(12) United States Patent
Lang

(10) Patent No.: US 11,801,114 B2
(45) Date of Patent: Oct. 31, 2023

(54) AUGMENTED REALITY DISPLAY FOR VASCULAR AND OTHER INTERVENTIONS, COMPENSATION FOR CARDIAC AND RESPIRATORY MOTION

(71) Applicant: Philipp K. Lang, Lexington, MA (US)

(72) Inventor: Philipp K. Lang, Lexington, MA (US)

( * ) Notice: Subject to any disclaimer, the term of this patent is extended or adjusted under 35 U.S.C. 154(b) by 503 days.

(21) Appl. No.: 16/644,603

(22) PCT Filed: Sep. 11, 2018

(86) PCT No.: PCT/US2018/050389
§ 371 (c)(1),
(2) Date: Mar. 5, 2020

(87) PCT Pub. No.: WO2109/051464
PCT Pub. Date: Mar. 14, 2019

(65) Prior Publication Data
US 2021/0137634 A1    May 13, 2021

Related U.S. Application Data

(60) Provisional application No. 62/698,710, filed on Jul. 16, 2018, provisional application No. 62/698,698, (Continued)

(51) Int. Cl.
*A61B 90/00* (2016.01)
*A61B 34/20* (2016.01)
(Continued)

(52) U.S. Cl.
CPC ............ *A61B 90/37* (2016.02); *A61B 5/0035* (2013.01); *A61B 5/0205* (2013.01);
(Continued)

(58) Field of Classification Search
None
See application file for complete search history.

(56) References Cited

U.S. PATENT DOCUMENTS

| 5,526,812 A | 6/1996 | Dumoulin et al. |
| 5,676,673 A | 10/1997 | Ferre et al. |

(Continued)

FOREIGN PATENT DOCUMENTS

| EP | 1028659 B1 | 2/2004 |
| GB | 2498833 B | 12/2016 |

(Continued)

OTHER PUBLICATIONS

Aguerreche L. et al., "Reconfigurable Tangible Devices for 3D Virtual Object Manipulation by Single or Multiple Users." VRST 2010, Nov. 2010, Hong Kong, Hong Kong SAR China. inria-00534095.

(Continued)

*Primary Examiner* — Sean D Mattson
(74) *Attorney, Agent, or Firm* — Greenberg Traurig, LLP; Natalie Salem; Barry Schnidler

(57) ABSTRACT

Devices and methods for performing an interventional vascular procedure with visual guidance using one or more optical head mounted displays are disclosed. Devices and methods for compensating the display of an optical head mounted display for cardiac and/or respiratory motion are disclosed.

17 Claims, 19 Drawing Sheets

Related U.S. Application Data filed on Jul. 16, 2018, provisional application No. 62/556,894, filed on Sep. 11, 2017.

(51) Int. Cl.
| | | |
|---|---|---|
| *H04N 13/332* | (2018.01) | |
| *A61B 5/318* | (2021.01) | |
| *A61B 5/00* | (2006.01) | |
| *A61B 5/0205* | (2006.01) | |
| *A61B 5/11* | (2006.01) | |
| *A61B 90/50* | (2016.01) | |
| *A61B 5/0245* | (2006.01) | |

(52) U.S. Cl.
CPC ............ *A61B 5/1102* (2013.01); *A61B 5/318* (2021.01); *A61B 34/20* (2016.02); *A61B 90/36* (2016.02); *A61B 90/39* (2016.02); *H04N 13/332* (2018.05); *A61B 5/0245* (2013.01); *A61B 5/7289* (2013.01); *A61B 2034/2057* (2016.02); *A61B 2034/2065* (2016.02); *A61B 2090/363* (2016.02); *A61B 2090/365* (2016.02); *A61B 2090/372* (2016.02); *A61B 2090/3945* (2016.02); *A61B 2090/502* (2016.02)

(56) References Cited

U.S. PATENT DOCUMENTS

| | | |
|---|---|---|
| 5,800,352 A | 9/1998 | Ferre et al. |
| 5,803,089 A | 9/1998 | Ferre et al. |
| 5,829,444 A | 11/1998 | Ferre et al. |
| 5,873,822 A | 2/1999 | Ferre et al. |
| D415,146 S | 10/1999 | Hori |
| 5,967,980 A | 10/1999 | Ferre et al. |
| 6,175,756 B1 | 1/2001 | Ferre et al. |
| 6,341,231 B1 | 1/2002 | Ferre et al. |
| 6,396,497 B1 | 5/2002 | Reichlen |
| 6,445,943 B1 | 9/2002 | Ferre et al. |
| 6,599,247 B1 | 7/2003 | Stetten |
| 6,714,810 B2 | 3/2004 | Grzeszczuk et al. |
| 7,130,676 B2 | 10/2006 | Barrick |
| 7,774,044 B2 | 8/2010 | Sauer et al. |
| 7,812,815 B2 | 10/2010 | Banerjee et al. |
| 8,320,612 B2 | 11/2012 | Knobel et al. |
| 8,730,266 B2 | 5/2014 | Brown et al. |
| 8,989,843 B2 | 3/2015 | Chien |
| 9,068,820 B2 | 6/2015 | Kosmecki et al. |
| 9,068,824 B2 | 6/2015 | Findeisen et al. |
| 9,123,155 B2 | 9/2015 | Cunningham et al. |
| 9,183,560 B2 | 11/2015 | Abelow |
| 9,215,293 B2 | 12/2015 | Miller |
| 9,299,138 B2 | 3/2016 | Zellner et al. |
| 9,310,559 B2 | 4/2016 | Macnamara |
| 9,311,284 B2 | 4/2016 | Warila et al. |
| 9,389,424 B1 | 7/2016 | Schowengerdt |
| 9,417,452 B2 | 8/2016 | Schowengerdt et al. |
| 9,429,752 B2 | 8/2016 | Schowengerdt et al. |
| 9,503,681 B1 | 11/2016 | Popescu et al. |
| 9,547,940 B1 | 1/2017 | Sun et al. |
| 9,582,717 B2 | 2/2017 | Lee et al. |
| 9,792,721 B2 | 10/2017 | Kosmecki et al. |
| 9,861,446 B2 | 1/2018 | Lang |
| 9,980,780 B2 | 5/2018 | Lang |
| 10,078,221 B2 | 9/2018 | Pilkinton et al. |
| 10,136,952 B2 | 11/2018 | Couture et al. |
| 10,154,239 B2 | 12/2018 | Casas |
| 10,159,530 B2 | 12/2018 | Lang |
| 10,278,777 B1 | 5/2019 | Lang |
| 10,292,768 B2 | 5/2019 | Lang |
| 10,368,947 B2 | 8/2019 | Lang |
| 10,405,927 B1 | 9/2019 | Lang |
| 10,603,113 B2 | 3/2020 | Lang |
| 10,743,939 B1 | 8/2020 | Lang |
| 10,799,296 B2 | 10/2020 | Lang |
| 10,849,693 B2 | 12/2020 | Lang |
| 11,013,560 B2 | 5/2021 | Lang |
| 11,172,990 B2 | 11/2021 | Lang |
| 2001/0041838 A1 | 11/2001 | Holupka et al. |
| 2002/0082498 A1 | 6/2002 | Wendt et al. |
| 2002/0016349 A1 | 11/2002 | Sauer |
| 2005/0113846 A1 | 5/2005 | Carson |
| 2005/0215879 A1 | 9/2005 | Chuanggui |
| 2005/0028146 A1 | 12/2005 | Marquart et al. |
| 2005/0267353 A1 | 12/2005 | Marquart et al. |
| 2005/0281465 A1 | 12/2005 | Marquart et al. |
| 2006/0142739 A1 | 6/2006 | Disilestro et al. |
| 2007/0015999 A1 | 1/2007 | Heldreth et al. |
| 2007/0035511 A1 | 2/2007 | Banerjee et al. |
| 2007/0038944 A1 | 2/2007 | Carignano et al. |
| 2007/0236514 A1 | 10/2007 | Agusanto et al. |
| 2007/0276234 A1 | 11/2007 | Shahidi |
| 2009/0068620 A1 | 3/2009 | Knobel et al. |
| 2009/0089081 A1 | 4/2009 | Haddad |
| 2009/0138019 A1 | 5/2009 | Wasielewski |
| 2009/0267805 A1 | 10/2009 | Jin et al. |
| 2011/0190637 A1 | 8/2011 | Knobel et al. |
| 2012/0226150 A1 | 9/2012 | Balicki et al. |
| 2013/0093829 A1 | 4/2013 | Rosenblatt et al. |
| 2013/0096373 A1 | 4/2013 | Chabanas et al. |
| 2013/0116574 A1 | 5/2013 | Knobel et al. |
| 2013/0169683 A1 | 7/2013 | Perez et al. |
| 2013/0172730 A1 | 7/2013 | Cohen |
| 2013/0223702 A1 | 8/2013 | Holsing et al. |
| 2013/0261503 A1 | 10/2013 | Sherman et al. |
| 2013/0261504 A1 | 10/2013 | Claypool et al. |
| 2013/0261633 A1 | 10/2013 | Thornberry |
| 2013/0293578 A1* | 11/2013 | Leung ............... A61B 34/20 345/633 |
| 2013/0296682 A1 | 11/2013 | Clavin et al. |
| 2013/0326364 A1 | 12/2013 | Latta et al. |
| 2014/0081659 A1 | 3/2014 | Nawana et al. |
| 2014/0085203 A1 | 3/2014 | Kobayashi |
| 2014/0088941 A1 | 3/2014 | Banerjee et al. |
| 2014/0118335 A1 | 5/2014 | Gurman |
| 2014/0135746 A1 | 5/2014 | Schoepp |
| 2014/0198190 A1 | 7/2014 | Okumu |
| 2014/0218366 A1 | 8/2014 | Kosmecki et al. |
| 2014/0275760 A1 | 9/2014 | Lee et al. |
| 2014/0303491 A1 | 10/2014 | Shekhar et al. |
| 2014/0334670 A1 | 11/2014 | Guigues et al. |
| 2015/0100067 A1 | 4/2015 | Cavanagh et al. |
| 2015/0206218 A1 | 7/2015 | Banerjee et al. |
| 2015/0366628 A1 | 12/2015 | Ingmanson |
| 2016/0163105 A1 | 6/2016 | Hong et al. |
| 2016/0182877 A1 | 6/2016 | DeLuca |
| 2016/0191887 A1 | 6/2016 | Casas |
| 2016/0206379 A1 | 7/2016 | Flett et al. |
| 2016/0220105 A1 | 8/2016 | Duret |
| 2016/0225192 A1 | 8/2016 | Jones et al. |
| 2016/0228193 A1 | 8/2016 | Moctezuma de la Barrera et al. |
| 2016/0287337 A1 | 10/2016 | Aram et al. |
| 2016/0324580 A1 | 11/2016 | Esterberg |
| 2016/0381256 A1 | 12/2016 | Aguirre-Valencia |
| 2017/0027651 A1 | 2/2017 | Esterberg |
| 2017/0035517 A1 | 2/2017 | Geri et al. |
| 2017/0071673 A1 | 3/2017 | Ferro et al. |
| 2017/0108930 A1 | 4/2017 | Banerjee et al. |
| 2017/0160549 A1 | 6/2017 | Badiali et al. |
| 2017/0178375 A1 | 6/2017 | Benishti et al. |
| 2017/0202633 A1 | 7/2017 | Liu |
| 2017/0231714 A1 | 8/2017 | Kosmecki et al. |
| 2017/0258526 A1 | 9/2017 | Lang |
| 2017/0296292 A1* | 10/2017 | Mahmood ............ A61B 34/20 |
| 2018/0049622 A1 | 2/2018 | Ryan et al. |
| 2018/0116728 A1 | 5/2018 | Lang |
| 2018/0125584 A1 | 5/2018 | Lang |
| 2018/0256256 A1 | 9/2018 | May et al. |
| 2018/0263704 A1 | 9/2018 | Lang |
| 2019/0000564 A1 | 1/2019 | Navab et al. |
| 2019/0110842 A1 | 4/2019 | Lang |
| 2019/0192226 A1 | 6/2019 | Lang |
| 2019/0216452 A1 | 7/2019 | Nawana et al. |

(56) References Cited

U.S. PATENT DOCUMENTS

| | | |
|---|---|---|
| 2019/0262078 A1 | 8/2019 | Lang |
| 2019/0380784 A1 | 12/2019 | Lang |
| 2020/0060767 A1 | 2/2020 | Lang |
| 2020/0246074 A1 | 8/2020 | Lang |
| 2020/0305980 A1 | 10/2020 | Lang |
| 2021/0022808 A1 | 1/2021 | Lang |
| 2021/0106386 A1 | 4/2021 | Lang |
| 2021/0267691 A1 | 9/2021 | Lang |

FOREIGN PATENT DOCUMENTS

| | | |
|---|---|---|
| WO | 9325157 | 12/1993 |
| WO | 2005088539 | 9/2005 |
| WO | 2010/034117 A1 | 4/2010 |
| WO | 2014057352 A1 | 4/2014 |
| WO | 2015/110859 A1 | 7/2015 |
| WO | 2015145395 | 10/2015 |
| WO | 2015145395 A1 | 10/2015 |
| WO | 2016028828 | 2/2016 |
| WO | 2016162789 | 10/2016 |
| WO | 2016195401 | 12/2016 |
| WO | 2016207628 | 12/2016 |
| WO | 2016207628 A1 | 12/2016 |
| WO | 2017145155 A1 | 8/2017 |
| WO | 2018/085417 A1 | 5/2018 |
| WO | 2018/085691 A1 | 5/2018 |
| WO | 2018/052966 A1 | 10/2018 |

OTHER PUBLICATIONS

Azuma, R., "A survey of augmented reality." Teleoperators and Virtual Environments, vol. 6, Issue 4, Aug. 1997, pp. 355-385.

Bajura, M., et al., "Merging Virtual Objects with the Real World: Seeing Ultrasound Imagery Within the Patient.", In Proceedings of SIGGRAPH '92, 1992, New York: ACM Press, pp. 203-210.

Benford, S. et al., "User embodiment in collaborative virtual environments", Proceedings of the SIGCHI conference on Human factors in computing systems, CHI '95, pp. 242-249, 1995.

Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.

Billinghurst, et al., "The MagicBook: A Transitional AR Interface.", Computers and Graphics, Nov. 2001, pp. 745-753.

Billinghurst, M., et al., "Experiments with Face to Face Collaborative AR Interfaces.", Virtual Reality Journal, vol. 4, No. 2, (2002).

Billinghurst, M., et al., "Collaborative Mixed Reality.", Communications of the ACM 2002, vol. 45 Issue 7, pp. 64-70 (2002).

Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.

Cruz-Neira C. et al., "The cave: audio visual experience automatic virtual environment.", Commun. ACM, vol. 35, No. 6, pp. 64-72, Jun. 1992.

Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).

Gee A, et al., "Processing and visualizing three-dimensional ultrasound data.", The British Journal of Radiology, vol. 77, S186-S193, (2004).

Gonzalez, Smart Multi-Level Tool for Remote Patient Monitoring Based on a Wireless Sensor Network and Mobile Augmented Reality, Sensors, Sep. 2014; 14(9): 17212-17234.

Gorbert, M. et al., "Triangles: Tangible Interface for Manipulation and Exploration of Digital Information Topography.", Proceedings of CHI '98, Apr. 18-23, 1998, @ 1998 ACM.

Ishii, H., et al., "Iterative Design of Seamless Collaboration Media.", Communications of the ACM, vol. 37, No. 8, Aug. 1994, pp. 83-97.

Maier-Hein, L. et al., "Towards Mobile Augmented Reality for On-Patient Visualization of Medical Images.", Bildverarbeitung für die Medizin 2011: Algorithmen—Systeme—Anwendungen Proceedings des Workshops vom 20.-22. März 2011 in Lübeck (pp. 389-393).

Medeiros D. et al., "Proposal and evaluation of a tablet-based tool for 3D virtual environments.", SBC Journal on 3D Interactive Systems, vol. 4, No. 2, pp. 30-40, (2013).

Nicolau, "Augmented Reality in Laparoscopic Surgical Oncology.", Surgical Oncology, vol. 20, pp. 89-201 (2011).

Salmi Jamali, S. et al., "Utilising Mobile-Augmented Reality for Learning Human Anatomy.", 7th World Conference on Educational Sciences, (WCES-2015), Feb. 5-7, 2015, Novotel Athens Convention Center, Athens, Greece.

Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2xILmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1lz_TUFgILvsRhShqXDrSM63OcvvjISzpUoBvsC2LsOmHqf-zifqdYe1ctf0D0MDM78YhH-u7w9JUfxuLDGVUxUi9hDQLZo.

Watsen, K., et al., "A Handheld Computer as an Interaction Device to a Virtual Environment.", Proceedings of the International Projection Technologies Workshop, Stuttgart, Germany, May 10-11, 1999.

Wellner, P., "Interacting with Paper on the DigitalDesk.", Communications of the ACM. 36, 7, 87-96, (1993).

Yamazaki, K. et al., "Gesture Laser and Gesture Laser Car—Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.

Yang H. et al., "Exploring collaborative navigation.", Proceedings of the 4th international conference on Collaborative virtual environments, CVE, pp. 135-142, (2002).

Wang H. et al., "Precision insertion of percutaneous sacroiliac screws using a novel augmented reality-based navigation system: a pilot study"., Intl. Orthop. (SICOT) 2016, 40: 1941-1947.

International Search Report and Written Opinion in International Application No. PCT/US2018/50389 dated Jan. 4, 2019.

Sauer et al., "An Augmented Reality Navigation System with a Single-Camera Tracker: System Design and Needle Biopsy Phantom Trial", Proceedings of the 5th International Conference on Medical Image Computing and Computer-Assisted Intervention—Part II, pp. 116-124, Sep. 2002.

Sauer et al., "Augmented Workspace: Designing an AR Testbed", Proceedings IEEE and ACM International Symposium on Augmented Reality, pp. 47-53, Munich 2000.

Scuderi et al., "Total Knee Arthroplasty with a Novel Navigation System Within the Surgical Field", Orthopedic Clinics, vol. 45, Issue 2, pp. 167-173, Apr. 2014.

Shen et al., "3D Augmented Reality with Integral Imaging Display", Proceedings of SPIE—The International Society for Optical Engineering, vol. 9867, Article No. 9867OY, Apr. 2016.

Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.

Tong et al., "Scanning 3D Full Human Bodies Using Kinects", IEEE Transactions on Visualization and Computer Graphics, vol. 18, Issue 4, pp. 643-650, Apr. 1, 2012.

Trevisan et al., "Towards Markerless Augmented Medical Visualization", AMI-ARCS, pp. 57-66, 2004.

Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.

(56) References Cited

OTHER PUBLICATIONS

Vercauteren et al., "Real Time Autonomous Video Image Registration for Endomicroscopy: Fighting The Compromises", Three-Dimensional and Multidimensional Microscopy: Image Acquisition and Processing XV., vol. 6861, p. 68610C. International Society for Optics and Photonics, Feb. 12, 2008.
Vogt et al., "Reality Augmentation for Medical Procedures: System Architecture, Single Camera Marker Tracking, and System Evaluation", International Journal of Computer Vision, vol. 70, No. 2, pp. 179-190, 2006.
Vogt, Sebastian, "Real-Time Augmented Reality for Image-Guided Interventions", PhD Thesis, Nürnberg: Der Technischen Fakultät der Universität Erlangen, 2009.
Wang et al., "3D Modeling from Wide Baseline Range Scans Using Contour Coherence", Proceedings of the IEEE Conference on Computer Vision and Pattern Recognition, pp. 4018-4025, 2014.
Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.
Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.
Ye et al., "Accurate 3D Pose Estimation From a Single Depth Image", IEEE International Conference on Computer Vision (ICCV), pp. 731-738, Nov. 2011.
Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.
Bauer, Sebastian, Doctoral Thesis, "Rigid and Non-Rigid Surface Registration for Range Imaging Applications in Medicine", urn:nbn:de:bvb:29-opus4-54665, Nov. 27, 2014.
Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.
Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.
Bauer et al., "Real-Time Range Imaging in Health Care: A Survey", Time-of-Flight and Depth Imaging, Sensors, Algorithms, and Applications. Lecture Notes in Computer Science, vol. 8200, pp. 228-254, 2017.
Birkfellner et al., "Computer-enhanced stereoscopic vision in a head-mounted operating binocular", Physics in Medicine & Biology, vol. 48, No. 3, pp. 49-57, Feb. 7, 2003.
Birkfellner et al., "In-Vitro Aassessment of a Registration Protocol for Image Guided Implant Dentistry", Clinical Oral Implants Research, vol. 12, Issue 1, pp. 69-78, Feb. 2001.
Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.
Maurer et al., "Augmented-Reality Visualization of Brain Structures with Stereo and Kinetic Depth Cues: System Description and Initial Evaluation with Head Phantom", Proceedings, vol. 4319, Medical Imaging 2001: Visualization, Display, and Image-Guided Procedures, pp. 445-456, May 28, 2001.
Blackwell et al., "Augmented Reality and Its Future in Orthopaedics", Clinical Orthopaedics & Related Research, vol. 354, pp. 111-122, Sep. 1998.
Abe et al., "A Novel 3D Guidance System Using Augmented Reality for Percutaneous Vertebroplasty", Journal of Neurological Spine, vol. 19, pp. 492-501, Oct. 2013.

Castillo et al., "Augmented Reality for Assistance of Total Knee Replacement", Journal of Electrical and Computer Engineering, vol. 2016, Article 9358369, pp. 1-6, 2016.
Catani et al., "Knee Surgery Using Computer Assisted Surgery and Robotics", Springer Heidelberg Publishing, Book, pp. 1-221, 2013.
Cui et al., "KinectAvatar: Fully Automatic Body Capture Using a Single Kinect", ACCV'12 Proceedings of the 11th International Conference on Computer Vision—vol. 2, pp. 133-147, Nov. 2012.
DeLambert et al., "Electromagnetic Tracking for Registration and Navigation in Endovascular Aneurysm Repair: A Phantom Study" European Journal of Vascular and Endovascular Surgery, vol. 43, pp. 684-689, 2012.
Draelos, Mark, "The Kinect Up Close: Modifications for Short-Range Depth Imaging", NC State Theses and Dissertations, pp. 1-88, Mar. 26, 2012.
Ferrari et al., "Video See-Through in the Clinical Practice", 1st International Workshop on Engineering Interactive Computing Systems for Medicine and Health Care, EICS4Med. vol. 727, pp. 19-24, 2011.
Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.
Flusser et al., "Image Fusion: Principles, Methods and Applications", Tutorial EISIPCO 2007 Lecture Notes.
Germano et al., Advanced Techniques in Image-Guided Brain and Spine Surgery, Thieme Medical Publishers, Incorporated, 2002.
Hayashibe et al., "Surgical Navigation Display System Using vol. Rendering of Intraoperatively Scanned CT Images", Computer Aided Surgery, vol. 11, No. 5, pp. 240-246, Sep. 2006.
Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Dec. 12, 2013.
Hua et al., "A 3D Integral Imaging Optical See-Through Head-Mounted Display", Optical Society of America, vol. 22, No. 11, pp. 1-8, Jun. 2, 2014.
Jiang et al., "A Robust Automated Markerless Registration Framework for Neurosurgery Navigation", The International Journal of Medical Robotics and Computer Assisted Surgery, vol. 11, pp. 436-447, Oct. 19, 2014.
Jolesz, Ferenc A., Textbook, "Intraoperative Imaging and Image-Guided Therapy", Springer Science & Business Media, 893 pages, Jan. 14, 2014.
Kanade et al., "Simulation, Planning, and Execution of Computer-Assisted Surgery", Proceedings of the NSF Grand Challenges Workshop, 1996.
Kersten-Oertel et al., "The State of the Art of Visualization in Mixed Reality Image Guided Surgery", Computerized Medical Imaging and Graphics, vol. 37, pp. 98-112, Jan. 2013.
Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.
Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.
Liao et al., "Surgical Navigation by Autostereoscopic Image Overlay of Integral Videography", IEEE Transactions on Information Technology in Biomedicine, vol. 8, No. 2, pp. 114-121, Jun. 2004.
Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.
Lievin et al., "Stereoscopic Augmented Reality System for Computer-Assisted Surgery", International Congress Series, vol. 1230, pp. 107-111, Jun. 2001.
Liu et al., "An Optical See-Through Head Mounted Display with Addressable Focal Planes" IEEE International Symposium on Mixed and Augmented Reality, Cambridge, UK, pp. 33-42, Oct. 3, 2008.

(56) References Cited

OTHER PUBLICATIONS

Maier-Hein et al., "Optical Techniques for 3D Surface Reconstruction in Computer-Assisted Laparoscopic Surgery", Medical Image Analysis, vol. 17, pp. 974-996, May 3, 2013.
Menozzi et al., "Development of Vision-Aided Navigation for a Wearable Outdoor Augmented Reality System", IEEE Plans, Position Location and Navigation Symposium, Article No. 6851442, pp. 760-772, 2014.
Muller et al., "Automatic Multi-Modal ToF/CT Organ Surface Registration", Bildverarbeitung für die Medizin, pp. 154-158, Mar. 2011.
Noonan et al., "The Design and Initial Calibration of an Optical Tracking System Using the Microsoft Kinect", IEEE Nuclear Science Symposium Conference Record, pp. 3614-3617, Oct. 2011.
Okamura, Allison, "Tracking and Surgical Navigation, Registration", Stanford Lecture 8: ME 328: Medical Robotics, pp. 1-19, Spring 2013.
Pauly et al., "Machine Learning-Based Augmented Reality for Improved Surgical Scene Understanding", Computerized Medical Imaging and Graphics, vol. 1280, pp. 1-6, Jun. 2014.
Peters et al., Textbook, "Image-Guided Interventions, Technology and Applications", Springer Science and Business Media, 576 pages, 2018.
Ren et al., "Marker-Based Surgical Instrument Tracking Using Dual Kinect Sensors", IEEE Transactions on Automation Science and Engineering, vol. 11, No. 3, pp. 921-924, Jul. 2014.
Rinaldi et al., Textbook, "Computer-Guided Applications for Dental Implants, Bone Grafting, and Reconstructive Surgery", Elsevier Inc., 556 pages, 2016.
Robinett et al., "A Computational Model for the Stereoscopic Optics of a Head-Mounted Display", Proceedings vol. 1457, Stereoscopic Displays and Applications II, pp. 140-160, 1991.
Rolland et al., "A Comparison of Optical and Video See-through Head-mounted Displays", Proceedings vol. 2351, Telemanipulator and Telepresence Technologies, pp. 293-307, Dec. 21, 1995.
Rolland et al., "Optical Versus Video See-Through Head-Mounted Displays in Medical Visualization", Presence: Teleoperators and Virtual Environments, vol. 9, Issue 3, pp. 287-309, Jun. 2000.
Rosman et al., "Articulated Motion Segmentation of Point Clouds by Group-Valued Regularization", Eurographics Workshop on 3D Object Retrieval, EG 3DOR, pp. 77-84, May 2012.
"3D Optical Microscopy for Orthopedic Implants"; Bruker Nano Surfaces, Jun. 17, 2016.
"A Look into the Body—Augmented Reality in Computer Aided Surgery", Department of Informatics, Research—Highlights; Technische Universitat Munchen.
Armstrong et al., "A Heads-Up Display for Diabetic Limb Salvage Surgery: A View Through the Google Looking Glass", Journal of Diabetes Science and Technology 2014, vol. 8(5) 951-956.
Besl PJ, Mckay ND. 2, 1992. A method for registration of 3-D shapes. IEEE Trans PAMI, vol. 14, pp. 239-256.
Bichlmeier et al., "Virtually Extended Surgical Drilling Device: Virtual Mirror for Navigated Spine Surgery"; MICCAI 2007, Part I, LNCS 4791, pp. 434-441.
Chandak, "MEMS Based Wireless Controlled Robot with Voice and Video Camera"; International Journal of Scientific & Engineering Research, vol. 5, Issue 4, Apr. 2014.
Charbonnier et al., "Real Virtuality: Perspectives offered by the combination of Virtual Reality headsets and Motion Capture", Artanim, Real Virtuality White Paper, Aug. 23, 2015.
Chen et al., "Development of a surgical navigation system based on augmented reality using an optical see-through head-mounted display"; Journal of Biomedical Informatics 55 (2015) 124-131.
Elmi-Terander et al., "Surgical Navigation Technology Based on Augmented Reality and Integrated 3D Intraoperative Imaging"; Spine Surgery, vol. 41, No. 21, pp. E1303-1311, 2016.
Fritz et al., "Augmented Reality Visualization with Use of Image Overlay Technology for MR Imaging—guided Interventions: Assessment of Performance in Cadaceric Shoulder and Hip Arthrography at 1.5T"; Radiology: vol. 265, No. 1, Oct. 2012, pp. 254-259.

Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).
Garrido-Jurado, S.; Muñoz-Salinas, R.; Madrid-Cuevas, F. J.; Marín-Jiménez, M. J. (2014): Automatic generation and detection of highly reliable fiducial markers under occlusion. In: Pattern Recognition 47 (6), S. 2280-2292. DOI: 10.1016/j.patcog.2014.01.005.
Gavaghan et al., "Augmented Reality Image Overlay Projection for Image Guided Open Liver Ablation of Metastatic Liver Cancer"; C.A. Linte et al. (Eds.): AE-CAI 2011, LNCS, pp. 36-46, 2012.
Gromov et al., "What is the optimal alignment of the tibial and femoral components in knee arthroplasty?: An overview of the literature"; Acta Orthopaedica 2014; 85(5): 480-487.
Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.
Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.
Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.
Hinterstoisser, S.; Lepetit, V.; Benhimane, S.; Fua, P.; Navab, N. (2011a): Learning Real-Time Perspective Patch Rectification. In: International Journal of Computer Vision (IJCV), Springer. DOI: 10.1007/s11263-010-0379-x.
Hoff, "Fusion of Data from Head-Mounted and Fixed Sensors"; First International Workshop on Augmented Reality, 1, 1998, pp. 1-15.
Holographic weapon sight—Wikipedia https://en.wikipedia.org/wiki/Holographic_weapon_sight retrieved on Nov. 22, 2016.
Ji et al., "Real-Time Eye, Gaze, and Face Pose Tracking for Monitoring Driver Vigilance"; Real-Time Imaging 8, pp. 357-377, 2002.
Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.
Kolodzey et al., "Wearable technology in the operating room: a systematic review"; GMJ Innov 2017; 3:55-63.
Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.
Lamata et al., "Augmented Reality for Minimally Invasive Surgery: Overview and Some Recent Advances"; Augmented Reality, Jan. 2010.
Lindert et al., "The use of a head-mounted display for visualization in neuroendoscopy", Computer Aided Surgery, 2004; 9(6): 251-256.
Lorensen WE, Cline HE. [ed.], in M.C. Stone. 1987. Marching cubes: A high resolution 3d surface construction algorithm. Proceedings of SIGGRAPH 87. pp. 163-169.
Melzer, "Head-Mounted Displays", The Avionics Handbook, 2001.
MicroVision 2015 Annual Report and Proxy Statement for 2016 Annual Meeting of Shareholders.
Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.
Nikou et al., "Augmented Reality Imaging Technology for Orthopaedic Surgery", Operative Techniques in Orthopaedics, vol. 10, No. 1 Jan. 2000: pp. 82-86.
Ortega et al., "Usefulness of a head mounted monitor device for viewing intraoperative fluoroscopy during orthopaedic procedures", Arch Orthop Trauma Surg (2008) 128:1123-1126.
Paprosky et al., "Intellijoint Hip: a 3D mini-optical navigation tool for improving intraoperative accuracy during total hip arthroplasty"; Med Devices (Auckl). 2016; 9: 401-408.

(56) References Cited

OTHER PUBLICATIONS

Ponce et al., "Emerging Technology in Surgical Education: Combining Real-Time Augmented Reality and Wearable Computing Devices", The Cutting Edge, Nov. 2014, vol. 37, No. 11.
Qian, Long; Azimi, Ehsan; Kazanzides, Peter; Navab, Nassir (2017): Comprehensive Tracker Based Display Calibration for Holographic Optical See-Through Head-Mounted Display.
Rhodes, "A brief history of wearable computing", MIT Wearable Computing Project.
Rosenthal et al., "Augmented Reality Guidance for Needle Biopsies: A Randomized, Controlled Trial in Phantoms"; MICCAI 2001, LNCS 2208: 240-248.
Sanko, "Microvision's Nomad Augmented Vision System: The How and the Why"; SID Pacific Northwest Chapter Meeting, Jun. 11, 2003.
State et al., "Stereo Imagery from the UNC Augmented Reality System for Breast Biopsy Guidance", MMVR 2003.
Tan, D. J.; Tombari, F.; Ilic, S.; Navab, N. (2015): A Versatile Learning-Based 3D Temporal Tracker. Scalable, Robust, Online. In: 2015 IEEE International Conference on Computer Vision (ICCV), S. 693-701.
Traub, J., Stefan, P., Heining, S.M., Sielhorst, T., Riquarts, C., Eulerz, E., Navab, N. (2006): Hybrid Navigation Interface for Orthopedic and Trauma Surgery. R. Larsen, M. Nielsen, and J. Sporring (Eds.): MICCAI 2006, LNCS 4190, pp. 373-380.
Wang et al., "Augmented Reality 3D Displays with Micro Integral Imaging"; Journal of Display Technology, Oct. 2014.
Wilson et al., "Validation of Three-Dimensional Models of the Distal Femur Created from Surgical Navigation Point Cloud Data"; CAOS 2015.
Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.
Anderson et al., "Virtual annotations of the surgical field through an augmented reality transparent display", The Visual Computer, vol. 32, Issue 11, pp. 1481-1498, Nov. 2016.
Baker et al., "The Emergence of Augmented Reality in Orthopaedic Surgery and Education", The Orthopaedic Journal at Harvard Medical School, vol. 16, pp. 8-16, Jun. 2015.
Daniel and Ramos, "Augmented Reality for Assistance of Total Knee Replacement", Journal of Electrical and Computer Engineering, vol. 2016, Article ID 9358369, Hindawi Publishing Corporation.
Davies et al., "Computer Assisted Orthopaedic Surgery", 8th Annual Meeting of CAOS—International Proceedings, Apr. 2008.
Fritz et al., "Augmented Reality Visualization with Image Overlay for MRI-Guided Intervention: Accuracy for Lumbar Spinal Procedures with a 1.5-T MRI System", Vascular and Interventional Radiology, AJR: 198, Mar. 2012.
George et al., "Low Cost Augmented Reality for Training of MRI-Guided Needle Biopsy of the Spine", Medicine Meets Virtual Reality 16, pp. 138-140, IOS Press, 2008.
Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013; 37(2): 83-97, DOI: 10.1016/j.compmedimag.2012.12.002.
Moore et al., "Image Guidance for Spinal Facet Injections Using Tracked Ultrasound", MICCAI 2009, Part I, LNCS 5761, pp. 516-523 2009.
Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.
Blackwell et al., "An Image Overlay System for Medical Data Visualization", In: Wells W.M., Colchester A., Delp S. (eds) Medical Image Computing and Computer-Assisted Intervention—MICCAI'98. MICCAI 1998. Lecture Notes in Computer Science, vol. 1496. Springer, Berlin, Heidelberg; pp. 232-240.

* cited by examiner

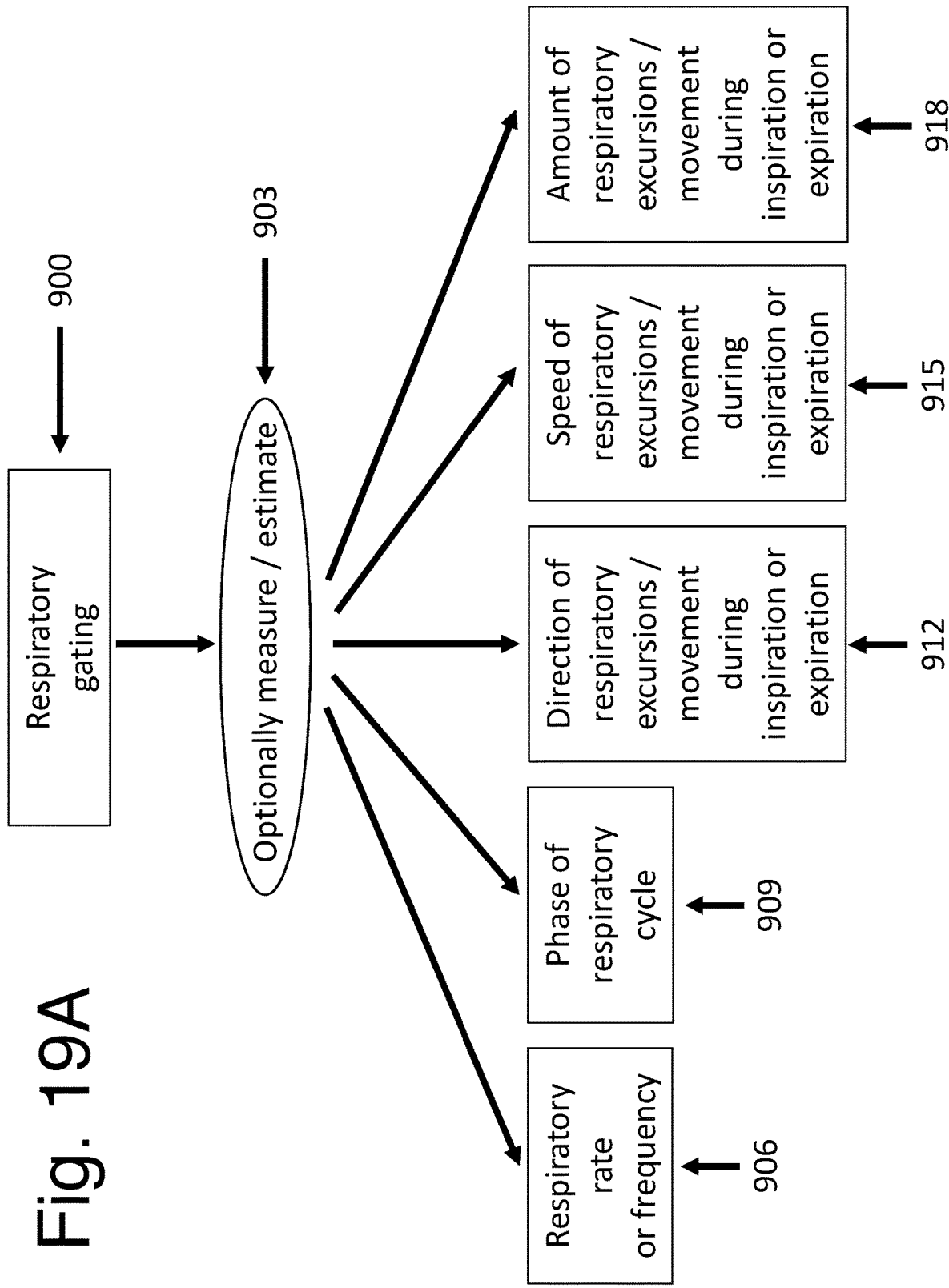

AUGMENTED REALITY DISPLAY FOR VASCULAR AND OTHER INTERVENTIONS, COMPENSATION FOR CARDIAC AND RESPIRATORY MOTION

RELATED APPLICATIONS

This application is a U.S. national phase application under 35 U.S.C. 371 of PCT International Application No. PCT/US2018/050389, filed Sep. 11, 2018, which claims the benefit of and priority to U.S. Provisional application Ser. No. 62/556,894, filed Sep. 11, 2017, to U.S. Provisional Application Ser. No. 62/698,710, filed Jul. 16, 2018, and to U.S. Provisional Application Ser. No. 62,698/698, filed Jul. 16, 2018, the entire contents of each of which are hereby incorporated by reference in their entireties.

TECHNICAL FIELD

The present disclosure relates to devices and methods for performing an interventional procedure with visual guidance using an optical head mounted display. The present disclosure relates to devices and methods for performing various interventional or surgical procedures with visual guidance using an optical head mounted display with cardiac and/or respiratory gating of the displayed virtual data.

BACKGROUND

With vascular interventions, pre-operative imaging studies of the patient can be used. The imaging studies can be displayed in the interventional suite on an external computer monitor and the patient's anatomy, e.g. landmarks such as vessels, vascular branches, vascular trees, bones, and/or organs, can be registered in relationship to the information displayed on the monitor. Since the interventional field and vascular access is in a different location and has a different view coordinate system for the surgeon or interventionalist's eyes than the external computer monitor, hand-eye coordination can be challenging for the surgeon or interventionalist. Thoracic and/or abdominal tissues and/or organs can move as a result of cardiac and/or respiratory motion.

SUMMARY

According to some embodiments, devices, systems, methods and techniques for gating and/or moving the display of virtual data by one or more optical head mounted displays using cardiac and/or respiratory gating information are provided.

Some embodiments relate to a system comprising an optical head mounted display, and a computer system with one or more processors, wherein the optical head mounted display is configured to display a computer-generated virtual image of an anatomic structure of a patient or of a device or instrument aligned with an anatomic landmark or the anatomic structure of a patient, wherein the one or more processors are configured to receive data of the respiratory cycle of the patient, wherein the one or more processors are configured to maintain the alignment of the virtual image with the anatomic landmark or anatomic structure of the patient through at least a portion of the respiratory cycle of the patient by synchronizing the display of the virtual image based on the data of the respiratory cycle of the patient. In some embodiments, the synchronizing includes changing the coordinates of the virtual image displayed by the optical head mounted display in x-, y-, and/or z-direction based on the data of the respiratory cycle of the patient. In some embodiments, the synchronizing includes displaying sequentially two or more virtual images by the optical head mounted display, wherein each virtual image includes data from a different phase of the respiratory cycle. In some embodiments, the synchronizing includes changing the coordinates of the virtual image displayed by the optical head mounted display in x-, y-, and/or z-direction based on the data of the respiratory cycle of the patient and displaying sequentially two or more virtual images by the optical head mounted display, wherein each virtual image includes data from a different phase of the respiratory cycle.

In some embodiments, the one or more processor is configured to match one or more virtual images displayed by the optical head mounted display to the data of the respiratory cycle of the patient. In some embodiments, the virtual image is a three-dimensional digital representation corresponding to at least one portion of a physical anatomic landmark, a physical anatomic structure, or a physical tissue. In some embodiments, the virtual image is a three-dimensional digital representation corresponding to at least one portion of a physical anatomical target for surgical or other medical intervention. In some embodiments, the virtual image is a three-dimensional digital representation corresponding to at least one portion of a physical device or a physical instrument.

In some embodiments, the data of the respiratory cycle of the patient comprises at least one of (a) one or more of a frequency of the patient's respiratory cycle, (b) a phase of the respiratory cycle, (c) a direction of respiratory movement or excursion of the diaphragm, physical landmark, physical structure, physical tissue, physical organ or physical target, (d) a speed of respiratory movement or excursion of the diaphragm, physical landmark, physical structure, physical tissue, physical organ or physical target, or (e) an amount of movement or excursion of the diaphragm, physical landmark, physical structure, physical tissue, physical organ or physical target.

In some embodiments, the physical anatomic landmark, physical structure or physical tissue of the patient are not directly visible through the optical head mounted display. In some embodiments, the physical anatomic landmark, physical structure or physical tissue of the patient are below a skin, inside a pericardium, inside a pleura, inside a peritoneum, inside an organ, underneath an organ surface, or underneath a tissue surface.

In some embodiments, the virtual image is derived from imaging data. In some embodiments, the imaging data are acquired using respiratory gating. In some embodiments, the respiratory gating comprises measuring one or more parameters of the respiratory cycle of the patient and tagging the imaging data with the measured parameter of the phase of the respiratory cycle during which the imaging data were acquired. In some embodiments, the data of the respiratory cycle of the patient are measured using one or more markers applied to the chest wall, abdominal wall, organ, tissue, or tissue surface, and using an image capture, camera or video system. In some embodiments, the data of the respiratory cycle of the patient are measured using imaging. In some embodiments, the virtual image is aligned with onto a corresponding physical landmark, physical structure or physical tissue through at least a portion of the respiratory cycle.

In some embodiments, the one or more processor is configured to compute a synchronized movement of the virtual image displayed by the optical head mounted display using the data of the respiratory cycle of the patient to maintain alignment of the virtual image with a physical landmark, a physical anatomic structure or a physical tissue of the patient through at least a portion of the respiratory cycle.

In some embodiments, the one or more processor is configured to compute a synchronized sequence of virtual images from different phases of the respiratory cycle displayed by the optical head mounted display using the data of the respiratory cycle of the patient to maintain alignment of the virtual image with a physical landmark, a physical anatomic structure or a physical tissue of the patient through at least a portion of the respiratory cycle.

In some embodiments, the optical head mounted display is a see through optical head mounted display.

In some embodiments, the one or more processor is configured to maintain the alignment of the virtual image with the anatomic landmark or anatomic structure of the patient through the entire respiratory cycle of the patient.

In some embodiments, the instrument comprises one of a grasper, vein valve cutter, vein extirpation set or extraction instrument. In some embodiments, the device comprises one of a catheter, catheter tip, guidewire, sheath, stent, coil, implant or vascular prosthesis.

In some embodiments, the physical anatomic landmark comprises a vascular structure, a cardiac structure, neural structure, a neurovascular structure, or combinations thereof. In some embodiments, the physical structure comprises a vessel, an artery, a vein, a coronary artery, a cerebral artery, a cerebral vein, a lymph vessel, a duct, a urether, a urethra, a cavity, or combinations thereof. In some embodiments, the physical tissue comprises epicardium, myocardium, cardiac tissue, cardiac valves, neural tissue, lymphatic tissue or combinations thereof.

In some embodiments, the physical anatomic landmark comprises a target for surgical or other medical intervention. In some embodiments, the physical structure comprises a vessel, an artery, a vein, an aorta, an inferior vena cava, a pulmonary artery, a pulmonary vein, or combinations thereof. In some embodiments, the physical tissue of the patient comprises one or more of a heart, a lung, a liver, a spleen, a pancreas, a gallbladder, a kidney, a tumor, a lesion, or combinations thereof.

Other embodiments relate to a method comprising (a) generating by a computer system a virtual image of an anatomic structure of a patient or of a device or instrument, (b) displaying the computer-generated virtual image by the optical head mounted display so as to align the virtual image with an anatomic landmark or an anatomic structure of a patient, and (c) receiving data of the respiratory cycle of the patient, wherein the display of the computer-generated virtual image is configured to be aligned with the anatomic landmark or anatomic structure of the patient through at least a portion of the respiratory cycle of the patient by synchronizing by the computer system the display of the virtual image based on the data of the respiratory cycle of the patient to maintain the alignment of the virtual image with the anatomic landmark or anatomic structure of the patient through at least a portion of the respiratory cycle of the patient.

Other embodiments relate to a system comprising an optical head mounted display, and a computer system with one or more processors, wherein the optical head mounted display is configured to display a computer-generated virtual image aligned with an anatomic landmark or an anatomic structure of a patient, wherein the one or more processors are configured to receive data of the cardiac cycle of the patient, and wherein the one or more processors are configured to maintain the alignment of the virtual image with the anatomic landmarks or anatomic structures of the patient through at least a portion of the cardiac cycle of the patient by synchronizing the display of the virtual image based on the data of the cardiac cycle of the patient.

In some embodiments, the synchronizing includes changing the coordinates of the virtual image displayed by the optical head mounted display in x-, y-, and/or z-direction based on the data of the cardiac cycle of the patient. In some embodiments, the synchronizing includes displaying sequentially two or more virtual images by the optical head mounted display, wherein each virtual image includes data from a different phase of the cardiac cycle. In some embodiments, the synchronizing includes changing the coordinates of the virtual image displayed by the optical head mounted display in x-, y-, and/or z-direction based on the data of the cardiac cycle of the patient and displaying sequentially two or more virtual images by the optical head mounted display, wherein each virtual image includes data from a different phase of the cardiac cycle.

In some embodiments, the one or more processor is configured to match one or more virtual images displayed by the optical head mounted display to the data of the cardiac cycle of the patient.

In some embodiments, the virtual image is a three-dimensional digital representation corresponding to at least one portion of a physical anatomic landmark, a physical anatomic structure, or a physical tissue. In some embodiments, the virtual image is a three-dimensional digital representation corresponding to at least one portion of a physical anatomical target for surgical or other medical intervention. In some embodiments, the virtual image is a three-dimensional digital representation corresponding to at least one portion of a physical device or a physical instrument.

In some embodiments, the data of the patient's cardiac cycle include one or more of (a) a heart rate, (b) phase of the cardiac cycle, (c) phase of systole or diastole, (d) direction of cardiac or vascular movement or pulsation, (e) speed of cardiac or vascular movement or pulsation, (f) amount of cardiac or vascular movement or pulsation, or (g) the amount of cardiac or vascular related movement or excursion of a physical anatomic landmark, physical structure, physical tissue, physical organ or physical target. In some embodiments, the physical anatomic landmark, physical structure or physical tissue of the patient are not directly visible through the optical head mounted display. In some embodiments, the physical anatomic landmark, physical structure or physical tissue of the patient are below a skin, inside a pericardium, inside a pleura, inside a peritoneum, inside an organ, underneath an organ surface, or underneath a tissue surface. In some embodiments, the In some embodiments, the virtual image is derived from imaging data. In some embodiments, the imaging data are acquired using cardiac gating. In some embodiments, the cardiac gating comprises measuring one or more parameters of the cardiac cycle of the patient and tagging the imaging data with the measured parameter of the phase of the cardiac cycle during which the imaging data were acquired. In some embodiments, the data of the cardiac cycle of the patient are measured using one or more markers applied to the chest wall, abdominal wall, organ, tissue, or tissue surface, and using an image capture, camera or video system. In some embodiments, the data of the cardiac cycle of the patient are measured using imaging.

In some embodiments, the display of the virtual image is aligned with onto a corresponding physical landmark, physical structure or physical tissue through at least a portion of the cardiac cycle.

In some embodiments, the one or more processor is configured to compute a synchronized movement of the virtual image displayed by the optical head mounted display using the data of the cardiac cycle of the patient to maintain alignment of the virtual image with a physical landmark, a physical anatomic structure or a physical tissue of the patient through at least a portion of the cardiac cycle.

In some embodiments, the one or more processor is configured to compute a synchronized sequence of virtual images from different phases of the cardiac cycle displayed by the optical head mounted display using the data of the cardiac cycle of the patient to maintain alignment of the virtual image with a physical landmark, a physical anatomic structure or a physical tissue of the patient through at least a portion of the cardiac cycle.

In some embodiments, the optical head mounted display is a see through optical head mounted display.

In some embodiments, the instrument comprises one of a grasper, vein valve cutter, vein extirpation set, extraction instrument. In some embodiments, the device comprises one of a catheter, catheter tip, guidewire, sheath, stent, coil, implant, or vascular prosthesis. In some embodiments, the one or more processor is configured to maintain the alignment of the virtual image with the anatomic landmark or anatomic structure of the patient through the entire cardiac cycle of the patient.

In some embodiments, the physical anatomic landmark comprises a vascular structure, a cardiac structure, neural structure, a neurovascular structure, or combinations thereof. In some embodiments, the physical structure comprises a vessel, an artery, a vein, a coronary artery, a cerebral artery, a cerebral vein, a lymph vessel, a duct, a urether, a urethra, a cavity, or combinations thereof. In some embodiments, the physical tissue comprises epicardium, myocardium, cardiac tissue, cardiac valves, neural tissue, lymphatic tissue or combinations thereof.

In some embodiments, the physical anatomic landmark comprises a target for surgical or other medical intervention. In some embodiments, the physical structure comprises a vessel, an artery, a vein, an aorta, an inferior vena cava, a pulmonary artery, a pulmonary vein, or combinations thereof. In some embodiments, the physical tissue of the patient comprises one or more of a heart, a lung, a liver, a spleen, a pancreas, a gallbladder, a kidney, a tumor, a lesion, or combinations thereof.

Other aspects relate to a method comprising (a) generating by a computer system a virtual image of an anatomic structure of a patient or of a device or instrument, (b) displaying the computer-generated virtual image by the optical head mounted display so as to align the virtual image with an anatomic landmark or an anatomic structure of a patient, and (c) receiving data of the cardiac cycle of the patient, wherein the display of the computer-generated virtual image is configured to be aligned with the anatomic landmark or anatomic structure of the patient through at least a portion of the cardiac cycle of the patient by synchronizing by the computer system the display of the virtual image based on the data of the cardiac cycle of the patient to maintain the alignment of the virtual image with the anatomic landmark or anatomic structure of the patient through at least a portion of the cardiac cycle of the patient.

Other embodiments relate to a system comprising nan optical head mounted display, and a computer system comprising a computer monitor and one or more processors, wherein the optical head mounted display, the computer monitor, and a patient are registered in a coordinate system, wherein the one or more computer processors are configured to display an intra-operative angiogram of the patient on the computer monitor, wherein the one or more computer processors are configured to track an instrument or a device in the coordinate system, wherein the instrument or device is registered in the coordinate system, wherein the optical head mounted display is configured to display a virtual pre-operative vascular 3D image aligned with one or more corresponding vascular structures represented in the angiogram of the patient displayed on the computer monitor, wherein the optical head mounted display is configured to display a virtual 3D image of the tracked instrument or device aligned with at least one of the corresponding intra-operative angiogram of vascular structures of the patient displayed on the computer monitor or the virtual pre-operative vascular 3D image displayed by the optical head mounted display.

In some embodiments, the intra-operative angiogram includes one or more of a 2D angiogram, a biplanar angiogram, a 3D angiogram, a vascular run-off or bolus chase.

In some embodiments, the virtual pre-operative vascular 3D image includes one or more of an ultrasound image, an echocardiogram image, a CT scan image, an MRI scan image, a CT angiogram image, an MR angiogram image. In some embodiments, the pre-operative vascular 3D image includes 3D data.

In some embodiments, the pre-operative vascular 3D image is registered with the intra-operative angiogram using a 3D-2D registration.

In some embodiments, the tracking of the instrument or device is image based. In some embodiments, the instrument or device comprises one or more radiopaque markers. In some embodiments, the instrument or device comprises one or more receivers, transmitter coils, sensors, IMU's or combinations thereof.

In some embodiments, the computer monitor is a stand-alone computer monitor.

In some embodiments, the optical head mounted display is a see through optical head mounted display.

In some embodiments, the device is an intravascular or endoluminal device or wherein the instrument is an intravascular or endoluminal instrument. In some embodiments, the device is one of a catheter, catheter tip, guidewire, sheath, stent, coil, implant, or vascular prosthesis. In some embodiments, the instrument is one of a grasper, vein valve cutter, vein extirpation set, or extraction instrument.

Some embodiments relate to a method comprising (a) registering an optical head mounted display, a computer monitor, an instrument or a device, and a patient in a coordinate system;

displaying an intra-operative angiogram of a patient on the computer monitor, (b) generating using a computer processor a virtual pre-operative vascular 3D image, (c) tracking the instrument or the device in the coordinate system, (d) displaying using the optical head mounted display the virtual pre-operative vascular 3D image so that the virtual pre-operative vascular 3D image is aligned with one or more corresponding vascular structures represented in the intra-operative angiogram of the patient displayed on the computer monitor, and (e) displaying a virtual 3D image of the tracked instrument or device aligned with at least one of the corresponding intra-operative angiogram of vascular structures displayed on the computer monitor or aligned with the virtual pre-operative vascular 3D image displayed by the optical head mounted display.

BRIEF DESCRIPTION OF THE DRAWINGS

Illustrative, non-limiting example embodiments will be more clearly understood from the following detailed description taken in conjunction with the accompanying drawings.

FIG. 19A is a diagram showing an example of respiratory gating for measuring or estimating one or more of respiratory rate or frequency, the phase of the respiratory cycle, the direction of respiratory excursions or movement during inspiration or expiration, the speed of respiratory excursions or movement during inspiration or expiration or the amount of respiratory excursions or movement during inspiration or expiration, according to some embodiments.

DETAILED DESCRIPTION

Figure 1:
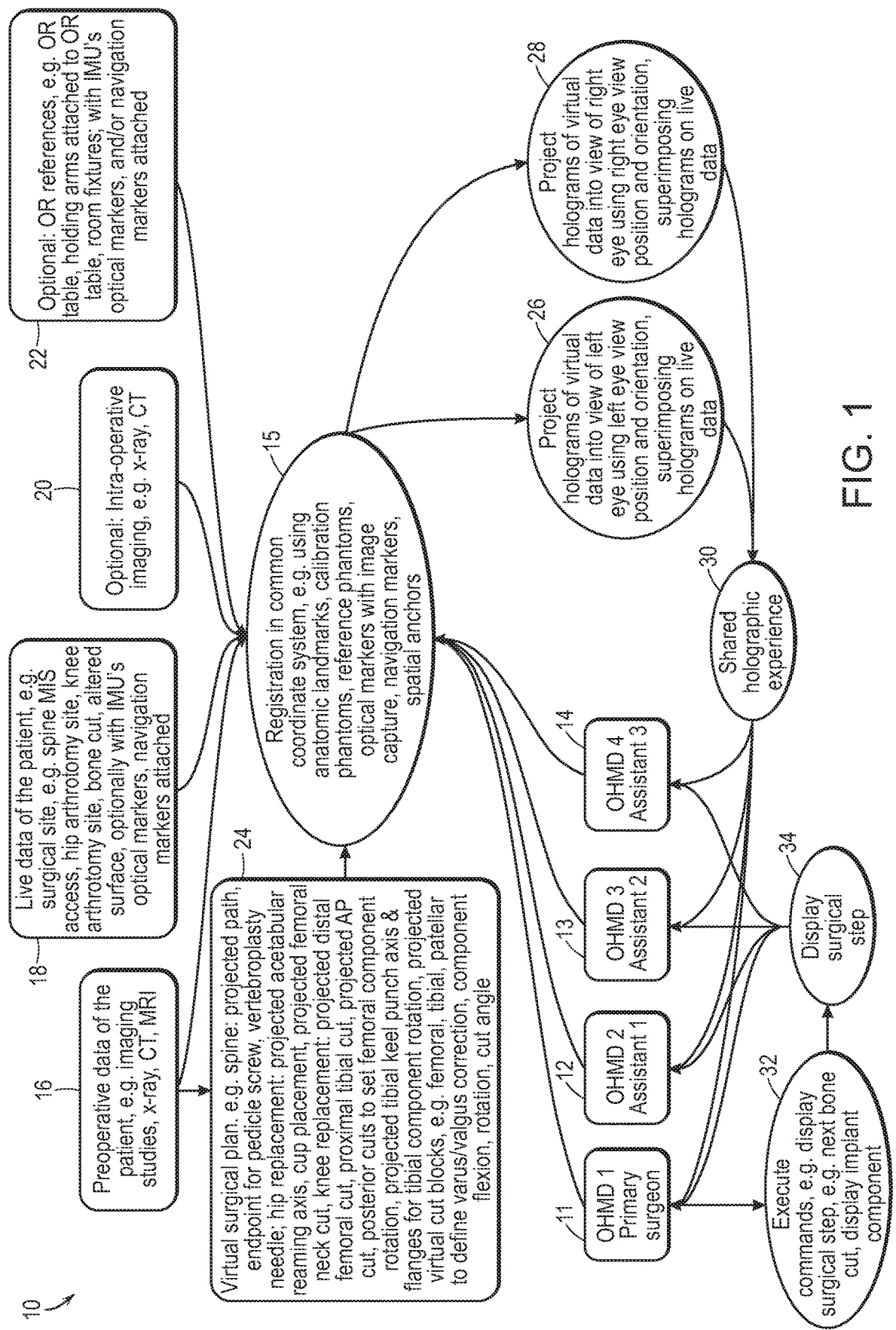
FIG. 1 is an illustrative flow chart showing the use of multiple OHMDs for multiple viewer's, e.g. a primary surgeon or interventionalist, second surgeon or interventionalist, surgical assistant(s) and/or nurses(s) according to some embodiments of the present disclosure.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

The term "live data" of the patient, as used herein, includes the surgical or interventional site, anatomy, anatomic structures or tissues and/or pathology, pathologic structures or tissues of the patient as seen by the surgeon or interventionalist's or viewer's eyes without information from virtual data, stereoscopic views of virtual data, or imaging studies. The term live data of the patient does not include internal or subsurface tissues or structures or hidden tissues or structures that can only be seen with assistance of imaging studies, a computer monitor or OHMD.

The terms real surgical, surgical-interventional, vascular-interventional, or interventional, actual surgical, surgical-interventional, vascular-interventional, or interventional, physical surgical, surgical-interventional, vascular-interventional, or interventional, and surgical, surgical-interventional, vascular-interventional, or interventional, can be used interchangeably throughout the application; the terms real surgical, surgical-interventional, vascular-interventional, or interventional, actual surgical, surgical-interventional, vascular-interventional, or interventional, physical surgical, surgical-interventional, vascular-interventional, or interventional, and surgical, surgical-interventional, vascular-interventional, or interventional, do not include virtual surgical, surgical-interventional, vascular-interventional, or interventional. Physical surgical, surgical-interventional, vascular-interventional, interventional, or vascular instruments can be re-useable or disposable or combinations thereof. Physical surgical, surgical-interventional, vascular-interventional, interventional, or vascular instruments can be patient specific. The term virtual surgical, surgical-interventional, vascular-interventional, interventional, or vascular instrument does not include real surgical, surgical-interventional, vascular-interventional, interventional, or vascular instrument, actual surgical, surgical-interventional, vascular-interventional, interventional, or vascular instrument, physical surgical, surgical-interventional, vascular-interventional, interventional, or vascular instrument and surgical, surgical-interventional, vascular-interventional, interventional, or vascular instrument.

The terms "virtual data" or "virtual image" as used throughout the specification can include virtual 3D models, e.g. virtual 3D models extracted from or generated based on scans, images, image data sets, volume data sets, spirals, e.g. from pre- or intra-operative imaging, e.g. ultrasound, CT, MRI, SPECT, PET, echocardiography, CTA, MRA.

The terms real surgical, surgical-interventional, vascular-interventional, interventional, or vascular device, actual surgical, surgical-interventional, vascular-interventional, interventional, or vascular device, physical surgical, surgical-interventional, vascular-interventional, interventional, or vascular device and surgical, surgical-interventional, vascular-interventional, interventional, or vascular device are used interchangeably throughout the application; the terms real surgical, surgical-interventional, vascular-interventional, interventional, or vascular device, actual surgical, surgical-interventional, vascular-interventional, interventional, or vascular device, physical surgical, surgical-interventional, vascular-interventional, interventional, or vascular device and surgical, surgical-interventional, vascular-interventional, interventional, or vascular device do not include virtual surgical, surgical-interventional, vascular-interventional, interventional, or vascular devices. The physical surgical, surgical-interventional, vascular-interventional, interventional, or vascular devices can be surgical, surgical-interventional, vascular-interventional, interventional, or vascular devices provided by manufacturers or vendors. The term virtual surgical, surgical-interventional, vascular-interventional, interventional, or vascular device does not include real surgical, surgical-interventional, vascular-interventional, interventional, or vascular device, actual surgical, surgical-interventional, vascular-interventional, interventional, or vascular device, physical surgical, surgical-interventional, vascular-interventional, interventional, or vascular device and surgical, surgical-interventional, vascular-interventional, interventional, or vascular device.

The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical, surgical-interventional, vascular-interventional, interventional, or vascular implants can be a stent, e.g. a vascular stent, a biliary stent, another form of stent, stents with our without drug coating, a coil, etc. The term virtual implant or implant component does not include real implant or implant component, actual implant or implant component, physical implant or implant component and implant or implant component.

The terms "image capture system", "video capture system", "image or video capture system", "image and/or video capture system, and/or optical imaging system" can be used interchangeably. In some embodiments, a single or more than one, e.g. two or three or more, image capture system, video capture system, image or video capture system, image and/or video capture system, and/or optical imaging system can be used in one or more locations e.g. in one, two, three, or more locations), for example integrated into, attached to or separate from an OHMD, attached to an OR or interventional table, attached to a fixed structure in the OR or interventional suite, integrated or attached to or separate from an instrument, integrated or attached to or separate from an endoscope, integrated or attached to or separate from a catheter, integrated or attached to or separate from a guide wire, internal to the patient's skin, internal to a surgical or interventional site, internal to a target tissue, internal to an organ, internal to a cavity (e.g. an abdominal cavity or a bladder cavity or a cistern or a CSF space), internal to a vascular lumen or a vascular structure, internal to a vascular bifurcation, internal to a vascular wall, internal to an aneurysm, internal to a vascular flap, internal to a bowel, internal to a small intestine, internal to a stomach, internal to a biliary structure, internal to a bile duct, internal to a pancreatic duct, internal to a urethra and or urether, internal to a renal pelvis, external to the patient's skin, external to a surgical or interventional site, external to a target tissue, external to an organ, external to a cavity (e.g. an abdominal cavity or a bladder cavity or a cistern or a CSF space), external to a vascular lumen, external to a vascular bifurcation, external to a vascular wall, external to an aneurysm, external to a vascular flap, external to a bowel, external to a small intestine, external to a stomach, external to a biliary structure, external to a pancreatic duct, external to a urethra and or urether, and/or external to a renal pelvis. In some embodiments, the position and/or orientation and/or coordinates of the one or more image capture system, video capture system, image or video capture system, image and/or video capture system, and/or optical imaging system can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ described in the specification or known in the art.

Tracking of the one or more image capture system, video capture system, image or video capture system, image and/or video capture system, and/or optical imaging system can, for example, be advantageous when the one or more 3D scanners are integrated into or attached to an instrument, an endoscope, and/or when they are located internal to any structures, e.g. inside a cavity or a lumen, e.g. a vascular lumen.

Virtual and/or physical devices or implants can include, for example, catheters, wires, guidewires, sheaths, thrombectomy devices, thrombectomy systems, revascularization devices or systems, stents (e.g. endovascular stents, biliary stents, coated stents, drug eluting stents), coils, grafts (e.g. vascular grafts, valve grafts or graft valves), patches, vascular prostheses, scaffolding prostheses, e.g. open pore, cardiac valves, cardiac valve replacements, cardiac valve repair systems, electrodes, electric probes, electrophysiologic probes, ablation devices, pacemakers, pacemaker leads or electrodes, etc.

Virtual and/or physical instruments can include, for example, graspers, vein valve cutters, vein extirpation sets, extraction instruments, etc.

Physical instruments or devices or implants can be coated or uncoated.

The term "respiratory cycle" refers to the complete sequence of events in the lung and chest from the beginning of an inspiration to the beginning of the following inspiration: a complete inspiration and expiration. The respiratory cycle is the process of breathing in and out. When a patient breathes in, it can be called inspiration or inhalation, and the patient's lungs are expanding. Expiration or exhalation, or breathing out, is the part of the cycle when the lungs deflate. Inhalation begins with the contraction of the muscles attached to the rib cage; this causes an expansion in the chest cavity. The onset of contraction of the diaphragm results in expansion of the intrapleural space and an increase in negative pressure. This negative pressure generates airflow because of the pressure difference between the atmosphere and the alveoli. Air enters, inflating the lung through either the nose or mouth into the pharynx and trachlea, entering the bronchi, bronchioli and alveoli. Expiration or exhalation is the flow of the breath out of an organism. In humans it is the movement of air from the lungs out of the airways, to the external environment during breathing. This can happen due to elastic properties of the lungs, as well as the internal intercostal muscles which can lower the rib cage and decrease thoracic volume. As the thoracic diaphragm relaxes during exhalation, it can cause the tissue to rise superiorly and put pressure on the lungs to expel the air. During forced exhalation, expiratory muscles including the abdominal muscles and internal intercostal muscles can generate abdominal and thoracic pressure, which can force air out of the lungs. Tidal volume is the amount of air that enters the lungs in a normal breath. Vital capacity is the maximum amount of air a patient exhales after the deepest breath possible.

Throughout the specification, the terms "diaphragmatic movement", "diaphragmatic motion", "movement of the diaphragm", "motion of the diaphragm" and any descriptions of movement of the diaphragm or terms or embodiments pertaining to the movement of the diaphragm can include movement, e.g. contraction or relaxation, of the intercostal muscles, movement of the chest wall and/or rib cage and/or abdomen and organs, anatomic structures, lesions, tumors or targets for surgical or other intervention contained therein. Data or parameters that can be measured during the respiratory cycle include, for example, the frequency of the respiratory cycle, the phase of the respiratory cycle, e.g. full inspiration, partial inspiration, full expiration, partial expiration, early inspiration, mid inspiration, late inspiration, early expiration, mid expiration, late expiration, and/or the direction of respiratory movement or excursion, and/or the speed of respiratory movement or excursion, and/or the amount of movement or excursion during the respiratory cycle. Data or parameters that can be measured during the respiratory cycle can include, for example, one or more of the frequency of the respiratory cycle, or the phase of the respiratory cycle, e.g. full inspiration, partial inspiration, full expiration, partial expiration, early inspiration, mid inspiration, late inspiration, early expiration, mid expiration, late expiration, or the direction of respiratory movement or excursion of the diaphragm and/or intercostal muscles and/or rib cage, or the direction of respiratory movement or excursion of a physical organ or physical tissue or a target, or the speed of respiratory movement or excursion of the diaphragm and/or intercostal muscles and/or rib cage, or the speed of respiratory movement or excursion of a physical organ or physical tissue or a target, or the amount of movement or excursion of the diaphragm and/or intercostal muscles and/or rib cage, or the amount of respiratory movement or excursion of a physical organ or physical tissue or a target.

Sensors and/or devices and/or techniques and/or modalities and/or systems to obtain data and/or measurements from the respiratory cycle include, but are not limited to, for example, thoracic belts, bellows, cushions, markers, e.g. optical markers or navigation markers, video imaging, navigation systems, fluoroscopy, computed tomography, scintigraphy, SPECT, and PET, and any other test or imaging modality known in the art for this purpose. Any of these sensors, devices, techniques and/or modalities described in the specification or known in the art can be used for obtaining data or measurements from the respiratory cycle and/or for respiratory gating and/or for synchronizing the display of virtual data by one or more optical head mounted displays with the moving lung, pulmonary structures or tissues, heart, cardiac structures or tissues, chest or chest wall structures, tissues or organs, abdominal structures, tissues or organs, or vessels or surrounding and/or adjacent tissues or organs of a patient. The term "cardiac cycle" refers to the complete sequence of events in the heart from the beginning of one beat to the beginning of the following beat: a complete heartbeat including systole and diastole. The cardiac cycle is the sequence of the human heart from the beginning of one heartbeat to the beginning of the next. It consists of two periods: diastole—when the myocardium relaxes and refills with blood, and systole when the myocardium contracts and the heart pumps blood. In a healthy heart and with an exemplary heart rate of 70 to 75 beats per minute, each cardiac cycle can take about 0.8 seconds to complete the cycle. The heart has two atrial and two ventricular chambers, paired in the left heart and the right heart. At the beginning of the cardiac cycle, e.g. during ventricular diastole, the blood is received into both ventricles through both atria; then, for example near the end of ventricular diastole, the two atria begin to contract (atrial systole), and each atrium pumps blood into the ventricle. During ventricular systole the ventricles are contracting and ejecting two separate blood streams from the heart, one to the lungs and one to the aorta, while the two atria are relaxing (atrial diastole).

The mitral and tricuspid valves, also known as the atrioventricular (AV) valves, open during ventricular diastole to permit filling. Late in the filling period the atria begin to contract (atrial systole) forcing a blood into the ventricles under pressure. Initiated by electrical signals from the sinoatrial node, the ventricles start contracting (ventricular systole), and as pressure against the valves increases the AV valves are closed, which stops the blood volumes in the ventricles from flowing in. Due to the myocardial contraction of ventricular systole, pressure in the ventricles rises quickly, exceeding the pressure in the trunks of the aorta and the pulmonary arteries and causing the requisite valves (the aortic and pulmonary valves) to open—which results in blood being ejected from the ventricles corresponding to the ejection stage of the cardiac cycle. After ventricular pressures fall below their peak(s) and below those in the aorta and pulmonary arteries, the aortic and pulmonary valves close again.

This is followed by a period during which pressure within the ventricles begins to fall significantly, and thereafter the atria begin refilling as blood returns to flow into the right atrium from the vena cavae and into the left atrium from the pulmonary veins. As the ventricles begin to relax, the mitral and tricuspid valves open again, and the completed cycle returns to ventricular diastole and a new beginning of the cardiac cycle. Blood pressure increases and decreases during the cardiac cycle. The movements of cardiac muscle are coordinated by a series of electrical impulses produced by pacemaker cells found within the sinoatrial node and the atrioventricular node. Cardiac muscle is composed of myocytes. In an electrocardiogram, electrical systole initiates the atrial systole at the P wave deflection of a steady signal; and it starts contractions, systole, of the ventricles at the Q deflection of the QRS complex.

Data or parameters that can, for example, be measured during a cardiac cycle include, but are not limited to heart rate, phase of the cardiac cycle, e.g. on an ECG, phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target.

Sensors and/or devices and/or techniques and/or modalities and/or systems to obtain data and/or measurements from the cardiac cycle include, but are not limited to, for example, ECG, pulse measurements, pulse oximetry, echocardiography (including transesophageal echocardiography), ultrasound, computed tomography, CT angiography, magnetic resonance imaging (MRI), MR angiography, nuclear heart scan, scintigraphy, SPECT, PET, angiography, and any other test or imaging modality known in the art for this purpose. Any of these sensors, devices, techniques and/or modalities described in the specification or known in the art can be used for obtaining data or measurements from the cardiac cycle and/or for cardiac gating and/or for synchronizing the display of virtual data by one or more optical head mounted displays with the beating, moving heart, heart structures and/or heart tissues and/or vessels and/or surrounding tissues of a patient.

Wearable devices can be used to obtain one or more cardiac or respiratory data or measurements. Wearable devices can include or incorporate one or more sensors, techniques, modalities or systems to obtain data from or about the cardiac and/or respiratory cycle. Wearable devices can include optical head mounted displays, e.g. see through or non-see through, watches, smart phones, or devices attached to the human body, e.g. a patient, a surgeon, and/or an interventionalist.

A vessel and/or vascular structure can be an artery or can be a vein. The vessel and/or vascular structure can be of neurovascular, cardiac, pulmonary, abdominal, pelvic, extremity and/or any other location. The vessel and/or vascular structure can be normal and/or pathologic.

The terms "align" or "aligning" can include the terms "superimpose", and "superimposing". The terms "align" or "aligning" can include the terms "overlay", and "overlaying". The terms "align" or "aligning" can include superimposing two corresponding features, e.g. surfaces, surface structures, volumes, shapes, landmarks, walls, edges, perimeters, outlines, of virtual data or a virtual image, e.g. a virtual object, such as, an organ, tissue, structure, device, or instrument, and a physical object, such as, an organ, tissue, structure, device, or instrument.

The terms "align" or "aligning" can include superimposing two corresponding features, e.g. surfaces, surface structures, volumes, shapes, landmarks, walls, edges, perimeters, outlines, of virtual data or a virtual image, e.g. a virtual object, such as, an organ, tissue, structure, device, or instrument, and a physical object, such as, an organ, tissue, structure, device, or instrument, wherein the virtual object and the physical object are different. For example, the virtual object can be a virtual device, such as a catheter or an implant, and the physical object can be a vessel or an organ.

The virtual data or virtual image, e.g. a virtual object, such as, an organ, tissue, structure, device, or instrument, can be a 3D or 2D electronic or virtual representation or placement indicator of a physical object, such as, an organ, tissue, structure, device, or instrument.

The virtual data or virtual images can include multiple virtual objects or virtual representations, such as, an organ, tissue, structure, device, or instrument, and can include 3D or 2D electronic or virtual representations or placement indicators of multiple physical objects, such as, an organ, tissue, structure, device, or instrument or multiples thereof.

The virtual data or virtual image can be a virtual representation of the same physical object, organ, tissue, structure, device, implant or instrument. For example, the virtual object can be a device, such as a virtual implant, and the physical object can be the corresponding physical implant. For example, the virtual object can be an organ or tissue and the physical object can be the corresponding physical organ or tissue.

The terms "align" or "aligning" can include superimposing the virtual data or a virtual image, e.g. the virtual object, such as, organ, tissue, structure, device, or instrument, on the surface or relative to the surface or inside the same physical object, such as, organ, tissue, structure, device, or instrument. For example, the virtual object can be a three-dimensional image of a vessel, e.g. an artery or a vein, or a vascular branch, or a vascular tree and the physical object can be the physical vessel, physical vascular branch or physical vascular tree.

The virtual data or virtual image can be a virtual representation of a virtual device, or instrument placed on the surface or inside the physical object, organ, tissue, or structure. The terms "align" or "aligning" can include superimposing virtual data or a virtual image, e.g. a virtual device, implant or instrument, on the surface or inside a different physical object, organ, tissue, or structure. For example, the virtual object can be a catheter and the virtual object can be displayed inside at least a portion of a physical vessel, e.g. an artery or a vein. Or, for example, the virtual object can be a stent or an aneurysm clip aligned with a physical vascular wall or a physical aneurysm wall or a physical aneurysm neck and displayed by one or more OHMDs inside the physical vessel or aneurysm.

The terms "align" or "aligning" can include superimposing two corresponding features, e.g. surfaces, surface structures, volumes, shapes, landmarks, walls, edges, perimeters, outlines, of a first set of virtual data or a first virtual image, e.g. a first virtual object, such as, an organ, tissue, structure, device, or instrument, and a second set of virtual data or a second virtual image, e.g. a second virtual object, such as, an organ, tissue, structure, device, or instrument.

The terms "align" or "aligning" can include superimposing two corresponding features, e.g. surfaces, surface structures, volumes, shapes, landmarks, walls, edges, perimeters, outlines, of a first set of virtual data or a first virtual image, e.g. a first virtual object, such as, an organ, tissue, structure, device, or instrument, and a second set of virtual data or a second virtual image, e.g. a second virtual object, such as, an organ, tissue, structure, device, or instrument, wherein the first virtual object and the second virtual object can be different. For example, the first virtual object can be a virtual device, such as a catheter or an implant, e.g. displayed by an OHMD, and the second virtual object can be a virtual representation of a vessel or an organ, e.g. displayed by the OHMD or a computer monitor. The superimposing can, for example, also be performed using registration of the first virtual object, e.g. the catheter inside a vessel, and second virtual object, e.g. the vessel imaged using angiography, in a common coordinate system, with the registration as described in the specification or known in the art.

The first and second set of virtual data or virtual images, e.g. a virtual object, such as, an organ, tissue, structure, device, or instrument, can be a 3D or 2D electronic or virtual representation or placement indicator of a physical object, such as, an organ, tissue, structure, device, or instrument.

The first and second set of virtual data or virtual images can include multiple virtual objects or virtual representations, such as, an organ, tissue, structure, device, or instrument, and can include 3D or 2D electronic or virtual representations or placement indicators of multiple physical objects, such as, an organ, tissue, structure, device, or instrument or multiples thereof.

The first and second set of virtual data or virtual images can be different virtual representations of the same physical object, organ, tissue, structure, device or instrument. For example, the first and second set of virtual data or virtual images can be generated using different techniques or modalities or imaging systems or methods. For example, the first set of virtual data or virtual images can be from a pre-operative imaging study, e.g. an x-ray, ultrasound, echocardiogram, CT scan, MRI scan, CTA, MRA, scintigram, radionuclide heart scan, SPECT scan or PET scan. The second set of virtual data or virtual images can be from an intra-operative imaging study, e.g. an angiogram (2D, biplanar, 3D), ultrasound or echocardiogram. The first set of virtual data or virtual images can, for example, be displayed by an OHMD. The second set of virtual data or virtual images can be displayed by an OHMD or a computer monitor. The first set of virtual data or virtual images and the second set of virtual data or virtual images can be registered in the same coordinate system and can be superimposed, for example when both are displayed in the OHMD or, for example, by registering the computer monitor in the coordinate system and superimposing the first set of virtual data displayed by the OHMD superimposed onto the corresponding features, e.g. structures, surfaces, geometries, of the second set of virtual data or virtual images displayed by the computer monitor.

The first set of virtual data or virtual images can be a virtual representation of a virtual device, or instrument placed on the surface or inside a second set of virtual data or virtual images, which can be a virtual object, organ, tissue, or structure. The terms "align" or "aligning" can include superimposing the first set of virtual data or virtual images, e.g. a virtual device or instrument, on the surface or inside the second set of virtual data or virtual images, e.g. a virtual object, organ, tissue, or structure. For example, the first virtual object can be a catheter (e.g. a tracked catheter) and the first virtual object can be displayed inside at least a portion of a second virtual object which can be a virtual vessel, e.g. an artery or a vein. The movement of a tracked catheter can be displayed by the OHMD superimposed onto or inside a virtual display of the virtual vessel, e.g. the virtual artery or vein thereby allowing the interventionalist to see the movement of the tracked catheter in 3D in the OHMD display, for example as it enters a vascular ostium or an aneurysm. Or, for example, the first virtual object can be a virtual stent (optionally tracked) or a virtual aneurysm clip (optionally tracked) aligned with a second virtual object which can be a virtual vascular wall or a virtual aneurysm wall or a virtual aneurysm neck and displayed by one or more OHMDs.

A first set of virtual data can be generated by a first computer system with one or more computer processors. A second set of virtual data can be generated by a second computer system with one or more computer processors. The first computer system and the second computer system can be different. Yet in some embodiments the first computer system and the second computer system can be the same.

The term "synchronize" or "synchronizing" can include moving virtual data, e.g. from a scan, image, image data set, volume data set, or spiral acquired pre-operatively or intra-operatively, in the display of an OHMD. Using a computer system with one or more computer processors, the moving by the display of the OHMD can be triggered or performed using one or more data or parameters obtained from the respiratory and/or cardiac cycle of the patient. The moving can be reflective of and/or or correspond to, for example, a movement or excursion or pulsation of the heart, the lung, and/or a vessel measured using respiratory and/or cardiac gating techniques in the patient described in the specification or known in the art. The amount of movement (amplitude) can be adjusted based on the amount of respiratory and/or cardiac movement (amplitude). The amount of movement (amplitude) can also be adjusted based on the distance of the OHMD to the patient and/or a computer monitor (if virtual data or images are, for example, aligned with, superimposed onto or overlaid onto a computer monitor). Thus, the OHMD can move virtual data or virtual images, e.g. from a pre-operative scan, that can match the movement of the tissues and/or organs during the cardiac and/or respiratory cycle of the patient, e.g. during an intervention; in this manner, the computer system can maintain the display of the virtual data or virtual images superimposed onto and/or aligned with the corresponding anatomic structures, tissues and/or organs both inside the physical patient and/or in virtual data acquired, for example, (e.g. in real-time) from the physical patient, e.g. an intra-operative angiogram, run-off or bolus chase study, e.g. displayed by the OHMD and/or a computer monitor.

The term "synchronize" or "synchronizing" can include displaying sequential virtual data, e.g. virtual data, for example, scans, images, image data sets, volume data sets, spirals, from sequential time points, time intervals, time segments, by the OHMD. The scans, images, image data sets, volume data sets, spirals can optionally be marked or coded with the specific time point, time interval, time segment of the phase of the respiratory and/or cardiac cycle during which the scan, images, image data sets, volume data sets, spiral were acquired, for example in a pre-operative scan, e.g. a CT or MRI. A computer system with one or more computer processors can then be used to display virtual data or virtual images from the time sequence of scans, images, image data sets, volume data sets, spirals obtained at the different time points, time intervals, time segments of the respiratory and/or cardiac cycle, e.g. from a pre-operative image acquisition or scan, that correspond to the phase of the respiratory or cardiac cycle of the patient, e.g. during an interventional procedure. Thus, the OHMD can display sequential virtual data or virtual images, e.g. from a pre-operative scan, that can match the phase of the cardiac and/or respiratory cycle of the patient, e.g. during an intervention; in this manner, the computer system can maintain the display of the virtual data or virtual images superimposed onto and/or aligned with the corresponding anatomic structures, tissues and/or organs both in the physical patient and/or in virtual data acquired, for example in real-time, from the physical patient, e.g. an intra-operative angiogram, run-off or bolus chase study, e.g. displayed by the OHMD and/or a computer monitor.

The term "synchronize" or "synchronizing" can include a combination of moving of virtual data and display of sequential virtual data, e.g. from two or more time points, time intervals or time segments of the respiratory and/or cardiac cycle.

The terms "standalone computer monitor" or "computer monitor" can be used interchangeably. A standalone computer monitor or computer monitor can be part of a computer system with one or more computer processors. In some embodiments, a computer monitor can be separate from the computer system for operating one or more optical head mounted displays and/or for generating a coordinate system and/or for registering and/or tracking objects in the coordinate system. In some embodiments, a computer monitor can be part of a computer system for operating one or more optical head mounted displays and/or for generating a coordinate system and/or for registering and/or tracking objects in the coordinate system.

Representative devices, systems, techniques and methods for augmented reality guidance are provided in U.S. Pat. No. 9,861,446 and in Patent Application No. PCT/US18/13774, which are hereby incorporated by reference in their entirety. Representative devices, systems, techniques and methods for improving the accuracy of augmented reality guidance are provided in Patent Application No. PCT/US18/12459 which are hereby incorporated by reference in their entirety.

In some embodiments, one or more physical surgical, surgical-interventional, vascular-interventional, interventional, or vascular instruments, tools and/or implants or devices can be tracked. Tracking can be achieved using, for example, one or more RF transmitters or IMU's or combinations thereof integrated into or attached to the surgical, surgical-interventional, vascular-interventional, interventional, or vascular instruments, tools and/or implants. Tracking of one or more surgical, surgical-interventional, vascular-interventional, interventional, or vascular instruments, tools and/or implants can be achieved using, for example, x-ray based techniques as are described, for example, in Baert et al., 2000 [S. A. M. Baert, W. J. Niessen, E. H. W. Meijering, A. F. Frangi, M. A. Viergever (2000) Guide wire tracking in interventional radiology, In Proceedings of the 14th Computer Assisted Radiology and Surgery, CARS 2000, pp 537-542, H. U. Lemke, M. W. Vannier, K. Inamura, A. G. Farman and K. Doi (Eds.), Springer.]. Tracking of one or more surgical, surgical-interventional, vascular-interventional, interventional, or vascular instruments, tools and/or implants can be achieved using labels or phantoms integrated into or attached to the surgical, surgical-interventional, vascular-interventional, interventional, or vascular instruments, tools and/or implants, which can be detected by an imaging modality, e.g. as described in Peeters et al. 2006 [J. M. Peeters, J-H. Seppenwoolde, C. J. Bakker, L. W. Bartels. A safe and practical guide wire for use during passive tracking in endovascular interventional procedures. Proc. Intl. Soc. Mag. Reson. Med. 14 (2006) 3354]. Tracking of one or more surgical, surgical-interventional, vascular-interventional, interventional, or vascular instruments, tools and/or implants can be performed using any other technique known in the art. Tracking of one or more surgical, surgical-interventional, vascular-interventional, interventional, or vascular instruments, tools and/or implants can be performed internal to the patient's skin, internal to a surgical or interventional site, internal to a target tissue, internal to an organ, internal to a cavity (e.g. an abdominal cavity or a bladder cavity or a cistern or a CSF space), or internal to a vascular lumen or a vascular structure, internal to a vascular bifurcation, internal to a vascular wall, internal to an aneurysm, internal to a vascular flap, internal to a bowel, internal to a small intestine, internal to a stomach, internal to a biliary structure, internal to a bile duct, internal to a pancreatic duct, internal to a urethra and or urether, internal to a renal pelvis, external to the patient's skin, external to a surgical or interventional site, external to a target tissue, external to an organ, external to a cavity (e.g. an abdominal cavity or a bladder cavity or a cistern or a CSF space), external to a vascular lumen, external to a vascular bifurcation, external to a vascular wall, external to an aneurysm, external to a vascular flap, external to a bowel, external to a small intestine, external to a stomach, external to a biliary structure, external to a pancreatic duct external to a urethra and or urether, and/or external to a renal pelvis.

In some embodiments, a single or more than one, e.g. two or three or more, 3D scanners can be present in one or more locations (e.g. in one, two, three, or more locations), for example integrated into, attached to or separate from an OHMD, attached to an OR table, attached to a fixed structure in the OR, integrated or attached to or separate from an instrument, integrated or attached to or separate from an arthroscope, integrated or attached to or separate from an endoscope, a guidewire, a catheter, internal to the patient's skin, internal to a surgical site, internal to a target tissue, internal to an organ, internal to a cavity (e.g. an abdominal cavity or a bladder cavity or a cistern or a CSF space, and/or internal to a vascular lumen), internal to a vascular bifurcation, internal to a bowel, internal to a small intestine, internal to a stomach, internal to a biliary structure, internal to a urethra and or urether, internal to a renal pelvis, external to the patient's skin, external to a surgical site, external to a target tissue, external to an organ, external to a cavity (e.g. an abdominal cavity or a bladder cavity or a cistern or a CSF space, and/or external to a vascular lumen), external to a vascular bifurcation, external to a bowel, external to a small intestine, external to a stomach, external to a biliary structure, external to a urethra and or urether, and/or external to a renal pelvis. In some embodiments, the position and/or orientation and/or coordinates of the one or more 3D scanners can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ mentioned in the specification or known in the art. Tracking of the one or more 3D scanners can, for example, be advantageous when the one or more 3D scanners are integrated into or attached to an instrument, an arthroscope, an endoscope, and/or when they are located internal to any structures, e.g. inside a cavity or a lumen.

In some embodiments, one or more image capture system, video capture system, image or video capture system, image and/or video capture system, and/or optical imaging system can be used in conjunction with one or more 3D scanners, e.g. in any of the foregoing locations and/or tissues and/or organs and any other location and/or tissue and/or organ described in the specification or known in the art.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Some aspects of the invention relate to devices, systems and methods for positioning a virtual path, virtual plane, virtual tool, virtual surgical instrument or virtual implant component in a mixed reality environment using a head mounted display device, optionally coupled to one or more processing units.

With guidance in mixed reality environment, a virtual surgical catheter, guidewire, endo- or extravascular guide, tool, instrument or implant can be superimposed onto the physical structures of the patient or surgical or vascular interventional site. Further, the physical catheter, guidewire, endo- or extravascular guide, tool, instrument or implant can be aligned with the virtual surgical catheter, guidewire, endo- or extravascular guide, tool, instrument or implant displayed or projected by the OHMD. Thus, guidance in mixed reality environment does not need to use a plurality of virtual representations of the catheter, guidewire, endo- or extravascular guide, tool, instrument or implant and does not need to compare the positions and/or orientations of the plurality of virtual representations of the virtual catheter, guidewire, endo- or extravascular guide, tool, instrument or implant.

In various embodiments, the OHMD can display one or more of a virtual surgical tool, virtual surgical instrument including a virtual surgical guide, virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual device, estimated or predetermined non-visualized portions for one or more devices or implants or implant components or surgical instruments or surgical tools, and/or one or more of a predetermined tissue change or alteration.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a a surgical site, a vessel, a vascular structure, an OHMD, a surgical tool or instrument, a trial implant, an implant component or an implant.

In some embodiments, multiple coordinate systems can be used instead of a common or shared coordinate system. In this case, coordinate transfers can be applied from one coordinate system to another coordinate system, for example for registering the OHMD, live data of the patient including the surgical site, virtual instruments and/or virtual implants and physical instruments and physical implants. Coordinate systems can also include sub-coordinate systems.

The term surgical can be used interchangeably with the terms vascular, cardiovascular or neurovascular or interventional throughout the application. The term surgical plan can be used interchangeably with the terms vascular interventional plan, cardiovascular interventional plan, neurovascular interventional plan or interventional plan. For example, a virtual surgical plan can be a virtual interventional plan or a virtual vascular interventional plan.

The term "intervention" as used throughout the specification can include a vascular intervention, cardiac intervention, neurosurgical intervention, neurovascular intervention, biliary intervention, urologic intervention, gynecologic intervention or any other medical or surgical intervention.

The terms physical organ, physical tissue, physical surface, physical structure or targets on the surface of the patient, e.g. an exposed surface, or inside the patient or inside an organ and/or cavity as used throughout the specification can include vascular structures, vessels, arteries, veins, cardiac structures, epicardium, myocardium, cardiac tissue, cardiac valves, coronary arteries, neural structures, neural tissue, neurovascular structures, cerebral arteries, cerebral veins, lymphatic tissue, lymph vessels, ducts, e.g. biliary ducts, a urether, a urethra, cavities, e.g. inside an organ, e.g. a bladder or a kidney, e.g. a renal pelvis, or an abdominal cavity or pleural cavity. Thus, for example, respiratory gating or cardiac gating as described in the specification can be used for the display of virtual data by one or more OHMDs. Virtual data displayed by one or more OHMDs can be synchronized e.g. using a computer system with one or more computer processors configured for moving virtual data, using respiratory and/or cardiac gating information to maintain superimposition and/or alignment of the virtual data with the one or more physical organs, physical tissues, physical surfaces, physical structures or targets during portions of or the entire respiratory cycle and/or during portions of or the entire cardiac cycle. Thus, in an example, virtual data displayed by one or more OHMDs can be synchronized, e.g. using a computer system with one or more computer processors configured for moving virtual data, using respiratory and/or cardiac gating information to maintain superimposition and/or alignment of the virtual data, e.g. a pre-operative imaging study, e.g. a spiral CT angiography, with one or more physical vessels or one or more physical vessels imaged, for example in real time, during an intervention, during portions of or the entire respiratory cycle and/or during portions of or the entire cardiac cycle. In some embodiments, the display of the virtual data, displayed by one or more OHMDs, is configured, using respiratory and/or cardiac gating information, so that the superimposition and/or alignment of the virtual data with the one or more physical organs, physical tissues, physical surfaces, physical structures or targets during portions of or the entire respiratory cycle and/or during portions of or the entire cardiac cycle is maintained. The computer system can include one or more computer processors configured to receive input or data from devices or systems configured to measure one or more parameters of the patient's respiratory cycle.

Optical Head Mounted Displays

In some embodiments, a pair of glasses is utilized. The glasses can include an optical head-mounted display. An optical head-mounted display (OHMD) can be a wearable display that has the capability of reflecting projected images as well as allowing the user to see through it. Various types of OHMDs can be used. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the OHMDs include, but are not limited to touchpad or buttons, smartphone controllers, speech recognition, and gesture recognition. Advanced interfaces are possible, e.g. a brain—computer interface.

Optionally, a computer or server or a workstation can transmit data to the OHMD. The data transmission can occur via cable, Bluetooth, WiFi, optical signals and any other method or mode of data transmission known in the art. The OHMD can display virtual data, e.g. virtual data of the patient, in uncompressed form or in compressed form. Virtual data of a patient can optionally be reduced in resolution when transmitted to the OHMD or when displayed by the OHMD.

When virtual data are transmitted to the OHMD, they can be in compressed form during the transmission. The OHMD can then optionally decompress them so that uncompressed virtual data are being displayed by the OHMD.

Alternatively, when virtual data are transmitted to the OHMD, they can be of reduced resolution during the transmission, for example by increasing the slice thickness of image data prior to the transmission. The OHMD can then optionally increase the resolution, for example by re-interpolating to the original slice thickness of the image data or even thinner slices so that virtual data with resolution equal to or greater than the original virtual data or at least greater in resolution than the transmitted data are being displayed by the OHMD.

In some embodiments, the OHMD can transmit data back to a computer, a server or a workstation. Such data can include, but are not limited to:

- Positional, orientational or directional information about the OHMD or the operator or surgeon or interventionalist wearing the OHMD
- Changes in position, orientation or direction of the OHMD
- Data generated by one or more IMU's
- Data generated by markers (radiofrequency, optical, light, other) attached to, integrated with or coupled to the OHMD
- Data generated by a surgical navigation system attached to, integrated with or coupled to the OHMD
- Data generated by an image and/or video capture system attached to, integrated with or coupled to the OHMD
- Parallax data, e.g. using two or more image and/or video capture systems attached to, integrated with or coupled to the OHMD, for example one positioned over or under or near the left eye and a second positioned over or under or near the right eye
- Distance data, e.g. parallax data generated by two or more image and/or video capture systems evaluating changes in distance between the OHMD and a surgical field or an object
- Motion parallax data
- Data related to calibration or registration phantoms (see other sections of this specification)
- Any type of live data of the patient captured by the OHMD including image and/or video capture systems attached to, integrated with or coupled to the OHMD
  - For example, alterations to a live surgical site
  - For example, use of certain surgical instruments detected by the image and/or video capture system
  - For example, use of certain medical devices or trial implants detected by the image and/or video capture system
- Any type of modification to a surgical plan
  - Portions or aspects of a live surgical plan
  - Portions or aspects of a virtual surgical plan Radiofrequency tags used throughout the embodiments can be of active or passive kind with or without a battery.

Exemplary optical head mounted displays include the ODG R-7, R-8 and R-8 smart glasses from ODG (Osterhout Group, San Francisco, CA), the NVIDIA 942 3-D vision wireless glasses (NVIDIA, Santa Clara, CA) and the Microsoft HoloLens (Microsoft, Redmond, WI).

The Microsoft HoloLens is manufactured by Microsoft. It is a pair of augmented reality smart glasses. Hololens can use the Windows 10 operating system. The front portion of the Hololens includes, among others, sensors, related hardware, several cameras and processors. The visor includes a pair of transparent combiner lenses, in which the projected images are displayed. The HoloLens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present.

The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor.

Hololens has an Intel Cherry Trail SoC containing the CPU and GPU. HoloLens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. HoloLens includes a IEEE 802.11ac Wi-Fi and Bluetooth 4.1 Low Energy (LE) wireless connectivity. The headset uses Bluetooth LE and can connect to a Clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application FreeForm, integrating HoloLens with the Autodesk Fusion 360 cloud-based 3D development application, and others.

HoloLens utilizing the HPU can employ sensual and natural interface commands—voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized.

The HoloLens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around.

The Microsoft HoloLens App for Windows 10 PC's and Windows 10 Mobile devices can be used by developers to run apps and to view live stream from the HoloLens user's point of view, and to capture augmented reality photos and videos.

Almost all Universal Windows Platform apps can run on Hololens. These apps can be projected in 2D. Select Windows 10 APIs are currently supported by HoloLens. Hololens apps can also be developed on Windows 10 PC's. Holographic applications can use Windows Holographic APIs. Unity (Unity Technologies, San Francisco, CA) and Vuforia (PTC, Inc., Needham, MA) are some apps that can be utilized. Applications can also be developed using DirectX and Windows API's.

Computer Graphics Viewing Pipeline

Figure 10A:
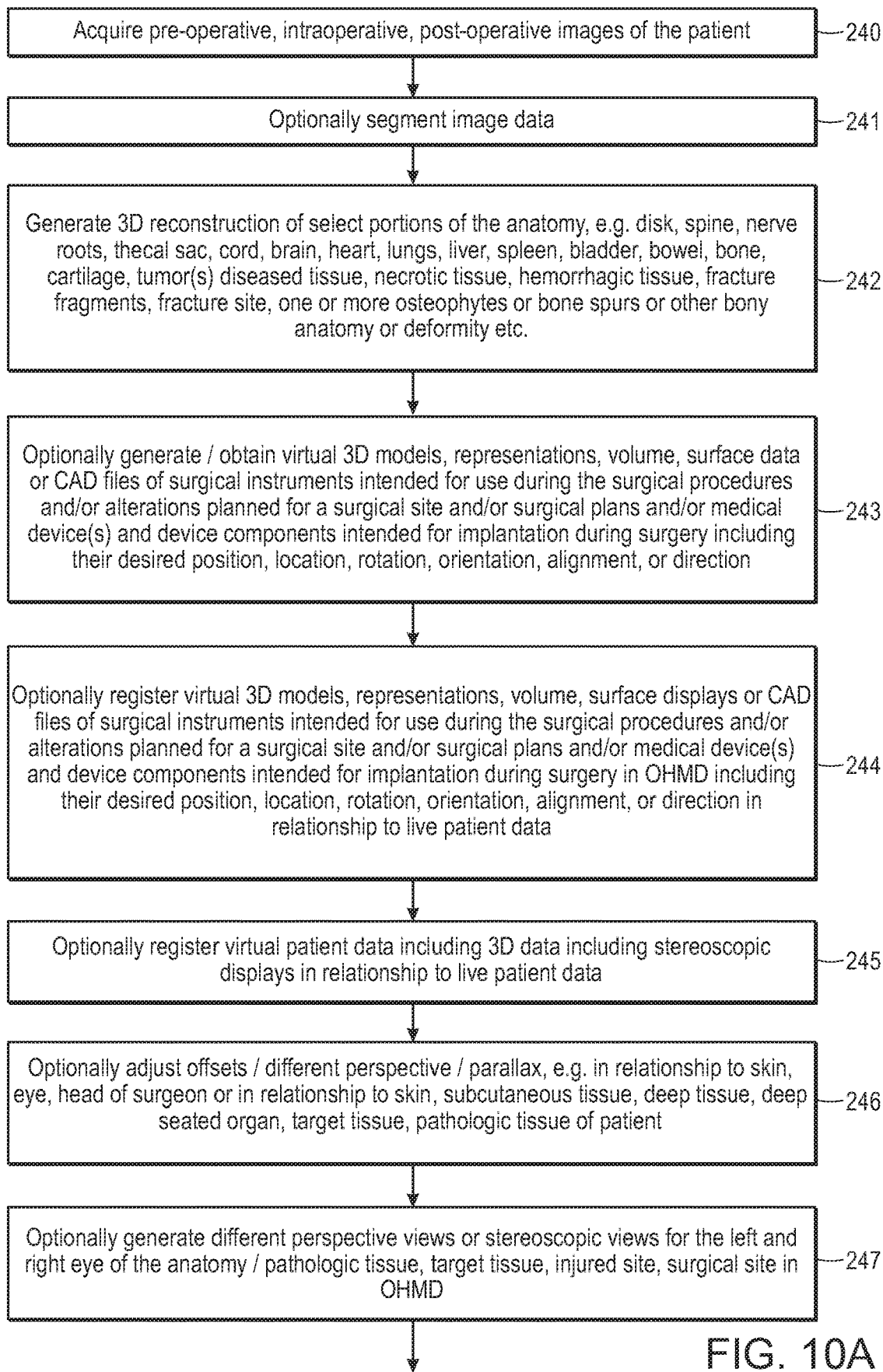
FIGS. 10A, B and C are flow charts summarizing model generation, registration and view projection for one or more OHMDs, e.g. by a primary surgeon or interventionalist, second surgeon or interventionalist, surgical assistant nurse, or others according to some embodiments of the present disclosure.
Figure 10B:
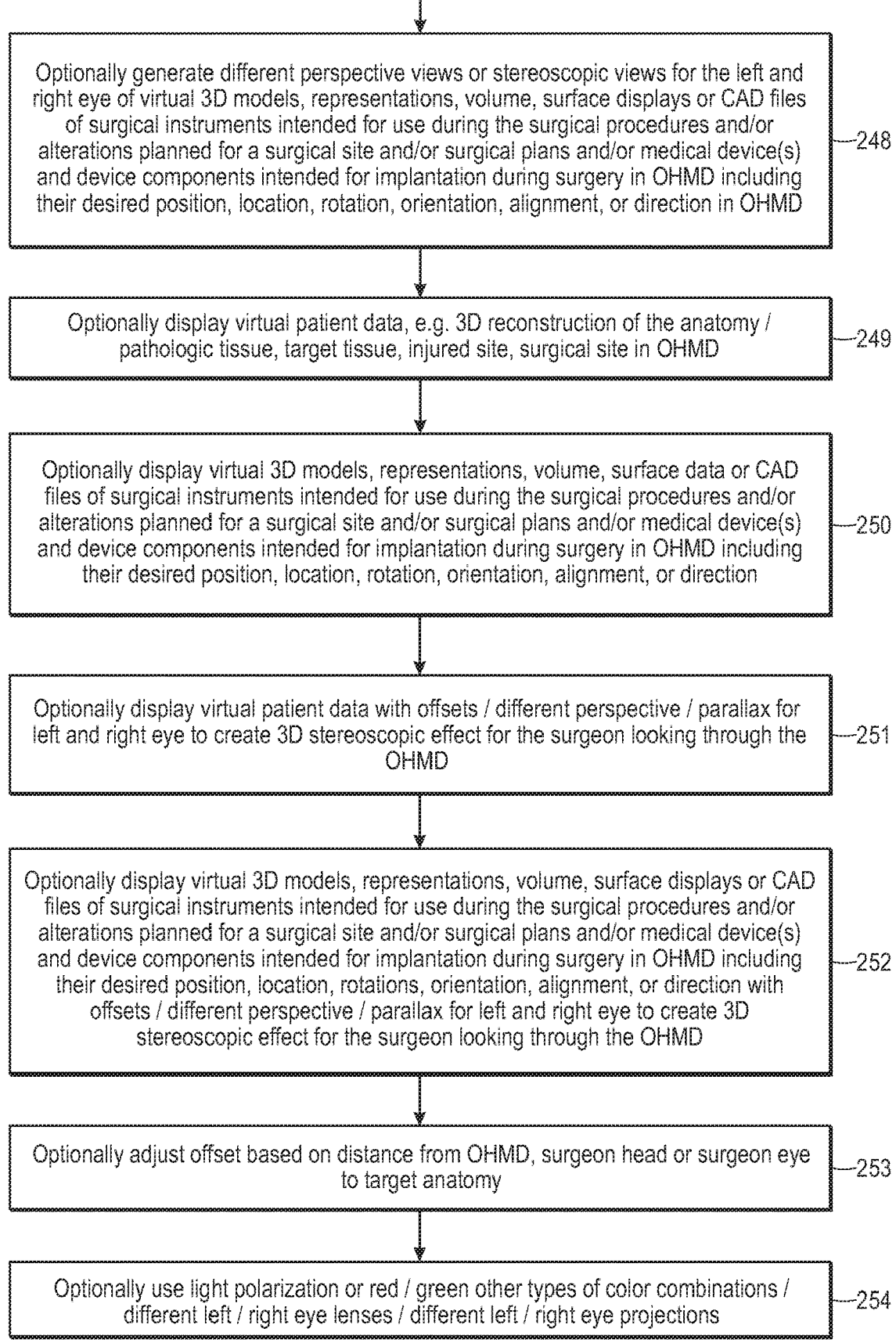
Figure 10C:
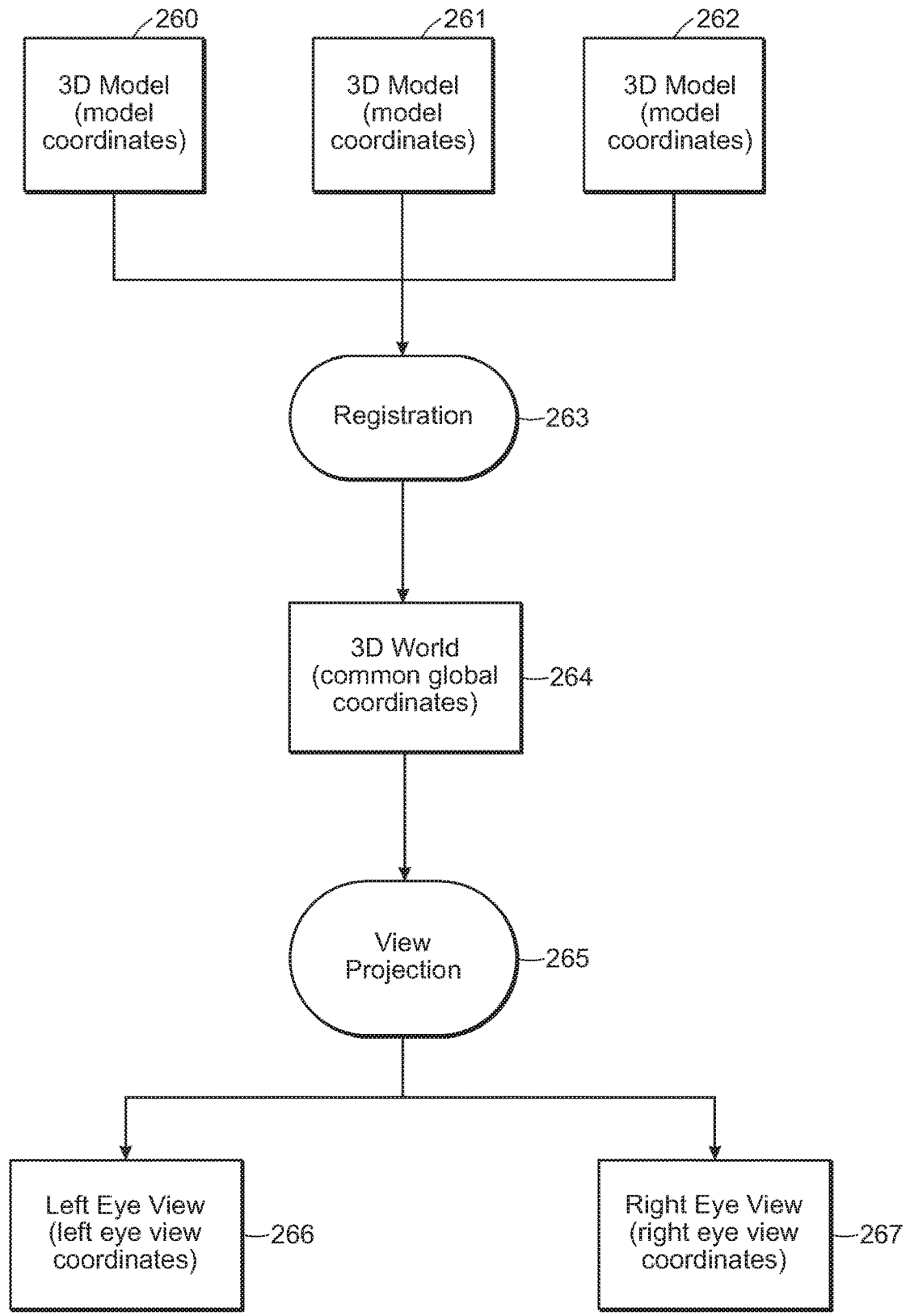

In some embodiments, the optical head mount display uses a computer graphics viewing pipeline that consists of the following steps to display 3D objects or 2D objects positioned in 3D space or other computer-generated objects and models FIG. 10C:

1. Registration
2. View projection

Registration:

The different objects to be displayed by the OHMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality OHMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

Once all objects to be displayed have been registered and transformed into the common global coordinate system, they are prepared for viewing on a display by transforming their coordinates from the global coordinate system into the view coordinate system and subsequently projecting them onto the display plane. This view projection step uses the viewpoint and view direction to define the transformations applied in this step. For stereoscopic displays, such as an OHMD, two different view projections can be used, one for the left eye and the other one for the right eye. For augmented reality OHMDs the position of the viewpoint and view direction relative to the physical environment can be known in order to correctly superimpose the computer-generated objects with the physical environment. As the viewpoint and view direction change, for example due to head movement, the view projections are updated so that the computer-generated display follows the new view.

Positional Tracking Systems

In certain embodiments, the position and/or orientation of the OHMD can be tracked. For example, in order to calculate and update the view projection of the computer graphics view pipeline as described in the previous section and to display the computer-generated overlay images in the OHMD, the view position and direction needs to be known.

Different methods to track the OHMD can be used. For example, the OHMD can be tracked using outside-in tracking. For outside-in tracking, one or more external sensors or cameras can be installed in a stationary location, e.g. on the ceiling, the wall or on a stand. The sensors or camera capture the movement of the OHMD, for example through shape detection or markers attached to the OHMD or the user's head. The sensor data or camera image is typically processed on a central computer to which the one or more sensors or cameras are connected. The tracking information obtained on the central computer is then used to compute the view projection. The view projection can be computed on the central computer or on the OHMD.

In another embodiment, the inside-out tracking method is employed. One or more sensors or cameras are attached to the OHMD or the user's head or integrated with the OHMD. The sensors or cameras can be dedicated to the tracking functionality. In other embodiments, the data collected by the sensors or cameras is used for positional tracking as well as for other purposes, e.g. image recording or spatial mapping. Information gathered by the sensors and/or cameras is used to determine the OHMD's position and orientation in 3D space. This can be done, for example, by detecting optical, infrared or electromagnetic markers attached to the external environment. Changes in the position of the markers relative to the sensors or cameras are used to continuously determine the position and orientation of the OHMD.

Data processing of the sensor and camera information is typically performed by a mobile processing unit attached to or integrated with the OHMD, which allows for increased mobility of the OHMD user as compared to outside-in tracking. Alternatively, the data can be transmitted to and processed on the central computer.

Inside-out tracking can also utilize markerless techniques. For example, spatial mapping data acquired by the OHMD sensors can be aligned with a virtual model of the environment, thus determining the position and orientation of the OHMD in the 3D environment. Alternatively, or additionally, information from inertial measurement units can be used. Potential advantages of inside-out tracking include greater mobility for the OHMD user, a greater field of view not limited by the viewing angle of stationary cameras and reduced or eliminated problems with marker occlusion.

Eye Tracking Systems

The present disclosure provides for methods of using the human eye including eye movements and lid movements as well as movements induced by the peri-orbital muscles for executing computer commands. Also provided are methods of executing computer commands by way of facial movements and movements of the head.

Command execution induced by eye movements and lid movements as well as movements induced by the peri-orbital muscles, facial movements and head movements can be advantageous in environments where an operator does not have his hands available to type on a keyboard or to execute commands on a touchpad or other hand—computer interface. Such situations include, but are not limited, to industrial applications including automotive and airplane manufacturing, chip manufacturing, medical or surgical procedures and many other potential applications.

In some embodiments, the optical head mount display can include an eye tracking system. Different types of eye tracking systems can be utilized. The examples provided below are in no way thought to be limiting. Any eye tracking system known in the art now can be utilized.

Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections. Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, optical or video-based eye trackers can be used. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retroreflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations.

The optical tracking method can include tracking movement of the eye including the pupil as described above. The optical tracking method can also include tracking of the movement of the eye lids and also periorbital and facial muscles.

In some embodiments, the eye-tracking apparatus is integrated in an optical head mounted display. In some embodiments, head motion can be simultaneously tracked, for example using a combination of accelerometers and gyroscopes forming an inertial measurement unit (see below).

In some embodiments, electric potentials can be measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments. A sampling rate of 15, 20, 25, 30, 50, 60, 100, 120, 240, 250, 500, 1000 Hz or greater can be used.

Any sampling frequency is possibly. In many embodiments, sampling rates greater than 30 Hz will be preferred.

Measuring Location, Orientation, Acceleration

The location, orientation, and acceleration of the human head, portions of the human body, e.g. hands, arms, legs or feet, as well as portions of the patient's body, e.g. the patient's head or extremities, including the hip, knee, ankle, foot, shoulder, elbow, hand or wrist and any other body part, can, for example, be measured with a combination of gyroscopes and accelerometers. In select applications, magnetometers may also be used. Such measurement systems using any of these components can be defined as inertial measurement units (IMU). As used herein, the term IMU relates to an electronic device that can measure and transmit information on a body's specific force, angular rate, and, optionally, the magnetic field surrounding the body, using a combination of accelerometers and gyroscopes, and, optionally, magnetometers. An IMU or components thereof can be coupled with or registered with a navigation system or a robot, for example by registering a body or portions of a body within a shared coordinate system. Optionally, an IMU can be wireless, for example using WiFi networks or Bluetooth networks.

Pairs of accelerometers extended over a region of space can be used to detect differences (gradients) in the proper accelerations of frames of references associated with those points. Single- and multi-axis models of accelerometer are available to detect magnitude and direction of the acceleration, as a vector quantity, and can be used to sense orientation (because direction of weight changes), coordinate acceleration (so long as it produces g-force or a change in g-force), vibration, shock. Micromachined accelerometers can be utilized in some embodiments to detect the position of the device or the operator's head.

Piezoelectric, piezoresistive and capacitive devices can be used to convert the mechanical motion into an electrical signal. Piezoelectric accelerometers rely on piezoceramics or single crystals Piezoresistive accelerometers can also be utilized. Capacitive accelerometers typically use a silicon micro-machined sensing element.

Accelerometers used in some of the embodiments can include small micro electro-mechanical systems (MEMS), consisting, for example, of little more than a cantilever beam with a proof mass.

Optionally, the accelerometer can be integrated in the optical head mounted devices and both the outputs from the eye tracking system and the accelerometer(s) can be utilized for command execution.

With an IMU, the following exemplary information can be captured about the operator and the patient and respective body parts including a moving: Speed, velocity, acceleration, position in space, positional change, angular orientation, change in angular orientation, alignment, orientation, and/or direction of movement and or speed of movement (e.g. through sequential measurements). Operator and/or patient body parts about which such information can be transmitted by the IMU include, but are not limited to: head, chest, trunk, shoulder, elbow, wrist, hand, fingers, arm, hip, knee, ankle, foot, toes, leg, inner organs, e.g. brain, heart, lungs, liver, spleen, bowel, bladder, etc.

Any number of IMU's can be placed on the OHMD, the operator and/or the patient and, optionally, these IMU's can be cross-referenced to each other within a single or multiple coordinate systems or, optionally, they can be cross-referenced in relationship to an OHMD, a second and third or more OHMD's, a navigation system or a robot and one or more coordinate systems used by such navigation system and/or robot. A navigation system can be used in conjunction with an OHMD without the use of an IMU. For example, navigation markers including infrared markers, retroreflective markers, RF markers can be attached to an OHMD and, optionally, portions or segments of the patient or the patient's anatomy. The OHMD and the patient or the patient's anatomy can be cross-referenced in this manner or registered in one or more coordinate systems used by the navigation system and movements of the OHMD or the operator wearing the OHMD can be registered in relationship to the patient within these one or more coordinate systems. Once the virtual data and the live data of the patient and the OHMD are registered in the same coordinate system, e.g. using IMUs, optical markers, navigation markers including infrared markers, retroreflective markers, RF markers, and any other registration method described in the specification or known in the art, any change in position of any of the OHMD in relationship to the patient measured in this fashion can be used to move virtual data of the patient in relationship to live data of the patient, so that the visual image of the virtual data of the patient and the live data of the patient seen through the OHDM are always aligned, irrespective of movement of the OHMD and/or the operator's head and/or the operator wearing the OHMD. Similarly, when multiple OHMD's are used, e.g. one for the primary surgeon or interventionalist and additional ones, e.g. two, three, four or more, for other surgeon or interventionalists, assistants, residents, fellows, nurses and/or visitors, the OHMD's worn by the other staff, not the primary surgeon or interventionalist, will also display the virtual representation(s) of the virtual data of the patient aligned with the corresponding live data of the patient seen through the OHMD, wherein the perspective of the virtual data that is with the patient and/or the surgical site for the location, position, and/or orientation of the viewer's eyes for each of the OHMD's used and each viewer. The foregoing embodiments can be achieved since the IMU's, optical markers, RF markers, infrared markers and/or navigation markers placed on the operator and/or the patient as well as any spatial anchors can be registered in the same coordinate system as the primary OHMD and any additional OHMD's. The position, orientation, alignment, and change in position, orientation and alignment in relationship to the patient and/or the surgical site of each additional OHMD can be individually monitored thereby maintaining alignment and/or superimposition of corresponding structures in the live data of the patient and the virtual data of the patient for each additional OHMD irrespective of their position, orientation, and/or alignment in relationship to the patient and/or the surgical site. Referring to FIG. 1, a system 10 for using multiple OHMDs 11, 12, 13, 14 for multiple viewer's, e.g. a primary surgeon or interventionalist, second surgeon or interventionalist, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. an organ, a tissue, a vascular intervention site, a vascular structure, an altered surface can be measured, for example using one or more IMUS, optical markers, navigation markers, image or video capture systems and/or spatial anchors.

The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUS, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon or interventionalist wearing OHMD 1 11 can execute commands 32, e.g. to display the next predetermined bone cut, e.g. from a virtual surgical plan or an imaging study or intra-operative measurements, which can trigger the OHMDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual OHMD for their respective view angle or perspective by registering live data of the patient, e.g. the surgical field, and virtual data of the patient as well as each OHMD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

Fusing Physical World with Imaging and Other Data of A Patient

In some embodiments, an operator such as a surgeon or interventionalist may look through an OHMD observing physical data or information on a patient, e.g. a surgical site or changes induced on a surgical site, while pre-existing data of the patient are superimposed onto the physical visual representation of the live patient.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other.

The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the disclosure; this list is not exhaustive, but only exemplary. Anyone skilled in the art can identify other scanning or imaging techniques that can be used. For a detailed description of illustrative scanning and imaging techniques, see for example, Bushberg et al. The Essential Physics of Medical Imaging, $3^{rd}$ edition, Wolters, Kluwer, Lippincott, 2012.

- X-ray imaging, 2D, 3D, supine, upright or in other body positions and poses, including analog and digital x-ray imaging
- Digital tomosynthesis
- Angiography, e.g. single plane, bi-planar, 3D rotational angiography, Angiographic run-offs, angiographic bolus studies, angiographic flow studies, e.g. single plane, bi-planar, 3D rotational angiography
- Cone beam CT
- Ultrasound, including, for example, 2D and 3D imaging with addl. Doppler flow studies
- Doppler ultrasound
- Elastography, e.g. using ultrasound or MRI
- CT
- MRI
  including, for example, fMRI, diffusion imaging, stroke imaging, MRI with contrast media
- Functional MRI (fMRI), e.g. for brain imaging and functional brain mapping
- Magnetic resonance spectroscopy
- PET
- SPECT-CT
- PET-CT
- PET-MRI
- Upright scanning, optionally in multiple planes or in 3D using any of the foregoing modalities, including x-ray imaging, ultrasound etc.
- Contrast media
  e.g. iodinated contrast agents for x-ray and CT scanning, or MRI contrast agents.
  contrast agents can include antigens or antibodies for cell or tissue specific targeting
  other targeting techniques, e.g. using liposomes, can also be applied
  molecular imaging
    To highlight metabolic abnormalities in the brain and target surgical instruments towards area of metabolic abnormality
  any contrast agent known in the art can be used.
- 3D optical imaging, including
- Laser scanning
- Confocal imaging, e.g. including with use of fiberoptics, single bundle, multiple bundles
- Confocal microscopy, e.g. including with use of fiberoptics, single bundle, multiple bundles
- Optical coherence tomography
- Photogrammetry
- Stereovision (active or passive)
- Triangulation (active or passive)
- Interferometry Phase shift imaging
Active wavefront sampling
Structured light imaging
Other optical techniques to acquire 3D surface information
Combination of imaging data, e.g. optical imaging, wavefront imaging, interferometry, optical coherence tomography and/or confocal laser imaging or scanning
Image fusion or co-display of different imaging modalities, e.g. in 2D or 3D, optionally registered, optionally more than two modalities combined, fused or co-displayed, e.g. optical imaging, e.g. direct visualization or through an arthroscope, and/or laser scan data, e.g. direct visualization or through an arthroscope, and/or virtual data, e.g. intra-articular, extra-articular, intra-osseous, hidden, not directly visible, and/or external to skin, and/or confocal imaging or microscopy images/data, e.g. direct visualization or through an arthroscope In embodiments, 3D scanning can be used for imaging of the patient and/or the surgical site and/or anatomic landmarks and/or pathologic structures and/or tissues (e.g. damaged or diseased cartilage or exposed subchondral bone) and/or the surgeon or interventionalist's hands and/or fingers and/or the OR table and/or reference areas or points and/or marker, e.g. optical markers, in the operating room and/or on the patient and/or on the surgical field. 3D scanning can be accomplished with multiple different modalities including combinations thereof, for example, optical imaging, e.g. using a video or image capture system integrated into, attached to, or separate from one or more OHMD's, laser scanning, confocal imaging, optical coherence tomography, photogrammetry, active and passive stereovision and triangulation, interferometry and phase shift principles and/or imaging, wavefront sampling and/or imaging. One or more optical imaging systems or 3D scanners can, for example, be used to image and/or monitor, e.g. the coordinates, position, orientation, alignment, direction of movement, speed of movement of, Anatomic landmarks, patient surface(s), organ surface(s), tissue surface(s), pathologic tissues and/or surface(s), e.g. for purposes of registration, e.g. of the patient and/or the surgical site, e.g. one or more bones or cartilage, and/or one or more OHMD's, e.g. in a common coordinate system The surgeon or interventionalist's hands and/or fingers, e.g. for
Monitoring steps in an interventional procedure. Select hand and/or finger movements can be associated with corresponding surgical steps. When the 3D scanner system detects a particular hand and/or finger movement, it can trigger the display of the corresponding surgical step or the next surgical step, e.g. by displaying a predetermined virtual path, e.g. for a catheter, a virtual instrument, a virtual device etc.
Executing virtual commands, e.g. using gesture recognition or a virtual interface, e.g. a virtual touch pad
One or more OHMDs, e.g. registered in a common coordinate system, e.g. with the surgical site and/or the surgeon or interventionalist's hands and/or fingers The use of optical imaging systems and/or 3D scanners for registration, e.g. of the surgical site and/or one or more OHMDs can be helpful when markerless registration is desired, e.g. without use of optical markers, e.g. with geometric patterns, and/or IMU's, and/or LED's, and/or navigation markers. The use of optical imaging systems and/or 3D scanners for registration can also be combined with the use of one or more of optical markers, e.g. with geometric patterns, and/or IMU's, and/or LED's, and/or navigation markers.

In embodiments, one or more 3D models and/or 3D surfaces generated by an optical imaging system and/or a 3D scanner can be registered with, superimposed with and/or aligned with one ore more 3D models and/or 3D surfaces generated by another imaging test, e.g. a CT scan, MRI scan, PET scan, other scan, or combinations thereof, and/or a 3D model and/or 3D surfaces generated from or derived from an x-ray or multiple x-rays, e.g. using bone morphing technologies, as described in the specification or known in the art.

With optical imaging systems or 3D scanners, a virtual 3D model can be reconstructed by postprocessing single images, e.g. acquired from a single perspective. In this case, the reconstruction cannot be performed in real time with continuous data capture. Optical imaging systems or 3D scanners can also operate in real time generating true 3D data.

For example, with confocal microscopy using, for example, an active triangulation technique, a projector can project a changing pattern of light, e.g. blue light, onto the surgical field, e.g. an articular surface exposed by arthroscopy or a bone or a soft-tissue, e.g. using projection grids that can have a transmittance random distribution and which can be formed by sub regions containing transparent and opaque structures. By using elements for varying the length of the optical path, it can possible, for each acquired profile, to state a specific relationship between the characteristic of the light and the optical distance of the image plane from the imaging optics. A light source can produce an illumination beam that can be focused onto the surface of the surgical field, e.g. the articular surface. An image sensor can receive the observation beam reflected by the surface of the target object. A focusing system can focus the observation beam onto the image sensor. The light source can split into a plurality of regions that can be independently regulated in terms of light intensity. Thus, the intensity of light detected by each sensor element can be a direct measure of the distance between the scan head and a corresponding point on the target object.

Parallel confocal imaging can be performed, e.g. by shining an array of incident laser light beams, e.g. passing through focusing optics and a probing face, on the surgical field, e.g. an articular surface, a bone or a soft-tissue. The focusing optics can define one or more focal planes forward to the probe face in one or more positions which can be changed, e.g. by a motor or other mechanism. The laser light beams can generate illuminated spots or patterns on the surgical field and the intensity of returning light rays can be measured at various positions of the focal plane determining spot-specific positions yielding a maximum intensity of the reflected light beams. Data can be generated which can represent the topology of the three-dimensional structure of the surgical field, e.g. an articular surface, e.g. exposed and/or visible and/or accessible during arthroscopy, a bone or a soft-tissue. By determining surface topologies of adjacent portions or tissues, e.g. an adjacent articular surface or bone or soft-tissue, from two or more different angular locations and then combining such surface topologies, a complete three-dimensional representation of the entire surgical field can be obtained. Optionally, a color wheel can be included in the acquisition unit itself. In this example, a two-dimensional (2D) color image of the 3D structure of the surgical field, e.g. an articular surface, a bone or a soft-tissue, can also be taken at the same angle and orientation with respect to the structure. Thus, each point with its unique coordinates on the 2D image can correspond to a similar point on the 3D scan having the same x and y coordinates. The imaging process can be based on illuminating the target surface with three differently-colored illumination beams (e.g. red, green or blue light) combinable to provide white light, thus, for example, capturing a monochromatic image of the target portion of the surgical field, e.g. an articular surface, a bone, a cartilage or a soft-tissue, corresponding to each illuminating radiation. The monochromatic images can optionally be combined to create a full color image. Three differently-colored illumination beams can be provided by means of one white light source optically coupled with color filters.

With optical coherence tomography (OCT), using, for example, a confocal sensor, a laser digitizer can include a laser source, e.g. coupled to a fiber optic cable, a coupler and a detector. The coupler can split the light from the light source into two paths. The first path can lead to the imaging optics, which can focus the beam onto a scanner mirror, which can steer the light to the surface of the surgical field, e.g. an articular surface, e.g. as seen or accessible during arthroscopy, a cartilage, a bone and/or a soft-tissue. A second path of light from the light source can be coupled via the coupler to the optical delay line and to the reflector. The second path of light, e.g. the reference path, can be of a controlled and known path length, as configured by the parameters of the optical delay line. Light can be reflected from the surface of the surgical field, e.g. an articular surface, a cartilage, a bone and/or a soft-tissue, returned via the scanner mirror and combined by the coupler with the reference path light from the optical delay line. The combined light can be coupled to an imaging system and imaging optics via a fiber optic cable. By utilizing a low coherence light source and varying the reference path by a known variation, the laser digitizer can provide an optical coherence tomography (OCT) sensor or a low coherence reflectometry sensor. The focusing optics can be placed on a positioning device in order to alter the focusing position of the laser beam and to operate as a confocal sensor. A series of imaged laser segments on the object from a single sample/tissue position can be interlaced between two or multiple 3D maps of the sample/tissue from essentially the same sample/tissue position. The motion of the operator between each subframe can be tracked mathematically through reference points. Operator motion can optionally be removed.

Active wavefront sampling and/or imaging can be performed using structured light projection. The scanning system can include an active three-dimensional imaging system that can include an off-axis rotating aperture element, e.g. placed in the illumination path or in the imaging path. Out-of-plane coordinates of object points can be measured by sampling the optical wavefront, e.g. with an off-axis rotating aperture element, and measuring the defocus blur diameter. The system can include a lens, a rotating aperture element and an image plane. The single aperture can help avoid overlapping of images from different object regions and can help increase spatial resolution. The rotating aperture can allow taking images at several aperture positions. The aperture movement can make it possible to record on a CCD element a single exposed image at different aperture locations. To process the image, localized cross correlation can be applied to reveal image disparity between image frames.

In another embodiment, a scanner can use a polarizing multiplexer. The scanner can project laser sheet onto the surgical cite, e.g. an articular surface, e.g. as exposed or accessible during arthroscopy, a cartilage, damaged, diseased or normal, a subchondral bone, a cortical bone etc., and can then utilize the polarizing multiplexer to optically combine multiple views of the profile illuminated by the sheet of laser light. The scanner head can use a laser diode to create a laser beam that can pass through a collimating lens which can be followed by a sheet generator lens that can convert the beam of laser light into a sheet of laser light. The sheet of laser light can be reflected by a folding mirror and can illuminate the surface of the surgical field. A system like this can optionally combine the light from two perspectives onto a single camera using passive or active triangulation. A system like this system can be configured to achieve the independence of lateral resolution and depth of field. In order to achieve this independence, the imaging system, can be physically oriented so as to satisfy the Scheimpflug principle. The Scheimpflug principle is a geometric rule that describes the orientation of the plane of focus of an optical system wherein the lens plane is not parallel to the image plane. This enables sheet of light based triangulation systems to maintain the high lateral resolution required for applications requiring high accuracy, e.g. accuracy of registration, while providing a large depth of focus.

A 3D scanner probe can sweep a sheet of light across one or more tissue surfaces, where the sheet of light projector and imaging aperture within the scanner probe can rapidly move back and forth along all or part of the full scan path, and can display, for example near real-time, a live 3D preview of the digital 3D model of the scanned tissue surface(s). A 3D preview display can provide feedback on how the probe is positioned and oriented with respect to the target tissue surface.

In other embodiments, the principle of active stereophotogrammetry with structured light projection can be employed. The surgical field can be illuminated by a 2D array of structured illumination points. 3D models can be obtained from the single image by triangulation with a stored image of the structured illumination onto a reference surface such as a plane. A single or multiple camera can be used. To obtain information in z-direction, the surgical site can be illuminated by a 2D image of structured illumination projected from a first angle with respect to the surgical site. Then the camera can be positioned at a second angle with respect to the surgical site, to produce a normal image containing two-dimensional information in x and y direction as seen at that second angle. The structured illumination projected from a photographic slide can superimpose a 2D array of patterns over the surgical site and can appear in the captured image. The information in z-direction is then recovered from the camera image of the surgical site under the structured illumination by performing a triangulation of each of the patterns in the array on the image with reference to an image of the structured illumination projected on a reference plane, which can also be illuminated from the first angle. In order to unambiguously match corresponding points in the image of the surgical site and in the stored image, the points of the structured illumination can be spatially-modulated with two-dimensional random patterns which can be generated and saved in a projectable medium. Random patterns are reproducible, so that the patterns projected onto the surgical site to be imaged are the same as the corresponding patterns in the saved image.

Accordion fringe interferometry (AFI) can employ light from two point sources to illuminate an object with an interference fringe pattern. A high precision digital camera can be used to record the curvature of the fringes. The degree of apparent fringe curvature coupled with the known geometry between the camera and laser source enable the AFI algorithms to digitize the surface of the object being scanned. AFI can offer advantages over other scanners as lower sensitivity to ambient light variations and noise, high accuracy, large projector depth of field, enhanced ability to scan shiny and translucent surfaces, e.g. cartilage, and the ability to scan without targets and photogrammetric systems. A grating and lens can be used.

Alternatively, coherent point source of electromagnetic radiation can also be generated without a grating and lens. For example, electromagnetic radiation can be emitted from a pair or pairs of optical fibers which can be used to illuminate target objects with interferometric fringes. Consequently, movement of a macroscopic grating which requires several milliseconds or more to effect a phase shift can be avoided. A fiber-based phase shifter can be used to change the relative phase of the electromagnetic radiation emitted from the exit ends of two optical fibers in a few microseconds or less. Optical radiation scattered from surfaces and subsurface regions of illuminated objects can be received by a detector array. Electrical signals can be generated by a detector array in response to the received electromagnetic radiation. A processor receives the electrical signals and calculates three-dimensional position information of tissue surfaces based on changes in the relative phase of the emitted optical radiation and the received optical radiation scattered by the surfaces. Sources of optical radiation with a wavelength between about 350 nm and 500 nm can be used; other wavelengths are possible.

Other optical imaging systems and/or 3D scanners can use the principle of human stereoscopic vision and the principle of linear projection: if straight lines are projected onto an object the lines will be curved around the object. This distortion of the lines allows conclusions to be drawn about the surface contour.

With any of the optical imaging and/or 3D scanner techniques, if there are holes in the acquisition and/or scan and/or 3D surface, repeat scanning can be performed to fill the holes. The scanned surface can also be compared against a 3D surface or 3D model of the surgical site, e.g. an articular surface, a cartilage, damaged or diseased or normal, a subchondral bone, a bone and/or a soft-tissue, obtained from an imaging study, e.g. an ultrasound, a CT or MRI scan, or obtained via bone morphing from x-rays as described in other parts of the specification. Discrepancies in surface geometry between the 3D model or 3D surface generated with the optical imaging system and/or the 3D scanner and the 3D surface or 3D model obtained from an imaging study or bone morphing from x-rays, can be determined; similarly, it can be determined if the surfaces or 3D models display sufficient commonality to allow for registration of the intra-operative 3D surface or 3D model obtained with the optical imaging system and/or 3D scanner and the 3D surface or 3D model obtained from the pre-operative imaging study or bone morphing from x-rays. If there is not sufficient commonality, additional scanning can be performed using the optical imaging and/or 3D scanner technique, for example in order to increase the spatial resolution of the scanned data, the accuracy of the scanned data and/or to fill any holes in the model or surface. Any surface matching algorithm known in the art can be utilized to register overlapping surface areas and thereby transform all surface portions into the same coordinate space, for example the Iterative Closest Point method described in Besl et al., A Method for Registration of 3-D Shapes; 1992; IEEE Trans PAMI 14(2): 239-255.

Optionally, with any of the foregoing embodiments, the optical imaging system or 3D scanner can have a form of boot or stabilization advice attached to it, which can, for example, be rested against and moved over the target tissue, e.g. an articular surface, a bone or a soft-tissue. The boot or stabilization device can help maintain a constant distance between the scanner and the target tissue. The boot or stabilization device can also help maintain a constant angle between the scanner and the target tissue. For example, a boot or stabilization device can be used with an optical imaging system or scanner used during an interventional procedure.

Multi-Dimensional Imaging, Reconstruction and Visualization Various embodiments can be practiced in one, two, three or more dimensions. The following is an exemplary list of potential dimensions, views, projections, angles, or reconstructions that can be applied; this list is not exhaustive, but only exemplary. Anyone skilled in the art can identify additional dimensions, views, projections, angles or reconstructions that can be used. Exemplary dimensions are listed in Table 1.

TABLE 1

Exemplary list of potential dimensions, views, projections, angles, or reconstructions that can be displayed using virtual representations with optical head mounted display(s), optionally stereoscopic $1^{st}$ dimension: superoinferior, e.g. patient physical data
$2^{nd}$ dimension: mediolateral, e.g. patient physical data
$3^{rd}$ dimension: anteroposterior, e.g. patient physical data
$4^{th}$-$6^{th}$ dimension: head motion (and with it motion of glasses/OHMD) in 1, 2 or 3 dimensions
$7^{th}$-$9^{th}$ dimension: instrument motion in 1, 2 or 3 dimensions, e.g. in relationship to surgical field, organ or head including head motion
$10^{th}$-$13^{th}$ dimension: arm or hand motion in 1, 2 or 3 dimensions, e.g. in relationship to surgical field, organ or head including head motion
$14^{th}$-$16^{th}$ dimension: virtual 3D data of patient, obtained, for example from a scan or intraoperative measurements
$17^{th}$-$19^{th}$ dimension: vascular flow; in 1, 2 or 3 dimensions, e.g. in relationship to surgical field, organ or head including head motion
$20^{th}$-$22^{nd}$ dimension: temperature map (including changes induced by cryo- or hyperthermia), thermal imaging, in 1, 2 or 3 dimensions, e.g. in relationship to surgical field
$25^{th}$-$28^{th}$ dimension: metabolic map (e.g. using MRS, PET-CT, SPECT-CT), in 1, 2 or 3 dimensions, e.g. in relationship to surgical field
$29^{th}$-$32^{nd}$ dimension: functional map (e.g. using fMRI, PET-CT, SPECT-CT, PET, kinematic imaging), in 1, 2 or 3 dimensions, e.g. in relationship to surgical field or patient

TABLE 1-continued

Exemplary list of potential dimensions, views, projections, angles, or reconstructions that can be displayed using virtual representations with optical head mounted display(s), optionally stereoscopic $33^{rd}$-$35^{th}$ dimension: confocal imaging data and/or microscopy data in 1, 2, or 3 dimensions, e.g. in relationship to surgical field or patient, e.g. obtained through an endoluminal probe or direct visualization/imaging of an exposed surface $36^{th}$-$38^{th}$ dimension: optical imaging data in 1, 2 or 3 dimensions, e.g. in relationship to surgical field or patient, e.g. obtained through an endoluminal probe or direct visualization/imaging of an exposed surface $39^{th}$-$40^{th}$ dimension: laser scan data in 1, 2 or 3 dimensions, e.g. in relationship to surgical field or patient, e.g. obtained through an endoluminal probe or direct visualization/imaging of an exposed surface Any oblique planes are possible. Any perspective projections are possible. Any oblique angles are possible. Any curved planes are possible. Any curved perspective projections are possible. Any combination of 1D, 2D, and 3D data between the different types of data is possible.

Registering Virtual Data with Live Data Seen Through Optical Head Mounted Display In some embodiments, virtual data of a patient can be superimposed onto live data seen through the optical head mounted display. The virtual data can be raw data in unprocessed form, e.g. preoperative images of a patient, or they can be processed data, e.g. filtered data or segmented data.

Data Segmentation

Figure 2:
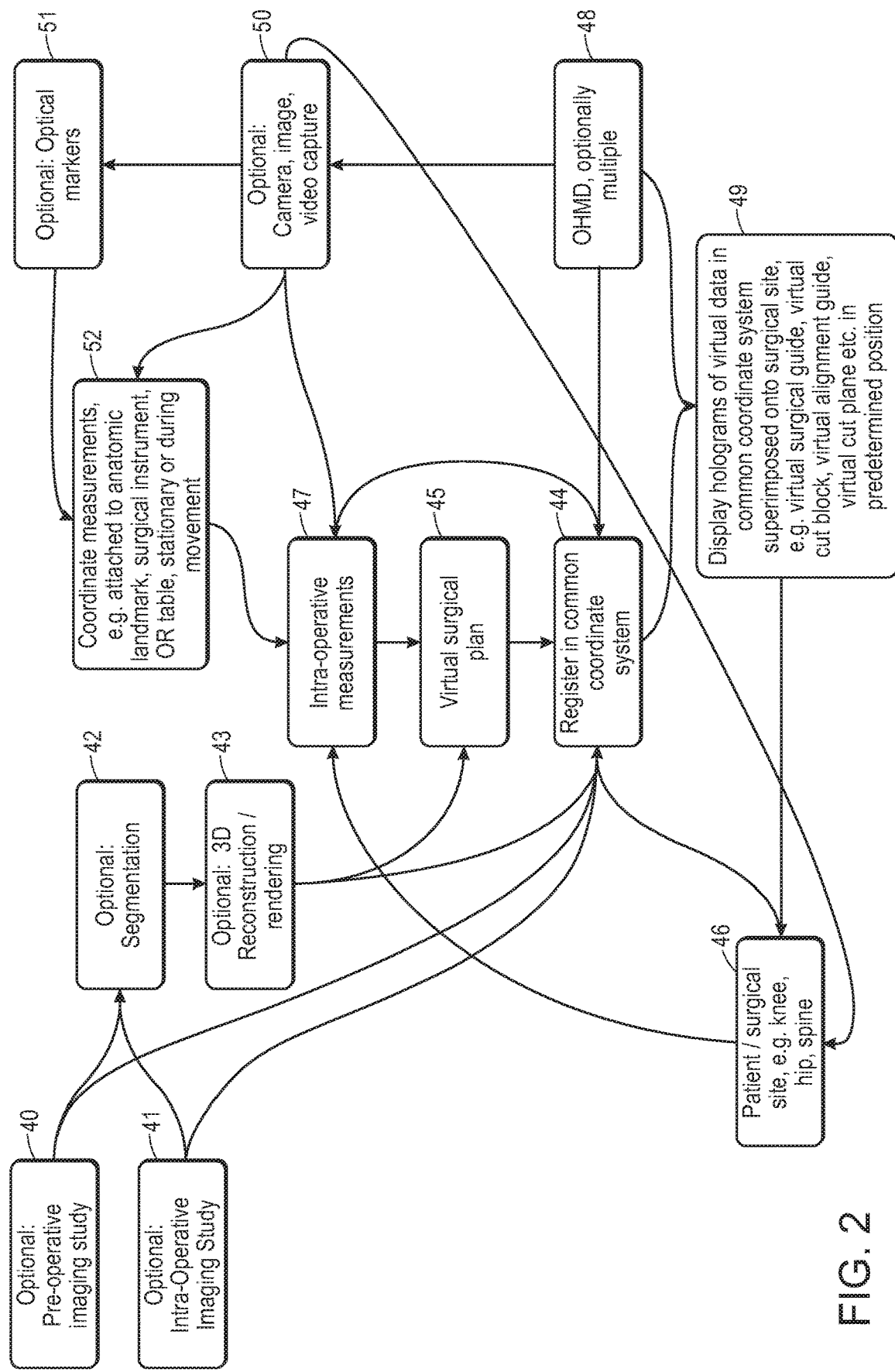
FIG. 2 shows a workflow for segmentation and select subsequent steps according to some embodiments of the present disclosure.

When images of the patient are superimposed onto live data seen through the optical head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (Math Works, Natick, Mass.). A representative workflow for segmentation and subsequent is provided in FIG. 2. An optional pre-operative imaging study can be obtained. An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. An optical head mounted display 48 can project or display digital holograms of virtual data or virtual data 49 superimposed onto and aligned with the surgical site. The OHMD 48 is configured to use a built-in camera or image capture or video capture system 50 to optionally detect and/or measure the position and/or orientation and/or alignment of one or more optical markers 51, which can be used for the coordinate measurements 52, which can be part of the intra-operative measurements 47.

Software and Algorithms for Registration

Registration of virtual data with live data can be performed using a variety of techniques know in the art. These include, but are not limited to, surface registration algorithms such as the Iterative Closest Point algorithm, statistical models, Active Shape Models, mutual information-based or other volume registration algorithms, object recognition, pattern recognition or computer vision techniques, deep learning or other artificial intelligence methods. The processed data can, for example, consist of mesh data, parametric surface data, point cloud data, volume data or a combination thereof. These methods are known in the art and have been implemented in publicly and/or commercially available code libraries and application programming interfaces (API's), such as the Insight Segmentation and Registration Toolkit (ITK), the open-source computer vision library OpenCV, Elastix, Plastimatch, or the Medical Image Registration Toolkit (MIRTK).

Superimposition of Virtual Data and Live Data by the OHMD

In some embodiments, segmented data or raw data can be superimposed on the patient's live data seen through the optical head mounted display. This superimposition can occur in unregistered form, i.e. the patient's virtual data may not be aligned with the live data seen through the optical head mounted display. In this case, the operator who is wearing the OHMD may move his/her head in a direction of orientation that will superimpose corresponding features of virtual data and live patient data. The surgeon or interventionalist or operator can also move and re-orient the virtual data using other means, e.g. a trackball or a virtual display interface displayed in the OHMD, unrelated to the surgeon or interventionalist/operator head movement. The operator can adjust the magnification of the live data so that the size, shape, length, thickness of certain features of the virtual data matches that of the live data for a given distance to the object/patient.

For example, during brain surgery, the surgeon or interventionalist may visually in live data look at the exposed gyri and sulci of the patient's brain. The OHMD can display a virtual 3D model of the gyri and sulci of the patient. The surgeon or interventionalist can optionally adjust the magnification of the 3D model so that the model will match the size or width or the length of the corresponding gyri and sulci in the live data. The surgeon or interventionalist can optionally adjust the transparency or opacity of the virtual data displayed in the OHMD. The ratio of virtual vs. live data transmitted through the OHMD can be 1:10, 1:9, 1:8, 1:5, 1:2, 1:1, 2:1, 3:1, 5:1, 8:1, 10:1, as well as fractions or multiples thereof. Any combination of transparency or opacity of virtual data and live data is possible. The surgeon or interventionalist can move his/her head in a direction or orientation that will superimpose virtual features, e.g. the patient's gyri and sulci, with the live patient data.

Once the data have been superimposed, the surgeon or interventionalist can optionally register the virtual data with the live data. This registration can be as simple as described here, e.g. a visual confirmation from the surgeon or interventionalist that virtual and live data are substantially matching or substantially superimposed. At this time, the surgeon or interventionalist can optionally reference the virtual data and/or the coordinate system of the virtual data in 2, 3 or more dimensions with the live data and/or the coordinate system of the live data. Once the data are registered, the surgeon or interventionalist can move his/her head into any desired position or orientation, for example for viewing the patient's brain or a lesion and adjacent, e.g. sensitive, anatomy from different view angles. The IMU of the OHMD will register the head movement, the direction of the head movement, the new head position and head orientation. The change in location and orientation of the surgeon or interventionalist's head can be simultaneously or, if desired, non-simultaneously applied to the virtual data which can now be superimposed with the resultant new position and orientation in relationship to the live data. In addition, when the surgeon or interventionalist moves his/her head or body further away from the target anatomy, the change in position and the increase in distance from the target anatomy can be measured by the IMU. Depending on the distance from the IMU, a magnification or minification factor can be applied to the virtual data so that the size, shape and dimensions of the virtual data will, in some embodiments, be close to or match the size, shape and dimensions of the live data, irrespective of the distance, location and orientation of the surgeon or interventionalist's head.

For purposes of registration of virtual data and live data, the OHMD can be optionally placed in a fixed position, e.g. mounted on a stand or on a tripod. While the OHMD is placed in the fixed position, live data can be viewed by the surgeon or interventionalist and they can be, optionally recorded with a camera and/or displayed on a monitor. Virtual data can then be superimposed and the matching and registration of virtual data and live data can be performed. At this point, the surgeon or interventionalist or an operator can remove OHMD from the fixed position and the surgeon or interventionalist can wear the OHMD during the surgical procedure.

The virtual data can optionally be displayed using a different color, e.g. red, green, yellow etc. Optionally, only the outline of select features of the virtual data may be displayed. For example, these features can be the sulci of the patient's brain (e.g. with a black line or black or lines with other colors), with no visualization of the gyri that these sulci border. Or, for example, only a lesion, e.g. a tumor such as, in the example of the brain, glioblastoma, can be displayed. Or combinations of virtual data of normal tissue and pathologic tissue can be displayed.

The virtual data can be registered with the live data seen through the optical head mounted display. The registration can occur using any method known in the art for registering or cross-referencing virtual and live data, in 2, 3, or more dimensions.

In some embodiments, the registration of the virtual data and the live data will be maintained through the vascular or interventional procedure. In some embodiments, the registration of the virtual data and the live data will be maintained during select portions of the vascular or interventional procedure or the vascular or interventional plan, which can be or can include a virtual, e.g. a preoperatively generated, vascular or interventional plan.

In some embodiments disclosure, the superimposition of the virtual data and the live data by the OHMD occurs simultaneously. In some embodiments, the superimposition of the virtual data and the live data by the OHMD is not simultaneous. For example, the virtual data can be superimposed intermittently.

Virtual data can be transparent, translucent or opaque. If virtual data are opaque, they may be displayed intermittently so that the operator or surgeon or interventionalist can see how they project in relationship to the live data of the patient.

If combinations of virtual data are displayed simultaneously with the live data, the different types of virtual data can be displayed with different colors. Representative combinations of virtual and live data are provided below. The following is only illustrative in nature and by no means meant to be limiting:

Live data: the patient's brain; surgically exposed gyri and sulci.

Live data: surgical instrument, e.g. biopsy needle or cutting tool

Virtual data: the patient's brain with gyri and sulci derived and optionally segmented from an imaging modality, e.g. a CT scan or an MRI scan Virtual data: a brain tumor, deep seated inside the brain Virtual data: the same surgical instrument currently used by the surgeon or interventionalist, in a virtual representation of the instrument, the virtual data indicating the desired orientation, location or direction of the surgical instrument.

Any of the foregoing virtual data can be displayed in two dimensions or three dimensions. Multi-dimensional displays as outlined in other sections of the specification are possible.

For example, the patient's normal tissue, e.g. normal brain tissue, can optionally be displayed in two dimensions, e.g. using grey level images, while the patient's abnormal tissue, e.g. a stroke, a hemorrhage or a tumor, can be displayed in three dimensions. Any combination of 2D, 3D, and multi-dimensional images is possible for display by the OHMD; any combination of 2D, 3D, and multi-dimensional images can be superimposed on live patient data by the OHMD.

The virtual 2D, 3D, and multi-dimensional data can be generated or acquired by different data acquisition technologies, e.g. different imaging tests etc.

Locking or Moving of Virtual Data

In some embodiments, virtual data can be locked in relationship to the surgeon or interventionalist or operator or in relationship to the patient or a certain target anatomy within a patient. This means even if the surgeon or interventionalist moves his or her head or the body or parts of the patient's anatomy are being moved, the virtual data will not move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or interventionalist or operator moves his or her head or body during the surgical procedure, the virtual data will not move, but are being displayed within the same location.

In some embodiments, virtual data can move in relationship to the surgeon or interventionalist or operator or in relationship to the patient or a certain target anatomy within a patient. This means if the surgeon or interventionalist moves his or her head or the body or parts of the patient's anatomy are being moved, the virtual data will move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or interventionalist or operator moves his or her head or body during the surgical procedure, the virtual data will move and change location and orientation the same way how the surgeon or interventionalist moves his/her head or body, typically reflecting the change in perspective or view angle that the surgeon or interventionalist obtained by moving his or her head or body.

Optionally the moving of the virtual data can be at greater virtual distance or greater angle or lesser virtual distance or lesser angle than the movement of the surgeon or interventionalist's head or body.

Improving the Accuracy of Moving or Re-Orienting Virtual Data Once registration between virtual data and physical data has occurred, the moving or re-orienting of virtual data to follow, for example, the surgeon or interventionalist's head movements or body movements or operating arm or hand movements, or the movements of the patient or certain body parts of the patient can be accomplished, for example, by monitoring the movement and change in location and/or orientation of the surgeon or interventionalist's head using the IMU of the OHMD.

In some embodiments, optical or RF tracker's or other tracking devices known in the art can be applied to the OHMD and/or the patient including select body parts or target tissues of the patient. Using standard surgical navigation techniques known in the art, the spatial location of the optical or RF trackers can be recorded, for example for a starting pose or position or location. Movement of the trackers, e.g. induced by movement of the surgeon or interventionalist's head or body or by movement of at least a part of the patient, can then be tracked using the navigation system. The information on positional change, orientational change or movement direction of the surgeon or interventionalist's head or the patient or both can then be used to update the virtual data, or the display of the virtual data in the OHMD, or both correspondingly. In this manner, the virtual data and the live data can be superimposed by the OHMD, typically in an accurate manner.

Optionally, positional, orientational, directional data and the like generated by the IMU can be used in conjunction with such data generated by a surgical navigation system. A combination of data can be beneficial for more accurate measurement of changes in position or orientation of the surgeon or interventionalist's head, body, operating arm, hand, or the patient.

Use of Virtual Data in 2 or More Dimensions

In some embodiments, the OHMD can display a 2D virtual image of the patient. The image can be a transmission type image, e.g. an x-ray or CT scout scan. The image can be a cross-sectional image of select anatomy of the patient. The image can be an original image or a reformatted, reconstructed or segmented or partially segmented image of the patient.

In some embodiments, a surgeon or interventionalist will look through the OHMD at the patient's live data, e.g. the exposed brain surface with the patient's gyri and sulci. The surgeon or interventionalist can register virtual data of the patient, e.g. an MRI scan of the patient's brain, relative to the patient's live data. Registration can occur in 2, 3 or more dimensions. Registration of virtual data in relationship to live data can include registration of different types of virtual data, e.g. different types of normal or diseased tissue, different imaging modalities used, different dimensions used for different types of normal or diseased tissue etc. More than one 2D scan plane can be displayed simultaneously. These 2D scan planes can be parallel or non-parallel, orthogonal or non-orthogonal at variable angles.

Scrolling Through, Moving of Virtual Data Superimposed Onto Live Data

In some embodiments, a surgeon or interventionalist or operator may optionally scroll through a set of consecutive or non-consecutive virtual 2D image data as well as 3D image data which are being superimposed onto the patient's live data, typically live data from the same anatomic region, e.g. a brain, an organ, a tissue, a vascular intervention site, a vascular structure, a vascular tree, a vascular flow or contrast study etc. The scrolling can be directed through any type of user interface, known in the art. For example, a surgeon or interventionalist can use a virtual interface projected by the OHMD where he or she can move a virtual arrow up or down or left or right to scroll the images backward or forward or, for example, to rotate the images or to display them in different multiplanar angles or to change the view angle or projection angle.

Optionally, the surgeon or interventionalist can scroll through the virtual image data or move virtual image data by moving his or her head back and forth, e.g. for scrolling backward or forward in a virtual image volume. The surgeon or interventionalist can move his or her head left or right for example, to rotate the images or to display them in different multiplanar angles or to change the view angle or projection angle of a 3D image.

Optionally, the surgeon or interventionalist can scroll through the virtual image data by moving his or her hand or finger or any other body part back and forth, e.g. for scrolling backward or forward in a virtual image volume. The surgeon or interventionalist can move his or her hand or finger or any other body part back and forth left or right for example, to rotate the images or to display them in different multiplanar angles or to change the view angle or projection angle. The surgeon or interventionalist can move his or her hand or finger in a spinning or rotating movement to spin or rotate the virtual data. Any combination of head or hand or eye and other body signals can be used for changing the display of the virtual data. Optionally, these display changes of the virtual data can be executed in the OHMD using the same location, position, orientation, angular, direction and movement related changes that are made by the surgeon or interventionalist's body part used to trigger the change in display. Alternatively, any one of location, position, orientation, angular, direction and movement related changes of the virtual data can be executed using a magnification factor or a minification factor in relationship to the changes in location, position, orientation, angular, direction and movement of the surgeon or interventionalist's body part. These magnification or minification factors can be linear or non-linear, e.g. exponential or logarithmic. In some embodiments, the further the surgeon or interventionalist's body part controlling the movement of the virtual data in the OHMD display moves away from its original position, the greater the induced change on the movement of the virtual data in the OHMD. In some embodiments, the further the surgeon or interventionalist's body part controlling the movement of the virtual data in the OHMD display moves away from its original position, the smaller the induced change on the movement of the virtual data in the OHMD.

Use of Virtual Data in 3 or More Dimensions

In some embodiments, the OHMD can display a 3D virtual image of the patient. A 3D representation of the patient can include a 3D display of different types of anatomy, for example in an area of intended surgery or a surgical site.

A 3D reconstruction of image data or other data of the patient can be generated preoperatively, intraoperatively and/or postoperatively. A virtual 3D representation can include an entire anatomic area or select tissues or select tissues of an anatomic area. Different tissues can be virtually displayed by the OHMD in 3D using, for example, different colors. Normal tissue(s) and pathologic tissue(s) can be displayed in this manner.

Normal tissue can, for example, include brain tissue, heart tissue, lung tissue, liver tissue, vascular structures, bone, cartilage, spinal tissue, intervertebral disks, nerve roots. Any tissue can be visualized virtually by the OHMD.

Registration of Virtual Data and Live Data of a Patient, for Example Relative to a Surgical Site In some embodiments, virtual data of a patient displayed by an OHMD and live data of a patient seen through an OHMD are spatially registered in relationship to each other, for example in a common coordinate system, for example with one or more optical OHMD's in the same common coordinate system. Virtual and physical surgical instruments and implant components can also be registered in the common coordinate system. Spatial co-registration can have the benefit that the simultaneous display of virtual and live data of the patient is not affected or less affected when the surgeon or interventionalist moves his or her head or body, when the OHMD moves or when the patient moves. Thus, the view perspective of the live data of the patient seen by the surgeon or interventionalist's eyes through the OHMD, e.g. the live surgical field, can stay the same as the view perspective of the virtual data of the patient seen by the surgeon or interventionalist's eyes through the display of the OHMD unit, e.g. the virtual surgical field, virtual surgical plane, virtual paths, virtual cut paths or planes, projected into the surgeon or interventionalist's eyes, even as the surgeon or interventionalist moves his or her head or body. In this manner, the surgeon or interventionalist does not need to re-think or adjust his hand eye coordination since live data of the patient seen through the surgeon or interventionalist's eye and virtual data of the patient seen through the OHMD display are superimposed, which is fundamentally different from other approaches such as surgical navigation which employ a separate computer monitor in the OR with a view angle for the surgeon or interventionalist that is different than his or her view angle for the live data of the patient and the surgical field. Also, with surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations the first and the second virtual instruments are compared.

With guidance in mixed reality environment, e.g. with stereoscopic display like an electronic holographic environment, a virtual surgical guide, tool, instrument or implant can be superimposed onto the surgical site, e.g. an organ or a tumor. Further, the physical guide, tool, instrument or implant can be aligned with the 2D or 3D representation of the virtual surgical guide, tool, instrument or implant. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, virtual data can move in relationship to the surgeon or interventionalist or operator or in relationship to the patient or a certain target anatomy within a patient. This means if the surgeon or interventionalist moves his or her head or the body or parts of the patient's anatomy are being moved, the virtual data will move in the OHMD display. For example, once registration of the OHMD, the virtual data of the patient and the live data of the patient in a common coordinate system has occurred, the OHMD can display a virtual image of a target tissue or adjacent tissue. The virtual image of the target tissue or adjacent tissue can be, for example, an image of or through a tumor or other type of pathologic tissue or an organ, a tissue, a vascular intervention site, a vascular structure. As the surgeon or interventionalist or operator moves his or her head or body during the surgical procedure, the virtual data will move and change location and orientation the same way how the surgeon or interventionalist moves his/her head or body, typically reflecting the change in perspective or view angle that the surgeon or interventionalist obtained by moving his or her head or body. The virtual data can also include a medical device, such as a vascular device, wherein the virtual data of the vascular device shows its intended location, orientation or path in relationship to a vessel or organ intended for placement or passage.

In some embodiments, registration is performed with at least three or more points that can be superimposed or fused into a common object coordinate system for virtual data and live data. Registration can also be performed using a surface or a 3D shape of an anatomic structure present in both virtual data and live data of the patient. In this case the virtual surface can be moved until it substantially matches the live surface of the patient or the virtual shape can be moved until it substantially matches the live shape of the patient.

Registration of virtual data of a patient and live data of a patient can be achieved using different means. The following is by no means meant to by limiting, but is only exemplary in nature.

Registration of Virtual Patient Data and Live Patient Data Using Directly or Indirectly Connected Object Coordinate Systems Registration of virtual and live data of the patient can be performed if the virtual data, e.g. imaging data of the patient, are acquired with the patient located in a first object coordinate system and the live data, e.g. during surgery, are observed or acquired with the patient located in a second object coordinate system, wherein the first and the second object coordinate system can be connected by direct, e.g. physical, or indirect, e.g. non-physical, means. A direct connection of the first and second object coordinate system can be, for example, a physical connection between the first and second object coordinate system. For example, the patient can be moved from the first to the second object coordinate system along the length of a tape measure. Or the patient can be scanned inside a scanner, e.g. a CT scanner or MRI scanner, and the scanner table can be subsequently moved out of the scanner for performing a surgical procedure with the patient still located on the scanner table. In this case, the scanner table can be a form of physical connection between the first and the second object coordinate system and the length of the table movement between the scan position and the outside the scanner position (for the live data, e.g. the surgical procedure) can define the coordinate transformation from the first to the second object coordinate system.

An indirect connection between the first (virtual data) and second (live data) object can be established if the patient is moved between the acquiring the virtual data, e.g. using an imaging test, and the live data, e.g. while performing a surgical procedure, along a defined path, wherein the direction(s) and angle(s) of the path are known so that the first and the second object coordinate system can be cross-referenced and an object coordinate transfer can be applied using the known information of the defined path and virtual data of the patient, live data of the patient and the OHMD can be registered in a common coordinate system. Virtual and physical surgical instruments and implant components can also be registered in the common coordinate system.

Registration of virtual patient data and live patient data is also possible without directly or indirectly connected object coordinate systems using other means and methods as will be explained in the following paragraphs and columns, for example when the patient performed one or more movements of unknown direction, length or magnitude. Combinations of all different registration methods described in the specification are possible, e.g. for switching registration methods during a procedure or for simultaneously using multiple registration methods, e.g. for enhancing the accuracy of the registration.

Registration Using Spatial Mapping

Live data, e.g. live data of the patient, the position and/or orientation of a physical instrument, the position and/or orientation of an implant component, the position and/or orientation of one or more OHMD's, can be acquired or registered, for example, using a spatial mapping process. This process creates a three-dimensional mesh describing the surfaces of one or more objects or environmental structures using, for example and without limitation, a depth sensor, laser scanner, structured light sensor, time of flight sensor, infrared sensor, or tracked probe. These devices can generate 3D surface data by collecting, for example, 3D coordinate information or information on the distance from the sensor of one or more surface points on the one or more objects or environmental structures. The 3D surface points can then be connected to 3D surface meshes, resulting in a three-dimensional surface representation of the live data. The surface mesh can then be merged with the virtual data using any of the registration techniques described in the specification.

The live data can be static, or preferably, it can be continuously updated with additional information to incorporate changes in the position or surface of the one or more objects or environmental structures. The additional information can, for example be acquired by a depth sensor, laser scanner, structured light sensor, time of flight sensor, infrared sensor, or tracked probe.

For initial spatial mapping and updating of mapping data, commonly available software code libraries can be used. For example, this functionality can be provided by the Microsoft HoloToolkit or the Google Project Tango platform. Various techniques have been described for spatial mapping and tracking including those described in U.S. Pat. No. 9,582,717, which is expressly incorporated by reference herein.

Registration of Virtual Patient Data and Live Patient Data Using Visual Anatomic Features a) Visual registration of virtual patient data in relationship to live patient data by the surgeon or interventionalist or operator In some embodiments, a surgeon or interventionalist or operator can visually align or match virtual patient data with live patient data. Such visually aligning or matching of virtual patient data and live patient data can, for example, be performed by moving the OHMD, for example via movement of the head of the operator who is wearing the OHMD. In this example, the virtual patient data can be displayed in a fixed manner, not changing perspective as the operator moves the OHMD. The operator will move the OHMD until the live patient data are aligned or superimposed onto the fixed projection of the virtual patient data. Once satisfactory alignment, matching or superimposition of the live patient data with the virtual patient data has been achieved, the surgeon or interventionalist can execute a registration command, for example via a voice command or a keyboard command. The virtual patient data and the live patient data are now registered. At this point, upon completion of the registration, the virtual patient data will move corresponding to the movement of the OHMD, for example as measured via the movement of an integrated IMU, image and field of view tracking, e.g. using anchor points in an image or field of view using an image and/or video capture system, and/or an attached navigation system with optical or RF or other trackers, which can be attached to the patient, the surgical site, a bone or any other tissue of the patient, the surgeon or interventionalist, the surgeon or interventionalist's arm, the surgeon or interventionalist's head or an OHMD worn by the surgeon or interventionalist.

Thus, once a satisfactory alignment or match has been achieved the surgeon or interventionalist can execute a command indicating successful registration. The registration can include changes in at least one of position, orientation, and magnification of the virtual data and the live data in order to achieve the alignment or match. Magnification applied to the virtual data can be an indication of the distance from the OHMD or the surgeon or interventionalist's head to the matched tissue. As a means of maximizing the accuracy of the registration, the estimated distance between the OHMD and the target tissue or the skin surface or other reference tissue can be confirmed with an optional physical measurement of the distance, in particular if the OHMD is, for example, in a fixed position, e.g. on a stand or tripod, which may be used optionally during the initial registration. Upon successful alignment or matching, the surgeon or interventionalist command can register, for example, the virtual patient data and the live patient data or images and the OHMD in the same common coordinate system. Virtual and physical surgical instruments and implant components can also be registered in the common coordinate system.

In some embodiments, the visual anatomic data can be, for example, gyri of the brain or osteophytes or bone spurs or pathologic bone deformations or tumor nodes or nodules, e.g. on the surface of a liver or a brain, or vascular branches and their respective shape or geometry.

Figure 3:
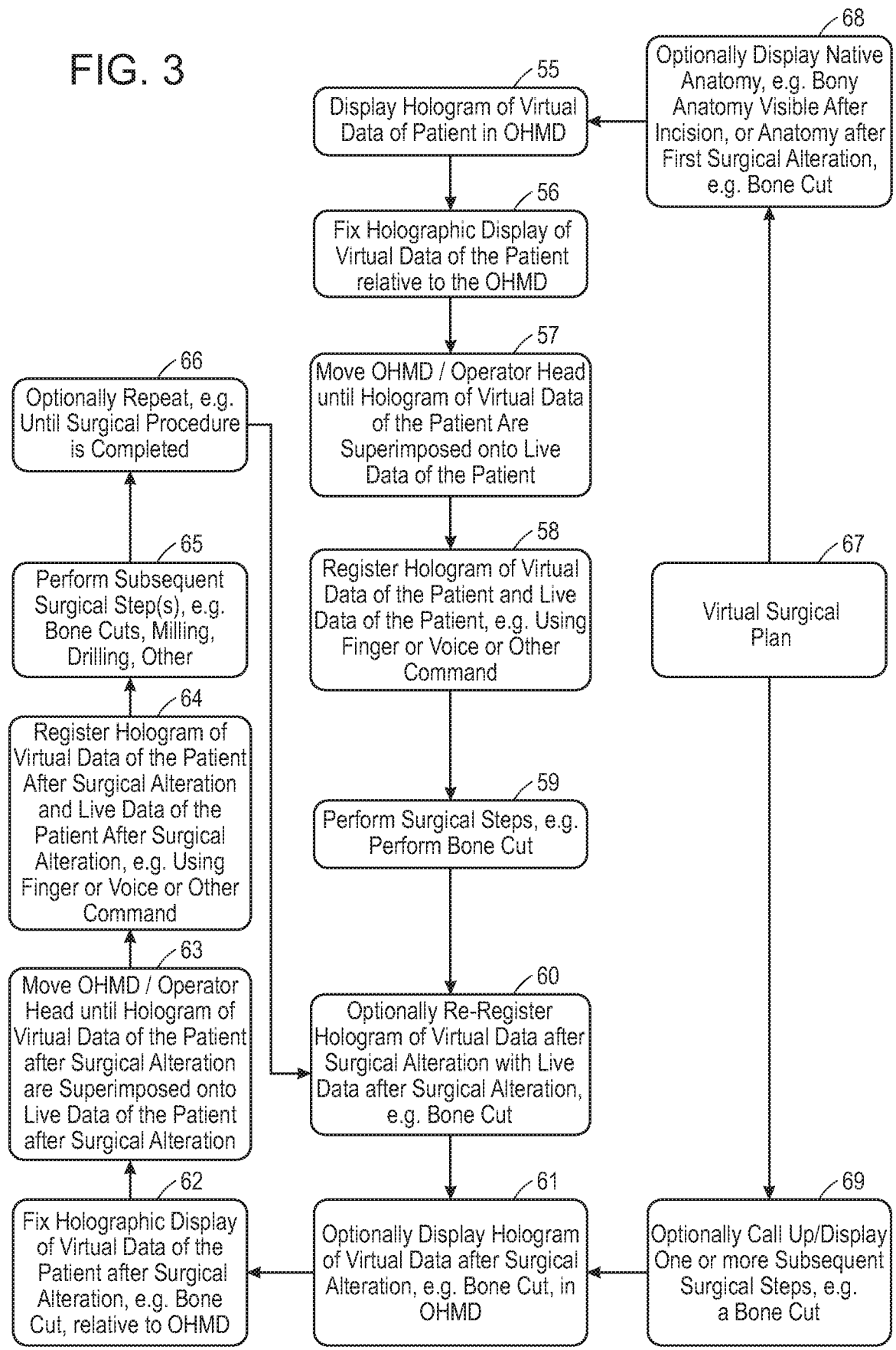
FIG. 3 is a flow chart illustrating an example of registering a digital hologram for an initial surgical step, performing the surgical step and re-registering one or more digital holograms for subsequent surgical steps according to some embodiments of the present disclosure.

In some embodiments, the registration of virtual patient data and live patient data using the methods described herein can be repeated after one or more surgical steps have been performed. In this case, the surgically altered tissue or tissue surface or tissue contour or shape, e.g. shape of a bone after milling or reaming, or tissue perimeter, e.g. perimeter of a bone cut, or tissue volume or other tissue features, e.g. a shape or volume of a vessel, an aneurysm, a vascular structure, a tumor after an intervention, e.g. an ablation or a coiling, in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, with substantially identical view angle of the virtual data of the patient seen by the surgeon or interventionalist's eyes through the display of the OHMD unit and the live data of the patient seen by the surgeon or interventionalist's eyes through the OHMD unit. The matching, superimposing and/or registering of the live data of the patient and the virtual data of the patient after the surgical tissue alteration can be performed using the same methods described in the foregoing or any of the other registration methods described in the specification or any other registration method known in the art. Referring to FIG. 3, FIG. 3 illustrates an example of registering a digital hologram or virtual data for an initial surgical step, performing the surgical step and re-registering one or more holograms for subsequent surgical steps. An optical head mounted display can project or display a digital hologram of virtual data or virtual data of the patient 55. The digital hologram can optionally be fixed to the OHMD so that it will move with the movement of the OHMD 56. The operator can move the OHMD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon or interventionalist can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the OHMD 61. The digital hologram of the virtual data or virtual data after the surgical alteration can optionally be fixed relative to the OHMD so that it will move with the movement of the OHMD 62. The operator can move the OHMD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon or interventionalist can then perform one or more predetermined subsequent surgical steps, e.g. bone cuts, milling or drilling 65. The preceding steps can optionally be repeated until the surgical procedures is completed 66. A virtual surgical plan 67 can be utilized. Optionally, the native anatomy of the patient including after a first surgical alteration can be displayed by the OHMD 68. The OHMD can optionally display digital holograms of subsequent surgical steps 69.

b) Automatic or semi-automatic registration of virtual patient data in relationship to live patient data using image processing and/or pattern recognition and matching techniques c) In some embodiments, image processing techniques, pattern recognition techniques or deep learning/artificial neural-network based techniques can be used to match virtual patient data and live patient data. Optionally, image processing and/or pattern recognition algorithms can be used to identify certain features, e.g. gyri or sulci on the brain surface of virtual data of a patient. An ear including its unique shape can also be used for the purpose of matching virtual patient data and live patient data.

For example, with brain surgery, the patient can be placed on the operating table. Optionally, cleaning or sterilization fluid can be applied to the shaved skull, for example using betadine. The OHMD can be placed over the patient, either on a tripod or worn by the operator, for example with the head of the patient turned sideways over the live patient's ear and lateral skull. The OHMD will be placed over an area of the live patient that includes the virtual data of the patient to be displayed.

Virtual data of the patient can be displayed in the OHMD. The virtual data of the patient can include, for example, a visualization of the patient's skin or other data, e.g. the patient's ear or nose, for example derived from preoperative MRI data. The virtual data of the patient's skin or other structures, e.g. the patient's ear or nose, can be displayed simultaneous with the live patient data. The virtual data of the patient can then be moved, re-oriented, re-aligned and, optionally, magnified or minified until a satisfactory alignment, match or superimposition has been achieved. Optionally, the OHMD can be moved also during this process, e.g. to achieve a satisfactory size match between virtual data and live data of the patient, optionally without magnification or minification of the virtual data of the patient. Once a satisfactory alignment, match or superimposition has been achieved between virtual data and live data of the patient, the operator can execute a command indicating successful registration. Changes in position, orientation, or direction of the OHMD, for example as measured via an integrated IMU, image and field of view tracking, e.g. using anchor points in an image or field of view using an image and/or video capture system, and/or a navigation system attached to the OHMD, can be used to move the virtual patient data with the view of the live patient data through the OHMD, with substantially identical object coordinates of the virtual data of the patient and the live data of the patient, thereby maintaining registration during the course of the surgery irrespective of any movements of the OHMD, e.g. head movement by the operator wearing the OHMD, and ensuring that the virtual data of the patient is correctly superimposed with the live data of the patient when projected into the surgeon or interventionalist's view.

After successful registration of the virtual patient data to the patient's skin or other structures, e.g. an ear or a nose, the operator or an assistant can apply a marker or calibration or registration phantom or device on the patient, for example close to the intended site of a craniotomy. The marker or calibration or registration phantom or device will not be covered by any drapes or surgical covers that will be placed subsequently. A secondary registration of the virtual patient data to the live patient data can then occur, by registering the virtual patient data to the live patient data, using the live marker or calibration or registration phantom or device placed on the patient and by cross-referencing these to the live data of the patient's skin or other structures, e.g. an ear or a nose. This can be achieved, for example, by registering the patient's skin or other structures, e.g. an ear or a nose, in the same coordinate system as the marker or calibration or registration phantom or device placed on the patient, e.g. by co-registering the virtual patient data of the patient's skin or other structures, e.g. an ear or a nose or an osteophyte or bone spur or other bony anatomy or deformity, with the live data of the marker or calibration or registration phantom or device. The distance, offset, angular offset or overall difference in coordinates between the patient's skin or other structures, e.g. an ear or nose or an osteophyte or bone spur or other bony anatomy or deformity, to the marker or calibration or registration phantom or device attached to the patient can be measured and can be used to switch the registration of the virtual patient data to the live patient data from the live data of the patient's skin or other structures, e.g. an ear or a nose, to the live data of the marker or calibration or registration phantom or device. Optionally, registration can be maintained to both the live data of the patient's skin or other structures, e.g. an ear or a nose, and the live data of the marker or calibration or registration phantom or device. Optionally, the system can evaluate if registration to the live data of the patient's skin or other structures, e.g. an ear or a nose, or to the live data of the marker or calibration or registration phantom or device is more accurate and the system can switch back and forth between either. For example, if the distance increases or decreases from the OHMD to the patient's skin or other structure, e.g. an ear or a nose, beyond a certain level, e.g. a threshold, which can be optionally predefined, or if some of them is partially covered by a drape, the system can switch the registration to the live data of the marker or calibration or registration phantom or device. The reverse is possible. Or, if the angle from the OHMD increases or decreases beyond a certain level, e.g. a threshold, which can be optionally predefined, to the patient's skin or other structure, e.g. an ear or a nose or an osteophyte or bone spur or other bony anatomy or deformity, the system can switch the registration to the live data of the marker or calibration or registration phantom or device. The reverse is possible.

The operator or the assistants can then place sterile drapes or surgical covers over the site, however preferably not covering the marker or calibration or registration phantom or device. Registration can be maintained via the live data of the marker or calibration or registration phantom or device attached to the patient, e.g. adjacent to or inside a craniotomy site. Image processing and/or pattern recognition of the live data of the patient can then be performed through the OHMD, e.g. using a built-in image capture apparatus and/or a 3D scanner for capturing the live data of the patient or image and/or video capture systems and/or a 3D scanner attached to, integrated with or coupled to the OHMD.

Virtual and live data features or patterns can then be matched. The matching can include a moving and/or reorienting and/or magnification and/or minification of virtual data for successful registration with the live data of the patient and superimposition of both. Virtual and live data can include an osteophyte or bone spur or other bony anatomy or deformity. Combination of (a) and (b), e.g. automatic registration with manual adjustment option, e.g. by moving the virtual image data in relation to the live image data after image processing software and/or pattern recognition software and/or matching software have identified a potential match or performed an initial matching, which can then be followed by manual/operator based adjustments. Alternatively, manual/operator based matching and registration can be performed first, followed then by fine-tuning via software or algorithm (image processing, pattern recognition, etc.) based matching and registration. Virtual and live data can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Anatomic Landmarks In some embodiments, a surgeon or interventionalist can identify select anatomic landmarks on virtual data of the patient, e.g. on an electronic preoperative plan of the patient, and on live data of the patient. For example, the surgeon or interventionalist can identify a landmark by placing a cursor or a marker on it on an electronic image of the virtual data of the patient and by clicking on the landmark once the cursor or marker is in the desired location. The surgeon or interventionalist can then identify the same landmarks live in the patient. For example, as the surgeon or interventionalist looks through the OHMD, the surgeon or interventionalist can point with the finger or with a pointing device at the corresponding anatomic landmark in the live data. The tip of the pointer or the tip of the finger can, optionally, include a tracker which locates the tip of the pointer or the finger in space. Such locating can also be done visually using image and/or video capture and/or a 3D scanner, e.g. in a stereoscopic manner through the OHMD for more accurate determination of the distance and location of the pointer or finger in relationship to the OHMD. An image and/or video capture system and/or a 3D scanner can also be attached to, integrated with or coupled to the OHMD. Virtual and live data can include an osteophyte or bone spur or other bony or vascular anatomy or deformity.

Representative anatomic landmarks that can be used for registration of virtual and live data of the patient can include (but are not limited to):

Skull and brain: A portion of a calvarium; A portion of an occiput; A portion of a temporal bone; A portion of a occipital bone; A portion of a parietal bone; A portion of a frontal bone; A portion of a facial bone; A portion of a facial structure; A portion or an entire bony structure inside the skull; Portions or all of select gyri; Portions or all of select sulci; A portion of a sinus; A portion of a venous sinus; A portion of a vessel; A portion of an ear; A portion of an outer auditory canal Organs: A portion of an organ, e.g. a superior pole or inferior pole of a kidney; An edge or a margin of a liver, a spleen, a lung; A portion of a hepatic lobe; A portion of a vessel; A portion of a hiatus, e.g. in the liver or spleen; A portion of a uterus Someone skilled in the art can identify other anatomic landmarks of hard tissues, soft-tissues and or organs including brain that can be used for registration of virtual data (including optionally including virtual surgical plans) and live data of the patient and the OHMD in a common coordinate system. Virtual and physical surgical instruments and implant components can also be registered in the common coordinate system.

In some embodiments, the OHMD can display an arbitrary virtual plane over the surgical field. The arbitrary virtual plane can be moveable using a virtual or other interface. For example, the arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the OHMD can capture the movement of the surgeon or interventionalist's finger(s) in relationship to the touch area; using gesture tracking software, the virtual plane can then be moved by advancing the finger towards the touch area in a desired direction.

The OHMD can display the arbitrary virtual plane in any location initially, e.g. projected onto or outside an interventional field, e.g. a vessel, a femoral or other puncture site, a vascular structure. The OHMD can optionally display the arbitrary virtual plane at a defined angle, e.g. orthogonal or parallel, relative to a fixed structure in the operating room, which can, for example, be recognized using one or more cameras, image capture or video capture systems and/or a 3D scanner integrated into the OHMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The OHMD can detect these one or more optical markers and determine their coordinates and, with that, the horizontal plane of the operating room table. The arbitrary virtual plane can then be displayed perpendicular or at another angle relative to the operating room table. The virtual arbitrary plane can be perpendicular to the operating table or at another predefined or predetermined angle relative to the OR table. Using a virtual interface, e.g. a touch area on the virtual surgical plane and gesture tracking, the OHMD can detect how the surgeon or interventionalist is moving the virtual arbitrary plane. Optionally, the virtual arbitrary plane can maintain its perpendicular (or of desired other angle) orientation relative to the OR table while the surgeon or interventionalist is moving and/or re-orienting the plane; a perpendicular orientation can be desirable when the surgeon or interventionalist intends to make a perpendicular cut. A different angle can be desirable, when the surgeon or interventionalist intends to make a cut with another orientation.

Using the touch area or other virtual interface, the surgeon or interventionalist can then move the arbitrary virtual plane into a desired position, orientation and/or alignment. The moving of the arbitrary virtual plane can include translation and rotation or combinations thereof in any desired direction using any desired angle or vector. The surgeon or interventionalist can move the arbitrary virtual plane to intersect with select anatomic landmarks or to intersect with select anatomic or biomechanical axes. The surgeon or interventionalist can move the arbitrary virtual plane to be tangent with select anatomic landmarks or select anatomic or biomechanical axes.

Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual devices can be virtually projected or displayed and automatically or using a virtual or other user interface moved, oriented or aligned to coincide, to be tangent with, to intersect, to be offset with, to be partially or completely superimposed with internal, subsurface, or hidden patient anatomy, internal, subsurface, or hidden pathology, internal, subsurface, or hidden anatomic axes, internal, subsurface, or hidden vessels or vascular structures, internal, subsurface, or hidden anatomic planes, internal, subsurface, or hidden 3D shapes, internal, subsurface, or hidden 2D and/or 3D geometries, internal, subsurface, or hidden 3D surfaces, and/or internal, subsurface, or hidden 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual devices can be virtually projected or displayed and automatically or using a virtual or other user interface moved, oriented or aligned to coincide, to be tangent with, to intersect, to be offset with, to be partially or completely superimposed with external patient anatomy, external pathology, external anatomic axes, external anatomic planes, external 3D shapes, external 2D and/or 3D geometries, external 3D surfaces, and/or external 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with patient anatomy directly visible to the operator's eye, e.g. without using a display of an OHMD, pathology directly visible to the operator's eye, e.g. without using a display of an OHMD, anatomic axes directly visible to the operator's eye, e.g. without using a display of an OHMD, biomechanical including mechanical axes directly visible to the operator's eye, e.g. without using a display of an OHMD, anatomic planes directly visible to the operator's eye, e.g. without using a display of an OHMD, 3D shapes directly visible to the operator's eye, e.g. without using a display of an OHMD, 2D and/or 3D geometries directly visible to the operator's eye, e.g. without using a display of an OHMD, 3D surfaces directly visible to the operator's eye, e.g. without using a display of an OHMD, and/or 3D volumes directly visible to the operator's eye, e.g. without using a display of an OHMD, of any organs, soft-tissues or hard tissues of the patient. Patient anatomy can include an implantation site, a bone for implanting a medical device, a soft-tissue for implanting a medical device, an anatomic structure adjacent to an implantation site, e.g. an adjacent tooth with which a dentist can virtually align a virtual implant component.

After the moving, orienting or aligning, the coordinate information of the 2D and/or 3D virtual shapes or outlines or surfaces can then be measured. Optionally, based on the coordinate information, additional intraoperative measurements can be performed and/or, optionally, a virtual surgical plan can be developed or modified using the information.

In any of the embodiments, the OHMD display of virtual data, e.g. of one or more of virtual surgical tool, virtual surgical instrument including a virtual surgical guide, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, virtual device, non-visualized portions for one or more devices or surgical instruments or surgical tools, and/or one or more of a predetermined tissue change or alteration can be performed in relationship to and/or with a predetermined location, orientation, and/or alignment to a normal, damaged and/or diseased organ, tissue, tissue surface, vessel, heart, valve. The predetermined location, orientation, and/or alignment can be external and/or internal to a normal, damaged and/or diseased organ, tissue, tissue surface, vessel, heart, valve. The predetermined location, orientation, and/or alignment can be tangent with and/or intersecting with a normal, damaged and/or diseased organ, tissue, tissue surface, vessel, heart, valve. The intersecting can be at one or more predetermined angles. The predetermined location, orientation, and/or alignment can be at an offset to a normal, damaged and/or diseased vessel or vascular structure, e.g. an offset of 0.5, 1.0, 1.5, 2.0, 3.0, 4.0, 5.0, 7.0, 10.0, 15.0, 20.0 mm, or a range from 0.1 to 50 mm in x, y and/or z-direction relative to the normal, damaged and/or diseased organ, tissue, tissue surface, vessel, heart, valve. For example, a virtual surgical guide and/or any virtual placement indicators for a physical surgical guide can be projected by one or more OHMDs so that at least portions of the virtual surgical guide and/or virtual placement indicators (e.g. a virtual path, e.g. for a catheter) are tangent with, intersecting with and/or offset with a normal, damaged and/or diseased organ, tissue, tissue surface, vessel, heart, valve of the patient.

In embodiments, the OHMD display of virtual data, e.g. of one or more of virtual surgical tool, virtual surgical instrument including a virtual surgical guide, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration, can be superimposed onto and/or aligned with the corresponding anatomic structure, e.g. a target tissue or an exposed tissue surface, e.g. an exposed tissue surface, seen directly through the see-through optical head mounted display (as they would be seen by the surgeon or interventionalist without wearing an OHMD). The surgeon or interventionalist can then, for example, move a physical instrument, surgical guide, surgical tool, implant, implant component, device to align with the virtual projection.

In some embodiments, the registration of virtual patient data and live patient data using the methods described herein including anatomic landmarks can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art. Optionally, different anatomic landmarks can also be used for the first registration and any of the subsequent registrations. Or the same anatomic landmarks can be used for the first registration and any of the subsequent registrations.

Using Light Sources for Referencing Live Anatomic Landmarks

The tracker or pointing device can also be a light source, which can, for example, create a red point or green point created by a laser on the patient's tissue highlighting the anatomic landmark intended to be used for registration. A light source can be chosen that has an intensity and/or a color that will readily distinguish it from the live tissue of the patient. The laser or other light source can optionally be integrated into or attached to the OHMD. For example, the laser or the light source can be integrated into or attached to a bridge connecting the frame pieces between the left and the right eye portion of the OHMD, for example over the nasal region.

Image and/or video capture and/or a 3D scanner, for example integrated into or attached to or coupled to the OHMD, can be used to identify the location of the light on the patient's tissue or the patient's anatomic landmark. Once the light has been directed to the desired location on the live data of the patient, specifically, the live landmark of the patient, registration can be performed by executing a registration command, registering the live data of the patient with the virtual data of the patient, e.g. the live landmark with the laser or other light being reflected of it and the corresponding virtual landmark of the patient. This process can be repeated for different anatomic landmarks, e.g. by pointing the light source at the next live anatomic landmark of the patient, confirming accurate placement or pointing, the light, e.g. a red or green laser point being reflected from the live patient landmark can be captured via the image and/or video capture device and/or 3D scanner, and the next anatomic live landmark can be registered with the corresponding virtual anatomic landmark of the patient. Virtual and live data can include an osteophyte or bone spur or other bony anatomy or deformity. In this manner, the OHMD, live data of the patient and virtual data of the patient can be registered in a common coordinate system. Virtual and physical surgical instruments and implant components can also be registered in the common coordinate system.

In some embodiments, more than one live and virtual anatomic landmark of the patient will be used, e.g. two, three or more.

In some embodiments, ultrasound or a radiofrequency transmitter can be used to pinpoint certain live anatomic landmarks. For example, an ultrasonic transmitter or a radiofrequency transmitter can be integrated into a point device, for example the tip of a pointing device. When the tip touches the desired live anatomic landmark, the transmitter can transmit and ultrasonic or RF signal which can be captured at a receiving site, optionally integrated into the OHMD. Optionally, for example as a means of increasing the accuracy of live data registration, multiple receiving sites can be used in spatially different locations. Virtual and live data can include an osteophyte or bone spur or other bony anatomy or deformity.

In some embodiments, the dimensions of the pointer have been previously scanned and registered with the OHMD. The image and/or video capture system attached to, integrated with or coupled to the OHMD can recognize the pointer in the live data and can identify the tip of the pointer. When the tip of the pointer touches the live landmark on the patient that corresponds to the landmark in the virtual data, the surgeon or interventionalist can, for example, click to indicate successful cross-referencing. The two data points can then optionally be fused or superimposed in a common coordinate system. Virtual and live data and data points can include or can be generated from an osteophyte or bone spur or other bony anatomy or deformity. Virtual and physical surgical instruments and implant components can also be registered in the common coordinate system.

Anatomic landmarks can include an unaltered surface shape, e.g. skin, facial features, e.g. the tip of the nose, a distance between both eyes, the location of an ear, the shape of the ear. Anatomic landmarks can also be bony landmarks, e.g. a medial or lateral malleolus, a tibial tuberosity, a medial or lateral epicondyle, a trochlear notch, a spinous process etc. Virtual and live data and virtual and live anatomic landmarks can include an osteophyte or bone spur or other bony anatomy or deformity.

Optionally, a live anatomic surface can be used for registration purposes. In this embodiment, the live anatomic surface can be derived, for example, using a light scanning, infrared scanning or ultrasound technique, or ultrasonic scanning technique during the surgery. The live surfaces of the patient that are detected and generated in this manner can be matched or aligned with virtual surfaces of the patient, for example obtained preoperatively using an imaging test such as x-ray imaging, ultrasound, CT or MRI or any other technique known in the art. Virtual and live data and anatomic surfaces can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Implantable or Attachable Markers or Calibration or Registration Phantoms or Devices Including Optical Markers In some embodiments, a surgeon or interventionalist is optionally using implantable or attachable markers to register virtual data of the patient with live data of the patient. This embodiment can, for example, be useful if the surgery is very extensive and results in the removal of tissue in the surgical site, as can be the case during brain surgery, e.g. removal of a brain tumor, liver surgery, e.g. removal of a liver tumor, and many other types of surgery. Virtual and live data can include an osteophyte or bone spur or other bony anatomy or deformity.

The terms implantable markers, attachable markers, skin markers, soft-tissue markers, calibration or registration phantoms or devices, and image capture markers as used throughout the application can include optical markers, e.g. optical markers with different geometric shapes or patterns, with QR codes, with bar codes, with alphanumeric codes. Implantable or attachable markers or calibration or registration phantoms or devices can be implanted prior to the actual surgery and can be included in pre-, intra- and/or postoperative imaging. Implantable or attachable markers or calibration or registration phantoms or devices can be implanted on or attached to osteophytes or bone spurs or other bony anatomy or deformity.

If the implantable or attachable markers or calibration or registration phantoms or devices are present in the virtual image data, the surgeon or interventionalist can optionally identify the implantable or attachable markers or calibration or registration phantoms or devices after an incision as he or she gains access to the target tissue and the implantable markers placed next to the target tissue or inside the target tissue. Such implantable or attachable markers or calibration or registration phantoms or devices can, for example, include radiation beets or metallic beets, for example also used for stereographic imaging or registration.

Alternatively, implantable or attachable markers or calibration or registration phantoms or devices can be placed during the surgery and, for example using an image and/or video capture system and/or 3D scanner attached to, integrated with or coupled to the OHMD, the location of the implantable or attachable markers or calibration or registration phantoms or devices can be determined. The location of the implantable or attachable markers or calibration or registration phantoms or devices on the patient in the live data of the patient can then be matched with the location of the anatomic structure to which the implantable or attachable markers or calibration or registration phantoms or devices is attached in the virtual data of the patient. For example, the anatomic structure in the virtual and live data can include an osteophyte or bone spur or other bony anatomy or deformity. In some embodiments, a pointer or pointing device can optionally include implantable or attachable markers or calibration or registration phantoms or device or optical markers followed by image capture through the OHMD or other image and/or video capture device and/or 3D scanner attached to, integrated with or coupled to the OHMD and registration of the tip of the pointer. In this manner, the OHMD, the implantable or attachable markers or calibration or registration phantoms or devices including optical markers and, through the use of the implantable or attachable markers or calibration or registration phantoms or devices including optical markers, the anatomic structures, pathologic structures, instruments, implant components and any other objects to which one or more implantable or attachable markers or calibration or registration phantoms or devices including optical markers can be attached, as well as the virtual data of the patient can be registered in a common coordinate system. Virtual and physical surgical instruments and implant components can also be registered in the common coordinate system.

Implantable or attachable markers or calibration or registration phantoms or devices can include rigid or fixed registration markers. Such rigid or fixed registration markers can be used to maintain registration as surgical field is being altered. A rigid or fixed registration marker can, for example, be a screw or a pin. Virtual and live data can include an osteophyte or bone spur or other bony anatomy or deformity. The rigid or fixed registration marker can be attached to the osteophyte or bone spur or other bony anatomy or deformity. In some embodiments, the medical device that is being implanted or a component thereof that has been, for example, already temporarily or permanently attached to the patient's tissue, e.g. an osteophyte or bone spur or bony anatomy or deformity, or the anatomic site or the surgical site can be used as an implantable or attachable marker or calibration or registration phantom or device during the surgery, for example while subsequent steps of the surgery are being completed. Such subsequent steps can, for example, include the implantation of additional components of the medical device. Any other rigid or fixed registration marker or implantable device can be used in this manner for different types of surgeries of the human body.

The one or more implantable or attachable markers or calibration or registration phantoms or devices can be attached to bone, cartilage, soft-tissues, organs or pathologic tissues such as osteophytes or bone spur or other bony anatomy or deformity, etc.

The one or more implantable or attachable markers or calibration or registration phantoms or devices can optionally include optical markers, retroreflective markers, infrared markers, or RF markers or any other marker device described in the art.

Optical markers are markers that can reflect light within the visible spectrum, i.e. the portion of the electromagnetic spectrum that is visible to the human eye, with wavelengths from about 390 to 700 nm or a frequency band from about 430-770 THz. Optical markers can also reflect light that includes a mix of different wavelengths within the visible spectrum. The light reflected by the optical markers can be detected by an image and/or video capture system integrated into, attached to or separate from the OHMD. Optical markers can be detected with regard to their location, position, orientation, alignment and/or direction of movement and/or speed of movement with use of an image and/or video capture system integrated into, attached to or separate from the OHMD with associated image processing and, optionally, pattern recognition software and systems. Optical markers can include markers with select geometric patterns and/or geometric shapes that an image and/or video capture system, for example integrated into, attached to or separate from the OHMD, can recognize, for example using image processing and/or pattern recognition techniques. Optical markers can include markers with select alphabetic codes or patterns and/or numeric codes or patterns and/or alphanumeric codes or patterns or other codes or patterns, e.g. bar codes or QR codes, that an image and/or video capture system, for example integrated into, attached to or separate from the OHMD, can recognize, for example using image processing and/or pattern recognition techniques. QR codes or quick response codes include any current or future generation matrix code including barcode. Barcodes and QR codes are machine readable optical labels that can include information, for example, about the patient including patient identifiers, patient condition, type of surgery, about the surgical site, the patient's side operated, one or more surgical instruments, one or more implant components, including type of implant used and/or implant size. A QR code can use different standardized encoding modes, e.g. numeric, alphanumeric, byte/binary, and/or kanji to store data. Other encoding modes can be used. Any current and/or future version of QR codes can be used. QR codes using single or multi-color encoding can be used. Other graphical markers, such as the ones supported by the Vuforia (PTC, Needham, Mass.) augmented reality platform, can be used as well.

A bar code, QR code or other graphical marker can be the optical marker. A bar code, QR code or other graphical marker can be part of an optical marker or can be integrated into an optical marker. The same QR code or bar code or other graphical marker can contain information related to the patient and/or the surgical site, e.g. patient identifiers, age, sex, BMI, medical history, risk factors, allergies, site and side (left, right), spinal level to be operated information related to inventory management, e.g. of surgical instruments and/or implants or implant components, e.g. left vs. right component, selected component size (match against virtual surgical plan and/or templating and/or sizing)

and can be used to obtain information about the location, position, orientation, alignment and/or direction of movement, and/or speed of movement, if applicable, of the surgical site, surgically altered tissue, one or more surgical instruments and one or more trial implants and/or implant components.

Geometric patterns, geometric shapes, alphabetic, numeric, alphanumeric, and other codes or patterns including bar codes and QR codes included in or part of one or more optical markers can be predefined and, optionally, stored in database accessible by an image and/or video capture system and associated image processing software and pattern recognition software. Geometric patterns, geometric shapes, alphabetic, numeric, alphanumeric, and other codes or patterns including bar codes and QR codes included in or part of one or more optical markers can be in 2D and some of it in 3D. For example, one or more planar or 2D patterns can be used in select embodiments. Alternatively, select 3D geometric shapes can be used, e.g. cubes, cuboids, prisms, cones, cylinders, spheres. Any 3D shape can be used including irregular shapes and/or asymmetric shapes. The 3D geometric shape can include 2D geometric patterns and/or alphabetic, numeric, alphanumeric, and other codes or patterns including bar codes and QR codes on one or more surfaces. For example, if a cuboid or other 3D shape is used for an optical marker, the same or different geometric patterns and/or alphabetic, numeric, alphanumeric, and other codes or patterns including bar codes and QR codes can be included in, affixed to or integrated into one or more of its surfaces or faces, e.g. two opposing surfaces or two adjacent surfaces oriented, for example, perpendicularly. 2D geometric patterns and/or alphabetic, numeric, alphanumeric, and other codes or patterns including bar codes and OR codes included in, affixed to or integrated into one or more surfaces or faces of a 3D geometric shape can be used to determine the orientation of select surfaces or faces of the geometric shape including the optical marker and, with that, the orientation and/or alignment of the surface or face and with that the geometric shape, for example in relationship to a surgical site, a surgical alteration, e.g. a cut bone surface or a reamed bone surface, a surgical instrument and/or one or more implant components including trial implants. In this manner, movement of a limb or surgical site can be tracked in embodiments. For example, an optical marker with a 3D shape can be attached to a trochlea or an anterior tibia. The optical marker can have a first surface with a first geometric pattern. The optical marker can have a second surface with a second geometric pattern. The first surface with the first geometric pattern can, for example, be anteriorly facing. The second surface with the second geometric pattern can, for example, be medially or laterally facing. When the operator looks through the OHMD, optionally with one or more video systems integrated into, attached to or separate from the OHMD, at the optical marker and the video system, in this example, detects predominantly the first surface, the information can be used to indicate that the tissue or organ is in a frontal, e.g. non-rotated position; if the video system detects a different ratio of first vs. second surface visible or detectable, e.g. with a larger portion of the second surface visible or detectable, the information can be used to indicate that the tissue or organ is in a somewhat or more rotated position. Similarly, a third surface with a third geometric pattern can be superior or inferior facing. If the video detects that a greater portion of the third surface is visible or detectable, the information can indicate that the tissue or organ is in a more flexed position. Any combination is possible.

A 3D optical marker can, optionally, not have distinct surfaces with distinct geometric patterns, but can include a continuum of the same or, optionally changing, geometric patterns along its 3D surface or 3D surfaces. The location and/or or position and/or orientation and/or coordinates of the changing, different portions of the geometric pattern along the 3D surface(s) can be known, e.g. prior to tracking a surgical site, a surgical instrument, an implant, a medical device or a limb or bone, e.g. during movement. A video system integrated into, attached to or separate from the OHMD can detect the location and/or position and/or orientation and/or coordinates of one or more of the different portions of the geometric patterns and can use the information to track a surgical site, a surgical instrument, an implant, a medical device or a limb or bone, e.g. during movement.

The detection of one or more surfaces with geometric patterns or one or more portions of geometric patterns, e.g. on a 2D optical marker or a 3D optical marker, can be used to trigger one or more computer demands. Similarly, the disappearance of one or more surfaces with geometric patterns or one or more portions of geometric patterns or an entire geometric pattern can be used to trigger one or more computer demands. Such computer commands can, for example, include activating a motion tracking mode, de-activating a motion tracking mode, activating an OHMD display, de-activating an OHMD display, displaying a surgical step, e.g. a next surgical step or a prior surgical step, displaying a proposed correction for a surgical step, initiating an alarm, terminating an alarm, displaying a surgical instrument, tracking a surgical instrument, displaying a next surgical instrument, displaying an implant component, displaying a medical device, tracking any of the foregoing, terminating any of the foregoing commands. Someone skilled in the art can recognize other commands that can be initiated or executed in this manner. Such commands can also be used, for example, to initiate action by a robot, e.g. activating a robot to guide an omnidirectional catheter.

In another embodiment, one or more video systems or cameras integrated into, attached to or separate from an OHMD can detect a change in angular orientation of a 2D or 3D optical marker and/or geometric pattern and/or portions of one or more of the foregoing; the change in angular orientation detected in this manner can also be used to trigger or execute one or more commands.

Geometric patterns and/or geometric shapes, alphabetic, numeric, alphanumeric, and other codes or patterns including bar codes and QR codes can be in color or black and white. Geometric patterns and/or geometric shapes and/or alphabetic, numeric, alphanumeric, and other codes or patterns including bar codes and QR codes can include portions that include color and black and white sections, portions that include only color and portions that are only black and white. Geometric shapes can include faces or surfaces that include color and black and white, faces or surfaces that include only black and white, and faces or surfaces that include only color. Different colors and different color codes can be used for different faces or surfaces of a geometric shape part of an optical marker. Different colors and different color codes can be used for different geometric patterns and/or geometric shapes and/or alphabetic, numeric, alphanumeric, and other codes or patterns including bar codes and QR codes. Different colors and different color codes can be used for different optical markers. Different colors, e.g. red, blue, green, orange, cyan etc., can be used for different geometric patterns and/or geometric shapes and/or alphabetic, numeric, alphanumeric, and other codes or patterns including bar codes and QR codes. Different colors, e.g. red, blue, green, orange, yellow, pink, cyan can be used for different optical markers. Different optical markers can optionally be associated with different surgical steps and/or different surgical instruments and/or different implant components; the use of a particular marker can be recognized by an image and/or video capture system integrated into, attached to or separate from the OHMD using standard image processing and/or pattern recognition software, including, optionally a database of patterns, e.g. with their associations with a particular surgical step and/or surgical instruments. As the image and/or video capture system recognizes a particular optical marker in the field of view, for example based on a particular geometric patterns and/or geometric shape and/or alphabetic, numeric, alphanumeric, and other codes or patterns including bar codes and QR codes used, it can then optionally display the corresponding surgical step and/or surgical instrument and/or implant component associated with that optical marker.

2D geometric patterns, alphabetic, numeric, alphanumeric, and other codes or patterns including bar codes and QR codes or combinations thereof, optionally with color and/or black and white coding, included in, affixed to or integrated into one or more surfaces or faces of a 3D geometric shape can be used to determine the orientation and/or alignment of select surfaces or faces of the geometric shape and, with that, the orientation and/or alignment of the geometric shape and/or the optical marker, for example in relationship to an anatomic landmark, a surgical site, a surgical alternation, a surgical instrument and/or one or more implant components. One or more 2D geometric patterns, alphabetic, numeric, alphanumeric, and other codes or patterns including bar codes and QR codes, optionally with color and/or black and white coding, included in, affixed to or integrated into an optical marker can be used to determine the orientation and/or alignment of the optical marker, which can, for example, be affixed to or integrated into an anatomic landmark, a surgical site, a surgical alternation, e.g. a cut bone surface or a reamed bone surface, a surgical instrument and/or one or more implant components including trial implants. Optical markers can be affixed to an anatomic landmark, a surgical site, a surgical alteration, e.g. a cut bone surface or a reamed bone surface, or a drill hole of the patient and the corresponding anatomic landmark, surgical site, or surgical alternation can be identified in the virtual data of patient thereby enabling registration of the virtual data and the live data of the patient in the same coordinate system.

Executing Commands Using Optical Markers: Optical markers can be hidden or removed. The hiding or removal of an optical marker can be used to trigger a computer command. For example, a camera integrated into, attached to or separate from an OHMD can monitor the presence of an optical marker. If the optical marker is hidden, for example by placing a drape over it or by covering it with the surgeon or interventionalist's or the surgical assistant's hand, or removed, the hiding or removal can trigger a command. The command can, for example, be to initiate a different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Un-hiding the optical marker can be used to reverse the command, e.g. to return to a prior display state or display type of the optical head mounted display(s). Un-hiding the optical marker can also be used to advance to yet different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. The hiding or removal can include hiding or removing only a portion of the optical marker. For example, when an optical marker has a 3D shape, for example with select 2D portions and 2D geometric patterns or continuous, optionally changing 3D geometric pattern(s), one or more of the 2D portions or 2D geometric patterns can optionally be hidden or removed, for example by manually or through other means removing the 2D portion or 2D geometric pattern or continuous, optionally changing 3D geometric pattern(s) from the 3D shape of the optical marker; this is feasible, for example, when the 2D portion or 2D geometric pattern is attached to or inserted into the optical marker with the attachment or insertion mechanism providing the capability for removal of the 2D portion or 2D geometric pattern. Alternatively, a 3D portion of the 3D shape of the optical marker can be removed or hidden. Such removal or hiding can also trigger one or more commands as described in the foregoing embodiments, e.g. to initiate a different display, to turn on or turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Optical markers can be added or re-displayed. The re-displaying of an optical marker can be used to trigger a computer command. For example, a camera integrated into, attached to or separate from an OHMD can monitor the presence of an optical marker. If the optical marker is re-displayed, for example by removing a drape from it or by uncovering it by removing the surgeon or interventionalist's or the surgical assistant's hand, or added, the adding or re-displaying can trigger a command. The command can, for example, be to initiate a different display, to turn on or to turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. Hiding or removing the optical marker can be used to reverse the command, e.g. to return to a prior display state or display type of the optical head mounted display(s).

Re-displaying or adding then the optical marker again can also be used to advance to yet different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. The adding or re-displaying can include adding or re-displaying only a portion of the optical marker. For example, when an optical marker has a 3D shape, for example with select 2D portions and 2D geometric patterns or a 3D geometric pattern, one or more of the 2D portions or 2D geometric patterns or 3D geometric patterns can optionally be added or re-displayed, for example by manually or through other means adding the 2D portion or 2D geometric pattern or 3D geometric pattern to the 3D shape of the optical marker; this is feasible, for example, when the 2D portion or 2D geometric pattern or 3D geometric pattern can be attached to or inserted into the optical marker with the attachment or insertion mechanism providing the capability for adding or re-displaying the 2D portion or 2D geometric pattern or 3D geometric pattern. Alternatively, a 3D portion of the 3D shape of the optical marker can be added or re-displayed. Such adding or re-displaying can also trigger one or more commands as described in the foregoing embodiments, e.g. to initiate a different display, to turn on or turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Similarly, the activation, e.g. turning on, of one or more LED's or the de-activation, e.g. turning off, of one or more LED's can be detected by one or more camera systems integrated into, attached to or separate from the OHMD and can be used to trigger or reverse one or more commands, e.g. to initiate a different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Optical markers on OHMD's: Optical markers can also be attached to an OHMD including multiple OHMD's if multiple OHMD's are used during a surgery. Optionally, optical markers, e.g. with QR codes, can be used to differentiate a first from a second, third, fourth and/or more OHMD's. One or more optical markers can optionally be attached to the operating room table and they can be registered in a coordinate system, for example the same coordinate system in which the one or more OHMD's, the patient, and portions of the surgical site can be registered. One or more optical markers can optionally be attached to other structures in the operating room including fixed structures, e.g. walls, and movable structures, e.g. OR lights, and they can be registered in a coordinate system, for example the same coordinate system in which the one or more OHMDs, the patient, and portions of the surgical site can be registered. In this example, optical markers can also be mounted to fixed structures on holding arms or extenders, optionally moveable and, for example, of known dimensions, orientations, lengths and angles.

Optical markers attached to fixed structures such as OR walls can be used to enhance the accuracy of room recognition and spatial mapping, in particular when the coordinates and/or the angles and/or distances between different optical markers are known. Optical markers attached to fixed structures such as OR walls can also be used to enhance the determination of the location and pose and change in location or pose or the coordinates and change in coordinates of one or more optical head mounted displays, which can assist with increasing the accuracy of the display of virtual data and their superimposition on corresponding live data.

Optical markers attached to movable structures can be used to track their location in the operating room. Optical markers attached to OR lights can be used to estimate the direction of light and the orientation and/or trajectory of shadows in the OR or a room. If the orientation and/or trajectory of shadows in the OR or the room is known, virtual shadowing or shading with the same or similar orientation or trajectory can be applied to virtual data display by the OHMD.

Different coordinate systems can be used. For example, a global coordinate system, can include one or more of a femoral coordinate system, tibial coordinate system, ankle coordinate system, hip coordinate system, acetabular coordinate system, humeral coordinate system, glenoid coordinate system, vertebral coordinate system etc. Someone skilled in the art can readily recognize other sub-coordinate systems in the global coordinate system.

In some embodiments, an optical marker, for example with one or more specific geometric shapes, geometric patterns, alphabetic, numeric, alphanumeric, and other codes or patterns including bar codes and QR codes or combinations thereof, can be assigned to a virtual surgical step. The marker can, for example, include written text defining the surgical step or corresponding to the surgical step, which can be the immediately preceding surgical step or the next surgical step, for example in a virtual surgical plan. In some embodiments, the text can be a number, for example a number corresponding to a particular surgical step, e.g. 1— for femoral artery puncture, 2— for guidewire placement, 3— for sheath placement, 4— for advancing catheter, 5— for stent placement. The number can be recognized by the image and/or video capture system, which can then display the virtual view for the corresponding surgical step, e.g. for 1—a cut plane for the distal femoral cut or a virtual outline of the corresponding physical distal femoral cut block. A combination of numbers and text can be used and the image and/or video capture system and associated software and optional pattern recognition software and systems can recognize the numbers and text and trigger a command to display the corresponding virtual view of the corresponding virtual surgical step, e.g. 1— for femoral artery puncture, 2— for guidewire placement, 3— for sheath placement, 4— for advancing catheter, 5— for stent placement etc.

Optical markers can be included in, integrated into or attached to the instrument or device. The optical markers can include a text or alphanumeric code for the surgeon or interventionalist that designates, for example, a specific surgical step, e.g. 1— for femoral artery puncture, 2— for guidewire placement, 3— for sheath placement, 4— for advancing catheter, 5— for stent placement etc. The optical markers can also include one or more specific geometric shapes, geometric patterns, alphabetic, numeric, alphanumeric, and other codes or patterns including bar codes and QR codes or combinations thereof. The one or more specific geometric shapes, geometric patterns, alphabetic, numeric, alphanumeric, and other codes or patterns including bar codes and QR codes or combinations thereof can be specific for the surgical (e.g. interventional) step, corresponding, for example, to the lettering or alphanumeric code that indicates the surgical step to the surgeon or interventionalist. An image and/or video capture system integrated into, attached to or separate from the OHMD can detect the one or more specific geometric shapes, geometric patterns, alphabetic, numeric, alphanumeric, and other codes or patterns including bar codes and QR codes or combinations thereof as the optical marker(s) enters the field of view; the specific geometric shapes, geometric patterns, alphabetic, numeric, alphanumeric, and other codes or patterns can be recognized using image processing and/or pattern recognition software triggering, for example, a command to display corresponding virtual surgical step in the OHMD superimposed onto the surgical field with the view angle for the surgeon or interventionalist aligned with the surgical field or target anatomy or bone cut. The image and/or video capture system can detect when the optical marker is not present in the field of view any longer, triggering, for example a command to turn off the OHMD display, e.g. as a means of preserving battery power, or the display of the completed surgical step or to switch to the display of the next surgical step and corresponding virtual display.

One or more optical markers can be used to determine the position, location, orientation, alignment and/or direction of a device or instrument with use of an image and/or video capture system integrated into, attached to or separate from the OHMD. For example, after the initial registration or any subsequent registration of the patient, the surgical site, the OHMD, optionally an image and/or video capture system integrated into, attached to or separate from the OHMD, the virtual data and/or the live data of the patient have been performed, the image and/or video capture system can detect an optical marker included in, integrated into, and/or attached to the surgical instrument. Since the location, position, alignment and/or orientation of the optical marker on the surgical instrument are known and the dimensions, e.g. at least one of them, or geometry of the surgical instrument are known, the image and/or video capture system can track the optical marker and the surgical instrument with regard to its location, position, orientation, alignment and/or direction of movement.

In another example, two or more optical markers can be integrated into or attached to different, optionally defined locations along the long axis of a device or instrument. An image and/or video capture system can detect the two or more optical markers and their respective location can be determined. With the location of the two or more optical markers captured and defined by the image and/or video capture system, the long axis of the device or instrument can be determined; other axes can be determined in addition to the long axis or instead of the long axis. With the location of the optical markers on the device or instrument known, the long axis or other axis of the device or instrument known, any portions of the device or instrument hidden by the tissue, e.g. below the skin and/or inside or within a vessel or vascular structure, can be estimated and can optionally be displayed by the OHMD in addition to the virtual or intended path or projected path or any other aspects of a virtual surgical plan. Rather than using two or more optical markers in the foregoing embodiment, an optical marker long enough or wide enough or deep enough to define one or more axes of a device or instrument can also be used.

Optionally, when two or more optical markers are used included in, integrated into or attached to a surgical instrument, the optical markers, can be arranged at the same angles, e.g. parallel or on the same axis, or at different angles, e.g. orthogonal angles or non-orthogonal angles.

This can be particularly useful, when the optical markers include one or more of a geometric shape, geometric pattern, alphabetic, numeric, alphanumeric, and other codes or patterns including bar codes and QR codes or combinations thereof. By arranging the optical markers and any associated geometric shapes, geometric patterns, alphabetic, numeric, alphanumeric, and other codes or patterns including bar codes and QR codes or combinations thereof in this manner, the angular orientation of the surgical instrument or an axis can be determined in a more accurate manner. For example, at certain view angles from an image and/or video capture system integrated into or attached to an OHMD select geometric shapes, geometric patterns, alphabetic, numeric, alphanumeric, and other codes or patterns including bar codes and QR codes or combinations thereof of a first optical marker on a surgical instrument or an anatomic landmark may be only partially visualized or not visualized at all due to the angular orientation; when a second optical marker is oriented at a different angle, location and/or orientation on the same surgical instrument or an anatomic landmark, the view angle from the image and/or video capture system integrated into or attached to the OHMD to the second optical marker can allow for a complete or a more complete visualization of the one or more geometric shapes, geometric patterns, alphabetic, numeric, alphanumeric, and other codes or patterns including bar codes and QR codes or combinations thereof, thereby allowing a more accurate determination of the angular orientation of the second optical marker and, with that, the surgical instrument. In addition, the respective projections of the first optical marker and/or the second optical marker measured by the image and/or video capture system, optionally paired with any parallax information when two or more cameras are used, e.g. one positioned near the left eye and another positioned near the right eye, can be used to more accurately determine their relative position and the position of the surgical instrument.

An image and/or video capture system integrated into or attached to or separate from an OHMD can detect an optical marker included in, integrated into or attached to a device or instrument as it enters the surgeon or interventionalist's field of view triggering a command to display the predetermined path or plane or a virtual display of the device or instrument or other display mode or type of the virtual surgical plan, for example with the intended position, location and/or alignment and/or direction for the intended surgical step; as the optical marker with the surgical instrument exits the surgeon or interventionalist's field of view, the image and/or video capture system can detect it triggering a command to stop the display of the predetermined path or the virtual display of the surgical instrument or other aspects of the virtual surgical plan, optionally switching to the next surgical step and corresponding virtual display. In a spinal procedure as well as select other procedures, the next surgical step can involve the same side of the patient or the opposite side of the patient at the same spinal level, where the corresponding virtual display for the next surgical step for a given level and side can be initiated by the OHMD display. The next surgical step can involve the same side of the patient or the opposite side of the patient at an adjoining or different spinal level, where the corresponding virtual display for the next surgical step for a given level and side can be initiated by the OHMD display.

Optical markers can include one or more QR codes. QR codes can be part of or can be embedded in a geometric pattern or geometric shape included in an optical marker. Optical markers can be a QR code.

If an optical marker is attached to a surgical instrument, the attachment can occur in a defined location and/or position and/or alignment, for example at an end of the surgical instrument. The attachment can include, for example, an opening with a stop thereby defining the location and/or position and/or alignment of the optical marker on the surgical instrument. With this type of attachment and other attachments that secure the marker in a defined location, position and/or orientation on the surgical instrument, an image and/or video capture system can detect the optical marker and its location, position and/or orientation can be used to determine the location, position, and/or orientation of the surgical instrument, e.g. a pin, including its tip or frontal portion inside the patient due to their defined spatial relationship and due to the known geometry of the surgical instrument.

In some embodiments, an optical marker can be used to determine or identify the position, location, orientation, alignment, dimensions, axis or axes, plane or planes of a surgical alteration. For example, if a bone cut or tissue ablation has been performed in a surgical step, one or more optical markers can be attached to the cut bone to determine one or more of its position, location, orientation, alignment, dimensions, shape, geometry, axis or axes, plane or planes. For example, one, two or more optical markers can be placed near or attached to the periphery or the edge of the cut bone or surgical alteration, e.g. tissue ablation; an image and/or video capture system integrated into, attached to or separate from the OHMD can detect the location, position, and/or orientation of the optical markers and software can be used, for example, to analyze the location, position, and/or orientation information of the optical markers to derive information on the periphery and/or edge and/or shape of the cut bone or surgical alteration. One, two or more optical markers can be placed near or attached to the cut bone or surgical alteration; an image and/or video capture system integrated into, attached to or separate from the OHMD can detect the location, position, and/or orientation of the optical markers and software can be used, for example, to analyze the location, position, and/or orientation information of the optical markers to derive information on the shape or geometry of the cut bone or surgical alteration. If the bone cut is planar, one or more optical markers with a planar bone facing surface or one or more optical markers attached to a carrier or instrument, e.g. a plastic piece, with a planar bone facing surface can be held against, affixed to or attached to the cut bone surface; an image and/or video capture system integrated into, attached to or separate from an OHMD can then be used to detect the one or more optical markers and software can be used, for example, to analyze the location, position and/or orientation information of the one or more optical markers to derive information on the location and/or position and/or orientation and/or alignment of the plane of the bone cut, including for example in relationship to other anatomic landmarks and/or other optical markers. The carrier or instrument for the optical marker can be transparent or semi-transparent so that the surgeon or interventionalist can check or confirm that the carrier or instrument and the attached optical marker(s) are flush against the bone cut prior to determining or confirming, for example, the plane of the bone cut.

Optical markers on fixed structures in the OR: In some embodiments, one or more optical marker and/or LED's can be attached to an operating room (OR) table. If the optical marker is parallel to the OR table, a single marker can be sufficient to determine the principal plane of the OR table, e.g. the horizontal plane, which can be the plane on which the patient is resting, for example in supine, prone, lateral or oblique or other positions known in the art. This can be aided by using optical marker and/or LED's that include a surface or plane that is parallel or perpendicular or at a defined angle to the OR table and that is large enough to be detected by the camera, image or video capture system integrated into, attached to or separate from the OHMD. For example, such a plane of the optical marker can measure 1×1 cm, 2×2 cm, 2×3 cm, 4×4 cm, 4×6 cm and so forth. Alternatively, multiple, e.g. two, three or more, optical marker and/or LED's can be used to determine a plane through the markers corresponding to the principal plane of the OR table or a plane parallel to the principal plane of the OR table or, for example, a plane vertical to the OR table or, for example, a plane at a defined angle to the OR table. If the OR table is hidden by surgical drapes, one or more magnetic or otherwise attachable bases can be attached to the OR table prior to placing the drapes. After the drapes have been placed, one or more magnetic or otherwise attachable optical marker and/or LED's can be affixed to the magnetic bases or attachment mechanisms with the interposed surgical drapes. The magnetic base can be radiopaque which can help identify the location, orientation and/or coordinates of the optical marker(s) in radiographic images or other images using ionizing radiation. Alternatively, one or more holding arms or extenders of known geometry can be attached to the OR table and one or more optical marker and/or LED's can be attached to or can be integrated into the holding arms or extenders. An image and/or video capture system integrated into, attached to or separate from the OHMD can then identify the location, position, orientation and/or alignment of the one or more optical marker and/or LED's. The resultant information can be used to determine the principal plane of the OR table on which the patient is lying. One or more OHMD's can be referenced using, for example, an image and/or video capture system integrated into or attached to the OHMD relative to the OR table and/or the attached optical marker and/or LED's. Once the principal plane of the OR table is determined in the system, virtual surgical steps can be planned in the virtual surgical plan of the patient in relationship to the principal plane of the OR table. One or more anatomic axes or biomechanical axes or vascular axes or geometries or combinations thereof can also be referenced to the OR table in this manner, e.g. the principal plane of the OR table, a plane parallel to the OR table, a plane perpendicular to the OR table, a plane oblique to the OR table or combinations thereof.

One or more optical marker and/or LED's attached to or referencing the OR table can also serve as a fixed reference for the one or more OHMDs during a surgical procedure. This can be useful, for example, when the patient and/or the extremity and/or the surgical site moves during the procedure. A fixed reference to the OR table can aid in maintaining registration of the one or more OHMDs and the virtual surgical plan and the live data of the patient and/or OR.

In some embodiments, one or more optical marker and/or LED's can be placed on or attached to the patient in the area of the surgical field and/or in an area away from the surgical field. An image and/or video capture system integrated into, attached to or separate from the OHMD can be used to identify the one or more optical marker and/or LED's and to determine their location, position, orientation and/or alignment. The image and/or video capture system can also, optionally, determine the location, position, orientation and/or alignment of one or more optical marker and/or LED's attached to or referencing the OR table. The system can reference the coordinates and/or the spatial relationship of the one or more optical marker and/or LED's attached to the patient in the area of the surgical field and/or in an area away from the surgical field and the one or more optical marker and/or LED's attached to or referencing the OR table. In this manner, if the patient's body moves during the procedure, e.g. during an interventional procedure, the movement between the one or more optical marker and/or LED's attached to the patient in the area of the surgical field and/or in an area away from the surgical field and the one or more optical marker and/or LED's attached to or referencing the OR table and the change in coordinates of the one or more optical marker and/or LED's attached to the patient in the area of the surgical field and/or in an area away from the surgical field can be detected and the amount of movement, direction of movement and magnitude of movement can be determined; the resultant information can, for example, be used to update or adjust or modify a virtual surgical plan or to update or adjust or modify the display of the virtual surgical plan or virtual surgical steps or virtual displays for the movement of the patient, including for example by updating, moving or adjusting one or more aspects or components of the virtual surgical plan including one or more of a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or surgical instruments or surgical tools, and/or one or more of a predetermined tissue change or alteration using the new patient coordinates or the new coordinates of the surgical field.

Radiopaque optical markers: In some embodiments, portions of the optical marker or the entire optical marker can be radiopaque, so that the optical marker can also be visible on a radiograph or angiogram or other imaging studies that utilize ionizing radiation including, for example, fluoroscopy, digital tomosynthesis, cone beam CT, and/or computed tomography.

Different levels or degrees of radiopacity can be present in different portions or areas of the optical marker. Different levels or degrees of radiopacity can be utilized to encode information. For example, different levels of radiopacity can be used to encode information also contained, for example, in an optically readable alphanumeric code, bar code or QR or other code. The different levels of radiopacity can optionally be arranged in a bar like thickness distribution, which can optionally mirror portions or all of the information contained in a bar code. The different levels of radiopacity can optionally be arranged in a point or square like thickness distribution, which can optionally mirror portions of the information contained in a QR code. Different radiopacity can be obtained by varying the thickness of the metal, e.g. lead. Radiopaque optical marker and/or LED's with information encoded in such manner can, for example, be manufactured using 3D metal printers. They can also be CNC machined, e.g. from bar stock or cast blanks. Optical markers can include portions that are radiopaque and portions that are not radiopaque. Radiopaque portions can include radiopaque elements, e.g. radiopaque struts, disks, sphere and/or other shapes. Any shape known in the art can be used. The optical marker can be attached to the radiopaque elements and/or radiopaque portions. The optical marker can be integrated into the radiopaque elements and/or radiopaque portions. The optical marker can be separate from the radiopaque elements and/or radiopaque portions, e.g. at a defined or known distance, defined or known angle and/or defined or known geometric and/or spatial arrangement.

The radiopaque portions of the optical marker can include information on laterality, e.g. L for left and R for right, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. The radiopaque portions of the optical marker can include information on anatomical site visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. Image processing techniques and/or software can be applied to the radiographic information including the optical marker and radiographically encoded information such as laterality and/or site and the information included in the radiograph can be compared against the information included on the optical scan. If any discrepancies are detected, an alert can be triggered, which can, for example, be displayed in the OHMD.

Multiple partially or completely radiopaque optical markers can be used. The radiopaque optical markers can be applied at different locations and in different planes around the surgical site. In spinal surgery, for example, one, two, three or more radiopaque optical markers can be applied to the skin around the spinal levels for the intended surgery; one, two, three or more radiopaque optical markers can be attached to a pin, drill or screw inserted into a spinous process and/or a pedicle or other spinal element; one, two, three or more radiopaque optical markers can be applied to the patient's flank or abdomen.

In some embodiments, the system performance can be tested. System performance tests can, for example, measure a phantom including two or more optical markers at known locations, positions, orientations and/or alignment. With the coordinates of the two or more optical markers known along with the distance(s) and angle(s) between the markers, the accuracy of performing distance measurements and/or angle measurements and/or area measurements and/or volume measurements using an image and/or video capture system integrated into, attached to or separate from the OHMD can be determined. In addition, by repeating the measurements, the reproducibility and/or precision of performing distance measurements and/or angle measurements and/or area measurements and/or volume measurements using an image and/or video capture system integrated into, attached to or separate from the OHMD can be determined. The accuracy and/or the reproducibility and/or the precision of performing distance measurements and/or angle measurements and/or area measurements and/or volume measurements using an image and/or video capture system integrated into, attached to or separate from the OHMD can be determined for static and dynamic conditions. Static conditions can be conditions where a patient, a surgical site, an organ or a tissue do not move. Dynamic conditions can be conditions where a patient, a surgical site, an organ or a tissue move during the image capture. Measurements for static conditions and for dynamic conditions can be performed for different view angles and distances of the image and/or video capture system integrated into, attached to or separate from the OHMD. More than one image and/or video capture system integrated into, attached to or separate from the OHMD can be used leveraging information from multiple view angles or leveraging parallax information. Measurements for static conditions and for dynamic conditions can be performed with the OHMD at rest, not moving. Measurements for static conditions and for dynamic conditions can be performed with the OHMD not at rest, but moving, for example moving with the operators head.

TABLE 2 shows exemplary tests with various combinations of test conditions and test parameters for which the accuracy and the reproducibility and/or the precision of the measurements can be determined. Any combination is possible. Other parameters, e.g. reproducibility of color temperature (e.g. in Kelvin), can be measured. Other statistical tests can be applied. All measurements and all statistical determinations and parameters can be assessed for static, dynamic, OHMD at rest and OHMD moving conditions including at different angles and distances of the image and/or video capture system to the target anatomy and/or test apparatus and/or phantom.

|  | Coordinates of optical markers | Distance between optical markers | Angle between optical markers | Area enclosed by optical markers | Volume of optical marker(s) | Volume enclosed by multiple optical markers | Axis defined by two or more optical markers | Speed of Movement of optical marker | Direction of movement of optical marker |
|---|---|---|---|---|---|---|---|---|---|
| Accuracy | X | X | X | X | X | X | X | X | X |
| Reproducibility/ | X | X | X | X | X | X | X | X | X |
| Static | X | X | X | X | X | X | X | | |
| Dynamic | X | X | X | X | X | X | X | X | X |
| OHMD at rest | X | X | X | X | X | X | X | X | X |
| OHMD moving | X | X | X | X | X | X | X | X | X |

Once the accuracy and/or the reproducibility and/or the precision of performing distance measurements and/or angle measurements and/or area measurements and/or volume measurements and/or coordinate measurements using one or more image and/or video capture system integrated into, attached to or separate from the OHMD has been determined, threshold values can, for example, be defined that can indicate when the system is operating outside a clinically acceptable performance range. The threshold values can be determined using standard statistical methods known in the art. For example, when a view angle and/or a distance or a movement speed of an image and/or video capture system integrated into an OHMD indicate that a measurement value can fall outside two standard deviations of the system performance including overall system performance, it can trigger an alert to the surgeon or interventionalist that the display of virtual data, e.g. portions of a virtual surgical plan, virtual projected paths or virtual planes, e.g. virtual cut planes, may not be accurate. A binary, e.g. yes, no, system can be used for triggering an alert that the image and/or video capture system and/or the OHMD display are operating outside a clinically acceptable performance range, e.g. exceeding certain view angles, exceeding or being below certain distances to the target anatomy, or exceeding an acceptable movement speed. Alternatively, a sliding scale can be used as the system enters progressively into a range outside the clinically acceptable performance range. The sliding scale can, for example, be a color scale from green to red with mixed colors in between. The sliding scale can be an acoustic signal that increases in intensity or frequency the further the system operates outside the clinically acceptable range. The sliding scale can be a vibration signal that increases in intensity or frequency the further the system operates outside the clinically acceptable range. In some embodiments, the OHMD can optionally turn off the display of any virtual data of the patient, e.g. virtual plan information, virtual surgical guides or virtual planes or intended paths, or one or more desired or predetermined alignment axes, anatomical axes, biomechanical axes and/or rotation axes when one or more test data indicate that the system is operating outside its clinically acceptable performance range. When test data indicate that the system is operating again inside the clinically acceptable performance range, the OHMD display can turn back on. System tests including accuracy tests and reproducibility tests can be performed intermittently, e.g. every 3 seconds, 5 seconds, 10 seconds, 20 seconds, 30 seconds, 1 minutes, 2 minutes and so forth. System tests can be performed continuously. System tests can be performed intermittently or continuously but limited to times when virtual data are displayed by the OHMD. System tests can be performed intermittently or continuously but limited to times when surgical steps that require high accuracy or reproducibility are being performed. Such steps requiring high accuracy or high reproducibility can be identified for example by the surgeon or interventionalist through voice commands or other commands or they can be identified in the virtual surgical plan, e.g. automatically or by surgeon or interventionalist choice.

In some embodiments, radiopaque and non-radiopaque optical markers can optionally be attached to or applied to extenders that increase the distance of the optical marker from the patient's skin. Such extenders can, for example, be anchored in a spinous process, a pedicle or other spinal element or a femoral condyle or tibial tubercle via a pin, drill or screw. The use of extenders with attached radiographic optical markers can increase the accuracy of registration between radiographic data and image capture data, for example when AP and lateral radiographs are used. The use of extenders with attached optical markers can help define anatomic or instrument axes and other information when image capture is used. When two or more markers are used with extenders and the markers are separated by a distance greater than the spatial resolution of the image and/or video capture system, the accuracy in determining, for example, an axis between the two markers can increase, for example as the length of the extender and the distance between the markers increases. Optical markers can be visible with other imaging modalities, e.g. MRI, nuclear scintigraphy, SPECT or PET. Optical markers can, for example, be doped with an MRI contrast agent such as Gadolinium-DTPA so that they are MRI visible. Optical markers can, for example, be doped with an isotope or positron emitter so that they are SPECT or PET visible.

When an optical marker includes a QR code or when a QR code is used as an optical marker, it can also address inventory management issues and quality concerns before, during and after surgery. Operating the wrong side of a patient is a common quality problem related to surgery, which can have devastating consequences for the patient. Similarly, in spinal surgery, operating the wrong spinal level can result in serious injury of the patient. Optical markers used for determining the location, position, orientation, alignment and/or direction of travel, if applicable, of a patient, a surgical site, an organ or a tissue, a surgical instrument, a trial implant and/or an implant component can also include information any of the following using, for example, bar codes or QR codes included in, integrated into or attached to the optical marker: Patient identifiers; Patient demographics, e.g. age, sex, height, BMI; Patient medical history; Patient risk factors; Patient allergies; Side to be operated, e.g. left vs. right; Site to be operated; Portions of virtual surgical plan (e.g. resection amounts, resection levels for a given surgical step, position and/or orientation of bone cuts, implant rotation, implant flexion, Intended depth, location, position, orientation, direction, coordinates of burring, Intended depth, location, position, orientation, direction, coordinates of reaming, intended depth, location, position, orientation, direction, coordinates of milling, Offset, Intended implant component axes/alignment; Templating or sizing related information (e.g. Size of selected implant component, Side of implant component, left vs. right); Inventory management information (e.g. Version, type, model of instrument used, Lot number of instrument used, Place of manufacture of instrument used, Date of manufacture of instrument used, Date of first sterilization of instrument used, Number of sterilization cycles applied to instrument used, Date of last sterilization of instrument used, Sterilization center used, Sterilization method used, Recommended sterilization method, Discrepancy between recommended sterilization method and sterilization method use, optionally with alert (e.g. transmitted optically using OHMD), Date instrument delivered to hospital or surgery center, Version, type, model of implant component used, Lot number of implant component used, Place of manufacture of implant component used, Date of manufacture of implant component used, Date of sterilization of implant component used, Type of sterilization of implant component used, Allowed shelf life of implant component, e.g. for given packaging and/or sterilization method, Date implant component delivered to hospital or surgery center, Any other information relevant to inventory management).

Optionally, QR codes that include some of this information can also be separate from the optical marker. In some embodiments, separate bar code and/or QR code readers can be used prior to, during and/or after the surgery to read the information included on the bar codes and/or QR codes. In some embodiments, an image and/or video capture system integrated into or attached to or separate from the OHMD can be used to read the information included on the bar codes and/or QR codes. The information read from the bar code and/or QR code can then, for example, be compared against portions of the virtual surgical plan and/or, for example, the physical patient's side prepared for surgery, e.g. left vs. right, the physical patient site prepared for surgery, e.g. spinal level L4 vs. L5 (as seen, for example, on radiographs), the physical surgery executed, the physical instrument selected, the physical implant trial selected, the physical implant component selected.

When a pin or a screw is placed in a surgical site including a surgical site, an organ or a tissue, for example also in a spinal level, e.g. a spinous process or pedicle, with an integrated or attached optical marker with a QR code or when an instrument, a trial implant, and/or an implant component with an integrated or attached optical marker with a QR code enters the field of view of a bar code and/or QR code reader and/or an image and/or video capture system integrated or attached to the OHMD, or enters the proximity of the surgical field or surgically altered tissue, the information on the bar code or QR code on the physical pin or screw, the physical instrument, the physical trial implant, and/or the physical implant component can be read and compared against the intended surgical site information and/or the intended laterality information and/or the virtual surgical plan and/or the intended sizing information and/or the intended templating information. In the example of a spinal level, the bar code and/or QR code reader and/or the image and/or video capture system integrated or attached to the OHMD, can read the QR code identifying the intended spinal level and side (left vs. right) for a pin or a pedicle screw or other device(s). The information can be compared to the virtual surgical plan of the patient and/or x-ray information. For example, intra-operative x-rays can be used by the system to automatically or semi-automatically or user-operated identify spinal levels, e.g. counting up from the sacrum, e.g. by detecting the sacral endplate and opposing endplates and/or pedicles. If the system detects a discrepancy in spinal level or laterality between the information read from the pin, screw or device and the integrated or attached optical marker and bar code or QR code, the virtual surgical plan and/or the radiographic information, it can trigger an alert to check the device, check the surgical plan, and/or to re-confirm the side or the vascular branch. The foregoing example is not limited to radiographic information; other imaging tests known in the art, e.g. CT, MRI, etc., can be used for determining or identifying the anatomic site and side, including for spinal levels.

If the reading of the QR code indicates a discrepancy in any of the information embedded in the QR code, e.g. site, laterality, level, portions or aspects of virtual surgical plan, sizing or templating information, vs. the physical live data during the surgery, e.g. the physical position or spinal level or laterality of the inserted pin or screw, the physical instrument used, the physical trial implant used, and/or the physical implant component used, an alert can be triggered, for example in the OHMD or on a computer monitor used for planning, display, or modifying the virtual surgical plan. The alert can be visual, e.g. red warning signs or stop signs or alert signs displayed, or acoustic, or a vibration, or combinations thereof. Any other alert known in the art can be used.

For example, when a surgeon or interventionalist is operating on a patient to replace a tissue with a device, one or more device components or an attached holder or packaging label or sterile package can include an optical marker including a QR marker. The QR marker can indicate the laterality, e.g. left femoral component vs. right femoral component. If the scrub technician accidentally hands the surgeon or interventionalist a right device component for implantation into the patient's left side, an image and/or video capture system integrated or attached to the OHMD that the surgeon or interventionalist is wearing can read the QR code as the surgeon or interventionalist takes the femoral component and as the femoral component with the attached optical marker and QR code enters the surgeon or interventionalist's field of view or enters the proximity of the surgical field. The image and/or video capture system and related system software can read the QR code identifying that the implant component is for a right side; the system software can then compare the information to the virtual surgical plan of the patient or the templating and/or sizing information which can indicate that a left side intervention was planned, then triggering an alert that an incorrect femoral component has entered the field of view of the surgeon or interventionalist or has entered into the proximity of the surgical field, as for example demarcated by another optical marker. The alert can assist the surgeon or interventionalist in correcting the error by switching to the correct side component.

Arrangement of optical markers inside sterile barriers indicating use of a medical device: In another example, when a surgeon or interventionalist is operating on a place a vascular device, e.g. a stent, one or more device components or an attached holder or packaging label or sterile package can include an optical marker including a QR marker. Optionally, the optical marker, e.g. including a QR code, barcode or other inventory management code can be included inside the sterile package. In some embodiments, the sterile package can include a first and a second sterile barrier. A QR code, barcode or other inventory management code can be included inside the first sterile barrier. A QR code, barcode or other inventory management code can be included inside the second sterile barrier. A QR code, barcode or other inventory management code can be included inside the first and the second sterile barrier. Optionally a QR code, barcode or other inventory management code reader can be used to read the code when the first and/or second sterile barrier is opened. The QR code, barcode or other inventory management code are intentionally placed and/or arranged inside the sterile barrier so that they can only be read or detected once the first and/or second sterile barrier is opened, e.g. by removing a cover or seal from the package, indicating and/or confirming the use of the medical device, which can trigger the billing charge or invoice, for example. The QR code, barcode or other inventory management code can be not visible, can be hidden and/or can be obscured inside the sterile barrier so that they are only exposed with the opening of the sterile package and so that they can only be read or detected once the first and/or second sterile barrier is opened, e.g. by removing a cover or seal from the package, indicating and/or confirming the use of the medical device, which can trigger the billing charge or invoice, for example. The QR code, barcode or other inventory management code can be intentionally not visible, can be intentionally hidden and/or can be intentionally obscured inside the sterile barrier so that they are only exposed with the opening of the sterile package and so that they can only be read or detected once the first and/or second sterile barrier is opened, e.g. by removing a cover or seal from the package, indicating and/or confirming the use of the medical device, which can trigger the billing charge or invoice, for example. A camera or image capture system and/or 3D scanner integrated into, attached to or separate from the OHMD can detect and/or read the QR code, bar code or other inventory management codes. Thus, for example, when a nurse, surgical assistant or surgeon or interventionalist, opens the first sterile barrier, a QR code, bar code or other inventory management code readers including, for example, a camera or image and/or video capture system and/or 3D scanner integrated into, attached to or separate from the OHMD, e.g. the OHMD worn by the nurse, surgical assistant or surgeon or interventionalist, can read the QR code, bar code or other inventory management code sending a signal that the first sterile barrier of the implant component has been opened. When a nurse, surgical assistant or surgeon or interventionalist opens the second sterile barrier, a QR code, bar code or other inventory management code readers including, for example, a camera or image and/or video capture system and/or 3D scanner integrated into, attached to or separate from the OHMD, e.g. the OHMD worn by the nurse, surgical assistant or surgeon or interventionalist, can read the QR code, bar code or other inventory management code sending a signal that the second sterile barrier of the implant component has been opened. The opening of the first and/or the second sterile barrier can trigger a signal or command indicating that the implant component has been used during the surgery; the signal or command can be transmitted to the hospital management system or the manufacturer, e.g. to their respective inventory management system, triggering one or more additional commands, e.g. to replenish the inventory for the used implant component and/or the pay the manufacturer for the used implant component and/or to generate a purchase order and/or an invoice to the hospital. The QR marker can indicate the size of the device. If the scrub technician accidentally hands the surgeon or interventionalist a wrong size device, an image and/or video capture system integrated or attached to the OHMD that the surgeon or interventionalist is wearing can read the QR code as the surgeon or interventionalist takes the device and as the device with the attached optical marker and QR code enters the surgeon or interventionalist's field of view or enters the proximity of the surgical field. The image and/or video capture system and related system software can read the QR code identifying size of the device; the system software can then compare the information to the virtual surgical plan of the patient or the templating and/or sizing information which can indicate that a different size device was planned, then triggering an alert that an incorrect size device has entered the field of view of the surgeon or interventionalist or has entered into the proximity of the surgical field, as for example demarcated by another optical marker. The alert can assist the surgeon or interventionalist in correcting the error by switching to the correct size device.

An image and/or video capture system and/or a bar code and/or QR code reader integrated into, attached to or separate from the OHMD can also be used to read embedded information on the virtual surgical instruments and/or implant components for inventory management and billing and invoicing purposes. For example, the image and/or video capture system and/or a bar code and/or QR code reader can detect which instruments were used, monitor their frequency of use, and when a certain recommended frequency of used has been reached, the system can trigger an alert to send the instrument for servicing. In some embodiments, the image and/or video capture system and/or a bar code and/or QR code reader can detect which instruments were used and trigger an alert to send the instruments used for sterilization. In some embodiments, the image and/or video capture system and/or a bar code and/or QR code reader can detect which disposable instruments were used and trigger an alert in the system to replenish the supply and send new, additional disposable instruments to replace the ones used. In some embodiments, the image and/or video capture system and/or a bar code and/or QR code reader can detect which implant components and other chargeable components were used and trigger an alert in the system to replenish the supply and send new, additional implant to replace the ones used; the alert can also trigger a command to generate an invoice to the hospital and/or surgery center and to monitor payment.

Any of the foregoing embodiments can be applied to any surgical step and any surgical instrument or implant component during any type of surgery, e.g. a vascular interventional procedure.

In some embodiments, pins or other implantable or attachable markers or calibration or registration phantoms or devices including optical markers can be placed initially, for example in a bone or an osteophyte or bone spur or other bony anatomy or deformity. Registration of virtual image data, for example using anatomic landmarks or locations or an osteophyte or bone spur or other bony anatomy or deformity, where the pins have been physically placed and optionally marking those on an electronic image, and live patient data can be performed. The pins can be optionally removed then, for example if they would interfere with a step of the surgical procedure. After the step of the surgical procedure has been performed, e.g. a bone cut, the pins can optionally be re-inserted into the pin holes remaining in the residual bone underneath the bone cut and the pins can be used for registered the virtual data of the patient with the live data of the patient even though the surgical site and anatomy has been altered by the surgical procedure.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Patient Specific Markers or Templates Various techniques have been described for registering virtual patient data with live patient data using patient specific markers or templates including those described in WO9325157A1, which is expressly incorporated by reference herein.

In some embodiments, pre-operative imaging is performed to acquire 3D data of the patient. The pre-operative imaging can, for example, entail ultrasound, CT or MRI, any of the foregoing, optionally with administration of a contrast agent.

The pre-operative imaging can include a single area or region. Alternatively, the pre-operative imaging can include scanning through portions of multiple anatomic areas.

The pre-operative imaging can also entail imaging in one or more positions, e.g. prone, supine, upright, flexion, extension, lateral bending. Data obtained from scans with the patient in different positions can optionally be combined or fused.

The patient specific marker or template can be developed from CT, MRI or ultrasound scans as well as x-ray imaging. Principally, any multi-planar 2D or 3D imaging modality is applicable, in particular when it provides information on surface shape or provides information to derive estimates of surface shape of an anatomic region. The patient specific marker or template can include one or more surfaces that are designed or manufactured to fit in a soft-tissue shape, e.g. the shape of a thigh or calf or lower back, or thoracic region, or neck region, or foot or ankle region, or shoulder region; Soft-tissue shape in different body poses or positions, e.g. in prone position or in supine position or in lateral position; Ligament of a patient; Labrum of a patient; Meniscus of a patient; Organ shape of a patient; Organ rim or edge of a patient, e.g. a liver edge or spleen edge.

Different imaging tests can be particularly amenable for a given tissue. For example, if the patient specific marker or template is designed to fit the cartilage shape of the patient, MRI and ultrasound or CT arthrography are ideally suited to provide the surface information. If the patient specific marker or template is intended to fit the subchondral bone shape or cortical bone shape, CT can be used, although MRI and ultrasound can also provide information on bone shape.

Patient specific markers or templates can be manufactured using different materials, e.g. ABS or nylon or different types of plastics or metals. They can be machined, e.g. from a blank, wherein a CAD/CAM process transfers the patient specific shape information into the milling machines. They can also be produced using stereolithography or 3D printing techniques known in the art. If 3D printing is used, any residual powder can be removed using an air cleaning operation and/or a water bath. 3D printing can be performed using powder based or liquid resin based approaches, including, but not limited to continuous liquid interface production.

Patient specific markers or templates can include or incorporate optical markers, e.g. optical markers with different geometric shapes or patterns, with QR codes, with bar codes, with alphanumeric codes. Optionally, geometric shapes or patterns, QR codes, bar codes, alphanumeric codes can be printed, for example when 3D printing is used for manufacturing patient specific markers or templates. 3D printing can be performed with software, e.g. Materialise Magics (Materialise, Leuven, Belgium), and hardware known in the art, e.g. 3D printers from 3D Systems, Rock Hill, SC, or Concept Laser, Lichtenfels, Germany.

Patient specific markers or templates can be made with different material properties. For example, they can be non-elastic, semi-elastic or elastic. They can be hard. They can be solid or include hollow spaces or openings. They can be opaque. Patient specific markers or templates can be semi-opaque. Patient specific markers can be transparent. In some embodiments, a patient specific marker or template can be semi-opaque or semi-transparent. However, when the patient specific marker or templates comes in contact with the patient and the patient specific surface(s) of the marker or template achieves a good fit with the corresponding surface of the patient, the patient specific marker or template becomes transparent due to the tissue moisture on the corresponding surface of the patient.

Representative, non-limiting examples of patient surfaces to which patient specific markers or templates can be designed and/or fitted include:

Skull and brain: A portion of a calvarium; A portion of an occiput; A portion of a temporal bone; A portion of an occipital bone; A portion of a parietal bone; A portion of a frontal bone; A portion of a facial bone; A portion or an entire bony structure inside the skull; Portions or all of select gyri; Portions or all of select sulci; A portion of a sinus; A portion of a venous sinus; A portion of a vessel Organs: A portion of an organ, e.g. a superior pole or inferior pole of a kidney; An edge or a margin of a liver, a spleen, a lung; A portion of a hepatic lobe; A portion of a vessel; A portion of a hiatus, e.g. in the liver or spleen; A portion of a uterus.

The patient specific marker or template can be designed or fitted to any of the previously mentioned tissues, if applicable for a particular anatomic region, e.g. cartilage, subchondral bone, cortical bone, osteophytes etc. The patient specific marker or template can be designed or fitted to normal tissue only. The patient specific marker or template can be designed or fitted to abnormal or diseased tissue only. The patient specific marker or template can be designed or fitted to combinations of normal and abnormal or diseased tissue. Patient specific markers can be used to register one or more normal or pathologic tissues or structures in a common coordinate system, for example with one or more OHMD's and virtual data of the patient. Virtual and physical surgical instruments and devices can also be registered in the common coordinate system.

The patient specific marker or template can be designed using virtual data of the patient, e.g. from a pre-operative imaging study such as a CT scan, MRI scan or ultrasound scan. The patient specific marker or template includes one or more surfaces that are designed and/or manufacture to achieve a close fit with a corresponding surface of the patient.

In some embodiments, a surgeon or interventionalist or an operator can apply the patient specific marker or template to the corresponding tissue of the patient. Once a satisfactory fit has been achieved and the two corresponding surfaces are substantially in contact, the patient specific marker or template can be used to register the virtual data of the patient and an optional virtual surgical plan with the live data of the patient. By applying the patient specific marker or template to its corresponding surface(s) on the patient, the surgeon or interventionalist is effectively identifying corresponding structures or surfaces in the virtual data and the live data of the patient.

The position, location and/or orientation of the patient specific marker or template can then be determined in relationship to the OHMD. Any of the embodiments described herein can be applied for determining the position, location and/or orientation of the patient specific marker or template in relationship to the OHMD. For example, the side of the patient specific marker or template that is opposite the patient specific surface can include certain standardized geometric features, e.g. rectangles, triangles, circles and the like, that can be readily recognized by an image and/or video capture system integrated into or attached to or coupled to the OHMD. In alternative embodiments, the patient specific marker or template can include one or more IMU's, including, for example, accelerometers, magnetometers, and gyroscopes, similar, for example, to the OHMD. In some embodiments, the patient specific marker or template can include one or more radiofrequency tags or markers or retroreflective markers and its position, location and/or orientation can be captured by a surgical navigation system. Radiofrequency tags can be active or passive. Optionally, the OHMD may also include one or more radiofrequency tags or markers or retroreflective markers and its position, location and/or orientation can also be captured by the surgical navigation system and cross-referenced to the patient specific marker or template. The patient specific marker or template can also include light sources, such as lasers or LED's. A laser can be projected, for example, on a wall or a ceiling and the OHMD can be referenced in relationship to that. An LED attached to or integrated into the patient specific marker or template can be recognized, for example, by an image and/or video capture system integrated into or attached to r coupled to the OHMD.

In an additional embodiment, one or more of the surgical instruments and/or one or more of the implantable devices used during the surgery can include certain standardized geometric features, e.g. rectangles, triangles, circles and the like, that can be readily recognized by an image and/or video capture system integrated into or attached to or coupled to the OHMD. In alternative embodiments, one or more of the surgical instruments and/or one or more of the implantable devices used during the surgery can include one or more IMU's, including, for example, accelerometers, magnetometers, and gyroscopes, similar, for example, to the OHMD. In some embodiments, one or more of the surgical instruments and/or one or more of the implantable devices used during the surgery can include one or more radiofrequency tags or markers or retroreflective markers and its position, location and/or orientation can be captured by a surgical navigation system. Optionally, the OHMD may also include one or more radiofrequency tags or markers or retroreflective markers and its position, location and/or orientation can also be captured by the surgical navigation system and cross-referenced to the patient specific marker or template and/or the one or more of the surgical instruments and/or one or more of the implantable devices used during the surgery. One or more of the surgical instruments and/or one or more of the implantable devices used during the surgery can also include light sources, such as lasers or LED's. A laser can be projected, for example, on a wall or a ceiling and the OHMD and the patient can be referenced in relationship to that. An LED attached to or integrated into the one or more of the surgical instruments and/or one or more of the implantable devices used during the surgery can be recognized, for example, by an image and/or video capture system integrated into or attached to or coupled to the OHMD. Optionally, multiple LED's can be used. Optionally, two or more of the multiple LED's emit light with different wavelength or color. The two or more LED's can be located in spatially defined locations and orientations, e.g. at a pre-defined or fixed distance and at one or more pre-defined or fixed angles. In this manner, the two or more LED's can be located by an image and/or video capture system integrated into, attached to or separate from the OHMD and their measured distance and/or angles as seen through the image and/or video capture system can, for example, be used to determine the distance and or orientation of the operator to the target anatomy, e.g. when the image and/or video capture system is close to the operator's eyes. By using LED's with different wavelength or color, the image and/or video capture system can differentiate between different LED's; when the LED's are arranged in a known spatial orientation, this information can be helpful for increasing the accuracy of the registration and/or for obtaining accurate distance, angle, direction and/or velocity measurements. The use of two or more LED's with different wavelength and color and measurements or registration as described above are applicable throughout the specification in all embodiments that incorporate the use of LED's or that are amenable to using LED's. Optionally, the patient specific marker or template and, optionally, one or more of the surgical instruments and/or one or more of the implantable devices used during the surgery can also include color markings, optionally with different geometric shapes or located or oriented at different, known locations and different, known angles, that can be used, for example, by an image and/or video capture system integrated into or attached to or coupled to an OHMD to recognize such patterns and, for example, to estimate distances and angles, e.g. from the surgical site to the OHMD, or distances and angles between two markings, two surgical instruments or medical device components.

Optionally, the patient specific marker or template and, optionally, one or more of the surgical instruments and/or one or more of the implantable devices used during the surgery can also include scales, e.g. of metric distances, inches, or angles that can be used, for example, by an image and/or video capture system integrated into or attached to or coupled to an OHMD to recognize such scales or angles and, for example, to estimate distances and angles, e.g. from the surgical site to the OHMD, or distances and angles between two surgical instruments or medical device components.

In some embodiments, the patient specific marker or template can be attached to the corresponding surface of the patient or to an adjacent surface of the patient, for example using tissue glue such as fibrin glue or a pin or a staple.

In some embodiments, the patient specific marker or template can include openings or guides, for example for accepting a surgical instrument or tool such as a bur, a saw, a reamer, a pin, a screw and any other instrument or tool known in the art.

By cross-referencing virtual patient data and live patient data with use of a patient specific marker or template and, optionally, one or more of the surgical instruments and/or one or more of the implantable devices used during the surgery and an OHMD, any coordinate information, distance information, axis information, functional information contained in the virtual patient data can now be available and used during the surgery.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Intraoperative Imaging In some embodiments, intraoperative imaging, for example using x-ray imaging or CT imaging and/or ultrasound imaging, can be performed. Virtual patient data obtained intraoperatively using intraoperative imaging can be used to register virtual patient data obtained preoperatively, for example using preoperative x-ray, ultrasound, CT or MRI imaging. The registration of preoperative and intraoperative virtual data of the patient and live data of the patient in a common coordinate system with one or more OHMDs can be performed, for example, by identifying and, optionally, marking corresponding landmarks, surfaces, object shapes, e.g. of a surgical site or target tissue, in the preoperative virtual data of the patient, the intraoperative virtual data of the patient, e.g. on electronic 2D or 3D images of one or more of the foregoing, and the live data of the patient. Virtual preoperative, virtual intraoperative and live data can include an osteophyte or bone spur or other bony anatomy or deformity. Virtual and physical surgical instruments and implant components can also be registered in the common coordinate system.

This embodiment can be advantageous when the amount of information obtained with intraoperative imaging is, for example, anatomically or in other ways more limited than the amount of information available with preoperative imaging or vice versa.

For example, intraoperative imaging may be performed using x-ray imaging, which is commonly only two-dimensional in nature. X-ray imaging can be augmented through image acquisition in more than one plane, e.g. orthogonal planes or one or more planes separated by a defined angle. Intraoperative x-ray images can be used to identify certain landmarks or shapes that can then be registered to preoperative imaging and/or live data of the patient during surgery. Preoperative imaging can, optionally, include 3D image data, for example obtained with CT or MRI. Acquisition of intraoperative images in multiple planes can be helpful to more accurately define the location of certain landmarks, contours or shapes intended for use in a registration of preoperative virtual data, intraoperative virtual data and live data of the patient. For purposes of clarification, intraoperative virtual data of the patient can be intraoperative images of the patient in 2D or 3D.

Optionally, the distance of the x-ray tube from the patient resulting in x-ray magnification can be factored into any registration in order to improve the accuracy of the registration of virtual preoperative data of the patient and virtual intraoperative data of the patient or live data of the patient. The intraoperative x-ray images can then be registered and, optionally, superimposed onto the preoperative data of the patient or the live data of the patient in the projection by the OHMD. The intraoperative virtual data of the patient can be registered to the live data of the patient, for example by touching the corresponding anatomic landmarks with a pointing device or a needle or a pin inserted through the skin and by cross-referencing the location of the tip of the live data pointing device with the intraoperative virtual data of the patient. In this manner, any one of preoperative virtual data of the patient, intraoperative virtual data of the patient, and live data of the patient and combinations thereof can be co-registered. Two or three of these data sets, preoperative virtual data of the patient, intraoperative virtual data of the patient, and live data of the patient, can optionally be seen in the OHMD. However, in many embodiments, intraoperative imaging may only be used for enhancing the accuracy of the registration of preoperative virtual data of the patient and live data of the patient and, for example, preoperative virtual data of the patient and/or a medical device intended for placement in a surgical site will be displayed by the OHMD together with the view of the live data of the patient or the surgical site.

In some embodiments, the registration of virtual patient data and live patient data using the techniques described herein can be repeated after one or more surgical steps have been performed and, optionally, intraoperative imaging can be repeated. In this case, the surgically altered tissue or tissue surface or tissue contour or tissue perimeter or tissue volume or other tissue features in the live patient or in the intraoperative repeat imaging data of the patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Skin Markers or Soft-Tissue Markers In some embodiments, skin markers and soft-tissue markers, calibration or registration phantoms or devices can be used for registering preoperative virtual data, optionally intraoperative virtual data such as data obtained from intraoperative x-ray imaging, and live data seen through the OHMD in a common coordinate system with one or more OHMD's. Virtual and physical surgical instruments and implant components can also be registered in the common coordinate system. For example, an initial registration between preoperative virtual data and live data of the patient can happen at the beginning of the procedure. The initial registration can, for example, be performed using corresponding anatomic landmarks, surfaces or shapes, or using intraoperative imaging resulting in intraoperative virtual data or any of the other embodiments described herein. The registration can be used, for example, to place the virtual data and the live data and the optical head mounted display into a common coordinate system. Skin markers, calibration or registration phantoms or devices can then be applied. Virtual and physical surgical instruments and implant components can also be registered in the common coordinate system. Alternatively, or in addition, soft-tissue markers, calibration or registration phantoms or devices can be applied. Typically, more than one, such as two, three, four or more skin markers and soft-tissue markers, calibration or registration phantoms or devices will be applied. For clarity, the terms implantable markers, attachable markers, skin markers, soft-tissue markers, calibration or registration phantoms or devices as used through the application can include optical markers, e.g. optical markers with different geometric shapes or patterns, with QR codes, with bar codes, with alphanumeric codes. Skin markers and soft-tissue markers, calibration or registration phantoms or devices can, for example, be applied to the skin or the soft-tissue using a form of tissue compatible adhesive, including fibrin glue and the like. In some embodiments, one, two, three, four or more skin markers and soft-tissue markers, calibration or registration phantoms or devices can be included in a surgical drape or dressing or a transparent film applied to the skin prior to the procedure. The skin markers and soft-tissue markers, calibration or registration phantoms or devices can then be registered in the live data and cross-referenced to virtual data. The skin markers and soft-tissue markers, calibration or registration phantoms or devices can subsequently be used, for example, when the surgical site is altered and the landmarks, surface or shape that was used for the initial registration of virtual and live data have been altered or removed and cannot be used or cannot be used reliably for maintaining registration between virtual data and live data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

Registration of Virtual Patient Data and Live Patient Data Using Calibration or Registration Phantoms With Defined Dimensions or Shapes In some embodiments, calibration or registration phantoms with defined dimensions or shapes can be used to perform the registration of virtual data of the patient and live data of the patient. The calibration or registration phantoms can be of primarily two-dimensional or three-dimensional nature. For example, a calibration or registration phantom can be arranged or located primarily in a single plane. Other calibration phantoms can be located in multiple planes, thereby creating the opportunity for registration using more than one planes. For clarity, the terms calibration or registration phantoms, implantable markers, attachable markers, skin markers, soft-tissue markers, or devices as used through the application can include optical markers, e.g. optical markers with different geometric shapes or patterns, with QR codes, with bar codes, with alphanumeric codes.

Such calibration or registration phantoms can be, for example, attached to the patient's skin. The calibration or registration phantom can be integrated or attached to a surgical drape. The calibration or registration phantom can be attached to the patient's tissue. The calibration or registration phantom can be part of or a component of a medical device. The part or component of the medical device will typically have known dimensions. By using calibration or registration phantoms, as well as other markers, the live data of a patient and the virtual data of the patient can be registered in a common coordinate system, for example with one or more OHMDs. Virtual and physical surgical instruments and implant components can also be registered in the common coordinate system.

In some embodiments, the calibration or registration phantom includes known dimensions, angles or geometric 2D or 3D shapes. For example, the calibration or registration phantom can include structures such as circles, ovoids, ellipses, squares, rectangles, complex 2D geometries, 2D geometries with one or more defined distances, 2D geometries with one or more defined angles spheres, egg shaped structures, cylinders, cubes, cuboids, complex 3D geometries or shapes, 3D geometries with one or more defined distances, 3D geometries with one or more defined angles, 3D geometries with one or more defined surfaces Optionally, the calibration or registration phantoms can be radiopaque if pre-operative or intra-operative imaging is performed using an imaging modality with ionizing radiation, e.g. x-ray imaging, fluoroscopy in 2D or 3D, CT, cone beam CT etc.

In some embodiments, the calibration or registration phantom can be MRI visible or nuclear scintigraphy or SPECT visible or PET visible, for example by including portions or containers in the phantom containing Gadolinium-DTPA doped or radionuclide doped or PET isotope emitting water. Any contrast agent or MRI or nuclear scintigraphy or SPECT or PET visible agent known in the art can be used in this fashion.

In some embodiments, the calibration or registration phantom includes retroreflective markers or features which facilitate detection by an image and/or video capture system. The calibration or registration phantom can also be highlighted against the patient's tissue(s) including blood as well as surgical drapes through a choice of select colors, e.g. a bright green, bright blue, bright yellow, bright pink etc. Color combinations are possible. Any color or color combination known in the art can be used.

The calibration or registration phantom can optionally include LED's, optionally battery powered. More than one LED can be used. The LED's can emit a light of a known color, hue and intensity, preferably selected to be readily identifiable by the image and/or video capture system and any segmentation techniques or algorithms used for detecting the location, position and/or orientation of the LED's.

The LED's can be arranged in a spatially defined way, with two or more LED's arranged at a defined distance or distances, at a defined angle or angles, in substantially the same plane or different planes. If LED's are arranged in different planes, the spatial orientation of the planes is for example known and defined.

When two or more LED's are used, the two or more LED's can emit light utilizing different wavelengths, colors, intensity and, optionally also, blinking frequency. In this manner, an image and/or video capture system integrated into, attached to or separate from the OHMD can recognize each different LED based on one or more of their different wavelength, color, intensity and/or blinking frequency. When the LED's are arrange in a spatially defined and known manner, e.g. using known distances or angles within the same plane or different planes, the identification of each individual LED and the change in distances and angles measured by the image and/or video capture system can be used to determine the position, location and/or orientation of the OHMD and/or the operator's head (e.g. if the image and/or video capture system is integrated into the OHMD or attached to the OHMD) or, in some applications, the movement of the patient or body part to which the calibration or registration phantom and LED's are attached.

LED's used throughout the specification can be re-useable. LED's used throughout the specification can also be disposable, optionally with integrated, disposable battery cells/batteries. LED's can be operated utilizing wires, e.g. connected to a power supply and/or connected to a wired user interface or control unit. LED's can be wireless, e.g. without attached power supply (e.g. battery operated) and/or connected to a wireless (e.g. WiFi, Bluetooth) control unit.

LED's can be connected and/or organized in LIF networks. One or more LIF networks can be used, for example, to transmit or receive data or information back and forth from the one or more OHMDs to a control unit or computer, optionally with a user interface. In this example, LED's participating or connected in the one or more LIF networks can be integrated into or attached to the OHMD. LED's participating or connected in the one or more LIF networks can be attached to or, when applicable, integrated into any location or site on the surgeon or interventionalist, the OR staff, the patient, the surgical site, one or more OHMDs, one or more navigation systems, one or more navigation markers, e.g. retroreflective markers, infrared markers, RF markers; one or more optical markers, calibration or registration phantoms.

An LIF network can also be used to transmit or receive data or information about the spatial position, orientation, direction of movement, speed of movement etc. of individual LED's. The same LED's whose relative position, orientation, direction of movement, speed of movement, e.g. in relationship to the surgeon or interventionalist or the patient or the surgical site, is being measured, e.g. using an image and/or video capture system, can be used to transmit or receive information in the LIF network, optionally using different wavelengths, color, frequency, blinking patterns depending on the type of data being transmitted. The information can be about the position, orientation, direction of movement, speed of movement of individual LED's. The information can also be data that are being transmitted or received by the OHMD. The information can be the information or data that are being displayed by the OHMD. The information can be information generated or received by navigation markers, RF markers. The information can be information captured by one or more image and/or video capture systems or cameras. 1, 2, 3, 4 or more LED's can be connected to or attached to the patient, the target anatomy, the surgical site, the surgical site after a first, second or more surgical alterations, for example executed using a virtual surgical plan, the OHMD, a second, third and/or additional OHMDs, for example worn by a second surgeon or interventionalist, a scrub nurse, other OR personnel, the hand, forearm, upper arm and or other body parts of the surgeon or interventionalist/operator.

The relative position, orientation, movement, direction of movement, velocity of movement of each LED can be determined, for example using one or more image and/or video capture systems, e.g. integrated into, attached to or separate from the one or more OHMDs, e.g. when the one or more LED's emit light utilizing different wavelengths, colors, intensity and, optionally also, blinking frequency.

The calibration or registration phantom can optionally include one or more lasers, optionally battery powered. More than one laser can be used. The laser can emit a light of a known color, hue and intensity, for example selected to be readily identifiable by the image and/or video capture system and any segmentation techniques or algorithms used for detecting the location, position and/or orientation of the laser.

The laser can be arranged in a spatially defined way, with two or more lasers arranged at a defined distance or distances, at a defined angle or angles, in substantially the same plane or different planes. If lasers are arranged in different planes, the spatial orientation of the planes can be known and defined.

The calibration or registration phantom can optionally include radiofrequency (RF) transmitters, optionally battery powered. More than one RF transmitter can be used. The RF transmitters can transmit a signal or signals selected to be readily identifiable by an RF receiver system used for detecting the location, position and/or orientation of the RF transmitters. One or more RF transmitters can transmit signals with different frequency and intensity, thereby permitting differentiation of the different RF transmitters by the RF receiver system.

The RF transmitters can be arranged in a spatially defined way, with two or more RF transmitters arranged at a defined distance or distances, at a defined angle or angles, in substantially the same plane or different planes. If RF transmitters are arranged in different planes, the spatial orientation of the planes is can be known and defined.

The calibration or registration phantom can optionally include ultrasound (US) transmitters, optionally battery powered. More than one US transmitter can be used. The US transmitters can transmit a signal or signals selected to be readily identifiable by an US receiver or transducer system used for detecting the location, position and/or orientation of the US transmitters. One or more US transmitters can transmit signal with different frequency and intensity, thereby permitting differentiation of the different US transmitters by the US receiver or transducer system.

The US transmitters can be arranged in a spatially defined way, with two or more US transmitters arranged at a defined distance or distances, at a defined angle or angles, in substantially the same plane or different planes. If US transmitters are arranged in different planes, the spatial orientation of the planes is can be known and defined.

Calibration phantoms or registration phantoms can be used for pre-operative imaging and/or for intraoperative imaging and/or image capture of live data, for example using an image and/or video capture system attached to or integrated into the OHMD or coupled to the OHMD or separate from the OHMD. Virtual preoperative, virtual intraoperative and live data can include an osteophyte or bone spur or other bony anatomy or deformity.

If the same calibration or registration phantom is used for pre-operative imaging and for intra-operative imaging, optionally, the imaging can be performed using the same imaging modality, e.g. x-ray imaging, and, for example, using the same orientation of the patient in relationship to the x-ray source and the detector system and, for example using the same distance of the patient in relationship to the x-ray source and the detector system. Using this approach, the anatomic structures visualized on the pre-operative imaging and intra-operative imaging can be superimposed and registered, optionally in the same coordinate system.

In the event, the calibration or registration phantom has been positioned differently on the patient for the pre-operative imaging and for the intraoperative imaging data acquisition, the difference in location or position or coordinates can be determined using the co-registration of the anatomic data visualized on the pre-operative imaging and intra-operative imaging. An adjustment for the difference in phantom location from the pre-operative to the intraoperative data can be performed; this adjustment can optionally be defined as a phantom offset between pre-operative and intra-operative data. Virtual preoperative, virtual intraoperative and live data can include an osteophyte or bone spur or other bony anatomy or deformity.

As an alternative to the anatomic registration from the anatomic structures visualized on the pre-operative imaging and intra-operative imaging, the registration between pre-operative imaging data and intra-operative live data visualized through the OHMD or an attached, integrated or separate image and/or video capture system can be performed alternatively now using the calibration or registration phantom as visualized or as identified optically during the surgery, for example using the phantom offset between pre-operative and intra-operative data.

In general, the initial registration of virtual data and live data is possible using any of the techniques described herein, e.g. using anatomic features, anatomic landmarks, intraoperative imaging etc. Then co-registration of the calibration or registration phantom, e.g. in the same coordinate system, can be performed. If initial registration fails during the surgical procedure, registration can be maintained using the calibration or registration phantom. For this purpose, the position, location, orientation and/or alignment of the calibration or registration phantom will be continuously or intermittently monitored using an image and/or video capture system, which can be integrated into or attached to the OHMD or coupled to the OHMD or separate from the OHMD.

In some embodiments, the preoperative imaging can entail a cross-sectional imaging modality, e.g. computed tomography, which can optionally generate 3D data of the patient, e.g. in the form of a spiral or a helical CT scan and, optionally, a 3D reconstruction. The 3D data of the patient, e.g. the spiral or helical CT scan or 3D reconstruction, can be re-projected into a 2D image, creating an x-ray like transmission image of the patient, e.g. of the bony structures of the patient including, but not limited to an osteophyte or bone spur or other bony anatomy or deformity. Optionally, this 2D re-projection of the 3D data, e.g. CT data, can be performed using the same plane or projection or view angle and, for example, the same or similar magnification as can be used subsequently during surgery with an intraoperative x-ray imaging test. The film-focus and, optionally, object distance of the x-ray system used for the intraoperative imaging part can be known at the time of the re-projection of the preoperative 3D data, so that the magnification of the patient or anatomic data resulting for a given intraoperative film-focus and optionally object distance will be matched or reflected in the re-projected pre-operative data. If the film-focus and, optionally, object distance of the x-ray system used for the intraoperative imaging part is not known at the time of the re-projection of the preoperative 3D data, the magnification of the re-projected data can be adjusted when they are visualized with and optionally superimposed onto the 2D intraoperative imaging data of the patient or anatomic data resulting for a given intraoperative film-focus and optionally object distance so that the magnification of both re-projected and intraoperative imaging data will be matched or substantially similar. Such matching in magnification can be achieved, for example, by aligning certain features or anatomic landmarks or pathologic tissues including an osteophyte or bone spur or other bony anatomy or deformity in the pre-operative re-projected data with the intraoperative data and adjusting the magnification until the feature or landmarks are substantially superimposed or substantially matching. With this approach, pre-operative imaging data can use the benefit of 3D data including, for example, more accurate three-dimensional placement of an implant component. Similarly, certain anatomic landmarks or features can be detected and utilized for surgical planning in the 3D data set. When the 3D data are then re-projected into a 2D re-projection or view, anatomic landmarks, features or data or pathologic data can be readily matched up or aligned with corresponding anatomic landmarks, features or data or pathologic data in the corresponding portions of the intraoperative 2D imaging study, e.g. intraoperative x-rays. Thus, while different 3D preoperative and 2D intraoperative imaging modalities can be used, 2D re-projection allows for cross-referencing and, optionally, co-registration of the 2D and 3D data sets. Any 2D and 3D imaging modality known in the art can be used in this manner.

In additional embodiments, the calibration/registration phantom can be used

1.) To estimate distance, position, orientation of OHMD from the patient, for primary or back-up registration, for example used in conjunction with an image and/or video capture system integrated into, attached to or coupled to or separate from the OHMD 2.) To estimate distance, position, orientation of target tissue or surgical site underneath the patient's skin, e.g. after cross-registration with pre-operative and/or intra-operative imaging data 3.) To estimate the path of a surgical instrument or to estimate the location of a desired implantation site for a medical device or implant or transplant 4.) To update a surgical plan The calibration or registration phantom can be used in physical time mode, using physical time registration, for example using an image and/or video capture system integrated into, attached to, coupled to, or separate from the OHMD, which can optionally operate in physical time mode. Physical time mode can, for example, mean that image capture is performed with more than 5 frames/sec, 10 frames/sec, 15 frames/sec, 20 frames/sec, 30 frames/sec etc.

If images generated with the image and/or video capture system are segmented or, for example, image processing or pattern recognition is performed, this can optionally be performed on each frame generated with the image and/or video capture system.

Alternatively, segmentation or image processing or pattern recognition can be performed on a subset of the image frames captured with the image and/or video capture system. Segmentation, image processing or pattern recognition data can be averaged between frames. The foregoing embodiments are applicable to all embodiments in this specification that utilize image capture.

The calibration or registration phantom can be used in non-physical time mode, e.g. an intermittent mode, for example using an image and/or video capture system integrated into, attached to, coupled to, or separate from the OHMD, which can optionally operate in intermittent mode. Intermittent mode use of the calibration or registration phantom can be performed, for example, by using a timer or timing device, wherein image capture and registration is performed every 10 seconds, 8 seconds, 5 seconds, 3 seconds, 2 seconds, 1 second etc.

In some embodiments, real-time and intermittent registration using the calibration or registration phantom will be selected or designed so that the data generated will for example not exceed the temporal resolution of the image and/or video capture system and/or the temporal resolution of the segmentation or image processing or pattern recognition used for the registration.

In any of the foregoing embodiments, the accuracy of registration can optionally be improved by using multiple registration points, patterns, planes or surfaces. In general, the accuracy of registration will improve with an increasing number of registration points, patterns, planes or surfaces. These may, in some embodiments, not exceed the spatial resolution of the image and/or video capture system. In some embodiments, these may exceed the spatial resolution of the image and/or video capture system. In that situation, optionally, down-sampling of data can be performed, e.g. by reducing the effective spatial resolution in one, two or three planes or by reducing the spatial resolution in select areas of the field of view seen through the OHMD or visualized in the virtual data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

To Estimate Distance, Position, Orientation of OHMD from the Patient

If registration of virtual patient data and live patient data has occurred using any of the techniques or techniques described in this specification and if the calibration or registration phantom is also registered in relationship to the live patient data, the calibration or registration phantom can be used to maintain registration, for example on an intermittent or a real-time basis, including while the surgeon or interventionalist or operator moves his or her head or body. The calibration or registration phantom can, for example, not be moved during the surgery. If the calibration or registration phantom needs to be moved, it may optionally be re-registered in relationship to any live patient data, virtual patient data, pre-operative data and intra-operative data.

In this and related embodiments, the calibration or registration phantom will be identified with regard to its location, position, orientation, alignment, surfaces or shape using an image and/or video capture system and, optionally, segmentation, image processing or pattern recognition and any other techniques known in the art for identifying an object in image data. The image and/or video capture system can be integrated into or attached to the OHMD. The image and/or video capture system can be coupled to or separate from the OHMD. The image and/or video capture system will be used to determine the location, position, orientation, alignment, surfaces or shape of the calibration or registration phantom in relationship to the patient, the operator and/or the OHMD.

Any other techniques known in the art, including as described in this specification, that can be used to determine the location, position, orientation, alignment, surfaces or shape of the calibration or registration phantom in relationship to the patient, the operator and/or the OHMD, can be used, including, but not limited to surgical navigation including optical or RF tracking, laser based distance measurements and the like.

The calibration or registration phantom can be used for primary or back-up registration. Optionally, synchronized registration can be used, wherein, for example, more than one technique of registration is used simultaneously to maintain registration between virtual patient data and live patient data, for example by simultaneously maintaining registration between virtual patient data and live patient data using one or more calibration or registration phantoms in conjunction with maintaining registration using corresponding anatomic landmarks or surfaces between virtual patient data and live patient data. If synchronized registration is used, optionally, rules can be applied to resolve potential conflicts between a first and a second registration technique for registering virtual and live patient data.

For example, with an image and/or video capture system integrated into or attached to the OHMD or coupled to the OHMD, any change in the position, location or orientation of the surgeon or interventionalist's or operator's head or body will result in a change in the perspective view and visualized size and/or shape of the calibration or registration phantom. The change in perspective view and visualized size and/or shape of the calibration or registration phantom can be measured and can be used to determine the change in position, location or orientation of the surgeon or interventionalist's or operator's head or body, which can then be used to maintain registration between the virtual patient data and the live patient data, by moving the virtual patient data into a position, location, orientation and/or alignment that ensures that even with the new position location or orientation of the surgeon or interventionalist's or operator's head or body the registration is maintained and the virtual and the live patient data are, for example, substantially superimposed or matched where desired. Similarly, when more than one OHMD is used, e.g. one for the primary surgeon or interventionalist, a second OHMD for an assistant, a third OHMD for a resident, a fourth OHMD for a scrub nurse and a fifth OHMD for a visitor, with an image and/or video capture system integrated into or attached to each of the different OHMDs or coupled to each of the different OHMDs, any change in the position, location or orientation of the user's or viewer's head or body will result in a change in the perspective view and visualized size and/or shape of the calibration or registration phantom. The change in perspective view and visualized size and/or shape of the calibration or registration phantom can be measured and can be used to determine the change in position, location or orientation of the user's or viewer's head or body, which can then be used to maintain registration between the virtual patient data and the live patient data, by moving the virtual patient data into a position, location, orientation and/or alignment that ensures that even with the new position location or orientation of the user's or viewer's head or body the registration is maintained and the virtual and the live patient data are, for example, substantially superimposed or aligned or matched where desired, with substantially identical view angle of the virtual data of the patient seen by the viewer's left eye through the display of the OHMD unit and the live data of the patient seen by the viewer's left eye through the OHMD unit and substantially identical view angle of the virtual data of the patient seen by the viewer's right eye through the display of the OHMD unit and the live data of the patient seen by the viewer's right eye through the OHMD unit for each of the OHMD used.

In some embodiments, the calibration or registration phantom can be used to check the accuracy of an integrated or attached or coupled or separate image and/or video capture system.

In a further embodiment, the calibration or registration phantom can be used to calibrate an integrated or attached or coupled or separate image and/or video capture system.

In some embodiments, the calibration or registration phantom can be used to calibrate the IMU, e.g. for distance measurements, movement, distance to object, since calibration or registration phantom includes known geometries, e.g. known distances or angles.

Registration of Virtual Patient Data and Live Patient Data Accounting for Tissue Deformation In some embodiments, tissue deformation, a shape change or removal of tissue caused by the surgery or surgical instruments can be simulated in the virtual data. The resultant simulated virtual data can then be registered related to the live patient data, either before and/or after deformation, alteration of shape or removal of tissue of the live patient. The tissue deformation, shape change or removal of tissue caused by the surgery or surgical instruments can include the shape alteration or removal of one or more osteophytes or bone spurs or other bony anatomy or deformity. The virtual data of the patient and the live data of the patient can be registered in a common coordinate system, for example with one or more OHMDs. Virtual and physical surgical instruments and implant components can also be registered in the common coordinate system.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. Re-registration of live patient data and virtual patient data can be particularly helpful if the surgical alteration or surgical step has led to some tissue deformation. For example, the re-registration can be performed by matching, superimposing, and/or registering tissues that have not been performed by the surgical step or surgical alteration. Alternatively, the re-registration can be performed by matching, superimposing and/or registering deformed live patient data, e.g. from surgically deformed tissue, with virtual patient data that simulate the same tissue deformation after the virtual surgical step, e.g. an osteophyte or tissue removal.

Registration of Virtual Patient Data and Live Patient Data at Multiple Time Points, for Example at Different Stages of a Surgical Procedure In some embodiments, registration of virtual patient data and live patient data can occur at multiple time points, for example during different phases of tissue removal or implantation of a medical device. For select or each time point, e.g. for select or all stages of the surgical procedure, the live data of the patient and the virtual data of the patient can be registered in a common coordinate system, for example with one or more OHMDs. Virtual and physical surgical instruments can also be registered in the common coordinate system.

Registration of virtual patient data and live patient data can be performed using, for example, the vascular shape prior to a procedure. The registration of virtual and live patient data can be repeated using different registration sites, surfaces or landmarks after tissue has been removed, or after a contrast medium, e.g. an x-ray dye has been injected. The registration can now occur to a newly created landmark, created by the surgical procedure, or, for example, a newly created surface, e.g. created by the surgical procedure. Thus, some aspects of the invention allow for multiple time point registration of virtual patient data and live patient data, for example by registered virtual patient data to the live patient data prior to surgical alteration and after one or more surgical alterations. In this manner, it is possible to re-register multiple times as surgical field changes.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using CAD Files or Data or 3D Files or Data, e.g. of a Medical Device In some embodiments, a CAD file or CAD data of a medical device can be displayed by the OHMD and superimposed on live data of the patient. The CAD file or CAD data can be a medical device intended for use or implantation during the surgical procedure. Any type of CAD file or CAD data or any type of 3D file or 3D data of a medical device, a surgical instrument or an implantable device can be superimposed and registered in relationship to the live data of the patient including normal anatomy or pathologic tissue, e.g. one or more osteophytes or bone spurs or other bony anatomy or deformity or soft-tissue or neoplastic tissue or abnormality in a common coordinate system, for example with one or more OHMDs. Physical surgical instruments and implant components can also be registered in the common coordinate system.

Medical devices can include non-biologic as well as biologic devices, e.g. tissue scaffolds, cells, cell matrices etc. that can be implanted in a human body.

In some embodiments, multiple CAD files and/or 3D files of virtual data can be superimposed onto the live data of the patient. For example, CAD files can be CAD files of a medical device available in different sizes or shapes. Virtual 2D or 3D data of the patient, for example obtained from a preoperative imaging test, can be superimposed onto live data of the patient, e.g. a surgical site. The surgeon or interventionalist can then optionally introduce a 3D CAD file of a medical device into the display by the OHMD. The surgeon or interventionalist can check the size or shape of the medical device in relationship to the virtual 2D or 3D data of the patient and/or the live data of the patient. If the surgeon or interventionalist is not satisfied with the projected size or shape of the medical device in relationship to the virtual 2D or 3D data of the patient and/or the live data of the patient, the surgeon or interventionalist can select a different CAD file of a medical device with a different size and/or shape, project the CAD file optionally onto the virtual 2D or 3D data of the patient and the live data of the patient in the OHMD display and repeat the process as many times as needed until the surgeon or interventionalist is satisfied with the resultant size or shape of the selected medical device in relationship to the virtual 2D or 3D data of the patient and/or the live data of the patient.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, CAD files simulating the virtual surgical step or surgical alteration in the virtual patient data can be matched, superimposed or registered with live patient data after the physical surgical step or surgical alteration in the live patient. In this manner, live and virtual data can be re-registered after the surgical step or surgical alteration.

Registration of Virtual Patient Data and Live Patient Data Using Non-Anatomic Data Registration of virtual data of the patient and live data of the patient can be performed using data other than anatomic or pathologic structures. Registration can be performed, for example, based on motion data, kinematic data in the live data which can then be registered to an estimate or simulated center of rotation in the virtual data of the patient). Registration can be performed using metabolic data, for example using an area of high 18 FDG-PET uptake in a PET scan or PET-MRI or PET CT, which can be, for example matched to an area of increased body temperature in a target surgical site. Registration can be performed using functional data, e.g. using functional MRI studies. Virtual data and live data of the patient can be registered in a common coordinate system, for example with one or more OHMDs. Virtual and physical surgical instruments and implant components can also be registered in the common coordinate system.

Optionally, different types of data, e.g. anatomic, motion, kinematic, metabolic, functional, temperature and/or vascular flow data can be used alone or in combination for registered virtual and live data of the patient.

The registration of virtual patient data and live patient data using the techniques described herein can be repeated after one or more surgical steps have been performed using non-anatomic data. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, optionally using non-anatomic data. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient data and Live Patient Data After Performing One or More Surgical Alterations to the Tissue or the Surgical Site In some embodiments, the registration of virtual patient data and live patient data using the techniques described herein can be repeated after one or more surgical steps have been performed and virtual data and live data of the patient can be registered in a common coordinate system after select steps or each surgical step or tissue alteration, for example with one or more OHMD's. Virtual and physical surgical instruments and implant components can also be registered in the common coordinate system after select steps or each surgical step or tissue alteration. The surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The matching, superimposing and/or registering of the live data of the patient and the virtual data of the patient after the surgical tissue alteration can be manual, semi-automatic or automatic using information about the surgically altered tissue or tissue surface or tissue contour or tissue perimeter or tissue volume or other tissue features. Automated re-registration can, for example, be performed using an image and/or video capture system integrated into, attached to or separate from the OHMD which can capture information about the surgically altered tissue or tissue surface or tissue contour or tissue perimeter or tissue volume or other tissue features in the live patient data after the surgical alteration and compare the information to information in the virtual data of the patient, e.g. for the virtual data after performing the comparable step in a virtual surgical plan.

The surgical alteration or surgical steps can include, but are not limited to the listed in the following: Exemplary surgical alterations or steps applied to various patient tissues, e.g. bone, skin, fat, organ tissue, e.g. liver, spleen, kidney, intestines, gallbladder, lung, heart, thyroid, brain etc.: Cutting, drilling, pinning, radiofrequency ablation, heat ablation, cryoablation, cauterization, tissue resection, tissue removal, resection of a neoplasm, fracture fixation, trauma repair, trauma reconstruction, soft-tissue repair, soft-tissue reconstruction, tissue grafting, placement of a registration marker or calibration phantom on the tissue surface or inside the tissue, placement of a surgical instrument, placement of a device or a component thereof, placement of a tissue graft, placement of a tissue matrix, placement of a transplant, placement of a catheter, e.g. an indwelling catheter, placement or injection of cells, e.g. stem cells, injection of a drug.

Optionally, the registration procedures described herein can be repeated after performing a surgical step. Optionally, the registration procedures described herein can be repeated after multiple surgical steps. Optionally, the registration procedures described herein can be repeated after each surgical step. Optionally, the registration procedures described herein can be repeated after major surgical steps. Optionally, the registration procedures described herein can be repeated when the surgeon or interventionalist wants to achieve high surgical accuracy. Optionally, the registration procedures described herein can be performed or repeated when the surgeon or interventionalist is concerned that the initial registration performed prior to the surgical step or surgical alteration was not accurate or is not accurate any longer or is affected by the surgical step or surgical alteration.

In some embodiments, the change on the patient's tissue induced by the surgical alteration or the surgical step can be known or estimated, for example as part of the virtual surgical plan using the virtual data of the patient. Surgical alterations and/or surgical steps applied to patient tissues can include any of the surgical alterations and/or surgical steps listed in the foregoing examples, although any alteration to a patient's tissue known in the art can be included. The alteration and/or the change induced on the patient's tissue by the surgical alteration or surgical step can be estimated, for example in the virtual surgical plan and/or the virtual data of the patient. Exemplary changes induced on the patient's tissue by the surgical alteration or surgical step are tabulated in Table 3, which is only exemplary in nature and in no way meant to be limiting:

TABLE 3: Exemplary changes induced on the patient's tissue by a surgical alteration or surgical step. These changes can be induced in the live patient. These changes can also be planned/intended or simulated, e.g. for projection by one or more OHMDs, e.g. in a virtual surgical plan.

Change in tissue surface area
Change in tissue volume
Change in tissue surface shape
Change in tissue surface topography
Change in tissue perimeter (e.g. from uncut to cut surface, or from cut surface 1 to cut surface 2)
Change in tissue surface roughness
Change in tissue surface texture
Change in tissue surface color
Change in tissue surface reflexivity (e.g. reflected light or ultrasound)
Change in tissue surface area with different color (e.g. color change induced by surgical alteration)
Change in tissue surface perimeter, e.g. cut vs. uncut tissue surface
Change in tissue temperature
Change in tissue elasticity
Change in tissue composition, e.g. fat content (e.g. marrow fat on a cut bone surface)

Any of the foregoing changes can include all of the tissue or only a portion of the tissue. The embodiments can be directed towards all of the tissue or only partial tissue or portions of the tissue.

Following initial registration of the live data of the patient with the virtual data of the patient using any of the techniques described in the specification or known in the art, a first or any subsequent surgical alteration or surgical step can be performed inducing changes to the patient's tissue. The surgical alteration or surgical step can be performed with optional guidance through the OHMD display, e.g. by displaying one or more of virtual surgical tool, virtual surgical instrument including a virtual surgical guide or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration.

Once a surgical alteration or surgical step has been performed or induced on a patient's tissue in the live patient, the physical changes induced or the resultant tissue appearance and/or tissue properties/characteristics can be determined in the live data of the patient/the live patient. The physical changes induced or the resultant tissue appearance and/or tissue properties/characteristics can be determined in the live data of the patient/the live patient using any technique known in the art for assessing tissue appearance, tissue properties and/or characteristics including, for example, area, volume, shape, topography, roughness, texture, color, reflexivity, area with different color, perimeter, temperature, elasticity, and/or composition. For example, an image and/or video capture system integrated into, attached to or separate from an OHMD can be used to assess one or more of an area, shape, topography, roughness, texture, color, reflexivity, area with different color, perimeter, temperature, elasticity, and/or composition of a surgically altered tissue. Tissue probes, e.g. temperature probes, elasticity probes, can be used to assess characteristics and/or properties of the surgically altered tissue. Mechanical probes, e.g. with one or more attached optical markers, LED's, infrared markers, retroreflective markers, RF markers, navigation markers and/or IMU's can be used to touch the tissue surface or perimeter and, for example, to circle a perimeter or to follow and assess a tissue topography of a surgically altered tissue.

Figure 4:
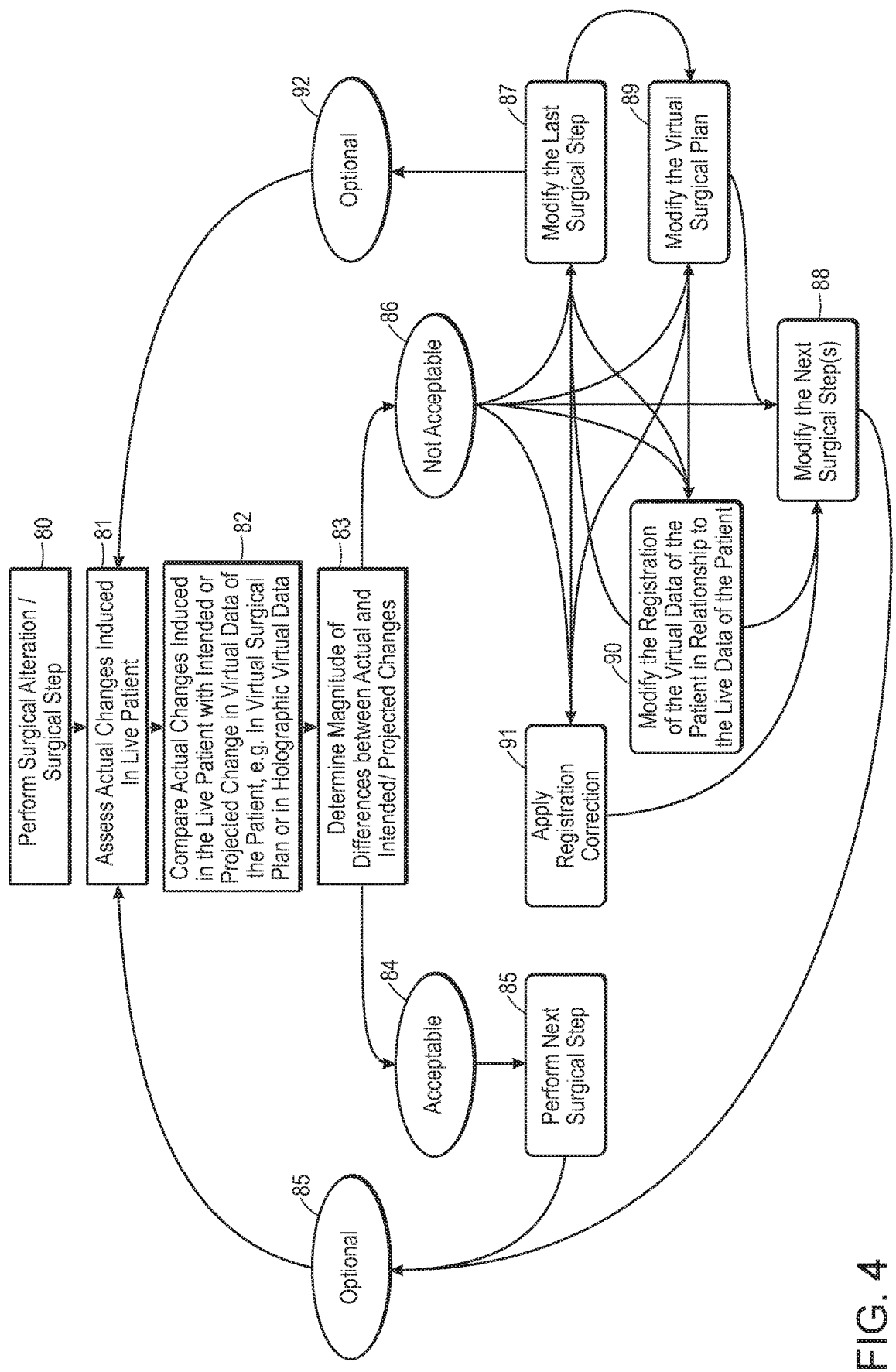
FIG. 4 is an illustrative flow chart showing different methods of addressing inaccuracies between the changes induced by a surgical step and the intended, projected or predetermined changes in the virtual data of the patient according to some embodiments of the present disclosure.

The physical appearance, properties and/or characteristics of the surgically altered tissue can be assessed using any of the foregoing techniques or any of the techniques described in the specification or known in the art. The physical appearance, properties and/or characteristics of the surgically altered tissue can optionally be compared to the estimated or intended change or post-alteration appearance, e.g. surface area, volume, shape, topography, properties and/or characteristics of the tissue in the virtual data of the patient, for example the virtual surgical plan. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed: If the differences are deemed to be insignificant, for example, if they fall below an, optionally predefined, threshold in distance or angular deviation, the surgical procedure and subsequent surgical steps can continue as originally planned, e.g. in the virtual surgical plan. If the differences are deemed to be significant, for example, if they fall above an, optionally predefined, threshold in distance or angular deviation, the surgeon or interventionalist or the operator can have several options. The process and the options are also shown in illustrative form in FIG. 4: The surgeon or interventionalist can perform a surgical step 80. The surgeon or interventionalist can then assess the actual changes induced in the live patient 81. The surgeon or interventionalist can compare the actual changes induced in the live patient with the predetermined changes in the virtual data of the patient, e.g. in a virtual surgical plan or in a virtual 3D display 82. The magnitude of the difference(s) between the actual and the predetermined changes can be determined 83. If they are acceptable 84, the surgeon or interventionalist can perform the next surgical step 85. Optionally 85, the steps 81, 82, 83 can be repeated for the next surgical step. If the difference(s) between the actual and the predetermined changes are not acceptable 86, the surgeon or interventionalist has several means of addressing the difference(s), modify the last surgical step 87, modify the next surgical step 88, modify the virtual surgical plan 89, modify the registration of the virtual data of the patient in relationship to the live data of the patient 90, or apply registration correction 91. After the last surgical step has been modified 87, optionally 92, the steps 81, 82, 83 can be repeated for the next surgical step.

A) Modify the Last Surgical Step so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification is more similar to and, optionally, more closely replicates the intended virtual appearance, virtual properties and/or virtual characteristics in the virtual data of the patient, e.g. a virtual surgical plan of the patient. This option can, for example, be chosen if the operator or surgeon or interventionalist is of the opinion that the last surgical step was subject to an inaccuracy, e.g. by a fluttering or deviating saw blade or a misaligned pin or a misaligned reamer or impactor or other problem, and should correct the inaccuracy. Once the modification has been completed, the surgeon or interventionalist or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or interventionalist or operator can optionally repeat option A, or revert to options B or C.

B) Modify the Next Surgical Step(s) so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification in the next surgical step(s) is more similar to and, optionally, more closely replicates the intended virtual appearance, virtual properties and/or virtual characteristics in the virtual data of the patient, e.g. a virtual surgical plan of the patient after the virtual modification in the next virtual surgical step(s). This option can, for example, be chosen if the operator or surgeon or interventionalist is of the opinion that the last surgical step was subject to an inaccuracy, e.g. by a fluttering or deviating saw blade or a misaligned pin or a misaligned reamer or impactor or other problem, and he or she should correct the inaccuracy in the next surgical step(s). Once the modification has been completed with the next surgical step(s), the surgeon or interventionalist or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or interventionalist or operator can optionally repeat option A and/or B and/or revert to options C and/or D and/or E.

C) Modify the Virtual Surgical Plan of the patient so that the virtual appearance, virtual properties and/or virtual characteristics (including, for example, shape, volume and dimensions, cut plane, perimeter or surface/surface area of a cut plane/tissue plane, drill depth, angle, rotation, implant site etc.) of the surgically altered tissue in the virtual data of the patient after the modification is/are more similar to and, optionally, more closely replicates the physical appearance, physical properties and/or physical characteristics in the physical live data of the patient after the physical surgical alteration. This option can, for example, be chosen if the operator or surgeon or interventionalist is of the opinion that the last surgical step was accurate or accounted for unexpected variations in tissue conditions that were not accounted for in the virtual surgical plan. If the modified surgical plan is modified in this manner, all subsequent virtual surgical steps can then be referenced off the last or preceding physical surgical step, thereby maintaining continuity of the procedure. The OHMD can then be used for projecting all or some of the subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration. The subsequent virtual surgical steps are thus modified to allow completion of the procedure and, optionally, placement of an implant or implant component or device or graft or transplant taking into account the one or more modified preceding physical surgical steps. Optionally, the modified subsequent virtual surgical steps can be further modified based on local tissue conditions/characteristics after the virtual or physical modification, for example, if subsequent surgical steps were to fall into a tissue void or would result in impairment of implant component placement.

D) Modify the Registration of the Virtual Data of the Patient in Relationship to the Live Data of the Patient. The operator or surgeon or interventionalist can optionally repeat the registration procedure using any of the techniques described in the specification or known in the art for registering the virtual data of the patient, including, for example the virtual surgical plan, in relationship to the live data of the patient after the physical surgical alteration. Once the virtual data of the patient and the live data of the patient after the surgical alteration have been re-registered, all subsequent virtual surgical steps displayed by the OHMD and any related virtual surgical plan can be referenced off the re-registration of the virtual and live data of the patient. For example, the OHMD can then be used after the re-registration for projecting all subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration.

E). Apply Registration Correction. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed and can be used to apply a coordinate correction, coordinate adjustment or coordinate transfer of registration of the virtual data of the patient, including, optionally, the virtual surgical plan, and the live data of the patient, e.g. for any subsequent surgical steps or surgical procedures. For example, the OHMD can then project/display all subsequent virtual surgical steps using the coordinate correction or adjustment or transfer, e.g. by projecting one or more of virtual surgical tool, virtual surgical instrument including virtual surgical guide or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration using the coordinate correction, adjustment and/or transfer.

Any combinations of the foregoing Options A, B, C, D and/or E are possible.

If an image and/or video capture system is used to measure/capture the physical changes, e.g. change in surface/surface area, perimeter, perimeter shape, and/or shape of the cut surface or otherwise modified or altered surface, the data/images captured by the image and/or video capture system can be corrected for any angular distortion or projection, for example if the camera(s) is/are positioned at an angle other than 90 degrees relative to the cut surface or otherwise modified or altered surface. Similarly, the physical changes measured by the image and/or video capture system, e.g. the size of the surface/surface area, perimeter, perimeter shape, and/or shape of the cut surface or otherwise modified or altered surface, can be corrected or adjusted for the distance between the camera or image and/or video capture system and the changed surface/surface area, perimeter, perimeter shape, and/or shape of the cut surface or otherwise modified or altered surface. The angle and/or the distance of the image and/or video capture system to the physical changes, e.g. surface/surface area, perimeter, perimeter shape, and/or shape of the cut surface or otherwise modified or altered surface, can be assessed, for example, using one or more RF markers, optical markers, navigation markers including, but not limited to, infrared markers, retroreflective markers, RF markers, LED's, and/or IMU's attached to the image and/or video capture system, and/or the OHMD, and/or the patient, and/or the cut, modified or altered surface.

If the physical position, alignment, orientation, surface, surface area, perimeter, perimeter shape, and/or shape of the cut surface differ from the virtually intended/projected position, alignment, orientation, surface, surface area, perimeter, perimeter shape, and/or shape of the cut surface, the software can, optionally, determine a virtually modified position, alignment, orientation, surface, surface area, perimeter, perimeter shape, and/or shape of the cut surface that would more closely resemble the physical position, alignment, orientation, surface, surface area, perimeter, perimeter shape, and/or shape of the cut surface. The difference in coordinates between the virtually modified position, alignment, orientation, surface, surface area, perimeter, perimeter shape, and/or shape of the cut surface and the physical position, alignment, orientation, surface, surface area, perimeter, perimeter shape, and/or shape of the cut surface can then be used to determine any coordinate correction, adjustment or transfer for subsequent virtual surgical steps. The coordinate correction, adjustment or transfer can then by applied to the OHMD displays, for example when the OHMD displays in any subsequent surgical steps one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration using the coordinate correction, adjustment and/or transfer.

If a tissue cut is performed, for example with a scalpel or a saw, the registration procedure can be repeated after the tissue cut has been placed. In this case, the cut tissue surface of the live patient or portions thereof or the perimeter of the cut tissue surface of the live patient or portions thereof or the surface area of the cut tissue surface of the live patient or portions thereof or the volume of the removed tissue of the live patient or portions thereof can be matched to or superimposed and/or registered with the corresponding cut tissue surface of the virtual data or portions thereof or the perimeter of the cut tissue surface of the virtual data or portions thereof or the surface area of the cut tissue surface of the virtual data or portions thereof or the volume of the removed tissue of the virtual data or portions thereof in the virtual surgical plan. Once an adequate match of the live and virtual cut surfaces has been obtained, registration can optionally be repeated.

If a tissue cut is performed, the registration procedure can be repeated after the tissue cut has been completed. In this case, the cut tissue surface of the live patient or portions thereof or the perimeter of the cut tissue surface of the live patient or portions thereof can be matched to or superimposed onto and/or registered with the corresponding cut tissue surface or portions thereof in the virtual surgical plan or the perimeter of the cut tissue surface in the virtual surgical plan or portions thereof. Once an adequate match of the live and virtual cut surfaces has been obtained, registration can optionally be repeated.

If a radiofrequency ablation, heat ablation, cryoablation, or cauterization is performed, the registration procedure can be repeated after the radiofrequency ablation, heat ablation, cryoablation, or cauterization has been performed. In this case, the ablated or cauterized tissue surface of the live patient or portions thereof or the perimeter of the ablated or cauterized tissue surface of the live patient or portions thereof or the surface area of the ablated or cauterized tissue surface of the live patient or portions thereof or the volume of the removed tissue of the live patient or portions thereof can be matched to or superimposed and/or registered with the corresponding ablated or cauterized tissue surface of the virtual data or portions thereof or the perimeter of the ablated or cauterized tissue surface of the virtual data or portions thereof or the surface area of the ablated or cauterized tissue surface of the virtual data or portions thereof or the volume of the removed tissue of the virtual data or portions thereof in the virtual surgical plan. Once an adequate match of the live and virtual ablated or cauterized surfaces has been obtained, registration can optionally be repeated. If a placement of a medical implant component, a trial implant, a tissue graft, a tissue matrix, a transplant, a catheter, a surgical instrument or an injection of cells or a drug is performed, the registration procedure can be repeated after the surgical step or surgical alteration has been performed. In this case, the altered tissue of the live patient or portions thereof, the altered tissue surface of the live patient or portions thereof, or the perimeter of the altered tissue surface of the live patient or portions thereof, or the surface area of the altered tissue surface of the live patient or portions thereof, or the volume of the removed tissue of the live patient or portions thereof can be matched to or superimposed and/or registered with the corresponding altered tissue of the virtual data or portions thereof, altered tissue surface of the virtual data or portions thereof, or the perimeter of the altered tissue surface of the virtual data or portions thereof, or the surface area of the altered tissue surface of the virtual data or portions thereof, or the volume of the removed tissue of the virtual data or portions thereof in the virtual surgical plan. Once an adequate match of the live and virtual altered tissue has been obtained, registration can optionally be repeated.

Libraries of Surgical Instruments

In some embodiments, the system includes libraries of surgical instruments for different surgical procedures. The concept of a virtual library of surgical instruments used in a virtual surgical plan and optionally displayed by an OHMD during the live surgery, e.g. superimposed onto the physical surgical instruments to provide positional, orientation or directional guidance of the physical surgical instrument according to the virtual and/or intended surgical plan, is applicable to any surgical procedure, e.g. cardiovascular procedures, thoracic or pulmonary procedures, neurological procedures, urological procedures, gynecological procedures, hepatic or other inner organ procedures, intestinal procedures and/or musculoskeletal procedures. Virtual and physical surgical instruments and implant components can be registered in a common coordinate system, for example with one or more OHMD's and live data of the patient; the OHMD can project or display a virtual representation of the virtual surgical instrument.

In some embodiments, a virtual library of surgical instruments can correspond to a physical library of surgical instruments during surgery. Optionally, only a few, select surgical instruments can be included in the virtual library of surgical instruments. These few select surgical instruments can, for example, be the ones used for the principal, key surgical steps, or select sub-steps. Alternatively, all surgical instruments used during the live surgery can be included in a virtual library of virtual surgical instruments.

The virtual library of virtual surgical instruments can include these instruments in various file formats. In some embodiments, CAD file formats can be used. In general, any type of surface representation, 2D or 3D shape representation 3D volume representation, 3D display and different file formats can be used in a virtual surgical plan, followed by optional display by the OHMD during surgery.

Any surgical instruments used in any other surgical procedure can be utilized in a virtual surgical plan and/or can be displayed by the OHMD.

All of the above surgical instruments can be provided in different sizes and/or diameters and/or widths and/or lengths and/or shapes and/or dimensions, for example based on the size or dimensions of the physical implant, implant component and/or medical device used.

Virtual Placement, Virtual Fitting/Selection of Good or Best Fitting Device, Determination of Preferred Virtual Orientation, Determination of Preferred Virtual Alignment, Determination and/or Selection of Preferred Virtual Anchor/Attachment/Fixation Member in the Live, Physical Surgical Site of the Patient An optical head mounted display can display or project virtual representations, stereoscopic or non-stereoscopic of one or more virtual implants, virtual implant components and/or virtual medical devices and virtual instruments with or without the use of pre-operative or intra-operative imaging. The surgical field can be seen by the surgeon or interventionalist using a see-through OHMD or, when using a virtual reality type OHMD, by imaging it with one or more cameras or video systems, optionally integrated into, attached to or separate from the OHMD, and by projecting the video stream or select or intermittent images with the OHMD. By displaying a virtual implant, virtual implant component and/or virtual medical device and/or virtual instrument projected over the surgical field, the virtual implant, virtual implant component and/or virtual medical device and/or virtual instrument can be placed into a desired position, for example, in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual placing or placement of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site. The surgeon or interventionalist can evaluate the fit of the virtual implant, virtual implant component and/or virtual medical device and/or virtual instrument and can visually select a good or best fitting virtual implant, virtual implant component and/or virtual medical device in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual fitting and/or selecting a good or best fitting virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon or interventionalist can evaluate the shape of a virtual implant, virtual implant component and/or virtual medical device and/or virtual instrument and can visually select the virtual implant, virtual implant component and/or virtual medical device with regard to its shape in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual evaluation of the shape of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon or interventionalist can also determine the preferred position and/or orientation and/or alignment of the virtual implant, virtual implant component and/or virtual medical device and/or virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance. The virtual determining of a preferred position and/or orientation and/or alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon or interventionalist can determine the preferred alignment of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance. The virtual aligning and/or virtual evaluation of the alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon or interventionalist can determine the preferred function of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site, and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more functional tests, which can include any of these parameters and the virtual implant, virtual implant component and/or virtual medical device and virtual instrument. The virtual determining of the preferred function of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site, and/or one or more functional tests, which can include any of these parameters and the virtual implant, virtual implant component and/or virtual medical device and virtual instrument.

The surgeon or interventionalist can determine and/or select a preferred virtual anchor, attachment or fixation member for the virtual implant, virtual implant component and/or virtual medical device and virtual instrument, in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance, for example when simultaneously projecting a registered and superimposed imaging study of the patient, e.g. an x-ray, an ultrasound, a CT, an MRI or a PET scan, e.g. for demonstrating underlying tissue such as bone and bone stock. The virtual determination and/or virtual selection of a preferred virtual anchor, attachment or fixation member of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, bone stock, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site. Table 4 shows non-limiting examples of select medical devices amenable to one or more of virtual placement, virtual fitting/selection of good or best fitting device, determination of preferred virtual orientation, determination of preferred virtual alignment, determination and/or selection of preferred virtual anchor/attachment/fixation member.

Table 4: Non-Limiting Examples of Select Medical Devices Amenable to One or More of Virtual Placement, Virtual Fitting/Selection of Good or Best Fitting Device, Evaluation of Virtual Shape with Selection of Device with Preferred Shape, Evaluation of Virtual Function with Selection of Device with Preferred Function, Determination of Preferred Virtual Orientation, Determination of Preferred Virtual Alignment, Determination and/or Selection of Preferred Virtual Anchor/Attachment/Fixation Member

TABLE 4

Non-Limiting Examples of Select Medical Devices Amenable to One or More of Virtual Placement, Virtual Fitting/Selection of Good or Best Fitting Devices, Evaluation of Virtual Shape with Selection of Device with Preferred Shape, Evaluation of Virtual Function with Selection of Device with Preffered Function, Determined of Preferred Virtual Orientation, Determination of Preferred Virtual Alignment, Determination and/or Selection of Preferred Virtual Anchor/Attachment/Fixation Member

|  | 1 Virtual placement of virtual device | 2 Evaluate virtual fit, select best fitting device | 3 Evaluate virtual shape, select device with preferred shape | 4 Evaluate virtual function, select device with preferred function | 5 Determine preferred virtual position | 6 Determine preferred virtual orientation | 7 Determine preferred virtual alignment | 8 Determine/ select preferred virtual anchor/ attachment |
|---|---|---|---|---|---|---|---|---|
| Biliary stent | ✓ | ✓ | ✓ | ✓ | ✓ | ✓ | ✓ | ✓ |
| Hepatic stent | ✓ | ✓ | ✓ | ✓ | ✓ | ✓ | ✓ | ✓ |
| Uretheral stent | ✓ | ✓ | ✓ | ✓ | ✓ | ✓ | ✓ | ✓ |
| Urethral stent | ✓ | ✓ | ✓ | ✓ | ✓ | ✓ | ✓ | ✓ |
| Other stents | ✓ | ✓ | ✓ | ✓ | ✓ | ✓ | ✓ | ✓ |
| Intravascular filter, e.g. vena cava filter | ✓ | ✓ | ✓ | ✓ | ✓ | ✓ | ✓ | ✓ |
| Cardiopulmonary bypass, including various components, e.g. connectors, clamps, other components | ✓ | ✓ | ✓ | ✓ | ✓ | ✓ | ✓ | ✓ |
| Wire | ✓ |  |  |  | ✓ | ✓ | ✓ | ✓ |
| Shunt/tube, e.g. vascular, lymphatic, biliary, hepatic, central nervous system, cerebrospinal fluid, other | ✓ | ✓ | ✓ | ✓ | ✓ | ✓ | ✓ | ✓ |
| Surgical mesh, e.g. for hernia repair, vaginal/uterine prolapse, urinary incontinence | ✓ | ✓ | ✓ | ✓ | ✓ | ✓ | ✓ | ✓ |
| Seeds, e.g. metal, radiation, isotope seeds | ✓ | ✓ | ✓ | ✓ | ✓ | ✓ | ✓ | ✓ |
| Biliary catheter | ✓ |  | ✓ | ✓ | ✓ | ✓ | ✓ |  |
| Vascular catheter | ✓ |  | ✓ | ✓ | ✓ | ✓ | ✓ |  |
| Clip | ✓ | ✓ | ✓ | ✓ | ✓ | ✓ | ✓ | ✓ |
| Staple | ✓ | ✓ | ✓ | ✓ | ✓ | ✓ | ✓ | ✓ |
| Spinal cord stimulator | ✓ | ✓ | ✓ | ✓ | ✓ | ✓ | ✓ | ✓ |
| Peripheral nerve stimulator | ✓ | ✓ | ✓ | ✓ | ✓ | ✓ | ✓ | ✓ |
| Arteriovenous shunt device | ✓ | ✓ | ✓ | ✓ | ✓ | ✓ | ✓ | ✓ |
| Arteriovenous fistula device | ✓ | ✓ | ✓ | ✓ | ✓ | ✓ | ✓ | ✓ |
| Vascular port | ✓ | ✓ | ✓ | ✓ | ✓ | ✓ | ✓ |  |
| Intraventricular port | ✓ | ✓ | ✓ | ✓ | ✓ | ✓ | ✓ |  |
| Vagus nerve stimulator | ✓ |  | ✓ | ✓ | ✓ | ✓ | ✓ | ✓ |
| Magnetic/thermal rods for prostate | ✓ |  | ✓ | ✓ | ✓ | ✓ | ✓ | ✓ |
| Tissue anchor | ✓ | ✓ | ✓ | ✓ | ✓ | ✓ | ✓ | ✓ |
| Implantable radiofrequency transponder system | ✓ |  | ✓ | ✓ | ✓ | ✓ | ✓ | ✓ |
| Endoscopic suture plication system | ✓ |  | ✓ | ✓ | ✓ | ✓ | ✓ | ✓ |
| Hypertension electrical nerve stimulation system | ✓ |  | ✓ | ✓ | ✓ | ✓ | ✓ | ✓ |
| Tissue scaffold | ✓ | ✓ | ✓ | ✓ | ✓ | ✓ | ✓ | ✓ |
| Mesh for chest wall repair | ✓ | ✓ | ✓ | ✓ | ✓ | ✓ | ✓ | ✓ |
| Pacemaker | ✓ |  | ✓ | ✓ | ✓ | ✓ | ✓ |  |
| Pacemaker lead, including tip | ✓ |  | ✓ | ✓ | ✓ | ✓ |  | ✓ |
| Vascular graft | ✓ | ✓ | ✓ | ✓ | ✓ | ✓ | ✓ | ✓ |
| Vascular stent | ✓ | ✓ | ✓ | ✓ | ✓ | ✓ | ✓ | ✓ |
| Prosthetic heart valve, e.g. mitral, tricuspid, aortic, pulmonary valve | ✓ | ✓ | ✓ | ✓ | ✓ | ✓ | ✓ | ✓ |
| Allograft or autograft heart valve, e.g. mitral, tricuspid, aortic, pulmonary valve | ✓ | ✓ | ✓ | ✓ | ✓ | ✓ | ✓ | ✓ |

TABLE 4-continued

Non-Limiting Examples of Select Medical Devices Amenable to One or More of Virtual Placement, Virtual Fitting/Selection of Good or Best Fitting Devices, Evaluation of Virtual Shape with Selection of Device with Preferred Shape, Evaluation of Virtual Function with Selection of Device with Preffered Function, Determined of Preferred Virtual Orientation, Determination of Preferred Virtual Alignment, Determination and/or Selection of Preferred Virtual Anchor/Attachment/Fixation Member

| | 1 Virtual placement of virtual device | 2 Evaluate virtual fit, select best fitting device | 3 Evaluate virtual shape, select device with preferred shape | 4 Evaluate virtual function, select device with preferred function | 5 Determine preferred virtual position | 6 Determine preferred virtual orientation | 7 Determine preferred virtual alignment | 8 Determine/ select preferred virtual anchor/ attachment |
|---|---|---|---|---|---|---|---|---|
| Cardiac valve repair devices, e.g. mitral valve repair devices | ✓ | ✓ | ✓ | ✓ | ✓ | ✓ | ✓ | ✓ |
| Intra-ventricular catheter | ✓ | | ✓ | ✓ | ✓ | ✓ | ✓ | ✓ |
| Intra-ventricular electrode | ✓ | | ✓ | ✓ | ✓ | ✓ | ✓ | ✓ |
| Coronary guide wire | ✓ | ✓ | ✓ | ✓ | ✓ | ✓ | ✓ | ✓ |
| Coronary catheter | ✓ | ✓ | ✓ | ✓ | ✓ | ✓ | ✓ | ✓ |
| Atrial appendage closure system | ✓ | | ✓ | ✓ | ✓ | ✓ | ✓ | ✓ |
| Epicardial pacing electrode | ✓ | | ✓ | ✓ | ✓ | ✓ | ✓ | ✓ |
| Implantable aneurysm pressure sensor | ✓ | | ✓ | ✓ | ✓ | ✓ | ✓ | |
| Long-term implanted intra-vascular catheter | ✓ | ✓ | ✓ | ✓ | ✓ | ✓ | ✓ | |
| Pericardial patch | ✓ | ✓ | ✓ | ✓ | ✓ | ✓ | ✓ | ✓ |
| Neurovascular guide wire | ✓ | ✓ | ✓ | ✓ | ✓ | ✓ | ✓ | |
| Neurovascular catheter | ✓ | ✓ | ✓ | ✓ | ✓ | ✓ | ✓ | |
| Neurovascular coil | ✓ | ✓ | ✓ | ✓ | ✓ | ✓ | ✓ | ✓ |
| Guide wire | ✓ | ✓ | ✓ | ✓ | ✓ | ✓ | ✓ | |
| Catheter | ✓ | ✓ | ✓ | ✓ | ✓ | ✓ | ✓ | |
| Coil | ✓ | ✓ | ✓ | ✓ | ✓ | ✓ | ✓ | ✓ |
| Aneurysm clip | ✓ | ✓ | ✓ | ✓ | ✓ | ✓ | ✓ | ✓ |
| Hemodialysis catheter | ✓ | | ✓ | ✓ | ✓ | ✓ | ✓ | |
| Drug eluting stent | ✓ | ✓ | ✓ | ✓ | ✓ | ✓ | ✓ | ✓ |
| Vessel guard or cover | ✓ | ✓ | ✓ | ✓ | ✓ | ✓ | ✓ | |
| Endovascular suturing system | ✓ | | ✓ | ✓ | ✓ | ✓ | ✓ | ✓ |

1. Virtual placement of virtual device includes, for example, virtual placement of one or more virtual devices using computer (e.g. PC) based interface, acoustic interface, and/or virtual interface (e.g. gesture recognition), other interface; e.g. with 1, 2, 3, 4, 5, 6 degrees of freedom, optionally alternating, e.g. in one direction followed by another direction or rotation; for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

2. Evaluate virtual fit, select good or best fitting device, e.g. from library of virtual devices, pre-existing CAD files, STL files etc., e.g. with different size, dimensions, geometry, shape, function, anchor/attachment mechanisms, anchor/attachment size, dimensions, geometry, shape; optionally each of the foregoing and/or following for different components, component combinations; select good or best fitting device for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/ tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

3. Evaluate virtual shape, select device with preferred shape, e.g. from library of virtual devices, pre-existing CAD files, STL files etc., e.g. with different size, dimensions, geometry, shape, function, anchor/attachment mechanisms, anchor/attachment size, dimensions, geometry, shape; optionally each of the foregoing and/or following for different components, component combinations; select device with preferred shape for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

4. Evaluate virtual function select device with preferred function e.g. from library of virtual devices, pre-existing CAD files, STL files etc., e.g. with different size, dimensions, geometry, shape, function, anchor/attachment mechanisms, anchor/attachment size, dimensions, geometry, shape, function; optionally each of the foregoing and/or following for different components, component combinations; select device with preferred function for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, function articular/tissue/organ/vascular surface/dimension/radius, radii/curvature/geometry/shape/volume, anatomical and/or biomechanical axis/axes, function; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, function, other portion of articular/tissue/organ/vascular surface/dimension/radius, radii/curvature/geometry/shape/volume/function or opposing articular/tissue/organ/vascular surface/dimension/radius, radii/curvature/geometry/shape/volume, anatomical and/or biomechanical axis/axes, function; including same or different tissues) and/or adjacent or subjacent or opposing or articulating or connected medical devices (including, for example, their dimensions, radius, radii, curvature, geometry, shape, placement position, orientation and/or alignment, function, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

5. Determine preferred virtual position, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.
6. Determine preferred virtual orientation, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.
7. Determine preferred virtual alignment, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.
8. Determine and/or select preferred virtual anchor/attachment/fixation member (length, width, diameter, size, dimensions, radius, radii, geometry, shape, location, position, orientation, alignment, function) (monoblock or modular, e.g. attachable) and/or placement, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data Numeric references In Table 4 are used for purposes of cross-referencing text associated with headings. Numeric references are not meant to imply a particular sequence. Some embodiments can be practiced in variable order or sequence, simultaneously or sequentially. In some embodiments for some devices, all of virtual placement, evaluating virtual fit, selecting good or best fitting implant, evaluating virtual shape, selecting implant with preferred shape, evaluating virtual function, selecting implant with preferred function, determining virtual position, virtual orientation, virtual alignment and determination and/or selection of preferred anchor/attachment/fixation member can be applied. In some embodiments for some devices, only one or more, but not all of virtual placement, evaluating virtual fit, selecting good or best fitting implant, evaluating virtual shape, selecting implant with preferred shape, evaluating virtual function, selecting implant with preferred function, determining virtual position, virtual orientation, virtual alignment and determination and/or selection of preferred anchor/attachment/fixation member can be applied.

"✓" denotes can be used or applied. Table 4 is only exemplary and not meant to be limiting. Virtual placement of a virtual device and/or implant component and/or instrument can include, for example, virtual placement of one or more virtual devices and/or implant components and/or instruments using a computer (e.g. PC) based interface, acoustic interface, and/or virtual interface, e.g. using gesture recognition, and/or other interface; e.g. with 1, 2, 3, 4, 5, 6 degrees of freedom, optionally alternating, e.g. in one direction followed by another direction or rotation; for example, using live data, e.g. visible through a see-through OHMD or imaged with a camera or scanner, e.g. a 3D laser scanner, or a confocal imaging system, and displayed by the OHMD, and optionally virtually moving, aligning and/or superimposing a virtual device and/or implant component and/or instrument in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues. These can be the same or different tissues.

Virtual placement can include virtually moving, aligning, superimposing and/or attaching a virtual device and/or implant component and/or instrument in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues.

Virtual placement can include virtually moving, aligning, superimposing and/or attaching a virtual device and/or implant component and/or instrument in relationship to one or more external features of an adjacent or subjacent or opposing or articulating or connected medical devices and/or implant components and/or instruments including, for example, one or more of their dimensions, radius, radii, curvature, geometry, shape, placement position, orientation and/or alignment, e.g. relative to landmarks and/or anatomic or biomechanical axis/axes. Virtual placement of virtual device and/or implant component and/or instrument can include, for example, virtually moving, aligning, superimposing and/or attaching a virtual device and/or implant component and/or instrument in relationship to one or more target anatomic and/or pathologic structure(s) for placement and/or alignment and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues. These can be the same or different tissues.

Virtual placement can include virtually moving, aligning, superimposing and/or attaching a virtual device and/or implant component and/or instrument in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues.

Virtual placement can include virtually moving, aligning and/or superimposing a virtual device and/or implant component and/or instrument in relationship to one or more internal, optionally hidden or not directly accessible features of an adjacent or subjacent or opposing or articulating or connected medical devices and/or implant components and/or instruments including, for example, one or more of their dimensions, radius, radii, curvature, geometry, shape, placement position, orientation and/or alignment, e.g. relative to landmarks and/or anatomic or biomechanical axis/axes.

Virtual placement can include virtually moving, aligning and/or superimposing a virtual device and/or implant component and/or instrument in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for virtual placement can be combined.

Evaluating the virtual fit and/or selecting a good fitting or the best fitting device and/or implant component and/or instrument can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component combinations.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/ geometry/shape/volume, and/or anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a good fitting or the best fitting device and/or implant component and/or instrument can be combined.

Evaluating the virtual shape and/or selecting a device and/or implant component and/or instrument with a preferred shape can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component combinations.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a device and/or implant component and/or instrument with a preferred shape can be combined.

Evaluating the virtual function and/or selecting a device and/or implant component and/or instrument with a preferred function can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, shape and/or function. The foregoing and/or following embodiments can be applied to different components and/or component combinations.

Evaluating and/or selecting a device and/or implant component and/or instrument with a preferred function can, for example, include moving, aligning, superimposing and/or projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/ACTIVE shape/function/volume, anatomical and/or biomechanical axis/axes and/or function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/ACTIVE curvature/geometry/shape, function/volume, anatomical and/or biomechanical axis/axes, and/or function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues. Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a device and/or implant component and/or instrument with a preferred function can be combined.

Determining the preferred position of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred position of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred position of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred position of a device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred position of a device and/or implant component and/or instrument can be combined.

Determining the preferred orientation of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred orientation of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred orientation of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred orientation of a device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred orientation of a device and/or implant component and/or instrument can be combined.

Determining the preferred alignment of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred alignment of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred alignment of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred alignment of a device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred alignment of a device and/or implant component and/or instrument can be combined.

Determining and/or selecting a preferred virtual anchor and/or attachment and/or fixation member, e.g. with regard to one or more of length, width, diameter, size, dimensions, radius, radii, geometry, shape, surface properties, location, position, orientation, alignment, and/or function, for example in a monoblock or modular, e.g. attachable, configuration can include selecting the virtual anchor and/or attachment and/or fixation member from a library of virtual devices and/or implant components and/or virtual anchors and/or attachments and/or fixation members, including, for example, using pre-existing CAD files and/or STL files and/or other files of the device and/or implant component and/or virtual anchors and/or attachments and/or fixation members, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component and/or anchor and/or attachment and/or fixation member combinations.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to live data, e.g. visible through a see-through OHMD, e.g. visible with the bare eye without an OHMD, and/or imaged with camera and/or scanner and displayed by the OHMD.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining and/or selecting a preferred virtual anchor and/or attachment and/or fixation member can be combined.

Virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can, for example, include moving, aligning, superimposing and/or projecting and/or attaching the virtual device and/or device components and/or implant components and/or instruments in relationship to live data, e.g. external data, e.g. visible through a see-through OHMD, e.g. visible with the bare eye without an OHMD, and/or imaged with camera and/or scanner and displayed by the OHMD, and/or live data, e.g. internal data, e.g. not visible through a see-through OHMD, e.g. not visible with the bare eye without an OHMD, e.g. hidden inside the tissue, and/or can, for example, include moving, aligning, superimposing and/or projecting and/or attaching the virtual device and/or device components and/or implant components and/or instruments in relationship to one or more external or internal target anatomic and/or pathologic structure(s) for placement and/or alignment and/or superimposition and/or attachment using, for example, an external or internal margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes, and/or can, for example, include moving, aligning, superimposing and/or projecting and/or attaching the virtual device and/or device components and/or implant components and/or instruments in relationship to one or more surrounding and/or adjacent and/or subjacent and/or opposing external or internal anatomic and/or pathologic structure(s) using, for example, an external or internal margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes, and/or can, for example, include moving, aligning, superimposing and/or projecting and/or attaching the virtual device and/or device components and/or implant components and/or instruments in relationship to one or more external or internal features of an adjacent and/or subjacent and/or opposing and/or articulating and/or connected external or internal medical device and/or implant component and/or instrument including, for example, their dimensions, radius, radii, curvature, geometry, shape, placement position, orientation and/or alignment, e.g. relative to landmarks and/or anatomic or biomechanical axis/axes, and/or can, for example, include moving, aligning, superimposing and/or projecting and/or attaching the virtual device and/or device components and/or implant components and/or instruments in relationship to one or more externally projected and/or internally projected virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data, and/or or any combinations of the foregoing, and can be based on a single or a multiple parameters, i.e. can be single or multi-parametric, e.g. by determining, evaluating, assessing, considering, using, for example, any one or more of the foregoing, e.g. by determining, evaluating, assessing, considering, using, for example, any one or more of external or internal target anatomic and/or pathologic structure(s), for example, an external or internal margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes, and/or surrounding and/or adjacent and/or subjacent and/or opposing external or internal anatomic and/or pathologic structure(s), for example, an external or internal margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes, and/or external or internal features of an adjacent and/or subjacent and/or opposing and/or articulating and/or connected external or internal medical device and/or implant component and/or instrument including, for example, their dimensions, radius, radii, curvature, geometry, shape, placement position, orientation and/or alignment, e.g. relative to landmarks and/or anatomic or biomechanical axis/axes, and/or externally projected and/or internally projected virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

The foregoing is only illustrative in nature and not meant to be limiting. Someone skilled in the art can recognize other landmarks, sites, shapes, pathology etc. that can be used in this manner.

In some embodiments, the OHMD can display an arbitrary virtual implant, virtual implant component and/or virtual medical device and virtual instrument over the surgical field, in a location directly visible, e.g. through a see through optical head mounted display or visible by a camera attached to a non-see through optical head mounted display, or in a location not directly visible, e.g. a subsurface location, with optional display of one or more subsurface organs, tissues or structures by one or more optical head mounted displays. The projection can be a 2D outline similar to radiographic templates, optionally derived from radiographic templates, or a 3D image, e.g. a 3D CAD file of the virtual implant, virtual implant component and/or virtual medical device and virtual instrument. The arbitrary virtual implant, virtual implant component and/or virtual medical device and virtual instrument can, for example, be a virtual implant, virtual implant component and/or virtual medical device and virtual instrument selected from the middle of a size range or a shape range or function range. The arbitrary virtual implant, virtual implant component and/or virtual medical device and virtual instrument can be selected based on surgeon or interventionalist preferences. The arbitrary virtual implant, virtual implant component and/or virtual medical device and virtual instrument can be the most common size used in a particular patient population. The arbitrary virtual implant, virtual implant component and/or virtual medical device and virtual instrument can be moveable using a computer (e.g. PC based), virtual, acoustic, or other interface. For example, the virtual representation of the arbitrary virtual implant, virtual implant component and/or virtual medical device and virtual instrument can include a "touch area", wherein gesture recognition software, for example the one provided by Microsoft with the Microsoft Hololens including, for example, the integrated virtual "drag function" for holograms can be used to move the arbitrary virtual implant, virtual implant component and/or virtual medical device and virtual instrument. For example, one or more cameras integrated or attached to the OHMD can capture the movement of the surgeon or interventionalist's finger(s) in relationship to the touch area; using gesture tracking software, the arbitrary virtual implant, virtual implant component and/or virtual medical device and virtual instrument can then be moved by advancing the finger towards the touch area in a desired direction. A surgeon or interventionalist can, for example, also "hold" the arbitrary virtual implant, virtual implant component and/or virtual medical device and virtual instrument by closing two fingers, e.g. thumb and index finger, over the touch area and then moving the fingers in the desired direction, thereby moving the arbitrary virtual implant, virtual implant component and/or virtual medical device and virtual instrument into the desired position and/or orientation on the patient's tissue, e.g. inside a vessel. Movement can be possible with 6 degrees of freedom. When the thumb and index finger reach the virtual touch area and close over the touch area, the location of the thumb and index finger in the touch area can be recognized by the gesture recognition system, triggering a command that the surgeon or interventionalist can move the virtual implant by moving the thumb and index finger with 1, 2, 3, 4, 5 or 6 degrees of freedom. When the surgeon or interventionalist opens the thumb and index finger, e.g. widens the distance between the thumb and index finger so that one or both fingers are not aligned with their respective touch areas anymore, the gesture recognition system can optionally recognize this opening of thumb and index finger triggering a command, for example, to fixate the virtual implant in its last position and/or orientation with the coordinates of the last position and/or orientation. The last position and/or orientation can be, for example, a position and/or orientation where the implant component is tangent with at least a portion of an external margin or periphery or rim of a surgical site, an organ or a tissue and/or where the implant component is tangent with at least a portion of the surgical site, an organ or a tissue.

In embodiments, one or more virtual medical devices, virtual implants, virtual implant components, virtual implant portions, virtual anchors, attachment or fixation members, and/or virtual instruments and/or virtual surgical tools can be moved, aligned, superimposed, projected or attached using one or more assistive tool. Such assistive tools can, for example, include handheld devices. The one or more assistive tools can be tracked using any of the tracking means described in the specification, including combinations thereof, including, but not limited to, optical markers, e.g. with one or more geometric patterns, and/or LED's, for example tracked using an image and/or video capture system or camera system integrated into, attached to or separate from an OHMD, navigation markers, e.g. infrared or RF marker's, e.g. tracked with a navigation system, IMU's, calibration phantoms, and/or reference phantoms. The one or more assistive tools can also be tracked using intrinsic tracking methods. The one or more assistive tools can also be directly recognized by one or more image capture systems or video systems and/or 3D scanners integrated into, attached to or separate from an OHMD, wherein the direct recognition and tracking allows to track the one or more assistive tools in one or more coordinate systems, e.g. a common coordinate system. In embodiments, a handheld device can have a wand, baton, stick, dowel, like shape, which can be tracked directly, e.g. using one or more image capture or video capture systems and/or 3D scanners, or optionally with one or more optical markers, LED's, navigation markers, IMU's, phantom's and the like attached to a first and, optionally, a second end. The surgeon or interventionalist can hold the wand, baton, stick or dowel like handheld device, for example, between a thumb and an index or other finger. The surgeon or interventionalist can execute commands, e.g. a virtual command or a voice command, to activate direct tracking or tracking of the wand, baton, stick or dowel like handheld device or to stop tracking of the wand, baton, stick or dowel like handheld device. One or more assistive tools can also be attached to the surgeon or interventionalist, e.g. the surgeon or interventionalist's wrist or arm. As the surgeon or interventionalist moves the wrist or arm, the position, orientation, alignment, direction of movement and/or speed of movement can be tracked. As the system tracks the position and/or orientation, and/or alignment and/or direction of movement and/or speed of movement, e.g. in a common coordinate system or any coordinate system, the position and/or orientation, and/or alignment and/or direction of movement and/or speed of movement can be translated into a corresponding position and/or orientation, and/or alignment and/or direction of movement and/or speed of movement or corresponding change in position and/or orientation, and/or alignment and/or direction of movement and/or speed of movement of the one or more projected virtual medical device, virtual implant or implant component, virtual anchor, attachment or fixation member, and/or virtual instrument. Thus, in this example, by moving the handheld device or assistive tool the surgeon or interventionalist can effect a movement of the virtual medical device, virtual implant or implant component, virtual anchor, attachment or fixation member, and/or virtual instrument displayed by the OHMD and the surgeon or interventionalist can virtually position, orient, align, superimpose or project the virtual medical device, virtual implant or implant component, virtual anchor, attachment or fixation member, and/or virtual instrument onto the physical anatomy or pathology of the patient, the physical surgical site, a resected tissue, a resected bone or cartilage, a hidden tissue, an area deep inside the tissue, e.g. inside a bone, a physical medical device present in the tissues of the patient and/or any surrounding, adjacent or subjacent tissues. As the surgeon or interventionalist moves the one or more assistive tools and the position, orientation, alignment, direction and/or speed of movement is tracked, the corresponding change in position, orientation, alignment, direction and/or speed of movement and/or coordinates of the virtual medical device, virtual implant, virtual implant component, virtual anchor, attachment or fixation member, and/or virtual instrument can be the same or can be less or more. For example, changes in position, orientation, alignment, direction and/or speed of movement and/or coordinates of the assistive tool can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1.5:1, 2:1, 3:1, 4:1, 5:1 or any other ratio. In this example, the movement of the virtual device, virtual implant, virtual implant component, virtual anchor, attachment or fixation member, virtual instrument and/or virtual surgical tool is smaller than the movement of the assistive tool, which can help the surgeon or interventionalist placing the virtual device, virtual implant, virtual implant component, virtual instrument and/or virtual surgical tool with high accuracy over an intended area, e.g. an implantation site. In another example, changes in position, orientation, alignment, direction and/or speed of movement and/or coordinates of the assistive tool can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1:1.5, 1:2, 1:3, 1:4, 1:5 or any other ratio. In this example, the movement of the virtual device, virtual implant, virtual implant component, virtual anchor, attachment or fixation member, virtual instrument and/or virtual surgical tool is larger than the movement of the assistive tool, which can help the surgeon or interventionalist placing the virtual device, virtual implant, virtual implant component, virtual instrument and/or virtual surgical tool with high speed over an intended area, e.g. an implantation site. The surgeon or interventionalist or an operator can optionally change these ratios. Non-linear ratios can be applied. For example, at the beginning of a virtual placement or alignment or fitting or selection, the movement of the virtual device, virtual implant, virtual implant component, virtual anchor, attachment or fixation member, virtual instrument or virtual surgical tool can intentionally be larger than the movement of the assistive tool in order to facilitate quick and time efficient placement, alignment and/or evaluation or any of the foregoing steps, including the ones tabulated in Table 4. As the procedure progresses, the movement of the virtual device, virtual implant, virtual implant component, virtual anchor, attachment or fixation member, virtual instrument or virtual surgical tool can intentionally be smaller than the movement of the assistive tool in order to facilitate accurate and reproducible placement, alignment and/or evaluation or any of the foregoing steps, including the ones tabulated in Table 4.

Alternatively, when the assistive tool and/or the virtual device, virtual implant, virtual implant component, virtual anchor, attachment or fixation member, virtual instrument or virtual surgical tool is in the periphery of the surgical field or the visual field of the surgeon or interventionalist, the movement of the virtual device, virtual implant, virtual implant component, virtual anchor, attachment or fixation member, virtual instrument or virtual surgical tool can be larger than the movement of the assistive tool in order to facilitate quick and time efficient placement or movement of the virtual device, virtual implant, virtual implant component, virtual anchor, attachment or fixation member, virtual instrument or virtual surgical tool towards or in the center of the surgical field or visual field of the surgeon or interventionalist. As the assistive tool and/or the virtual device, virtual implant, virtual implant component, virtual anchor, attachment or fixation member, virtual instrument or virtual surgical tool approaches the center of the surgical field or the visual field of the surgeon or interventionalist, the movement of the virtual device, virtual implant, virtual implant component, virtual anchor, attachment or fixation member, virtual instrument or virtual surgical tool can be smaller than the movement of the assistive tool in order to facilitate accurate and reproducible placement or movement of the virtual device, virtual implant, virtual implant component, virtual anchor, attachment or fixation member, virtual instrument or virtual surgical tool. The ratio, magnitude and speed of change in coordinates can change in a stepwise fashion or a continuous fashion, e.g. based on the location of the assistive tool or the virtual device, virtual implant, virtual implant component, virtual anchor, attachment or fixation member, virtual instrument or virtual surgical tool, e.g. from the periphery to the center of the surgical field and/or the visual field of the surgeon or interventionalist. The change can be automatic, e.g. based on coordinates of the assistive tool or the virtual device, virtual implant, virtual implant component, virtual anchor, attachment or fixation member, virtual instrument or virtual surgical tool in relationship to the surgical field and/or the OHMD, semi-automatic with user interaction, or manual with user interaction only. User interaction can be performed using any of the interfaces described in the specification, e.g. PC based, mouse based, voice based, gesture recognition based etc.

In embodiments using direct tracking, e.g. using one or more image capture or video capture systems and/or 3D scanners integrated into, attached to or separate from the OHMD, the surgeon or interventionalist can effect a movement of the virtual medical device, virtual implant or implant component, virtual anchor, attachment or fixation member, and/or virtual instrument displayed by the OHMD using finger, hand or arm movements which are tracked directly with the one or more image capture or video capture systems and/or 3D scanners, and the surgeon or interventionalist can virtually position, orient, align, superimpose or project the virtual medical device, virtual implant or implant component, virtual anchor, attachment or fixation member, and/or virtual instrument onto the physical anatomy or pathology of the patient, the physical surgical site, a resected tissue, a resected bone or cartilage, a hidden tissue, an area deep inside the tissue, e.g. inside a bone, a physical medical device present in the tissues of the patient and/or any surrounding, adjacent or subjacent tissues. Any of the foregoing embodiments described for assistive tools can also be applied to direct tracking. Changes in position, orientation, alignment, direction and/or speed of movement and/or coordinates of the surgeon or interventionalist's fingers, hands' or arms' can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1.5:1, 2:1, 3:1, 4:1, 5:1 or any other ratio. In this example, the movement of the virtual device, virtual implant, virtual implant component, virtual anchor, attachment or fixation member, virtual instrument and/or virtual surgical tool is smaller than the movement of the surgeon or interventionalist's finger(s), hand(s) or arm(s), which can help the surgeon or interventionalist placing the virtual device, virtual implant, virtual implant component, virtual instrument and/or virtual surgical tool with high accuracy over an intended area, e.g. an implantation site. In another example, changes in position, orientation, alignment, direction and/or speed of movement and/or coordinates of the surgeon or interventionalist's finger(s), hand(s) or arm(s) can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1:1.5, 1:2, 1:3, 1:4, 1:5 or any other ratio. In this example, the movement of the virtual device, virtual implant, virtual implant component, virtual anchor, attachment or fixation member, virtual instrument and/or virtual surgical tool is larger than the movement of the surgeon or interventionalist's finger(s), hand(s) or arm(s), which can help the surgeon or interventionalist placing the virtual device, virtual implant, virtual implant component, virtual instrument and/or virtual surgical tool with high speed over an intended area, e.g. an implantation site. The surgeon or interventionalist or an operator can optionally change these ratios. Non-linear ratios can be applied. For example, at the beginning of a virtual placement or alignment or fitting or selection, the movement of the virtual device, virtual implant, virtual implant component, virtual anchor, attachment or fixation member, virtual instrument or virtual surgical tool can intentionally be larger than the movement of the surgeon or interventionalist's finger(s), hand(s) or arm(s) in order to facilitate quick and time efficient placement, alignment and/or evaluation or any of the foregoing steps, including the ones tabulated in Table 4. As the procedure progresses, the movement of the virtual device, virtual implant, virtual implant component, virtual anchor, attachment or fixation member, virtual instrument or virtual surgical tool can intentionally be smaller than the movement of the surgeon or interventionalist's finger(s), hand(s) or arm(s) in order to facilitate accurate and reproducible placement, alignment and/or evaluation or any of the foregoing steps, including the ones tabulated in Table 4.

Alternatively, when the surgeon or interventionalist's finger(s), hand(s) or arm(s) and/or the virtual device, virtual implant, virtual implant component, virtual anchor, attachment or fixation member, virtual instrument or virtual surgical tool is in the periphery of the surgical field or the visual field of the surgeon or interventionalist, the movement of the virtual device, virtual implant, virtual implant component, virtual anchor, attachment or fixation member, virtual instrument or virtual surgical tool can be larger than the movement of the surgeon or interventionalist's finger(s), hand(s) or arm(s) in order to facilitate quick and time efficient placement or movement of the virtual device, virtual implant, virtual implant component, virtual anchor, attachment or fixation member, virtual instrument or virtual surgical tool towards or in the center of the surgical field or visual field of the surgeon or interventionalist. As the surgeon or interventionalist's finger(s), hand(s) or arm(s) and/or the virtual device, virtual implant, virtual implant component, virtual anchor, attachment or fixation member, virtual instrument or virtual surgical tool approaches the center of the surgical field or the visual field of the surgeon or interventionalist, the movement of the virtual device, virtual implant, virtual implant component, virtual anchor, attachment or fixation member, virtual instrument or virtual surgical tool can be smaller than the movement of the assistive tool in order to facilitate accurate and reproducible placement or movement of the virtual device, virtual implant, virtual implant component, virtual anchor, attachment or fixation member, virtual instrument or virtual surgical tool. The ratio, magnitude and speed of change in coordinates can change in a stepwise fashion or a continuous fashion, e.g. based on the location of the surgeon or interventionalist's finger(s), hand(s) or arm(s) and/or the virtual device, virtual implant, virtual implant component, virtual anchor, attachment or fixation member, virtual instrument or virtual surgical tool, e.g. from the periphery to the center of the surgical field and/or the visual field of the surgeon or interventionalist. The change can be automatic, e.g. based on coordinates of the surgeon or interventionalist's finger(s), hand(s) or arm(s) and/or the virtual device, virtual implant, virtual implant component, virtual anchor, attachment or fixation member, virtual instrument or virtual surgical tool in relationship to the surgical field and/or the OHMD, semi-automatic with user interaction, or manual with user interaction only. User interaction can be performed using any of the interfaces described in the specification, e.g. PC based, mouse based, voice based, gesture recognition based etc. The OHMD can display the virtual implant component in any location initially, e.g. projected onto or outside the surgical field. The OHMD can optionally display the virtual implant component at a defined angle, e.g. orthogonal or parallel, relative to a fixed structure in the operating room, which can, for example, be recognized using one or more cameras, image capture or video capture systems and/or 3D scanner integrated into the OHMD and spatial recognition software such as the one provided by Microsoft with the Microsoft Hololens or which can be recognized using one or more attached optical markers or navigation markers including, but not limited to, infrared or RF markers. For example, one or more optical markers can be attached to an extension of the operating table. The OHMD can detect these one or more optical markers and determine their coordinates and, with that, the horizontal plane of the operating room table. The virtual implant component can then be displayed perpendicular or at another, e.g. predetermined, angle relative to the operating room table. The virtual implant component can be displayed at a defined, e.g. predetermined, angle to one or more anatomic or biomechanical axes, e.g. a mechanical and/or anatomic and/or rotational axis, for example when it was previously determined. The virtual implant component can be displayed or projected tangent with one or more anatomic landmarks. The virtual implant component can be displayed intersecting one or more anatomic landmarks. The surgeon or interventionalist can move the virtual implant component to align it in the desired location and/or orientation over the implantation site. The surgeon or interventionalist can then evaluate the size of the virtual implant component and the fit of the virtual implant component by evaluating the size and fit of the virtual representation of the implant component superimposed onto the intended implantation site. The surgeon or interventionalist can move and align the virtual implant component so that, for example, its external surface co-locates, e.g. has similar or substantially the same coordinates, as the external surface of the intended implantation site, including, for example, the articular surface or an opposing articular surface. The surgeon or interventionalist can evaluate implant overhang or undersizing in different regions of the size, e.g. a trochlea, a medial and lateral condyle in the central or distal weight-bearing regions, in other weight-bearing regions, in high flexion regions and the surgeon or interventionalist can move, e.g. translate, flex or rotate the implant component to optimize coverage and minimize potential overhang.

The OHMD can display the other portions of the virtual implant component which project underneath the external surface of the implantation site including any bone cuts or other implant features for bone fixation, such as a surface facing a burred bone surface, e.g. for manual burring or burring with a robot, or a peg or strut or a keel for fixation. If the virtual implant component is too large for an implantation site, for example resulting in implant overhang over the patient's bone, the surgeon or interventionalist can cancel the virtual display of the particular size of virtual implant component displayed and the surgeon or interventionalist can select a smaller virtual implant component from the library of virtual and physical implant components. If the virtual implant component is too small for an implantation site, for example resulting in poor coverage of the patient's bone, the surgeon or interventionalist can cancel the virtual display of the particular size of virtual implant component displayed and the surgeon or interventionalist can select a larger virtual implant component from the library of virtual and physical implant components. If the implant has a shape that resembles the patient's shape poorly, e.g. in the area of the articular surface(s), the surgeon or interventionalist can cancel the virtual display of the virtual implant component displayed and the surgeon or interventionalist can select a virtual implant component with a different shape from the library of virtual and physical implant components. Such different shape can, for example, be different distal and/or posterior condylar offsets, different medial and lateral condylar widths, different medial and lateral tibial shapes, e.g. on the articulating surfaces and/or on the tibial component perimeter, different medial and lateral polyethylene thicknesses, different trochlear flange shapes and/or heights, different patellar shapes and/or sizes. In this manner, the surgeon or interventionalist can optimize the implant size and fit in three-dimensions in the actual surgical site, rather than reverting to pre-operative sizing and fitting using, for example, 2D x-rays or 3D imaging studies, e.g. CT and MRI. If an implantation site is characterized by one or more asymmetries, e.g. in an internal organ, the surgeon or interventionalist can optionally size and fit one or more asymmetric implant components, optionally with different asymmetries and geometries, for the implantation site.

The surgeon or interventionalist can move the virtual implant component to place it and/or align and/it or orient in a desired position, location, and/or orientation over the implantation site for a given patient. Since the moving and aligning is performed over the live implantation site of the patient, the surgeon or interventionalist can optimize the implant position, location, and/or orientation. The surgeon or interventionalist can further modify and/or optimize the position, location, and/or orientation of the virtual implant component and, with that, the physical implant component for a desired function in an implantation site, e.g. a desired flexion angle, rotation angle, range of motion, ligamentous laxity, desired movement.

The surgeon or interventionalist can align at least a portion of the external surface of the virtual implant component with at least a portion of the external surface of the implantation site, including one or more of normal cartilage, damaged or diseased cartilage, subchondral bone, cortical bone, a portion of the articular surface, the entire articular surface, a portion of an opposing articular surface, the entire opposing articular surface. After the surgeon or interventionalist has placed, aligned and/or oriented the virtual implant component superimposed in the desired position and/or orientation over or aligned with the live implantation site, the coordinates of the virtual implant component can be saved, e.g. in a common coordinate system in which the OHMD and the implantation site can also be registered. The saved coordinates of the virtual implant component can, optionally be incorporated in a virtual surgical plan, which can optionally also be registered in the common coordinate system. The OHMD can subsequently display one or more digital holograms of one or more virtual surgical instruments and/or virtual implant components wherein the position, location, and/or orientation of the one or more digital holograms of the one or more virtual surgical instruments and/or virtual implant components are derived from or take into consideration the saved coordinates of the virtual implant component.

The surgeon or interventionalist can move the virtual device, using a virtual or other interface, e.g. a "touch zone" on the virtual representation of the virtual device, e.g. with image or video capture and/or 3D scan of the surgeon or interventionalist's hand and/or fingers and/or gesture tracking, and superimpose it onto the patient's anatomic structures. If the virtual device is too large for an implantation site, the surgeon or interventionalist can cancel or discard the virtual display of the particular size of virtual device displayed and the surgeon or interventionalist can select a smaller device from the library of virtual devices.

In embodiments, an OHMD can project a 3D anatomic model of a vessel, a vascular structure or a vascular tree. The 3D anatomic model can, for example, be a "standard vessel", for example with a shape averaged from a population sample, or obtained, for example from data such as from the Visible Human Project. The surgeon or interventionalist can project, move, align and/or superimpose the 3D model onto the patient's vessel, e.g. relative to the external surface of the vessel.

The display of virtual data, e.g. of aspects of a virtual surgical plan, of virtual planes, of virtual placement indicators, of projected paths, virtually displaying a device and/or instrument, including, for example, a virtual surgical guide, virtually placing a device and/or instrument, virtually evaluating and/or selecting a good fitting or the best fitting device and/or instrument, evaluating the virtual shape and/or selecting a virtual device and/or instrument with a preferred shape, evaluating the virtual function and/or selecting a device and/or instrument with a preferred virtual function, virtually determining the preferred position of a device and/or instrument, virtually determining the preferred orientation of a device and/or instrument, virtually determining the preferred alignment of a device and/or instrument, and/or virtually determining and/or selecting a preferred virtual anchor and/or attachment and/or fixation member can be performed in any of the embodiments in relationship to and/or with a predetermined location, orientation, and/or alignment to a vessel, a vascular tree or a vascular structure.

In some embodiments, an intra-operative 2D or 3D imaging study can be performed, e.g. one or more x-rays or a CT scan. The intra-operative imaging study can be registered in a common coordinate system with the surgical site. The OHM D can display one or more digital holograms of subsurface anatomy of the patient, hidden or obscured by overlying skin, soft-tissue and/or bone.

Virtual Surgical Plans

Virtual and physical surgical instruments and implant components can be registered in a common coordinate system, for example with one or more OHMD's and live data of the patient. When pre-operative imaging studies, intra-operative imaging studies or intra-operative measurements are registered in a common coordinate system with one or more OHMD's using, for example, anatomic features, anatomic landmarks, implantable and attachable markers, calibration and registration phantoms including optical markers, LED's with image capture, navigation markers, infrared markers, RF markers, IMU's, or spatial anchors and spatial recognition, one or more of an instrument or implant position, orientation, alignment can be predetermined using the information from the pre- and intra-operative imaging studies and/or the intra-operative measurements.

In some embodiments, a surgeon or interventionalist or an operator can develop a virtual surgical plan. The virtual surgical plan can include the virtual removal of select tissues, e.g. bone or cartilage or soft-tissue, e.g. for installing or implanting a medical device. The virtual surgical plan can include removal of a tumor or other tissues. The virtual surgical plan can include placing a graft or a transplant. Any surgical procedure known in the art can be simulated in a virtual surgical plan, for example catheterization procedures, placement of stents, placement of vascular devices, removal of vascular devices.

A virtual surgical plan can be developed using intra-operative data or measurements, including measurements obtained using one or more optical markers which can, for example, be detected using one or more cameras, an image capture system, a video capture system and/or 3D scanner integrated into, attached to or separate from an OHMD. The one or more cameras, an image capture system, a video capture system and/or 3D scanner integrated into, attached to or separate from an OHMD can, for example, detect the coordinates of one or more optical markers attached to the surgical site, e.g. a bone or cartilage, an altered surgical site, e.g. a bone cut, the operating room table, an extension of the operating room table, and/or fixture structures in the operating room, e.g. walls. The one or more cameras, an image capture system, a video capture system and/or 3D scanner integrated into, attached to or separate from an OHMD can detect the one or more optical markers in static positions and/or dynamic, moving positions. The coordinates (x, y, z) of the optical markers can be measured in static and dynamic conditions.

Any other sensor described in the specification, e.g. IMU's, navigation markers, e.g. infrared markers and/or RF markers, LED's, can be used for obtaining intraoperative measurements and can be combined, for example with optical marker measurements, for deriving intra-operative measurements and for generating and/or developing a virtual surgical plan.

Intra-operative measurements using one or more cameras, an image capture system, a video capture system and/or 3D scanner integrated into or attached to an OHMD can be beneficial when measurements are desired to be obtained from the view angle of the surgeon or interventionalist or, when multiple OHMDs are used, from the view angle of a surgical assistant or second surgeon or interventionalist. Intra-operative measurements using one or more cameras, an image capture system, a video capture and/or 3D scanner separate from an OHMD can be advantageous when measurements are desired to be obtained from a view angle other than the surgeon or interventionalist or, when multiple OHMDs are used, from a view angle other than of a surgical assistant or second surgeon or interventionalist. Pre-operative data, e.g. pre-operative imaging studies or kinematic studies of a patient can also be incorporated into a virtual surgical plan. Pre-operative data alone can be used to develop a virtual surgical plan.

The virtual surgical plan can be developed with use of a computer or computer workstation as well as a local or remote computer or computer network. The computer or computer workstation can include one or more displays, keyboard, mouse, trackball, mousepad, joystick, human input devices, processor, graphics processors, memory chips, storage media, disks, and software, for example for 3D reconstruction, surface displays, volume displays or CAD design and display, as well as optional CAM output. The software can include one or more interfaces for CAD design, for displaying the patient's anatomy, for displaying virtual surgical instruments and for displaying virtual implants, implant components, medical devices and/or medical device components.

The different anatomic and pathologic structures as well as the different virtual instruments, e.g. virtual surgical guides, virtual devices and/or device components can optionally be displayed simultaneously on the same screen or screen section or non-simultaneously, e.g. on different screens, on the same screen at different times, or no different screen sections. The different anatomic and pathologic structures including hidden and/or obscured or partially hidden and/or obscured anatomic and pathologic structures as well as the different virtual instruments, e.g. virtual surgical guides, virtual devices and/or virtual device components can optionally be displayed using different colors or different shading. Some of the different anatomic and pathologic structures as well as the different virtual instruments, e.g. virtual surgical guides or virtual devices and/or virtual device components can optionally be displayed in a form of outline mode or pattern mode, where only the outline or select features or patterns of the anatomic and pathologic structures as well as the virtual instruments, e.g. virtual surgical guides, virtual devices and/or virtual device components are being displayed, for example with solid, dotted or stippled lines or geometric patterns.

Figure 5:
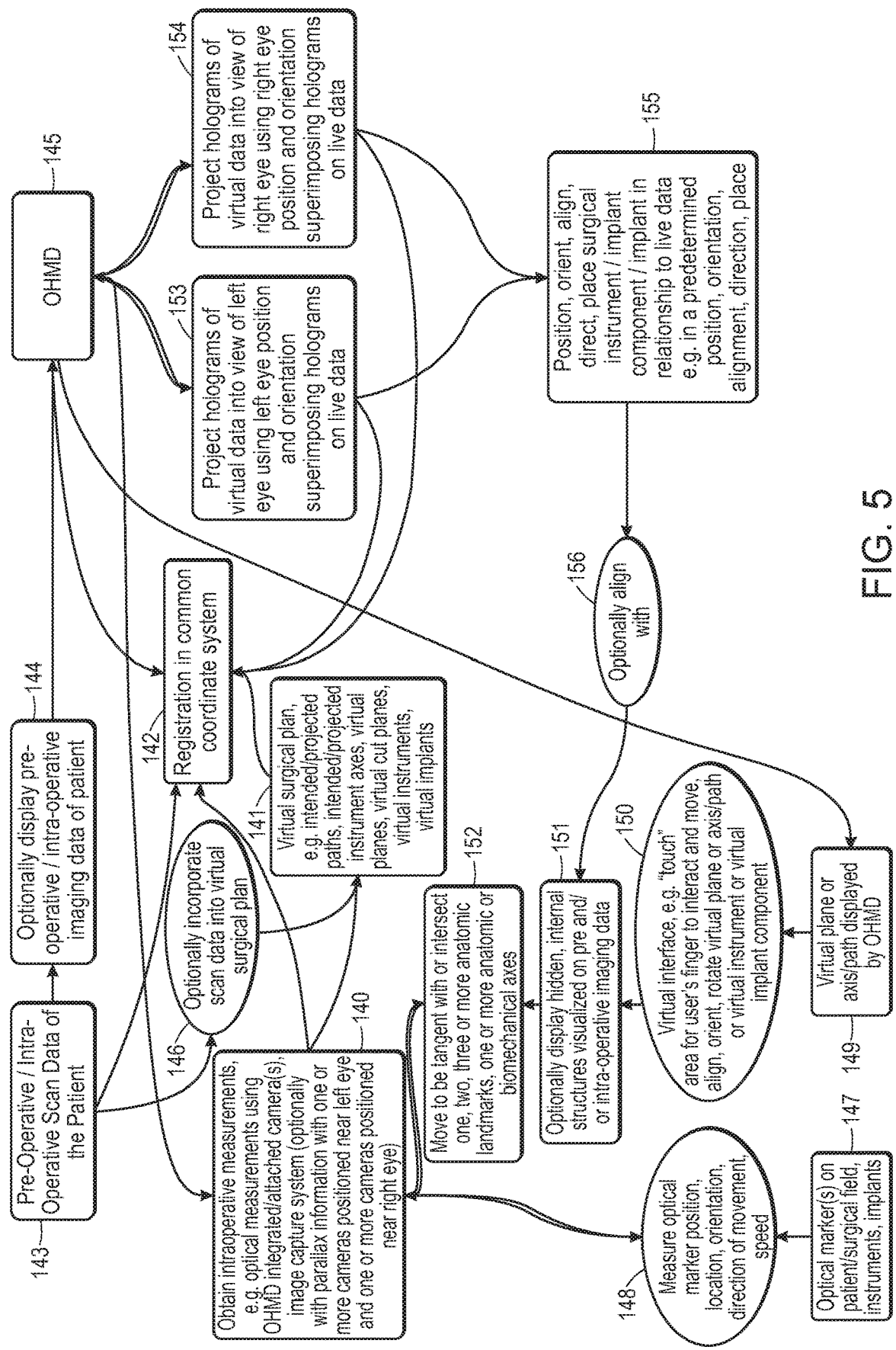
FIG. 5 is an illustrative flow chart showing how a virtual surgical plan can be generated using intraoperative data, e.g. intra-operative measurements, for example measurements obtained with one or more cameras, an image capture system or a video capture system and/or a 3D scanner integrated into, attached to or separate from an optical head mount display according to some embodiments of the present disclosure.

FIG. 5 shows how a virtual surgical plan 141 can be generated using intraoperative data, e.g. intra-operative measurements 140, for example measurements obtained with one or more cameras, an image capture system or a video capture system and/or 3D scanner integrated into, attached to or separate from an optical head mount display. Intraoperative measurements 140 can be utilized to generate a virtual surgical plan 141 (e.g. a virtual interventional vascular plan) which can be registered in a common coordinate system 142. The intraoperative measurements 140 can also be directly registered in the common coordinate system 142. Preoperative (e.g. from an ultrasound, CTA, MRA, echocardiogram) and/or intraoperative scan data (e.g. from an angiogram, run-off or bolus chase) 143 can be generated and can be optionally displayed 144 in two or three dimensions in an OHMD 145. Preoperative and/or intraoperative scan data 143 can optionally be incorporated 146 in the virtual surgical plan (e.g. a virtual interventional vascular plan) 141. Optical markers 147 can be present on the patient, the surgical field, surgical instruments or implants and can be measured with regard to their position, location, orientation, direction of movement and/or speed 148. A virtual plane or path or axis 149 (e.g. for placing a device (e.g. a catheter)) can be displayed by the OHMD 145 and, using a virtual interface 150, the plane or path or axis, as well as optionally virtual implants or instruments, can be moved by the surgeon or interventionalist. Optionally, the OHMD 145 can display hidden or internal structures 151, e.g. visualized on preoperative or intraoperative imaging studies or combinations of both, and the surgeon or interventionalist or the software can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying electronic holograms with virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Figure 6:
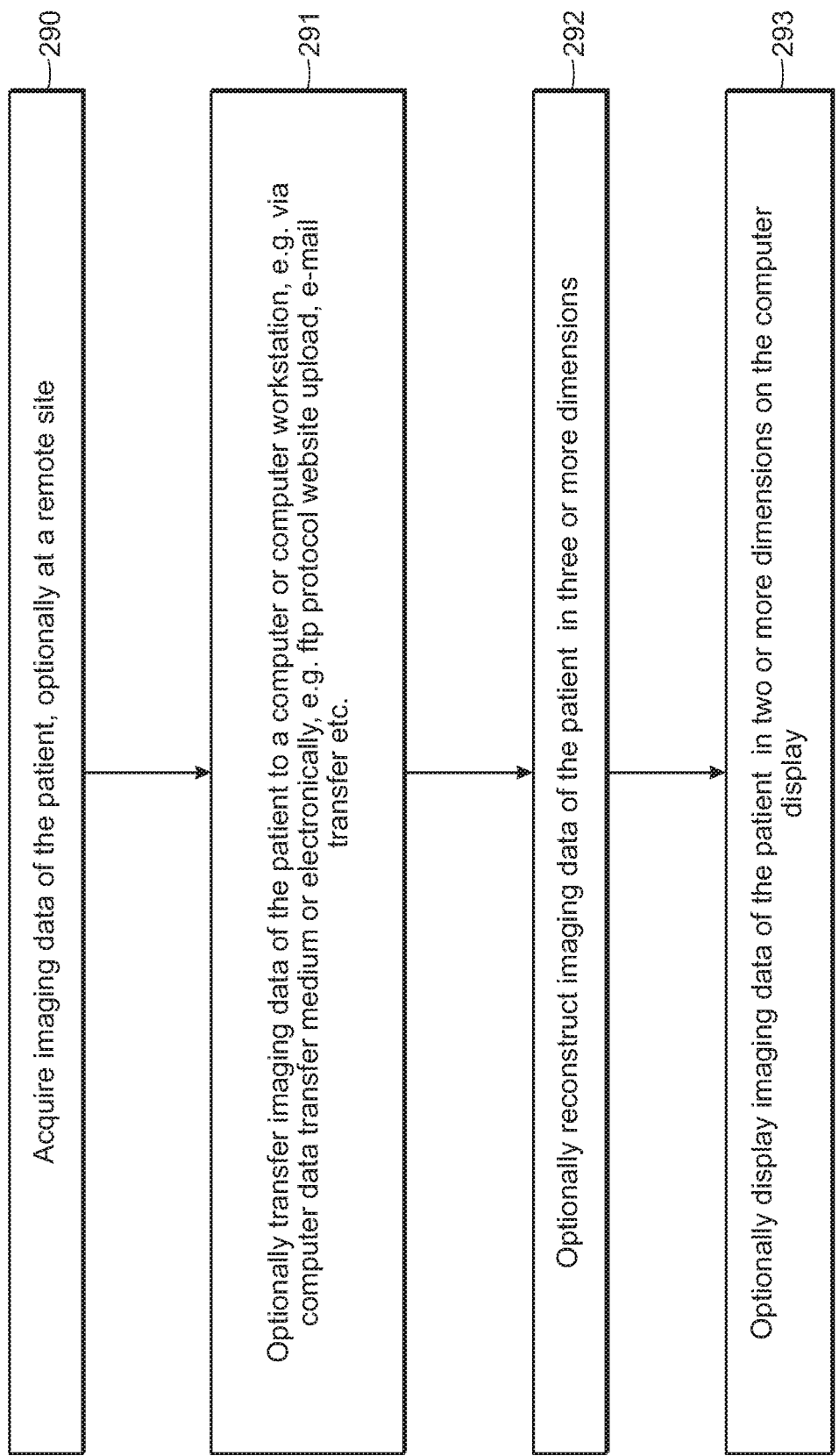
FIG. 6 is an exemplary workflow for generating a virtual surgical plan according to some embodiments of the present disclosure.

FIG. 6 is another exemplary workflow for generating a virtual surgical plan. Imaging data of a patient are acquired, e.g. at a site remote from the operating room 290. The imaging data can be transferred to a computer or workstation, e.g. via electronic data transfer routines such as ftp or internet 291. The imaging data of the patient can be reconstructed in three dimensions 292. The imaging data can be displayed in two or three dimensions on a computer display 293 or OHMD.

Figure 7:
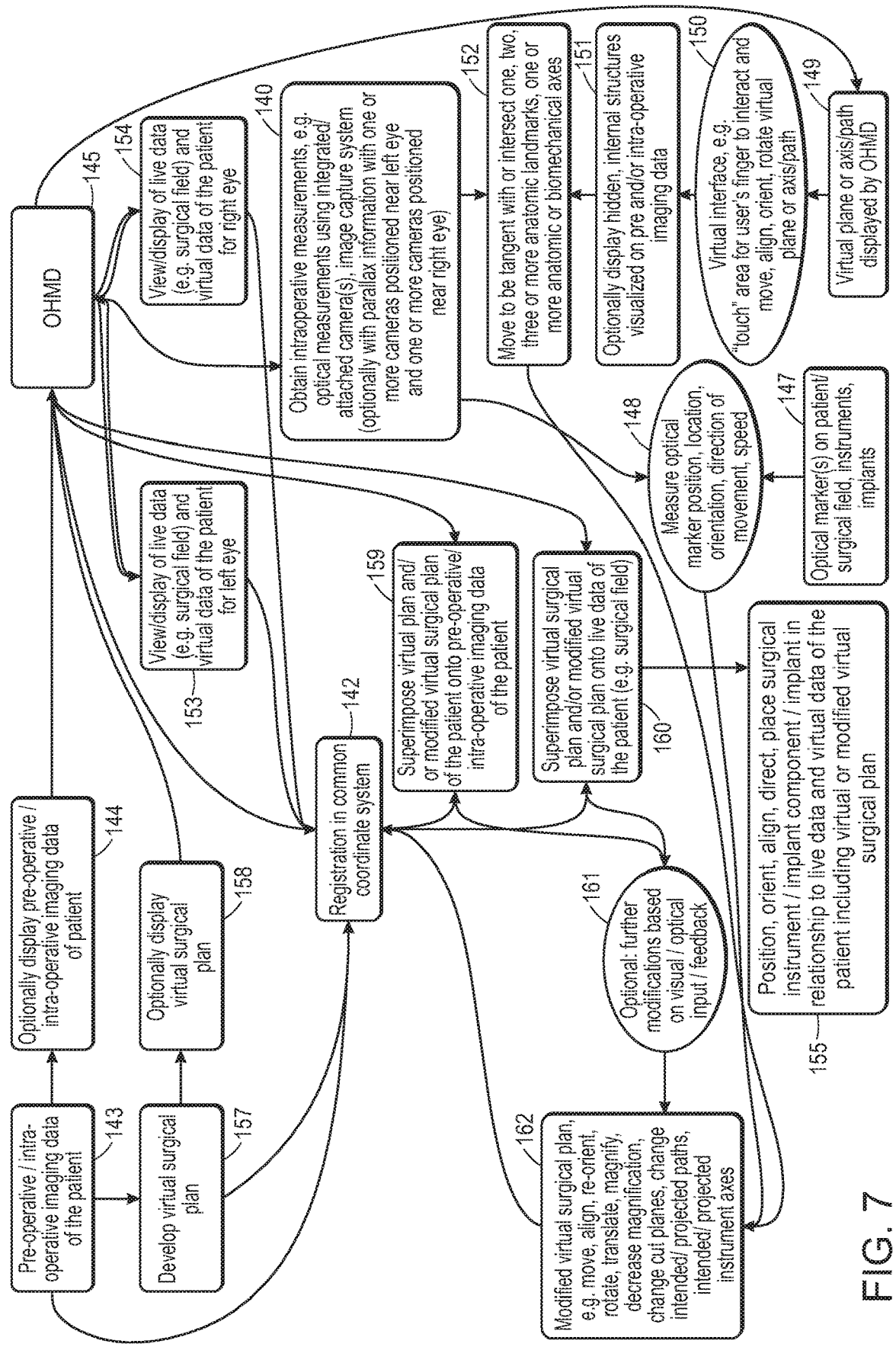
FIG. 7 is an illustrative flow chart showing how a virtual surgical plan can be modified using intraoperative data, e.g. intraoperative measurements according to some embodiments of the present disclosure.

FIG. 7 shows an example how a virtual surgical plan 157 (e.g. for an interventional vascular procedure) can be modified using intraoperative data, e.g. intraoperative measurements 140. The virtual surgical plan 157 can be developed using pre-operative and intra-operative imaging data of the patient 143, e.g. an ultrasound, CTA, MRA, an angiogram. The virtual surgical plan 157 can be registered in a common coordinate system 142. Preoperative and/or intraoperative scan data 143 can be generated and can be optionally displayed 144 in two or three dimensions in an OHMD 145. Preoperative and/or intraoperative scan data 143 can be used to develop the virtual surgical plan 157 which can be optionally displayed 158 by the OHMD 145. Optical markers 147 can be present on the patient, the surgical field, instruments or devices and can be measured with regard to their position, location, orientation, direction of movement and/or speed 148. A virtual plane or path or axis 149 can be displayed by the OHMD 145 and, using a virtual interface 150, the plane or path or axis, as well as optionally virtual devices or instruments, can be moved by the surgeon or interventionalist. For example, using a graphical user interface, the surgeon can move a device or a stent, e.g. along a vascular wall or inside a vascular lumen. A surgeon can virtually place a device inside a vascular lumen or an aneurysm or any other vascular structure, while observing the vascular lumen, aneurysm, or vascular structure and the device placement in the OHMD display. In some embodiments, a virtual path can be a path fora device, e.g. a catheter. In some embodiments, the virtual path can be compared to tracking data of the device, e.g. using any of the tracking methods and techniques described in the specification or known in the art. Optionally, the OHMD 145 can display hidden or internal structures 151, e.g. visualized on preoperative or intraoperative imaging studies or combinations of both, and the surgeon or interventionalist can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Intraoperative measurements 140 can be utilized to generate or modify a virtual surgical plan 157. The virtual surgical plan 157 and/or a modified virtual surgical plan 162 can optionally be superimposed on pre-operative and intraoperative imaging data of the patient 159. The virtual surgical plan 157 and/or a modified virtual surgical plan 162 can optionally be superimposed on pre-operative and intraoperative imaging data of the patient 159. The modified virtual surgical plan 162 can be further modified based on visual or optical feedback or input 161 and it can be used to position, orient, align, direct, place one or more virtual or physical instruments, implant components and/or implants in a predetermined position 155. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

In some embodiments, one or more of a virtual surgical tool, virtual surgical instrument including a virtual surgical guide, or a virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration can be moved, re-oriented and/or re-aligned by the surgeon or interventionalist using a virtual or other interface. For example, the virtual representation of the one or more of a virtual surgical tool, virtual surgical instrument including a virtual surgical guide or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument or virtual device, non-visualized portions for one or more devices or implants or implant components or surgical instruments or surgical tools, and/or one or more of a predetermined tissue change or alteration can include a "touch area", wherein an image or video capture system and/or 3D scanner and gesture recognition software, for example the one provided by Microsoft with the Microsoft Hololens including, for example, the integrated virtual "drag function" for holograms can be used to move the virtual data. For example, one or more cameras integrated or attached to the OHMD can capture the movement of the surgeon or interventionalist's finger(s) in relationship to the touch area; using gesture tracking software, the hologram(s) can then be moved by advancing the finger towards the touch area in a desired direction. A surgeon or interventionalist can, for example, also "hold" the hologram(s) by closing two fingers, e.g. thumb and index finger, over the touch area and then moving the fingers in the desired direction.

Placement Rules, Selection Rules, Design Rules

A virtual surgical plan can optionally include placement rules for surgical instruments and/or medical devices, implants or implant components. These placement rules can be based on standard rules of surgery or on standard surgical techniques, e.g. placement rules for a vascular stent or an aneyrusym coil. Placement rules or selection rules or design rules for a virtual surgical plan can be based on the patient's anatomy, desired implant, component or medical device position, location, orientation, rotation or alignment, one or more anatomical axes, one or more biomechanical axes, one or more rotational axes, a desired function of an implant, implant component or medical device. Placement rules or selection rules or design rules for a surgical plan can be used, for example, to select an implant. Placement rules or selection rules or design rules can include implant, implant component, or medical device dimensions or shape. Placement rules or selection rules or design rules can include avoidance of certain soft-tissues, vessels or neural structures as well as other sensitive tissues or structures, e.g. ligaments intended to be preserved. Placement rules, selection rules or design rules of a virtual surgical plan can include demographic information of the patient, e.g. weight, height, age, gender, other information such as bone mineral density or structure, clinical history, history of prior fractures, or functional information, e.g. on motion of a surgical site, an organ or a tissue, or metabolic information, e.g. for certain organs or pathologic tissues. Automatic placement of a virtual medical device, device component or implant is possible, for example based on anatomic criteria, pathologic criteria, or functional criteria using placement rules, selection rules or design rules for virtual surgical plans. Placement of a virtual medical device using placement rules, selection rules or design rules can be manual, semi-automatic or automatic. Manual, semi-automatic or automatic placement rules will typically require a software and a user interface.

The surgeon or interventionalist can receive 2D or 3D or multi-dimensional information of the patient. The information can be displayed, for example using a display screen, e.g. a computer screen separate from the OHMD or the OHMD. The surgeon or interventionalist can mark anatomic structures or pathologic structures on the computer screen using the 2D or 3D or multi-dimensional information of the patient. The information can optionally be segmented or can be modified, for example using image processing techniques known in the art. The marking can be performed using the display of the OHMD unit, e.g. using a virtual user interface.

The surgeon or interventionalist can also mark sensitive tissue, e.g. nerves, brain structure, vessels etc., that the surgeon or interventionalist wants to preserve or protect during the surgery. Such sensitive structure(s) can be highlighted, for example using different colors, when the virtual surgical plan and the related anatomic data or pathologic tissue information is being transmitted to or displayed by the OHMD. The surgical plan can be designed, adapted or modified so that sensitive structures are avoided or only minimally perturbed. For example, if a virtual surgical plan would result in an interference between a surgical instrument, e.g. a scalpel, a saw, a drill or a bur and a sensitive structure such as a vessel or a nerve, the virtual surgical plan can be adapted or modified by moving the position, location, orientation and/or direction of the virtual surgical instrument in order to avoid any interference or contact of the sensitive structure(s) with the surgical instrument. The marking can be performed using the display of the OHMD unit, e.g. using a virtual user interface. For example, the surgeon or interventionalist can optionally point at or circle with his or her finger sensitive structure on the live surgical site including by optionally touching the sensitive tissue. One or more cameras, an image or video capture system and/or 3D scanner integrated into, attached to or separate from the OHMD can detect the finger movement and can highlight the sensitive areas pointed out or circled by the surgeon or interventionalist's finger.

In some embodiments, if an interference or contact between the surgical instrument and one or more sensitive structures cannot be avoided (in the virtual data and/or the live or physical surgery), the virtual surgical plan can be adapted or modified to move, typically at least partially, the sensitive structure(s), for example using tissue retractors, in order to minimize or reduce any interference or contact of the surgical instrument with the sensitive structure(s).

In some embodiments, if an interference or contact between the surgical instrument and one or more sensitive structures cannot be avoided (in the virtual data and/or the live or physical surgery), the virtual surgical plan can be adapted or modified to protect, at least partially, the sensitive structure(s), for example using a virtual and in the live patient physical metal or plastic shield which can optionally be interposed between the sensitive structure(s) and the surgical instrument in order to minimize or reduce any interference or contact of the surgical instrument with the sensitive structure(s).

The surgeon or interventionalist can mark the desired location, position, orientation, and or alignment of a graft, transplant or an implant or components thereof. Implant materials can include organic and inorganic matter. Implant materials can include biologic and non-biologic matter.

With the implantation of any medical device, the surgeon or interventionalist can indicate the desired location, position, orientation, alignment of the medical device. Thus, the virtual surgical plan can show the desired location, position, orientation, or alignment of a medical device. The virtual surgical plan can also show the desired location, position, orientation, or alignment of a medical device relative to neighboring tissue. Neighboring tissue can be the tissue of the same organ. Neighboring tissue can also be the tissue of adjacent sensitive structures, e.g. vessel, nerves, other organs and the like.

The surgeon or interventionalist can optionally simulate different locations, positions, orientations or alignments of a medical device. The simulation of different locations, positions, orientations or alignments of a medical device can be particularly helpful when the medical device entails more than one component.

With these multicomponent devices, the surgeon or interventionalist can plan the placement of individual components in the virtual surgical plan and the surgeon or interventionalist can optionally evaluate their location, position, orientation or alignment relative to each other. The surgeon or interventionalist can then make adjustments to the placement, e.g. the position, location, orientation, rotation or alignment of one or more of the components in the virtual plan and, optionally later, in the live surgery.

Optionally, the surgeon or interventionalist can also test the function of these components in relationship to each other. For example, in a surgical plan for an artificial intervertebral disk, the software can allow the surgeon or interventionalist to virtually simulate spinal flexion or extension or lateral bending to the left and right with one or more of the medical device components included in the virtual surgical plan or the motion simulation. The surgeon or interventionalist can repeat the virtual surgical plan or the simulation with different degrees of flexion or extension or lateral bending to the left and the right and/or with differently sized or shaped medical devices or medical device components. If there is interchangeability of parts or components between different sizes and shapes or a medical device, the surgeon or interventionalist can optionally repeat the virtual surgical plan or the simulation using such different size components, e.g. a large size polyethylene insert or spacer with a medium size metal backing components or vice versa.

The surgeon or interventionalist can optionally superimpose medical device components with different size and/or shapes on the information and select the device component(s) that best fit the patient or that best match the patient.

In some embodiments, when, for example, a virtual surgical plan is developed using pre-operative data, e.g. pre-operative imaging data, the information is sent from the surgeon or interventionalist's or operator's office, e.g. a radiology office, to a central site, e.g. for image processing or for generating an initial draft surgical plan resulting in processed data or information. The processed information can be transmitted back to the surgeon or interventionalist or the operator. The surgeon or interventionalist or the operator can review the draft surgical plan. The surgeon or interventionalist or the operator can accept the draft surgical plan. The surgeon or interventionalist or the operator can optionally modify the draft surgical plan. The accepted or modified draft surgical plan can optionally be transmitted back to the central site. The central site can, for example, generate instructions to ship certain medical device components that the surgeon or interventionalist has accepted or selected with the accepted or modified surgical plan.

When intra-operative data are used for developing the virtual surgical plan, the surgeon or interventionalist can develop portions or the entire virtual surgical plan on his or her own, for example using a computer, standard hardware components, display and software in his or her office, a computer, standard hardware components, display and software in the operating room, or the optical head mount display, e.g. using a virtual interface, or combinations thereof. Different computers including the OHMD can be connected via a network, e.g. a WiFi or LiFi network.

The surgeon or interventionalist can optionally incorporate pre-operative data into the virtual surgical plan. Any of the foregoing can be registered in the common coordinate system and optionally virtually displayed by the OHMD.

In some embodiments, aspects of the surgical plan, e.g. the intended location of a medical device that the surgeon or interventionalist is planning to implant can be displayed by the OHMD superimposed onto the live data. The intended location can be indicated, for example, by a virtual medical device component that is a representation of the medical device component selected for implantation. The virtual medical device component displayed by the OHMD in superimposition with the live data can be displayed, for example, in its final desired position. The surgeon or interventionalist can then intraoperatively place or insert the medical device component aligning the physical device with the virtual device component.

In some embodiments, the intended location of a graft, transplant, medical device or other implantable can be indicated using virtual markers or targets displayed by the OHMD simultaneous with the live data of the patient. The surgeon or interventionalist can then align the graft, transplant, medical device or other implantable with the virtual markers or targets or the surgeon or interventionalist can direct the graft, transplant, medical device or other implantable towards the virtual markers or targets.

A visual or acoustic or other warning signal can be emitted or provided if the surgeon or interventionalist/operator deviates from the surgical plan. The visual warning signal can be provided by the OHMD, e.g. a red background flashing in the display of the virtual data or a color change, e.g. to red, of the virtual data.

In some embodiments, the virtual surgical plan can start by selecting or designing a desired implant or implant component or medical device size and/or dimension and/or shape based on the patient's anatomy, surgical site, pathologic conditions, deformity and other information including but not limited to a desired location, position, orientation, rotation or alignment in relationship to one or more anatomic or rotational or biomechanical axes. The selection or design of the desired size and/or dimension and/or shape can be followed by the placement of the implant, implant component or medical device in the desired location, position, orientation, rotation or alignment in relationship to one or more anatomic or biomechanical axes, the patient's anatomy surgical site, pathologic conditions or deformity. The process can be iterative. For example, the implant or implant component or medical device selection or design can be followed by a desired placement, which can be followed by changes in the selection or design of the implant or implant component or medical device selection, which can be followed by adjustments in placement and so forth. The iterative process can be automatic or semiautomatic.

Once the final implant selection or design and placement have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments, the virtual surgical plan can start by placing a virtual implant or implant component or medical device in a desired location, position, orientation, rotation or alignment in relationship to one or more anatomic or biomechanical axes, the patient's anatomy surgical site, pathologic conditions or deformity. The implant used for this initial or final placement can be an implant selected from an average, a minimum or a maximum size, dimension or shape or combinations thereof. The placing of the implant or implant component or medical device can then be followed by the selection or design of a desired implant or implant component or medical device size and/or dimension and/or shape. The process can be iterative. For example, placement of the implant or implant component or medical device can be followed by a selection or design of the desired the implant or implant component or medical device size, dimension or shape, which can be followed by changes in the placement of the implant or implant component or medical device, which can be followed by changes in the selection or design of size, dimension or shape and so forth. The iterative process can be automatic or semiautomatic.

Once the final implant placement and selection or design have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments, the virtual surgical plan can start out with the initial surgical step as defined, for example, in the surgical technique. This can be followed optionally by each or some of the subsequent surgical steps, for example only the major steps. The virtual surgical plan can then continue up to the selection and/or design and placement of the implant in the virtual data of the patient. If the resultant selection and/or design and/or placement of the implant, implant component or medical device differs from the desired result, for example as defined in the surgical plan or as desired by the surgeon or interventionalist, any of the foregoing surgical steps, the placement and/or the selection or the design of the implant, implant component or medical device can be modified. This process can be iterative, manual, semi-automatic or automatic until the desired virtual surgical plan, implant, implant component or medical device selection and/or design or placement are achieved.

Figure 8:
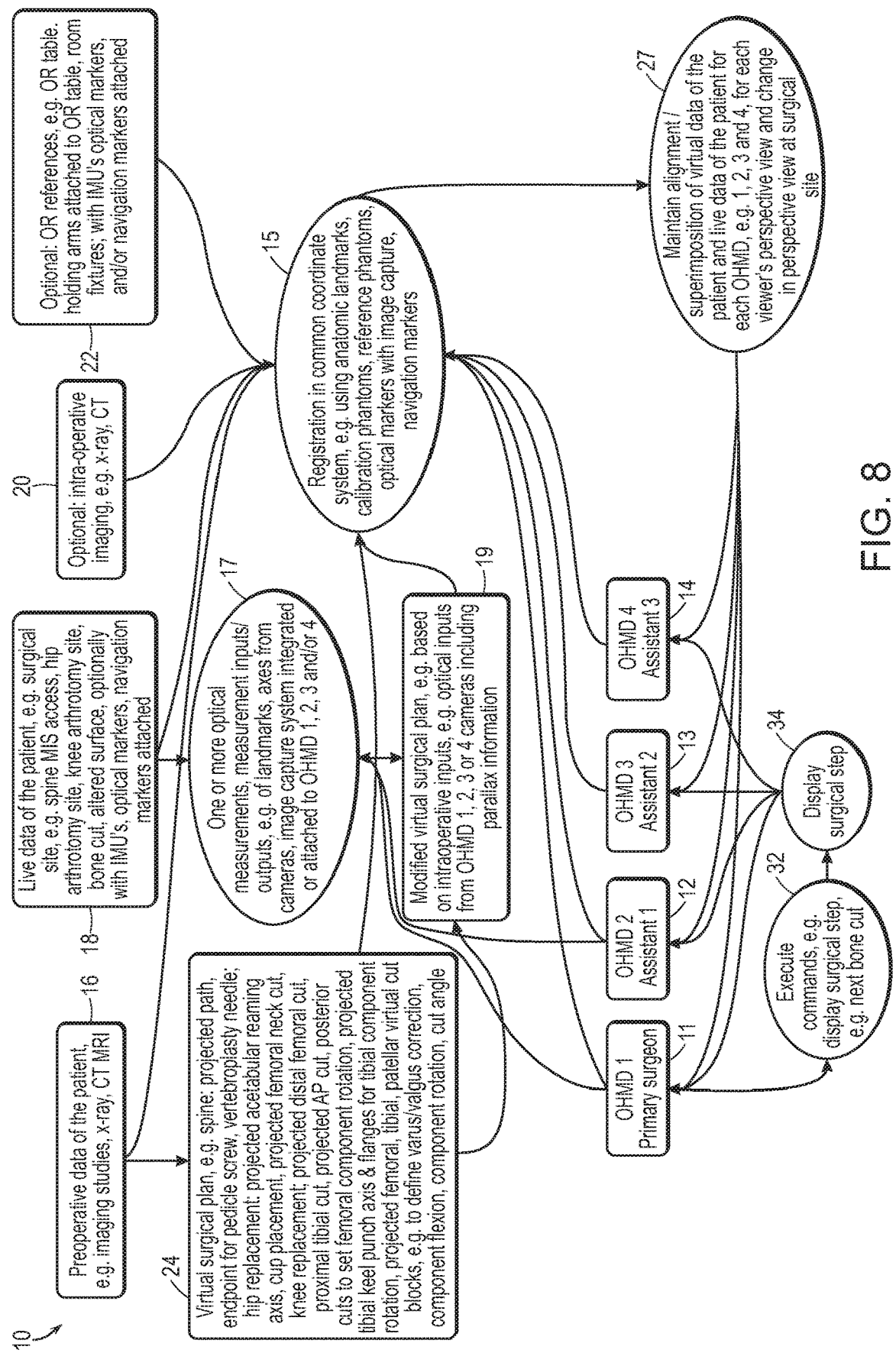
FIG. 8 is an illustrative flow chart showing how multiple OHMDs can be used during a surgery, for example by a first surgeon or interventionalist, a second surgeon or interventionalist, a surgical assistant and/or one or more nurses and how a surgical plan can be modified and displayed during the procedure by multiple OHMDs while preserving the correct perspective view of virtual data and corresponding live data for each individual operator according to some embodiments of the present disclosure.

FIG. 8 shows an illustrative example how multiple OHMDs can be used during a surgery, e.g. an interventional vascular procedure, for example by a first surgeon or interventionalist, a second surgeon or interventionalist, a surgical assistant and/or one or more nurses and how a surgical plan can be modified and displayed during the procedure by multiple OHMDs while preserving the correct perspective view of virtual data and corresponding live data for each individual operator. A system 10 for using multiple OHMDs 11, 12, 13, 14 for multiple viewer's, e.g. a primary surgeon or interventionalist, second surgeon or interventionalist, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient, e.g. vascular images from an ultrasound, CTA or MRA, can also be registered in the common coordinate system 15. Live data 18 of the patient, for example from the surgical site, e.g. a an organ, a tissue, a vascular intervention site, a vascular structure, a brain, an aneurysm, optionally with minimally invasive access, an altered surface or tissue, e.g. after a coagulation or infusion of a caustic substance (e.g. alcohol) or a chemotherapeutic drug, can be measured, for example using one or more IMU's, optical markers, navigation markers, image or video capture systems and/or 3D scanner and/or spatial anchors. The live data 18 of the patient can be registered in the common coordinate system 15. Intra-operative imaging studies 20, e.g. an angiogram, can be registered in the common coordinate system 15. OR references, e.g. an OR table or room fixtures can be registered in the common coordinate system 15 using, for example, optical markers IMU's, navigation markers or spatial mapping 22. The pre-operative data 16, e.g. a pre-operative imaging test, e.g. an ultrasound, CTA or MRA, or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can maintain alignment and superimposition of virtual data of the patient and live data of the patient for each OHMD 11, 12, 13, 14 for each viewer's perspective view and position and head position and orientation 27. Using a virtual or other interface, the surgeon or interventionalist wearing OHMD 1 11 can execute commands 32, e.g. to display the next predetermined interventional step, e.g. the placement of a device (for example, a stent), e.g. from a virtual surgical plan or an imaging study or intra-operative measurements, which can trigger the OHMDs 11, 12, 13, 14 to project virtual data of the next surgical (e.g. interventional vascular) step 34 superimposed onto and aligned with the surgical site in a predetermined position and/or orientation. Any of the OHMDs 11, 12, 13, 14 can acquire one or more optical measurements or measurement inputs, e.g. of anatomic landmarks, axes from cameras, anatomic axes, biomechanical axes, 17, using for example an integrated or attached camera, image capture or video system. By using multiple OHMDs 11, 12, 13, 14 from different view angles with multiple cameras, image capture or video systems, the accuracy of the measurements can optionally be improved. Optionally, parallax measurements can be performed using the multiple OHMDs 11, 12, 13, 14 from different view angles with multiple cameras, image capture or video systems. The one or more optical measurements can be used to modify the virtual surgical plan 19, optionally using the information from multiple OHMDs 11, 12, 13, 14. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Tissue Morphing

In some embodiments, the shape of one or more of the patient's tissues, such as a vessel or an organ, can be estimated or morphed in three dimensions intra-operatively, e.g. during the surgery. The estimating or morphing of the patient's tissue shape, e.g. bone shape, cartilage shape, or organ shape, can help reduce or obviate the need for pre-operative imaging and, in select embodiments, intra-operative imaging.

In some embodiments, 2D preoperative data can be used and the shape of one or more of the patient's tissues, such as a vessel or an organ, can be estimated or morphed in three dimensions pre-operatively, e.g. prior to surgery.

Tissue Morphing Using Pre-Operative Imaging or Intra-Operative Imaging

In some embodiments, one or more two-dimensional images of the patient can be obtained. These images can, for example, include one or more x-rays of the patient. X-rays can be obtained using digital acquisition techniques. X-rays can also be obtained using conventional film based technique, in which case the x-rays can be subsequently digitized using a scanner. X-rays can be obtained with the patient in upright, supine and/or prone position. X-rays can be obtained with the patient in weight-bearing and in non-weight-bearing position. In some embodiments, x-rays are obtained intra-operatively, for example with the patient already positioned and placed for the intended surgical procedure.

The x-ray data of the patient can be transferred into a computer. Optionally, image processing can be applied to segment select patient tissues, such as a bone or vertebra or vertebral structure, subchondral bone, cortical bone, osteophytes. Image processing can, for example, also be applied to determine the edge of select patient tissues, such as a bone or vertebra or vertebral structure, subchondral bone, cortical bone, osteophytes. When subchondral bone has been identified and/or derived from the images, including a subchondral bone curvature and/or geometry and/or shape, a cartilage shape, curvature or geometry can be superimposed or added to the subchondral bone shape.

In some embodiments, the 2D x-rays images can be used to derive information about the dimensions and shape of the anatomic structure(s) included in the x-ray. Some of this information can be, for example: Anatomic landmark(s); Distances and/or dimensions between two or more known landmarks/structures; Angles between landmarks; Anatomic axes; Biomechanical axes; Curvature information; Curvature information of a bone surface;

Curvature information of a subchondral bone surface; Curvature information of an articular surface; Change in curvature from convex to concave; Change in curvature from concave to convex; Surface information; Edge information; Shape information, e.g. when information from multiple x-rays images obtained with different projection or beam angles is combined or aggregated; Length information, e.g. in AP, ML, SI direction, AP, ML, SI plane, oblique planes; Width information, e.g. in AP, ML, SI direction, AP, ML, SI plane, oblique planes; Depth information, e.g. in AP, ML, SI direction, AP, ML, SI plane, oblique planes.

Any of the foregoing information can be external on the surgical field, e.g. directly visible through a see-through OHMD or the eye of a surgeon or interventionalist without an OHMD and/or on an accessible surface. Any of the information can be internal to the surgical field, e.g. not directly visible through a see-through OHMD display or the eye of a surgeon or interventionalist without an OHMD and/or not on an accessible surface and/or hidden by other tissue, e.g. bone, cortical bone and/or soft-tissue.

For any of the embodiments, landmarks, distances, dimensions, surfaces, edges, angles, axes, curvatures, shapes, lengths, widths, depths and/or other features can be external on the surgical field, e.g. directly visible through a see-through OHMD or the eye of a surgeon or interventionalist without an OHMD and/or on an accessible surface; landmarks, distances, dimensions, surfaces, edges, angles, axes, curvatures, shapes, lengths, widths, depths and/or other features can be internal to the surgical field, e.g. not directly visible through a see-through OHMD display or the eye of a surgeon or interventionalist without an OHMD and/or not on an accessible surface and/or hidden by other tissue, e.g. bone, cortical bone and/or soft-tissue.

The 3D shape, volume or surface or curvature of the tissue can, for example, be estimated by filling in the information, e.g. intermediate or connecting landmarks, distances, dimensions, surfaces, edges, angles, axes, curvatures, shapes, lengths, widths, depths and/or other features between known landmarks, distances, dimensions, surfaces, edges, angles, axes, curvatures, shapes, lengths, widths, depths and/or other features derived from the one, two, three or more x-ray images. The 3D shape, volume or surface or curvature of the tissue can, for example, be estimated by interpolating surfaces between multiple points or by fitting splines.

In some embodiments, a standard model of the tissue can be used and can be deformed using one or more of the known landmarks, distances, dimensions, surfaces, edges, angles, axes, curvatures, shapes, lengths, widths, depths and/or other features derived from the x-ray images, including using landmarks, distances, dimensions, surfaces, edges, angles, axes, curvatures, shapes, lengths, widths, depths and/or other features external on the surgical field, e.g. directly visible through a see-through OHMD or the eye of a surgeon or interventionalist without an OHMD and/or on an accessible surface and/or landmarks, distances, dimensions, surfaces, edges, angles, axes, curvatures, shapes, lengths, widths, depths and/or other features internal to the surgical field, e.g. not directly visible through a see-through OHMD display or the eye of a surgeon or interventionalist without an OHMD and/or not on an accessible surface and/or hidden by other tissue, e.g. bone, cortical bone and/or soft-tissue. Such deformations can be performed using various statistical models known in the art.

In some embodiments, a database or library of bone models and tissue models can be used. The one or more of these anatomic landmarks, distances, dimensions, surfaces, edges, angles, axes, curvatures, shapes, lengths, widths, depths and/or other features, e.g. external or internal, can be used to identify a standard bone shape and/or a standard cartilage shape by comparing the one or more landmarks, distances, dimensions, surfaces, edges, angles, axes, curvatures, shapes, lengths, widths, depths and/or other external or internal features with data in a reference database of reference patients and/or reference bone and/or cartilage shapes and by selecting a 3D model that most closely matches the selected landmarks, distances, dimensions, surfaces, edges, angles, axes, curvatures, shapes, lengths, widths, depths and/or other features. The reference database can be, for example, an anatomic reference database from cadaver data. Such scan data can be used to generate a database of 3D shapes of patients with different age, gender, ethnic background, race, weight, height and/or BMI.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment throughout the specification including for all other clinical applications, e.g. brain surgery, liver surgery, cancer surgery etc.

In some embodiments, a standard model, optionally already deformed using the patient's landmarks, distances, dimensions, surfaces, edges, angles, axes, curvatures, shapes, lengths, widths, depths and/or other features, can be combined or fused with a model selected from a database using the patient's landmarks, distances, dimensions, surfaces, edges, angles, axes, curvatures, shapes, lengths, widths, depths and/or other features. In some embodiments, the model selected from the database can be deformed and/or adapted using the patient's landmarks, distances, dimensions, surfaces, edges, angles, axes, curvatures, shapes, lengths, widths, depths and/or other features. Such deformations can be performed using various statistical models known in the art.

The foregoing description of techniques to estimate or morph the three-dimensional shape of a patient's bone is only exemplary in nature and is in no way meant to be limiting. It can be applied to the estimation and morphing of the 3D shape of a vessel or vascular structure. Someone skilled in the art will readily recognize other means to estimate the shape of the patient's bone in three dimensions. Any technique known in the art for determining or estimating the three-dimensional shape of a bone from two-dimensional data can be used.

Any technique known in the art for modeling and displaying the three-dimensional shape of a bone from two-dimensional data can be used. The resultant 3D model of the patient's bone using any of these techniques can then be displayed by one or more OHMDs, e.g. superimposed onto the patient's live, physical anatomy or surgical site.

Bone and/or Tissue Morphing Using Optical Probes and/or 3D Scanners and/or Image and/or Video Capture Systems In some embodiments, an image and/or video capture system and/or 3D scanner integrated into, attached to or separate from the OHMD can be used to image the patient's tissue and/or organ surface. With the position, orientation, alignment and/or direction of movement of the image and/or video capture system(s) and/or 3D scanner(s) optionally known, e.g. in a common coordinate system, for example using optical markers, navigation markers including infrared markers, retroreflective markers, RF markers, LEDs and/or IMUs, spatial mapping, and/or depth mapping, images of the patient's tissue and/or organ surface can be acquired from multiple viewpoints or continuously and, using software and image processing as described in Data Segmentation or spatial mapping techniques as described in Spatial Mapping, images can be used to derive one or more 3D volumes, 3D surfaces and/or 3D shapes of the patient's tissue and/or organ. The accuracy of such image acquisitions and reconstruction of 3D volumes, 3D surfaces and/or 3D shapes can optionally be enhanced with image and/or video capture systems and/or 3D scanners that use two or more cameras and/or scanners, which can be used to generated parallax information and/or stereoscopic information of the same structures, wherein, for example, the parallax and/or stereoscopic information can be used to enhance the accuracy of the reconstructions. Alternatively, the information from two or more cameras can be merged by averaging the 3D coordinates or detected surface points or other geometric structures such as planes or curved surfaces.

In some embodiments, 3D laser scanners or depth sensors known in the art, such as, for example, the Structure laser scanner provided by Occipital Inc., can be used to image the surface of the patient's tissue and/or organ. Other 3D scanners known in the art can be used.

Any laser scanning, optical or light scanning technique known in the art for determining, estimating or deriving the 3D volume, 3D surface or 3D shape of a structure known in the art can be used.

In some embodiments, the 3D scanner or image and/or video capture system and/or 3D scanner can be attached to an arm or tripod. Images of the patient's tissue and/or organ can be acquired at a constant distance. Images of the patient's tissue and/or organ can be acquired at a variable distance. The laser or optical scanner can optionally be used to measure the distance to the patient's tissue and/or organ during the image acquisition. Using the laser's starting position or the starting position of the image and/or video capture system and/or 3D scanner and/or at least one of an optical marker, navigation marker including infrared markers, retroreflective markers, RF markers, LED and/or IMU, the position, orientation, alignment and/or direction of movement of the image and/or video capture system and/or 3D scanner can be known throughout the acquisition allowing for magnification correction and optional view angle adjustments and/or projection and/or surface generation calculation and/or adjustments and/or corrections.

Combining Pre-Operative and Intra-Operative Data

In some embodiments, 2D or 3D data obtained intra-operatively with a mechanical probe, opto-electronic probe, RF probe, optical probe, image and/or video capture system, laser scanner and/or 3D scanner can be combined with pre-operative data, e.g. pre-operative imaging data and/or a virtual surgical plan.

The 2D or 3D data obtained intra-operatively can, for example, include dimensional information, geometric information, curvature information, volume information, shape information, and/or surface information of the tissue, organ, e.g. a vessel or vascular structure.

Optionally, adjustments or corrections can be applied to data obtained pre-operatively and/or intra-operatively.

In some embodiments, 2D or 3D pre-operative data can be combined with 2D or 3D intra-operative data. A virtual surgical plan can be developed or derived based on the combined data. If a virtual surgical plan has already been developed pre-operatively, the virtual surgical plan can be modified intra-operatively using intra-operative 3D scan information.

In some embodiments, 3D surfaces morphed from 2D pre-operative data, e.g. using one or more pre-operative x-rays, can be combined with 3D surfaces derived intra-operatively, e.g. derived using an intra-operative laser and/or 3D scanner. 2D data obtained pre-operatively and/or intra-operatively using 2D to 3D tissue morphing, e.g. vessel morphing, for example as described in the specification, and morphed into a 3D model can be displayed stereoscopically and/or non-stereoscopically using one or more OHMD displays. In addition, any of a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration can be displayed by the OHMD concurrent with the 2D to 3D morphed 3D model, e.g. bone model, stereoscopically or non-stereoscopically. The one or more of a virtual surgical tool, virtual surgical instrument including a virtual surgical guide or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration can be planned using the 2D to 3D morphed 3D model, for example using a virtual surgical plan.

In some embodiments, at least one or more of the same landmarks, distances, dimensions, surfaces, edges, angles, axes, curvatures, shapes, lengths, widths, depths and/or other features used for 2D to 3D tissue morphing, can be used for intra-operative registration of live data and virtual data, e.g. pre-operative data, of the patient by identifying the at least one or more of the corresponding landmarks, distances, dimensions, surfaces, edges, angles, axes, curvatures, shapes, lengths, widths, depths and/or other features in the live data, using, for example, some of the techniques described in the specification. In this manner, the accuracy of registration can, for example, by improved by using real, physical data used for 2D to 3D tissue morphing, as compared to morphed data, for registration of the physical patient anatomy, e.g. a surgical site, with the virtual data.

Figure 9:
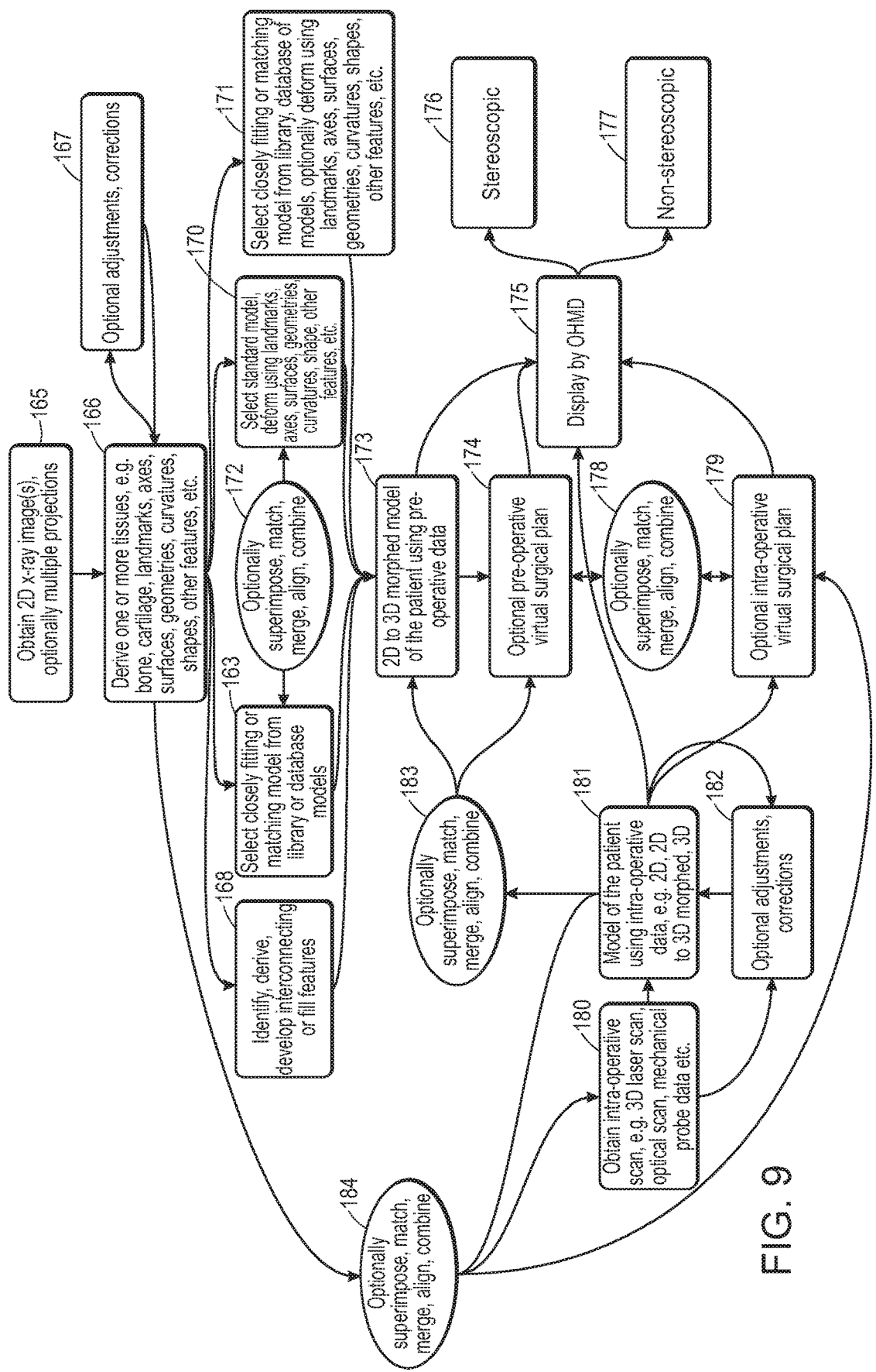
FIG. 9 is an illustrative flow chart showing how 2D to 3D morphed data can be used or applied.

FIG. 9 is an example how 2D to 3D morphed data can be used or applied. The example is in no way meant to be limiting. In this example, 2D x-ray images or 2D angiograms can be obtained, optionally with multiple projections 165. One or more tissues, e.g. bone, cartilage, a vessel, an artery, a vein, their landmarks, shapes and or geometries or other features can be derived 166 and can be optionally adjusted 167. Interconnecting or fill features can be determined 168, a closely fitting or matching model can be selected from a library or database of models 169, a standard model can be selected and optionally be deformed 170 using the shapes, geometries or features 166, a closely fitting or matching model can be selected from a library or database of models 171 and deformed using the information in 166. Steps and processes in 168, 169, 170, and 171 can optionally be combined 172. Steps and processes 168, 169, 170, 171, and 172 can be used to generate a 2D to 3D morphed model 173, which can be used to generate pre-operative virtual surgical plan 174. Throughout the specification, the term virtual surgical plan can be a virtual interventional plan for vascular procedures. The morphed model 173 and the pre-operative virtual surgical plan 174 can be displayed by one or more OHMD's 175, optionally stereoscopic 176 or non-stereoscopic 177. An intra-operative virtual surgical plan 179, e.g. for virtual interventional plan for vascular procedures, can optionally be superimposed, merged, matched or aligned with the pre-operative virtual surgical plan 174, e.g. for virtual interventional plan for vascular procedures. An intra-operative scan or probe data 180, e.g. from a catheter tracking, can be used to generate a model of the patient using intra-operative data, e.g. 2D, 2D to 3D morphed, 3D 181, which can optionally be superimposed, matched, merged or aligned 173 with the morphed model of the patient using pre-operative data 173 or the pre-operative virtual surgical plan 174. Optional adjustments to the model of the patient using intra-operative data 181 can be made 182.

Virtual Data and Live Data Seen Through One or More OHMDs

A virtual surgical plan using, for example, virtual data of the patient, can be used to develop or determine any of the following for placing or directing a surgical tool, a surgical instrument, a trial implant component, a trial implant, an implant component, an implant, a device including any type of biological treatment or implant or matrix known in the art:
Predetermined start point; Predetermined start position; Predetermined start orientation/alignmen; Predetermined intermediate point(s); Predetermined intermediate position(s); Predetermined intermediate orientation/alignment; Predetermined end point; Predetermined end position; Predetermined intermediate orientation/alignment; Predetermined path; Predetermined plane (e.g. for placing or orienting a surgical instrument or a device); Predetermined cut plane (e.g. for directing surgical instruments and/or for placing or orienting a device); Projected contour/outline/cross-section/surface features/shape/projection; Predetermined depth marker or depth gauge, predetermined stop, optionally corresponding to a physical depth marker or depth gauge on the physical surgical instrument or device; Predetermined angle/orientation/rotation marker, optionally corresponding to a physical angle/orientation/rotation marker on the physical surgical tool, surgical instrument, trial implant, implant component, implant or device; Predetermined axis, e.g. rotation axis; Predetermined axis of the physical surgical instrument, or device, e.g. a long axis, a horizontal axis, an orthogonal axis; Estimated/projected non-visualized portions of device/surgical instrument, e.g. using image capture or markers attached to device/surgical instrument with known geometry; Predetermined virtual tissue change/alteration.

Any of the foregoing, e.g. an outline of a device or a surgical instrument, can be displayed in 2D and/or in 3D, optionally alternatingly. When the surgeon or interventionalist looks from the side, e.g. at an angle, the visualization can optionally switch to a 3D display to show the desired angular orientation of the cut and/or the blade in relationship to the bone. The display can also remain in 2D mode. The switching between 2D and 3D display can be manual, e.g. through a voice command or a command on a virtually projected keyboard or a virtually projected user interface, or automatic, e.g. based on the position and/or orientation of the operator's head and/or the OHMD in relationship to the surgical site (e.g. operator head/OHMD in frontal orientation relative to surgical site, or close to including 90 degree side (near orthogonal) orientation, or angular, non-90 degree side orientation, e.g. 30, 40, 50, 60, 70 degree angles).

A 2D or 3D Display Can Also Include Multiple Cut Planes

If the surgeon or interventionalist elects to change or adjust any of a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration used in the one or more virtual surgical plans using, for example, a virtual interface displayed by the OHMD display, e.g. a finger slider or finger tab to move and/or rotate a virtual cut plane by virtually touching it, or any other interface, including, for example, a finger command or a voice command, the virtual representation of the virtual data can move accordingly and the virtual data displayed in the OHMD can be updated accordingly in the surgeon or interventionalist's display. The change in position and/or orientation of the virtual representation of the virtual data can also be seen in other OHMD's, e.g. worn by a second surgeon or interventionalist, a resident, a scrub nurse or a PA, and the projection of the virtual data can also be updated accordingly in a second, third or any additional OHMD units used, for example, by a second surgeon or interventionalist, a resident, a scrub nurse or a PA during the surgery. Optionally, the virtual interface or any other interface to change or adjust one or more of the virtual data can only be available for the surgeon or interventionalist's OHMD unit, i.e. the lead OHMD unit, while the other OHMD units can operate as slave units that simply follow the display of the lead OHMD unit. In this manner, potential intraoperative errors, for example with a non-surgeon or interventionalist modifying virtual data or aspects of the virtual surgical plan, can be avoided. Optionally, the lead can be passed over to any of the other units, in which case the surgeon or interventionalist's OHMD unit can operate as a slave unit. This can be beneficial when complex changes are required to the virtual surgical plan and/or the virtual data of the patient, which may require a separate person to implement such changes, while the surgeon or interventionalist is managing the physical operation in the live patient.

In some embodiments, the OHMD unit of the surgeon or interventionalist can capture the live data of the patient using one or more image and/or video capture systems and/or 3D scanners integrated into or attached to the OHMD. The captured live data of the patient can then be transmitted in electronic, digital form as live stream to slave OHMD units, optionally together with the virtual data of the patient, e.g. superimposed onto or co-displayed with the virtual data of the patient. Alternatively, the slave units in this example can be non-see through virtual reality (VR) systems such as the Google Daydream system or the Zeiss VR One system and others known in the art.

A virtual surgical plan can be used to define a predetermined start point for a surgical tool, a surgical instrument, a trial implant component, a trial implant, an implant component, an implant, a device. A start point can be, for example, the entry at the patient's skin. If pre-operative imaging, e.g. ultrasound, CT and/or MRI, is used for developing the surgical plan, the skin can be located in the imaging data and the start point can be defined at an area typically near the intended surgical site. A start point can also be defined at a select soft-tissue depth, e.g. 5, 8 or 10 cm into the soft-tissue, e.g. subcutaneous tissue or muscle or other tissues or organ tissue. A start point can be defined at the surface of an organ, e.g. a liver or a spleen or a kidney or a bladder or a brain. A start point can be defined at an anatomic landmark or in relationship to an anatomic landmark of an organ, e.g. a rim of a liver, a liver portal, an entry of an inferior vena cava into the liver, an entry of a portal vein into the liver, a superior or inferior pole of a kidney, a renal hilum. A start point can be defined at a bone surface or bony landmark The one or more of a virtual surgical tool, virtual surgical instrument including a virtual surgical guide or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration used in the one or more virtual surgical plans can be highlighted in the one or more OHMD displays using various techniques known in the art, including but not limited to: Colored display; Grey scale display; Shaded display; Patterned display, e.g. squares, lines, bars; Line display, e.g. solid, stippled, dotted; Arrow display; Target like display; Intermittent display, e.g. blinking or flashing; Appearing or disappearing display; Magnified display; Minified display For example, a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration is displayed by the OHMD multiple colors can be chosen.

For example, a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration can be highlighted using an arrow display. The arrows can be aligned with the direction of the one or more surgical tools, surgical instruments, implant components, implants or devices. The arrows can also not be aligned with the direction of the one or more surgical tools, surgical instruments, implant components, implants or devices. The arrows can be orthogonal to the direction of the one or more surgical tools, surgical instruments, implant components, implants or devices. The arrows can be aligned with the one or more surgical tools, surgical instruments, implant components, implants or devices. The arrows cannot be orthogonal with the one or more surgical instruments or devices. One or more arrows can directly point at the one or more of a virtual surgical tool, virtual surgical instrument including a virtual surgical guide or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration. The one or more arrows can optionally be magnified or minified. The one or more arrows can optionally be displayed intermittently, e.g. blinking or flashing. The one or more arrows can optionally be appearing or disappearing. For example, the one or more arrows can disappear when the predetermined end point is reached by the physical surgical instrument or device.

The one or more of a virtual surgical tool, virtual surgical instrument or virtual device, one or more predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices (e.g. implants or implant components) or surgical instruments or surgical tools, and/or one or more of a predetermined tissue change or alteration can be highlighted using a target like display. More than one target-like display can be used.

The target-like display can, for example, be positioned over a starting point, one or more intermediate points, an end point, a starting position, one or more intermediate positions, an end position, a intended path, predetermined plane, predetermined cut plane, a predetermined axis of the physical surgical tool, surgical instrument, trial implant, implant component, implant or device. A line or an axis oriented in orthogonal fashion through the target and passing through the center of one or more targets can optionally be aligned with a predetermined path, predetermined plane, predetermined cut plane, or predetermined axis of the physical surgical tool, surgical instrument, trial implant, implant component, implant or device, and/or one or more of a predetermined tissue change/alteration.

An intermittent, e.g. blinking or flashing display can be used to show one or more of a virtual surgical tool, virtual surgical instrument including a virtual surgical guide or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are not aligned with one or more of the virtual surgical tool, virtual surgical instrument including a virtual surgical guide or virtual device, one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are aligned with one or more of the one or more of a virtual surgical tool, virtual surgical instrument including a virtual surgical guide or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration.

An intermittent display can optionally change colors or have intermittent, varying color schemes. For example, a blinking or flashing red color can turn into solid, not intermittent green color when one or more of the physical surgical tool, surgical instrument, trial implant, implant component, implant and/or devices are aligned with one or more of a virtual surgical tool, virtual surgical instrument including a virtual surgical guide or virtual device, or one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration.

An intermittent display can, for example, highlight if and when one or more of the surgical tool, surgical instrument, trial implant, implant component, implant or device are not aligned with one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration in the OHMD can turn from a solid color, e.g. green or blue, to a blinking or flashing red color. Different colors can be chosen for intermediate versus final, end positions, e.g. blue for intermediate and green for final/end.

An appearing or disappearing display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device inside the OHMD. An appearing or disappearing display can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. In this example, the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can appear in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can disappear in the OHMD display when alignment is achieved again. The reverse can be possible, e.g. with the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device disappearing when alignment is not achieved and appearing when alignment is achieved.

A magnified or minified display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. The OHMD can also, optionally, provide or superimpose a magnified or minified display of the virtual anatomy or virtual data of the patient, for example after registration with the live anatomy/live data of the patient. The unmagnified, magnified or minified virtual anatomy or virtual data of the patient can be displayed by the OHMD simultaneously, e.g. with use of different colors, grey scale or patterns, or alternatingly with the unmagnified, magnified or minified display by the OHMD of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. In some embodiments, the magnification (including no magnification) or minification of the display of the virtual anatomy or virtual data of the patient can be the same as the magnification (including no magnification) or minification of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. Virtual anatomy or virtual data of the patient as used in the foregoing includes all virtual data of the patient, including, for example, data from vascular flow studies, metabolic imaging, kinematic data and the like.

A magnified or minified display by the OHMD can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. In this example, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be magnified or minified in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be set to zero magnification or minification or can go from magnified to minified or from minified to magnified in the OHMD display when alignment is achieved again.

If more than one a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device are displayed by the OHMD, any combination of display styles or techniques, e.g. multi-colored, grey scale, shaded, patterned, line, arrow, target, intermittent, appearing, disappearing, magnified, minified is possible. In some embodiments, different display styles or techniques can be chosen for different predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device.

Two-dimensional and three-dimensional displays One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in two dimensions. One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in three dimensions. One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in two dimensions and/or three dimensions, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device in three dimensions can be possible.

Stereoscopic and Non-Stereoscopic Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in a non-stereoscopic manner in three dimensions, with similar view angle of the virtual data of the patient seen by the surgeon's eyes through the display of the OHMD unit and the live data of the patient seen by the surgeon's eyes through the OHMD unit.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in a stereoscopic manner in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device can be displayed by the OHMD in a stereoscopic and/or a non-stereoscopic display, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device in a non-stereoscopic manner with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument or virtual device in a stereoscopic manner can be possible.

When stereoscopic projection is used by the OHMD, the display for the left eye and the right eye can be adjusted for the surgeon or interventionalist's or operator's inter-ocular distance, including, for example, the inter-pupillary distance. For example, the distance between the left pupil and the right pupil can be measured prior to operating the OHMD. Such measurements can be performed using an image and/or video capture system and/or 3D scanner integrated into, attached to or separate from the OHMD. Such measurements can also be performed using any other technique known in the art, including, for example, mechanical rulers, optical measurement tools and standard tools used by optometrists.

Adjusting the OHMD Unit Including the Display

In some embodiments, once the inter-ocular, e.g. the inter-pupillary distance, of the surgeon or interventionalist or operator is known, it can be entered into the display system interface and/or software and the 3D projection of the left and the right eye can be adjusted for the user. For example, with a narrow inter-ocular or inter-pupillary distance, the projection for the left eye and the right eye can be moved closer to the nose so that the center of the left and the right projections will be aligned with the center of the left eye/pupil and the right eye/pupil. With a wide inter-ocular or inter-pupillary distance, the projection for the left eye and the right eye can be moved further away from the nose so that the center of the left and the right projections will be aligned with the center of the left eye/pupil and the right eye/pupil. Different user settings can be stored in the system, e.g. by user name. In this manner, when a different user is placing the OHMD on his or her head, the user or the system can call up their preferred user settings, including their respective inter-ocular or inter-pupillary distance. User settings can be called up, for example, using a visual or optical keyboard interface, projected by the OHMD, where the operator can select virtual buttons. User settings can also be called up using voice commands, keyboards and any other known technique or technique for executing user commands.

Refresh Rates, Addressing Image Flicker

In many embodiments, a fast refresh rate can be desirable, e.g. 15 Hz, 20 Hz, 25 Hz, or 30 Hz, 50 Hz, 70 Hz, 80 Hz, 100 Hz, 120 Hz, 150 Hz, 175 Hz, 200 Hz or greater. When higher refresh rates are used, the spatial resolution of the display of the virtual data can optionally be reduced if bandwidth and transmission speed and/or display speed reach their limits.

Alternatively, there can be an alternating of a high-resolution display, e.g. 1920×1080 pixel resolution, and lower resolution, e.g. 1024×768 pixel resolution. The ratio of high to lower resolution images can be 1:1, 2:1, 3:1, 1:2, 1:3, with any other combination possible.

Some users physicalize no flicker with refresh rates of 30 Hz, sometimes less. Other users can feel or experience flicker with refresh rates of 70 Hz or faster. If a user is experiencing flicker effects or a flicker feeling with the display of virtual data, the user can have the option of increasing the refresh rate and, optionally, decreasing the display resolution if necessary, for example for reasons of bandwidth or transmission speed. The user can also select alternating resolutions, e.g. 1920×1080 pixel resolution intermixed with 1024×768 pixel resolution; any other pixel resolution and combination of pixel resolutions is possible. In this manner, the user can select the setting that will yield a pleasant, substantially flicker free display while at the same time maintaining sufficient spatial and/or temporal resolution to enable an accurate physical/virtual work environment.

In some embodiments, the display will automatically turn of and, optionally, turn on depending where the user and/or surgeon or interventionalist directs the view.

Managing Display, Hardware, Software or Bandwidth Limitations

In some embodiments, the display of the OHMD unit can display a subset of the data and/or images representing a smaller portion of the field of view visible through the OHMD or displayable by the display of the OHMD unit, using, for example, only a portion of the available display. If data from a pre-operative or intra-operative imaging study, e.g. x-rays, a CT scan, an MRI scan, are displayed, the data or images displayed by the OHMD can also be targeted to a volume smaller than the original scan volume or area covered by the imaging study in order to decrease the amount of data displayed. In addition, the data or images displayed by the OHMD can also be targeted to a volume or area smaller than the volume or area to be operated or smaller than the volume or area of the surgical site. This embodiment can, for example, be useful, when the software environment limits the amount of surface points or nodes displayed or limits the size or amount of the data displayed by the OHMD. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD.

This smaller portion of the field of view visible through the OHMD or displayable by the display of the OHMD unit, smaller, targeted volume from an imaging study, or the volume or area smaller that the volume or area of the surgical site can be targeted to portions of the surgical site or to anatomic landmarks.

A targeted area or smaller portion of the field of view visible through the OHMD or displayable by the display of the OHMD, a smaller, targeted volume from an imaging study, or a volume or area smaller that the volume or area of the surgical site can also be defined with use of one or more anatomic landmarks, e.g. a vascular structure (including as seen on a vascular imaging study). One or more of the same landmarks that have been/are being used for registration of virtual data and live data of the patient can be used for defining or identifying a target area or a smaller portion of the field of view visible through the OHMD or displayable by the display of the OHMD. The landmarks can be identified using, for example, an image and/or video capture system and/or 3D scanner integrated into, attached to or separate from an OHMD.

The landmarks can be identified by attaching optionally one or more optical markers, navigation markers including infrared markers, retroreflective markers, RF markers, surgical navigation, LED's, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or interventionalist or operator.

By limiting the display to such a smaller portion of the field of view visible through the OHMD or displayable by the display of the OHMD or target area, a smaller, targeted volume from an imaging study, or a volume or area smaller that the volume or area of the surgical site the amount of data displayed can be reduced. In addition, the amount of data transmitted, e.g. using a WiFi, Bluetooth or LiF network can also be reduced.

Viewing 2D Computer Monitors Through an OHMD Unit

In some embodiments, the OHMD system can detect, e.g. automatically, if the surgeon or interventionalist or operator is looking at a computer or display monitor separate from the OHMD, for example, with use of an image and/or video capture system and/or 3D scanner integrated into, attached to or separate from the OHMD. The standalone or separate computer or display monitor can be used, for example, to display image data, e.g. of a patient, or to concurrently display virtual data displayed by the OHMD. The image and/or video capture system and/or 3D scanner can, for example, capture the outline of the computer or display monitor, e.g. round, square or rectangular, and the software can, optionally, automatically match, superimpose or align the items or structures displayed by the OHMD with the items or structures displayed by the standalone or separate computer or display monitor. Alternatively, the user, operator and/or surgeon or interventionalist can execute a command, e.g. a voice command or a command using a virtual finger/keyboard interface, indicating that he or she is looking at the standalone or separate computer or display monitor and the software can then match, superimpose or align the items or structures displayed by the OHMD with the items or structures displayed by the standalone or separate computer or display monitor. The OHMD system can match, superimpose, or align all of the structures displayed by the standalone or separate computer monitor. The OHMD system can match, superimpose or align a portion of the structures displayed by the standalone or separate computer monitor.

The OHMD can display the structures displayed by the standalone or separate computer monitor using the same color. The OHMD can display the structures displayed by the standalone or separate computer monitor using different colors. The OHMD can display structures not displayed by the standalone or separate computer monitor using a different color or greyscale or contrast than that used by the standalone or separate computer monitor.

The OHMD can display the structures displayed by the standalone or separate computer monitor using the same greyscale and/or contrast used by the standalone or separate computer monitor. The OHMD can display the structures displayed by the standalone or separate computer monitor using a different greyscale and/or contrast used by the standalone or separate computer monitor.

The OHMD can display the structures displayed by the standalone or separate computer monitor using the same image intensity used by the standalone or separate computer monitor. The OHMD can display the structures displayed by the standalone or separate computer monitor using a different image intensity used by the standalone or separate computer monitor, e.g. brighter or less bright.

In some embodiments, a standalone or separate computer or display monitor located in a user area, e.g. an operating room or a surgical suite, can be used as a calibration or reference or registration phantom for the OHMD unit including the frame and display position, orientation and/or alignment and/or direction of movement. The monitor can have a round, rectangular or square shape of known dimensions. An image and/or video capture system and/or 3D scanner integrated into, attached to or separate from the OHMD can be used to capture one or more images of the monitor. Since the dimensions of the monitor are known, the size, shape or dimensions, for example along its edges, or the area of the monitor on the captured image(s) can be used to determine the distance of the OHMD to the monitor; the shape of the circle, oval, rectangle or square can be used to determine the angle of the OHMD relative to the monitor. If the image and/or video capture system and/or 3D scanner integrated into or attached to the OHMD uses two or more cameras, the difference in shape of the circle, oval, rectangle or square detected between a first, second and any additional cameras can be used to increase the accuracy of any estimates of the angular orientation of the OHMD to the display monitor, e.g. by calibrating the measurement of a first camera against a second camera against a third camera and so forth. If two or more cameras are used integrated into or attached to different portions of the OHMD frame, e.g. the left side of the frame and the right side of the frame, the difference in projection of the monitor circle, oval, rectangle or square between the two cameras can also be used to estimate the user's head position and/or orientation and/or alignment and/or the position and/or orientation and/or alignment of the OHMD frame in relationship to the user's head and/or face.

In some embodiments, the user and/or surgeon or interventionalist can optionally look at the display monitor through the OHMD while maintaining his or her head in a neutral position, e.g. with no neck abduction, adduction, flexion, extension or rotation. This head position can be used to calibrate the position of the OHMD display in relationship to the target area and/or the patient and/or the surgical site, e.g. during an initial registration or a subsequent registration. This head position can also be used to calibrate the position of the OHMD unit/frame in relationship to the user's and/or the surgeon or interventionalist's head and face. Optionally, the user and/or surgeon or interventionalist can place his or her head on a chin stand or head holder for purposes of this calibration or registration. This process of using an external computer or display monitor as a reference for calibration and/or registration purposes can be performed at the beginning of an activity and/or a surgical procedure, e.g. as part of an initial registration process. This process of using an external display monitor as a reference for calibration and/or registration purposes can also be performed during an activity or after an activity and/or surgical procedure, for example when there is concern that the OHMD unit may have moved relative to the user's and/or surgeon or interventionalist's face.

In some embodiments, the position, location, orientation, and/or alignment of the outline of the standalone or separate computer or display monitor can be monitored, for example using an image and/or video capture system and/or 3D scanner integrated into, attached to or separate from the OHMD. Optionally, the position, location, orientation and/or alignment of the outline of the standalone or separate computer or display monitor can be monitored using attached optical markers, navigation markers including infrared markers, retroreflective markers, RF markers, LED's and/or IMU's as well as any other techniques described in the specification or known in the art for determining and/or tracking the position, location, orientation and/or alignment of an object. With the position, location, orientation and/or alignment of the standalone or external computer or display monitor known, the position, location, orientation, alignment and/or direction of movement of the OHMD unit can be tracked in relationship to it, e.g. via an image and/or video capture system and/or 3D scanner integrated into or attached to the OHMD or optical markers, navigation markers including infrared markers, retroreflective markers, RF markers, LED's and/or IMU's integrated into it or attached to it. As the position, location, orientation, alignment and/or direction of movement of the OHMD unit can be tracked, the display of the OHMD unit can at all times or, if preferred, intermittently, display the same structures, or at least a portion or subset thereof, displayed by the standalone or separate computer or display monitor, spatially matched. If the standalone or separate computer or display monitor occupies only a portion of the visual field covered by the OHMD display, the OHMD display can match the displayed structures with the structures displayed by the standalone or separate computer or display monitor only for the portion of the visual field occupied by the standalone or separate computer or display monitor. Optionally, the OHMD display can display structures extending beyond the portion of the visual field occupied by the standalone or separate computer or display monitor. The structures extending beyond the portion of the visual field occupied by the standalone or separate computer or display monitor can be continuous with the structures displayed by the standalone or separate computer or display monitor. The structures outside the portion of the visual field occupied by the standalone or separate computer or display monitor can be separate and/or from the structures displayed by the standalone or separate computer or display monitor. For example, in addition to displaying one or more structures matching or corresponding to what is displayed by the standalone or separate computer or display monitor, the OHMD display can display items such as vital signs or patient demographics, or pre-operative imaging studies in those portions of the visual field that do not include the standalone or separate computer or display monitor. This can be useful when the user, operator and/or surgeon or interventionalist is not looking at the patient.

In some embodiments, the OHMD can display surgical field related information, e.g. details or aspects of a virtual surgical plan, e.g. intended/projected cut planes, or anatomic information of the patient, e.g. from a pre-operative imaging study, when the user or surgeon or interventionalist is looking at the surgical field; the OHMD can display portions of information or all of the information displayed by a standalone or separate computer or display monitor, for example in 3D while the standalone or separate computer or display monitor display can be in 2D, when the user or surgeon or interventionalist is looking at the standalone or separate computer or display monitor; the OHMD can display non-surgical field related information and non-standalone or separate computer or display monitor related or displayed information when the user or surgeon or interventionalist is neither looking at the surgical field nor at the standalone or separate computer or display monitor or when the surgical field and/or the standalone or separate computer or display monitor occupy only a portion of the visual field covered by the OHMD display. The switching or toggling between surgical field related information, standalone or separate computer or display monitor information and other information by the OHMD display can be automatic, for example via image capture and related image processing and recognition which area the user or surgeon or interventionalist is currently looking at, e.g. optionally demarcated by optical markers, navigation markers including infrared markers, retroreflective markers, RF markers, and/or LED's, or it can be via commands executed by the user or surgeon or interventionalist, e.g. voice commands or finger/keyboard commands, for example using a virtual keyboard displayed by the OHMD display.

The OHMD can display information related to the information displayed on the standalone or separate computer display or monitor in two dimensions or three dimensions, the latter stereoscopically or non-stereoscopically. Any number of combinations of displays can be applied between the display by the OHMD display and the display by the standalone or separate computer or monitor display. For example, when the computer or monitor displays shows a pre-operative or intra-operative imaging study of the patient, these can be displayed in 2D (e.g. cross-sectional) or 3D using pseudo-3D display techniques, for example with surface reconstruction and shading. Overlaying or superimposing, for example, a true 3D, e.g. stereoscopic 3D, view of the anatomy from the pre- or intra-operative imaging study and/or virtual surgical plan of the patient using the OHMD display onto the same anatomic structures and/or virtual surgical plan displayed in 2D or pseudo 3D by the standalone or separate computer or display monitor can be beneficial for the surgeon or interventionalist as he or she executes surgical plans or plans next surgical plans during a procedure.

In some embodiments, the display of the OHMD unit or the standalone or separate computer or display monitor can display functional and/or time studies of the patient, e.g. the surgeon or interventionalist moving a leg or an arm of the patient using real-time fluoroscopic imaging, while the other of the two display modalities can simultaneously display and/or superimpose static images. For example, the standalone or separate computer or display monitor can display 2D or 3D function and/or time studies, e.g. captured using real-time 2D single or biplane fluoroscopy or captured using 3D CT fluoroscopy, while the display of the OHMD unit can superimpose 2D or 3D non-stereoscopic or 3D stereoscopic images of the corresponding anatomy.

The OHMD display can optionally display some virtual data, e.g. pre-operative images and/or image reconstructions, of the patient in 2D, while it can display other virtual data, e.g. aspects or components of the virtual plan, e.g. intended cut planes, in 3D. Similarly, the OHMD display can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

The following is an exemplary list of select possible combinations of 2D, 3D non-stereoscopic and stereoscopic displays by the OHMD and 2D and pseudo 3D displays of the standalone or separate computer or display monitor. The list in Table 6 is in no way meant to be limiting of the disclosure.

Table 6: Examples of possible combinations of display modes or types by the display of the OHMD unit and the display of the standalone or separate computer or display monitor.

TABLE 6

Examples of possible combinations of display modes or types by the display of the OHMD unit and the display of the standalone or separate computer or display monitor.

| OHMD Display | | | | | Standalone or Separate Computer or Display Monitor | | | |
|---|---|---|---|---|---|---|---|---|
| 2D | 3D Non-Stereoscopic | 3D Stereoscopic | 3D Non-Stereoscopic with Function/Time | 3D Stereoscopic with Function/Time | 2D | Pseudo 3D | 2D with Function/Time | Pseudo 3D with Function/Time |
| X | | | | | X | | | |
| X | | | | | | X | | |
| X | | | | | | | X | |
| X | | | | | | | | X |
| | X | | | | X | | | |
| | X | | | | | X | | |
| | X | | | | | | X | |
| | X | | | | | | | X |
| | | X | | | X | | | |
| | | X | | | | X | | |
| | | X | | | | | X | |
| | | X | | | | | | X |

TABLE 6-continued

Examples of possible combinations of display modes or types by the display of the OHMD unit and the display of the standalone or separate computer or display monitor.

| OHMD Display 2D | 3D Non-Stereoscopic | 3D Stereoscopic | 3D Non-Stereoscopic with Function/Time | 3D Stereoscopic with Function/Time | Standalone or Separate Computer or Display Monitor | | | |
|---|---|---|---|---|---|---|---|---|
| | | | | | 2D | Pseudo 3D | 2D with Function/Time | Pseudo 3D with Function/Time |
| | | | X | | X | | | |
| | | | X | | | X | | |
| | | | X | | | | X | |
| | | | X | | | | | X |
| | | | | X | X | | | |
| | | | | X | | X | | |
| | | | | X | | | X | |
| | | | | X | | | | X |

X denotes type of display mode used

The standalone or separate computer or display monitor can optionally display some virtual data, e.g. pre-operative images and/or image reconstructions, of the patient in 2D, while it can display other virtual data, e.g. aspects or components of the virtual plan, e.g. intended cut planes, in pseudo 3D, e.g. with perspective views and shading. Similarly, the standalone or separate computer or display monitor can optionally display some virtual data, e.g. pre-operative images and/or image reconstructions, of the patient in 3D, while it can display other virtual data, e.g. aspects or components of the virtual plan, e.g. intended pin or drill placement, in 2D.

Aspects or components of the virtual surgical plan can, for example, include one or more of the following: a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device.

In an additional embodiment, the OHMD display can optionally display some of the aspects or components of the virtual surgical plan in 2D and other aspects and components in 3D, stereoscopic or non-stereoscopic. For example, the OHMD display can display a intended cut plane in 3D stereoscopic or non-stereoscopic, while it can display a virtual cut block as an outline in 2D, for example projected with a stereoscopic 3D view of the underlying tissue to be cut. The OHMD display can display a virtual surgical instrument, e.g. a reamer in 3D, e.g. stereoscopic or non-stereoscopic, and it can project the intended reaming axis in 2D or in 3D.

The standalone or separate computer or display monitor can optionally co-display some of the aspects or components of the virtual surgical plan in 2D and other aspects and components in pseudo 3D, optionally with different colors. For example, the standalone or separate computer or display monitor can display an intended cut plane in pseudo 3D, while it can display a virtual cut block as an outline in 2D, for example projected on a pseudo 3D view of the underlying tissue to be removed. The computer or display monitor can display a virtual device in pseudo 3D, and it can project its intended central axis.

The different 2D and 3D displays by the OHMD display and the standalone or separate computer or display monitor can be displayed and viewed simultaneously, in many embodiments substantially or partially superimposed. Since the user or surgeon or interventionalist can view the standalone or separate computer or display monitor through the OHMD display, the user or surgeon or interventionalist can experience a combination of 2D and 3D display information, e.g. of virtual anatomy of the patient and/or aspects of the virtual surgical plan, not previously achievable.

TABLE 7

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | Standalone or Separate Computer or Display Monitor |||||||||||||||||||| 
|---|---|---|---|---|---|---|---|---|---|---|---|---|---|---|---|---|---|---|---|---|
| | Virtual Anatomic Data of the Patient |||| Components of Virtual Surgical Plan of the Patient |||| Virtual Surgical Instruments |||| Virtual Implant or Trial Implant Components |||| Intra-Operative Imaging of the Patient ||||
| OHMD Display | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| Virtual Anatomic Data of the Patient | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | | X | | X | | X | | X | | X | | X | | X | | X | | X | |
| Components of Virtual Surgical Plan of the Patient | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | | X | | X | | X | | X | | X | | X | | X | | X | | X | |
| Virtual Surgical Instruments | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | | X | | X | | X | | X | | X | | X | | X | | X | | X | |
| Virtual Implant or Trial Implant Components | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |

TABLE 7-continued

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | Standalone or Separate Computer or Display Monitor | | | | | | | | | | | | | | | | | | | |
|---|---|---|---|---|---|---|---|---|---|---|---|---|---|---|---|---|---|---|---|---|
| | Virtual Anatomic Data of the Patient | | | | Components of Virtual Surgical Plan of the Patient | | | | Virtual Surgical Instruments | | | | Virtual Implant or Trial Implant Components | | | | Intra-Operative Imaging of the Patient | | | |
| OHMD Display | 2D | Pseudo 3D | 2D with Function/ Time | Pseudo 3D with Function/ Time | 2D | Pseudo 3D | 2D with Function/ Time | Pseudo 3D with Function/ Time | 2D | Pseudo 3D | 2D with Function/ Time | Pseudo 3D with Function/ Time | 2D | Pseudo 3D | 2D with Function/ Time | Pseudo 3D with Function/ Time | 2D | Pseudo 3D | 2D with Function/ Time | Pseudo 3D with Function/ Time |
| 3D Non-Stereoscopic with Function/Time | X | X | X | X | X | X | X | X | X | X | X | X | X | X | X | X | X | X | X | X |
| 3D Stereoscopic with Function/Time | X | X | X | X | X | X | X | X | X | X | X | X | X | X | X | X | X | X | X | X |
| Intra-Operative Imaging of the Patient | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | X | X | X | X | X | X | X | X | X | X | X | X | X | X | X | X | X | X | X |

X denotes type of display mode combinations used or possible

Virtual data of the patient including anatomy, e.g. pre-operative imaging, and/or aspects and/or components of a virtual surgical plan, and/or virtual surgical instruments and/or virtual implants or implant components and/or intra-operative imaging of the patient can be displayed using different colors, greyscale values and image intensities by the display of the OHMD unit and the display of the standalone or separate computer or display monitor.

Intra-operative imaging of the patient can include, for example, x-ray imaging, laser scanning, 3D scanning or mechanical probe scanning of an organ or a tissue. Intra-operative X-ray images, laser scans, 3D scans, mechanical probe scans, pre-operative imaging data of the patient including 2D and 3D reconstructions, aspects or components of a virtual surgical plan, virtual surgical instruments, and/or virtual implants and implant components can be displayed simultaneously and, optionally, superimposed by the display of the OHMD unit and the display of the standalone or separate computer or display monitor. If two or more imaging modalities or pre-operative and intra-operative imaging studies are co-displayed, they can optionally be anatomically matched and they can optionally be displayed using the same projection plane or, optionally, different projection planes.

If 2D views are co-displayed with 3D views or pseudo 3D views by the OHMD display alone, by the standalone or separate computer or display monitor alone, or the two together and partially or completely superimposed, the 2D views can optionally be displayed using certain standard projections, e.g. AP, lateral, oblique; the standard projection, e.g. AP, lateral and oblique, can optionally be referenced to the live data of the patient, e.g. the corresponding planes with the patient positioned on the OR table, or to the data of the patient displayed on the standalone or separate computer or display monitor. Standard projections or standard views can also include view angles from the patient's side, front, top, bottom, or oblique views.

Dynamic views or functional views, for example with two or three spatial dimensions and a time dimension can be displayed by the display of the OHMD unit and/or the display of the standalone or separate computer or display monitor, optionally superimposed onto or co-displayed with static images, e.g. 2D or 3D, by the second display unit, e.g. the display of the OHMD unit or the display of the standalone or separate computer or display monitor. Such dynamic views or functional views can include kinematic studies of an organ or a tissue, e.g. obtained with an intraoperative laser or 3D scanner, which can be used by a surgeon or interventionalist to obtain scans of the organ or tissue at different angles, e.g. 0, 10, 15, 20, 30, 40, 45, 50, 60, 70, 80, 90, 100, 110, 120, 130, 140, 150 degrees etc. Any other type of dynamic scan, which can include a time element or time dimension or a functional element or functional dimension can be displayed by the display of the OHMD unit and/or the display of the standalone or separate computer or display monitor.

In some embodiments, the display of the OHMD unit can be used for displaying lower resolution data and/or images, while the display of the display of the standalone or separate computer or display monitor can be used for displaying corresponding or matching or overlapping higher resolution data and/or images. This embodiment can be particularly useful when, for example, the maximum available display resolution of the OHMD is lower than desirable for a particular application or surgical procedure. This embodiment can also be useful, when the software environment limits, for example, the amount of surface points or nodes displayed or limits the available resolution. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in available spatial resolution for the display of the data and/or images by the OHMD. By viewing the lower resolution data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the higher resolution data and/or images on the display of the standalone or separate computer or display monitor the viewer can have the concurrent benefit of viewing the data and/or images in high resolution.

In some embodiments, the display of the OHMD unit can be used for displaying static data and/or images, while the display of the standalone or separate computer or display monitor can be used for displaying corresponding or matching or overlapping dynamic data and/or images, e.g. images demonstrating a function, e.g. a time element or dimension including a change in condition or function monitored over a time period. This embodiment can be particularly useful when, for example, the refresh rate of the OHMD display is lower than desirable for a particular application or surgical procedure. This embodiment can also be useful, when the software environment limits, for example, the amount of data and/or images displayed. This embodiment can also be useful when a WiFi or Bluetooth or other wireless connection is used for connecting the OHMD with limitations in bandwidth and/or data transmission, thereby limiting the amount of data being transmitted to the OHMD and, ultimately, displayed, in particular when this limitation implies a limitation in available temporal and/or spatial resolution for the display of the data and/or images by the OHMD. By viewing the static data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the dynamic data and/or images on the display of the standalone or separate computer or display monitor the viewer can have the concurrent benefit of viewing the dynamic data and/or images, optionally in high resolution.

In some embodiments, the display of the OHMD unit can be used for displaying a subset of the data and/or images representing a smaller portion of the field of view displayed by the standalone or separate computer or display monitor, while the display of the display of the standalone or separate computer or display monitor can be used for displaying corresponding or matching or overlapping higher data and/or images using the full intended field of view of patient data. This embodiment can, for example, be useful, when the software environment limits the amount of surface points or nodes displayed or limits the size of the data displayed by the OHMD. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD. By viewing data and/or images with a smaller, more narrow field of view through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the data and/or images with the full field of view on the display of the standalone or separate computer or display monitor the viewer can have the concurrent benefit of viewing the data and/or images using the full intended field of view of patient data. When 3D views are superimposed onto or co-displayed with 2D views by the display of the OHMD unit and the display of the standalone or separate computer or display monitor or when multiple 2D views are superimposed or co-displayed by the display of the OHMD unit and the display of the standalone or separate computer or display monitor, they can be anatomically matched, for example using corresponding landmarks and/or using common coordinates. They can also have different view angles, e.g. a view angle as the patient is positioned on the OR table, a view angle from the side, front, top, bottom, or oblique views. Thus, the OHMD display can, for example, show a stereoscopic 3D view of the patient's virtual anatomy, e.g. from a pre-operative imaging study, while the standalone or separate computer or display monitor can show a matching AP or lateral intra-operative radiographic view or a matching pseudo 3D laser view of the patient.

The matching of data displayed by the display of the OHMD unit and the display of the standalone or separate computer or display monitor can be achieved in different ways, e.g. using Matching of data and/or image using coordinates; Matching of data and/or image using content; Combinations of matching of data and/or image coordinates and data and/or image content.

In some embodiments, data and/or images displayed by the OHMD and data and/or images displayed by the standalone or separate computer or display monitor can be matched using known image coordinates and can then optionally be partially or completely superimposed, e.g. as the user and/or surgeon or interventionalist moves his or her head and/or body while looking at the standalone or separate computer or display monitor. For example, if the OHMD is registered in space, e.g. with regard to the patient and/or the surgical site and/or the standalone computer or display monitor and/or the image data displayed on the standalone computer or display monitor, data and/or images displayed by the OHMD and/or displayed by the standalone computer or display monitor can be in the same or a common coordinate system, which can allow the matching or superimposition of the display by the OHMD with the display by the standalone or separate computer or display monitor, when portions or all of the separate computer or display monitor are included in the field of view of the user or surgeon or interventionalist through the OHMD.

In some embodiments, when both the display of the OHMD and the display of the separate computer or display monitor are registered in the same coordinate system, which can include that the image data displayed by the one or more OHMDs and the image data displayed by the separate computer or display monitor are registered in the same coordinate system, the OHMD can display then a set of data and/or images at least partially matching the coordinates and/or anatomic features, e.g. in 2D or 3D, of the data and/or images of the separate computer or display monitor. For example, the OHMD can display stereoscopic 3D views that share common coordinates and/or anatomic features, e.g. in 2D or 3D, with a pseudo 3D visualization displayed by the standalone or separate computer or display monitor. Such common coordinates can, for example, be corner points or edges or select geometric features and/or locations which can be superimposed then in the resultant composite OHMD/standalone monitor view that the user or surgeon or interventionalist sees. The OHMD can also, for example, display a stereoscopic 3D view of live data of the patient or virtual data of the patient or both, while the standalone or separate computer or display monitor displays a 2D view, e.g. a pre-operative imaging study, of the patient. The 2D plane or view display by the standalone or separate computer or display monitor can have the same or common coordinates and/or anatomic features, e.g. in 2D or 3D, with the corresponding 2D plane embedded in or contained in the 3D data and/or images displayed by the OHMD which can be matched or superimposed then in the resultant composite OHMD/standalone monitor view that the user or surgeon or interventionalist sees. Alternatively, in a similar example, if the OHMD provides only a surface display, for example, the periphery or outline or select peripheral points of the 2D plane displayed by the standalone or separate computer or display monitor can have the same or common coordinates and/or anatomic features, e.g. in 2D or 3D, with corresponding surface points and/or anatomic features, e.g. in 2D or 3D, in the location corresponding to the 2D plane in the 3D data and/or images displayed by the OHMD.

The data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching. In some embodiments, the surgical table can be moved. The movement of the surgical table can translate into a comparable movement of the patient and/or the surgical site in x, y, and/or z direction. When the magnitude and direction of the table movement is known, it can be used to move the common coordinate system by a corresponding amount or direction for matching or superimposing the data and/or images displayed by the OHMD and the data and/or images displayed by the standalone or separate display monitor. For example, if the OHMD displays live data of the patient, e.g. captured through an image and/or video capture system and/or 3D scanner integrated into, attached to or separate from the OHMD, and/or virtual data of the patient and/or virtual data of the patient superimposed onto live data of the patient and the standalone or separate computer or display monitor displays a pre-operative imaging study of the patient, the surgical table and the patient can be moved and the display of the live or virtual data by the OHMD can be moved by a corresponding amount, thereby maintaining registration including registration to the data displayed on the standalone or separate computer or display monitor.

In some embodiments, the data and/or images displayed by the OHMD and the data and/or images displayed by the standalone or separate computer or display monitor can be cross-registered and, for example, moved into a shared or common coordinate system with use of an image and/or video capture system and/or 3D scanner integrated into, attached to, or separate from the OHMD, capturing the data displayed by the standalone or separate computer or display monitor. For example, the standalone or separate computer or display monitor can display data from a real-time intra-operative imaging study of the patient, including, for example, imaging during movement of the patient or surgical table or both. Standard image processing techniques can, for example, recognize anatomic landmarks or features on the data or images displayed on the standalone or separate computer or display monitor and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features. In embodiments, the process can be applied with use of an image capture or video capture system or a 3D scanner capturing the information from the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the OHMD. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the OHMD.

In embodiments, the process can be applied with use of an image capture or video capture system or a 3D scanner capturing the information from the standalone or separate computer monitor or display, by comparing, registering, matching, moving, aligning and/or superimposing images obtained in a pre-operative imaging study, e.g. displayed by the OHMD, with data and/or images acquired with an intra-operative imaging system, e.g. displayed by the standalone or separate computer monitor or display. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images obtained in a pre-operative imaging study, e.g. displayed by the OHMD, with data and/or images acquired with an intra-operative imaging system, e.g. displayed by the standalone or separate computer monitor or display.

Image processing techniques can, for example, recognize anatomic landmarks or features on the data or images acquired by the real-time imaging system and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features.

In the foregoing embodiments, the data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching.

Matching of images displayed by the OHMD and a standalone or separate computer or display monitor can also be performed by combining coordinate based matching, e.g. using the same coordinate system for both displays, and landmark based matching using any of the foregoing techniques. Someone skilled in the art will readily recognize other means of coordinate matching and landmark matching.

In some embodiments, the magnification of the items displayed by the OHMD can be adjusted so that it is reflective of, corresponds to, is smaller or larger than the magnification used by the standalone or separate computer or display monitor. Alternatively, the standalone or separate computer or display monitor can have one or more markers, e.g. one or more LED's, that an image and/or video capture system and/or 3D scanner, e.g. integrated into, attached to or separate from the OHMD, can detect which, in turn, can then trigger the adjustment of the magnification of the items displayed by the OHMD, e.g. based on the distance of the OHMD to the monitor. In some embodiments, an image and/or video capture system and/or 3D scanner integrated into, attached to or separate from the OHMD can visualize the size and shape (round, oval, ellipsoid, rectangular, square) of the standalone or separate computer or display monitor; using standard image processing techniques and geometry, the size and shape can then be used to derive the distance and angle of the OHMD relative to the standalone or separate computer or display monitor. If more than one camera is used, additional parallax information (difference in size and/or shape of the standalone or separate computer or display monitor) can be used to further estimate or improve the estimation of the distance or angle of the OHMD to the standalone or separate computer or display monitor. The resultant estimation of the distance and/or angle of the OHMD display to the standalone or separate computer or display monitor can then optionally be used to match the magnification of the data displayed by the standalone or separate computer or display monitor or to display at a higher or lower magnification than the data display by the standalone or separate computer or display monitor.

Similarly, the OHMD can detect, e.g. automatically, if the surgeon or interventionalist or operator is not looking at the standalone or separate computer or display monitor, for example, with use of an image and/or video capture system and/or 3D scanner integrated into, attached to or separate from the OHMD. The image and/or video capture system and/or 3D scanner can, for example, detect that the outline of the standalone or separate computer or display monitor (e.g. round, square, rectangular) is not present in the captured image data and the software can then automatically adjust the magnification of the items displayed by the OHMD so that it is reflective of or corresponds to the distance of the OHMD or the surgeon or interventionalist's eyes to the patient's surgical site, or is smaller or larger than that. Alternatively, a standalone or separate computer or display monitor can have one or more markers, e.g. one or more LED's or optical markers, that the image and/or video capture system and/or 3D scanner can detect; in this case, when the image captures system notices that the one or more LED's or optical markers are not included in the image capture data, the software can then automatically adjust the magnification of the items displayed by the OHMD so that it is reflective of or corresponds to the distance of the OHMD or the surgeon or interventionalist's eyes to the patient's surgical site, or is smaller or larger than that. Similarly, markers or LED's placed on the patient's surgical site can be detected by the OHMD including an image and/or video capture system and/or 3D scanner integrated into, attached to or separate from the OHMD thereby triggering an adjustment in magnification so that it is reflective of, corresponds to the distance of the OHMD or the surgeon or interventionalist's eyes to the patient's surgical site, or is smaller or larger than that when the surgeon or interventionalist or operator is looking at the patient's surgical site.

In some embodiments, the OHMD can be used to display data and/or images instead of a standalone or separate computer or display monitor. Optionally, the OHMD can replace the standalone or separate computer or display monitor. In some embodiments, the OHMD can display the live data from the patient's surgical site and project them for the surgeon or interventionalist and superimpose them with virtual data. The OHMD can also display one or more aspects or components of the virtual surgical plan, e.g. projected paths for one or more surgical instruments, or it can display one or more virtual implants or implant components. In this embodiment, the OHMD can optionally match the magnification of the one or more projected paths, and/or one or more surgical instruments and/or one or more virtual implants or implant components relative to the magnification of the live data from the patient. The OHMD can also apply a larger or smaller magnification and/or size than the magnification of the live data from the patient for the one or more projected paths and/or virtual surgical instruments, and/or one or more virtual implants or implant components. The live data of the patient can be seen through the transparent display of the OHMD. Alternatively, the display can be partially or completely opaque and the live data can be capture through an image and/or video capture system and/or 3D scanner integrated into, attached to or separate from the OHMD and then subsequently be displayed by the OHMD display.

In some embodiments, for example when the OHMD is the primary display unit, the OHMD can be non-transparent to light or minimally transparent to light reflected from the patient's surgical field and can display, for example, live (electronic) images collected by the image and/or video capture system and/or 3D scanner and, optionally, it can display, in addition, aspects or components of the virtual surgical plan, e.g. one or more projected paths for one or more physical surgical instruments, probes, pointers, and/or one or more virtual instruments and/or one or more virtual implants or implant components (optionally with various chosen matching or non-matching magnifications). In this setting, the OHMD can also display electronic images of the physical surgical instruments and or devices and their respective movements, for example captured with an image and/or video capture system and/or 3D scanner integrated into, attached to, or separate from the OHMD (with various chosen matching or non-matching magnifications).

The OHMD can be permanently non-transparent to light or minimally transparent to light reflected from the patient's surgical field. Alternatively, the degree of transparency can be variable, for example with use of one or more optical filters, e.g. polarizing light filters, in front of or integrated into the OHMD or electronic, e.g. LCD, or optical filters in front or integrated into the OHMD, or via intensity adjustments. The OR theater can optionally use light sources, e.g. polarized or filtered light that will support modulation or aid with adjustments of the transparency of the OHMD to light reflected from the patient's surgical field.

Magnified Displays

Magnified displays of the following structures and/or devices can be shown with an OHMD for example for one or more of the following, simultaneously or non-simultaneously:
  Physical anatomy (e.g. using intra-operative imaging with optional magnification or demagnification)
    Static
    Dynamic, e.g. with functional or time element or dimension
  Virtual anatomy, e.g. from pre-operative imaging study
  Aspects or components of a virtual surgical plan, e.g. a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide, or virtual device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide, or virtual device
  Virtual surgical instrument(s)
  Virtual implant(s) or implant component(s) In some embodiments, the OHMD display can display live data of the patient captured through an image and/or video capture system and/or 3D scanner integrated into, attached to or separate from the OHMD with higher magnification than the live data seen through transparent portions of the OHMD by the user's or surgeon or interventionalist's eye. Thus, the live data of the patient captured through an image and/or video capture system and/or 3D scanner integrated into, attached to or separate from the OHMD can be displayed in a magnified manner for a given distance of the OHMD display to the surgical field. This has the benefit that select structures can be seen with greater detail, for example offering a low power microscopic, magnified view of portions or all of the surgical field. The distance of the OHMD to the surgical field can be determined using techniques described in the specification, e.g. optical markers, navigation markers including infrared markers, retroreflective markers, RF markers, IMU's, LED's and any other technique known in the art. The distance of the OHMD to a separate or standalone computer monitor or display can be considered in addition to the magnification of any images displayed using the standalone computer monitor or display in order to match the structures and the magnification of the structures displayed by the separate or standalone computer monitor with the OHMD display.

The magnified display of live data can be performed while partially or completely blending out live data seen through the OHMD, e.g. with the OHMD turned partially or completely opaque to light emitted from the surgical field and primarily or only data displayed captured through the image and/or video capture system and/or 3D scanner. The magnified display of live data captured through the image and/or video capture system and/or 3D scanner can be superimposed on live data seen through one or more partially or completely transparent portions of the OHMD. In this example, the magnified display of the live data can be a portion of the surgical field seen through the OHMD. Optionally, a declining gradient of magnification can be applied to the live data so that the magnified live data can blend in seamlessly or near seamlessly with the non-magnified live data, e.g. the live data seen through one or more partially or completely transparent portions of the OHMD.

The magnification of a portion or all of the live data captured through an image and/or video capture system and/or 3D scanner can be at preset levels, e.g. 1.5×, 2.0×, 3.0×, 4.0×, or 5.0× or any other magnification level, e.g. a range from 0-1×, 0-5×, 0-10×, 0-20×. The magnification can be continuous, e.g. on a sliding scale. The magnification can be selected by the user and/or surgeon or interventionalist, for example using voice commands, eye commands or using a virtual keyboard interface displayed by the OHMD. Virtual data can optionally be displayed with the same magnification as the live data. Optionally, virtual data can be displayed with no magnification or lesser or greater magnification than live data.

In some embodiments, the OHMD display can display virtual data of the patient with higher magnification than the live data seen through transparent portions of the OHMD by the user's or surgeon or interventionalist's eye. Thus, the virtual data of the patient can be displayed in a magnified manner for a given distance of the OHMD display to the surgical field. This has the benefit that select structures or aspects of components of a virtual surgical plan can be seen with greater detail, for example offering a low power microscopic, magnified view of portions or all of the virtual data. The distance of the OHMD to the surgical field can be determined using techniques described in the specification, e.g. optical markers, navigation markers including infrared markers, retroreflective markers, RF markers, IMU's, LED's and any other technique known in the art.

The magnified display of virtual data can be performed while partially or completely blending out live data seen through the OHMD, e.g. with the OHMD turned partially or completely opaque to light emitted from the surgical field and primarily or only virtual data displayed. The magnified display of virtual data captured through the image and/or video capture system and/or 3D scanner can be superimposed on live data seen through one or more partially or completely transparent portions of the OHMD. In this example, the magnified display of the virtual data can be a portion of the surgical field seen through the OHMD. Optionally, a declining gradient of magnification can be applied to the virtual data so that the magnified virtual data can blend in seamlessly or near seamlessly with the non-magnified live data, e.g. the live data seen through one or more partially or completely transparent portions of the OHMD.

The magnification of a portion or all of the virtual data can be at preset levels, e.g. 1.5×, 2.0×, 3.0×, 4.0×, or 5.0× or any other magnification level, e.g. a range from 0-1×, 0-2×, 0-3×, 0-5×, 0-10×, 10-20×. The magnification can be continuous, e.g. on a sliding scale. The magnification can be selected by the user and/or surgeon or interventionalist, for example using voice commands, eye commands or using a virtual keyboard interface displayed by the OHMD.

Both portions or all of live data and virtual data can be displayed using magnification or no magnification. Non-limiting examples of possible magnification combinations between live data and virtual data are provided below.

TABLE 8

Exemplary, non-limiting combinations of magnifications of live data and/or virtual data.

| Virtual data | Live data, e.g. as captured by image capture system and displayed by DHMD | | | | |
| --- | --- | --- | --- | --- | --- |
| | Original size | Portions magnified | All magnified | Portions minified | All minified |
| Original size | X | X | X | X | X |
| Portions magnified | X | X | X | X | X |
| All magnified | X | X | X | X | X |
| Portions minified | X | X | X | X | X |
| All minified | X | X | X | X | X |

X denotes type of magnification mode combinations used or possible

The magnification of live data and virtual data can be the same. The magnification of live data and virtual data can be different. Virtual data can be partially, e.g. affecting only part of the displayed virtual data, or all magnified. Live data can be partially, e.g. affecting only part of the displayed live data, or all magnified. Virtual data can be magnified while live data are not magnified. Live data can be magnified while virtual data are not magnified. Any combination is possible.

The term magnification includes also displays wherein the live data or the virtual data are displayed in a format or with a magnification that is smaller than live data seen through transparent portions of the OHMD for a given distance.

The magnification can be applied around a central point, e.g. an anchor point, an anatomic landmark, a pin entry into a bone, a screw head, or central axis of the field of view of the OHMD, a pin axis or a screw axis. When a central point is used, the coordinates of the central point in the live data of the patient as seen by the surgeon or interventionalist's right eye through the OHMD unit will be the same as the view coordinates of the central point in the virtual data of the patient seen by the surgeon or interventionalist's right eye projected by the display of the OHMD unit; the coordinates of the central point in the live data of the patient as seen by the surgeon or interventionalist's left eye through the OHMD unit will be the same as the view coordinates of the central point in the virtual data of the patient seen by the surgeon or interventionalist's left eye projected by the display of the OHMD unit. When a central axis is used, the coordinates of the central axis in the live data of the patient as seen by the surgeon or interventionalist's right eye through the OHMD unit will be the same as the view coordinates of the central axis in the virtual data of the patient seen by the surgeon or interventionalist's right eye projected by the display of the OHMD unit; the coordinates of the central axis in the live data of the patient as seen by the surgeon or interventionalist's left eye through the OHMD unit will be the same as the view coordinates of the central axis in the virtual data of the patient seen by the surgeon or interventionalist's left eye projected by the display of the OHMD unit. When stereoscopic projection is used with the left and right displays of the OHMD unit, the view coordinates for the left display and the right display of the OHMD unit will be different for the left eye and the right eye; the difference in view coordinates is a reflection of the parallax. For example, when the user or surgeon or interventionalist elects to turn on magnification of live and/or virtual data, the magnification can be applied around the central point of the last unmagnified field of view. The system including its software can optionally apply the magnification automatically around the central point of the last field of view. Alternatively, the user and/or surgeon or interventionalist can use a different central point or central axis as the center around which the live and/or virtual data are being magnified. The central point or central axis can, for example, coincide with the center of a pedicle, when spinal surgery is contemplated. The central axis can coincide with an acetabular or femoral axis, e.g. an anteversion axis. The central axis can, for example, be a predetermined path. The central point can be the center of a vessel or vascular structure. The central axis can be a vascular axis. The central point, can, for example, be an endpoint. The central point or central axis for magnification can be pre-selected for various anatomic sites or surgical fields or surgeries contemplated, e.g. coiling of an aneurysm. Using, for example, one or more image and/or video capture systems and/or 3D scanner integrated into, attached to or separate from the OHMD, or using intra-operative imaging, one or more anatomic structures can optionally be identified using standard image processing techniques (e.g. the acetabulum and its center) and the central point or central axis for any magnified views can optionally be set or defined automatically.

In some embodiments, the magnification of the OHMD display can be matched with the magnification of a computer monitor, e.g. in the OR, so that corresponding tissues shown by the OHMD and/or the computer monitor are displayed using the same magnification and can, for example, be substantially aligned or superimposed between the OHMD and the computer monitor display.

Displaying Surgical Instruments and/or Medical Devices/Implantables

In some embodiments, surgical instruments or medical devices or implantables can be displayed virtually with the live data of the patient. The virtual data surgical instrument or virtual implantable can be shown by the OHMD superimposed onto the live data of the patient including the live data surgical instrument.

The OHMD can show the virtual surgical instrument or the virtual implantable indicating the desired orientation or direction or placement of the virtual surgical instrument or the virtual implantable, for example using a virtual surgical plan. Optionally, the OHMD can display directional markers such as an intended path derived from a surgical plan to help guide the surgeon or interventionalist direct the physical surgical instrument or the physical implantable.

The physical surgical instrument or physical implantable can be scanned preoperatively to derive its shape and/or dimensions for subsequent display of a derived shape or dimension of a virtual representation of the surgical instrument or the implantable by the OHMD. Alternatively, a CAD file or 3D file of the surgical instrument or the implantable can be used. Preoperative scanning of the surgical instrument or the implantable can be performed using any technique known in the art. Scanning of the surgical instrument or the implantable can be performed by the OHMD, for example using a built-in image capture device. Scanning of the surgical instrument or the implantable can be performed by a separate image capture device.

In some embodiments, scanning of the surgical instrument or the implantable can occur in two or more dimensions. The more dimensions are used typically the more accurate the resultant virtual representation of the surgical instrument or the implantable.

If an image capture device is used, e.g. one attached to or integrated into the OHMD or coupled to or separate from the OHMD, the surgical instrument or the implantable can be scanned in one, two or more projections, positions or orientation, e.g. by moving the OHMD or the surgical instrument or implantable into different positions or orientations. In some embodiments, the surgical instrument or the implantable can be placed on a tray or fixture for this purpose, which allows to move the surgical instrument or the implantable into different positions and, optionally, to rotate the surgical instrument or the implantable. In some embodiments, the distance between the surgical instrument or the implantable and the image capture device, including an image capture device attached to or integrated into the OHMD or coupled to or separate from the OHMD, is fixed, while the surgical instrument or the implantable are being scanned.

Scans of the physical surgical instrument or implantable can then be used to derive a virtual 2D or 3D representation of the surgical instrument or the implantable.

By scanning the surgical instrument or the implantable intraoperatively, the surgeon or interventionalist has great flexibility in using different surgical instruments or implantables which he can change and modify and, optionally, integrate into his physical or virtual surgical plan.

The surgeon or interventionalist can optionally store each surgical instrument or implantable that has been scanned in this manner in a virtual library of surgical instruments or implantables. The virtual surgical instruments or implantables stored in this manner can be named and stored for future use in subsequent surgical procedures in other patients. By storing the virtual surgical instruments or implantables the need for repeat scans of the same surgical instrument or same type or shape of implantable is obviated.

In some embodiments, the surgeon or interventionalist can use the virtual data of the surgical instrument or implantables that were previously generated in a new surgical plan for another, new patient. The surgeon or interventionalist can select a desired virtual surgical instrument or implantable from the virtual library and use the virtual surgical instrument or the virtual implantable in his or her virtual surgical plan.

When the surgeon or interventionalist performs the physical surgery and the OHMD displays optionally the virtual surgical instrument or implantable, optionally superimposed onto or displayed near the physical surgical instrument or implantable, the software can optionally compare the size and shape of the physical surgical instrument or implantable with that of the previously selected virtual surgical instrument or implantable. Alternatively, the surgeon or interventionalist can visually compared the size and/or shape of the virtual and the physical surgical instrument or implantable.

If a size and/or shape mismatch is detected, the software can send an alert or alarm to the surgeon or interventionalist, e.g. visual or audible, that indicates a mismatch. A mismatch can indicate to the surgeon or interventionalist that the accuracy of registration of virtual data and live data has been compromised and that re-registration may be required. A mismatch can also indicate to the surgeon or interventionalist that the wrong physical surgical instrument or implantable has been selected in comparison to the previously identified virtual surgical instrument or implantable. In this case, the surgeon or interventionalist can check the virtual surgical plan or the physical surgical plan and modify either or both, for example by selecting a different size or shape virtual or live surgical instrument or implantable.

Stereoscopic and Non-Stereoscopic 3D Display of Virtual Data of the Patient with Superimposition on Live Data of the Patient In some embodiments, the OHMD can display a virtual 2D or 3D image of the patient's normal or diseased tissue or an organ or a surgical site or target tissue with a view angle or a perspective or projection that is different for the display for the left eye compared to the display for the right eye resulting in a stereoscopic projection of the anatomy or the pathologic tissue. The virtual data of the patient is thus superimposed on the live data of the patient, e.g. the surgical site, for the left and right eye of the surgeon or interventionalist, respectively, using both the left and the right view angle for the surgeon or interventionalist. This means that two separate views are rendered from the virtual 2D or 3D data sets, one for the left eye and one for the right eye. Multidimensional views exceeding three dimensions generated for the left eye and the right eye are possible. For example, in addition to the virtual anatomy of the patient vascular flow can be displayed separately for the left eye and the right eye. The difference in perspective between the left eye and the right eye projection of virtual data or parallax can be selected or programmed so that it will change, for example, with the distance of the OHMD, the surgeon or interventionalist's head or the surgeon or interventionalist's eye in relationship to the target site, surgical site or target tissue. The distance between the surgeon or interventionalist's or operator's eyes can also be taken into account. In some embodiments, the difference in perspective or parallax will be selected or programmed so that a 3D effect is generated in a stereoscopic 3D manner or effect. The difference in perspective or parallax can change depending on any changes in the distance of the OHMD, the surgeon or interventionalist's or operator's head or the surgeon or interventionalist's or operator's eye in relationship to the target site, surgical site or target tissue. For example, as the surgeon or interventionalist or operator moves away from the target site, surgical site or target tissue, the difference in perspective or parallax can decrease. As the surgeon or interventionalist or operator moves towards the target site, surgical site or target tissue, the difference in perspective or parallax can increase. The decrease or increase can be linear, non-linear, exponential or algorithmic. Any other mathematical function is possible. In some embodiments, the difference in perspective or parallax will change similar to the change experienced by the human eye as the surgeon or interventionalist or operator moves towards or away from a target.

The distance of the OHMD, the surgeon or interventionalist's or operator's head or the surgeon or interventionalist's or operator's eye in relationship to the target site, surgical site or target tissue can be measured via image capture, anatomic landmark embodiments, image capture used in conjunction with calibration or registration phantoms, surgical navigation or any of the other embodiments described in this specification and or spatial mapping. The distance and any changes in distance of the OHMD, the surgeon or interventionalist's or operator's head or the surgeon or interventionalist's or operator's eye in relationship to the target site, surgical site or target tissue can be used to change the difference in perspective views or parallax in views for the left eye and the right eye.

FIGS. 10A and 10B are flow charts summarizing model generation, registration and view projection for one or more OHMD's, e.g. by a primary surgeon or interventionalist, second surgeon or interventionalist, surgical assistant nurse, or others. Pre-operative, intra-operative or post-operative images of the patient can be acquired 240. The image data can optionally be segmented 241. 3D reconstructions of the patient's anatomy or pathology including multiple different tissues, e.g. using different colors or shading, can be generated 242. Virtual 3D models of surgical instruments and devices components can be generated which can include their predetermined position, location, rotation, orientation, alignment and/or direction 243. The virtual 3D models can be registered, for example in relationship to the OHMD and the patient 244. The virtual 3D models can be registered relative to the live patient data 245. Optionally, adjustments can be made for different view perspectives, parallax, skin, skin movement and other tissue specific issues 246. Different perspective views can be generated for the user's left eye and right eye to facilitate a stereoscopic viewing experience, e.g. like an electronic hologram, of the virtual models of subsurface or hidden anatomic or pathologic tissues 247 and the virtual 3D models of tools, instruments, implants and devices 248. Virtual patient data 249 and virtual 3D models of tools, instruments, implants and devices 250 can be displayed in the OHMD, optionally with different view perspectives adjusted for the left and the right eye of the user 251 and 252. Left eye and right eye offsets or parallax can optionally be adjusted based on the distance from the OHMD, surgeon or interventionalist head or surgeon or interventionalist eyes to the surgical site using, for example, depth sensors or spatial mapping or other registration techniques and also based on interocular distance 253. Polarization or color techniques for stereoscopic views 254 can be combined with electronic holograms such as those provided by the Microsoft Hololens.

In an alternative description in FIG. 10C, multiple 3D models 260, 261, 262 can be generated, e.g. one for subsurface anatomic or pathologic structures of the patient, one for virtual surgical tools or instruments and one for virtual surgical implant components. These can be registered, e.g. in a common coordinate system or multiple coordinate systems using coordinate transfers, also with the OHMD 263. Using shared coordinates for the different virtual 3D models 260, 261, 262 multiple viewers using multiple OHMD's can share a 3D World 264 with projection or display of one or more of the models onto the live data of the patient 265. The display can be generated separately for the left eye of each user using the user's left eye coordinates 266 and the right eye of each user using the user's right eye coordinates 267.

Stereoscopic views or different perspective views or views with a parallax for the left eye and the right eye can be generated for multiple virtual data sets or data volumes of the patient. Any of the dimensions listed in Table 1 or virtual structures, tissues or data mentioned in the application can be displayed separately for the left eye and the right eye using stereoscopic views or different perspective views or views with a parallax, simultaneously, non-simultaneously, or sequentially. In addition, any of the virtual data in Table 9 can be displayed using stereoscopic views or different perspective views or views with a parallax for the left eye and the right eye. Multiple of the data listed in Table 9 can be displayed simultaneously, non-simultaneously or sequentially, for example also with the live data or images of the patient seen through the OHMD, stereoscopically or non-stereoscopically:

TABLE 9: Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

TABLE 9A

Exemplary virtual data of the patient that can be displayed stereoscopically or non-stereoscopically Native anatomy, e.g.
   Gyri of the brain
   Venous sinus of the brain
   Arterial structures of the brain
   Brain lesion
   Brain tumor
   Liver margin
   Liver lobes
   Spleen margin
   Kidney, renal outline
   Any tumor affecting the human body
   Vascular trees, vascular branches, vascular structures, vessels, e.g. as listed in Table 12.

TABLE 9B

Exemplary virtual surgical sites and alterations to a surgical site that can be displayed stereoscopically or non-stereoscopically Alterations planned to surgical site, e.g.
   Tissue removal
   Removal of normal tissue
   Removal of diseased tissue
   Removal of neoplastic tissue
   Drilling
   Tissue transplants
   Organ transplants
   Partial or complete resections, e.g. of organs
   Placement of a device, e.g. placement of a stent

TABLE 9C

Exemplary virtual surgical instruments and surgical steps or procedures that can be displayed stereoscopically or non-stereoscopically Tissue cutters,
   e.g. scalpels, blades, drills, saws, burrs, reamers, broaches
Tissue ablation devices
   e.g. heat or cryotherapy
Robotic arms
Instruments attached to robotic arms
Endoscopy devices
Endoscopic cameras
Endoscopic cutting devices
Endoscopic ablation devices
A predetermined surgical path or predetermined placement or position, location, rotation, orientation, alignment, or direction of one surgical instrument
A predetermined surgical path or predetermined placement or position, location, rotation, orientation, alignment, or direction of more than one surgical instrument
A predetermined surgical path or predetermined placement or position, location, rotation, orientation, alignment, or direction of more than one surgical instrument used simultaneously
A predetermined surgical path or predetermined placement or position, location, rotation, orientation, alignment, or direction of more than one surgical instrument used non-simultaneously
A predetermined surgical path or predetermined placement or position, location, rotation, orientation, alignment, or direction of more than one surgical instrument used in succession
A predetermined surgical path or predetermined placement or position, location, rotation, orientation, alignment, or direction of more than one surgical instrument not used in succession

TABLE 9D

Exemplary virtual devices that can be displayed stereoscopically or non-stereoscopically Vascular stents
  Coronary stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Carotid stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Aortic stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Femoral stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
Cochlear implants including predetermined placement or position, location, rotation, orientation, alignment, for example in relationship to osseous structures, neural structures, auditory structures, the labyrinth
Retinal implants including predetermined placement or position, location, rotation, orientation, alignment, for example in relationship to osseous structures, neural structures, vascular structures
Neural implants including predetermined placement or position, location, rotation, orientation, alignment, for example in relationship to neural structures, vascular structures, osseous structures
Neuroprosthetics including predetermined placement or position, location, rotation, orientation, alignment, for example in relationship to neural structures, vascular structures, osseous structures
Implants for deep brain stimulation, e.g. for treatment of Parkinson's disease including predetermined placement or position, location, rotation, orientation, alignment, for example in relationship to neural structures, vascular structures, osseous structures The list in Table 9 is only exemplary and is not meant to be limiting. Any of the exemplary virtual data of the patient listed in Table 9A, exemplary virtual surgical sites and alterations to a surgical site listed in Table 9B, exemplary virtual surgical instruments and surgical steps or procedures listed in Table 9C, and exemplary virtual medical devices and implants listed in Table 9D can be displayed by the OHMD in two, three or more dimensions (e.g. as described also in Table 1), using stereoscopic as well as non-stereoscopic projections or view. Thus, the embodiments are not limited to stereoscopic displays and/or 2D displays and/or 3D displays. Any combination of virtual displays is possible, e.g. 3D stereoscopic patient anatomy or surgical site with 2D surgical instrument displays and/or 2D medical device displays, or 3D patient anatomy, with 3D non-stereoscopic surgical instrument display and/or 3D stereoscopic medical device display.

Aligning or Superimposing Physical Surgical Instruments with Virtual Surgical Instruments With virtual displays of the surgical instruments in the OHMD, the surgical instruments displayed in the virtual data can be representative of the physical surgical instruments used in the live patient and can have the same projected dimensions and shape as the physical surgical instruments. As indicated in Table 9, the virtual view of the virtual surgical instrument or instruments can, for example, indicate the predetermined position, location, rotation, orientation, alignment, direction of a surgical instrument. When the physical surgical instrument is aligned with and/or superimposed onto the virtual representation of the virtual surgical instrument, the surgical step can optionally be executed or the surgeon or interventionalist can elect to make adjustments to the position, location, rotation, orientation, alignment, direction of a physical surgical instrument relative to the virtual surgical instrument, for example on the basis of a ligament tension or ligament balance, e.g. in flexion or extension. The resultant alteration of the live surgical site induced by the surgical step in the live patient is typically consistent with the virtual surgical plan, when the virtual and physical surgical instruments are superimposed in their respective position, location, rotation, orientation, alignment, or direction.

More than one surgical step can be executed in this manner, e.g. by aligning the physical surgical instruments with the corresponding virtual surgical instruments using stereoscopic or non-stereoscopic displays of virtual surgical instruments. The aligning can be performed in two dimensions, three dimensions, and more than three dimensions. The aligning can be performed with stereoscopic and non-stereoscopic displays. More than one virtual surgical step can be planned utilizing the virtual surgical plan. Two or more virtual surgical steps can be planned. The virtual surgical steps can include the major surgical steps of the intended procedure, they can include optionally sub-steps, or, optionally, the entire procedure. When the physical surgical steps are executed after aligning one or more physical instruments with the virtual instruments in the corresponding surgical steps, each surgical step using the physical instruments is effectively image guided using, optionally, the virtual surgical plan with the operator or the surgeon or interventionalist using the image guidance information, for example from a preoperative scan or imaging study obtained at a time different from the surgical procedure, typically preceding the surgical procedure, and typically with the surgical site in a different object coordinate system at the time of the preoperative imaging when compared to the time of the surgical procedure. The display of the virtual surgical instruments can be stereoscopic or non-stereoscopic.

Thus, by aligning physical surgical instruments seen through the OHMD or displayed by the OHMD with virtual surgical instruments using stereoscopic or non-stereoscopic displays of virtual surgical instruments in the OHMD, it is possible to execute accurately on a surgical plan in the live patient using pre-existing image information and image guidance information, as defined, for example, in a virtual surgical plan. In addition, by aligning physical surgical instruments seen through the OHMD or displayed by the OHMD with virtual surgical instruments using stereoscopic or non-stereoscopic displays of virtual surgical instruments in the OHMD, it is possible to achieve an predetermined position, location, rotation, orientation, alignment, direction of a medical implant including, but not limited to, for example the implants listed in Table 9D.

The OHMD can show the one or more virtual surgical instruments with a continuous surface view, for example, using one color or multiple colors for different features of the instrument. The continuous surface display can include shading based on light sources used in the operating room and/or over the surgical field. The directional orientation of the OR light sources can, for example, be measured using image capture, optionally integrated into, attached to or separate from the OHMD. The OHMD can show the one or more virtual surgical instruments with an outline view which can be in 2D or in 3D. The outline view can include an outline of the entire virtual surgical instrument, for example in a particular plane or cross-sectional plane. The outline view can optionally only highlight select features of the virtual surgical instrument, e.g. a bone cutting surface or feature or a grip feature or combinations thereof. The OHMD can show two or more outline views, for example extending through or along the surface or the periphery of the virtual surgical instrument along different planes. These planes can be chosen to be different than at a 0 or 180 degree angles to each other. In some embodiments, the outline views can be orthogonal to each other. In this manner, even though the two or more outline views can be two-dimensional, the OHMD can still provide information to the surgeon or interventionalist or the operator on the intended orientation, position and/or direction of the surgical instrument in three-dimensions by providing two or more outline views with different angular orientations and by providing information on the x, y and z-axis alignment or position or orientation or direction of the surgical instrument. Outline views can help limiting the amount of information displayed by the OHMD, which can help the surgeon or interventionalist maintaining his or her focus on the surgical site, with full visibility of the surgical site. Outline view can help decrease the risk of obscuring important live information from the patient, e.g. a bleeding vessel, by inadvertently superimposing virtual data, e.g. 3D surface data, and obscuring portions of the live anatomy.

By aligning physical surgical instruments seen through the OHMD or displayed by the OHMD with virtual surgical instruments using stereoscopic or non-stereoscopic displays of virtual surgical instruments in the OHMD, it is possible to achieve certain alterations of a surgical site or certain implant placement or implant component placement in live patients that can, for example, determine at least one of a Surgical instrument position
Surgical instrument location
Surgical instrument orientation
Surgical instrument rotation
Surgical instrument alignment
Surgical instrument direction
Depth of advancement of a surgical instrument
Device position
Device location
Device orientation
Device rotation
Device alignment
Device position of two or more implant components in relationship to each other and/or in relationship to the patient
Device location of two or more implant components in relationship to each other and/or in relationship to the patient
Device orientation of two or more implant components in relationship to each other and/or in relationship to the patient
Device rotation of two or more implant components in relationship to each other and/or in relationship to the patient
Device alignment of two or more implant components in relationship to each other and/or in relationship to the patient Anatomic or pathologic structures and/or tissue including but not limited to one or more osteophytes or bone spurs or other bony anatomy or deformity or soft-tissue or neoplastic tissue or abnormality can be used for referencing the patient both in the virtual and in the live data and for determining or cross-referencing to the other anatomy the desired instrument or implant component position, location, orientation, rotation or alignment.

Aligning or Superimposing Physical Surgical Instruments or Physical Medical Devices with Virtual Alterations to a Surgical Site The OHMD can display virtual alterations to a surgical site superimposed onto the live surgical site prior to the physical alteration of the live surgical site. The virtual alterations to a surgical can be simulated using a virtual surgical plan. The virtual surgical alterations and/or the virtual surgical plan can be executed or displayed in two, three or more dimensions, optionally with a stereoscopic or non-stereoscopic display.

In some embodiments, the OHMD can display a virtual alteration to a surgical site. The operator or the surgeon or interventionalist can then align the physical surgical instrument selected to perform the intended alteration to the physical surgical site and align the physical surgical instrument with the virtual alteration of the surgical site. The virtual alteration can, for example, be the removal or shape modification of one or more osteophytes or bone spurs or other bony anatomy or deformity or soft-tissue or neoplastic tissue or abnormality. The operator or surgeon or interventionalist can then advance or move the physical surgical instrument into the direction of or into the physical surgical site, optionally while maintaining alignment of the physical instrument with the virtual alteration of the surgical site. In this manner, the operator or the surgeon or interventionalist can effect the desired change or alteration to the surgical site in the live patient, and the change or alteration achieved in the surgical site of the live patient is typically similar to or aligned with or consistent with the intended virtual change or alteration to the surgical site and, if applicable, the virtual surgical plan.

For example, a surgeon or interventionalist can plan to make a bone cut to a distal femur of a patient. The OHMD can display the virtual bone cut superimposed onto the uncut bone of the live patient. The virtual bone cut and the intended physical bone cut can, for example, remove or correct one or more osteophytes or bone spurs or other bony anatomy or deformity or soft-tissue. The surgeon or interventionalist can then align the saw blade of the physical bone saw with the planar surface of the intended bone cut in the virtual alteration of the bone surface displayed by the OHMD. By advancing the saw blade in the direction of the cut while maintaining alignment between the physical saw blade, e.g. the flat surface of the physical saw blade, and the planar surface of the virtual bone cut, the surgeon or interventionalist can achieve an accurate physical bone cut in the live patient. Alternatively, the surgeon or interventionalist can align a cutting tool or cut block or cut guide to guide a bone saw with the planar surface of the intended bone cut in the virtual alteration of the bone surface displayed by the OHMD; the cutting tool or cut block or cut guide can then optionally be affixed to the tissue and/or bone, for example using one or more pins or screws and the cut can be performed using the cutting tool, cut block or cut guide.

In another embodiment, by aligning with or directing physical surgical instruments or medical devices towards a display of virtual alterations to a surgical site in the OHMD it is possible to achieve certain alterations of a surgical site or certain implant placement or implant component placement in live patient that can, for example, determine at least one of a
- Surgical instrument position
- Surgical instrument location
- Surgical instrument orientation
- Surgical instrument rotation
- Surgical instrument alignment
- Surgical instrument direction
- Depth of advancement of a surgical instrument, e.g. for acetabular reaming
- Device position
- Device location
- Device orientation
- Device rotation
- Device alignment
- Device position of two or more device components in relationship to each other and/or in relationship to the patient
- Device location of two or more device components in relationship to each other and/or in relationship to the patient
- Device orientation of two or more device components in relationship to each other and/or in relationship to the patient
- Device rotation of two or more device components in relationship to each other and/or in relationship to the patient
- Device alignment of two or more device components in relationship to each other and/or in relationship to the patient Optionally, the surgeon or interventionalist can toggle the display of the virtual data between a display of the surgical site prior to the alteration and/or after the alteration. Optionally, the surgeon or interventionalist can advance the display of the virtual data several surgical steps so that, for example, not the next but one or more subsequent virtual alterations to the surgical site be displayed.

Optionally, the surgeon or interventionalist can use displays with different colors for simultaneously or non-simultaneously viewing the physical, live surgical site and the virtual surgical site before and after one or more consecutive or non-consecutive virtual alterations intended or planned for the surgical site, optionally superimposed onto the live or virtual surgical site before the one or more alterations are made.

Optionally, the virtual display of the planned alteration can be superimposed onto the physical surgical site after the surgical alteration has been made to check for the accuracy of the physical alteration in the live patient. If the surgeon or interventionalist notices a discrepancy between the planned virtual alteration and the physical alteration, the surgeon or interventionalist can modify the physical alteration.

If the surgeon or interventionalist notices a discrepancy between the planned virtual alteration and the physical alteration, the surgeon or interventionalist can optionally also modify the virtual alteration to match the physical alteration induced by the patient. The virtual surgical plan can then be modified, for example for one or more of the subsequent surgical steps or procedures so that the virtual surgical plan will continue to work with the physical surgical alterations achieved with or induced in the live patient. The modification of the virtual surgical plan can be performed manually by the operator or surgeon or interventionalist, semi automatically or automatically using the input from the physical surgical alteration induced in the patient.

Aligning Physical Medical Devices (e.g. Implants) with Virtual Medical Devices (e.g. Implants)

By aligning with or directing physical medical devices or medical device components towards a display of virtually implanted medical devices or medical device components, for example in their intended final virtual position, location, orientation, rotation or alignment, in the OHMD, it is possible to achieve predetermined implant placement or implant component placement in the live patient that can, for example, determine at least one of a physical, final
- Device position
- Device location
- Device orientation
- Device rotation
- Device alignment
- Device position of two or more device components in relationship to each other and/or in relationship to the patient
- Device location of two or more device components in relationship to each other and/or in relationship to the patient
- Device orientation of two or more device components in relationship to each other and/or in relationship to the patient
- Device rotation of two or more device components in relationship to each other and/or in relationship to the patient
- Device alignment of two or more device components in relationship to each other and/or in relationship to the patient The OHMD can show the one or more virtual and, optionally, virtually implanted medical devices or medical device components with a continuous surface view, for example, using one color or with multiple colors for different features of the device or for different device components. The continuous surface display can include shading based on light sources used in the operating room and/or over the surgical field. The directional orientation of the OR light sources can, for example, be measured using image capture, optionally integrated into, attached to or separate from the OHMD.

The OHMD can show the one or more virtual and, optionally, virtually implanted medical devices or medical device components with an outline view which can be in 2D or in 3D. The outline view can include an outline of the entire virtual medical device or virtual medical device component, for example in a particular plane or cross-sectional plane. The outline view can optionally only highlight select features of the virtual medical device or virtual medical device component, e.g. a bone facing surface or a surface between two or more components facing each other, or a linking portion of the device or component or combinations thereof. The OHMD can show two or more outline views, for example extending through or along the surface or the periphery of the virtual medical device or virtual medical device component along different planes. These planes can be chosen to be different than at a 0 or 180 degree angle to each other. In some embodiments, the outline views can be orthogonal to each other. In this manner, even though the two or more outline views can be two-dimensional, the OHMD can still provide information to the surgeon or interventionalist or the operator on the intended orientation, position and/or direction of the device or device component in three-dimensions by providing two or more outline views with different angular orientations and by providing information on the x, y and z-axis alignment or position or orientation of the device or device component. Outline views can help limiting the amount of information displayed by the OHMD, which can help the surgeon or interventionalist maintaining his or her focus on the surgical site, with full visibility of the surgical site. Outline view can help decrease the risk of obscuring important live information from the patient, e.g. an exposed nerve root, by superimposing virtual data in a reduced format.

Optionally, the surgeon or interventionalist can toggle the display of the virtual data between a display of one or more of the virtual medical device components and, optionally, the live medical device components.

Optionally, the surgeon or interventionalist can use displays with different colors for simultaneously or non-simultaneously viewing the two or more virtual medical device components, optionally superimposed onto or displayed with the physical medical device.

Optionally, the virtual display of the medical device or medical device component after virtual implantation can be superimposed onto the physical medical device or medical device component after the physical implantation or placement to check for the accuracy of the physical implantation or placement in the live patient. If the surgeon or interventionalist notices a discrepancy between the planned virtual position, location, orientation, rotation, alignment of the medical device or medical device components and the physical position, location, orientation, rotation, alignment of the physical medical device or medical device components, the surgeon or interventionalist can modify the physical device placement or the surgeon or interventionalist can utilize different device components.

Visors

In some embodiments, a visor or splash shield can be integrated into the OHMD to protect the surgeon or interventionalist including his or her eyes from bodily fluids, e.g. blood. In some embodiments, a visor or splash shield can be attached to the OHMD to protect the surgeon or interventionalist including his or her eyes from bodily fluids, e.g. blood. In some embodiments, a visor or splash shield can be placed in front of the OHMD to protect the surgeon or interventionalist including his or her eyes from bodily fluids, e.g. blood.

Color Coding

Optionally, the different surgical instruments, devices or device components can be color coded during the display in the OHMD. For example, the color coding in the OHMD display will correspond to the color coding of the physical surgical instruments, devices or device components, if applicable.

The foregoing color coding is only exemplary. Any colors, combination of colors, stripes, patterns can be used for identifying different sizes, dimensions, shapes, diameters, widths or lengths. Any instrument or device can be color coded.

Color coding is applicable to any surgical instrument, medical device or medical device component, e.g. also with vascular stents, cardiac devices, cardiac defibrillators etc.

Optionally, in addition to the color coding or as an alternative to color coding, the OHMD can display one or more numerical values next to the virtual surgical instrument or medical device, e.g. a thickness or diameter or a size from a sizing chart.

In some embodiments, the OHMD can recognize if there is a discrepancy in diameter, width, length, dimension, shape, or size of a physical surgical instrument or device and a virtual device chosen in a surgical plan. For example, an image and/or video capture system and/or 3D scanner integrated into, attached to or connected to the OHMD or separate from the OHMD can be used to image a surgical instrument, medical device or medical device component, optionally correct its diameter, width, length, dimension, shape, or size based on the distance of the surgical instrument or device from the image and/or video capture system and/or 3D scanner (e.g. using parallax based measurements or registration or calibration phantoms) and then determine if the physical medical device or medical device component chosen by the operator or surgeon or interventionalist matches that selected in the virtual surgical plan. If the physical surgical instrument or medical device or medical device component is mismatched, for example with regard to diameter, width, length, dimension, shape, or size relative to the virtual instrument or component, the system can provide a warning signal, such as an acoustic alert or a visual warning sign (e.g. a red exclamation mark displayed by the OHMD).

Partially Visible or Partially Obscured Instruments, Tools, Devices In certain situations during surgery or in certain surgical sites, one or more physical surgical instruments or tools or one or more physical devices, and systems for implantation may only be partially visible during aspects or a period of the surgery. This is particular the case with surgeries involving deep seated organs, e.g. a liver or a kidney, a brain, or deep seated, obscured or hidden body structures, where important parts of one or more physical surgical instruments or tools or one or more physical devices and systems for implantation may be at least partially obscured from view. This may be aggravated if the portion that is obscured from view is a portion that is inducing one or more alteration to a tissue surface, for example by electro-cautery, ablation, cutting or reaming or impacting. This reduction or limitation in visualization of the one or more physical surgical instruments or tools or one or more physical devices and systems for implantation can result in a decreased accuracy of the surgical technique and, for example, placement errors of a device, implant, implant component or system for implantation or potential complications.

In an embodiment, one or more of the physical surgical instruments or tools and/or one or more of the physical devices and systems for implantation can include certain standardized geometric features, e.g. rectangles, triangles, circles and the like, that can be readily recognized by an image and/or video capture system and/or 3D scanner integrated into or attached to or coupled to or separate from the OHMD. Alternatively, the image and/or video capture system and/or 3D scanner may simply recognize the visible geometric shapes, surfaces, features or portions of the one or more of the physical surgical instruments or tools and/or one or more of the physical devices and systems for implantation. The information can then be used to compute the shape, geometry, outline, surface or other features of the non-visualized, non-visible portions of the one or more of the physical surgical instruments or tools and/or one or more of the physical devices and systems for implantation. With any of the foregoing techniques, the position, location, orientation, alignment, motional direction, and/or trajectory of the one or more of the surgical instruments or tools and/or one or more of the devices, implants, implant components and systems for implantation can be determined even though the one or more of the surgical instruments or tools and/or one or more of the devices, implants, implant components and systems for implantation is only partially or incompletely visualized or visible in the surgical site.

The non-visualized or non-visible portions of the one or more of the physical surgical instruments or tools and/or one or more of the physical devices and systems for implantation can then optionally be displayed by the OHMD and projected onto the view of the surgical site. Optionally, the non-visualized or non-visible portions of the one or more of the physical surgical instruments or tools and/or one or more of the physical devices and systems for implantation can be displayed by the OHMD simultaneous with the one or more of the corresponding virtual surgical instruments or tools and/or one or more of the corresponding virtual devices, implants, implant components and systems for implantation. Different colors or display patterns can optionally be used to display and differentiate the virtual from the physical of the one or more of the surgical instruments or tools and/or one or more of the devices, implants, implant components and systems for implantation in the OHMD display. In alternative embodiments, one or more of the physical surgical instruments or tools and/or one or more of the physical devices and systems for implantation can include one or more IMU's, including, for example, with accelerometers, magnetometers, and gyroscopes, similar, for example, to the OHMD. In some embodiments, one or more of the physical surgical instruments or tools and/or one or more of the physical devices and systems for implantation can include one or more radiofrequency tags or markers or retroreflective markers and the like and its/their position, location and/or orientation can be captured by a surgical navigation system. Optionally, the OHMD may also include one or more radiofrequency tags or markers or retroreflective markers and the like and its position, location and/or orientation can also be captured by the surgical navigation system and cross-referenced to the one or more of the physical surgical instruments or tools and/or one or more of the physical devices and systems for implantation. One or more of the physical surgical instruments or tools and/or one or more of the physical devices and systems for implantation can also include light sources, such as lasers or LED's. A laser can be projected, for example, on a wall or a ceiling and the OHMD and the patient can be referenced in relationship to that. An LED attached to or integrated into the one or more of the physical surgical instruments or tools and/or one or more of the physical devices and systems for implantation can be recognized, for example, by an image and/or video capture system and/or 3D scanner integrated into or attached to or coupled to or separate from the OHMD.

With any of the foregoing techniques, the position, location, orientation, alignment, motional direction, and/or trajectory of the one or more of the physical surgical instruments or tools and/or one or more of the physical devices and systems for implantation can be determined even though the one or more of the physical surgical instruments or tools and/or one or more of the physical devices and systems for implantation is only partially or incompletely visualized or visible in the surgical site. A computer program or software can then optionally compute the shape, geometry, outline, surface of other features of the non-visualized, non-visible portions of the one or more of the physical surgical instruments or tools and/or one or more of the physical devices and systems for implantation. The non-visualized or non-visible portions of the one or more of the physical surgical instruments or tools and/or one or more of the physical devices and systems for implantation can then optionally be displayed by the OHMD and projected onto the view of the surgical site. Optionally, the non-visualized or non-visible portions of the one or more of the physical surgical instruments or tools and/or one or more of the physical devices and systems for implantation can be displayed by the OHMD simultaneous with the one or more of the corresponding virtual surgical instruments or tools and/or one or more of the corresponding virtual devices, implants, implant components and systems for implantation. Different colors or display patterns can optionally be used to display and differentiate the virtual from the physical of the one or more of the surgical instruments or tools and/or one or more of the devices, implants, implant components and systems for implantation in the OHMD display.

Difficult Lighting and Tissue Contrast Conditions

In certain situations during surgery or in certain surgical sites, the lighting conditions and tissue contrast may be such that any virtual anatomic data or structures, virtual surgical plans, virtual tool or instrument or device paths, virtual surgical instruments or tools and/or any virtual devices, implants, implant components and systems for implantation may be difficult to see in the OHMD display by the human operator. In any of these circumstances, the system can optionally allow the operator or the surgeon or interventionalist to change the display mode or it can actively change the display mode of one or more the virtual anatomic data or structures, virtual surgical plans, virtual tool or instrument or device paths, virtual surgical instruments or tools and/or the virtual devices, implants, implant components and systems for implantation, for example by changing the color, brightness, intensity, and/or contrast of one or more of the virtual anatomic data or structures, virtual surgical plans, virtual tool or instrument or device paths, virtual surgical instruments or tools and/or the virtual devices, implants, implant components and systems for implantation. Different changes in color, brightness, intensity, and/or contrast can be applied to different virtual data, e.g. virtual anatomic data or structures, virtual surgical plans, virtual tool or instrument or device paths, virtual surgical instruments or tools and/or the virtual devices, implants, implant components and systems for implantation.

The surgeon or interventionalist or operator or the software or the system may change the color of one or more of the virtual anatomic data or structures, virtual surgical plans, virtual tool or instrument or device paths, virtual surgical instruments or tools and/or the virtual devices, implants, implant components and systems for implantation. The surgeon or interventionalist or operator or the software or the system may change the brightness of one or more of the virtual anatomic data or structures, virtual surgical plans, virtual tool or instrument or device paths, virtual surgical instruments or tools and/or the virtual devices, implants, implant components and systems for implantation. The surgeon or interventionalist or operator or the software or the system may change the intensity of one or more of the virtual anatomic data or structures, virtual surgical plans, virtual tool or instrument or device paths, virtual surgical instruments or tools and/or the virtual devices, implants, implant components and systems for implantation. The surgeon or interventionalist or operator or the software or the system may change the contrast of one or more of the virtual anatomic data or structures, virtual surgical plans, virtual tool or instrument or device paths, virtual surgical instruments or tools and/or the virtual devices, implants, implant components and systems for implantation. The surgeon or interventionalist or the operator or the software or the system may change the display pattern of the one or more of the virtual anatomic data or structures, virtual surgical plans, virtual tool or instrument or device paths, virtual surgical instruments or tools and/or the virtual devices, implants, implant components and systems for implantation. For example, one or more of the virtual anatomic data or structures, virtual surgical plans, virtual tool or instrument or device paths, virtual surgical instruments or tools and/or the virtual devices, implants, implant components and systems for implantation may be displayed with a raster pattern or a line pattern or a point pattern or any other display pattern known in the art. Alternatively, one or more of the virtual anatomic data or structures, virtual surgical plans, virtual tool or instrument or device paths, virtual surgical instruments or tools and/or the virtual devices, implants, implant components and systems for implantation may be displayed with a temporally changing display pattern, including, but not limited to a blinking pattern or a flashing pattern, e.g. with only intermittent display of the virtual information. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "skeletonization pattern", wherein, for example, only key features or key outlines of one or more of the virtual anatomic data or structures, virtual surgical plans, virtual tool or instrument or device paths, virtual surgical instruments or tools and/or the virtual devices, implants, implant components and systems for implantation can be displayed. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "highlighting pattern" or mode, wherein, for example, key features or key outlines of one or more of the virtual anatomic data or structures, virtual surgical plans, virtual tool or instrument or device paths, virtual surgical instruments or tools and/or the virtual devices, implants, implant components and systems for implantation may be displayed using an enlargement of the feature or outline or a color or brightness or contrast or other display enhancement of the feature or outline. Optionally, less important features or outline components or portions may be reduced in display intensity or removed from the display. The foregoing display adjustments can be performed via operator controlled commands, e.g. manual or voice or other commands. Alternatively, these adjustments can be semi-automatic with operator input or automatic using, for example, information about brightness, contrast and/or color of the virtual and/or the live data of the patient as well as ambient light conditions, e.g. OR light intensity, light reflections, etc. For semi-automatic or automated adjustment of the display of select, one or more virtual data, e.g. virtual anatomic data or structures, virtual surgical plans, virtual tool or instrument or device paths, virtual surgical instruments or tools and/or the virtual devices, implants, implant components and systems for implantation, light intensity and contrast sensors can be employed which can optionally be integrated into, attached to or separate from one or more OHMDs. Alternatively, the information about color, brightness, intensity, contrast of the live data seen through the OHMD and/or ambient lighting conditions can be obtained through one or more image and/or video capture systems and/or 3D scanner integrated into, attached to or separate from the OHMD.

Any of the foregoing changes to the display of virtual anatomic data or structures, virtual surgical plans, virtual tool or instrument or device paths, surgical instruments or tools and/or the devices, implants, implant components and systems for implantation can also be applied to any partially obscured or non-visible portions of the physical surgical instruments or tools and/or the physical devices and systems for implantation.

Any of the virtual anatomic data or structures, virtual surgical plans, virtual tool or instrument or device paths, surgical instruments or tools and/or the devices, implants, implant components and systems for implantation described herein can be modified in the display using one or more of these techniques or any other technique of display modification known in the art.

In certain situations during surgery or in certain surgical sites, the lighting conditions and tissue contrast may be such that any obscured portions of the anatomy or obscured pathology or obscured target tissue(s) or deep seated, obscured or hidden portions of the anatomy or target tissue(s) or intended alterations to deep seated tissue(s) may be difficult to see in the OHMD display by the human operator. This includes also normal tissue and normal anatomic structures, hidden or obscured or deep seated. In any of these circumstances, the system can optionally allow the operator or the surgeon or interventionalist to change the display mode or the system can actively change the display mode of the anatomy or deep seated portions of the anatomy or target tissue(s) or intended alterations to deep seated, obscured or hidden tissue(s). For example, the surgeon or interventionalist or operator may change the color of the anatomy or deep seated, obscured or hidden portions of the anatomy or target tissue(s) or intended alterations to deep seated, obscured or hidden tissue(s). Alternatively, the surgeon or interventionalist or the operator may change the display pattern of the anatomy or deep seated, obscured or hidden portions of the anatomy or target tissue(s) or intended alterations to deep seated, obscured or hidden tissue(s). For example, the anatomy or deep seated, obscured or hidden portions of the anatomy or target tissue(s) or intended alterations to deep seated, obscured or hidden tissue(s) may be displayed with a raster pattern or a line pattern or a point pattern or any other display pattern known in the art. Alternatively, the anatomy or deep seated, obscured or hidden portions of the anatomy or target tissue(s) or intended alterations to deep seated, obscured or hidden tissue(s) may be displayed with a temporally changing display pattern, including, but not limited to a blinking pattern or a flashing pattern, e.g. with only intermittent display of the information. Alternatively, the anatomy or deep seated, obscured or hidden portions of the anatomy or target tissue(s) or intended alterations to deep seated, obscured or hidden tissue(s) may be displayed with a "skeletonization pattern", wherein, for example, only key features or key outlines of the anatomy or deep seated, obscured or hidden portions of the anatomy or target tissue(s) or intended alterations to deep seated, obscured or hidden tissue(s) may be displayed.

Alternatively, the anatomy or deep seated, obscured or hidden portions of the anatomy or target tissue(s) or intended alterations to deep seated, obscured or hidden tissue(s) may be displayed with a "highlighting pattern" or mode, wherein, for example, key features or key outlines of the anatomy or deep seated, obscured or hidden portions of the anatomy or target tissue(s) or intended alterations to deep seated, obscured or hidden tissue(s) may be displayed using an enlargement of the feature or outline or a color or brightness or contrast or other display enhancement of the feature or outline. Optionally, less important features or outline components or portions may be reduced in display intensity or removed from the display. Any of the tissues described herein, such as by way of example, a cerebral cortex, gyri, a pedicle, vertebral endplates, an anterior vertebral wall, a posterior vertebral wall, an acetabulum, vessels, nerves, tumors, can be modified in the display using one or more of these techniques or any other method of display modification known in the art.

Any of the foregoing adjustments in color, brightness, intensity, and/or contrast can be applied to 2D or 3D, stereoscopic and non-stereoscopic displays of one or more of the virtual anatomic data or structures, virtual surgical plans, virtual tool or instrument or device paths, virtual surgical instruments or tools and/or the virtual devices, implants, implant components and systems for implantation. If live data of the patient are not directly seen through the OHMD, but are captured through an image and/or video capture system and/or 3D scanner integrated into, attached to or separate from the OHMD and then displayed by the OHMD, optionally in combination with virtual anatomic data or structures, virtual surgical plans, virtual tool or instrument or device paths, virtual surgical instruments or tools and/or the virtual devices, implants, implant components and systems for implantation, the same or similar adjustments can be applied to one or more of the live data of the patient, e.g. select anatomic structures, or all of the live data of the patient.

In some embodiments, the virtual surgical plan incorporates data from a pre-operative scan. In some embodiments, the virtual surgical plan incorporates data from an intra-operative scan. In some embodiments, the virtual surgical plan incorporates data from a pre-operative scan and an intra-operative scan. The scan includes one or more x-rays, a CT scan, an MRI scan, an ultrasound or combinations thereof.

In some embodiments, the scan data are registered in the common coordinate system. In some embodiments, the registered scan data are displayed superimposed onto the surgical site by the optical head mounted display. In some embodiments, the scan data include a three-dimensional display of the surgical site.

In some embodiments, the registering step includes identifying one or more landmarks in the live surgical site. In some embodiments, one or more corresponding anatomic landmarks are identified in the patient's scan data.

In some embodiments, the registering step includes identifying one or more anatomic axes or biomechanical axes in the live surgical site. In some embodiments, the one or more corresponding anatomic axes or biomechanical axes are identified in the patient's scan data. In some embodiments, the registering step includes detecting one or more optical markers attached to one or more structures in the live surgical site. In some embodiments, the registering step includes detecting one or more optical markers attached to the OR table. In some embodiments, the detecting of the one or more optical markers includes determining one or more of a position, orientation, alignment, direction of movement or speed of movement of the one or more optical markers.

The optical marker can include a geometric pattern, a QR code, a barcode or combinations thereof. The QR code or barcode can be included in or integrated into or attached to the geometric pattern. In some embodiments, the optical head mounted display includes one or more cameras or image capture or video capture systems and/or 3D scanner. The one or more cameras or image capture or video capture system and/or 3D scanner s can detect the one or more optical markers including their coordinates (x, y, z).

In some embodiments, the optical marker includes information about implant inventory management. For example, the QR code can include information about implant inventory management.

In some embodiments, the one or more cameras or image capture or video capture systems and/or 3D scanner included in the optical head mounted display reads the inventory management in the QR and transmits it to another computer.

In some embodiments, the intraoperative measurement includes identifying coordinates (x, y, z) of a live anatomic landmark in the patient's organ or tissue using one or more optical markers. In some embodiments, the intraoperative measurement includes identifying coordinates (x, y, z) of an anatomic landmark in the intra-operative scan data.

In some embodiments, the one or more optical markers are radiopaque and their coordinates (x, y, z) can be detected in the intra-operative scan data.

In some embodiments, the optical markers are detected using the one or more cameras or image capture or video capture systems and/or 3D scanner included in the optical head mounted display and detected in the intra-operative scan data are registered in the common coordinate system.

In some embodiments, the intraoperative measurement includes obtaining information from a surgically altered surface.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane can be found by placing a virtual plane to be tangent with or intersect with one or more anatomic landmarks. The virtual plane can be placed using a virtual interface. In some embodiments, the virtual surgical plan includes predetermined path for a surgical instrument. In some embodiments, the virtual surgical plan includes a projected or intended cut plane. In some embodiments, the virtual surgical plan includes a virtual cut block projected in a desired or intended position, orientation and/or alignment. In some embodiments, the virtual surgical plan includes a projected or intended reaming, milling or impacting axis. In some embodiments, the virtual surgical plan includes a virtual surgical instrument displayed or projected in a desired or predetermined position, orientation, alignment and/or direction of movement. In some embodiments, the virtual surgical plan includes a virtual device displayed or projected in a desired or predetermined position, orientation and/or alignment.

In some embodiments, the scan data is obtained pre-operatively and/or intra-operatively. In some embodiments, the scan data include pre-operative and intra-operative scan data. In some embodiments, the scan data include one or more x-rays, a CT scan, an MRI scan, an ultrasound or combinations of the foregoing.

In some embodiments, the scan data are registered in the common coordinate system. In some embodiments, the registered scan data are displayed superimposed onto the surgical site by the optical head mounted display.

In some embodiments, the scan data include a three-dimensional display of the surgical site.

In some embodiments, the registering includes identifying one or more anatomic landmarks in the patient's scan data. In some embodiments, the registering includes identifying one or more corresponding landmarks in the live surgical site. In some embodiments, the registering includes identifying one or more anatomic axes or biomechanical axes in the patient's scan data. In some embodiments, the registering includes identifying one or more corresponding anatomic axes or biomechanical axes in the live surgical site.

In some embodiments, the registering includes detecting one or more optical markers attached to one or more structures in the live surgical site. In some embodiments, the registering includes detecting one or more optical markers attached to the OR table. In some embodiments, the detecting of the one or more optical markers includes determining one or more of a position, orientation, alignment, direction of movement or speed of movement of the one or more optical markers. The optical marker can include a geometric pattern, a QR code, a barcode or combinations thereof. The QR code or barcode can be included in or integrated into or attached to the geometric pattern. In some embodiments, the optical head mounted display includes one or more cameras or image capture or video capture systems and/or 3D scanner. The one or more cameras or image capture or video capture systems and/or 3D scanner can detect the one or more optical markers including their coordinates (x, y, z). In some embodiments, the optical marker includes information about implant inventory management. For example, the QR code can include information about implant inventory management. In some embodiments, the QR code includes information about implant inventory management. In some embodiments, the one or more cameras or image capture or video capture systems and/or 3D scanner included in the optical head mounted display reads the inventory management in the QR and transmits it to another computer. In some embodiments, the one or more optical markers are radiopaque and their coordinates (x, y, z) can be detected in the intra-operative scan data.

In some embodiments, the optical markers are detected using the one or more cameras or image capture or video capture systems and/or 3D scanner included in the optical head mounted display and detected in the intra-operative scan data are registered in the common coordinate system.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane is found by placing a virtual plane to be tangent with or intersect with one or more anatomic landmarks. The virtual plane can be placed using a virtual interface. In some embodiments, the intraoperative measurement includes obtaining information from a surgically altered surface.

In some embodiments, the adjusting or modifying the virtual surgical plan includes placing or moving a predetermined path for a surgical instrument. In some embodiments, the adjusting or modifying the virtual surgical plan includes the placing or moving of a virtual cut plane. In some embodiments, the adjusting or modifying the virtual surgical plan includes the placing or moving of a virtual cut block. In some embodiments, the adjusting or modifying the virtual surgical plan includes the placing or moving of a virtual reaming, milling or impacting axis. In some embodiments, the adjusting or modifying the virtual surgical plan includes the placing or moving of a virtual surgical instrument. In some embodiments, the adjusting or modifying the virtual surgical plan includes the placing or moving of a virtual surgical implant component.

According to some aspects, the method for preparing a procedure in a patient comprises registering the patient's surgical site and one or more]optical head mounted displays worn by a surgeon or interventionalist or surgical assistant in a common coordinate system, wherein the registration of the patient's surgical site in the common coordinate system is performed using one or more optical markers attached to the patient in or around the surgical site, wherein the optical marker includes one or more geometric patterns, wherein the optical markers are detected with a camera, an image capture or video system integrated into, attached to or separate from the optical head mounted display. In some embodiments, the optical marker includes at least one portion that is radiopaque. In some embodiments, internal structures of the patient or the surgical site are visualized using an imaging test with ionizing radiation. For example, the imaging test can be one or more x-rays and/or a CT scan.

In some embodiments, the radiopaque portions of the optical marker are detected on the imaging test using image processing software. In some embodiments, the radiopaque portions of the optical marker detected on the imaging test are cross-referenced with the visible portions of the optical marker detected with the camera, image capture or video system and wherein the information is used to register the internal structures of the patient or the surgical site in the common coordinate system.

In some embodiments, the optical head mounted display displays the internal structures of the patient or the surgical site superimposed onto the corresponding external surfaces of the patient or the surgical site. In some embodiments, the optical head mounted display superimposes a virtual surgical plan onto the corresponding external and internal structures.

The virtual surgical plan can be a predetermined path for a surgical device.

Throughout the specification, any embodiment described for one anatomic region can be applied to other anatomic regions, any imaging study including combination of imaging studies, e.g. vascular imaging studies, angiography, intracardiac imaging, echocardiography, any functional study including combinations of functional studies, e.g. intraventricular or electrophysiologic mapping, all of the foregoing in 2D, 3D, 4D or multiple dimensions.

In some embodiments, when a physical guide, tool, instrument or implant is aligned with or superimposed onto a virtual surgical guide, tool, instrument or implant displayed or projected by the OHMD, the aligning or superimposing can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, x, y, z. When the physical guide, tool, instrument or implant is aligned with or superimposed onto the virtual surgical guide, tool, instrument or implant displayed or projected by the OHMD, the aligning or superimposing can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

Registration Techniques

Anatomic landmarks can be detected and/or identified using pointers, e.g. with one or more attached optical markers, e.g. with geometric patterns, one or more navigation markers, one or more IMU's, one or more reference or calibration phantoms etc. Pointers or pointing devices can also be imaged and/or detected using optical imaging systems and/or 3D scanners.

Pointers or pointing devices and any other instruments including vascular instruments or devices can be tracked, e.g. using one or more optical markers, e.g. using geometric patterns, LED's, IMU's, navigation markers, e.g. RF or infrared markers, calibration and/or reference phantoms. The one or more optical markers, e.g. using geometric patterns, LED's, IMU's, navigation markers, e.g. RF or infrared markers, calibration and/or reference phantoms can be integrated into or attached to pointers or pointing devices and any other instruments including vascular instruments or devices. The one or more one or more optical markers, e.g. using geometric patterns, IMU's, navigation markers, e.g. RF or infrared markers, calibration and/or reference phantoms can be located outside the patient's body, e.g. external to a portal or vascular access, a surgical access or the patient's skin. The one or more optical markers, e.g. using geometric patterns, LED's IMU's, navigation markers, e.g. RF or infrared markers, calibration and/or reference phantoms can be located inside the patient's body. One or more optical markers, e.g. using geometric patterns, IMU's, navigation markers, e.g. RF or infrared markers, calibration and/or reference phantoms can be located both outside the patient's body, e.g. external to a portal, a surgical access or the patient's skin, and inside the patient's body, e.g. inside a cavity. In embodiments, it can be advantageous to track the one or more optical markers, e.g. using geometric patterns, LED's IMU's, navigation markers, e.g. RF or infrared markers, calibration and/or reference phantoms only outside the patient's body, e.g. when no optical imaging system and/or 3D scanner is available inside the patient's body or when an optical imaging system and/or 3D scanner is active with other tasks. In embodiments, it can be advantageous to track the one or more optical markers, e.g. using geometric patterns, LED's IMU's, navigation markers, e.g. RF or infrared markers, calibration and/or reference phantoms only inside the patient's body. In embodiments, it can be advantageous to track the one or more optical markers, e.g. using geometric patterns, LED's IMU's, navigation markers, e.g. RF or infrared markers, calibration and/or reference phantoms inside and outside the patient's body.

A navigation system can track navigation markers attached to one or more pointers or pointing devices and any other instruments including vascular instruments or devices. With the geometry of the one or more pointers or pointing devices and any other instruments including vascular instruments or devices known and the position, location and or orientation of the one or more navigation markers on the pointers or pointing devices and any other instruments including vascular instruments or devices known, the location, position, orientation, direction and/or coordinates of the tip or of other portions and/or geometries of the one or more pointers or pointing devices and any other instruments including vascular instruments or devices can be tracked outside and/or inside the patient's body, also in relationship to one or more target tissues and/or virtual surgical plans.

One or more optical imaging systems and/or 3D scanners can track one or more optical markers, e.g. with one or more geometric patterns, LED's, calibration and/or reference phantoms and/or reference marks (e.g. depth marks on the surface of a vascular instrument or device, e.g. starting at tip, and/or outside the skin) attached to or integrated into one or more pointers or pointing devices and any other instruments.

In embodiments, it can be advantageous to track the one or more optical markers, e.g. using geometric patterns, LED's IMU's, navigation markers, e.g. RF or infrared markers, calibration and/or reference phantoms both outside and inside the patient's body. In this example, the tracking data obtained outside the patient's body can be compared with the tracking data obtained inside the patient's body. Any differences in measured coordinates of the one or more pointers or pointing devices and any other instruments can be determined. If these differences exceed, for example, a threshold value, e.g. greater than 0.5, 1.0, 1.5, 2.0 mm or degrees in x, y and/or z-direction or angular orientation, it can trigger an alert. An alert can, for example, suggest to repeat the registration outside the patient's body, inside the patient's body or both. Any differences in coordinates of the one or more pointers or pointing devices and any other instruments including measured inside the patient's body as compared to measured outside the patient's body can optionally also be reconciled using, for example, statistical methods, e.g. using means, weighted means, medians, standard deviations etc. of measured coordinates.

One or more optical markers, e.g. using geometric patterns, LED's, navigation markers, e.g. RF, infrared markers, or IMU's, calibration and/or reference phantoms can also be attached to an optical imaging system and/or a 3D scanner for tracking the position, orientation, alignment, direction of travel and/or coordinates of the optical imaging system and/or 3D scanner. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located inside the patient's body. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located outside the patient's body, e.g. external to the target tissue, external to the surgical field, and/or external to the patient's skin. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located outside the patient's body and inside the patient's body. For example, when the optical imaging system and/or 3D scanner is moveable, e.g. inside the patient's body, outside the patient's body and/or both, the position of the optical imaging system and/or 3D scanner can also be tracked, e.g. using additional optical imaging systems and/or 3D scanners, which can also be inside the patient's body, outside the patient's body and/or both inside and outside the patient's body, and which can optionally be stationary. Similarly, when the optical imaging system and/or 3D scanner is moveable, e.g. inside the patient's body, outside the patient's body and/or both, the position of the optical imaging system and/or 3D scanner can also be tracked, e.g. using a navigation system, which can be stationary. By monitoring and/or tracking the position, orientation, alignment, direction of travel and/or coordinates of an optical imaging system and/or 3D scanner, the accuracy of any coordinate measurements and/or 3D surface measurements and/or any measurements of optical markers, LED's, IMU's, calibration and/or reference phantoms can be improved in embodiments. In embodiments, tracking the one or more optical imaging systems and/or 3D scanners outside and/or inside the patient's body (or any structure of the human body, e.g. an abdominal cavity, a lumen etc.) can be useful for directing the optical imaging system and/or 3D scanner to a desired location, for example for real-time imaging of a lesion or pathologic area with optional surgical intervention. In embodiments, tracking the one or more optical imaging systems and/or 3D scanners outside and/or inside the patient's body (or any other structure of the human body, e.g. an abdominal cavity, a lumen etc.) can be useful for improving the accuracy of any registration and/or tracking of surgical instruments and/or virtual sizing, fitting, aligning, placement of virtual implant components.

Surface Generation, Surface Registration

In embodiments, a virtual 3D model of the patient's anatomy, e.g. a target site and/or target tissue, can be generated from an imaging study, e.g. an x-ray, a CT scan, an MRI scan, a PET scan, a SPECT scan, a PET/CT scan, a SPECT/CT scan, an ultrasound. In embodiments, one or more x-rays can be used to generate and/or select a virtual 3D model of the patient.

Software Components to Display Virtual Model(s) Overlaid with the Live View of the Patient Using One or More OHMDs The markers attached to a first and/or a second articular surface and/or associated structures and/or the intra-articular 3D surfaces generated with the optical imaging system and/or 3D scanner can be continuously or intermittently tracked using, for example, an intra-articular optical imaging system and/or 3D scanner (which can also be tracked in a common coordinate system) and, using, for example, the spatial relationship between the virtual 3D model and the intra-articular markers and/or the intra-articular 3D surface as described in the preceding sections, the position and/or orientation of the display of the virtual 3D model, e.g. a 3D reconstruction of a CT or MRI scan or a 3D model generated based on x-rays, or other virtual data, e.g. or display of a virtual anchor, or a display of a virtual lesion, e.g. a bone marrow edema like lesion, can be overlaid onto and superimposed with the live anatomy of the patient and can be updated in real time. The overlaying and superimposition can be on the live physical anatomy of the patient and/or on a computer monitor, e.g. a computer monitor that displays images obtained from inside the patient's body, using, for example, the methods and techniques described in various parts of the specification including the section entitled "Viewing 2D Computer Monitors through an OHMD Unit". For example, when the surgeon or interventionalist looks at the patient, the virtual data can be superimposed onto and aligned with the patient's body without magnification using the OHMD. When the surgeon or interventionalist looks at the images of the patient's body on a 2D computer monitor, the virtual data can be superimposed onto and aligned with the displayed structures matching the monitor and/or display magnification of the displayed images.

The foregoing techniques and the embodiments of the specification can be applied to any number of vascular, cardiac, neurologic, cardiovascular or urologic applications.

Optical Markers

Data were obtained using an OHMD manufactured by Microsoft, the Microsoft Hololens (Microsoft, Redmond, WI). The Hololens can use, for example, Windows holographic APIs including Unity (Unity Technologies, San Francisco, CA) and Vuforia 6.2 (PTC, Inc., Needham, MA).

Registration of Optical Markers Using Microsoft Hololens and Vuforia 6.2

Figure 11:
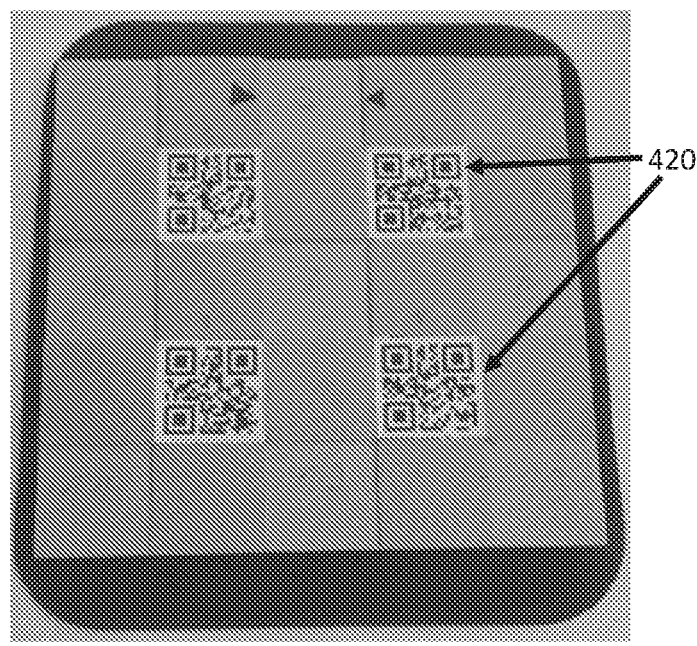
FIG. 11 shows a wooden board with 25 squares and four 4.0×4.0 cm optical markers.
Figure 12:
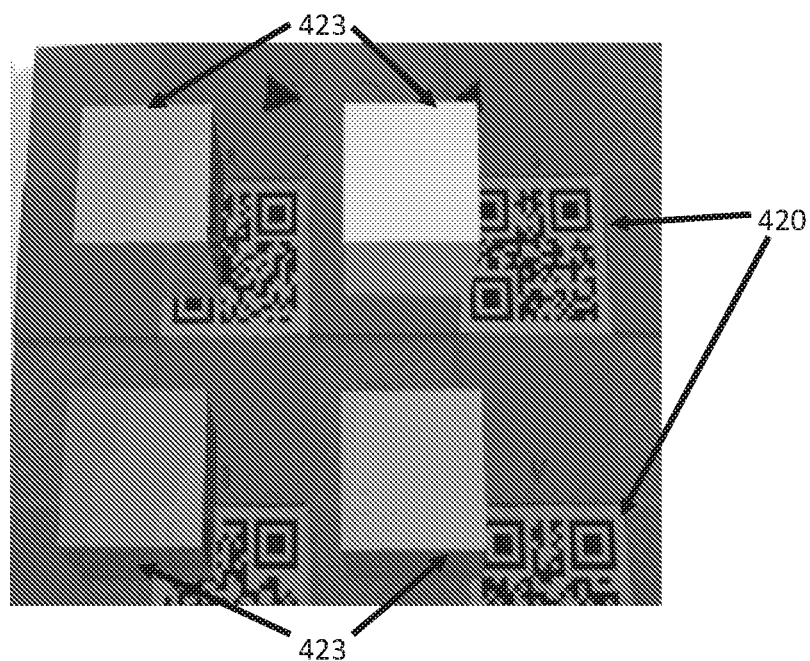
FIG. 12 shows an illustrative, non-limiting example of registration of four cubes in relationship to four optical markers using the image capture system of an OHMD.

FIG. 11 shows a wooden board with 25 squares which was prepared and four 4.0×4.0 cm optical markers 420 with four distinct QR codes were applied in equidistant locations, 4.0 cm apart. As seen in FIG. 12, a software routine was implemented to project four cubes 423 with dimensions of 4.0×4.0×4.0 cm superimposed onto the squares and to maintain registration over the squares irrespective of head movement. The results are shown in FIG. 12. The Microsoft Hololens was not able to maintain registration of the four cubes over the designated optical markers; the cubes were at times displaced by as much as 3-4 cm and were also tilted.

Registration of Optical Markers Using Hololens and OpenCV 2.4

Figure 13:
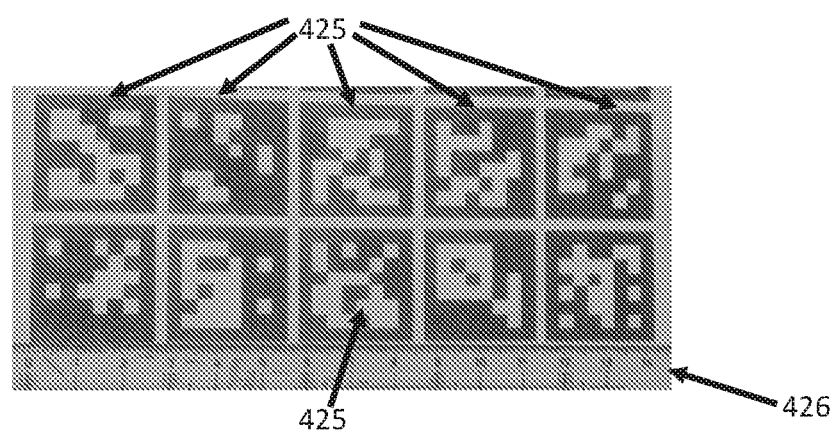
FIG. 13 shows an illustrative, non-limiting example of optical markers.
Figure 14:
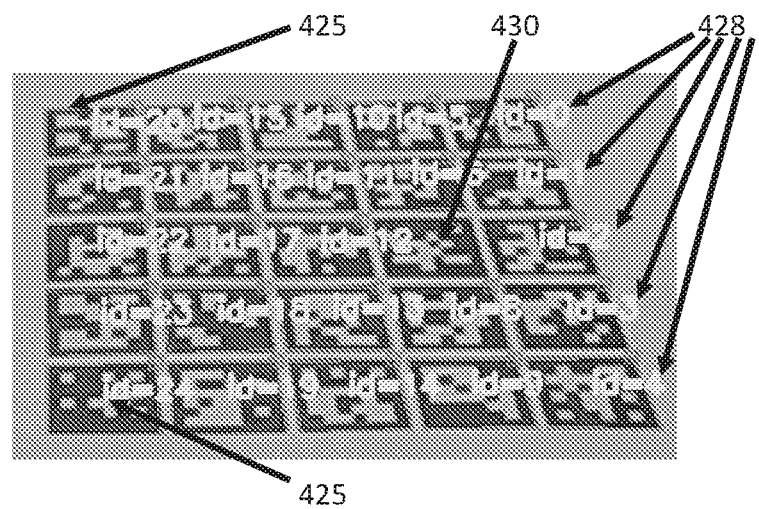
FIG. 14 shows an illustrative, non-limiting example of detection of optical markers using the image capture system of an OHMD.

OpenCV 2.4, an open source computer vision framework (Intel Inc., Santa Clara, CA), was implemented on the Hololens system using OpenCVForUnity. 25 As seen in FIG. 13, ArUco markers 425 available with OpenCV with a size of 2.8×2.8 cm were arranged at a distance of 3.0×3.0 cm. A cm scale 426 is shown at the bottom of FIG. 13. No further calibrations, e.g. camera calibration or calibration to reference frames, were performed. Using this approach shown with the results shown in FIG. 14, acquisition of the 25 markers 425 using the internal Hololens camera required 1 second, corresponding to approximately 40 ms per marker. Markers were consistently recognized as indicated by the displayed green marker ID number 428, with only few occasional drop outs with no green marker ID number displayed 430 as seen in FIG. 14.

Static Accuracy Measurements

Figure 15:
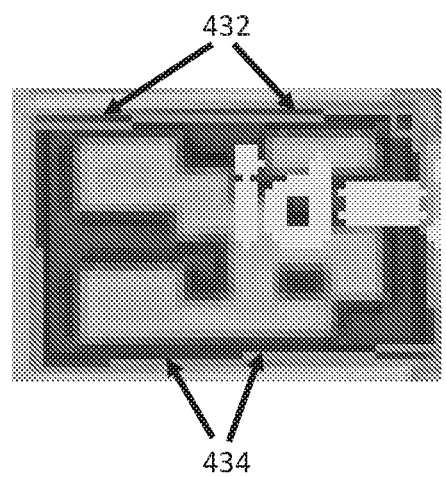
FIG. 15 shows an illustrative, non-limiting example of the accuracy of detecting an optical marker using a video camera integrated into an OHMD.

Markers were mounted on a wooden board with a size of 2.8×2.8 cm and arranged at a distance of 3.0×3.0 cm and static measurements of displacement of optically detected marker positions vs. actual marker positions were obtained at an angle of approximately 40 degrees between the Hololens and the board at a distance of approximately 32.5 cm to the center of the board. FIG. 15 shows an example comparing the actual marker dimensions (2.8×2.8 cm) and position in black 432 with the optically detected marker using the Hololens camera seen as red outline 434. The marker is not square in the image due to the angulation. The pixel size was approximately 0.5 mm in horizontal direction and 0.75 mm in vertical direction in this test. The data indicated sub-pixel accuracy which is why the following analysis of the data was implemented: Pixels at the superior, inferior, left and right border were considered incorrectly detected if more than half had a grey value lower than the average grey value (i.e. the grey value between black and the grey background). For example, the horizontal red line at the superior border in FIG. 15 would need to be exactly 1 pixel higher in order to be counted as correctly detected. Conversely, the inferior second and third horizontal red line from the left were counted as accurately detected. The percentage of each edge (superior, inferior, left, right) that was correctly detected was then determined, e.g. 100% for the superior edge and 50% for the inferior edge in FIG. 15. The analysis over the 25 markers showed that the maximum deviation between the optically detected marker position and the actual marker was 0.75 mm, i.e. one pixel size in vertical direction, with an average deviation between the optically detected marker position and the actual marker of 0.349 pixel=0.26 mm.

Dynamic Accuracy Measurements During Movement

Figure 16:
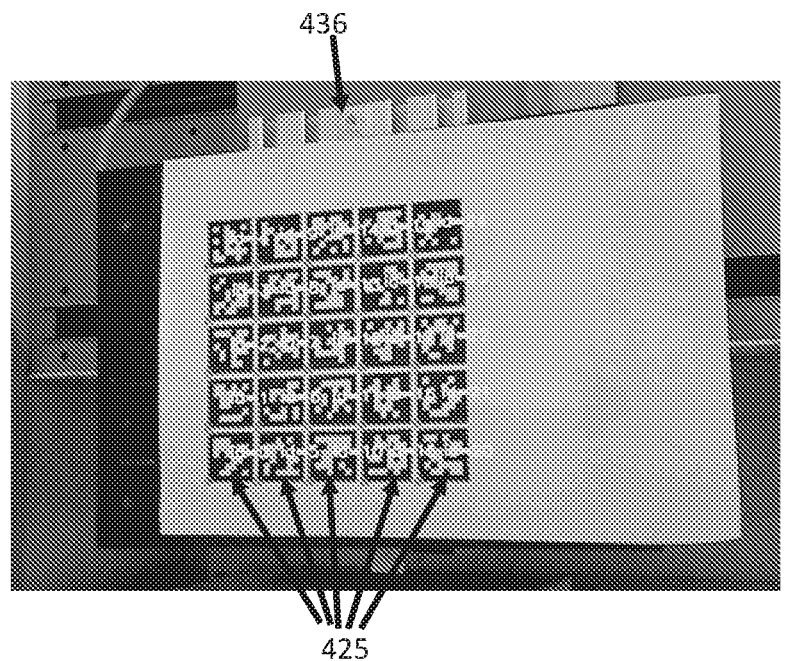
FIG. 16 shows an illustrative, non-limiting example of detection of optical markers during movement using an image capture or video camera system of an OHMD.

In FIG. 16, the board with 25 ArUco 425 markers measuring 2.8×2.8 cm arranged at 3.0 cm interval as described in the foregoing section was mounted on a CNC machine 436 (isel CPM 4030, isel, Eichenzell, Germany). The CNC machine was programmed to move the board in x and z direction at a defined speed of 7.5 cm per second to simulate surgeon or interventionalist head movement. At this speed the 25 markers were detected consistently with only intermittent dropouts of 1 or 2 markers. The pixel size in this experiment was approximately 0.58 mm. The maximum deviation between the optically detected marker position using the Hololens image and/or video capture system and the actual optical marker position in this experiment was 2 pixels corresponding to approximately 1.16 mm.

In a separate experiment, the accuracy regarding a movement in the y-direction was measured. The y-axis was directed into the image plane and corresponded to a movement towards to or away from the patient. The markers were again mounted on a moving CNC machine with the same velocity used in the prior experiment (7.5 cm per second). Four different snapshots were taken at distances from 30 cm to 68 cm away from the OHMD. The evaluation for all markers and the four different depths resulted in an average deviation between the optically detected positions using the Hololens image and/or video capture system and the actual marker position of 0.71±0.32 mm (mean±std). The largest deviation observed in this experiment was 1.75 mm and occurred at the greatest distance of 68 cm, which is beyond the typical work space of the surgeon or interventionalist. The accuracy of registration can be further enhanced by optimizing marker geometries and patterns, by using pre-existing knowledge about marker size and dimensions with size and dimensions known, e.g. in x and y direction or z direction or y and z direction or combinations of all three, and by using reference frames with optical markers attached to the patient and, optionally, the OR table. In addition, the implementation of a network of OHMDs using real-time spatial maps generated by each OHMD can further increase the accuracy of registration of the live image of the different OHMDs and the virtual data of the patient including a virtual surgical plan.

Developing Optical Markers for Biomedical Applications

Figure 17:
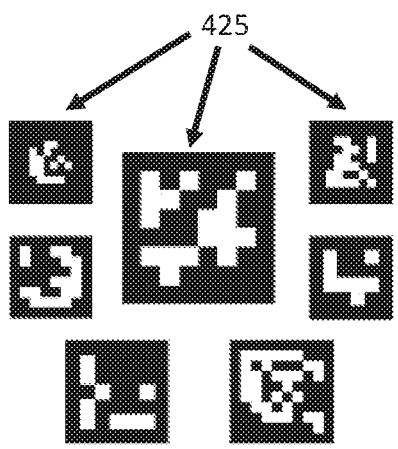
FIG. 17 shows an illustrative, non-limiting example of various optical markers with different dimensions and different geometric patterns.

In order to develop an optimal geometric pattern for detection and recognition using images from an OHMD's video camera for a particular biomedical application, candidate recognition can be tested for different parameters. FIG. 17 shows potential test candidates 425. The test candidates 425 can, for example, use ArUco patterns which utilize a square shape comprising a solid black border frame on the outside and a binary pattern inside as seen in FIG. 17. ArUco patterns can be developed based on OpenCV code. Any other optical marker and pattern can be used and optimized. In a first step in this example, an acceptable minimum size of a marker can be determined, for example for a desired registration accuracy, starting, for example, with a 4×4 binary pattern of 0.5 cm or 1.0 cm border length and increasing the size in 5 mm increments until the 10: tern is reliably detected with the video camera integrated in a Hololens or other OHMD. Any other marker patterns and dimensions can be used. Tests can be performed for different distances, angles, illuminance and light color parameters, for example like some of the exemplary parameters listed in Table 10. Tests can be performed using any possible parameter combinations, for example from Table 10 or any other set of parameters and parameter ranges. Tests can be conducted in static and moving conditions, e.g. at different speeds. A set-up with a CNC machine can be used for dynamic motion measurements, since speeds can be accurately programmed using this approach.

TABLE 14

Exemplary testing conditions and parameters. Any combination of parameters listed below as well as other parameters are possible.

| Distance (cm) | 35 | 50 | 75 |
|---|---|---|---|
| View angle (°) | 30 | 45 | 90 |
| Illuminance (lux) | 50 | 300 | 200 |
| Light color temperature (Kelvin) | 3000 | 4000 | 5000 |
| Static | ✓ | ✓ | ✓ |
| Dynamic, speed (cm/sec) | 3.25 | 7.5 | 15 |

ArUco optical markers can consist of multiple patterns and can be be attached to a plastic, metal or other material holder. Two shapes of holders, e.g. triangular vs. square, can be tested for performance: the detectability of each shape in the spatial maps acquired by the OHMD can be compared between the two shapes. Other shapes can be tested, e.q. rectangles, pentagon, sexagons, septagons, octagons, round, ovoid, elliptical, cubic, ellipoid, irregular shapes. Performance criteria can be position error as well as runtime and behavior in case of partial occlusion of markers. A radiopaque element can be attached to the markers in order to intraoperatively reference anatomic landmarks with fluoroscopy for determining the intended path of the surgical instruments or the intended placement of implant components. The edges of the radiopaque element can be aligned with the edges of the ArUco markers. Other geometric or density features of the radiopaque element can be aligned with features of the ArUco markers. Radiopaque elements or reference or calibration phantoms can be integrated or attached to optical markers. Radiopaque elements or reference or calibration phantoms can also be separate from optical markers at defined distances or geometric arrangements. A registration frame with attached optical markers or separate optical markers at defined distances or geometric arrangements to the registration frame can also be partially or completely radiopaque.

The software can utilize the OpenCV code and can be used to define a local marker coordinate system and pose of each marker. The MS Hololens spatial mapping library can be used to produce a surface mesh using depth camera scans; planes can be identified using the MS Hololens object detection library. Spatial mapping information can be used to define marker coordinates relative to the OHMD. Marker coordinates can be further refined using depth information based on the known shape and dimensional information of the markers. Scaling factors can be applied to the virtual data using the known shape and dimensional information of the markers. The spatial maps can be used to translate from local marker coordinate system, e.g. on a reference frame attached to the patient's back or the OR table, to global OHMD coordinates. The marker coordinate system can be used to determine coordinates of radiopaque elements, which can then be translated into global coordinates for registration with fluoroscopy data.

Registering Intra-Operative Fluoroscopic Images with Live Data of the Patient For merging fluoroscopy images with live images captured by an OHMD, a registration reference frame can be used. The frame can consist of rigid plastic rods made from a sterilizable plastic (e.g. PEEK) and arranged in a square or rectangular shape, e.g. with an edge length of 35 cm, 40 cm, 45 cm, 50 cm. Multiple frames can be used. Optionally, frame can be connectable, e.g. by including connectable members or mechanisms. Other materials, e.g. metal, can be used for the construction of the frame. Optionally, the frame can be radiopaque. An optical marker with an ArUco pattern and a radiopaque element can be attached to each corner of the frame. The markers can be attached at different heights (offsets) from the plane of the frame in order to avoid that the markers are co-planar and to ensure that at least some of the markers are not co-planar.

The registration algorithm can be prototyped and tested in the MATLAB development environment (Mathworks, Waltham, MA) and then ported to C# and the Microsoft Hololens platform or another OHMD. For performing the registration between fluoroscopy images and live images, the radiopaque marker elements can, for example, be located in the fluoroscopy image using graylevel thresholding and a template matching technique. The optical marker coordinates can be determined from the video image using the techniques described in the preceding sections. A single or multiple optical marker can be attached or integrated into the one or more frames. More than one optical marker can be used on a first side of the patient's anatomy, e.g. a left side or an anterior side. More than one optical marker can be used on a second side of the patient's anatomy, e.g. a right side or a posterior side.

The 3D model of the reference frame including its shape and dimension are known, so that a transformation matrix $T_1$ can be determined, which maps the positions of the markers, e.g. 4 markers $M_0$-$M_3$, in the model coordinate system to the coordinates of the optical markers, e.g. for the 4 optical markers $O_1$-$O_4$, as measured using the OHMD video image. This transformation matrix contains a rotation and a translation component.

Similarly, markers $M_0$-$M_3$ in the model coordinate system can be mapped to the markers $R_0$-$R_3$ identified in the fluoroscopy image using a transformation matrix $T_2$. $T_2$ can contain rotation, translation, projection and scaling components. The overall registration matrix $T_3$ between marker coordinates $R_0$-$R_3$ from the fluoroscopy image and coordinates $O_1$-$O_3$ derived from the video image results from the concatenation of the inverse of $T_1$ with $T_2$. This transformation can be used to merge and superimpose fluoroscopy images onto the live view. It can be updated to account for changes in position of the OHMD and/or the patient.

For this purpose, in order speed up the recalculation and allow for real time updating, only the optical marker coordinates can be updated. This will result in updates to $T_1$ and thus $T_3$ and assumes that the fluoroscopy image is not changing. If the fluoroscopy image is updated as well, a more time-consuming complete re-initialization of $T_1$, $T_2$ and $T_3$ as described can be triggered.

The accuracy of the registration can be tested. For example, the OHMD captures the location of the four optical markers on the edges of the registration frame placed on an OR table; a fluoroscopic image is obtained and the registration of live, optical data and fluoroscopic data using the reference markers is performed. Three square radiopaque lead phantoms measuring 1×1×1 cm are placed on the OR table within the bounds of the registration reference frame or adjacent to the registration frame. Using the registration transformations, the OHMD projects the fluoroscopy image into the live view, thus overlaying fluoroscopy and live views of the radiopaque lead phantoms. The difference between the projected, lead phantom in the fluoroscopy and the physical, visible phantom is captured similar to the technique shown in FIG. 12. The test is repeated for the distances and view angles listed in Table 10.

Using any of the foregoing techniques, fluoroscopic images of the patient can be registered with the live data of the patient including the live anatomy of the patient. If the surgical site is moving during the procedure, for example relative to the OR table or relative to the fluoroscopic images obtained prior to the movement, the fluoroscopic images displayed by the OHMD can be moved correspondingly reflecting any type of translation or rotation of the live surgical site to maintain registration between corresponding live anatomic landmarks and fluoroscopic landmarks using the techniques described above. Thus, fluoroscopy does not need to be repeated or can, optionally, be repeated intermittently which can help reduce radiation dose to the patient and the surgeon or interventionalist.

In certain situations the match between fluoroscopic images and also pre-operative or intra-operative x-ray images can be imperfect or partial, for example due to cone beam geometry of the x-ray beam or magnification affecting different parts of the patient's anatomy differently, e.g. depending on the angle of the x-ray tube. In order to mitigate this effect, registration can optionally be performed using radiopaque optical markers located on the side of the patient intended to be operated or radiopaque optical markers located near the intended surgical site. For example, in a spinal surgery, if the surgeon or interventionalist is planning to place a pedicle screw in the left L4 pedicle, radiopaque optical markers on the left side of a registration frame applied to the patient's back can optionally be used for the registation procedures, for example using the techniques described above. If the surgeon or interventionalist is planning to place a pedicle screw in the right L4 pedicle, radiopaque optical markers on the right side of a registration frame applied to the patient's back can optionally be used for the registation procedures, for example using the techniques described above. Optionally, markers present along the entire frame can be used.

Using any of the other registration techniques described in the specification, the registration can also be performed using corresponding anatomic landmarks in the live data of the patient and the radiographic or fluoroscopic data of the patient, e.g. the tip of a spinous process or several spinous processes which are readily accessible during surgery. If corresponding anatomic landmarks are used in the live data of the patient and the radiographic or fluoroscopic data of the patient, these can be chosen to be on the same side as the surgical site or near the surgical site to minimize the impact of distortions from cone beam geometry of the x-ray beam and to minimize any other distortions, e.g. from magnification affecting select parts of the anatomy further away from the x-ray tube. In this example, the x-ray tube and beam can be intentionally centered over the surgical site to decrease the effect of the cone beam geometry. Fluoroscopic images can be repeated with updated centering for the side to be operated on, for example, if the surgeon or interventionalist switches from a left T3 pedicle to a right T3 pedicle.

Co-Display of Intra-Operative Fluoroscopic Images with Live Data of the Patient

The display of fluoroscopic images, e.g. angiographic images, registered with the corresponding live data and anatomic landmarks of the patient and superimposed onto the corresponding live data and/or anatomic landmarks of the patient by the OHMD can be advantageous for any type of surgery that utilizes intra-operative fluoroscopy. Hand-eye coordination can be greatly improved by superimposing the fluoroscopic images directly onto the corresponding live data of the patient and/or anatomic structures using the OHMD. In addition, fluoroscopic images can be acquired less frequently or only intermittently, thereby reducing radiation dose. Such concurrent display of fluoroscopic images can, for example, be advantageous for interventional procedures, wherein the OHMD can display the fluoroscopic (e.g. angiographic) images superimposed onto the live anatomy of the patient, e.g. a vascular structure or vascular tree, and, optionally, wherein the OHMD can also display an intended path and/or endpoint for a surgical instrument superimposed onto the corresponding live structures of the patient and the display of the fluoroscopic images. Concurrent display by the OHMD of the fluoroscopic images superimposed onto the corresponding live data of the patient, e.g. anatomic structures and/or landmarks, and, optionally, the intended path and/or endpoint for a surgical instrument can help the surgeon or interventionalist in aiming or directing an instrument or a device. Optionally, the OHMD can also co-display a virtual image of any portions of the instrument or implant hidden inside the patient's tissue.

Optionally, the OHMD can also co-display a virtual image of any portions of the instrument or implant hidden inside the patient's tissue. The fluoroscopic (e.g. angiographic) image can be displayed by the OHMD in a plane parallel to the OR table or at a predetermined angle to the OR table and extending through a landmark.

Since the fluoroscopic image (e.g. angiographic) is a 2D image and the patient's anatomy is three-dimensional, fluoroscopic images can be displayed centered over an anatomic structure, e.g. as an anchor point, and/or aligned with or parallel with a plane defined by anatomic structures or the OR table. Any anatomic structure can be chosen to place the fluoroscopic (e.g. angiographic) image in tangent or intersecting fashion. Alternatively, the projection plane can be parallel to or at a predefined angle and, optionally, distance to the OR table, e.g. as determined using a video camera of an OHMD and one or more optical markers attached to the OR table, and can extend through an anatomic structure in intersecting or tangent fashion, e.g. one of the foregoing anatomic structures. Alternatively, the projection plane can be perpendicular to or at a predefined angle to the OR table, e.g. as determined using a video camera of an OHMD and one or more optical markers attached to the OR table, and can extend through one or more anatomic structures, e.g. one of the foregoing anatomic structures. Optionally, the projection plane can be parallel to the edge plane of the OR table or at a predefined angle to the edge of the OR table. The projection plane can be chosen to be near the area, tangent with or intersecting the area where the surgeon or interventionalist is operating.

The x-rays can be scaled to account for magnification. Using manual or automated image processing techniques to highlight anatomic landmarks or structures, the projections of the x-rays can optionally be aligned in the OHMD display so that they are directly superimposed with the corresponding live structure in the patient, which can be helpful, if the patient moved after the x-ray (e.g. angiographic) acquisition. For any of the foregoing examples, the projection plane can be selected to mirror the original beam direction or angle of the x-rays system or to be a derivative of the original beam direction or angle of the x-ray system. Someone skilled in the art can identify other anatomic areas or structures or anchor points for placing a virtual projection of an x-ray image or a fluoroscopic (e.g. angiographic) image so that it intersects or is tangent with the anatomic areas or structures or anchor points.

Co-Display of Pre-Operative Ultrasound, CT, MRI, SPECT and/or PET Scan Data with Live Data of the Patient In some embodiments, a surgeon or interventionalist can use one or more OHMD's to co-display a pre-operative CT scan or MRI scan of the patient with the patient's live intra-operative anatomy. The display of ultrasound, CT, MRI, SPECT and/or PET scan data, optionally displayed in 2D or 3D, registered with the corresponding live data and anatomic landmarks of the patient and superimposed onto the corresponding live data and/or anatomic landmarks of the patient by the OHMD can be advantageous for any type of surgery in which surgeon or interventionalists utilize pre-operative ultrasound, CT, MRI, SPECT and/or PET scan data. Hand-eye coordination can be greatly improved by superimposing the pre-operative ultrasound, CT, MRI, SPECT and/or PET scan data, optionally displayed in 2D or 3D, directly onto the corresponding live data of the patient and/or anatomic structures using the OHMD. Such concurrent display of pre-operative ultrasound, CT, MRI, SPECT and/or PET scan data, optionally displayed in 2D or 3D, can, for example, be advantageous for spinal surgery, wherein the OHMD can display the pre-operative ultrasound, CT, MRI, SPECT and/or PET scan data, optionally displayed in 2D or 3D, registered with and superimposed onto the live anatomy of the patient, e.g. skin, muscle or exposed spinal elements, and, optionally, wherein the OHMD can also display an intended path and/or endpoint for a surgical instrument superimposed onto the corresponding live structures of the patient and the display of the pre-operative ultrasound, CT, MRI, SPECT and/or PET scan data, optionally displayed in 2D or 3D. Concurrent display by the OHMD of the pre-operative ultrasound, CT, MRI, SPECT and/or PET scan data, optionally displayed in 2D or 3D, registered with and superimposed onto the corresponding live data of the patient, e.g. anatomic structures and/or landmarks, e.g. the center of a pedicle (live and/or virtual), and, optionally, the intended path and/or endpoint for a surgical instrument, an awl, or a pedicle screw can help the surgeon or interventionalist in aiming or directing an instrument or an implant, e.g. a pedicle screw. Optionally, the OHMD can also co-display a virtual image of any portions of the instrument or implant hidden inside the patient's tissue.

Optionally, the OHMD can also co-display a virtual image of any portions of the instrument or implant hidden inside the patient's tissue.

Projecting 2D Cross-Sectional Image Data with an OHMD

In some embodiments, ultrasound, CT, MRI, SPECT and/or PET can be displayed by the OHMD as a 2-dimensional (2D) cross-sectional image or as a 3-dimensional (3D) reconstruction. Since the patient's anatomy is three-dimensional, when 2D cross-sectional images are used, 2D images can be displayed centered over an anatomic structure, e.g. as an anchor point, and/or aligned with or parallel with a plane defined by anatomic structures or the OR table. Any other anatomic structure can be chosen to place the 2D cross-sectional cross-sectional image in tangent or intersecting fashion. Any of these structures can be selected for multiple spinal levels and the projection plane can be placed by the OHMD to intersect or be tangent with with three or more points chosen in this manner. Alternatively, the projection plane can be parallel to or at a predefined angle and, optionally, distance to the OR table, e.g. as determined using a video camera of an OHMD and one or more optical markers attached to the OR table, and can extend through an anatomic structure in intersecting or tangent fashion, e.g. one of the foregoing anatomic structures. Optionally, the projection plane can be parallel to the edge plane of the OR table or at a predefined angle to the edge of the OR table.

Network of OHMD Devices

In some embodiments, several OHMD devices can be interconnected to create a network for a shared experience of the augmented views. The devices can be organized in a client-server network where multiple OHMD clients are centralized around a single server. Thus, OHMD devices can be relieved of computing power when outsourcing tasks which are computational intensive (e.g. image processing) to the server. Moreover, battery life of the OHM D's can be significantly prolonged which makes this strategy applicable even in case of a single OHMD client. The server can by accessible in the OR. The server can have a computer monitor and user interface separate from the OHMD. In case of multiple clients, different data inputs from the various perspectives can be used by the server to increase the accuracy of the calculations (e.g. by averaging out errors). A technique to merge the spatial maps from multiple OHMD clients on the server can be implemented. Spatial maps consist of triangular meshes built from each OHM D's depth sensor information. Once spatial maps have been transferred from each OHMD to the server, the different meshes are combined into a combined, more accurate mesh using the following exemplary, non-limiting averaging algorithm: The data from a first OHMD is used as the baseline. From each face in the baseline mesh, a ray is cast along the surface normal of the face. Intersection points between the ray and all other meshes are calculated. A new vertex for the combined mesh is derived as the average of all intersection points along the ray. The new vertices from adjacent triangles in the baseline mesh are connected to form the faces in the combined mesh. The combined mesh is then transferred back to the individual OHMD's for refinement of the registration with the fluoroscopy data.

Exemplary User Interfaces

A standard user interface for surgical planning is implemented on the server in the OR. The server is configured to include a DICOM server for transfer of the fluoroscopic images of the patient. The interface allows a dual or multiple display mode of AP and lateral views, as well as any oblique views obtained. Using a standard mouse or track ball, the interface allows the surgeon or interventionalist to define entry points and vectors of instruments and pedicle screws. 3D coordinates of points and vectors of the plan are determined using a minimum of 2 approximately perpendicular fluoroscopy views. Other angles between the fluroscopy images or views are possible, known or defined or not known or defined. The planning data are displayed by the OHMD in addition to the fluoroscopic images and serve as input for to the real-time optical guidance during the intervention.

In addition, a prototype virtual interface for the path of a a pedicle screw is used using, for example, the Unity for HoloLens engine (Unity Technologies, San Francisco, CA). Unity's GestureRecognizer interface allows for recognition of different hold, navigation and manipulation functions. Additionally, the Gaze functionality is available for implementation of a cursor controlled by the user's view direction. Thus, in select application, the user's gaze is controlling the cursor including cursor movement. Closure of the eye lid can, for example, also be used as a command to execute a function. With the virtual interface, the planning can be performed on the fluoroscopic images displayed by the OHMD using gesture commands which are mapped to entry points and vectors. Any other finger symbols and movements can be used.

The accuracy of the virtual interface can tested in comparison to the standard interface developed for the PC implementation. The intended path is placed at a different time by the same operator using the virtual interface. The results of the intended path placement including its entry points and vector using the virtual interface are captured and are compared to the results obtained using the standard PC based interface as the ground truth. Standard interfaces and virtual interfaces can optionally be combined or can be available simultaneously.

Figure 18:
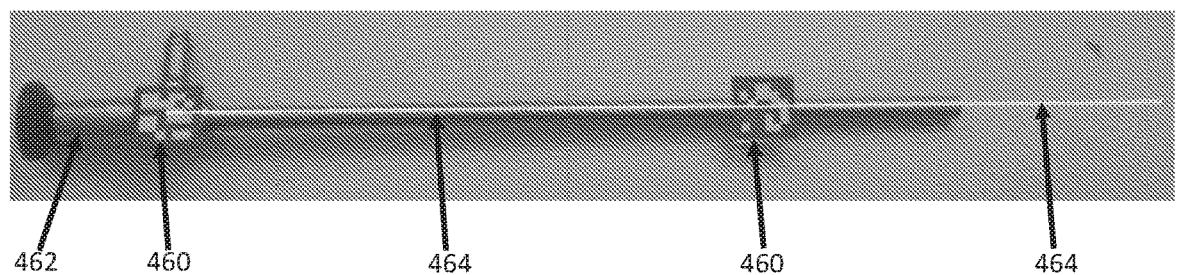
FIG. 18 shows an illustrative, non-limiting example of a surgical instrument with multiple optical markers attached for tracking the surgical instrument.

Tracking of surgical instruments, "painting" of patient surfaces Multiple different technical approaches are possible to track the surgical instruments in the surgeon or interventionalist's live view of the patient through the OHMD and to project the invisible parts of an instrument hidden by the tissue and its direction with the OMHD. None of these approaches are meant to be limiting, but are only exemplary in nature. Someone skilled in the art can recognize other approaches for tracking surgical instruments using embodiments described herein. Multiple optical markers 460 can be attached to a surgical instrument 462 as shown in FIG. 18. For example, the markers can be fixed at defined positions on the instrument. With the geometry of the instrument known, the position and orientation of the instrument can be calculated, e.g. for an instrument like an awl with a tip for which its rotary orientation is aligned with the pointing axis only two markers 460 are needed as shown in FIG. 18. More markers can be used, e.g. in different geometric locations on the instrument with overlapping or separate, distinct x, y, and z coordinates. The markers' 3D coordinates are recognized by the OMHD using the methods described in the preceding sections. Using the coordinates of a first and second marker, a vector 464, yellow line in FIG. 18, pointing in the direction of the tip is calculated and displayed by the OHMD to indicate the direction of the hidden portions of the instrument superimposed onto the surgical site, enabling the surgeon or interventionalist to align the physical awl or pedicle screw including its hidden portions with the intended path defined using the standard or virtual planning interface and also projected by the OHMD. Rather than using two or more markers, a single marker can be used, for example with sufficient geometric information, e.g. along the long axis or other axis of the instrument, for accurate coordinate determination, e.g. 2, 3, 4, 5, 6, 7, 8, 9 or 10 cm long and, for example, 1, 2, 3, 4, 5, 6, or 7 or other cm wide, depending also on the spatial resolution of the camera system. In general, the greater the spatial resolution of the camera or video system, the smaller the marker size that can be used for accurate coordinate and/or vector determination. In addition, smaller marker sizes can be possible when markers are stationary, e.g. rigidly attached to a non-moving anatomic part of the patient or the OR table. Larger marker sizes can be be used, for example, when markers are attached to a moveable anatomic landmark, e.g. a distal femoral condyle or a proximal tibial plateau, or a humerus, or a humeral tuberosity, or when they are attached to the OHMD and are thus, for example, subject to movement as the surgeon or interventionalist moves his or her head.

Another approach, which can be a fallback, uses pivoting, a mathematical technique for determining the position of the tip. With pivoting, the instruments tip is fixed in one position on the tissue while the whole instrument is moved. The attached optical markers move on a spherical surface. This leads, for example, to an accurate registration of an entry point. The accuracy of tracking the instruments can be measured, for example, by mounting them on a CNC machine using the methods described in the preceding sections. The accuracy of tracking instrument position and orientation can be tested for different parameter combinations, e.g. for parameters and parameter ranges selected from Table 10, for moving conditions at different speeds. Optionally, different instrument tracking techniques, e.g. the two foregoing examples, as well as tracking using attached IMU's or navigation markers can be combined. In another example, spatial maps can be used determine the coordinates of anatomical landmarks. Anatomical landmarks on the patient's physical anatomy can be digitized for registration with virtual models. For this purpose, the motion of a pointer instrument with optical markers, LED's or navigation markers or other markers attached can be tracked while its tip can be moved by the surgeon or interventionalist over the surface of the anatomical landmark, e.g. a femoral condyle, a tibial plateau, an articular surface or any other anatomical landmark. As the surgeon or interventionalist "paints" the landmark surface, the position of the instrument tip can be calculated from the optical markers, LED's or navigation markers or other. For example, the coordinates of multiple surface points can be determined as the pointer instrument is being moved along the surface, thereby generating a point cloud which can be used to define the surface. The touched or "painted" portions of the surface can optionally be displayed as a hologram in the OHMD for visual feedback to the surgeon or interventionalist by converting the recorded tip positions to a surface mesh. The density of points can be variable; higher density maps can be desirable when high spatial resolution and/or high registration accuracy is required, as can, for example, be the case during brain surgery or resection of a tumor in the brain or other organs or as can be necessary for placement of a medical device. The point cloud(s) or surface mesh can be registered with a virtual model, e.g. of the patient's anatomy, e.g. based on pre- or intra-operative scan data thereby registering, for example, intra-operative physical surface(s) and/or landmarks of the patient with virtual data, e.g. a pre-operative or intra-operative scan, imaging data or other virtual data including one or more virtual surgical plans. If the density of points is too low, the surgeon or interventionalist can be warned to add more points to the surface section, e.g. via visual feedback in the hologram or acoustic or other feedback. In addition to the dense mesh acquired via digitization of anatomic landmarks, a coarser, but more general spatial map can be generated by a depth camera. This spatial map can also consist of a 3-dimensional surface mesh, which can, for example, be read out using the OHMD's programming interface. This information can be used to supplement the digitized landmarks for registration.

The foregoing techniques and examples and any modifications thereof for using and optimizing optical markers, for optimizing geometric patterns of optical markers, for optimizing the shape of optical markers, for aligning optical markers and/or geometric patterns with radiopaque elements, for registering fluoroscopic images with the patient's live anatomy, for utilizing pre-existing information on the known size, shape and/or dimensions of one or more optical markers, for networks of OHMD's and combining multiple spatial maps, for various interfaces including virtual interfaces and for tracking surgical instruments are applicable to any type of surgical procedure, surgical instruments and devices.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

DEVICES, SYSTEMS AND METHODS FOR VASCULAR AND OTHER INCLUDING ENDOLUMINAL PROCEDURES

Virtual and/or physical devices or implants can include, for example, catheters, wires, guidewires, sheaths, thrombectomy devices, thrombectomy systems, revascularization devices or systems, stents (e.g. endovascular stents, biliary stents, coated stents, drug eluting stents), coils, grafts (e.g. vascular grafts, valve grafts or graft valves), patches, vascular prostheses, scaffolding prostheses, e.g. open pore, cardiac valves, cardiac valve replacements, cardiac valve repair systems, electrodes, electric probes, electrophysiologic probes, ablation devices, pacemakers, pacemaker leads or electrodes, etc.

Virtual and/or physical instruments can include, for example, graspers, vein valve cutters, vein extirpation sets, extraction instruments, etc.

Physical instruments or devices or implants can be coated or uncoated.

A vessel and/or vascular structure can be an artery or can be a vein. The vessel and/or vascular structure can be of neurovascular, cardiac, pulmonary, abdominal, pelvic, extremity and/or any other location. The vessel and/or vascular structure can be normal and/or pathologic.

In some embodiments a first set of 2D or 3D virtual data or virtual structures or objects, e.g. from a first imaging study, e.g. a pre-operative imaging test, and a second set of 2D or 3D virtual data or virtual structures or objects, e.g. a second imaging study, e.g. an intra-operative imaging test, including, for example, a 2D or 3D angiogram, can be superimposed onto each other or aligned with each other and can be maintained in superimposition and/or alignment, optionally including superimposition and/or alignment with the corresponding physical data of the patient, e.g. physical vessels or physical vascular structures. The superimposition and/or alignment of the first set of virtual data or structures or objects and the second set of virtual data or structures or objects and, optionally, the physical data or structures of the patient can be performed and can be displayed by the same one or more OHMD displays. The superimposition and/or alignment of the first set of virtual data or structures or objects with the second set of virtual data or structures or objects can be performed by one or more OHMDs, for example when the operator looks at a standalone or separate computer monitor and when the computer monitor displays, for example, the second set of virtual data or structures. The OHMD can be see-through or non see-through in some of these embodiments.

The see-through and/or the non see-through OHMD can include a video camera or image capture system, for example for capturing one or more images or video feed or stream from the physical patient, e.g. a surgical or interventional site (including for superimposition with the virtual data, structures or objects displayed by the OHMD), and/or from a computer monitor displaying, for example, virtual data of the patient, e.g. a pre- or intra-operative imaging study (including for superimposition with the virtual data, structures or objects displayed by the OHMD). A see-through OHMD can become a partially or complete non see-through OHMD, e.g. by blending out physical information directly visible to the operator and, optionally, by blending in video feed, e.g. from one or more image capture, camera or video systems integrated into, attached to or separate from the one or more OHMDs.

Display Options

Different display options can be applied to different embodiments. For example, a first set of 2D or 3D virtual data can be displayed by a standalone computer monitor. The first set of 2D or 3D virtual data, e.g. including pre-operative imaging studies or virtual device information or graphical representations, can be co-displayed and, optionally, superimposed and/or aligned with, for example using segmentation and/or registration performed by one or more computer processors configured for segmentation and/or registration and/or display generation of virtual data, a second or additional sets of 2D or 3D virtual data also displayed by the same standalone computer monitor. Since the display is by the standalone computer monitor, superimposition and/or alignment with the physical data or structures of the patient is not possible in this example.

A first set of 2D or 3D virtual data can be displayed by one or more OHMDs. The first set of 2D or 3D virtual data, e.g. including pre-operative imaging studies or virtual device information or graphical representations, can be superimposed and/or aligned with, for example using segmentation and/or registration performed by one or more computer processors configured for segmentation and/or registration and/or display generation of virtual data, and can be maintained superimposed and/or aligned with a second or additional sets of 2D or 3D virtual data displayed by a standalone computer monitor. Since the display of the second or additional sets of 2D or 3D virtual data is by the standalone computer monitor, superimposition and/or alignment with the physical data or structures of the patient is not possible in this example.

A first set of 2D or 3D virtual data can be displayed by one or more OHMDs. The first set of 2D or 3D virtual data, e.g. including pre-operative imaging studies or virtual device information or graphical representations, can be superimposed and/or aligned with, for example using segmentation and/or registration performed by one or more computer processors configured for segmentation and/or registration and/or display generation of virtual data, and can be maintained superimposed and/or aligned with a second or additional sets of 2D or 3D virtual data displayed by the one or more OHMD displays. Since the display of the second or additional sets of 2D or 3D virtual data is also by the one or more OHMD displays, superimposition and/or alignment with the physical data or structures of the patient is possible in this example. Thus, the display of the $1^{st}$ set of virtual data and/or the display of the $2^{nd}$ set or additional sets of virtual data by the one or more OHMDs can optionally be registered with, superimposed onto and/or aligned with and can be maintained superimposed onto and/or aligned with the physical data, physical structures, physical surfaces, physical tissues, physical organs of the patient, both in exposed, e.g. directly visible through a see-through optical head mounted display, or in hidden, e.g. subsurface location.

The superimposing and/or aligning and/or maintaining of the superimposing and/or aligning can be performed by one or more computer processors configured, for example, to segment virtual data, register virtual and/or physical data, track physical data, and/or display virtual data and/or move virtual data by the one or more OHMDs and/or synchronize virtual data displayed by the one or more OHMDs.

A first set of 2D or 3D virtual data can be displayed by one or more OHMD's. The first set of 2D or 3D virtual data, e.g. including pre-operative imaging studies or virtual device or instrument information or graphical representations, can be superimposed and/or aligned with, for example using segmentation and/or registration performed by one or more computer processors configured for segmentation and/or registration and/or display generation of virtual data, and can be maintained superimposed and/or aligned with a second or additional sets of 2D or 3D virtual data displayed by the one or more OHMD displays, for example, intra-operative imaging data, e.g. from an angiogram or vascular run-off and/or tracking data showing the movement of a virtual representation of a tracked physical device or instrument (e.g. a catheter). Since the display of the second or additional sets of 2D or 3D virtual data is also by the one or more OHMD displays, superimposition and/or alignment with the physical data or structures of the patient is possible in this example, but is not performed. Instead, the display of the 1" set of virtual data and/or the display of the $2^{nd}$ set or additional sets of virtual data by the one or more OHMDs can be projected onto an area of the operating room or interventional suite that is not occupied by the patient and/or a computer monitor. Optionally, this area can have a substantially dark or black background, optionally with little or no lighting, e.g. ambient lighting. The superimposing and/or aligning and/or maintaining of the superimposing and/or aligning can be performed by one or more computer processors configured, for example, to segment virtual data, register virtual data, track physical data, and/or display virtual data and/or move virtual data by the one or more OHMDs and/or synchronize virtual data displayed by the one or more OHMDs, for example using cardiac or respiratory gating data. The display of the virtual data in this example can be fixated in a predetermined or defined location, e.g. with predetermined coordinates, e.g. in an area of the operating room or interventional suite that is not occupied by the patient and/or a standalone computer monitor.

A first set of 2D or 3D virtual data can be displayed by one or more OHMDs. The first set of 2D or 3D virtual data, e.g. including pre-operative imaging studies or virtual device information or graphical representations, can be superimposed and/or aligned with, for example using segmentation and/or registration performed by one or more computer processors configured for segmentation and/or registration and/or display generation of virtual data, and can be maintained superimposed and/or aligned with a second or additional sets of 2D or 3D virtual data displayed by the one or more OHMD displays. Since the display of the second or additional sets of 2D or 3D virtual data is also by the one or more OHMD displays, superimposition and/or alignment with the physical data or structures of the patient is possible in this example, for example when the surgeon or interventionalist looks at the physical data or structures of the patient. The display of the 1" set of virtual data and/or the display of the $2^{nd}$ set or additional sets of virtual data by the one or more OHMDs can optionally not be fixated and can move with the surgeon's or the interventionalist's head. In some embodiments, only a first set of 2D or 3D virtual data can be displayed, e.g. by an OHMD. The first set of 2D or 3D virtual data can optionally be registered with the physical data or structures of the patient and can optionally be superimposed onto and/or aligned with and can optionally be maintained superimposed onto and/or aligned with the physical data or physical structures of the patient using, for example, one or more computer processors configured for the display of virtual data by one or more OHMDs, configured for registering virtual and/or physical data, configured for segmenting virtual data, and/or configured for tracking physical devices and/or instruments, e.g. catheters, guidewires, sheaths, stents, coils, implants etc.

Table 11 is an exemplary, non-limiting summary of different display options for superimposing two or more 2D and/or 3D models of virtual data including virtual tissues, surfaces, organs and/or structures of the patient and/or for superimposing one or more 2D and/or 3D models of virtual data with the physical data including physical tissues, surfaces, organs and/or structures of the patient.

TABLE 11

| Location of Display | $1^{st}$ Set(s) of 2D or 3D Virtual Data Displayed By | Superimposition and/or Alignment with $2^{nd}$ or Addl. Set(s) of 2D or 3D Virtual Data | $2^{nd}$ or Addl. Set(s) of 2D or 3D Virtual Data Displayed By | Superimposition and/or Alignment with Physical Data of the Patient | Physical Data of the Patient |
|---|---|---|---|---|---|
| Fixed on the standalone computer monitor | Standalone computer monitor | Projected with/onto and/or superimposed onto and/or aligned with | standalone computer monitor | Not applicable | Not applicable |
| Fixed on the standalone computer monitor (at least portions of) | One or more OHMD displays | projected onto and/or superimposed onto and/or aligned with | standalone computer monitor | Not applicable | Not applicable |

TABLE 11-continued

| Location of Display | $1^{st}$ Set(s) of 2D or 3D Virtual Data Displayed By | Superimposition and/or Alignment with $2^{nd}$ or Addl. Set(s) of 2D or 3D Virtual Data | $2^{nd}$ or Addl. Set(s) of 2D or 3D Virtual Data Displayed By | Superimposition and/or Alignment with Physical Data of the Patient | Physical Data of the Patient |
|---|---|---|---|---|---|
| Fixed on the patient | One or more OHMDs | co-projected or co-displayed with | one or more OHMDs | projected onto and/or superimposed onto and/or aligned with | a physical structure, tissue, surface, organ directly visible, e.g. exposed, or not directly visible, e.g. in sub-surface location |
| Fixed, e.g. at a space, e.g. an empty space, in the OR or interventional suite, e.g. not on a computer monitor, not on the patient | One or more OHMDs | co-projected or co-displayed with | one or more OHMDs | Not applicable | Not applicable |
| Not fixated, e.g. moveable with the operator's head | One or more OHMDS | co-projected or co-displayed with | one or more OHMDs | possible with | a physical structure, tissue, surface, organ directly visible, e.g. exposed, or not directly visible, e.g. in sub-surface location |
| Fixed on the patient | One or more OHMDs | Not applicable | Not applicable | projected onto and/or superimposed onto and/or aligned with | a physical structure, tissue, surface, organ directly visible, e.g. exposed, or not directly visible, e.g. in sub-surface location |

See-through and non see-through optical head mounted displays can be used in various embodiments. When non see-through optical head mounted displays, e.g. VR displays, are used, optionally an image capture, camera or video system integrated into, attached to or separated from the one or more OHMDs can be used to provide images and/or video feed from the interventional and/or surgical site to the eye of the surgeon and/or interventionalist.

The video feed can be configured by one or more computer processors to be registered with a $1^{st}$, $2^{nd}$ or additional sets of virtual data, e.g. from pre- or intra-procedural imaging generated by, for example, x-ray imaging, CTA, MRA, and/or 2D or 3D angiography. Alternatively, or in addition, see-through OHMDs can be configured to increase or decrease the luminosity and/or brightness and/or contrast of the virtual data and can be configured to increase or decrease the transparency for light transmitted from the physical site or structures of the patient so that in some embodiments a computer processor can be configured to blend out, e.g. intermittently or transiently, light transmitted form the physical site or structures and to display and make visible, for example primarily, or enhance the visibility of the $1^{st}$ set, $2^{nd}$ set or additional sets of virtual data.

Any of the 2D or 3D virtual data can include an arterial run-off, e.g. a peripheral run-off or an aortic run-off, optionally including bolus chasing. Bolus chasing can permit real-time visualization of the contrast bolus so that it can be followed, for example, peripherally with images, e.g. digital images, being acquired at a suitable frame rate. If the run-off and/or bolus chasing includes movement of the table on which the patient is positioned during the image acquisition, any 2D or 3D virtual data, e.g. from a pre-operative imaging study, e.g. a CTA or MRA or ultrasound, can be moved with the patient and/or table movement to maintain superimposition and/or alignment of a first 2D or 3D virtual data set, e.g. from the pre-operative imaging study, displayed by one or more OHMD's with a second or additional 2D or 3D virtual data sets, e.g. images obtained during the run-off and/or bolus chasing, displayed by the one or more OHMDs or a separate, standalone computer monitor using any of the combinations outlined in exemplary form in Tables 11, 13 and 14.

In any of the embodiments throughout the specification, one or more computer processors can be configured to measure one or more of a respiratory rate or frequency, the phase of the respiratory cycle, the direction of respiratory excursions or movement during inspiration or expiration, the speed of respiratory excursions or movement during inspiration or expiration or the amount of respiratory excursions or movement during inspiration or expiration. One or more computer processors can be configured to synchronize and/or move one or more OHMD displays using the one or more of the respiratory rate or frequency, the phase of the respiratory cycle, the direction of respiratory excursions or movement during inspiration or expiration, the speed of respiratory excursions or movement during inspiration or expiration or the amount of respiratory excursions or movement during inspiration or expiration. One or more computer processors can be configured to measure one or more of a heart rate, arrhythmias, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. One or more computer processors can be configured to move and/or synchronize one or more OHMD displays using the heart rate, arrhythmias, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. One or more computer processors can be configured to register virtual data with physical data of the patient, including considering and/or using respiratory and/or cardiac gating information. One or more computer processors can be configured to superimpose and/or align virtual data with physical data of the patient and to maintain the superimposing and/or aligning of virtual data with the physical data during portions of or the entire respiratory and/or cardiac cycle. One or more computer processors can be configured to superimpose and/or align individual virtual data, e.g. individual virtual tissues, surfaces, organs or structures, or groups of virtual data, e.g. groups of virtual tissues, surfaces, organs or structures, with corresponding invididual and/or groups of physical tissues, surfaces, organs or structures, optionally including cardiac and/or respiratory gating information. One or more computer processors can be configured to co-display and/or superimpose and/or align and/or to maintain the co-displaying and/or superimposing and/or aligning of a first set or sets of virtual data with a second set or additional sets of virtual data and/or physical data, e.g. corresponding physical structures, surfaces, tissues, organs or portions thereof. In any of the embodiments, the one or more computer processors can be the same or different. In any of the embodiments, the one or more computer processors can be part of the same or different computer systems, e.g. a computer system for a standalone computer monitor and/or a computer system for one or more OHMDs.

Superimposition and/or Alignment of Pre-Procedural and/or Intra-Procedural 2D and/or 3D Data for Cardiovascular, Neurovascular, General Vascular and Other Applications A 3D model of the vasculature and/or the heart can be generated using pre-operative 3D imaging data, for example a computed tomography (CT) scan or magnetic resonance imaging (MRI) scan. Preferably, the pre-operative 3D images are acquired using vascular enhancement such as CT angiography, e.g. spiral CT angiography, (with use of contrast media) or MR angiography with injection of a contrast agent or use of contrast enhancing MRI pulse sequences.

To generate the 3D vasculature and/or heart model from the 3D imaging data, suitable segmentation techniques known in the art can be applied that separate the vasculature tree from other structures and background in the images. These segmentation techniques can include, for example and without limitation, local or global thresholding or seed growing techniques. The segmentation techniques can be applied in 2D on each slice of the imaging data set separate or in 3D on the entire imaging data volume.

Typically, in contrast enhanced CT or MR angiograms, the vasculature, for example, flowing blood inside vessels or the heart, and the heart can appear brighter or darker than surrounding tissue. Therefore, a thresholding segmentation method in which voxels with an intensity or gray value above a specific threshold are classified as blood vessel can often be applied. The threshold can be applied globally to the entire dataset or vary based on local image characteristics and/or coil characteristics in the case of MRI and/or MR angiography. Seed growing techniques can use specific starting points in the image data set that can be classified as blood vessel and/or blood flow and can be determined automatically or manually. Based on local criteria, the surrounding voxels in the 3D neighborhood around the starting point can be analyzed and classified whether they also belong to a blood vessel or blood flow or not. For example, 6-connected, 18-connected, or 26-connected voxels or any other number of connected pixels or voxels around a current voxel can be classified. This process can be repeated until all image voxels in the image or in a Region of Interest (ROI) have been analyzed. The local criteria used to assess neighborhood voxels can include intensity or gray value differences relative to the current voxel. The local criteria can also take prior knowledge of the shape of the vasculature into account, e.g. by measuring the correlation between a group of neighborhood voxels and a cylindrical template.

In a similar fashion, the thresholding and seed growing techniques described above can also be applied to the pixels of the 2D projection images generated by the x-ray angiography, e.g. uni-planar and/or biplanar angiography and/or 3D angiography. In 2D seed growing, a 2D neighborhood around the current pixel can assessed for classification as blood vessel or flowing blood. This 2D neighborhood can include all 4-connected, 6-connected, or 8-connected pixels of the current pixel or any other number of connected pixels of the current pixel.

In order to overlay the 3D model of the vasculature and/or heart extracted from the preoperative scan using, for example, an optical head mounted display displaying the 3D model projected onto the 2D angiogram as, for example, displayed on a separate, stand-alone computer monitor, a 3D-2D registration can be performed. This registration can determine the optimal rotation, translation, scaling/magnification/minification and projection parameters that rigidly map and project 3D coordinates from the preoperative scan to 2D image coordinates of the x-ray angiogram. The rotation, translation, scaling/magnification/minification and projection parameters can result in an affine transformation that can, for example, be described as a 4×4 matrix. This transformation matrix can be used to transform coordinates from the coordinate system of the 3D model into the coordinate system of the 2D angiogram. The registration can also be split up into several separate components, for example by using separate transformation matrices for each of the rotation, translation, scaling/magnification/minification and projection parameters. Alternatively, there can be a transformation matrix for the transformation parameters within the 3D space (including rotation, translation and scaling/magnification/minification) and a separate transformation matrix for the projection from 3D coordinates into 2D coordinates.

Different methods are available to optimize the transformation parameters that define rotation, translation, scaling/magnification/minification and projection. The optimization can be based on matching of the 3D vs. 2D gray value data of the preoperative scan, or of the 3D and 2D models segmented using the methods described above, or any combination thereof.

The optimization technique can, for example, include a cost function that measures the degree of overlap between the projected 3D data and the 2D data. For example, the cost function can be based on mutual information between the projected gray value data of the preoperative scan and the x-ray gray value data. The cost function can also include the number of common pixels between the projected 3D model and the 2D model. The optimization can, for example, include an iterative search for the specific rotation, translation, scaling, and projection parameters for which the cost function is maximized or minimized. In addition to the rigid transformation defined by the rotation, translation, scaling/magnification/minification, and projection parameters a deformation field can be determined to model soft tissue deformations between the preoperative and intraoperative images. The deformation field can include elastic models or other physical models for the deformation of tissue to facilitate the optimization of the registration.

For the registration of 3D data with biplanar x-ray projections, the process can be accelerated by taking the known spatial relationship between the two 2D x-ray imaging planes into account. Instead of registering the 3D data with both 2D planes independently using the methods described above, the transformation for the second plane can be derived from that for the first plane by including an additional rotation factor.

Once the optimal transformation parameters for rotation, translation, scaling and projection of the 3D-2D registration have been found using any of the techniques described in the specification or known in the art, the first transformation matrix that includes the rotation, translation and scaling components can then be used for the overlay display of the 3D model on the 2D images, e.g. on a standalone or separate computer monitor or as displayed by one or more OHMDs. An optional offset can be added by including an additional translation component to vary the distance of the 3D model from the 2D images. This information can be used to create an overlay display or superimposition of the 3D model displayed by one or more OHMDs with a 2D or 3D angiogram or other vascular imaging study displayed by a separate or standalone computer monitor or display. This information can also be used to create an overlay display or superimposition of the 3D model displayed by one or more OHMDs with a 2D or 3D angiogram or other vascular imaging study co-displayed by the one or more OHMDs. Thus, a 3D model, e.g. including virtual data on a catheter, guidewire, stent, coil, implant or other intra-vascular or endoluminal device inside the vessel(s) or lumen including, optionally, tracking information for a tracked catheter, guidewire, stent, coil, implant or other intra-vascular or endoluminal device inside the vessel(s) or lumen, or a pre-operative imaging study, e.g. a CTA or MRA, can be displayed by one or more OHMD's and intra-operative 2D or 3D imaging information can be co-registered and co-displayed, e.g. using a 2D computer monitor or the OHMD, and superimposed and/or aligned with the 3D model. Thus, a 3D model, e.g. including virtual data on a catheter, guidewire, stent, coil, implant or other intra-vascular or endoluminal device inside the vessel(s) or lumen including, optionally, tracking information for a tracked catheter, guidewire, stent, coil, implant or other intra-vascular or endoluminal device inside the vessel(s) or lumen, or a pre-operative imaging study, e.g. a CTA or MRA, can be displayed by one or more OHMDs and intra-operative 2D or 3D imaging information can be co-registered and co-displayed, e.g. using a 2D computer monitor or the OHMD, and the 3D model can be superimposed and/or aligned with the intra-operative 2D or 3D imaging information.

The registration can be updated, for example to correct for patient or table movement. If the table movement is known, it can be directly included in the transformation parameters. For example, the registration can be updated to include an additional translation in the opposite direction for a table movement in the positive Z direction. If the table is raised or lowered, an additional translation in these directions can also be included. If the table is moved to the left or the right, an additional translation can also be included. The specific translation parameters will depend on the coordinate system used by the angiography or x-ray fluoroscopy system. The translation can consist of an x and/or a y and/or a z component.

Information on the direction and amount of table movement can be provided directly by the angiography system. If this information is not available, one or more markers can be attached to the table. The one or more markers can be navigation markers and/or optical markers as described elsewhere in this disclosure. The optical markers can be tracked by the OHMD or by a separate navigation system as described elsewhere in this disclosure. If tracking of the markers is performed by a separate navigation system, which can be fixed, the change in marker position is a direct indicator of the table movement and can be used to determine the corrective translation of the registration.

If tracking of the markers is performed by the OHMD, which itself is not stationary, any changes in the position and view direction of the OHMD need to be taken into account and compensated for. This can, for example, be done by using inside-out tracking information of the OHMD. This can also be accomplished by attaching one or more markers (e.g. retroreflective markers or markers with RF emitters for surgical navigation, or markers, e.g. with geometric patterns, for video imaging) to the x-ray imaging system that can also be tracked by the OHMD. Any relative movement between the markers attached to the table and the markers attached to the x-ray imaging system can then be measured and used for updating the registration parameters. The markers can optionally be radiopaque or include radiopaque elements. Any of the foregoing techniques, e.g. image based registration of 3D models and 2D or 3D angiograms and registration using table movement and related coordinates and/or marker movement can be combined.

In one embodiment, the 2D x-ray angiogram can be displayed as a virtual window in the OHMD. The 3D vasculature model, e.g. from a pre-operative imaging study such as a 3D ultrasound, a CTA or MRA, can then be superimposed on top of the 2D x-ray angiogram in front of or behind the virtual window. The virtual window displaying the 2D x-ray angiogram and the superimposed 3D vasculature model can move as the view direction of the OHMD changes, for example as the surgeon or interventionalist moves his or her head.

Alternatively, the virtual window and the 3D vasculature model can be fixed in 3D space. For this purpose, the position and view direction of the OHMD can, for example, be tracked internally using inside-out tracking, in which the OHMD position and view orientation can be determined using the OHMD's built-in sensors, e.g. one or more IMU's. The position and view direction of the OHMD can also be tracked outside-in, e.g. by attaching optical markers or other markers, e.g. navigation markers, to the OHMD, which are tracked by an external camera system, as described, for example, in the specification.

In another embodiment, the 2D x-ray angiogram is displayed on a separate, standalone computer screen that can be viewed through the OHMD. The 3D vasculature model can then be registered with the image on the computer screen using the methods described above or any method known in the art. It can be displayed superimposed over the 2D x-ray angiogram in front of and/or behind the computer screen. The position and orientation of the computer screen relative to the OHMD can be tracked by continuously updating the registration. It can also be tracked using inside-out tracking using the internal sensors of the OHMD, optionally supported by markers attached to the computer screen. Alternatively, outside-in tracking of the OHMD with external sensors can be used, e.g. by attaching markers to the OHMD, which can be tracked by an external camera system.

The display of the virtual data by the OHMD including the view angle or view perspective, including the 3D stereoscopic view angle or view perspective for the left and right eye, can change based on a number of parameters, including, for example, distance of OHMD to patient/interventional site (e.g. if virtual data projected onto interventional site, e.g. inside patient), distance of OHMD to 2D computer monitor (e.g. if 3D virtual data are superimposed onto and/or aligned with 2D intra-operative data, e.g. an intra-operative angiogram or run-off), head position, head angle, cardiac and/or respiratory gating and synchronization of the display of the virtual data with cardiac and/or respiratory gating data of the patient obtained during and/or before the procedure.

Any of the 2D or 3D virtual data in any of the embodiments throughout the specification can include an arterial run-off, e.g. a peripheral run-off or an aortic run-off, optionally including bolus chasing. Bolus chasing can permit real-time visualization of the contrast bolus so that it can be followed, for example, peripherally with images, e.g. digital images, being acquired at a suitable frame rate. If the run-off and/or bolus chasing includes movement of the table on which the patient is positioned during the image acquisition, any 2D or 3D virtual data, e.g. from a pre-operative imaging study, e.g. a CTA or MRA or ultrasound, can be moved with the patient and/or table movement to maintain superimposition and/or alignment of a first 2D or 3D virtual data set, e.g. from the pre-operative imaging study, displayed by one or more OHMDs with a second or additional 2D or 3D virtual data sets, e.g. images obtained during the run-off and/or bolus chasing, displayed by the one or more OHMDs or a separate, standalone computer monitor using any of the combinations outlined in exemplary form in Tables 11, 13 and 14. The moving of the 2D or 3D virtual data, e.g. from a first set of virtual data from a pre-operative imaging test such as a CTA, MRA or ultrasound, displayed, using a computer processor, by the one or more OHMDs can be accomplished using the image registration including 3D-2D transformation matrices or 3D-3D registration techniques and/or the known table movement, e.g. in x, y, and/or z-direction, and/or the measured movement of one or more markers applied to the table or the patient. The image registration can include selection and/or matching and/or superimposition and/or alignment of a different volume of interest from a pre-operative vascular imaging study, e.g. an ultrasound, echocardiogram, CTA or MRA, to match the run-off and/or bolus chasing images and to maintain the superimposition and/or alignment of the first virtual dataset displayed by the one or more OHMDs with the second virtual data set, i.e. the run-off and/or bolus chasing images, e.g. displayed by the one or more OHMDs or a standalone or separate computer monitor or display.

Tracking of Catheter, Guidewire, Sheath, Stent, Coil, Instrument, Implant, Vascular Prosthesis or Other Intra-Vascular or Endoluminal Instrument and/or Device with 3D Display by One or More OHMDs for Cardiovascular, Neurovascular, General Vascular and Other Applications Catheter or device tracking systems can be set up to determine the 2D or 3D position and orientation of the catheter and/or catheter tip or other device (e.g. a guidewire, sheath, stent, coil, instrument, implant, vascular prosthesis or other intra-vascular or endoluminal instrument and/or device), preferably with the ability to update the information in real time. Different methods are available for catheter tracking.

In some embodiments, image processing techniques can be applied to identify the catheter and/or catheter tip or other device (e.g. a guidewire, sheath, stent, coil, instrument, implant, vascular prosthesis or other intra-vascular or endoluminal instrument and/or device) in the x-ray angiography images. The catheter and/or catheter tip or other device (e.g. a guidewire, sheath, stent, coil, instrument, implant, vascular prosthesis or other intra-vascular or endoluminal instrument and/or device) can contain one or more radiopaque markers that can be visible on the x-ray images. To locate the catheter and/or catheter tip or other device (e.g. a guidewire, sheath, stent, coil, instrument, implant, vascular prosthesis or other intra-vascular or endoluminal instrument and/or device) in an x-ray image, for example, a 3D-2D registration can be performed to match a 3D model of the marker(s) on the catheter and/or catheter tip or other device (e.g. a guidewire, sheath, stent, coil, instrument, implant, vascular prosthesis or other intra-vascular or endoluminal instrument and/or device) with the projected marker of the catheter and/or catheter tip or other device (e.g. a guidewire, sheath, stent, coil, instrument, implant, vascular prosthesis or other intra-vascular or endoluminal instrument and/or device) on the x-ray image. The virtual 3D model of the marker(s) and/or the catheter and/or catheter tip or other device, e.g. a guidewire, sheath, stent, coil, instrument, implant, vascular prosthesis or other intra-vascular or endoluminal instrument and/or device, can then be displayed by one or more OHMDs, for example superimposed on a vascular structure or vascular tree or other structures of the patient displayed by a standalone or separate computer monitor or displayed by the OHMD. Alternatively, a search for the projected marker of the catheter and/or catheter tip or other device (e.g. a guidewire, sheath, stent, coil, instrument, implant, vascular prosthesis or other intra-vascular or endoluminal instrument and/or device) on the x-ray image can be performed by cross correlation of a tip template with the pixels in the x-ray image. After this step, the position and direction of the catheter tip in the 2D coordinate system of the x-ray image can be known. Biplanar angiography systems can utilize two separate x-ray sources in a fixed and known spatial configuration and allow for simultaneous visualization of two imaging planes. The spatial configuration of the two imaging planes can be orthogonal. In these systems, the marker localization algorithms described above can be applied to both imaging planes, resulting in a set of 2D coordinates of the marker of the catheter and/or catheter tip or other device (e.g. a guidewire, sheath, stent, coil, instrument, implant, vascular prosthesis or other intra-vascular or endoluminal instrument and/or device) for each imaging plane. Since the spatial configuration of the imaging planes is known, the separate 2D coordinates can be transformed back into 3D space, for example using a backprojection algorithm, which can result in position and orientation, e.g. coordinates in x, y, and/or z-direction, of the catheter and/or catheter tip or other device (e.g. a guidewire, sheath, stent, coil, instrument, implant, vascular prosthesis or other intra-vascular or endoluminal instrument and/or device) in 3D space.

Another catheter or device tracking technology can be based on magnetic resonance imaging (MRI). Active tracking capability of the catheter and/or catheter tip or other device (e.g. a guidewire, sheath, stent, coil, instrument, implant, vascular prosthesis or other intra-vascular or endoluminal instrument and/or device) can be provided by one or more miniature solenoid magnetic resonance receiver and/or transmitter coils integrated into portions, e.g. a tip, of the catheter and/or catheter tip or other device (e.g. a guidewire, sheath, stent, coil, instrument, implant, vascular prosthesis or other intra-vascular or endoluminal instrument and/or device). Using signal from the one or more receiver coils, a dedicated tracking MRI sequence, e.g. modified fast-field echo, can enable the localization of the position and, in case of multiple coils, orientation of the catheter and/or catheter tip or other device (e.g. a guidewire, sheath, stent, coil, instrument, implant, vascular prosthesis or other intra-vascular or endoluminal instrument and/or device). The derived position and/or orientation of the catheter and/or catheter tip or other device (e.g. a guidewire, sheath, stent, coil, instrument, implant, vascular prosthesis or other intra-vascular or endoluminal instrument and/or device) can be overlaid on a 3D dataset, e.g. a 3D dataset acquired prior to or during the interventional or surgical procedure. The 3D dataset, including the overlaid catheter position, can be displayed by the one or more OHMD's. The 3D dataset can be acquired and derived using the methods described in the specification.

Catheter tracking can also be performed using a sensor-based electromagnetic system. The system can consist of miniaturized sub-millimeter coil sensors embedded in the catheter and/or catheter tip or other device (e.g. a guidewire, sheath, stent, coil, instrument, implant, vascular prosthesis or other intra-vascular or endoluminal instrument and/or device). The coils generate electrical currents once placed within an alternating electromagnetic field generated by a transmitter unit and can be tracked in real time.

The tracking system can be co-registered with fluoroscopy imaging, for example by installing the transmitter unit within the fluoroscopy detector of the x-ray imaging system. Using this or similar hardware setups, fluoroscopic imaging and electromagnetic sensor tracking can be pre-aligned and auto-registered. This can allow for 3-dimensional real-time tracking of a sensor-equipped catheter and/or catheter tip or other device (e.g. a guidewire, sheath, stent, coil, instrument, implant, vascular prosthesis or other intra-vascular or endoluminal instrument and/or device) and projection of the catheter and/or catheter tip or other device (e.g. a guidewire, sheath, stent, coil, instrument, implant, vascular prosthesis or other intra-vascular or endoluminal instrument and/or device) onto the 3D models of the vasculature and/or heart and/or lungs and/or neurovascular anatomy derived from preoperative or intra-operative images by one or more OHMDs, compensated for cardiac movement due to heart-beat and organ motion during respiration and patient movement. A reference sensor attached to the patient's body can also provide information about the spatial relationship between the patient and the tracking field.

Catheter or device tracking methods that work independently from the x-ray fluoroscopy imaging, e.g. MRI-based tracking or electromagnetic tracking, do not require continuous updates of the x-ray image. Information about 3D position and orientation of the catheter and/or catheter tip or other device (e.g. a guidewire, sheath, stent, coil, instrument, implant, vascular prosthesis or other intra-vascular or endoluminal instrument and/or device) can be available continuously and in real-time. It can be projected continuously and in real-time onto pre-operative and/or intra-operative images and/or 3D models created from pre-operative and/or intra-operative images, e.g. graphical representations including one or more virtual catheter and/or catheter tip or other device (e.g. a guidewire, sheath, stent, coil, instrument, implant, vascular prosthesis or other intra-vascular or endoluminal instrument and/or device). In some embodiments, radiation exposure to the patient and the physician can be greatly reduced.

By superimposing and/or aligning a first virtual data set, e.g. a pre-operative 3D imaging study, displayed by one or more OHMDs with a second virtual data set, e.g. an intra-procedural imaging study such as a 2D, 3D angiogram including, for example, a run-off and/or bolus chase, displayed by the one or more OHMD's and/or a separate or standalone computer monitor or display, with optional superimposition and/or alignment of tracking data, e.g. from a catheter, catheter tip, guidewire, sheath, stent, coil, instrument, implant, vascular prosthesis or other intra-vascular or endoluminal instrument and/or device including virtual images, data or representations of the catheter, catheter tip, guidewire, sheath, stent, coil, instrument, implant, vascular prosthesis or other intra-vascular or endoluminal instrument and/or device displayed, with optional superimposition and/or alignment of a virtual 3D model or virtual image of the catheter, catheter tip, guidewire, sheath, stent, coil, instrument, implant, vascular prosthesis or other intra-vascular or endoluminal instrument and/or device, for example by the one or more OHMDs, superimposed onto and/or aligned with the 3D vascular tree from the first virtual data set or the 2D or 3D vascular tree from the second virtual data set, the display can facilitate the placing and/or advancing of the physical catheter guidewire, sheath, stent, coil, instrument, implant, vascular prosthesis or other intra-vascular or endoluminal instrument and/or device into a vascular ostium, e.g. the take-off of a vascular branch, for example hidden on the run-off behind a larger vessel, e.g. an aorta. For example, the vascular ostium and/or the direction of the take off cannot be visible on the intra-operative imaging study, e.g. the 2D or 3D angiogram including an optional vascular run-off and/or bolus chasing study, but it can be visualized on the superimposed and/or aligned pre-operative imaging study, e.g. a 3D CTA, ultrasound or MRA, displayed by the one or more OHMDs. The information, e.g. the first virtual dataset, e.g. a pre-operative 3D imaging study, registered with an intra-operative 2D or 3D angiogram, can also be used for directing, for example, a robot used or programmed for advancing a catheter guidewire, sheath, stent, coil, instrument, implant, vascular prosthesis or other intra-vascular or endoluminal instrument and/or device by providing 3D information (from the pre-operative imaging study) on the vascular tree, including, for example, the various branches, their orientation, their origin and/or take-off, registered with the intra-operative imaging study, e.g. a 2D, 3D angiogram including, for example, a run-off and/or bolus chase study.

Vascular trees and/or vascular branches that can be visualized in this manner using 5 or more dimensions can include, for example, the ones listed in Table 12.

TABLE 12

Vascular trees, vascular branches, vessels that can be visualized by one or more OHMDs in a first, second, third, and additional virtual datasets, stereoscopically or non-stereoscopically.

Arteries of the head and neck:
Superior thyroid group of arteries/vascular tree:
  superior laryngeal
  sternocleidomastoid branch
  infrahyoid branch
  cricothyroid branch
  glandular branches
Ascending pharyngealgroup of arteries/vascular tree:
  posterior meningeal
  pharyngeal branches
  inferior tympanic TABLE 12-continued Vascular trees, vascular branches, vessels that can be visualized by one or more OHMDs in a first, second, third, and additional virtual datasets, stereoscopically or non-stereoscopically.

Lingual group of arteries/vascular tree:
  suprahyoid
  dorsal lingual
  deep lingual
  sublingual
Facial group of arteries/vascular tree:
  cervical branches (ascending
palatine, tonsillar, submental, glandular)
  facial branches (inferior labial
  superior labial/nasal septum
  lateral nasal
  angular)
Occipital group of arteries/vascular tree:
  sternocleidomastoid
  meningeal
  occipital
  auricular
  descending
Posterior auricular group of arteries/vascular tree:
  stylomastoid
  stapedial
  auricular
  occipital
  parotid
Superior temporal group of arteries/vascular tree:
  transverse facial
  middle temporal (zygomatico-orbital)
  anterior auricular
  frontal
  parietal
Maxillary group of arteries/vascular tree:
Mandibular part
  anterior tympanic
  deep auricular
  middle meningeal (superior tympanic, petrosal)
  accessory meningeal
  inferior alveolar
Pterygoid part
  to muscles of mastication (deep temporal, pterygoid, masseteric)
  buccal
Pterygopalatine part
  posterior superior alveolar
  infraorbital (anterior superior alveolar)
  descending palatine (greater palatine, lesser palatine)
  artery of the pterygoid canal
  sphenopalatine (posterior septal branches, posterior lateral nasal)
  pharyngeal
Internal carotid
Cervical group of arteries/vascular tree:
  carotid sinus
Petrous group of arteries/vascular tree:
  Vidian
  caroticotympanic
Cavernous/ophthalmic group of arteries/vascular tree:
  orbital group: anterior ethmoidal
  posterior ethmoidal
  lacrimal (lateral palpebral)
  medial palpebral
  terminal (supraorbital, supratrochlear, dorsal nasal)
Ocular group of arteries/vascular tree: central retinal
  ciliary (short posterior, long posterior, anterior)
  Circulus arteriosus major
  hypophysial (superior, inferior)
Brain group of arteries/vascular tree:
  Circle of Willis
  ACA (anterior communicating, Recurrent artery of Heubner, Orbitofrontal artery)
  MCA (anterolateral central, Prefrontal artery, Superior terminal branch, Inferior terminal branch, Anterior temporal branch)
  posterior communicating
  anterior choroidal

TABLE 12-continued

Vascular trees, vascular branches, vessels that can be visualized by one or more OHMDs in a first, second, third, and additional virtual datasets, stereoscopically or non-stereoscopically.

Vertebral group of arteries/vascular tree:
  meningeal
  spinal (posterior, anterior)
  basilar: pontine
  labyrinthine
  cerebellar (AICA, SCA, PICA)
  cerebral (PCA)
  Thyrocervical trunk group of arteries/vascular tree:
inferior thyroid
  inferior laryngeal
  tracheal
  esophageal
  ascending cervical
  pharyngeal
  glandular branches
Transverse cervical group of arteries/vascular tree:
  superficial branch
  deep branch/dorsal scapular
    scapular anastomosis
Suprascapular group of arteries/vascular tree:
  acromial branch
  scapular anastomosis
Costocervical trunk group of arteries/vascular tree:
  deep cervical
  supreme Intercostal artery
Arteries of the chest:
Pulmonary artery
    Right
    Left (Ligamentum) arteriosum)
Heart
  Coronary circulation group of arteries/vascular tree:
  Right coronary:
    SA nodal
    AV nodal
    Atrial
    Right marginal
    Posterior interventricular
  Left coronary:
    Anterior interventricular
    Left circumflex (Left marginal)
Aorta
Sections
  Ascending aorta
  Aortic arch
  Descending aorta
  Thoracic aorta
  Abdominal aorta
  Aortic body
Aortic arch
Brachiocephalic
  Thyreoid
  Right subclavian
  Right common carotid
Left
common carotid
  External carotid
  Internal carotid
  Carotid body
  Carotid sinus
  Carotid bifurcation
Left
subclavian
  Internal thoracic: Anterior
intercostal
  Thymic
  Pericardiacophrenic
  Perforating branches
  terminal (Musculophrenic, superior epigastric)
  Costocervical trunk: Highest
intercostal (Posterior intercostal 1-2)
  Deep cervical
Descending aorta:
  Visceral: Bronchial
  Esophageal
  Mediastinal
  Posterior intercostal 3-11
  Subcostal
  Superior phrenic
Celiac tunk:
Left gastric
  Esophageal branches
Common hepatic
  Proper hepatic
    cystic
    Right gastric
  Gastroduodenal
    right gastroepiploic
    superior
pancreaticoduodenal
    supraduodenal
Splenic
  Pancreatic branches
    greater
    dorsal
  Short gastrics
  Left gastroepiploic
Superior mesenteric artery, group and vascular branches:
  Inferior pancreaticoduodenal
  Intestinal
    jejunal
    ileal
    arcades
    vasa recta
  Ileocolic
    colic
    anterior cecal
    posterior cecal
    ileal branch
    appendicular
  Right colic
  Middle colic
    Marginal
Suprarenal
  Middle suprarenal
Renal
  Inferior suprarenal
  Ureteral
Gonadal
  Testicular artery
  Ovarian artery
Lumbar
  Lumbar arteries
Inferior mesenteric
  Left colic
    Marginal
  Sigmoid
  Superior rectal
Common iliac
Internal iliac
Iliolumbar group and vascular branches:
  Lumbar branch
  Iliac branch
Superior vesicular artery
  Umbilical artery
    Medial umbilical ligament
  to ductus deferens
Obturator group and vascular branches:
  Anterior branch
    Pubic branch
  Posterior branch
    Acetabular branch
    Cruciate anastomosis
  Corona mortis
Middle rectal
  Vaginal branch/Prostatic
branch
Uterine group and vascular branches:
  Arcuate
  Vaginal branches
  Ovarian branches

TABLE 12-continued

Vascular trees, vascular branches, vessels that can be visualized by one or more OHMDs in a first, second, third, and additional virtual datasets, stereoscopically or non-stereoscopically.

Tubal branches
    Spiral
    Vaginal/Inferior vesical
Inferior gluteal group and vascular branches:
    Accompanying of sciatic nerve
    Cruciate anastomosis
Internal pudendal group and vascular branches:
    Inferior rectal
    Perineal
      posterior scrotal
      posterior labial
    Bulb of penis/vestibule
    Urethral
    Deep artery of the penis
      helicine
    Deep artery of clitoris
    Dorsal of the penis
    Dorsal of the clitoris
External iliac
    Inferior epigastric
      Corona mortis
    Deep circumflex iliac
    Femoral
      see arteries of lower limbs
Median sacral
    Coccygeal glomus
Arteries of the arm:
Axillary group of arteries/vascular tree:
Shoulder (before teres minor) group of arteries/vascular tree:
    Superior thoracic artery
    Thoracoacromial artery
      pectoral branch
      acromial branch
      clavicular branch
      deltoid branch
    Lateral thoracic artery
    Subscapular artery
      scapular anastomosis
      circumflex scapular artery
      thoracodorsal artery
    anterior humeral circumflex artery
    posterior humeral circumflex artery
Brachial group of arteries/vascular tree:
Forearm (before cubital fossa)
    profunda brachii
      radial collateral
      medial collateral
    ulnar collateral
      superior
      inferior
Radial artery group of arteries/vascular tree:
forearm
    radial recurrent
wrist/carpus
    Dorsal carpal branch
      dorsal carpal arch
    Palmar carpal branch
      deep palmar arch
hand
    Superficial palmar branch
      princeps pollicis
      radialis indicis artery
      superficial palmar arch
Median artery
    median artery
Ulnar artery
forearm
    ulnar recurrent
      anterior
      posterior
    common interosseous
      anterior
      posterior
        interosseous
recurrent
wrist/carpus
    Dorsal carpal branch
      dorsal carpal arch
    Palmar carpal branch
      superficial palmar arch
Arterial Arches group of arteries/vascular tree:
    Dorsal carpal arch
      dorsal metacarpal
      dorsal digital
    Palmar carpal arch
      superficial palmar arch
        common palmar digital
        proper palmar digital
      deep palmar arch
        palmar metacarpal
Arteries associated with the leg:
Inferior epigastric group of arteries/vascular tree:
    cremasteric ♂/round ligament ♀
Deep circumflex iliac group of arteries/vascular tree:
    no major branches
Femoral group of arteries/vascular tree:
In femoral canal
    superficial epigastric
    superficial circumflex iliac
    superficial external pudendal
    deep external pudendal
    (anterior scrotal ♂
Descending genicular
    saphenous branch
    articular branches
Profunda femoris
    medial circumflex femoral
      ascending
      descending
        superficial
        deep
        acetabular
    lateral circumflex femoral
      descending
      transverse
      ascending
    perforating
    Cruciate anastomosis
    Trochanteric anastomosis
Popliteal group of arteries/vascular tree:
Genicular group of arteries/vascular tree:
    superior
genicular (medial, lateral)
    middle genicular
    inferior
genicular (medial, lateral)
Sural group of arteries/vascular tree:
    no major branches
Anterior tibial group of arteries/vascular tree:
    tibial recurrent
      posterior
      anterior)
    anterior malleolar
      medial
      lateral
      dorsalis
pedis: tarsal (medial, lateral)
Tibial-fibular (Tibial-peroneal) trunk group of arteries/vascular tree:
    Posterior tibial
      circumflex fibular
      medial plantar
      lateral plantar
      fibular (peroneal)

TABLE 12-continued

Vascular trees, vascular branches, vessels that can be visualized by one or more OHMDs in a first, second, third, and additional virtual datasets, stereoscopically or non-stereoscopically.

Arches group of arteries/vascular tree:
  arcuate
    dorsal metatarsal
      first dorsal metatarsal
  deep plantar
  dorsal digital arteries
  plantar arch
    plantar metatarsal
      common plantar digital
      proper plantar digital

Catheter Steering

Different types of vascular catheters are available. Fixed curve catheters have a predefined distal curve shape near the tip.

Deflectable catheters feature a tip that can be pulled into a curve by using a wire connected to the tip. The tip returns to its original shape through natural springback. One type of deflectable catheter can move the tip in a single plane, for example a uni-directional catheter (the tip can be pulled in a single direction) or a bi-directional catheter (the tip can be pulled in two opposing directions).

Fixed curve, uni-directional or bi-directional catheters can be steerable, so that the orientation of the plane in which the tip is curved at the distal end can be rotated by turning or rotating the proximal end or handle of the catheter. The resulting tip orientation depends on the torque transmission (also known as torque transfer) from the proximal end to the distal end. With high torque transmission, there is almost like-for-like rotational movement of the tip with rotational movement of the proximal handle. With low torque transmission, the proximal handle has to be turned much further to effect a rotational movement of the tip.

Other types of deflectable catheters are 4-way deflectable or omnidirectional catheters. These devices have 4 wires connected to a distal pull ring. They can be pulled in 4 directions using a handle at the proximal end. By manipulating one or more pull wires simultaneously, the tip can be oriented in any direction. A robotic device can be used to control the pull wires. Omnidirectional catheters are not steered by rotating the proximal end of the catheter, but by changing the direction in which the tip is pulled instead.

In some embodiments, the control of steerable and omnidirectional catheters and tracking the catheter tip can be improved. For example, the orientation of the tip of a steerable catheter can be determined from the rotational position of its proximal end or handle. The relationship between the rotational travel of the distal tip and the rotational travel of the proximal handle can depend on torque transmission. If the torque transmission is known, it can be used as a correction factor when deriving the tip orientation from the rotational position of the proximal handle.

In one embodiment, the torque transmission can be determined pre-operatively prior to use of the catheter. For example, a bench test can be performed to measure the distal tip rotation angle for one or more varying rotational positions or rotation angles of the proximal handle. Using one or more measurements, a calibration curve or calibration function can be derived that allows for conversion of proximal into distal rotation angles and vice versa using, for example, a best fit method. Without limitation, the calibration curve or calibration function can be linear, quadratic, cubic, logarithmic, exponential, or any other type suitable for interpolating or approximating the series of one or more measurements.

The measurements can be performed for each individual catheter as part of the production process. The calibration curve or calibration function can be shipped with the catheter, e.g. printed on the instructions for use or in electronic or digital format.

Alternatively, the calibration curve or calibration function can be established once for a representative sample of one more catheters of a specific type and/or model.

The calibration curve or calibration function can then be incorporated into an electronic system, e.g. a computer system with one or more computer monitors, set up to predict the tip rotation based on handle rotation or vice versa. It can be entered manually or imported from a digital file. It can be imported from a QR code, e.g. on the catheter packaging. It can be imported from an RF tag, e.g. integrated into or attached to the catheter. It can also be built into the system, e.g. selectable based on type and/or model of the catheter.

In another embodiment, the torque transmission can be measured during the procedure. For this purpose, sensors can be built into the catheter or attached to the catheter. The sensors can be strain gauges. The sensors can also consist of elastic conductive wires that extend through the entire length of the catheter wall. Alternatively, multiple wires can extend through sub-segments of the catheter. As the catheter is torqued, the wire can change its length and cross-sectional area and therefore its electrical resistance. The change in resistance can be measured and used to determine the change in length. Based on the change in length of the wire, the torque transmission through the respective catheter segment through which the wire extends can be derived as the angle of rotation between the beginning and end of the wire segment. If the catheter is divided into multiple segments, the angles for each segment can be added up to determine the overall angle between the orientation of the proximal handle and the distal tip.

Once the torque transmission is known, either from pre-operative calibration measurements or intra-operative measurements, the tip orientation can be continuously predicted from the orientation of the proximal handle.

In one embodiment, markers can be attached to the handle that can be continuously tracked by the OHMD or a stand-alone navigation system or any other tracking means described in the specification. Any of the markers described in the specification can be used, including markers with one or more geometric patterns (e.g. a QR code).

The tracked orientation of the proximal handle can be converted into the tip orientation by applying the calibration curve or calibration function or, in case of sensor-based torque transmission measurements, by adding the angle derived from the sensor measurements. Once the tip orientation has been calculated, it can be visualized in the OHMD. For example, it can be displayed as a pointer or arrow inside the 3D vasculature model overlaid onto the patient as described herein. It can also be displayed in different colors, depending on whether the tip is pointing in a desired direction or not. For example, the OHMD software can allow the surgeon to identify a target location (e.g. a vascular bifurcation and/or a lesion and/or a target vessel or organ) in the 3D vasculature model where the catheter tip can be directed.

The OHMD software can then traverse the 3D vasculature model and determine which vessel branches the catheter needs to be directed into in order to reach the target location.

When the catheter approaches each branch point, the software can then visualize the catheter tip in green if it is directed towards the correct branch and green otherwise. The data can also be used to direct the catheter using a robot, e.g. an omnidirectional catheter with a robot controlling the pull wires.

In another embodiment, an actuator or robotic device attached to the proximal end of the catheter can be used to control the direction of the catheter tip by turning the proximal end. The orientation of the actuator in 3D space can be tracked using the tracking methods described in the specification. This includes attaching markers and tracking by the OHMD, an image capture, video capture, or camera system, a 3D scanner, or a navigation system. The rotational position of the proximal end of the catheter can be set by the actuator or robotic device. To change the rotation of the tip by a desired amount, the corresponding required rotation of the proximal end of the catheter can be calculated using the torque transmission and the position of the actuator or robotic device in 3D space. The required rotation of the proximal end can then be transferred to the actuator, e.g. using a wireless connection.

In another embodiment, haptic feedback can be provided through the handle, robotic device or actuator, based on the tracked position of the catheter tip. The haptic feedback can, for example, indicate to the physician when the catheter tip is oriented towards the lumen of a branching vessel. The haptic feedback can also indicate if the catheter tip is pointing in the right direction to move the catheter tip towards a desired target location identified in the 3D vasculature model. The haptic feedback can also indicate if the catheter tip is pointing in the wrong direction to move the catheter tip towards a desired target location identified in the 3D vasculature model. The haptic feedback can consist of vibrations or shaking of the handle, robotic device or actuator. The haptic feedback can be used with steerable or omnidirectional catheters.

Any of the methods, techniques and systems described above for catheter tracking, including image processing, radiopaque markers, biplanar angiography and fluoroscopy, magnetic resonance imaging and electromagnetic systems, can also be combined with haptic feedback through the handle, robotic device or actuator.

In one embodiment, the position and orientation can be tracked using, for example, image processing, radiopaque markers, angiography, fluoroscopy, magnetic resonance imaging or electromagnetic systems. A desired target location can be identified in the 3D vasculature model, e.g. through a graphical user interface, e.g. displayed by the OHMD or a computer monitor. The system can identify the path in the vasculature model from the current catheter tip location to the target location. The system can also determine the necessary rotation of the catheter tip needed to move from the current location to the target location. The system can determine the rotation needed to direct the catheter tip towards the lumen of a branching vessel.

Haptic feedback can then be provided to indicate to the physician when the catheter tip is oriented in the correct direction. Haptic feedback can also indicate in which direction the catheter tip needs to be rotated. The haptic feedback can consist of vibrations or shaking of the handle, robotic device or actuator. The haptic feedback can be used with steerable or omnidirectional catheters.

Viewing 2D Computer Monitors Through an OHMD Unit for Cardiovascular, Neurovascular, General Vascular and Other Applications In some embodiments, the OHMD system can detect, e.g. automatically, if the surgeon or interventionalist and/or radiologist and/or operator is looking at a computer or display monitor separate from the OHMD, for example, with use of an image and/or video capture system and/or 3D scanner integrated into, attached to or separate from the OHMD. The standalone or separate computer or display monitor can be used, for example, to display image data, e.g. of a patient, for example of a 2D or 3D angiogram, biplanar angiogram, or a vascular runoff, and/or to concurrently display virtual data displayed by the OHMD. The image and/or video capture system and/or 3D scanner can, for example, capture the outline of the computer or display monitor, e.g. round, square or rectangular, which can be detected by image processing software, and the software can, optionally, automatically match, superimpose or align the items or structures including vessels displayed by the OHMD with the items or structures including vessels displayed by the standalone or separate computer or display monitor. Alternatively, the user, operator and/or surgeon or interventionalist and/or radiologist can execute a command, e.g. a voice command or a command using a virtual finger/keyboard interface, indicating that he or she is looking at the standalone or separate computer or display monitor and the software can then match, superimpose or align the items or structures displayed by the OHMD with the items or structures displayed by the standalone or separate computer or display monitor. The OHMD system can match, superimpose, or align all of the structures including vessels displayed by the standalone or separate computer monitor. The OHMD system can match, superimpose or align a portion of the structures displayed by the standalone or separate computer monitor, e.g. only major vessels or vessels that have unique 2D and/or 3D shape criteria that can facilitate the matching of 2D and/or 3D intra-procedural angiographic data and 2D and/or 3D pre-procedural imaging data, e.g. generated with use of MRI angiography, CT angiography and/or ultrasound flow studies, diagnostic angiogram or any other imaging studies known in the art for imaging vascular flow.

The OHMD can display the structures and/or vessels displayed by the standalone or separate computer monitor using the same color. The OHMD can display the structures and/or vessels displayed by the standalone or separate computer monitor using different colors. The OHMD can display structures or vessels not displayed by the standalone or separate computer monitor using a different color or greyscale or contrast than that used by the standalone or separate computer monitor thereby, for example, highlighting branches of the vascular tree that are not visible on the 2D and/or 3D intra procedural angiographic data, e.g. branches of the vascular tree that are hidden behind dense radiopacity of a larger vessel positioned in front of a smaller vessel.

The OHMD can display the structures and/or vessels displayed by the standalone or separate computer monitor using the same greyscale and/or contrast used by the standalone or separate computer monitor. The OHMD can display the structures and/or vessels displayed by the standalone or separate computer monitor using a different greyscale and/or contrast used by the standalone or separate computer monitor. Optionally, the greyscale and/or contrast of the display by the one or more OHMD's, the display by the computer monitor or both, can be varied, e.g. automatically or by the user, for example using a graphical user interface. Optionally, the greyscale and/or contrast of the display by the one or more OHMD's, the display by the computer monitor or both can be optimized to maximize the contrast and differential visualization between pre- and intra-procedural images, e.g. pre-procedural 3D images superimposed onto one or more intra-procedural 2D or 3D images. The OHMD can display the structures and/or vessels displayed by the standalone or separate computer monitor using the same image intensity used by the standalone or separate computer monitor. The OHMD can display the structures and/or vessels displayed by the standalone or separate computer monitor using a different image intensity used by the standalone or separate computer monitor, e.g. brighter or less bright.

In some embodiments, a standalone or separate computer or display monitor located in a user area, e.g. an interventional radiology suite or a surgical radiologic suite, can be used as a calibration or reference or registration phantom for the OHMD unit including the frame and display position, orientation and/or alignment and/or direction of movement. The monitor can have a round, rectangular or square shape of known dimensions. An image and/or video capture system and/or 3D scanner integrated into, attached to or separate from the OHMD can be used to capture one or more images of the monitor. Since the dimensions of the monitor can be known, the size, shape or dimensions, for example along its edges, or the area of the monitor on the captured image(s) can be used to determine the distance and/or orientation and/or angle of the OHMD to the monitor; the shape of the circle, oval, rectangle or square can be used to determine the distance and/or orientation and/or angle of the OHMD relative to the monitor. If the image and/or video capture system and/or 3D scanner integrated into or attached to the OHMD uses two or more cameras, the difference in shape of the circle, oval, rectangle or square detected between a first, second and any additional cameras can be used to increase the accuracy of any estimates of the distance and/or angular orientation of the OHMD to the display monitor, e.g. by calibrating the measurement of a first camera against a second camera against a third camera and so forth. If two or more cameras are used integrated into or attached to different portions of the OHMD frame, e.g. the left side of the frame and the right side of the frame, the difference in projection of the monitor circle, oval, rectangle or square between the two cameras can also be used to estimate the user's head position and/or orientation and/or alignment and/or the position and/or orientation and/or alignment of the OHMD frame in relationship to the user's head and/or face.

In some embodiments, the surgeon or interventionalist and/or radiologist and/or user can optionally look at the display monitor through the OHMD while maintaining his or her head in a neutral position, e.g. with no neck abduction, adduction, flexion, extension or rotation, for example in a predefined location, e.g. with known coordinates within a common coordinate system. This head position can be used to calibrate the position of the OHMD display in relationship to the target area and/or the patient and/or the surgical/interventional radiologic site, e.g. during an initial registration or a subsequent registration. This head position can also be used to calibrate the position of the OHMD unit/frame in relationship to the user's and/or the surgeon or interventionalist and/or radiologist's head and face. Optionally, the user and/or surgeon or interventionalist and/or radiologist can place his or her head on a chin stand or head holder for purposes of this calibration or registration. This process of using an external computer or display monitor as a reference for calibration and/or registration purposes can be performed at the beginning of an activity and/or a surgical/interventional radiologic procedure, e.g. as part of an initial registration process. This process of using an external display monitor as a reference for calibration and/or registration purposes can also be performed during an activity or after an activity and/or surgical/interventional radiologic procedure, for example when there is concern that the OHMD unit may have moved relative to the user's and/or surgeon or interventionalist and/or radiologist's face. For example, the surgeon or interventionalist can return his or her head into the same pre-defined position, e.g. with known coordinates in the coordinate system, and the position of the optical head mounted display (with its coordinates) can be compared with an earlier measurement, for example to detect any movement of the optical head mounted display.

In some embodiments, the position, location, orientation, and/or alignment of the outline of the standalone or separate computer or display monitor can be monitored, for example using an image and/or video capture system and/or 3D scanner integrated into, attached to or separate from the OHMD. Optionally, the position, location, orientation and/or alignment of the outline of the standalone or separate computer or display monitor can be monitored using attached optical markers, navigation markers including infrared markers, retroreflective markers, RF markers, LED's and/or IMU's as well as any other techniques described in the specification or known in the art for determining and/or tracking the position, location, orientation and/or alignment of an object. With the position, location, orientation and/or alignment of the standalone or external computer or display monitor known, the position, location, orientation, alignment and/or direction of movement of the OHMD unit can be tracked in relationship to it, for example in a common coordinate system, e.g. via an image and/or video capture system and/or 3D scanner integrated into or attached to the OHMD or optical markers, navigation markers including infrared markers, retroreflective markers, RF markers, LED's and/or IMU's integrated into it or attached to it. As the position, location, orientation, alignment and/or direction of movement of the OHMD unit can be tracked, the display of the OHMD unit can at all times or, if preferred, intermittently, display the same structures, or at least a portion or subset thereof, displayed by the standalone or separate computer or display monitor, spatially matched and superimposed onto and/or aligned with the corresponding anatomic structures. If the standalone or separate computer or display monitor occupies only a portion of the visual field covered by the OHMD display, the OHMD display can match the displayed structures and/or vessels with the structures and/or vessels displayed by the standalone or separate computer or display monitor only for the portion of the visual field occupied by the standalone or separate computer or display monitor. Optionally, the OHMD display can display structures and/or vessels extending beyond the portion of the visual field occupied by the standalone or separate computer or display monitor. The structures and/or vessels extending beyond the portion of the visual field occupied by the standalone or separate computer or display monitor can be continuous with the structures and/or vessels displayed by the standalone or separate computer or display monitor. The structures outside the portion of the visual field occupied by the standalone or separate computer or display monitor can be separate and/or from the structures and/or vessels displayed by the standalone or separate computer or display monitor. For example, in addition to displaying one or more structures and/or vessels matching or corresponding to what is displayed by the standalone or separate computer or display monitor, the OHMD display can display items such as vital signs or patient demographics, or pre-operative imaging studies in those portions of the visual field that do not include the standalone or separate computer or display monitor. This can, for example, be useful when the user, operator and/or surgeon or interventionalist and/or radiologist is not looking at the patient.

In some embodiments, the OHMD can display surgical/interventional radiologic field related information, e.g. details or aspects of a virtual surgical/interventional radiologic plan, e.g. predetermined guide wire path, predetermined stent, coil or other vascular device position, orientation, alignment, fit, size, e.g. as predetermined using a pre-procedural imaging test, e.g. an MRA, CTA, ultrasound, diagnostic angiogram etc., or anatomic information of the patient, e.g. from a pre-procedural imaging study, when the user or surgeon or interventionalist and/or radiologist or radiologist is looking at the surgical/interventional radiologic field, e.g. the area of a diseased vessel inside the patient; the OHMD can display portions of information or all of the information displayed by a standalone or separate computer or display monitor, for example in 3D while the standalone or separate computer or display monitor display can be in 2D, when the user or surgeon or interventionalist and/or radiologist is looking at the standalone or separate computer or display monitor; the OHMD can display non-surgical/interventional radiologic field related information and non-standalone or separate computer or display monitor related or displayed information when the user or surgeon or interventionalist and/or radiologist is neither looking at the surgical/interventional radiologic/interventional radiologic field nor at the standalone or separate computer or display monitor or when the surgical/interventional radiologic field and/or the standalone or separate computer or display monitor occupy only a portion of the visual field covered by the OHMD display or visible to the surgeon and/or interventionalist through a see through optical head mounted display. The switching or toggling between surgical/interventional radiologic field related information, standalone or separate computer or display monitor information and other information by the OHMD display can be automatic, for example via image capture and related image processing and recognition which area the user or surgeon or interventionalist and/or radiologist is currently looking at, e.g. optionally demarcated by optical markers, navigation markers including infrared markers, retroreflective markers, RF markers, and/or LED's, or it can be via commands executed by the user or surgeon or interventionalist and/or radiologist, e.g. voice commands or finger/keyboard commands, for example using a virtual keyboard displayed by the OHMD display. For example, when optical markers are used, they can include one or more QR codes, wherein individual QR codes can designate or define the area that the surgeon and/or interventionalist is looking at e.g. an anesthesia area, a surgical field area, a standalone computer monitor with radiologic and/or imaging information, e.g. an angiogram, a standalone computer monitor with anesthesia information, a standalone computer monitor with OR supply information or OR schedule information, an OR supply area, an instrument area, an implant area.

The OHMD can display information related to the information, e.g. information about vascular structures, displayed on the standalone or separate computer display or monitor in two dimensions or three dimensions, the latter stereoscopically or non-stereoscopically. Any number of combinations of displays can be applied between the display by the OHMD display and the display by the standalone or separate computer or monitor display. For example, when the computer or monitor displays shows a pre-procedural or intra-procedural imaging study of the patient, these can be displayed in 2D (e.g. cross-sectional) or 3D using pseudo-3D display techniques, for example with surface reconstruction and shading. Overlaying or superimposing, for example, a true 3D, e.g. stereoscopic 3D, view of the anatomy from the pre- or intra-procedural imaging study and/or virtual surgical/interventional radiologic plan of the patient using the OHMD display onto the same anatomic structures, e.g. vessels, and/or virtual surgical/interventional radiologic plan displayed in 2D or pseudo 3D by the standalone or separate computer or display monitor can be beneficial for the surgeon or interventionalist and/or radiologist as he or she executes surgical/interventional radiologic plans or plans next surgical/interventional radiologic plans during a procedure.

In embodiments, the display of the OHMD unit and/or the standalone or separate computer or display monitor can display functional and/or time studies of the patient, e.g. vascular flow studies or bolus studies, while the other of the two display modalities can simultaneously display and/or superimpose static images. For example, the standalone or separate computer or display monitor can display 2D or 3D function and/or time studies, e.g. a vascular flow, an injection and/or a bolus study including, for example, bolus chasing, using single or biplane fluoroscopy or angiography or captured using digital subtraction angiography (DSA) or 3D rotation angiography (3DRA), while the display of the OHMD unit can superimpose 2D or 3D non-stereoscopic or 3D stereoscopic images of the corresponding anatomy, e.g. the vascular tree, e.g. from a pre-procedural CTA, MRA, ultrasound or diagnostic angiogram.

In embodiments, the standalone or separate computer or display monitor can show intra-procedural vascular information from a first imaging study, e.g. from an injection and/or a bolus study including, for example, bolus chasing, using single or biplane fluoroscopy or angiography or captured using digital subtraction angiography (DSA) or 3D rotation angiography (3DRA) or any other type of vascular flow or angiographic image obtained during the procedure. The images displayed on the standalone or separate computer or display monitor can, for example, also show a catheter and/or guide wire and/or other device inserted into one or more vessels or a vascular tree. One or more OHMDs can display information from a second, different imaging study, e.g. different with regard to time when it was acquired (including an earlier intra-procedural imaging study) and/or different with regard to imaging modality, e.g. CT, MRI, ultrasound. The second imaging study displayed be the one or more OHMDs can be superimposed and/or aligned with the first imaging study displayed by the separate, standalone computer monitor so that, for example, corresponding vessels or vascular branches, e.g. filled with x-ray or other contrast or dye, are substantially superimposed and/or aligned; the second imaging study displayed be the one or more OHMD's can be maintained [e.g. even in the presence of head movement by the operator] superimposed and/or aligned with the first imaging study displayed by the computer monitor so that, for example, corresponding vessels or vascular branches, e.g. filled with x-ray or other contrast or dye, are substantially superimposed and/or aligned with the vessels and/or vascular branches display by the separate, standalone computer monitor.

The second imaging study displayed by the one or more OHMDs can be three- or multi-dimensional and can be superimposed onto the first imaging study displayed by the separate or standalone computer monitor or display in a predetermined or predefined orientation. For example, if the first imaging study displayed by the separate or standalone computer monitor or display is oriented in a coronal plane relative to the patient, the second imaging study displayed by the one or more OHMDs can be oriented, superimposed onto and/or aligned with the first imaging study displayed by the separate or standalone computer monitor or display so that portions of vascular branches that are anatomically anterior to the substantially coronal plane, in this example, of the first imaging study displayed by the separate or standalone computer monitor or display can be projected by the one or more OHMDs in front of the separate or standalone computer monitor or display, e.g. by the same, greater, or lesser distance that the portion of the vascular branch is anatomically anterior to the substantially coronal imaging plane displayed on the standalone or separate computer monitor or display; portions of vascular branches that are anatomically posterior to the substantially coronal plane, in this example, of the first imaging study displayed by the separate or standalone computer monitor or display can be projected by the one or more OHMDs behind the separate or standalone computer monitor or display, e.g. by the same, greater, or lesser distance that the portion of the vascular branch is anatomically posterior to the substantially coronal imaging plane displayed on the standalone or separate computer monitor or display. Any other predetermined orientation of the second imaging study displayed by the one or more OHMDs relative to the first imaging study displayed by the separate or standalone computer monitor or display, for example with portions of vessels or vascular branches anatomically anterior to the plane of the first imaging study projected by the one or more OHMDs behind the separate or standalone computer monitor or display and with portions of vessels or vascular branches anatomically posterior to the plane of the first imaging study projected by the one or more OHMDs in front of the separate or standalone computer monitor or display.

If the first imaging study displayed by the separate or standalone computer monitor or display is oriented in a sagittal plane relative to the patient, the second imaging study displayed by the one or more OHMDs can be oriented, superimposed onto and/or aligned with the first imaging study displayed by the separate or standalone computer monitor or display so that portions of vascular branches that are anatomically left to the substantially sagittal plane, in this example, of the first imaging study displayed by the separate or standalone computer monitor or display, can be projected by the one or more OHMDs in front of the separate or standalone computer monitor or display, e.g. by the same, greater, or lesser distance that the portion of the vascular branch is anatomically left to the substantially sagittal imaging plane displayed on the standalone or separate computer monitor or display; portions of vascular branches that are anatomically right to the substantially sagittal plane, in this example, of the first imaging study displayed by the separate or standalone computer monitor or display, can be projected by the one or more OHMD's behind the separate or standalone computer monitor or display, e.g. by the same, greater, or lesser distance that the portion of the vascular branch is anatomically right to the substantially sagittal imaging plane displayed on the standalone or separate computer monitor or display. Any other predetermined orientation of the second imaging study displayed by the one or more OHMDs relative to the first imaging study displayed by the separate or standalone computer monitor or display, for example with portions of vessels or vascular branches anatomically left to the plane of the first imaging study projected by the one or more OHMDs behind the separate or standalone computer monitor or display and with portions of vessels or vascular branches anatomically right to the plane of the first imaging study projected by the one or more OHMDs in front of the separate or standalone computer monitor or display.

If the first imaging study displayed by the separate or standalone computer monitor or display is a transmission type image, e.g. an x-ray or an angiogram displaying a composite image of all body parts in the imaging beam or imaging direction, e.g. an x-ray beam, the principal plane of the first imaging study can be selected or determined or placed at a predetermined location in a common coordinate system, e.g. through the center of the patient's body part(s) interposed or included in the image, e.g. by the x-ray beam or at any other location, e.g. 5 cm, 10 cm, 15 cm, 20 cm, 25 cm from an anterior or posterior or medial or lateral skin surface or from the top of the OR table or imaging table. Using the coordinates of the selected plane in a common coordinate system, a 3D display or 3D data from a second imaging study, e.g. a prior imaging study such as a 3D CTA or 3D MRA or 3D ultrasound, can be registered with the first imaging study in the same coordinate system and displayed by the one or more OHMDs. If the first imaging study is then displayed on a separate or standalone computer monitor or display, the registration of the second imaging study relative to the first imaging study can be used to determine the display of the second imaging study by the one or more OHMDs superimposed and/or aligned with the first imaging study displayed by the separate or standalone computer monitor or display.

The distance of any structures, e.g. vessels or vascular branches, projected by the one or more OHMD's in front of or behind the separate or standalone computer monitor or display can be a reflection of the magnification of the first imaging study (by the imaging system and/or the separate or standalone computer monitor or display) and/or the distance of the object, tissue or organ or structure displayed by the one or more OHMDs from the principal plane of the first imaging study. For example, it can be a reflection of the distance of the object, tissue or organ or structure displayed by the one or more OHMDs from the principal plane of the first imaging study multiplied by a factor, which can be equal to, lesser than or greater than the magnification of the first imaging study.

In some embodiments, the one or more OHMDs can display virtual information about a tracked catheter, guidewire, stent, coil, implant or other intra-vascular or endoluminal device. The virtual information can include tracking information, e.g. coordinate information, of the tracked catheter, guidewire, stent, coil, implant or other intra-vascular or endoluminal device inside the vessel(s) or lumen, e.g. vessels or a lumen displayed in the first imaging study displayed by the separate or standalone computer monitor or display and/or vessels or a lumen displayed in the second imaging study, e.g. a 3D CTA or MRA, displayed by the one or more OHMDs. The tracking and/or coordinate information can be used to display a virtual tip or a virtual catheter, guidewire, stent, coil, implant or other intra-vascular or endoluminal device superimposed onto and/or aligned with vessels or a lumen displayed in the first imaging study displayed by the separate or standalone computer monitor or display and/or vessels or a lumen displayed in the second imaging study, e.g. a 3D CTA or MRA, displayed by the one or more OHMDs. In addition, the display by the separate or standalone computer monitor or display and/or the display by the one or more OHMDs can include virtual targets and/or a virtual path and/or virtual directional information for the virtual catheter, guidewire, sheath, stent, coil, instrument, implant, vascular prosthesis, or other intra-vascular or endoluminal instrument and/or device and the corresponding physical catheter, guidewire, stent, coil, instrument, implant or other intra-vascular or endoluminal instrument and/or device.

The display by the separate or standalone computer monitor or display and/or the display by the one or more OHMD's can include virtual data for the virtual catheter, guidewire, sheath, stent, coil, instrument, implant, vascular prosthesis, or other intra-vascular or endoluminal instrument and/or device and the corresponding physical catheter, guidewire, sheath, stent, coil, instrument, implant, vascular prosthesis, or other intra-vascular or endoluminal instrument and/or device including a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined contour or outline or cross-section or surface features or shape or projection, predetermined depth marker or depth gauge, predetermined stop, predetermined angle or orientation or rotation marker, predetermined axis, e.g. rotation axis, predetermined axis of the virtual surgical/interventional radiologic tool, virtual surgical/interventional radiologic instrument, virtual implant component, implant or device, e.g. stent, coil, vascular prosthesis, non-visualized portions for one or more devices or implants or implant components or surgical/interventional radiologic instruments or surgical/interventional radiologic tools, e.g. hidden behind another vessel or hidden inside a contrast bolus, or hidden inside a contrast column, or hidden inside a branching vessel, and/or one or more of a predetermined tissue change or alteration and/or one or more of a predetermined position and/or orientation of the virtual surgical/interventional radiologic tool, virtual surgical/interventional radiologic instrument, virtual implant component, implant or device. The virtual data can be displayed by the one or more OHMDs superimposed and/or aligned with the corresponding virtual data, e.g. from a first imaging study, displayed by the standalone or separate computer monitor or display, and they can be maintained superimposed onto and/or aligned with the corresponding virtual data, for example one or more vessels or one or more lumina, e.g. from a first imaging study, displayed by the standalone or separate computer monitor or display, e.g. using a computer processor for generating the display and/or aligning the display of the one or more OHMDs.

The virtual data can be displayed by the one or more OHMDs superimposed and/or aligned with the corresponding physical data of the patient, for example one or more physical vessels, physical vascular branches or physical lumina, and they can be maintained superimposed onto and/or aligned with the corresponding physical data of the patient, for example one or more physical vessels, physical vascular branches or physical lumina, e.g. using a computer processor for generating the display and/or aligning the display of the one or more OHMDs, for example when the surgeon or interventionalist looks, e.g. through a see through OHMD, at the physical patient and/or the physical surgical site or site subject to the interventional procedure.

In embodiments, for example when images are transferred to the OHMD using a WiFi connection, which can have bandwidth limitation, the more data intense data image set can be displayed using the standalone or separate computer or display monitor, the less data intense image set can be displayed using one or more OHMDs. In embodiments, the more data intense data image set can be displayed using the one or more OHMDs, while the less data intense image set can be displayed using the standalone or separate computer or display monitor.

The following is an exemplary list of select possible combinations of 2D, 3D non-stereoscopic and stereoscopic displays by the OHMD and 2D and pseudo 3D displays of the standalone or separate computer or display monitor. The list in Table 13 is in no way meant to be limiting.

TABLE 13

Examples of possible combinations of display modes or types by the display of the OHMD unit and the display of the standalone or separate computer or display monitor.

| OHMD Display | | | | | Standalone of Separate Computer or Display Monitor | | | |
|---|---|---|---|---|---|---|---|---|
| 2D | 3D Non-Stereoscopic | 3D Stereoscopic | 3D Non-Stereoscopic with Function/Time | 3D Stereoscopic with Function/Time | 2D | Pseudo 3D | 2D with Function/Time | Pseudo 3D with Function/Time |
| X | | | | | X | | | |
| X | | | | | | X | | |
| X | | | | | | | X | |
| X | | | | | | | | X |
| | X | | | | X | | | |
| | X | | | | | X | | |
| | X | | | | | | X | |
| | X | | | | | | | X |
| | | X | | | X | | | |
| | | X | | | | X | | |
| | | X | | | | | X | |
| | | X | | | | | | X |
| | | | X | | X | | | |
| | | | X | | | X | | |
| | | | X | | | | X | |
| | | | X | | | | | X |
| | | | | X | X | | | |

TABLE 13-continued

Examples of possible combinations of display modes or types by the display of the OHMD unit and the display of the standalone or separate computer or display monitor.

| OHMD Display | | | | | Standalone of Separate Computer or Display Monitor | | | |
|---|---|---|---|---|---|---|---|---|
| 2D Non-Stereoscopic | 3D Non-Stereoscopic | 3D Stereoscopic | 3D Non-Stereoscopic with Function/Time | 3D Stereoscopic with Function/Time | 2D | Pseudo 3D | 2D with Function/Time | Pseudo 3D with Function/Time |
| | | | | X | | X | | |
| | | | | X | | | X | |
| | | | | X | | | | X |

X denotes type of display mode used

The OHMD display can optionally display some virtual data, e.g. pre-procedural images and/or image reconstructions, of the patient in 2D, while it can display other virtual data, e.g. aspects or components of the virtual plan, e.g. an intended or predetermined stent or coil position, location, alignment and/or orientation, in 3D. Similarly, the OHMD display can optionally display some virtual data, e.g. pre-procedural images and/or image reconstructions, of the patient in 3D, while it can display other virtual data, e.g. aspects or components of the virtual plan, e.g. an intended guide wire trajectory, in 2D, e.g. as a line, or in 3D, e.g. as a 3D trajectory.

The standalone or separate computer or display monitor can optionally display some virtual data, e.g. pre-procedural images and/or image reconstructions, of the patient in 2D, while it can display other virtual data, e.g. aspects or components of the virtual plan, e.g. an intended or predetermined stent or coil position, location, alignment and/or orientation, in pseudo 3D, e.g. with perspective views and shading. Similarly, the standalone or separate computer or display monitor can optionally display some virtual data, e.g. pre-procedural images and/or image reconstructions, of the patient in 3D, while it can display other virtual data, e.g. aspects or components of the virtual plan, e.g. a trajectory of a guide wire, in 2D, e.g. as a line. Aspects or components of the virtual surgical/interventional radiologic plan can, for example, include one or more of the following: a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined contour or outline or cross-section or surface features or shape or projection, e.g. of a stent or coil, predetermined depth marker or depth gauge, e.g. of a guide wire, predetermined stop, predetermined angle or orientation or rotation marker, predetermined axis, predetermined axis of the virtual surgical/interventional radiologic tool, virtual surgical/interventional radiologic instrument, virtual implant, virtual implant component, virtual device, non-visualized portions of one or more devices or implants or implant components or surgical/interventional radiologic instruments or surgical/interventional radiologic tools, and/or one or more of a predetermined tissue change or alteration and/or one or more of a predetermined position and/or orientation of the virtual surgical/interventional radiologic tool, virtual surgical/interventional radiologic instrument virtual implant component, implant or device.

In an additional embodiment, the OHMD display can optionally display some of the aspects or components of the virtual surgical/interventional radiologic plan in 2D and other aspects and components in 3D, stereoscopic or non-stereoscopic. For example, the OHMD display can display a virtual stent in 3D stereoscopic or non-stereoscopic, while it can display a virtual guidewire as an outline in 2D or 3D, for example projected with a stereoscopic 3D view of the underlying tissue. The OHMD display can display a virtual surgical/interventional radiologic instrument, e.g. a wire in 3D, e.g. stereoscopic or non-stereoscopic, and it can project the predetermined path for the wire and/or a virtual sheath in 2D or in 3D.

The standalone or separate computer or display monitor can optionally co-display some of the aspects or components of the virtual surgical/interventional radiologic plan in 2D and other aspects and components in pseudo 3D, optionally with different colors. For example, the standalone or separate computer or display monitor can display a predetermined virtual stent or coil position, location, orientation, alignment in pseudo 3D, while it can display a virtual wire or sheath as an outline in 2D, for example projected on a pseudo 3D view of the underlying tissue and/or vessel(s). The standalone or separate computer or display monitor can display a virtual stent in pseudo 3D, and it can project its predetermined central axis in 2D.

The different 2D and 3D displays by the OHMD display and the standalone or separate computer or display monitor can be displayed and viewed simultaneously, in many embodiments completely, substantially or partially superimposed, and can be maintained completely, substantially or partially superimposed, e.g. by registering corresponding anatomic and/or vascular structures in the same coordinate system and by superimposing and/or aligning the anatomic and/or vascular structure displayed by the OHMD with the vascular structures displayed by the standalone or separate computer or display monitor thereby optionally creating a 5-dimensional or 6- or more dimensional display, e.g. 2D on the standalone or separate computer or display monitor and 3D on the superimposed one or more OHMD's. 6 or more dimensional displays can be used when, for example, flow information or functional information is included in one of the displays, e.g. the standalone or separate computer or display monitor or the one or more OHMD displays. If the 2D the standalone or separate computer or display monitor shows also functional information, e.g. in one or two directions, 6 or 7 different domains or dimensions or even more domains or dimensions, when accounting for functional, e.g. flow information, can be simultaneously seen by the surgeon or interventionalist, interventional radiologist and/or operator, e.g.

- 2D images of the vessels and/or vascular tree and/or the surrounding anatomy, e.g. bony landmarks, e.g. using a greyscale display, on the standalone or separate computer or display monitor
- 2D flow images and/or functional images, e.g. using color coding, on the standalone or separate computer or display monitor,
- a 3D display, e.g. of static vascular anatomy and/or surrounding anatomy, e.g. using a grey scale or a single color and, optionally multiple colors, provided by the one or more OHMD's registered and/or superimposed with the 2D images, stereoscopic or non-stereoscopic
- a 3D display of flow, optionally grey scale or color coded, e.g. with velocity information coded on a grey scale or color scale, provided by the one or more OHMDs registered and/or superimposed with the 2D images on the standalone or separate computer monitor or display and/or the 3D display of static vascular anatomy and/or surrounding anatomy, stereoscopic or non-stereoscopic
- Optionally, this can be further augmented by display of unsubtracted and/or subtracted images, e.g. on the standalone or separate computer or display monitor and/or one or more OHMDs, and, for example optionally by toggling or switching between unsubtracted and/or subtracted images, e.g. at a frequency of 0.5, 1.0, 1.5, 2.0, 3.0 Hz or any other frequency.

The 3D images displayed by the one or more OHMD can, for example, be images obtained and/or generated using a pre-procedural CT angiogram, MR angiogram, a diagnostic angiogram, and/or a 3D ultrasound, and/or any other imaging study of the vascular anatomy and/or pathology.

Since the user or surgeon or interventionalist and/or radiologist can view the standalone or separate computer or display monitor through the OHMD display, the user or surgeon or interventionalist and/or radiologist can experience a combination of 2D and 3D display information, e.g. of virtual anatomy of the patient and/or aspects of the virtual surgical/interventional radiologic plan, not previously achievable, e.g. in 5D and, optionally, more, as described above.

TABLE 14

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical/interventional radiologic plan, and/or virtual surgical/interventional radiologic instruments and/or virtual implants or implant components and/or intra-operative imaging of the patient.

| | Standalone or Separate Computer or Display Monitor | | | | | | | | | | | | | | | | | | | |
|---|---|---|---|---|---|---|---|---|---|---|---|---|---|---|---|---|---|---|---|---|
| | Virtual Anatomic Data of the Patient | | | | Components of Virtual Surgical Plan of the Patient | | | | Virtual Surgical Instruments | | | | Virtual Implant or Trial Implant Components | | | | Intra-Operative Imaging of the Patient | | | |
| OHMD Display | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| *Virtual Anatomic Data of the Patient* | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | | | X | X | | | X | X | | | X | X | | | X | X | | | X | X |
| 3D Stereoscopic with Function/Time | | | X | X | | | X | X | | | X | X | | | X | X | | | X | X |
| *Components of Virtual Surgical Plan of the Patient* | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | | | X | X | | | X | X | | | X | X | | | X | X | | | X | X |
| 3D Stereoscopic with Function/Time | | | X | X | | | X | X | | | X | X | | | X | X | | | X | X |
| *Virtual Surgical Instruments* | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | | | X | X | | | X | X | | | X | X | | | X | X | | | X | X |
| 3D Stereoscopic with Function/Time | | | X | X | | | X | X | | | X | X | | | X | X | | | X | X |
| *Virtual Implant or Trial Implant Components* | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |

TABLE 14-continued

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical/interventional radiologic plan, and/or virtual surgical/interventional radiologic instruments and/or virtual implants or implant components and/or intra-operative imaging of the patient.

| | Standalone or Separate Computer or Display Monitor | | | | | | | | | | | | | | | | | | | |
|---|---|---|---|---|---|---|---|---|---|---|---|---|---|---|---|---|---|---|---|---|
| | Virtual Anatomic Data of the Patient | | | | Components of Virtual Surgical Plan of the Patient | | | | Virtual Surgical Instruments | | | | Virtual Implant or Trial Implant Components | | | | Intra-Operative Imaging of the Patient | | | |
| OHMD Display | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| 3D Non-Stereoscopic with Function/Time | X | X | X | X | X | X | X | X | X | X | X | X | X | X | X | X | X | X | X | X |
| 3D Stereoscopic with Function/Time | X | X | X | X | X | X | X | X | X | X | X | X | X | X | X | X | X | X | X | X |
| Intra-Operative imaging of the Patient | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | X | X | X | X | X | X | X | X | X | X | X | X | X | X | X | X | X | X | X |

X denotes type of display mode combinations used or possible

Virtual data of the patient including anatomy, e.g. from pre-procedural imaging, and/or aspects and/or components of a virtual surgical/interventional radiologic plan, and/or virtual surgical/interventional radiologic instruments and/or tools and/or virtual implants or implant components and/or intra-operative imaging of the patient can be displayed using different colors, greyscale values and image intensities by the display of the OHMD unit and the display of the standalone or separate computer or display monitor thereby providing for visual differentiation of virtual data displayed by the one or more OHMDs and virtual data displayed be the standalone or separate computer or display monitor when both are substantially aligned and/or superimposed.

Intra-procedural imaging of the patient can include, for example, x-ray imaging, angiography, 2D and 3D angiography, biplanar angiography, digital subtraction angiography, and/or 3D scanning of the patient and/or ultrasound scanning, e.g. using one or more intravascular ultrasound probes, or any combination thereof. Intra-procedural x-ray imaging, angiography, 2D and 3D angiography, biplanar angiography, digital subtraction angiography, and/or 3D scanning of the patient and/or ultrasound scanning, e.g. using one or more intravascular ultrasound probes, including 2D and 3D reconstructions, aspects or components of a virtual surgical/interventional radiologic plan, virtual surgical/interventional radiologic instruments and/or tools, and/or virtual implants and implant components, e.g. stents or coils, can be displayed simultaneously and, optionally, anatomically superimposed and/or anatomically aligned by the display of the OHMD unit and the display of the standalone or separate computer or display monitor. If two or more imaging modalities or pre-procedural and intra-procedural imaging studies are co-displayed, they can optionally be anatomically matched and they can optionally be displayed using the same projection plane or, optionally, different projection planes.

If 2D views are co-displayed with 3D views or pseudo 3D views by the OHMD display alone, by the standalone or separate computer or display monitor alone, or the two together and partially or completely superimposed, the 2D views can optionally be displayed using certain standard projections, e.g. AP, lateral, oblique; the standard projection, e.g. AP, lateral and oblique, can optionally be referenced to the live data of the patient, e.g. the corresponding planes with the patient positioned on the interventional table, or to the data of the patient displayed on the standalone or separate computer or display monitor. Standard projections or standard views can also include view angles from the patient's side, front, top, bottom, or oblique views.

Dynamic views or functional views, for example with two or three spatial dimensions and a time dimension, e.g. vascular flow and/or bolus imaging and/or bolus tracking, can be displayed by the display of the OHMD unit and/or the display of the standalone or separate computer or display monitor, optionally superimposed onto or co-displayed with static images, e.g. 2D or 3D, by the second display unit, e.g. the display of the OHMD unit or the display of the standalone or separate computer or display monitor. Any other type of dynamic scan, which can include a time element or time dimension or a functional element or functional dimension can be displayed by the display of the OHMD unit and/or the display of the standalone or separate computer or display monitor.

In some embodiments, the display of the OHMD unit can be used for displaying lower resolution data and/or images, while the display of the display of the standalone or separate computer or display monitor can be used for displaying corresponding or matching or overlapping higher resolution data and/or images. This embodiment can be particularly useful when, for example, the maximum available display resolution of the OHMD is lower than desirable for a particular application or a surgical/interventional radiologic procedure. This embodiment can also be useful, when the software environment limits, for example, the amount of surface points or nodes displayed or limits the available resolution. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in available spatial resolution for the display of the data and/or images by the OHMD. By viewing the lower resolution data and/or images through the OHMD, the user can have, for example, the benefit of stereoscopic visualization, e.g. of the vascular tree and branches in 3D, or the benefit of viewing components or aspects of the surgical/interventional radiologic plan, e.g. a projected path, e.g. for a guide wire, a predetermined position, location, orientation and/or alignment and/or coordinates for a virtual implant, and/or a virtual implant, e.g. a stent or a coil, while by viewing simultaneously and/or with partial or complete anatomic superimposition and/or anatomic alignment the higher resolution data and/or images on the display of the standalone or separate computer or display monitor the viewer can have the concurrent benefit of viewing the data and/or images in high resolution.

In some embodiments, the display of the OHMD unit can be used for displaying static data and/or images, while the display of the standalone or separate computer or display monitor can be used for displaying corresponding or matching or overlapping dynamic data and/or images, e.g. images demonstrating a function and/or vascular flow and/or a time element or dimension including a change in condition or function monitored over a time period. This embodiment can be particularly useful when, for example, the refresh rate of the OHMD display is lower than desirable for a particular application or surgical/interventional radiologic procedure. This embodiment can also be useful, when the software environment limits, for example, the amount of data and/or images displayed. This embodiment can also be useful when a WiFi or Bluetooth or other wireless connection is used for connecting the OHMD with limitations in bandwidth and/or data transmission, thereby limiting the amount of data being transmitted to the OHMD and, ultimately, displayed, in particular when this limitation implies a limitation in available temporal and/or spatial resolution for the display of the data and/or images by the OHMD. By viewing the static data and/or images through the OHMD, the user can have, for example, the benefit of stereoscopic visualization or the benefit of viewing components or aspects of the surgical/interventional radiologic plan, e.g. a projected path, e.g. for a guide wire, e.g. in 3D, a predetermined position, location, orientation and/or alignment and/or coordinates for a virtual implant, and/or a virtual implant, e.g. a stent or a coil, or a vascular prosthesis, or a graft, or a patch, while by viewing simultaneously and/or with partial or complete superimposition the dynamic data and/or images on the display of the standalone or separate computer or display monitor the viewer can have the concurrent benefit of viewing the dynamic data and/or images, e.g. flow images, bolus studies, bolus chase studies, at high display frequency and, optionally, in high resolution.

In some embodiments, the display of the OHMD unit can be used for displaying a subset of the data and/or images representing a smaller portion of the field of view displayed by the standalone or separate computer or display monitor, while the display of the display of the standalone or separate computer or display monitor can be used for displaying corresponding or matching or overlapping higher resolution data and/or images including larger images, e.g. with larger field of view, using the full intended field of view of patient data. This embodiment can, for example, be useful, when the software environment limits the amount of surface points or nodes displayed or limits the size of the data displayed by the OHMD or when the display resolution of the OHMD is lower than the display resolution of the standalone or separate computer monitor. This embodiment can also be useful, for example, when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD. By viewing data and/or images with a smaller, more narrow field of view through the OHMD, the user can have, for example, the benefit of stereoscopic visualization or the benefit of viewing components or aspects of the surgical/interventional radiologic plan, e.g. a projected path, e.g. for a guide wire, a predetermined position, location, orientation and/or alignment and/or coordinates for a virtual implant, and/or a virtual implant, e.g. a stent or a coil, or a vascular prosthesis, or a graft, or a patch, while by viewing simultaneously and/or with partial or complete superimposition the data and/or images with the full field of view on the display of the standalone or separate computer or display monitor the viewer can have the concurrent benefit of viewing the data and/or images using the full intended field of view of patient data. When 3D views are superimposed onto or co-displayed with 2D views by the display of the OHMD unit and the display of the standalone or separate computer or display monitor or when multiple 2D views are superimposed or co-displayed by the display of the OHMD unit and the display of the standalone or separate computer or display monitor, they can be anatomically matched, for example using corresponding landmarks, e.g. a 2D or 3D outline of one or more vessels, or vascular branchings, or an organ, a tissue, a vascular intervention site, a vascular structure included in one or more angiographic images or in a pre-operative and/or an intra-operative imaging study, and/or using common coordinates. They can also have different view angles, e.g. a view angle as the patient is positioned on the interventional table, a view angle from the side, front, top, bottom, or oblique views. Thus, the OHMD display can, for example, show a stereoscopic 3D view of the patient's virtual anatomy, e.g. from a pre-procedural imaging study, while the standalone or separate computer or display monitor can show a matching AP or lateral intra-operative radiographic view or a matching pseudo 3D view of the patient.

The matching of data displayed by the display of the OHMD unit and the display of the standalone or separate computer or display monitor can be achieved in different ways, e.g. using Matching of data and/or image using coordinates
    Matching of data and/or image using content, e.g. image information, anatomic information visible on the one or more images
    Combinations of matching of data and/or image coordinates and data and/or image content In some embodiments, data and/or images displayed by the OHMD and data and/or images displayed by the standalone or separate computer or display monitor can be matched using known image coordinates and can then optionally be partially or completely superimposed, e.g. as the user and/or surgeon or interventionalist and/or radiologist moves his or her head and/or body while looking at the standalone or separate computer or display monitor. For example, if the OHMD is registered in space, e.g. with regard to the patient and/or the surgical/interventional radiologic site and/or the standalone computer or display monitor and/or the image data displayed on the standalone computer or display monitor, data and/or images displayed by the OHMD and/or displayed by the standalone computer or display monitor can be in the same or a common coordinate system, which can allow the matching or superimposition of the display by the OHMD with the display by the standalone or separate computer or display monitor, when portions or all of the separate computer or display monitor are included in the field of view of the user or surgeon or interventionalist and/or radiologist through the OHMD.

In some embodiments, when both the display of the OHMD and the display of the separate computer or display monitor are registered in the same coordinate system, which can include that the image data displayed by the one or more OHMD's and the image data displayed by the separate computer or display monitor are registered in the same coordinate system, the OHMD can display then a set of data and/or images at least partially matching the coordinates and/or anatomic features, e.g. in 2D or 3D, of the data and/or images of the separate computer or display monitor. For example, the OHMD can display stereoscopic 3D views that share common coordinates and/or anatomic features, e.g. in 2D or 3D, with a a 2D or pseudo 3D visualization displayed by the standalone or separate computer or display monitor. Such common coordinates can, for example, be corner points or edges or select geometric features and/or locations which can be superimposed then in the resultant composite OHMD/standalone monitor view that the user or surgeon or interventionalist and/or radiologist sees.

The OHMD can also, for example, display a stereoscopic 3D view of live data of the patient or virtual data of the patient or both, while the standalone or separate computer or display monitor displays a 2D view, e.g. a pre-procedural imaging study, of the patient. The 2D plane or view display by the standalone or separate computer or display monitor can have the same or common coordinates and/or anatomic features, e.g. in 2D or 3D, with the corresponding 2D plane embedded in or contained in the 3D data and/or images displayed by the OHMD which can be matched or superimposed then in the resultant composite OHMD/standalone monitor view that the user or surgeon or interventionalist and/or radiologist sees. Alternatively, in a similar example, if the OHMD provides only a surface display, for example, the periphery or outline or select peripheral points of the 2D plane displayed by the standalone or separate computer or display monitor can have the same or common coordinates and/or anatomic features, e.g. in 2D or 3D, with corresponding surface points and/or anatomic features, e.g. in 2D or 3D, in the location corresponding to the 2D plane in the 3D data and/or images displayed by the OHMD.

The data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching. In some embodiments, the surgical/interventional radiologic table can be moved. The movement of the surgical/interventional radiologic table can translate into a comparable movement of the patient and/or the surgical/interventional radiologic site in x, y, and/or z direction. When the magnitude and direction of the table movement is known, it can be used to move the common coordinate system by a corresponding amount or direction for matching or superimposing the data and/or images displayed by the OHMD and the data and/or images displayed by the standalone or separate display monitor. For example, if the OHMD displays live data of the patient, e.g. captured through an image and/or video capture system and/or 3D scanner integrated into, attached to or separate from the OHMD, and/or virtual data of the patient and/or virtual data of the patient superimposed onto live data of the patient and/or virtual data of the patient, e.g. from a pre-procedural imaging study, e.g. an MRA, CTA, diagnostic angiogram, ultrasound, etc., and/or aspects of a virtual surgical plan, e.g. a virtual stent, a virtual coil, a virtual vascular prosthesis, a virtual guide wire, a virtual wire, a virtual sheath, a virtual catheter etc., and the standalone or separate computer or display monitor displays a pre-procedural and/or intra-procedural imaging study of the patient, the surgical/interventional radiologic table and the patient can be moved and the display of the live or virtual data by the OHMD and/or by the standalone or separate computer monitor or display can be moved by a corresponding amount, thereby maintaining registration including registration to the data displayed on the standalone or separate computer or display monitor. In embodiments, the OHMD can display virtual data of the patient, e.g. from a pre-procedural imaging study, e.g. an MRA, CTA, diagnostic angiogram, ultrasound, etc., and/or aspects of a virtual surgical plan, e.g. a virtual stent, a virtual coil, a virtual vascular prosthesis, a virtual guide wire, a virtual wire, a virtual sheath, a virtual catheter etc., e.g. in 3D, stereoscopic and/or non-stereoscopic, while the separate and/or standalone computer and/or the OHMD can display intra-procedural images, e.g. from a 2D or 3D angiogram, digital subtraction angiogram, flow study, bolus study, bolus tracking etc., which can be automatically or continuously updated, e.g. in real time or near real time, e.g. as the table moves or as contrast and/or a bolus of contrast is injected or both. The image data and/or virtual data displayed by the OHMD, e.g. a 3D stereoscopic display from a pre-procedural imaging study, e.g. a CTA, MRA, ultrasound angiogram etc., can be moved by an amount and/or distance corresponding to the table movement in x, y, and/or z-direction thereby maintaining alignment and/or superimposition of corresponding anatomic structures in the virtual pre- and intra-procedural data, e.g. a vessel, a vascular bifurcation, a vessel origin. The image data and/or virtual data displayed by the OHMD, e.g. a 3D stereoscopic display from a pre-procedural imaging study, e.g. a CTA, MRA, ultrasound angiogram etc., can be moved by an amount and/or distance corresponding to the head movement of the operator and related movement of the OHMD in x, y, and/or z-direction thereby maintaining alignment and/or superimposition of corresponding anatomic structures, e.g. a vessel, a vascular bifurcation, a vessel origin. The alignment and/or superimposition of corresponding anatomic structures from pre- and intra-procedural imaging studies or data displayed by the one or more OHMD's and the standalone or separate computer monitor or display and/or the one or more OHMD's can be maintained, for example, by 1. Measuring the table movement in x, y and z-direction and applying a corresponding coordinate transfer of the OHMD display data in x, y, and z-direction
2. Measuring the OHMD movement in x, y and z-direction and applying a corresponding coordinate transfer of the OHMD display data in x, y, and z-direction
3. Measuring patient movement in x, y and z-direction and applying a corresponding coordinate transfer of the OHMD display data in x, y, and z-direction
4. Combinations of 1, 2, and/or 3.
5. Detecting the images obtained in the one or more new table positions, e.g. using an image capture or video capture system and/or a 3D scanner integrated into, attached to, or separate from the OHMD, e.g. every 0.001, 0.005, 0.01, 0.02, 0.05, 0.1, 0.2, 0.3, 0.5 seconds or for each frame, optionally segmenting the images, and matching the images using any of the registration techniques described in the specification, e.g. for registration of 3D pre-procedural imaging studies, displayed by one or more OHMDs, and intra-procedural imaging studies, e.g. an angiogram, digital substraction angiogram, 2D or 3D angiogram, flow study, bolus study, bolus tracking, displayed by the standalone computer monitor or display and/or the one or more OHMDs.
6. Obtaining the images from each table position and/or for each time point of the intra-procedural imaging study, e.g. during a flow study, bolus chase, bolus tracking, and/or cardiac and/or respiratory gated imaging study, optionally segmenting the images, and matching the images using any of the registration techniques described in the specification, e.g. for registration of 3D pre-procedural imaging studies, displayed by one or more OHMDs, and intra-procedural imaging studies, e.g. an angiogram, digital substraction angiogram, 2D or 3D angiogram, flow study, bolus study, bolus tracking, displayed by the standalone computer monitor or display and/or the one or more OHMDs.
7. Combinations of 5 and 6.

In some embodiments, the data and/or images displayed by the OHMD and the data and/or images displayed by the standalone or separate computer or display monitor can be cross-registered and, for example, registered in a shared or common coordinate system with use of an image and/or video capture system and/or 3D scanner integrated into, attached to, or separate from the OHMD, using one or more computer processors configured for capturing the data displayed by the standalone or separate computer or display monitor. In some embodiments, the data and/or images displayed by the OHMD and the data and/or images displayed by the standalone or separate computer or display monitor can be cross-registered and, for example, registered in a shared or common coordinate system with use of one or more computer processors configured to run image processing software, e.g. residing on a workstation, optionally connected to the standalone or separate computer monitor or display.

For example, the standalone or separate computer or display monitor can display data from an intra-procedural imaging study of the patient, e.g. a CT, a 2D or 3D angiogram, a digital subtraction angiogram, a flow study, a bolus tracking study, a bolus chase study, including, for example, imaging during movement of the patient and/or surgical/interventional radiologic table and/or movement of one or more OHMDs, e.g. on the surgeon or interventionalist's or radiologist's or operator's head. Image processing techniques can, for example, recognize anatomic landmarks or features on the data or images, e.g. a vascular bifurcation, a vascular diameter, obtained during the procedure and, for example, displayed on the standalone or separate computer or display monitor and/or the one or more OHMD displays and match these with the corresponding anatomic landmarks or features in the data and/or images obtained prior to the procedure, e.g. a pre-operative ultrasound, CTA or MRA, available, for example, for display by the one or more OHMDs. Illustrative, non-limiting examples of anatomic landmarks, features, surfaces, dimensions, shapes, and/or geometries and/or other features that can be detected and/or recognized, using one or more computer processors configured for detection of image features, include, for example:

A vessel
  An anteroposterior (AP), a mediolateral (ML), a superoinferior (SI) dimension of a vessel
A vascular surface
A curvature of a vessel, e.g. in a 2D image or a 3D image
A shape of a vessel
A geometry of a vessel
A vascular diameter
A vascular cross-sectional, e.g. in predetermined plane
A distance between two vascular branches
An angle between a main vessel and a branch originating from the vessel, e.g. between the aorta and a renal artery
A vascular pulsation, e.g. an amplitude of pulsation and/or vascular movement
A vascular plaque
Location of a vascular plaque, e.g. coordinates and/or in relation to other vascular structures, e.g. a vascular ostium and/or branching
Orientation of a vascular plaque, e.g. coordinates and/or in relation to other vascular structures, e.g. a vascular ostium and/or branching
Dimensions of a plaque
  AP, ML, SI and/or other dimensions of a plaque
Shape of a plaque
Volume of a vascular plaque
Calcified portion of a vascular plaque
Dimensions of calcified portion of a vascular plaque
Shape of calcified portion of a vascular plaque
Volume of calcified portion of a vascular plaque
An area of atherosclerosis in a vessel
Location of area of atherosclerosis, e.g. coordinates and/or in relation to other vascular structures, e.g. a vascular ostium and/or branching
Orientation of area of atherosclerosis, e.g. coordinates and/or in relation to other vascular structures, e.g. a vascular ostium and/or branching
Dimensions of area of atherosclerosis
  AP, ML, SI and/or other dimensions of an area of atherosclerosis
Shape of area of atherosclerosis
Volume of area of atherosclerosis
Calcified portion of area of atherosclerosis
Dimensions of calcified portion of area of atherosclerosis
Shape of calcified portion of area of atherosclerosis
Volume of calcified portion area of atherosclerosis
An arterial dissection
Location of arterial dissection, e.g. coordinates and/or in relation to other vascular structures, e.g. a vascular ostium and/or branching
Orientation of arterial dissection, e.g. coordinates and/or in relation to other vascular structures, e.g. a vascular ostium and/or branching
Dimensions of arterial dissection
  AP, ML, SI and/or other dimensions of arterial dissection
Shape of arterial dissection
Volume of arterial dissection
Calcified portion of arterial dissection
Dimensions of calcified portion of arterial dissection
Shape of calcified portion of arterial dissection
Volume of calcified portion of arterial dissection
Areas, volume of flow within an arterial dissection
An aneurysm
Location of an aneurysm, e.g. coordinates and/or in relation to other vascular structures, e.g. a vascular ostium and/or branching
Orientation of an aneurysm, e.g. coordinates and/or in relation to other vascular structures, e.g. a vascular ostium and/or branching
Dimensions of an aneurysm
  AP, ML, SI and/or other dimensions of an aneurysm
Shape of an aneurysm
Volume of an aneurysm
Calcified portion of an aneurysm
Dimensions of calcified portion of an aneurysm
Shape of calcified portion of an aneurysm
Volume of calcified portion of an aneurysm
Areas, volume of flow within an aneurysm
Bony structure and/or landmark and/or feature and/or geometry and/or shape in field of view imaged for evaluating vascular structures
Distance, angle, dimensions, geometry, shapes between bony structure and vascular structures, e.g. in 2D or 3D Any of these and other anatomic landmarks, features, surfaces, dimensions, shapes, and/or geometries and/or other features and combinations thereof can be used for matching, registering, moving, orienting, aligning, and/or superimposing a 2D, 3D or multi-dimensional pre-procedural imaging study and a 2D, 3D and/or multi-dimensional intra-procedural imaging study. Optionally, multiple pre-procedural and/or intra-procedural imaging studies can be registered, moved, oriented, aligned and/or superimposed using the standalone or separate computer monitor or display and/or one or more optical head mounted displays (see, for example, Tables 11, 13 and 14 for possible display combinations).

In embodiments, the OHMD can display the pre-procedural imaging study/studies and the standalone or separate computer monitor and/or the OHMD display can display the intra-procedural imaging study/studies. In embodiments, the OHMD can display the intra-procedural imaging study/studies and the standalone or separate computer monitor or display can display the pre-procedural imaging study/studies.

The OHMD can display the corresponding data and/or images, optionally superimposing and/or aligning the displayed data, e.g. pre-procedural data, based on matching one or more anatomic landmarks, features, surfaces, dimensions, shapes, and/or geometries and/or other features with virtual data obtained, for example, during the procedure. The matching of the one or more anatomic landmarks, features, surfaces, dimensions, shapes, and/or geometries and/or other features can, for example, occur by moving and/or translating and/or rotating the data or images available for display by the OHMD by an amount that will superimpose or match in a common coordinate system corresponding anatomic landmarks, features, surfaces, dimensions, shapes, and/or geometries and/or other features, e.g. as displayed by the standalone or separate computer monitor or display and/or the OHMD.

In embodiments, the process can be applied with use of an image capture or video capture system or a 3D scanner capturing the information from the standalone or separate computer monitor or display, by comparing, registering, matching, moving, aligning and/or superimposing images acquired with the intra-procedural imaging system, e.g. displayed by the standalone or separate computer monitor or display, with data and/or images obtained in a pre-procedural imaging study, e.g. displayed by the OHMD. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images acquired with the intra-procedural imaging system, e.g. displayed by the standalone or separate computer monitor or display, with data and/or images obtained in a pre-procedural imaging study, e.g. displayed by the OHMD or by comparing, registering, matching, moving, aligning and/or superimposing images acquired with the pre-procedural imaging system, e.g. displayed by the OHMD, with data and/or images obtained in an intra-procedural imaging study, e.g. displayed by the OHMD and/or the standalone computer monitor or display.

In embodiments, the process can be applied with use of an image capture or video capture system or a 3D scanner capturing the information, for example, from the standalone or separate computer monitor or display, by comparing, registering, matching, moving, aligning and/or superimposing images obtained in a pre-procedural imaging study, e.g. displayed by the OHMD, with data and/or images acquired with an intra-procedural imaging system, e.g. displayed by the standalone or separate computer monitor or display. In embodiments, the process can be applied directly, i.e. without use of an image capture or video capture system or a 3D scanner, using, for example, a computer workstation, optionally connected to the standalone or separate computer monitor or display, with a computer processor configured for comparing, registering, matching, moving, aligning and/or superimposing images obtained in a pre-procedural imaging study, e.g. displayed by the OHMD, with data and/or images acquired with an intra-procedural imaging system, e.g. displayed by the standalone or separate computer monitor or display.

A computer processor configured to run image processing software can, for example, recognize anatomic landmarks, features, surfaces, dimensions, shapes, and/or geometries and/or other features and combinations thereof on the data or images acquired by the intra-procedural imaging system and match these with the corresponding anatomic landmarks, features, surfaces, dimensions, shapes, and/or geometries and/or other features and combinations thereof in the data and/or images available for display by the OHMD, e.g. using pre-procedural imaging data. The OHMD can then display the corresponding data and/or images, optionally superimposing the data based on matching of anatomic landmarks, features, surfaces, dimensions, shapes, and/or geometries and/or other features and combinations thereof. The matching of anatomic landmarks, features, surfaces, dimensions, shapes, and/or geometries and/or other features and combinations thereof can, for example, occur by moving and/or translating the data or images available for display by the OHMD, using a computer processor configured for display and/or moving the virtual data, by an amount that will superimpose or match in a common coordinate system corresponding anatomic landmarks, features, surfaces, dimensions, shapes, and/or geometries and/or other features and combinations thereof, e.g. in a pre- and an intra-procedural imaging study including in pre- and intra-procedural virtual data sets.

In the foregoing embodiments, the data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with and/or aligned with the data and/or images displayed by the standalone or separate display monitor, the data and/or images displayed by the OHMD and the data and/or images displayed by the standalone or separate display monitor can be displayed with the same magnification in order to optimize the superimposition or matching. Matching of images displayed by the OHMD and a standalone or separate computer or display monitor can also be performed by combining coordinate based matching, e.g. using the same coordinate system for both displays, and matching of anatomic landmarks, features, surfaces, dimensions, shapes, and/or geometries and/or other features and combinations thereof using any of the foregoing techniques. Someone skilled in the art will readily recognize other means of coordinate matching and matching of anatomic landmarks, features, surfaces, dimensions, shapes, and/or geometries and/or other features and combinations thereof.

In some embodiments, the magnification of the items displayed by the OHMD can be adjusted so that it is reflective of, corresponds to, is smaller or larger than the magnification used by the standalone or separate computer or display monitor. Alternatively, the standalone or separate computer or display monitor can have one or more markers, e.g. one or more LED's or optical markers, e.g. with geometric patterns, that a computer processor connected to an image and/or video capture system and/or 3D scanner, e.g. integrated into, attached to or separate from the OHMD, and configured to detect the markers which detection, in turn, can then trigger the adjustment of the magnification of the items displayed by the OHMD, e.g. based on the distance of the OHMD to the monitor. In some embodiments, an image and/or video capture system and/or 3D scanner integrated into, attached to or separate from the OHMD can visualize the size and shape (round, oval, ellipsoid, rectangular, square) of the standalone or separate computer or display monitor; using a computer processor with image processing software configured to assess the geometry, the size and shape, the information can then be used to derive the distance and angle of the OHMD relative to the standalone or separate computer or display monitor. If more than one camera is used, additional parallax information (difference in size and/or shape of the standalone or separate computer or display monitor) can be used to further estimate or improve the estimation of the distance or angle of the OHMD to the standalone or separate computer or display monitor and/or for example a procedure or OR table with one or more attached markers or a patient with one or more attached markers. The resultant estimation of the distance and/or angle of the OHMD display to the standalone or separate computer or display monitor can then optionally be used to match the magnification of the data displayed by the standalone or separate computer or display monitor or to display at a higher or lower magnification than the data display by the standalone or separate computer or display monitor.

Similarly, the OHMD can detect, e.g. automatically, if the surgeon or interventionalist and/or radiologist or operator is not looking at the standalone or separate computer or display monitor, for example, with use of an image and/or video capture system and/or 3D scanner integrated into, attached to or separate from the OHMD. The image and/or video capture system and/or 3D scanner can, for example, detect that the outline of the standalone or separate computer or display monitor (e.g. round, square, rectangular) is not present in the captured image data and the software can the automatically adjust the magnification of the items displayed by the OHMD so that it is reflective of or corresponds to the distance of the OHMD or the surgeon or interventionalist and/or radiologist's eyes to the patient's surgical/interventional radiologic site, or is smaller or larger than that. Alternatively, a standalone or separate computer or display monitor can have one or more markers, e.g. one or more LED's or optical markers, that the image and/or video capture system and/or 3D scanner can detect; in this case, when the image captures system notices that the one or more LED's or optical markers are not included in the image capture data, the software can then automatically adjust the magnification of the items displayed by the OHMD so that it is reflective of or corresponds to the distance of the OHMD or the surgeon or interventionalist and/or radiologist's eyes to the patient's surgical/interventional radiologic site, or is smaller or larger than that. Similarly, markers or LED's placed on the patient's surgical/interventional radiologic site can be detected by the OHMD including an image and/or video capture system and/or 3D scanner integrated into, attached to or separate from the OHMD and a computer processor with software configured to detect the markers or LED's thereby triggering an adjustment in magnification so that it is reflective of, corresponds to the distance of the OHMD or the surgeon or interventionalist and/or radiologist's eyes to the patient's surgical/interventional radiologic site, or is smaller or larger than that when the surgeon or interventionalist and/or radiologist or operator is looking at the patient's surgical/interventional radiologic site.

In some embodiments, the OHMD can be used to display data and/or images instead of a standalone or separate computer or display monitor. Optionally, the OHMD can replace the standalone or separate computer or display monitor. In some embodiments, the OHMD can display the live data from the patient's surgical/interventional radiologic site and project them for the surgeon or interventionalist and/or radiologist and, optionally, superimpose them with virtual data. In some embodiments, the OHMD can display the intra-procedural imaging data of the patient, e.g. a 2D or 3D angiogram, a digital subtraction angiogram, a bolus study, a flow study, a bolus chase, and project them for the surgeon or interventionalist and/or radiologist and, optionally, superimpose them with other virtual data, e.g. from a pre-procedural imaging study, e.g. in 2D or 3D, e.g. an ultrasound, echocardiogram, CT, MRA, or vascular flow study. The OHMD can also display one or more aspects or components of the virtual surgical/interventional radiologic plan, e.g. projected paths for one or more surgical/interventional radiologic instruments, e.g. a guide wire, or it can display one or more virtual catheters, catheter tips, guide wires, sheaths, implants or implant components, e.g. a coil, a stent, or a vascular prosthesis. In this embodiment, the OHMD can optionally match the magnification of the one or more projected paths, e.g. using one or more computer processors configured for tracking a physical catheters, catheter tips, guide wires, sheaths, implants or implant components, e.g. a coil, a stent, or a vascular prosthesis, e.g. using one or more IMU's, RF transmitters, or electromagnetic coils or combinations thereof, and/or one or more of the physical catheters, catheter tips, guide wires, sheaths, implants or implant components, e.g. a coil, a stent, or a vascular prosthesis, relative to the magnification of the live data from the patient and/or the intra-procedural imaging data of the patient. The OHMD can also apply a larger or smaller magnification and/or size than the magnification of the live data from the patient for the one or more projected paths and/or virtual catheters, catheter tips, guide wires, sheaths, implants or implant components, e.g. a coil, a stent, or a vascular prosthesis, and/or one or more virtual implants or implant components. The live data of the patient and/or the intra-procedural imaging data can be seen through the transparent display of the OHMD. Alternatively, the display can be partially or completely opaque and the live data can be captured through an image and/or video capture system and/or 3D scanner integrated into, attached to or separate from the OHMD and then subsequently be displayed by the OHMD display.

In some embodiments, for example when the OHMD is the primary display unit, the OHMD can be non-transparent to light or minimally transparent to light reflected from the patient's surgical/interventional radiologic field and can display, for example, live (electronic) images collected by the image and/or video capture system and/or 3D scanner and/or can display the intra-procedural imaging study, e.g. a 2D or 3D angiogram, a digital subtraction angiogram, a bolus or flow study, and, optionally, it can display, in addition, for example aspects or components of the virtual surgical/interventional radiologic plan, e.g. one or more projected paths for one or more physical catheters, catheter tips, guide wires, sheaths, implants or implant components, e.g. a coil, a stent, or a vascular prosthesis or one or more tracked, virtual physical catheters, catheter tips, guide wires, sheaths, implants or implant components, e.g. a coil, a stent, or a vascular prosthesis (optionally with various chosen matching or non-matching magnifications). In this setting, the OHMD can also display electronic, virtual images of the physical surgical/interventional radiologic instruments, e.g. wires, and or devices, e.g. stents, coils or vascular prostheses, and their respective movements and/or orientation and/or alignment, for example captured with intra-procedural imaging (with various chosen matching or non-matching magnifications) or other tracking techniques, e.g. using coils, transmitters, IMU's etc.

The OHMD can be permanently non-transparent to light or minimally transparent to light reflected from the patient's surgical/interventional radiologic field. Alternatively, the degree of transparency to ambient light and/or to light reflected from the patient's surgical/interventional radiologic field can be variable, for example with use of one or more optical filters, e.g. polarizing light filters, in front of or integrated into the OHMD or electronic, e.g. LCD, or optical filters in front or integrated into the OHMD, or via intensity adjustments, or any combination thereof. The OHMD can include a visor, which can block portions or all of the field of view for ambient light. The visor can be partially transparent to external or ambient light; the visor can be non-transparent, e.g. completely blocking the transmission of ambient or external light through the visor. The visor can be moved in and out of position to block portions or all of the field of view using mechanical, electronic, magnetic, electromagnetic, and/or piezoelectric means. The visor can be partially or completely blocking the entry of ambient light. The visor can have multiple settings, e.g. blocking ⅓, ½, ⅔, ¾, ⅘, or 90% or more of the ambient light. Multiple, e.g. overlapping, visors can be used. For example, a first visor can yield a reduction in entry of ambient light and/or of light reflected from the patient's surgical/interventional radiologic field by 50%, e.g. by being partially transparent. A second visor, optionally overlapping the first visor, can yield a reduction in entry of ambient light and/or of light reflected from the patient's surgical/interventional radiologic field by 80% or 90%. A third visor, optionally overlapping the first and/or the second visor, can yield a reduction in entry of ambient light and/or of light reflected from the patient's surgical/interventional radiologic field by >90% or >95%. Any combination of filters and visors is possible. Any percentage of reduction in in entry of ambient light and/or of light reflected from the patient's surgical/interventional radiologic field is possible.

In another embodiments, a first visor can include a linearly or circularly polarizing light filter. In another embodiment, separate linearly or circularly polarizing light filter can be placed in front of the left eye and the right eye, integrated into, attached to or separate from the OHMD. Optionally, any of the polarizing light filters can be rotatable, e.g. using mechanical, electronic, magnetic, electromagnetic, and/or piezoelectric means. Polarizing light filter function can also be achieved with one or more LCD displays interposed between a surgical or interventional site/the patient and the eyes of the surgeon; the LCD display can be integrated into, attached to, or separate from the OHMD. The LCD display can be integrated into or part of a combiner, e.g. a combiner lens. By turning the LCD on and off, the polarizing light function can be turned on and off. A polarizing light filter can also be integrated into the combiner. With use of two polarizing light filters, it can optionally be possible to block all or most of the light that is incident from the operating room or interventional suite on the OHMD; blocking all or most of the light from the operating room or interventional suite can, for example, occur when the polarization axes of the two polarizing light filters (including one or two integrated into a combiner) are rotated such that they are perpendicular to each other. Blocking the light from the operating room or interventional suite partially can, for example, occur when the polarization axes of the two polarizing light filters (including one or two integrated into a combiner) are rotated such that they are near perpendicular to each other, but not completely perpendicular to each other. The light transmitted through the combiner can pass through only one or no polarizing light filter and can pass into the eye of the surgeon or interventionalist. In this manner, virtual data can be displayed by the OHMD, while ambient light and light from the operating room or interventional suite and/or the physical patient or the physical surgical site can be reduced, suppressed or cancelled. This can be useful during certain phases of a surgical or interventional procedure, for example when it is desirable to view virtual data of a patient, e.g. an intra-operative or a pre-operative 2D or 3D angiogram, and/or a virtual representation of a tracked device or instrument through one or more OHMDs without superimposition of objects or structures visible in the physical world. In any of the foregoing embodiments, the combiner can also have polarizing or other light filter function. Voice commands, gesture commands or any other commands and/or user interface can be used to turn an OHMD from fully transparent (see through) to partially transparent to non-transparent (non see through). When the OHMD is turned to non see through, optionally video feed from the operating room or interventional suite and/or the surgical site can be displayed in the OHMD, e.g. from a video system integrated into, attached to or separate from the OHMD, optionally superimposed with or co-displayed with other virtual data.

The interventional suite can optionally use light sources, e.g. polarized or filtered light that will support modulation or aid with adjustments of the transparency of the OHMD to light reflected from the patient's surgical/interventional radiologic field. Optionally, the vector of the polarized light emitted from the light sources, e.g. an OR lamp, can be modified so that it can, for example, pass through a polarization filter integrated into or attached to one or more OHMDs or so that it cannot pass through a polarization filter integrated into or attached to one or more OHMDs.

Magnified Displays

Magnified displays of the following structures and/or devices can be shown with an OHMD for example for one or more of the following, simultaneously or non-simultaneously:

Physical anatomy (e.g. using intra-procedural imaging with optional magnification or demagnification)
Static
Dynamic, e.g. with functional or time element or dimension, e.g. bolus study, flow study, bolus chase, study during table movement
Virtual anatomy, e.g. from pre-procedural imaging study
Aspects or components of a virtual surgical/interventional radiologic plan, e.g. a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined contour or outline or cross-section or surface features or shape or projection, predetermined depth marker or depth gauge, predetermined stop, predetermined angle or orientation or rotation marker, predetermined axis, e.g. rotation axis, predetermined axis of the virtual surgical/interventional radiologic tool, virtual surgical/interventional radiologic instrument, virtual implant component, implant or device, e.g. stent, coil, vascular prosthesis, non-visualized portions for one or more devices or implants or implant components or surgical/interventional radiologic instruments or surgical/interventional radiologic tools, e.g. hidden behind another vessel or hidden inside a contrast bolus, or hidden inside a contrast column, or hidden inside a branching vessel, and/or one or more of a predetermined tissue change or alteration and/or one or more of a predetermined position and/or orientation of the virtual surgical/interventional radiologic tool, virtual surgical/interventional radiologic instrument, virtual implant component, implant or device.

Virtual surgical/interventional radiologic instrument(s)
Virtual implant(s) or implant component(s) In some embodiments, the OHMD display can display live data of the patient captured through an image and/or video capture system and/or 3D scanner integrated into, attached to or separate from the OHMD or live data of the patient obtained with an intra-procedural imaging study, e.g. a 2D or 3D angiogram, a DSA, a bolus and/or flow study, with higher magnification than the live data seen through transparent portions of the OHMD by the user's or surgeon or interventionalist and/or radiologist's eye. Thus, the live data of the patient captured through an image and/or video capture system and/or 3D scanner integrated into, attached to or separate from the OHMD and/or live data obtained using an intra-procedural imaging test can be displayed in a magnified manner for a given distance of the OHMD display to the surgical/interventional radiologic field and/or the patient and/or the standalone or separate computer monitor. Data obtained using a pre-procedural imaging test can be displayed in a magnified manner for a given distance of the OHMD display to the surgical/interventional radiologic field and/or the patient and/or the standalone or separate computer monitor. This has the benefit that select structures can be seen with greater detail, for example offering a low power microscopic, magnified view of portions or all of the surgical/interventional radiologic field or portions or all of the target anatomy, e.g. a vessel or an anatomic area. The distance of the OHMD to the surgical/interventional radiologic field and/or a separate or standalone computer monitor or display can be determined using techniques described in the specification, e.g. optical markers, navigation markers including infrared markers, retroreflective markers, RF markers, IMU's, LED's, triangulation, parallax techniques, techniques using the known shape, dimensions and geometry of the standalone or separate computer monitor or display and any other technique known in the art. The distance of the OHMD to a separate or standalone computer monitor or display can be considered in addition to the magnification of any images displayed using the standalone computer monitor or display in order to match the structures or objects and the magnification of the structures or objects displayed by the separate or standalone computer monitor with the OHMD display.

The magnified display of live data including intra-procedural image data or pre-procedural image data can be performed while partially or completely blending out live data seen through the OHMD, e.g. with the OHMD turned partially or completely opaque to light emitted from the surgical/interventional radiologic field and primarily or only data displayed captured through the image and/or video capture system and/or 3D scanner. The magnified display of live data, e.g. intra-procedural image data of data captured through the image and/or video capture system and/or 3D scanner, can be superimposed on live data seen through one or more partially or completely transparent portions of the OHMD. In this example, the magnified display of the live data can be a portion of the surgical/interventional radiologic field seen through the OHMD.

Optionally, a declining gradient of magnification can be applied to the live data so that the magnified live data can blend in seamlessly or near seamlessly with the non-magnified live data, e.g. the live data seen through one or more partially or completely transparent portions of the OHMD.

The magnification of a portion or all of the live data captured through an image and/or video capture system and/or 3D scanner can be at preset levels, e.g. 1.5×, 2.0×, 3.0×, 4.0×, or 5.0× or any other magnification level, e.g. a range from 0-1×, 0-5×, 0-10×, 0-20×. The magnification can be continuous, e.g. on a sliding scale. The magnification can be selected by the user and/or surgeon or interventionalist and/or radiologist, for example using voice commands, eye commands or using a virtual keyboard interface displayed by the OHMD.

Virtual data can optionally be displayed with the same magnification as the live data. Optionally, virtual data can be displayed with no magnification or lesser or greater magnification than live data.

In some embodiments, the OHMD display can display virtual data of the patient with higher magnification than the live data seen through transparent portions of the OHMD by the user's or surgeon or interventionalist and/or radiologist's eye. Thus, the virtual data of the patient can be displayed in a magnified manner for a given distance of the OHMD display to the surgical/interventional radiologic field. This has the benefit that select structures or aspects of components of a virtual surgical/interventional radiologic plan can be seen with greater detail, for example offering a low power microscopic, magnified view of portions or all of the virtual data. The distance of the OHMD to the surgical/interventional radiologic field and/or the standalone or separate computer monitor or display can be determined using techniques described in the specification, e.g. optical markers, navigation markers including infrared markers, retroreflective markers, RF markers, IMU's, LED's, triangulation, parallax techniques, techniques using the known shape, dimensions and geometry of the standalone or separate computer monitor or display, and any other technique known in the art.

The magnified display of virtual data can be performed while partially or completely blending out live data seen through the OHMD, e.g. with the OHMD turned partially or completely opaque to light emitted from the surgical/interventional radiologic field and primarily or only virtual data displayed. The magnified display of virtual data captured through the image and/or video capture system and/or 3D scanner can be superimposed on live data seen through one or more partially or completely transparent portions of the OHMD. In this example, the magnified display of the virtual data can be a portion of the surgical/interventional radiologic field seen through the OHMD.

Optionally, a declining gradient of magnification can be applied to the virtual data so that the magnified virtual data can blend in seamlessly or near seamlessly with the non-magnified live data, e.g. the live data seen through one or more partially or completely transparent portions of the OHMD.

The magnification of a portion or all of the virtual data can be at preset levels, e.g. 1.5×, 2.0×, 3.0×, 4.0×, or 5.0× or any other magnification level, e.g. a range from 0-1×, 0-2×, 0-3×, 0-5×, 0-10×, 10-20×. The magnification can be continuous, e.g. on a sliding scale. The magnification can be selected by the user and/or surgeon or interventionalist and/or radiologist, for example using voice commands, eye commands or using a virtual keyboard interface displayed by the OHMD.

Both portions or all of live data and virtual data can be displayed using magnification or no magnification. Non-limiting examples of possible magnification combinations between live data and virtual data are provided below.

TABLE 15

Exemplary, non-limiting combinations of magnifications of live data and/or virtual data.

| Virtual data, e.g. obtained using a pre-procedural imaging test, e.g. a CTA or MRA or ultrasound or diagnostic angiogram | Live data, e.g. as obtained using an intra-procedural imaging test, e.g. a 2D or 3D angiogram, optionally displayed by a standalone or separate computer monitor or display | | | | |
|---|---|---|---|---|---|
| | Original size | Portions magnified | All magnified | Portions minified | All minified |
| Original size | X | X | X | X | X |
| Portions magnified | X | X | X | X | X |
| All magnified | X | X | X | X | X |
| Portions minified | X | X | X | X | X |
| All minified | X | X | X | X | X |

X denotes type of magnification mode combinations used or possible

The magnification of live data and virtual data can be the same. The magnification of live data and virtual data can be different. Virtual data can be partially, e.g. affecting only part of the displayed virtual data, or all magnified. Live data, including a 2D or 3D angiogram, DSA, flow study, bolus study, bolus chase, can be partially, e.g. affecting only part of the displayed live data, or all magnified. Virtual data, e.g. a virtual instrument or tool such as a guide wire or sheath and/or a virtual implant such as a stent, a coil, a vascular prosthesis, can be magnified while live data are not magnified. Live data can be magnified while virtual data are not magnified. Any combination is possible, also with the embodiments on superimposing an OHMD display with a standalone or separate computer monitor or display.

The term magnification includes also displays wherein the live data or the virtual data are displayed in a format or with a magnification that is smaller than live data seen through transparent portions of the OHMD for a given distance.

The magnification can be applied around a central point, e.g. an anchor point, an anatomic landmark, a guide wire, a sheath, a vascular device, a vascular implant, a contrast column, an opacified vessel and/or vascular structure, or central axis of the field of view of the OHMD, a pin axis or a screw axis. When a central point is used, the coordinates of the central point in the live data, e.g. an intra-procedural imaging study, of the patient as seen by the surgeon or interventionalist and/or radiologist's right eye through the OHMD unit will be the same as the view coordinates of the central point in the virtual data, e.g. a pre-procedural imaging study, of the patient seen by the surgeon or interventionalist and/or radiologist's right eye projected by the display of the OHMD unit; the coordinates of the central point in the live data, e.g. an intra-procedural imaging study, of the patient as seen by the surgeon or interventionalist and/or radiologist's left eye through the OHMD unit will be the same as the view coordinates of the central point in the virtual data, e.g. a pre-procedural imaging study, of the patient seen by the surgeon or interventionalist and/or radiologist's left eye projected by the display of the OHMD unit. When a central axis is used, the coordinates of the central axis in the live data of the patient as seen by the surgeon or interventionalist and/or radiologist's right eye through the OHMD unit will be the same as the view coordinates of the central axis in the virtual data of the patient seen by the surgeon or interventionalist and/or radiologist's right eye projected by the display of the OHMD unit; the coordinates of the central axis in the live data of the patient as seen by the surgeon or interventionalist and/or radiologist's left eye through the OHMD unit will be the same as the view coordinates of the central axis in the virtual data of the patient seen by the surgeon or interventionalist and/or radiologist's left eye projected by the display of the OHMD unit.

When stereoscopic projection is used with the left and right displays of the OHMD unit, the view coordinates for the left display and the right display of the OHMD unit will be different for the left eye and the right eye; the difference in view coordinates is a reflection of the parallax. For example, when the user or surgeon or interventionalist and/or radiologist elects to turn on magnification of live and/or virtual data, the magnification can be applied around the central point of the last unmagnified field of view. The system including its software can optionally apply the magnification automatically around the central point of the last field of view. Alternatively, the user and/or surgeon or interventionalist and/or radiologist can use a different central point or central axis as the center around which the live and/or virtual data are being magnified. The central point or central axis can, for example, coincide with the center of a vessel or a vascular bifurcation, e.g. a carotid bulb or bifurcation when carotid surgery is contemplated. The central axis can coincide with an vascular axis, e.g. a long axis of the aorta or a renal artery. The central axis can, for example, be a predetermined path, e.g. for a guide wire. The central axis can be a long axis of a wire or a stent or another vascular device or instrument. The central point, can, for example, be an endpoint, e.g. the terminal end of a wire or a sheath. The central point or central axis can, for example, be the center of a vascular bifurcation or the center of an aneurysm or a vascular malformation. The central point or central axis can, for example, be the center of a circle of Willis when brain surgery or vascular intervention is contemplated. The central point or central axis for magnification can be pre-selected for various anatomic sites or surgical/ interventional radiologic fields or surgeries contemplated, e.g. cardiac bypass surgery, cardiac valve replacement etc. Using, for example, one or more image and/or video capture systems and/or 3D scanner integrated into, attached to or separate from the OHMD, or using intra-procedural imaging, one or more non-vascular anatomic structures can optionally be identified, e.g. a bony landmark, structure of feature and the central point or central axis for any magnified views can optionally be set or defined using the non-vascular landmark, structure of feature.

View Patient/View Computer Monitor/Screen

In some embodiments, the magnification of the OHMD display can be matched with the magnification of a computer monitor, e.g. in the interventional suite, so that corresponding tissues shown by the OHMD and/or the computer monitor are displayed using the same magnification and can, for example, be substantially aligned or superimposed between the OHMD and the computer monitor display.

Display Considerations

In embodiments, one or more OHMDs can be the sole display, replacing a standalone or separate computer monitor or display. For this purpose, a white wall background can be present in sections of the interventional suite. Alternatively, the one or more OHMDs can blend out live data, e.g. reflected light, from the interventional suite and, for example, only display intra-procedural and/or pre-procedural imaging data or combinations thereof.

Cardiac and/or Respiratory Gating

In embodiments, pre-procedural imaging such as CTA, MRA and/or ultrasound can be performed with cardiac and/or respiratory gating. For this purpose, an EKG and/or a measurement of the respiratory cycle can be performed while the CTA, MRA and/or ultrasound images are obtained. In embodiments, one or more full sets of CTA, MRA or ultrasound images can be obtained through an entire cardiac and/or respiratory cycle. In embodiments, e.g. when performing vascular interventions involving the heart, the lungs, the cardiopulmonary system, abdominal organs, and EKG and/or measurements of the respiratory cycle can be performed while an intra-procedural imaging study, e.g. a 2D or 3D angiogram, a DSA, a contrast study, a flow study, a bolus study or a bolus tracking study is obtained.

One or more OHMD displays can then align and superimpose the vascular anatomy from pre-procedural imaging, e.g. a pre-procedural CTA, MRA or ultrasound, with the vascular anatomy seen during the intra-procedural imaging. The overlaying and/or aligning and/or superimposing can be performed by registering the pre-procedural images with the intra-procedural images using, for example, anatomic landmarks, features, surfaces, geometries, shapes, e.g. of vessels and/or vascular structures or underlying tissue such as bone; the overlaying and/or aligning and/or superimposing can also be performed by registering the pre-procedural images with the intra-procedural images with regard to cardiac cycle/cardiac gating and/or respiratory cycle/respiratory gating. For example, anatomically matched images from the same part of the cardiac cycle and/or respiratory cycle from a pre-procedural 3D CTA, 3D MRA or 3D ultrasound display can be aligned with and/or superimposed onto intra-procedural images, e.g. a 2D or 3D angiogram, a DSA, a contrast study, a flow study, a bolus study or a bolus tracking study, from a corresponding part of the cardiac cycle. Thus, pre-procedural images can be selected and/or matched and/or aligned and/or superimposed so that the matching, aligning and/or superimposing is done for corresponding parts of the cardiac and/or respiratory cycle, e.g. in addition to superimposing, aligning and/or matching on the basis of anatomic information.

Respiratory Gating

In some embodiments, respiratory gating can used to maintain the display of virtual data, e.g. a display of data from a pre-operative imaging study, e.g. an ultrasound, a pre-operative CT angiography or MR angiography, for example in 2D or 3D or 4D or more dimensions if a vascular flow study or functional study has been performed, or a virtual surgical plan or a virtual target or a virtual surgical guide, in relationship to physical data or physical structures of the patient, e.g. an organ, including a heart, a lung, a vessel, etc., through the respiratory cycle. Respiratory gating can used to maintain the display of virtual data, e.g. a display of data from a pre-operative imaging study, e.g. an ultrasound, a pre-operative CT angiography or MR angiography, for example in 2D or 3D or 4D or more dimensions if a vascular flow study or functional study has been performed, or a virtual surgical plan or a virtual target or a virtual surgical guide, superimposed onto and/or aligned with physical data or physical structures of the patient, e.g. an organ, including a heart, a lung, a vessel, etc., through the respiratory cycle. Thus, the movement of the physical data or physical structures of the patient with diaphragmatic motion can be accompanied by a corresponding movement of virtual data in one, two or three dimensions, optionally with the same, or, in some embodiments, different frequency, direction of movement, speed of movement and magnitude or amount of movement in one or more directions. The corresponding movement can be performed by one or more computer systems with one or more computer processors configured to display and/or move and/or superimpose and/or align virtual data by one or more OHMD displays. Respiratory expansion or contraction, corresponding to inspiration or expiration, can be detected using, for example, a thoracic belt, bellows, or cushion. The belt can, for example, be placed around the lower chest for chest breathers and around the mid abdomen for abdominal breathers. Multiple belts, bellows or cushions can be used. Impedance plesmythography devices that measure changes in electrical resistance across the chest with respiration can also be used. Spirometric devices that measure, for example, the movement of air in one or more portions of the airway can also be used to measure and/or monitor the respiratory cycle.

Use of Markers for Respiratory Gating

In some embodiments, techniques for monitoring the movement of one or more markers applied, for example, to the surface of the chest or the abdomen, can also be utilized for respiratory gating using, for example, a computer system with one or more computer processors configured to analyze one or more video feeds and/or configured to detect and/or measure marker motion. For example, the one or more markers can be retroreflective, similar to the markers used for surgical navigation systems. An infrared light source can be utilized to illuminate the area where the markers are applied or attached to the chest wall or abdominal wall or, for example, an organ surface, e.g. using fibrin glue, and the infrared light reflected by the markers can be utilized to measure or monitor respiratory motion, including respiratory frequency, direction of respiratory movement, e.g. in x-, y- and/or z- and/or any other direction, speed of respiratory movement, amount of respiratory movement, e.g. in x-, y- and/or z- and/or any other direction, etc. using one or more infrared receivers or cameras, such as the ones provided by Atracsys, Inc. (Atracsys, Inc. Le Mont-sur-Lausanne, Switzerland).

Any marker described in the specification or known in the art can be used. For example, an optical marker can be used. The optical marker can include a geometric pattern, a bar code, or a QR code. The bar code or QR code can encode the area or organ to which the marker has been applied or attached to. An image capture system, camera system, or video system integrated into, attached to or separate from one or more OHMDs can be used to monitor the movement of the marker caused by diaphragmatic motion. The marker and the one or more OHMDs can be registered in a common coordinate system. In this manner, movement of the OHMD in the coordinate system, e.g. through head movement of the surgeon or operator, can be differentiated from movement of the marker caused by diaphragmatic, respiratory motion.

The captured images or video images can be used to determine respiratory motion, including respiratory frequency, direction of respiratory movement, speed of respiratory movement, amount of respiratory movement, etc., in real time or retrospectively, using a computer system with one or more computer processors configured to analyze the captured images or video images. The image capture system, camera system, or video system can be attached to the OR table or can be attached to a stand separate from the OR table. The image capture system, camera system, or video system can be attached to an OR light.

If an organ is partially exposed or visible during the surgery, one or more markers can be attached to the visible portions of the organ and an image capture system, camera system, or video system integrated into, attached to or separate from one or more OHMDs can be used to monitor the movement of the marker caused by diaphragmatic motion. The movement of the marker and of the visible portions of the organ can be used to simulate the movement of the non-visible portions of the organ and/or any lesions or tumors inside the organ, hidden underneath the organ surface, using a computer system with one or more computer processors configured to simulate such movement.

In some embodiments, a 3D scanner or an imaging device, for example as described in the specification or as known in the art, can be used during the procedure to image an organ or a target area and to track any respiratory motion.

Superimposition and/or Alignment of Virtual Data by One or More OHMDs with Physical Data or Structures of the Patient Using Respiratory Gating In some embodiments, respiratory gating can be used to display and/or move virtual data displayed by one or more OHMDs using a computer system, for example, with one or more computer processors configured to synchronize the virtual data with the patient's respiratory cycle and, optionally, following the full or a partial amount of respiratory excursion, e.g. in mm or cm, e.g. by 5, 10, 15, 20, 25, 30, 35, 40, 45, 50, 55, 50 mm or any other amount of excursion in one or more directions, e.g. superior, inferior, anterior, posterior, medial or lateral or any oblique direction. In this manner, the display of the virtual data can be superimposed onto and/or aligned with corresponding physical structures of the patient and can be maintained in superimposition and/or alignment with the corresponding physical structures of the patient through at least portions of the respiratory cycle or the entire respiratory cycle.

Using a computer system with one or more computer processors configured to display and/or move virtual data in one or more OHMDs, the movement of the display of the virtual data by the one or more OHMDs can be performed to follow or mirror or to be synchronized with diaphragmatic movement and, for example, the associated movement of a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, or a target for surgical or other intervention associated with the patient's body, e.g. as it pertains to the frequency of the respiratory cycle, and/or the phase of the respiratory cycle, e.g. full inspiration, partial inspiration, full expiration, partial expiration, and/or the direction of respiratory movement or excursion, and/or the speed of respiratory movement or excursion, and/or the amount of excursion during the respiratory cycle. In some embodiments, the speed of movement, direction of movement, and/or amount of movement/excursion of a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, a device, an instrument, a catheter, a stent, or a target for surgical or other intervention associated with the patient's body can be the same as that of the diaphragm and/or the intercostal muscles, it can be less or it can be more. By synchronizing the display of the virtual data by the one or more OHMDs with the frequency of the respiratory cycle, and/or the phase of the respiratory cycle, e.g. full inspiration, partial inspiration, full expiration, partial expiration, and/or the direction of respiratory movement or excursion of the diaphragm or the direction of respiratory movement or excursion of a physical organ or physical tissue or a target, and/or the speed of respiratory movement or excursion of the diaphragm or the speed of respiratory movement or excursion of a physical organ or physical tissue or a target, and/or the amount of movement or excursion of the diaphragm or the amount of respiratory movement or excursion of a physical organ or physical tissue or a target, the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, a device, an instrument, a catheter, a stent, or a target for surgical or other intervention associated with the patient's body, during respiratory movement or excursion.

By moving the display of the virtual data, e.g. using one or more computer systems with one or more computer processors configured to generate the display of the virtual data, by the one or more OHMDs with the frequency of the respiratory cycle, and/or the phase of the respiratory cycle, e.g. full inspiration, partial inspiration, full expiration, partial expiration, and/or the direction of respiratory movement or excursion of the diaphragm or the direction of respiratory movement or excursion of a physical organ or physical tissue or a target, and/or the speed of respiratory movement or excursion of the diaphragm or the speed of respiratory movement or excursion of a physical organ or physical tissue or a target, and/or the amount of movement or excursion of the diaphragm or the amount of respiratory movement or excursion of a physical organ or physical tissue or a target, the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, or a device, an instrument, a catheter, a stent, or a target for surgical or other intervention associated with the patient's body, during respiratory movement or excursion during a portion of or during the entire respiratory cycle. One or more computer processors can be used for measuring the frequency of the respiratory cycle, and/or the phase of the respiratory cycle, e.g. full inspiration, partial inspiration, full expiration, partial expiration, and/or the direction of respiratory movement or excursion of the diaphragm or the direction of respiratory movement or excursion of a physical organ or physical tissue or a target, and/or the speed of respiratory movement or excursion of the diaphragm or the speed of respiratory movement or excursion of a physical organ or physical tissue or a target, and/or the amount of movement or excursion of the diaphragm or the amount of respiratory movement or excursion of a physical organ or physical tissue or a target. One or more computer processors can be used for moving the virtual data based on the one or more measurements. The one or more computer processors for obtaining the measurements and the one or more computer processors for moving the virtual data displayed by the one or more OHMDs can be the same or different computer processors.

Physical Data or Physical Structures in Exposed Areas or in Hidden Areas, e.g. Inside an Organ The physical data or physical structures of the patient, e.g. an organ or tissue or tissue surface, can be on a body surface or on an exposed surface, e.g. exposed through an incision or surgical alteration, e.g. a tissue removal, directly visible through a see through, e.g. augmented reality, optical head mounted display or visible directly by an image capture system, camera system or video system integrated into, attached to or separate from the one or more OHMDs. The physical data or physical structures or physical anatomic structures or physical tissues of the patient, e.g. an organ or tissue or tissue surface, can be inside the body, e.g. in a subsurface location, e.g. below a skin or inside a pericardium or a pleura or a peritoneum or inside an organ or underneath an organ surface, or underneath a tissue surface, and cannot be directly visible through a see through, e.g. augmented reality, optical head mounted display or not directly visible directly by an image capture systems, camera system or video system integrated into, attached to or separate from the one or more OHM Ds.

If the physical data or physical structures of the patient are located inside the body, e.g. in a subsurface location, e.g. below a skin or inside a pericardium or a pleura or a peritoneum or inside an organ or underneath an organ surface, or underneath a tissue surface, imaging can be performed prior to or at the time of a medical or surgical intervention to visualize the physical data or physical structures of the patient, e.g. pre-operatively or intra-operatively. The imaging can, for example, be performed using x-ray imaging, ultrasound, CT scan or MRI scan, SPECT scanning, PET scanning, radionuclide scanning or any other imaging modality known in the art. The imaging can be performed prior to and/or after administration of intravenous and/or intra-luminal and/or aerogenic contrast media. The image acquisition can be performed in select phases of the respiratory cycle. The image acquisition can also be performed throughout the respiratory cycle. Optionally, the image acquisition can be performed using one more computer systems with one or more computer processors configured to perform the image acquisition through the respiratory cycle to measure one or more of a frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target. Optionally, image acquisition can be performed through multiple respiratory cycles and the measured data can be averaged; optionally, other statistical models can be applied to the measured data.

For example, an ultrasound transducer can be applied in a fixed or static position to a body surface, a tissue surface, or an organ surface and ultrasound image acquisition can be performed to measure one or more of a frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target. The position and/or orientation of the ultrasound transducer can, for example be maintained with use of a stand and/or a holding arm. The ultrasound transducer can, for example, also be used to identify a target, e.g. a tumor or a lesion inside an organ.

One or more markers applied to the chest wall, abdominal wall, organ, tissue, or tissue surface can be used to measure respiratory movement including, for example, one or more of a frequency, phase, direction, speed and/or amount of movement or excursion using, for example, an image capture, camera or video system. The data obtained with use of the one or more markers and the data obtained with the imaging system, e.g. an ultrasound system, can optionally be compared, e.g. to identify any differences in marker measurements and imaging system measurements, with optional correction of such differences in the marker or imaging measurements.

After one or more image acquisitions, for example during a procedure, the surgeon or interventionalist can optionally discontinue the use of the imaging system; in some embodiments, the measured movement of the one or more markers or of the organ or tissue surface, e.g. as detected by a 3D scanner or video system, can then be used to compute or estimate the movement or excursion the physical data or physical structures of the patient, e.g. an organ or tissue or tissue surface, on an external and/or exposed surface or inside the body, e.g. in a subsurface location, e.g. below a skin or inside a pericardium or a pleura or a peritoneum or inside an organ or underneath an organ surface, or underneath a tissue surface with the respiratory movement or excursion, and the display of the virtual data by the one or more OHMDs can be moved synchronized with the frequency of the respiratory cycle, and/or the phase of the respiratory cycle, e.g. full inspiration, partial inspiration, full expiration, partial expiration, and/or with the direction of respiratory movement or excursion of the diaphragm, the physical organ or physical tissue or target, and/or with the speed of respiratory movement or excursion of the diaphragm, the physical organ or physical tissue or target, and/or the amount of movement or excursion of the diaphragm, the physical organ or physical tissue or target, and the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, or a target for surgical or other intervention associated with the patient's body, during respiratory movement or excursion.

The physical data or physical structures of the patient, e.g. an organ or tissue or tissue surface, can be inside the body, e.g. in a subsurface location, e.g. below a skin or inside a pericardium or a pleura or a peritoneum or inside an organ or underneath an organ surface, or underneath a tissue surface, and can be visible by an image capture system, camera system or video system inserted into or near the subsurface location, inside the pericardium, inside the pleura, inside the peritoneum, inside a cavity, inside a hollow organ, or inside a space created by a surgical instrument. By inserting the image capture system, camera system or video system into or near the subsurface location, inside the pericardium, inside the pleura, inside the peritoneum, inside a cavity, inside a hollow organ, or inside a space created by a surgical instrument, the physical data of the patient can be registered in a coordinate system, e.g. a coordinate system in which one or more OHMDs are also registered. By inserting the image capture system, camera system or video system into or near the subsurface location, inside the pericardium, inside the pleura, inside the peritoneum, inside a cavity, inside a hollow organ, or inside a space created by a surgical instrument, the image capture system, camera system or video system can also be used to image or capture respiratory motion, e.g. of the physical data or structures of the patient, including, for example, the frequency of the respiratory cycle, the phase of the respiratory cycle, e.g. full inspiration, partial inspiration, full expiration, partial expiration, the direction of respiratory movement or excursion of the physical organ or physical tissue or target, the speed of respiratory movement or excursion of the physical organ or physical tissue or target, or the amount of movement or excursion of the physical organ or physical tissue or target.

One or more markers applied to the chest wall, abdominal wall, organ, tissue, or tissue surface can be used to measure respiratory movement, e.g. using one or more computer systems with one or more computer processors configured to analyze a video stream and to measure marker movement, including, for example, one or more of a frequency, phase, direction, speed and/or amount of movement or excursion using, for example, an image capture, camera or video system. The data obtained with use of the one or more markers and the data obtained with the image capture system, camera system or video system inside the patient can optionally be compared, e.g. to identify any differences in marker measurements and image capture, camera or video system or imaging system measurements, with optional correction of such differences in the marker measurements.

In some embodiments, the measured movement of the one or more markers can then be used to compute or estimate the movement or excursion the physical data or physical structures of the patient, e.g. an organ or tissue or tissue surface, inside the body, e.g. in a subsurface location, e.g. below a skin or inside a pericardium or a pleura or a peritoneum or inside an organ or underneath an organ surface, or underneath a tissue surface with the respiratory movement or excursion, and the display of the virtual data by the one or more OHMDs can be moved with the frequency of the respiratory cycle, and/or the phase of the respiratory cycle, e.g. full inspiration, partial inspiration, full expiration, partial expiration, and/or the direction of respiratory movement or excursion of the physical organ or physical tissue or target, and/or the speed of respiratory movement or excursion of the physical organ or physical tissue or target, and/or the amount of movement or excursion of the physical organ or physical tissue or target, and the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, or a target for surgical or other intervention associated with the patient's body, during respiratory movement or excursion.

In some embodiments, the display of the virtual data can be aligned with and superimposed onto corresponding physical data or structures of the patient through the entire respiratory cycle, e.g. through all phases of inspiration or expiration. Thus, the display of the virtual data can be maintained aligned with and superimposed onto corresponding physical data or structures of the patient through the entire respiratory cycle, e.g. through all phases of inspiration or expiration. For example, a respiratory gating system can measure one or more of the frequency of the respiratory cycle, and/or the phase of the respiratory cycle, e.g. full inspiration, partial inspiration, full expiration, partial expiration, and/or the direction of respiratory movement or excursion, and/or the speed of respiratory movement or excursion and/or the amount of excursion of the respiratory cycle in one or more directions, e.g. superior, inferior, anterior, posterior, medial or lateral or any oblique direction. The measured data can be used to compute a synchronized movement of the virtual data by the one or more OHMDs to maintain superimposition and/or alignment of the virtual data onto the physical data or physical structures of the patient through the entire respiratory cycle.

In some embodiments, the display of the virtual data can be aligned with and superimposed onto corresponding physical data or structures of the patient through the portions of the respiratory cycle, e.g. through select phases of inspiration or expiration. Thus, the display of the virtual data can be maintained aligned with and superimposed onto corresponding physical data or structures of the patient through portions of the respiratory cycle, e.g. through select phases of inspiration or expiration. For example, a respiratory gating system can measure one or more of the frequency of the respiratory cycle, and/or the phase of the respiratory cycle, e.g. full inspiration, partial inspiration, full expiration, partial expiration, and/or the direction of respiratory movement or excursion, and/or the speed of respiratory movement or excursion and/or the amount of excursion of the respiratory cycle in one or more directions, e.g. superior, inferior, anterior, posterior, medial or lateral or any oblique direction. The measured data can be used to compute a synchronized movement of the virtual data by the one or more OHMDs to maintain superimposition and/or alignment of the virtual data onto the physical data or physical structures of the patient through portions of the respiratory cycle.

In some embodiments, a breath hold technique can be employed. Using any of the techniques described in the specification, one or more of the frequency of the respiratory cycle, and/or the phase of the respiratory cycle, e.g. full inspiration, partial inspiration, full expiration, partial expiration, and/or the direction of respiratory movement or excursion of the physical organ or physical tissue or target, and/or the speed of respiratory movement or excursion of the physical organ or physical tissue or target, and/or the amount of movement or excursion of the physical organ or physical tissue or target can be determined for the respiratory cycle. The position and/or orientation of the physical organ or physical tissue or physical structure or target can be determined, for example using imaging, for a given phase of the respiratory cycle, e.g. full expiration or full inspiration, or for the entire respiratory cycle or portions of the respiratory cycle. The patient can then be asked to fully exhale or fully inhale or to achieve any other phase of the respiratory cycle and then hold his or her breath, e.g. for 5, 10, 15, 20, or 30 seconds or any other amount of time. One or more OHMDs can then display the virtual data superimposed onto and/or aligned with the corresponding portions of the physical organ or physical tissue or physical structure or target for the given phase of the respiratory cycle and the associated position and/or coordinates of the physical organ or physical tissue or physical structure or target while the patient is maintaining the breath hold. Once the patient resumes breathing, the OHMD display can optionally fade or disappear; the OHMD display of the virtual data can be turned back on by the computer systems with the next breath hold, for example during the same or a different phase of the respiratory cycle compared to the prior breath hold. The OHMD display of the virtual data can be maintained superimposed onto and/or aligned with the corresponding physical organ or physical tissue or physical structure(s) on the surface, e.g. an exposed surface, of the patient or inside the patient or target on the patient's surface or inside the patient while the patient is holding his or her breath. The position and/or orientation of the display of the virtual data by the OHMD can be adjusted by one or more computer systems associated or connected to the one or more OHMDs so that the virtual data substantially match and/or are substantially aligned with and/or are substantially superimposed with the corresponding physical organ or physical tissue or physical structure(s) or target on the patient's surface or inside the patient, e.g. underneath the surface of an organ, for the given phase of the respiratory cycle and the associated position and/or coordinates of the physical organ or physical tissue or physical structure or target.

Optionally, the OHMD display of the virtual data can be stopped when the patient resumes breathing, e.g. as measured using a respiratory gating technique or device, e.g. a belt or marker with video system, and can be resumed and maintained when the patient performs the next breath hold.

In any of the embodiments, one or more OHMDs can be registered in the same coordinate system in which the patient or any portion of the patient, e.g. a physical organ, a physical surface, a physical tissue, or a physical target on the surface, e.g. an exposed surface, of the patient or inside the patient, are registered. Subcoordinate systems can be used within a common coordinate system. For example, one or more subcoordinate systems can be used for registering and/or tracking one or more portions of the patient; one or more subcoordinate systems can be used for registering and/or tracking one or more OHMDs. The subcoordinate systems can be referenced to the same common coordinate system. By registering and tracking the one or more physical organs, physical structures or targets of the patient and the one or more OHMDs in a common coordinate system, and by performing respiratory gating using any of the techniques described in the specification, and by moving the display of the virtual data by the one or more OHMDs using one or more of the measured frequency of the respiratory cycle, and/or the phase of the respiratory cycle, e.g. full inspiration, partial inspiration, full expiration, partial expiration, and/or the direction of respiratory movement or excursion of the physical organ or physical tissue or target, and/or the speed of respiratory movement or excursion of the physical organ or physical tissue or target, and/or the amount of movement or excursion of the physical organ or physical tissue or target, the display of the virtual data can be maintained aligned with and/or superimposed with the physical organ or physical tissue or physical structure(s) of the patient or the target for one or more portions of the respiratory cycle or the entire respiratory cycle, as well as for breath hold techniques.

FIG. 19A is an example of respiratory gating 900 for measuring or estimating 903 one or more of respiratory rate or frequency 906, the phase of the respiratory cycle 909, the direction of respiratory excursions or movement during inspiration or expiration 912, the speed of respiratory excursions or movement during inspiration or expiration 915 or the amount of respiratory excursions or movement during inspiration or expiration 918. The information can be used to move the display of virtual data by one or more OHMDs to maintain superimposition and/or alignment of the virtual data of the patient, for example a virtual surgical guide, e.g. a virtual axis for an instrument, with one or more physical organs, physical tissues, physical surfaces, physical structures or targets on the surface of the patient, e.g. an exposed surface, or inside the patient or inside an organ during at least portions of or the entire respiratory cycle.

Figure 19B:
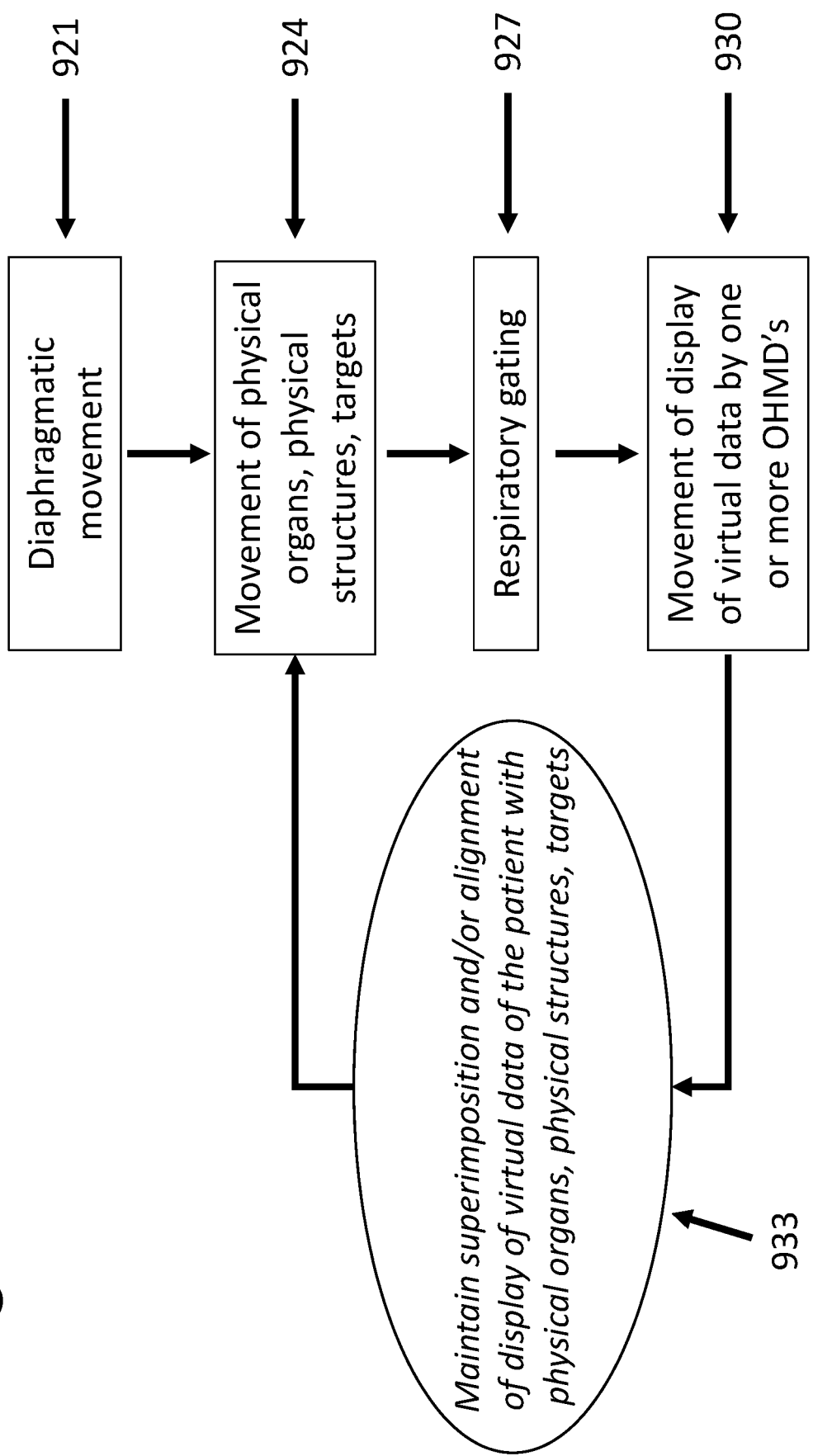
FIG. 19B is a diagram showing an example of a technique for maintaining superimposition and/or alignment of a display of virtual data with physical organs, physical structures or targets during at least portions of or the entire respiratory cycle, according to some embodiments.

FIG. 19B is an example of a technique for maintaining superimposition and/or alignment of a display of virtual data of the patient with physical organs, physical structures or targets during at least portions of or the entire respiratory cycle 933. Diaphragmatic movement 921 during inspiration or expiration can result in movement of one or more physical organs, physical structures, physical tissues, or physical surfaces 924 on the surface of the patient, e.g. a surgically exposed surface, or inside the patient, for example in a subsurface location or inside an organ, e.g. a vessel, during portions or all of the respiratory cycle. Respiratory gating 927 can be used to assess or estimate or measure one or more of the frequency of the respiratory cycle, and/or the phase of the respiratory cycle, e.g. full inspiration, partial inspiration, full expiration, partial expiration, and/or the direction of respiratory movement or excursion of the physical organ or physical tissue or target, and/or the speed of respiratory movement or excursion of the physical organ or physical tissue or target, and/or the amount of movement or excursion of the physical organ or physical tissue or target. The respiratory gating information can be used to move the display of virtual data by one or more OHMDs 930 consistent with, matching and/or synchronized with at least portions of the respiratory cycle and the associated respiratory movement of the one or more physical organs, physical structures, physical tissues, physical surfaces thereby maintaining superimposition and/or alignment of a display of virtual data with the one or more physical organs, physical structures, physical tissues, physical surfaces during at least portions of or the entire respiratory cycle 933.

For example, when OHMD guidance is desired for performing a renal biopsy or a puncture of the renal pelvis, e.g. for placing a nephrostomy tube, respiratory gating of the virtual data displayed by the one or more OHMDs, e.g. pre-procedural or intra-procedural 2D or 3D images of the patient's kidney, e.g. an ultrasound, can be performed. Imaging can be performed at the beginning of or during the procedure to visualize the physical data or physical structures of the patient. The imaging can, for example, be performed using x-ray imaging, ultrasound, CT scan or MRI scan or any other imaging modality known in the art. The image acquisition can be performed in select phases of the respiratory cycle. The image acquisition can also be performed throughout the respiratory cycle. Optionally, the image acquisition can be performed through the respiratory cycle using, for example, one or more computer systems with one or more computer processors configured to measure one or more of a frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target. The data obtained with use of the imaging system, e.g. an ultrasound system, can optionally be compared to data obtained using respiratory gating systems such as belts, bellows or cushions, spirometry, plesmythography, or markers with one or more infrared or video systems. Once a correlation between the imaging data and the respiratory gating system(s) has been established, e.g. specific image coordinates of the kidney or renal pelvis for a given or each phase of the respiratory cycle, the operator can optionally terminate the imaging procedure, while the respiratory gating and related data acquisition and analysis can continue.

By moving and synchronizing the display of the virtual data, in this example virtual data or images of the kidney or renal pelvis, with the respiratory movement of the physical kidney or physical renal pelvis as measured with the imaging system and/or the other respiratory gating systems, the OHMD display of the virtual data can be maintained superimposed and/or aligned with the physical kidney and/or renal pelvis during at least portions of or the entire respiratory cycle. The surgeon can thus see the virtual kidney and/or virtual renal pelvis displayed by the OHMD and projected inside the patient, registered with and superimposed and/or aligned with the physical kidney and/or physical renal pelvis, and maintained in superimposition and/or alignment with the physical kidney and/or physical renal pelvis during at least portions of or the entire respiratory cycle. The surgeon can then direct a physical surgical instrument, e.g. a trocar, towards the virtual renal pelvis projected by the OHMD and superimposed and maintained in superimposition with the physical renal pelvis during respiration and the surgeon can place the trocar inside the physical renal pelvis followed by the placement of the nephrostomy tube and the removal of the trocar. Optionally, the OHMD can also display virtual data of sensitive structures, e.g. adjacent arteries or veins or nerves, so that the surgeon can move the trocar away from the displayed virtual sensitive structures while advancing it towards the renal pelvis. The display of the virtual data of sensitive structures near or adjacent to the target tissue, e.g. a renal pelvis, by the OHMD can also be moved and synchronized with the respiratory movement of the physical sensitive structures and/or the physical kidney and/or renal pelvis so that the OHMD display of the virtual data of the sensitive structures of the patient can be maintained superimposed and/or aligned with the physical sensitive structures during at least portions of or the entire the respiratory cycle. In another example, when OHMD guidance is desired for resecting a tumor or metastasis inside an organ, respiratory gating of the virtual data displayed by the one or more OHMDs, e.g. pre-procedural or intra-procedural 2D or 3D images of the patient's organ and tumor or metastasis, e.g. an ultrasound, can be performed. Imaging can be performed at the beginning of or during the procedure to visualize the physical data or physical structures of the patient. The imaging can, for example, be performed using x-ray imaging, ultrasound, CT scan or MRI scan, PET scan, SPECT scan, or any other imaging modality known in the art. The image acquisition can be performed without respiratory gating, for example, when the imaging test is fast or when images are acquired during a breath hold. The image acquisition can be performed in select phases of the respiratory cycle. The image acquisition can also be performed throughout the respiratory cycle. Optionally, the image acquisition can be performed with respiratory gating and images can, optionally, be tagged with the respective part of the respiratory cycle during which they were acquired. Optionally, the image acquisition can be performed through the respiratory cycle to measure one or more of a frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target. The data obtained with use of the imaging system, e.g. an intra-operative ultrasound system using a sterile transducer probe, e.g. on the organ surface, can optionally be compared to data obtained using respiratory gating systems such as belts, bellows or cushions, spirometry, plesmythography, or markers with one or more infrared or video systems. Once a correlation between the imaging data and the respiratory gating system(s) has been established, e.g. specific image coordinates of the organ and/or the tumor or metastasis for a given or each phase of the respiratory cycle, the operator can optionally terminate the imaging procedure, while the respiratory gating and related data acquisition and analysis can continue.

By moving and synchronizing the display of the virtual data, in this example virtual data or images of the organ and/or tumor or metastasis, with the respiratory movement of the physical organ and/or physical tumor or metastasis as measured with the imaging system and/or the other respiratory gating systems, the OHMD display of the virtual data can be maintained superimposed and/or aligned with the physical organ and/or physical tumor or metastasis during at least portions of or the entire respiratory cycle. The surgeon can thus see the virtual organ and/or virtual tumor or metastasis displayed by the OHMD and projected inside the patient, registered with and superimposed and/or aligned with the physical organ and/or physical tumor or metastasis, and maintained in superimposition and/or alignment with the physical organ and/or physical tumor or metastasis during at least portions of or the entire respiratory cycle. The surgeon can then direct a physical surgical instrument, e.g. a scalpel or a needle or a thermocoagulation probe, or another instrument or another device towards the virtual organ and/or virtual tumor or metastasis projected by the OHMD and superimposed and maintained in superimposition with the physical organ and/or physical tumor or metastasis during respiration and the surgeon can place the scalpel or needle or thermocoagulation probe or other instrument or other device inside the physical organ and/or tumor or metastasis. Optionally, the OHMD can also display virtual data of sensitive structures, e.g. adjacent arteries or veins or nerves, so that the surgeon can move the scalpel or needle or thermocoagulation probe or other instrument or other device away from the displayed virtual sensitive structures while advancing it towards the renal pelvis. The display of the virtual data of sensitive structures near or adjacent to the target tissue, e.g. an organ and/or a target tissue, by the OHMD can also be moved and synchronized with the respiratory movement of the physical sensitive structures and/or the physical organ and/or tumor or metastasis so that the OHMD display of the virtual data of the sensitive structures of the patient can be maintained superimposed and/or aligned with the physical sensitive structures during at least portions of or the entire the respiratory cycle.

In some embodiments, respiratory gating can be used to synchronize virtual data with physical data of the patient, e.g. a physical organ that is moving due to respiratory motion. In this embodiment, the virtual data can be displayed by an AR or VR OHMD whenever a certain period or moment in the respiratory cycle is reached. For example, upon complete expiration or inspiration, can OHMD can display virtual data of a patient, e.g. a virtual axis for a puncture, onto the physical organ of the patient, e.g. deep inside the patient, e.g. below the abdominal wall, inside the peritoneum or inside the pleura or epicardium.

Respiratory gating can be performed using any system or method known in the art. In any of the embodiments, see through augmented reality optical head mounted displays can be used.

In any of the embodiments, non-see through virtual reality optical head mounted displays can be used; the use of VR optical head mounted displays can be accompanied by video capture of the physical data of the patient, e.g. a surgical site, onto which virtual data, e.g. virtual surgical guides or pre-operative imaging data, can optionally be superimposed.

In some embodiments, mechanical ventilation of the patient can be used. When mechanical ventilation is used, one or more of the frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target can be determined or influenced by the ventilator settings. The ventilator settings can then be used to move the display of virtual data by one or more OHMDs consistent with, matching and/or synchronized with at least portions of the respiratory cycle and the associated respiratory movement of the one or more physical organs, physical structures, physical tissues, physical surfaces thereby maintaining superimposition and/or alignment of a display of virtual data with the one or more physical organs, physical structures, physical tissues, physical surfaces during at least portions of or the entire respiratory cycle. The ventilator settings and related one or more of the frequency of the respiratory cycle, the phase of the respiratory cycle, e.g. full inspiration, partial inspiration, full expiration, partial expiration, the direction of respiratory movement or excursion of the diaphragm or the direction of respiratory movement or excursion of the physical organ or physical tissue or target, the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target can be transferred from the computer system of the ventilator, e.g. from one or more processors, to the computer systems including one or more processors of the one or more OHMDs, for example using direct cable, WiFi, LiFi or Bluetooth transfer protocols.

In some embodiments, supplemental respiratory gating using any of the techniques described in the specification can be performed while the patient is undergoing mechanical ventilation. The supplemental respiratory gating can be helpful to improve the accuracy of the determination of one or more of the speed of respiratory movement or excursion of the diaphragm or the speed of respiratory movement or excursion of the physical organ or physical tissue or target, or the amount of movement or excursion of the diaphragm or the amount of respiratory movement or excursion of the physical organ or physical tissue or target, which in turn can be used to optimize the movement of the display of the virtual data by the OHMD during the respiratory cycle for maintaining superimposition and alignment of the virtual data of the patient with the physical data of the patient, e.g. the physical organ or physical tissue or physical structures or target, during portions of or the entire respiratory cycle.

The shape of the chest and the shape of the organs and blood vessels inside the chest changes depending on the phase of the cardiac cycle and/or the respiratory cycle.

Pre-operative 3D imaging data used to generate a 3D model of the vasculature and/or the heart and/or the lungs can be acquired using respiratory and/or cardiac gating, which can synchronize the acquisition of the image data with the respiratory and/or cardiac cycle. Respiratory gating can, for example, be performed prospectively by tracking a patient's respiratory cycle, for example with an infrared camera and one or more reflective markers attached to the patient's body, e.g. the chest. Respiratory gating can measure the patient's respiratory pattern and motion, e.g. one or more of chest excursion over time as measured by movement of a reflective marker, the frequency of the respiratory cycle, and/or the phase of the respiratory cycle, e.g. full inspiration, partial inspiration, full expiration, partial expiration, and/or the direction of respiratory movement or excursion, and/or the speed of respiratory movement or excursion, and/or the amount of excursion during the respiratory cycle, and can display them, for example, as one or more cyclic waveforms. The cyclic waveforms can consist of repetitive periods that are usually identical or similar to each other. Any respiratory gating technique described in the specification or known in the art can be used. Image acquisition and/or image display, e.g. the display of one or more virtual images by an OHMD, can then, for example, be triggered at a specific phase during that waveform, for example during expiration or inspiration.

Image data can be acquired at the same phase, e.g. expiration, in different periods of the cyclic waveform. Image data can also be acquired at the same phase in the same period of the cyclic waveform, e.g. with multi-detector CT scanners or MRI scanners.

Image data acquired at the same phase in different locations can be combined. For example, CT or MRI data can be acquired in different locations at the same phase of the respiratory cycle. CT or MRI data can cover a spiral or volume of tissue, e.g. an upper third of the lung, a middle third of a lung, a lower third of a lung, a first portion of the heart, a second portion of the heart, a third portion of the heart, a fourth portion of the heart, etc., portions of an ascending aorta, portions of an aortic arch, portions of a descending aorta; different locations or volume data sets or spirals of the heart, lungs, vasculature, chest and/or abdomen can be acquired at the same phase of the respiratory cycle. Different locations or volume data sets or spirals of the heart, lungs, vasculature, chest and/or abdomen can be acquired at different phases of the respiratory cycle until ultimately the entire target anatomy, e.g. the heart, lung, vasculature, abdominal tissue or organs are covered or included in image data sets, volume data sets or spirals that include all phases of the respiratory cycle. The amount of tissue volume included in one image acquisition at the same phase of the respiratory cycle can depend on the speed of the image acquisition. The speed of the image acquisition can depend on multiple factors, e.g. spatial resolution, radiation dose (CT), number of detectors and detector rings used (CT), reconstruction algorithm, processor speed, gradient strength (MRI), field strength (MRI). If an image data set, volume data set or spiral cannot cover the entire anatomic structure of interest during one respiratory cycle, multiple image data sets, volume data sets or spirals from the same phase of the respiratory cycle can be acquired in different locations, sections or portions of the anatomic structure of interest, for example over multiple different respiratory cycles. Image data set, volume data sets or spirals acquired from the same phase of the respiratory cycle over multiple different respiratory cycles can then be combined, e.g. can be "stitched" together. For example, in CT imaging, various non-linear iterative reconstruction (IR) algorithms and/or linear filtered back projection (FBP) reconstruction algorithms can be used (see, for example, Haliburton S., et al., The role of advanced reconstruction algorithms in cardiac CT; Cardiovasc Diagn Ther, 2017, 7, 5, 527-538, which is hereby incorporated by reference in its entirety). Real-time or off console, off-line image reconstruction, e.g. after the image acquisition, can be used.

All image data, volume data and/or spirals from the same phase of the respiratory cycle, whether acquired during the same period or different period of the cyclic waveform of the respiratory cycle or any combination thereof, can be combined into one or more 3D imaging data sets that can be used to generate a 3D model of the vasculature and/or the heart and/or the lungs and/or abdominal structures, tissues or organs for that phase of the respiratory cycle and, for example, all phases of the respiratory cycle.

This process can be repeated for a different phase of the respiratory cycle, e.g. inspiration, e.g. early, mid, late inspiration, or expiration, e.g. early, mid late expiration. This allows for creation of different 3D models of the vasculature and/or the heart and/or the lungs and/or abdominal structures, tissues or organs for different phases of the respiratory cycle.

Cardiac Gating

In some embodiments, cardiac gating can be used. Cardiac gating can be performed using, for example, one or more computer system with one or more computer processors configured to obtain and/or to detect and/or to analyze ECG data and/or peripheral pulse data/measurements and/or vascular flow data/measurements, e.g. using ultrasound. Cardiac gating can be prospective and/or retrospective.

In some embodiments, cardiac gating can be used to maintain the display of virtual data, e.g. a display of data from a pre-operative imaging study, e.g. an ultrasound, a pre-operative CT angiography or MR angiography, a SPECT scan, a PET scan, or any other imaging modality, for example in 2D or 3D or 4D or more dimensions if a vascular flow study or functional study has been performed, or a virtual surgical plan or a virtual target or a virtual surgical guide, or a virtual device or instrument, e.g. a virtual catheter, a virtual guidewire, a virtual stent etc., in relationship to physical data or physical structures of the patient, e.g. a beating heart, a lung, a vessel, an artery, a vein, an aorta, an inferior vena cava, a coronary artery or vein etc., through at least portions of the cardiac cycle despite cardiac and/or associated vascular motion or vascular pulsation. Thus, the movement of the physical data or physical structures of the patient with cardiac motion or vascular motion or pulsation can be accompanied by a corresponding movement of virtual data of the patient in one, two or three dimensions, optionally with the same or, in some embodiments, different frequency, direction of movement, speed of movement and magnitude or amount of movement in one or more directions, including in three dimensions, e.g. using one or more computer system with one or more computer processors to generate the display of the virtual data by one or more OHMDs and/or to move the virtual data by one or more OHMDs, e.g. using the cardiac gating information.

Cardiac gating can be used to optimize the superimposition and/or alignment of virtual data onto physical data or physical structures of the patient, e.g. a beating heart, a lung, a vessel, an artery, a vein, an aorta, an inferior vena cava, a coronary artery or vein etc., through the cardiac cycle despite cardiac and/or associated vascular motion or pulsation. Cardiac gating can be used to maintain the superimposition and/or alignment of virtual data onto physical data or physical structures of the patient, e.g. a beating heart, a lung, a vessel, an artery, a vein, an aorta, an inferior vena cava, a coronary artery or vein etc., through the cardiac cycle despite cardiac and/or associated vascular motion or pulsation.

Different approaches can be used for cardiac gating. These include, for example, prospective ECG triggering and retrospective ECG gating of one or more OHMD displays. In some embodiments, cardiac gating can be performed for maintaining alignment and/or superimposition of virtual data onto physical data of the patient for portions of the cardiac cycle, e.g. diastole, including portions of diastole or all of diastole, and/or systole, e.g. portions of systole or all of systole. Prospective cardiac gating or triggering can, for example, use forward looking prediction of R-wave timing using ECG; any other wave can be used. In some embodiments, less cardiac motion or pulsation can occur during diastole; prospective ECG triggering can use the ECG signal to trigger the display by one or more OHMDs of the virtual data superimposed onto and/or aligned with the beating heart and/or a vessel, e.g. the aorta or IVC, moving secondary to cardiac motion and/or vascular flow or pulsation, during diastole, with optionally the display of the virtual data fading or disappearing or frozen during systole. Prospective ECG triggering can use the ECG signal to trigger the display by one or more OHMDs of the virtual data superimposed onto and/or aligned with the beating heart and/or a vessel, e.g. the aorta or IVC, moving secondary to cardiac motion and/or vascular flow or pulsation, during systole, with optionally the display of the virtual data fading or disappearing or frozen during diastole or any combination thereof, e.g. with the display of the virtual data maintained by one or more OHMDs over the physical structures of the heart and/or vessel(s) for portions of diastole and portions of systole. Prospective ECG triggering can use the ECG signal to trigger the display by one or more OHMDs of the virtual data superimposed onto and/or aligned with the beating heart and/or a vessel, e.g. the aorta or IVC, moving secondary to cardiac motion and/or vascular flow or pulsation, during systole, wherein the display of the virtual data moves with the beating heart and/or vessel, e.g. moves with any cardiac motion and/or vascular flow or pulsation, to maintain the virtual display superimposed with and/or aligned with the corresponding moving or beating physical structures of the patient, e.g. the beating heart and/or a vessel, e.g. the aorta or IVC. Prospective triggering techniques can be sensitive to heart rate changes and arrhythmias. In some embodiments, prospective triggering techniques can be effective only for certain heart rates, e.g. of less than 100 beats per minute, less than 90 beats per minute, less than 80 beats per minute and can perform poorly with arrhythmias, such as in atrial fibrillation.

Retrospective ECG gating techniques can be used in some embodiments. Retrospective gating techniques can allow faster coverage of the beating heart with the display of the virtual data by one or more OHMDs with superimposition and alignment of the virtual data onto the physical data or structures of the heart or one or more vessels for portions of or the entire cardiac cycle. Retrospective ECG gating or triggering techniques can use the ECG signal to trigger the display by one or more OHMDs of the virtual data superimposed onto and/or aligned with the beating heart and/or a vessel, e.g. the aorta or IVC, moving secondary to cardiac motion and/or vascular flow or pulsation, during systole, wherein the display of the virtual data moves with the beating heart and/or vessel, e.g. moves with any cardiac motion and/or vascular flow or pulsation, to maintain the virtual display superimposed with and/or aligned with the corresponding moving or beating physical structures of the patient, e.g. the beating heart and/or a vessel, e.g. the aorta or IVC.

In any of the embodiments throughout the specification, pre- or intra-operative imaging techniques for imaging the heart, lung, vessels and/or any organs can include axial CT scan, fast axial CT scan, electron beam CT scan, single helical CT scan, fan beam multi-detector CT scan, cone beam multi-detector CT scan, volume CT scan, flat panel CT scan, ultrafast spiral CT, any of the foregoing using injection of iodinated or other contrast media, ultrasound, e.g. 2D or 3D, ultrasound with Doppler flow studies, echocardiography including transesophageal echocardiography, MR imaging, e.g. with 2D or 3D Fourier transformation, MR angiography, angiography, e.g. single or bi-planar, or 3D angiography, SPECT scanning, PET scanning, nuclear heart imaging, myocardial perfusion scans, e.g. using rubidium-82, technetium-99m and thallium-201 or using any other radionuclide known in the art.

Use of Markers for Cardiac Gating

In some embodiments, techniques for monitoring the movement of one or more markers applied, for example, to the surface of the heart or a vessel, can also be utilized, e.g. using one or more computer system with one or more computer processors for analyzing a video stream and/or for detecting marker movement and/or for measuring marker movement. For example, the one or more markers can be retroreflective, similar to the markers used for surgical navigation systems. An infrared light source can be utilized to illuminate the area where the markers are applied or attached to the heart or the vessel or, for example, an organ surface, e.g. using fibrin glue, and the infrared light reflected by the markers can be utilized to measure or monitor cardiac and/or vascular motion or pulsation, including heart rate, direction of cardiac or vascular movement and/or pulsation, e.g. in x-, y- and/or z-direction, speed of cardiac or vascular movement and/or pulsation, amount of cardiac or vascular movement and/or pulsation, e.g. in x-, y- and/or z-direction, etc. using one or more infrared receivers or cameras, such as the ones provided by Atracsys, Inc. (Atracsys, Inc. Le Mont-sur-Lausanne, Switzerland).

Any marker described in the specification or known in the art can be used. For example, an optical marker can be used. The optical marker can include a geometric pattern, a bar code, or a QR code. The bar code or QR code can encode the area or organ to which the marker has been applied or attached to, e.g. a left ventricle, a right ventricle, a left atrium, and/or a right atrium, or an aorta or an IVC or one or more pulmonary arteries or veins. An image capture system, camera system, or video system integrated into, attached to or separate from one or more OHMDs can be used to monitor the movement of the marker caused by cardiac and/or vascular motion or pulsation. The marker(s) and the one or more OHMDs can be registered in a common coordinate system. In this manner, movement of the OHMD in the coordinate system, e.g. through head movement of the surgeon or operator, can be differentiated from movement of the marker caused by cardiac and/or vascular motion or pulsation, e.g. using one or more computer system with one or more computer processors configured to detect the movement of the different markers.

The captured images or video images can be used to determine cardiac and/or vascular motion or pulsation, including heart rate, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, etc., in real time or retrospectively. The image capture system, camera system, or video system can be attached to the OR table or can be attached to a stand separate from the OR table. The image capture system, camera system, or video system can be attached to an OR light.

If an organ, e.g. the heart or a vessel such as the IVC or aorta, is partially exposed or visible during the surgery, one or more markers can be attached to the visible portions of the organ, e.g. the heart, for example portions of pericardium, myocardium, a valve, a ventricle or an atrium, or an ischemic or infarcted area, and an image capture system, camera system, or video system integrated into, attached to or separate from one or more OHMDs can be used to monitor the movement of the marker caused by cardiac and/or vascular motion or pulsation. The movement of the marker and of the visible portions of the organ can be used to simulate the movement of the non-visible portions of the organ, e.g. the heart, for example portions of pericardium, myocardium, a valve, a ventricle or an atrium, or an ischemic or infarcted area, and/or any lesions, e.g. an ischemic area or an infarct, inside the organ, hidden underneath the organ surface, e.g. using one or more computer system with one or more computer processors configured to simulate the movement.

Superimposition and/or Alignment of Virtual Data by One or More OHMDs with Physical Data or Structures of the Patient Using Cardiac Gating In some embodiments, a 3D scanner or an imaging device, for example as described in the specification or as known in the art, can be used during the procedure to image the heart and/or vessels and to track any cardiac and/or vascular motion or pulsation.

In some embodiments, cardiac gating can be used to display and/or move virtual data displayed by one or more OHMDs synchronized with the patient's cardiac cycle and, optionally, following the full or a partial amount of cardiac and/or vascular movement and/or pulsation, e.g. in mm or cm, e.g. by 5, 10, 15, 20, 25, 30, 35, 40, 45, 50, 55, 50 mm or any other amount of movement in one or more directions, e.g. superior, inferior, anterior, posterior, medial or lateral or any oblique direction during at least portions or all of systole and/or diastole in order to maintain superimposition and/or alignment of virtual data with the corresponding physical data or structures of the patient. One or more computer system with one or more computer processors can move the virtual data in one or more directions by an amount and with a speed to maintain superimposition and/or alignment with the physical data of the patient, using one or more computer system with one or more computer processors configured, for example, to display and/or move virtual data.

The movement of the display of the virtual data by the one or more OHMDs can be performed to follow or mirror or to be synchronized with cardiac and/or vascular movement and/or pulsation and, for example, the associated movement of a physical organ or physical tissue, e.g. a lung, a vessel, an artery, a vein, an aorta, an inferior vena cava, a pulmonary artery or vein, a liver, a spleen, or a lesion including a focus of abnormal electric activity, e.g. in myocardium, or a target for surgical or other intervention associated with the patient's body, e.g. as it pertains to heart rate, phase of the cardiac cycle, e.g. on an ECG, phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, etc.

In some embodiments, the speed of movement, direction of movement, and/or amount of movement/excursion of a physical organ or physical tissue, e.g. a heart, a lung, a vessel, an artery, a vein, an aorta, an inferior vena cava, a pulmonary artery or vein, a liver, a spleen, a pancreas, a gallbladder, or a kidney, or a tumor or lesion, or a target for surgical or other intervention associated with the patient's body can be the same as that of the heart, it can be less or it can be more.

By synchronizing the display of the virtual data by the one or more OHMDs with the heart rate, phase of the cardiac cycle, e.g. on an ECG, phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target, the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a coronary artery or vein, a liver, a spleen, or a tumor or lesion including, for example, a focus of abnormal electric activity, e.g. in myocardium, a device, an instrument, a catheter, a stent, or a target for surgical or other intervention associated with the patient's body, during cardiac and/or vascular movement and/or pulsation or excursion during a portion of or during the entire cardiac cycle.

By moving the display of the virtual data by the one or more OHMDs, using one or more computer system with one or more computer processors configured for the display and/or the moving of the virtual data, with one or more of the heart rate, phase of the cardiac cycle, e.g. on an ECG, phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, and/or the amount of movement or excursion of the heart and/or vessels or the amount of cardiac and/or vascular movement and/or pulsation or excursion of a physical organ or physical tissue or a target, the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a liver, a spleen, a device, an instrument, a catheter, a stent, or a tumor or lesion, or a target for surgical or other intervention associated with the patient's body, during cardiac and/or vascular movement and/or pulsation or excursion or pulsation.

Physical Data or Physical Structures in Exposed Areas or in Hidden Areas, e.g. Inside an Organ The physical data or physical structures of the patient, e.g. an organ or tissue or tissue surface, can be on a body surface or on an exposed surface, e.g. exposed through an incision or surgical alteration, e.g. a tissue removal, directly visible through a see through, e.g. augmented reality, optical head mounted display or visible directly by an image capture system, camera system or video system integrated into, attached to or separate from the one or more OHMDs. For example, the physical data or physical structures of the patient can be a pericardium exposed after a sternotomy or thoracotomy. The physical data or structures of the patient can be one or more of a myocardium, an atrium, a ventricle, an aorta, an IVC, a pulmonary artery or vein, a coronary artery or vein, an endocardium, a heart valve, an infarct, an area of ischemia, e.g. myocardial ischemia, an area of abnormal mobility or contractility, e.g. in an ischemic or infarcted zone, an area of normal electrophysiologic activity, an area of abnormal electrophysiologic activity. The physical data of the patient can include one or more of a device, a cardiac valve replacement or repair, an instrument, a catheter, a guidewire, an electrode or electric or electrophysiologic probe or an ablation device or a stent, e.g. drug eluting or non-drug eluting.

The physical data or physical structures of the patient, e.g. an organ or tissue or tissue surface, can be inside the body, e.g. in a subsurface location, e.g. below a skin or inside a pericardium or a pleura or a peritoneum or inside an organ or underneath an organ surface, or underneath a tissue surface, and cannot be directly visible through a see through, e.g. augmented reality, optical head mounted display or not directly visible directly by an image capture system, camera system or video system integrated into, attached to or separate from the one or more OHMDs.

If the physical data or physical structures of the patient are located inside the body, e.g. in a subsurface location, e.g. below a skin or inside a pericardium or a pleura or a peritoneum or inside an organ or underneath an organ surface, or underneath a tissue surface, e.g. inside a myocardium, for example, a focus of abnormal electrophysiologic activity, a focus of abnormal mobility or contractility, an area of ischemia, an area of infarction, imaging can be performed to visualize the physical data or physical structures of the patient, e.g. pre-operatively or intra-operatively. The imaging can, for example, be performed using x-ray imaging, ultrasound, CT scan, SPECT scan, PET scan, or MRI scan or any other imaging modality known in the art. The image acquisition can be performed in select phases of the cardiac cycle. The image acquisition can also be performed throughout the cardiac cycle.

The imaging, for example using axial CT scan, fast axial CT scan, electron beam CT scan, single helical CT scan, fan beam multi-detector CT scan, cone beam multi-detector CT scan, volume CT scan, flat panel CT scan, ultrafast spiral CT, any of the foregoing using injection of iodinated or other contrast media, ultrasound, e.g. 2D or 3D, ultrasound with Doppler flow studies, echocardiography including transesophageal echocardiography, MR imaging, e.g. with 2D or 3D Fourier transformation, MR angiography, angiography, e.g. single or bi-planar, or 3D angiography, SPECT scanning, PET scanning, nuclear heart imaging, myocardial perfusion scans, e.g. using rubidium-82, technetium-99m and thallium-201 or using any other radionuclide known in the art, can be performed to assess one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or a portion of the heart; the imaging can be performed to identify global, e.g. through the entire heart, or regional, e.g. through a portion or anatomic area of the heart, abnormalities in one or more of the direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or a portion of the heart, using, for example, one or more computer system with one or more computer processors configured to analyze the images and to configured measure one or more of the foregoing parameters. One or more computer systems can utilize the measured heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or a portion of the heart and/or the measured global, e.g. through the entire heart, or regional, e.g. through a portion or anatomic area of the heart, abnormalities in one or more of the direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or a portion of the heart to adjust the movement of the virtual data by one or more OHMDs to match and/or to synchronize the movement of the virtual data with the movement of the physical data or physical structures of the patient including any motion or pulsation or contractility abnormalities of the physical data of the patient. By matching and/or synchronizing the movement of the virtual data with the movement of the physical data of the patient including any motion or pulsation or contractility abnormalities of the physical data, e.g. as detected on an imaging study, one or more OHMDs can superimpose and/or align the virtual data with the corresponding physical data and can maintain the superimposing and/or aligning of the virtual data with the corresponding physical data through a portion of or the entire cardiac cycle. Virtual data can include one or more of a virtual left atrium, a virtual right atrium, a virtual left ventricle, a virtual right ventricle, a virtual mitral valve, a virtual tricuspid valve, a virtual pulmonary valve, a virtual aortic valve, a virtual pericardium, a virtual myocardium, a virtual endocardium, a virtual coronary artery or vein, a virtual open or patent portion of a coronary artery or vein (e.g. projected by one or more OHMDs inside the physical coronary artery or vein), a virtual stenotic portion of a coronary artery or vein (e.g. projected by one or more OHMDs inside the physical coronary artery or vein), a virtual occluded portion of a coronary artery or vein (e.g. projected by one or more OHMDs inside the physical coronary artery or vein), a virtual aorta, a virtual IVC, a virtual pulmonary artery or vein, a virtual area of abnormal electrophysiologic activity (e.g. projected by one or more OHMDs inside physical myocardium), a virtual area of abnormal mobility or contractility (e.g. projected by one or more OHMDs inside physical myocardium), a virtual area of ischemia (e.g. projected by one or more OHMDs inside physical myocardium), a virtual area of infarction (e.g. projected by one or more OHMDs inside physical myocardium), a virtual area of healthy cardiac tissue, e.g. myocardium, a virtual area of normal electrophysiologic activity (e.g. projected by one or more OHMDs inside physical myocardium), and/or a virtual area of normal mobility or contractility, and/or a virtual device (e.g. projected by one or more OHMDs in its intended placement position or in the current position of the tracked physical device hidden inside the tissue or vessel), a virtual instrument (e.g. projected by one or more OHMDs in its intended placement position or in the current position of the tracked physical instrument hidden inside the tissue or vessel), a virtual catheter (e.g. projected by one or more OHMDs in its intended placement position or in the current position of the tracked physical catheter hidden inside the tissue or vessel), a virtual guidewire (e.g. projected by one or more OHMDs in its intended placement position or in the current position of the tracked physical guidewire hidden inside the tissue or vessel), a virtual stent (e.g. projected by one or more OHMDs in its intended placement position or in the current position of the tracked physical stent hidden inside the tissue or vessel), a virtual cardiac valve replacement or repair (e.g. projected by one or more OHMDs in its intended placement position or in the current position of the tracked physical cardiac valve replacement or repair hidden inside the tissue or vessel), or a virtual electrode or electric or electrophysiologic probe or an ablation device (e.g. projected by one or more OHMDs in its intended placement position or in the current position of the tracked physical electrode or electric or electrophysiologic probe or an ablation device hidden inside the tissue or vessel or atrium or ventricle). Corresponding physical data can include one or more of physical data or physical structures of the patient, e.g. a physical left atrium, a physical right atrium, a physical left ventricle, a physical right ventricle, a physical mitral valve, a physical tricuspid valve, a physical pulmonary valve, a physical aortic valve, a physical pericardium, a physical myocardium, a physical endocardium, a physical coronary artery or vein, a physical open or patent portion of a coronary artery or vein, a physical stenotic portion of a coronary artery or vein, a physical occluded portion of a coronary artery or vein an aorta, a physical IVC, a physical pulmonary artery or vein, a physical area of abnormal electrophysiologic activity, a physical area of abnormal mobility or contractility, a physical area of ischemia, a physical area of infarction, a physical area of healthy cardiac tissue, e.g. myocardium, a physical area of normal electrophysiologic activity, and/or a physical area of normal mobility or contractility, and/or a physical device, a physical instrument, a physical catheter, a physical guidewire, a physical stent, a physical cardiac valve replacement or repair, or a physical electrode or electric or electrophysiologic probe or an ablation device.

Combination, Fusion or Merging of Images for Display by an OHMD

In some embodiments, images of one or more different sections or portions of the heart or vessels obtained during the same phase of the same cardiac cycle can be combined or fused or merged, e.g. using one or more computer system with one or more computer processors configured for image fusion, and can subsequently be displayed by one or more OHMDs as one combined or fused or merged virtual data set including, for example, data derived from the images or displayed into the images by the one or more OHMDs, wherein the one or more OHMDs can maintain the display of the virtual data set(s) superimposed onto and/or aligned with the physical data or physical structures of the patient, e.g. the beating heart or select cardiac structures or vessels moving during the cardiac cycle or portions thereof.

In some embodiments, images of one or more different sections or portions of the heart or vessels obtained during the same phase of a different cardiac cycle can be combined or fused or merged and can subsequently be displayed by one or more OHMDs as one combined or fused or merged virtual data set including, for example, data derived from the images or displayed into the images by the one or more OHMDs, wherein the one or more OHMDs can maintain the display of the virtual data set(s) superimposed onto and/or aligned with the physical data or physical structures of the patient, e.g. the beating heart or select cardiac structures or vessels moving during the cardiac cycle or portions thereof.

In some embodiments, images of one or more different sections or portions of the heart or vessels obtained during a different phase of the same cardiac cycle can be combined or fused or merged and can subsequently be displayed by one or more OHMDs as one combined or fused or merged virtual data set including, for example, data derived from the images or displayed into the images by the one or more OHMDs, wherein the one or more OHMDs can maintain the display of the virtual data set(s) superimposed onto and/or aligned with the physical data or physical structures of the patient, e.g. the beating heart or select cardiac structures or vessels moving during the cardiac cycle or portions thereof.

In some embodiments, images of one or more different sections or portions of the heart or vessels obtained during a different phase of a different cardiac cycle can be combined or fused or merged and can subsequently be displayed by one or more OHMDs as one combined or fused or merged virtual data set including, for example, data derived from the images or displayed into the images by the one or more OHMDs, wherein the one or more OHMDs can maintain the display of the virtual data set(s) superimposed onto and/or aligned with the physical data or physical structures of the patient, e.g. the beating heart or select cardiac structures or vessels moving during the cardiac cycle or portions thereof.

In any of the embodiments throughout the specification, the one or more different sections or portions of the heart or vessels included in the virtual data or virtual data set(s) can include a left atrium, a right atrium, a left ventricle, a right ventricle, a mitral valve, a tricuspid valve, a pulmonary valve, an aortic valve, a pericardium, a myocardium, an endocardium, a coronary artery or vein, an open or patent portion of a coronary artery or vein, a stenotic portion of a coronary artery or vein, an occluded portion of a coronary artery or vein an aorta, an IVC, a pulmonary artery or vein, an area of abnormal electrophysiologic activity, an area of abnormal mobility or contractility, an area of ischemia, an area of infarction, an area of healthy cardiac tissue, e.g. myocardium, an area of normal electrophysiologic activity, or an area of normal mobility or contractility.

In any of the embodiments throughout the specification, the virtual data or virtual data set(s) of the patient can include a virtual device, a virtual instrument, a virtual catheter, a virtual guidewire, a virtual stent, a virtual cardiac valve replacement or repair, or a virtual electrode or electric or electrophysiologic probe or an ablation device. In any of the embodiments throughout the specification, the one or more virtual device, virtual instrument, virtual catheter, virtual guidewire, virtual stent, virtual cardiac valve replacement or repair, or virtual electrode or electric or electrophysiologic probe or an ablation device can be a 3D CAD file or a 3D surface reconstruction or a 3D volume file of the physical device, physical instrument, physical catheter, physical guidewire, physical stent, physical cardiac valve replacement or repair, or physical electrode or electric or electrophysiologic probe or an ablation device. In any of the embodiments throughout the specification, the one or more virtual device, virtual instrument, virtual catheter, virtual guidewire, virtual stent, virtual cardiac valve replacement or repair, or virtual electrode or electric or electrophysiologic probe or an ablation device can be a 2D or 3D outline or placement indicator of the physical device, physical instrument, physical catheter, physical guidewire, physical stent, or physical electrode or electric or electrophysiologic probe or an ablation device.

Techniques for fusing, merging, combining different imaging data and/or acquisitions are, for example, described in Desjardins B. and Kazerooni E. A., ECG Gated Cardiac CT, Am J. Roentgenology, vol. 182, issue 4, pp. 993-1010, which is hereby incorporated in its entirety. Techniques for fusing, merging, combining different imaging data and acquisitions are, for example, described in Bushberg et al. The Essential Physics of Medical Imaging, $3^{rd}$ edition, Wolters, Kluwer, Lippincott, 2012, which is hereby also incorporated in its entirety.

Imaging Including 3D Scanning

In some embodiments, an image acquisition can be performed through the cardiac cycle to measure (e.g. in addition to or instead of an ECG) one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion.

In some of the embodiments, image acquisition can be performed through multiple cardiac cycles and the measured data can be averaged; optionally, other statistical models can be applied to the measured data. Images can be processed by one or more computer system with one or more computer processors configured to analyze the images and/or configured to determine and/or configured to estimate any of the foregoing parameters.

For example, an ultrasound transducer can be applied in a fixed or static position to a body surface, a tissue surface, or an organ surface, e.g. a pericardium or a myocardium or an aortic surface, and ultrasound image acquisition can be performed to measure one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion. The position and/or orientation of the ultrasound transducer can, for example be maintained with use of a stand and/or a holding arm. The ultrasound transducer can, for example, also be used to identify a target, e.g. a tumor or a lesion inside an organ, e.g. an area of abnormal motion or pulsation, mobility or contractility inside a myocardium or on the surface of a myocardium. One or more markers applied to the chest wall, organ, tissue, or tissue surface, e.g. a pericardium or myocardium, can be used to measure cardiac or vascular movement and/or pulsation including, for example, one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion using, for example, an image capture, camera or video system. The data obtained with use of the one or more markers and the data obtained with the imaging system, e.g. an ultrasound system, can optionally be compared, e.g. to identify any differences in marker measurements and imaging system measurements, with optional correction of such differences in the marker or imaging measurements.

In any of the embodiments throughout the specification, markers can include radiopaque portions or radiopaque elements or portions doped with one or more contrast media, e.g. CT or MRI contrast media, or doped with one or more radioactive tracers, so that the markers can be readily identified, e.g. segmented, on any imaging studies.

Assessment of Motion or Pulsation Differences for Superimposition and/or Alignment of Virtual Data Projected by an OHMD with Physical Data or Structures Optionally, two or more markers can be applied to different portions of the same organ, e.g. a left atrium, a right atrium, a left ventricle, a right ventricle, a mitral valve, a tricuspid valve, a pulmonary valve, an aortic valve, a pericardium, a myocardium, an endocardium, a coronary artery or vein, an open or patent portion of a coronary artery or vein, a stenotic portion of a coronary artery or vein, an occluded portion of a coronary artery or vein an aorta, an IVC, a pulmonary artery or vein, an area of abnormal electrophysiologic activity, an area of abnormal mobility or contractility, an area of ischemia, an area of infarction, an area of healthy cardiac tissue, e.g. myocardium, an area of normal electrophysiologic activity, or an area of normal mobility or contractility. In this manner, differences in direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion or a portion of any of the foregoing can be detected, e.g. using one or more computer system with one or more computer processors configured to detect marker motion and/or to measure marker motion, and these differences can be used to synchronize corresponding portions of in the virtual data displayed by the one or more OHMDs with the physical organ or physical tissue or physical target or physical lesion or portion thereof.

For example, differences in direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, or the amount of cardiac and/or vascular related movement or excursion, e.g. in x-, y- and/or z- and/or any other direction, between a left atrium, a right atrium, a left ventricle, a right ventricle, a mitral valve, a tricuspid valve, a pulmonary valve, an aortic valve, a pericardium, a myocardium, an endocardium, a coronary artery or vein, an open or patent portion of a coronary artery or vein, a stenotic portion of a coronary artery or vein, an occluded portion of a coronary artery or vein an aorta, an IVC, a pulmonary artery or vein, an area of abnormal electrophysiologic activity, an area of abnormal mobility or contractility, an area of ischemia, an area of infarction, an area of healthy cardiac tissue, e.g. myocardium, an area of normal electrophysiologic activity, and/or an area of normal mobility or contractility can be detected and these differences can be used to synchronize, to align and/or to superimpose corresponding portions or structures in the virtual data displayed by the one or more OHMDs, e.g. a virtual left atrium, a virtual right atrium, a virtual left ventricle, a virtual right ventricle, a virtual mitral valve, a virtual tricuspid valve, a virtual pulmonary valve, a virtual aortic valve, a virtual pericardium, a virtual myocardium, a virtual endocardium, a virtual coronary artery or vein, a virtual open or patent portion of a coronary artery or vein (e.g. projected by one or more OHMDs inside the physical coronary artery or vein), a virtual stenotic portion of a coronary artery or vein (e.g. projected by one or more OHMDs inside the physical coronary artery or vein), a virtual occluded portion of a coronary artery or vein (e.g. projected by one or more OHMDs inside the physical coronary artery or vein), a virtual aorta, a virtual IVC, a virtual pulmonary artery or vein, a virtual area of abnormal electrophysiologic activity (e.g. projected by one or more OHMDs inside physical myocardium), a virtual area of abnormal mobility or contractility (e.g. projected by one or more OHMDs inside physical myocardium), a virtual area of ischemia (e.g. projected by one or more OHMDs inside physical myocardium), a virtual area of infarction (e.g. projected by one or more OHMDs inside physical myocardium), a virtual area of healthy cardiac tissue, e.g. myocardium, a virtual area of normal electrophysiologic activity (e.g. projected by one or more OHMDs inside physical myocardium), and/or a virtual area of normal mobility or contractility, and/or a virtual device (e.g. projected by one or more OHMDs in its intended placement position or in the current position of the tracked physical device hidden inside the tissue or vessel), a virtual instrument (e.g. projected by one or more OHMDs in its intended placement position or in the current position of the tracked physical instrument hidden inside the tissue or vessel), a virtual catheter (e.g. projected by one or more OHMDs in its intended placement position or in the current position of the tracked physical catheter hidden inside the tissue or vessel), a virtual guidewire (e.g. projected by one or more OHMDs in its intended placement position or in the current position of the tracked physical guidewire hidden inside the tissue or vessel), a virtual stent (e.g. projected by one or more OHMDs in its intended placement position or in the current position of the tracked physical stent hidden inside the tissue or vessel), a virtual cardiac valve replacement or repair (e.g. projected by one or more OHMDs in its intended placement position or in the current position of the tracked physical cardiac valve replacement or repair hidden inside the tissue or vessel), or a virtual electrode or electric or electrophysiologic probe or an ablation device (e.g. projected by one or more OHMDs in its intended placement position or in the current position of the tracked physical electrode or electric or electrophysiologic probe or an ablation device hidden inside the tissue or vessel or atrium or ventricle), and to maintain them in superimposition and/or alignment with the corresponding physical data or physical structures of the patient, e.g. a physical left atrium, a physical right atrium, a physical left ventricle, a physical right ventricle, a physical mitral valve, a physical tricuspid valve, a physical pulmonary valve, a physical aortic valve, a physical pericardium, a physical myocardium, a physical endocardium, a physical coronary artery or vein, a physical open or patent portion of a coronary artery or vein, a physical stenotic portion of a coronary artery or vein, a physical occluded portion of a coronary artery or vein an aorta, a physical IVC, a physical pulmonary artery or vein, a physical area of abnormal electrophysiologic activity, a physical area of abnormal mobility or contractility, a physical area of ischemia, a physical area of infarction, a physical area of healthy cardiac tissue, e.g. myocardium, a physical area of normal electrophysiologic activity, and/or a physical area of normal mobility or contractility, and/or a physical device, a physical instrument, a physical catheter, a physical guidewire, a physical stent, a physical cardiac valve replacement or repair, or a physical electrode or electric or electrophysiologic probe or an ablation device, during the entire or portions of the cardiac cycle.

Pre-operative and/or intra-operative imaging, e.g. prior to and/or during a procedure, including the use of 3D scanners and video imaging as described in the specification, can also be used to detect differences in direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, or the amount of cardiac and/or vascular related movement or excursion, e.g. in x-, y- and/or z- and/or any other direction, between a left atrium, a right atrium, a left ventricle, a right ventricle, a mitral valve, a tricuspid valve, a pulmonary valve, an aortic valve, a pericardium, a myocardium, an endocardium, a coronary artery or vein, an open or patent portion of a coronary artery or vein, a stenotic portion of a coronary artery or vein, an occluded portion of a coronary artery or vein an aorta, an IVC, a pulmonary artery or vein, an area of abnormal electrophysiologic activity, an area of abnormal mobility or contractility, an area of ischemia, an area of infarction, an area of healthy cardiac tissue, e.g. myocardium, an area of normal electrophysiologic activity, and/or an area of normal mobility or contractility, and these differences can be used to synchronize, to align and/or to superimpose corresponding portions or structures in the virtual data displayed by the one or more OHMDs, e.g. a virtual left atrium, a virtual right atrium, a virtual left ventricle, a virtual right ventricle, a virtual mitral valve, a virtual tricuspid valve, a virtual pulmonary valve, a virtual aortic valve, a virtual pericardium, a virtual myocardium, a virtual endocardium, a virtual coronary artery or vein, a virtual open or patent portion of a coronary artery or vein (e.g. projected by one or more OHMDs inside the physical coronary artery or vein), a virtual stenotic portion of a coronary artery or vein (e.g. projected by one or more OHMDs inside the physical coronary artery or vein), a virtual occluded portion of a coronary artery or vein (e.g. projected by one or more OHMDs inside the physical coronary artery or vein), a virtual aorta, a virtual IVC, a virtual pulmonary artery or vein, a virtual area of abnormal electrophysiologic activity (e.g. projected by one or more OHMDs inside physical myocardium), a virtual area of abnormal mobility or contractility (e.g. projected by one or more OHMDs inside physical myocardium), a virtual area of ischemia (e.g. projected by one or more OHMDs inside physical myocardium), a virtual area of infarction (e.g. projected by one or more OHMDs inside physical myocardium), a virtual area of healthy cardiac tissue, e.g. myocardium, a virtual area of normal electrophysiologic activity (e.g. projected by one or more OHMDs inside physical myocardium), and/or a virtual area of normal mobility or contractility, and/or a virtual device (e.g. projected by one or more OHMDs in its intended placement position or in the current position of the tracked physical device hidden inside the tissue or vessel), a virtual instrument (e.g. projected by one or more OHMDs in its intended placement position or in the current position of the tracked physical instrument hidden inside the tissue or vessel), a virtual catheter (e.g. projected by one or more OHMDs in its intended placement position or in the current position of the tracked physical catheter hidden inside the tissue or vessel), a virtual guidewire (e.g. projected by one or more OHMDs in its intended placement position or in the current position of the tracked physical guidewire hidden inside the tissue or vessel), a virtual stent (e.g. projected by one or more OHMDs in its intended placement position or in the current position of the tracked physical stent hidden inside the tissue or vessel), a virtual cardiac valve replacement or repair (e.g. projected by one or more OHMDs in its intended placement position or in the current position of the tracked physical cardiac valve replacement or repair hidden inside the tissue or vessel), or a virtual electrode or electric or electrophysiologic probe or an ablation device (e.g. projected by one or more OHMDs in its intended placement position or in the current position of the tracked physical electrode or electric or electrophysiologic probe or an ablation device hidden inside the tissue or vessel or atrium or ventricle), and to maintain them in superimposition and/or alignment with the corresponding physical data or physical structures of the patient, e.g. a physical left atrium, a physical right atrium, a physical left ventricle, a physical right ventricle, a physical mitral valve, a physical tricuspid valve, a physical pulmonary valve, a physical aortic valve, a physical pericardium, a physical myocardium, a physical endocardium, a physical coronary artery or vein, a physical open or patent portion of a coronary artery or vein, a physical stenotic portion of a coronary artery or vein, a physical occluded portion of a coronary artery or vein, a physical aorta, a physical IVC, a physical pulmonary artery or vein, a physical area of abnormal electrophysiologic activity, a physical area of abnormal mobility or contractility, a physical area of ischemia, a physical area of infarction, a physical area of healthy cardiac tissue, e.g. myocardium, a physical area of normal electrophysiologic activity, and/or a physical area of normal mobility or contractility, and/or a physical device, a physical instrument, a physical catheter, a physical guidewire, a physical stent, a physical cardiac valve replacement or repair, or a physical electrode or electric or electrophysiologic probe or an ablation device, during the entire or portions of the cardiac cycle. One or more computer system with one or more computer processors configured to display virtual data, and/or align, and/or superimpose virtual data onto corresponding virtual and/or physical data can be used for this purpose. Thus, by measuring one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart, cardiac tissues, or vessel(s) or blood flow or the amount of cardiac and/or vascular related movement or excursion of a physical organ or physical tissue or a target or a lesion and/or by detecting differences in phase of systole or diastole, e.g. atrial vs. ventricular, in direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, or the amount of cardiac and/or vascular related movement or excursion, e.g. in x-, y- and/or z- and/or any other direction, using, for example, one or more computer system with one or more computer processors configured for the measuring, one or more OHMDs can be synchronized using one or more of the foregoing data to maintain superimposition and/or alignment between virtual data and physical data or structures for one or more of the following virtual and corresponding physical data for portions of the cardiac cycle or the entire cardiac cycle (Table 16):

Table 16: Non-limiting examples of virtual data (left columns) that can be maintained in superimposition and/or alignment with corresponding physical data or structures (right columns)

TABLE 16

Non-limiting examples of virtual data (left columns) that can be maintained in superimposition and/or alignment with corresponding physical data or structures (right columns)

| | |
|---|---|
| virtual left atrium, | physical left atrium |
| virtual right atrium, | physical right atrium |
| virtual left ventricle, | physical left ventricle, |
| virtual right ventricle, | physical right ventricle, |
| virtual mitral valve, | physical mitral valve, |
| virtual tricuspid valve, | physical tricuspid valve, |
| virtual pulmonary valve, | physical pulmonary valve, |
| virtual aortic valve, | physical aortic valve, |
| virtual pericardium, | physical pericardium, |
| virtual myocardium, | physical myocardium, |
| virtual endocardium, | physical endocardium, |
| virtual coronary artery or vein, | physical coronary artery or vein, |
| virtual left coronary artery, | physical left coronary artery, |
| virtual right coronary artery, | physical right coronary artery, |
| virtual left marginal artery, | physical left marginal artery, |
| virtual left anterior descending artery, | physical left anterior descending artery, |
| virtual left interventricular artery, | physical left interventricular artery, |
| virtual diagonal branch, | physical diagonal branch, |
| virtual posterior descending artery, | physical posterior descending artery, |
| virtual right marginal artery, | physical right marginal artery, |
| virtual sinoatrial node artery, | physical sinoatrial node artery, |

TABLE 16-continued

Non-limiting examples of virtual data (left columns) that can be maintained in superimposition and/or alignment with corresponding physical data or structures (right columns)

| | |
|---|---|
| virtual endoluminal portion of a coronary artery or vein, | physical endoluminal portion of a coronary artery or vein, |
| virtual open or patent portion of a coronary virtual or vein, | physical open or patent portion of a coronary artery or vein, |
| virtual stenotic portion of a coronary artery or vein, | physical stenotic portion of a coronary artery or vein, |
| virtual occluded portion of a coronary artery or vein | physical occluded portion of a coronary artery or vein |
| virtual aorta, | physical aorta, |
| virtual IVC, | physical IVC, |
| virtual pulmonary artery | physical pulmonary artery |
| virtual pulmonary vein | physical pulmonary vein |
| virtual area of abnormal electrophysiologic activity, | physical area of abnormal electrophysiologic activity, |
| virtual area of abnormal mobility or contractility, | physical area of abnormal mobility or contractility, |
| virtual area of ischemia, | physical area of ischemia, |
| virtual area of infarction, | physical area of infarction, |
| virtual area of healthy cardiac tissue, e.g. myocardium, | physical area of healthy cardiac tissue, e.g. myocardium, |
| virtual area of epicardium, | physical area of epicardium, |
| virtual area of myocardium, | physical area of myocardium, |
| virtual area of endocardium, | physical area of endocardium, |
| virtual papillary muscle, | physical papillary muscle, |
| virtual area of normal electrophysiologic activity, | physical area of normal electrophysiologic activity, |
| virtual area of normal mobility or contractility, | physical area of normal mobility or contractility, |
| virtual device, | physical device, |
| virtual instrument, | physical instrument, |
| virtual catheter, | physical catheter, |
| virtual guidewire, | physical guidewire, |
| virtual stent, | physical stent, |
| virtual coil, | physical coil, |
| virtual extraction device, | physical extraction device, |
| virtual cardiac valve replacement, | physical cardiac valve replacement, |
| virtual cardiac valve repair, | physical cardiac valve repair, |
| virtual electrode or electric or electrophysiologic probe or an ablation device | physical electrode or electric or electrophysiologic probe or an ablation device |

Thus, a computer system including one or more computer processors, e.g. receiving input including data about heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of physical structures of the patient, and/or controlling the display of one or more OHMDs can match and/or synchronize the OHMD display(s) of one or more of a virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, virtual area of normal mobility or contractility, virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device with regard to one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of the displayed virtual data individually or in one or more groups, e.g. a left atrial group, a right atrial group, a left ventricular group, a right ventricular group, with a corresponding physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility, physical device, physical instrument, physical catheter, physical guidewire, physical stent, physical coil, physical extraction device, physical cardiac valve replacement, physical cardiac valve repair, or physical electrode or electric or electrophysiologic probe or an ablation device. By matching and/or synchronizing, using one or more computer system with one or more computer processors configured for such purpose, the one or more OHMD displays of one or more of a virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, virtual area of normal mobility or contractility, virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device with regard to one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of the displayed virtual data individually or in one or more groups, e.g. a left atrial group, a right atrial group, a left ventricular group, a right ventricular group, with a corresponding physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility, physical device, physical instrument, physical catheter, physical guidewire, physical stent, physical coil, physical extraction device, physical cardiac valve replacement, physical cardiac valve repair, or physical electrode or electric or electrophysiologic probe or an ablation device, the display of the one or more of a virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, virtual area of normal mobility or contractility, virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device can be maintained superimposed onto and/or aligned with the corresponding one or more of a physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility, physical device, physical instrument, physical catheter, physical guidewire, physical stent, physical coil, physical extraction device, physical cardiac valve replacement, physical cardiac valve repair, or physical electrode or electric or electrophysiologic probe or an ablation device during portions of or the entire cardiac cycle.

A pre-operative and/or intra-operative imaging test, e.g. x-ray imaging, cone beam CT, CT, MRI, CT angiography, e.g. in 2D and/or in 3D, CT cardiac motion studies, e.g. using ultrafast CT, MR angiography, MR cardiac motion studies, SPECT studies, PET studies, myocardial perfusion scans, e.g. using rubidium-82, technetium-99m and thallium-201, ultrasound and/or echocardiography including transesophageal echocardiography, as well as electrophysiological studies and/or mapping can be used, for example using one or more computer processors for analyzing images and/or for measuring movement of organs or tissues or tissues surfaces or anatomic landmarks, to measure and/or determine one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of one or more of a physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility, physical device, physical instrument, physical catheter, physical guidewire, physical stent, physical coil, physical extraction device, physical cardiac valve replacement, physical cardiac valve repair, or physical electrode or electric or electrophysiologic probe or an ablation device.

After measuring the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of the one or more of a physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility, physical device, physical instrument, physical catheter, physical guidewire, physical stent, physical coil, physical extraction device, physical cardiac valve replacement, physical cardiac valve repair, or physical electrode or electric or electrophysiologic probe or an ablation device, the data can optionally be grouped or aggregated in groups, for example using a computer processor configured to apply a classification or to utilize deep learning algorithms. The groups can be selected or classified to include physical data or structures with similar ranges of one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. The classification can be performed using artificial intelligence and/or deep learning. Thus, the grouping or selection to groups or classification to groups can be performed using individual tissue characteristics and similarities between different physical structures or tissues. For example, physical structures or tissues can be grouped into classes with similar one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. In any of the embodiments in the specification, groups can, for example, be a left atrial group, a right atrial group, an atrial group, a left ventricular group, a right ventricular group, a ventricular group, a valvular group, an arterial group, a venous group, a pulmonary arterial group, a pulmonary venous group, a vascular group. Any grouping is possible using, for example, anatomic, metabolic, physiologic, electrophysiologic and or functional criteria and/or classes or classifications. Alternatively, the grouping can also occur at the data acquisition level, e.g. during image acquisition of markers applied to an organ, e.g. a heart, or during pre- or intra-operative imaging, e.g. of a heart or a heart and lungs, e.g. using one or more computer processors configured to classify or group the acquired data. For example, tissues or structures can be grouped into a left atrial group, a right atrial group, an atrial group, a left ventricular group, a right ventricular group, a ventricular group, a valvular group, an arterial group, a venous group, a pulmonary arterial group, a pulmonary venous group, a vascular group, for example using echocardiography or myocardial perfusion scans, e.g. using rubidium-82, technetium-99m and thallium-201 or SPECT scanning or MRI scanning.

The one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured for individual physical data or structures, as shown in exemplary, non-limiting fashion in Table 16, can be applied to the corresponding virtual data, e.g. obtained using an imaging test or image processing or using overlay of graphical representations, also as shown in exemplary, non-limiting fashion in Table 16, on an individualized basis in order to maintain superimposition and/or alignment of individual virtual data with corresponding individual physical data.

For example, each individual virtual data set or structure, can be moved individually by the computer system of the one or more OHMDs using individually measured data about heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured for the individual corresponding physical data or structures. Thus, different virtual data can be moved by the one or more OHMDs using one or more different heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction in order to maintain superimposition and/or alignment of each individual virtual data set, group or structure with the corresponding individual physical data set, group or structure during portions of or the entire cardiac cycle.

The one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured or determined for groups or classes of physical data or structures, as shown in exemplary, non-limiting fashion in Table 16, can be applied to the corresponding groups or classes of virtual data as well as individual virtual data, e.g. obtained using an imaging test or image processing or using overlay of graphical representations, also as shown in exemplary, non-limiting fashion in Table 16, in order to maintain superimposition and/or alignment of groups or classes of virtual data and/or individual virtual data with corresponding groups or classes of physical data and/or individual physical data.

For example, each group or class of virtual data and/or each individual virtual data set or structure, can be moved individually by the computer system, including one or more computer processors configured for display and/or moving of virtual data, of the one or more OHMDs using individually measured or derived data or data measured or derived for one or more groups of patient data about heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured or derived for the individual corresponding physical data or structures or the corresponding groups or classes of physical data or structures. Thus, different virtual data including individual and/or groups or classes of virtual data can be moved by the one or more OHMDs using one or more different heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction in order to maintain superimposition and/or alignment of each individual virtual data set or structure and/or each group or class of virtual data with the corresponding individual physical data set or structure and/or each group or class of physical data during portions of or the entire cardiac cycle.

In any of the embodiments throughout the specification, imaging can be performed at rest and/or during physical activity or exercise and/or during stress or stress testing and/or during administration of drugs, e.g. for pharmacologic induced stress testing.

In some embodiments, the virtual data including individualized virtual data or groups or classes of virtual data, as shown in exemplary, non-limiting fashion in Table 16, can be synchronized and/or matched with regard to one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction to individualized physical data or groups or classes of physical data using the same value, a greater value or a lesser value for one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. Any combination is possible. Values can, for example, be selected in a manual or automated fashion. Values can, for example, be selected in order to optimize the superimposition and/or alignment of the virtual data with the physical data and/or to maintain the superimposition and/or alignment of the virtual data with the physical data for portions of or the entire cardiac cycle.

In some embodiments, one or more OHMDs can move a first, second, third and/or additional virtual data sets of the patient, e.g. using one or more computer processors configured for display and/or moving of virtual data, optionally with one or more of the same or one or more of a different heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, for example in reflection of differential heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction between different physical data, physical structures or different tissues; or, for example, in reflection of lesser or greater values selected for the moving of virtual data.

In any of the embodiments throughout the specification, a pre- or intra-operative imaging study and/or an image capture or video capture of marker coordinates and/or movements and/or an image capture or video capture or 3D scan of an organ, tissue, or structure, organ, tissue, or structure coordinates and/or organ, tissue, or structure movements can be correlated to other data, e.g. generated by other cardiac gating techniques, using, for example, ECG or pulse measurements, using, for example, one or more computer processors configured for data correlation. By establishing correlations between one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured by or estimated by a pre- or intra-operative imaging study and/or an image capture or video capture of marker coordinates and/or movements and/or an image capture or video capture or 3D scan of an organ, tissue, or structure with data obtained by other cardiac gating techniques, using, for example, ECG or pulse measurements, the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of one or more physical data or physical structures of the patient can be predicted using the data obtained by other cardiac gating techniques, using, for example, ECG or pulse measurements. Prediction rules and statistical models known in the art can be applied to predict the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of one or more physical data or physical structures of the patient. The prediction rules or correlations can be used to superimpose and/or align one or more virtual data, as listed, for example in Table 16, with corresponding physical data of the patient, as also listed, for example, in Table 16, and to maintain the superimposition and/or alignment of the virtual data with the physical data of the patient.

In any of the examples, a virtual image or virtual display of a physical device, physical instrument, physical catheter, physical guidewire, physical stent, physical coil, physical extraction device, physical cardiac valve replacement, physical cardiac valve repair, physical electrode or electric or electrophysiologic probe or an ablation device can be tracked in a coordinate system, e.g. a common coordinate system, using tracking techniques known in the art and described in the specification; the hidden portions of the tracked physical device, physical instrument, physical catheter, physical guidewire, physical stent, physical coil, physical extraction device, physical cardiac valve replacement, physical cardiac valve repair, physical electrode or electric or electrophysiologic probe or an ablation device can then be displayed by one or more OHMDs using the coordinate information, e.g. x, y, and z-coordinates in the common coordinate system, provided by the computer system of the tracking system in the form of a virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device projected superimposed and/or aligned with the anatomic structures with the corresponding coordinate information in the coordinate system, e.g. anatomic structures such as vessels into which the hidden portions of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device have been advanced into. The tracking can be intermittently or in real-time; the computer system can then update the coordinate information of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device intermittently or in real-time and the information can be used for updating the display of the virtual data, e.g. the virtual display of the hidden portions of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device by the one or more OHMDs. In addition, the position and/or orientation of the one or more OHMDs can be tracked in the same coordinate system, e.g. a common coordinate system, so that the display of the hidden portion of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device with the corresponding virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device can be maintained by the one or more OHMDs superimposed onto and/or aligned with the anatomic structures with the corresponding coordinate information in the common coordinate system, e.g. anatomic structures such as vessels into which the hidden portions of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device have been advanced into, even when the operator or surgeon moves his or her head.

In some embodiments, the one or more OHMDs can display, e.g. using a computer processor configured for display and/or registration of virtual data and/or registration and/or tracking of physical data, both the virtual data including the hidden portions of the tracked physical device, physical instrument, physical catheter, physical guidewire, physical stent, physical coil, physical extraction device, physical cardiac valve replacement, physical cardiac valve repair, or physical electrode or electric or electrophysiologic probe or an ablation device in the form of a virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device and anatomic structures of the patient hidden, for example, below a surface, e.g. an organ surface such as a pericardium or chest wall, wherein the anatomic structures can include one or more of a virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, virtual area of normal mobility or contractility. Optionally, the display of one or more of the virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, or virtual area of normal mobility or contractility can be executed by the one or more OHMDs with individual values, e.g. for each or several of the displayed structures, or grouped values for subgroups of the displayed structures, or with the same value for all displayed structures with regard to one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction between different physical data, physical structures or different tissues.

If a patient has an arrhythmia, the arrhythmia including one or more of the associated heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of one or more physical data or physical structures of the patient can be determined using one or more of the cardiac gating techniques known in the art or described in the specification including ECG and/or imaging, e.g. with echocardiography, and one or more of the virtual data, e.g. one or more of a virtual left atrium, virtual right atrium, virtual left ventricle, virtual right ventricle, virtual mitral valve, virtual tricuspid valve, virtual pulmonary valve, virtual aortic valve, virtual pericardium, virtual myocardium, virtual endocardium, virtual coronary artery or vein, virtual left coronary artery, virtual right coronary artery, virtual left marginal artery, virtual left anterior descending artery, virtual left interventricular artery, virtual diagonal branch, virtual posterior descending artery, virtual right marginal artery, virtual sinoatrial node artery, virtual endoluminal portion of a coronary artery or vein, virtual open or patent portion of a coronary virtual or vein, virtual stenotic portion of a coronary artery or vein, virtual occluded portion of a coronary artery or vein, virtual aorta, virtual IVC, virtual pulmonary artery, virtual pulmonary vein, virtual area of abnormal electrophysiologic activity, virtual area of abnormal mobility or contractility, virtual area of ischemia, virtual area of infarction, virtual area of healthy cardiac tissue, e.g. myocardium, virtual area of epicardium, virtual area of myocardium, virtual area of endocardium, virtual papillary muscle, virtual area of normal electrophysiologic activity, or virtual area of normal mobility or contractility, or one or more of a virtual device, virtual instrument, virtual catheter, virtual guidewire, virtual stent, virtual coil, virtual extraction device, virtual cardiac valve replacement, virtual cardiac valve repair, or virtual electrode or electric or electrophysiologic probe or an ablation device can be synchronized with the physical data and/or physical structures, e.g. using one or more computer processors configured for data synchronization, using one or more of the measured heart rate, arrhythmia, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction of one or more of the physical left atrium, physical right atrium, physical left ventricle, physical right ventricle, physical mitral valve, physical tricuspid valve, physical pulmonary valve, physical aortic valve, physical pericardium, physical myocardium, physical endocardium, physical coronary artery or vein, physical left coronary artery, physical right coronary artery, physical left marginal artery, physical left anterior descending artery, physical left interventricular artery, physical diagonal branch, physical posterior descending artery, physical right marginal artery, physical sinoatrial node artery, physical endoluminal portion of a coronary artery or vein, physical open or patent portion of a coronary physical or vein, physical stenotic portion of a coronary artery or vein, physical occluded portion of a coronary artery or vein, physical aorta, physical IVC, physical pulmonary artery, physical pulmonary vein, physical area of abnormal electrophysiologic activity, physical area of abnormal mobility or contractility, physical area of ischemia, physical area of infarction, physical area of healthy cardiac tissue, e.g. myocardium, physical area of epicardium, physical area of myocardium, physical area of endocardium, physical papillary muscle, physical area of normal electrophysiologic activity, physical area of normal mobility or contractility. Thus, even in the presence of an arrhythmia involving the entire heart or sections or portions of the heart, the display of the virtual data by one or more OHMD systems can be superimposed and/or aligned with the physical data or structures of the patient and can be maintained superimposed and/or aligned with the physical data or structures of the patient. Arrhythmias can include, for example one or more of a premature atrial contraction, premature ventricular contractions (PVCs), atrial fibrillation, atrial flutter, paroxysmal supraventricular tachycardia (PSVT), accessory pathway tachycardias, AV nodal reentrant tachycardia, ventricular fibrillation, ventricular tachycardia, long QT syndrome, bradyarrhythmias, sinus node dysfunction, or heart block.

Thus, also in the presence of an arrhythmia affecting select structures of the heart, groups of structures of the heart or groups of anatomic areas, or the entire heart, the one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured for individual physical data or structures, as shown in exemplary, non-limiting fashion in Table 16, can be applied to the corresponding virtual data, e.g. obtained using an imaging test or image processing or using overlay of graphical representations, also as shown in exemplary, non-limiting fashion in Table 16, on an individualized basis in order to maintain superimposition and/or alignment of individual virtual data with corresponding individual physical data.

For example, in the presence of an arrhythmia, each individual virtual data set or structure, can be moved individually by the computer system of the one or more OHMDs using individually measured data about heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured for the individual corresponding physical data or structures. Thus, different virtual data can be moved by the one or more OHMDs using one or more different heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction in order to maintain superimposition and/or alignment of each individual virtual data set, group or structure with the corresponding individual physical data set, group or structure during portions of or the entire cardiac cycle also in the presence of an arrhythmia.

The one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured or determined for groups or classes of physical data or structures, as shown in exemplary, non-limiting fashion in Table 16, can be applied to the corresponding groups or classes of virtual data as well as individual virtual data, e.g. obtained using an imaging test or image processing or using overlay of graphical representations, also as shown in exemplary, non-limiting fashion in Table 16 also in the presence of an arrhythmia, in order to maintain superimposition and/or alignment of groups or classes of virtual data and/or individual virtual data with corresponding groups or classes of physical data and/or individual physical data. Such groups or classes of physical data or such individual data can, for example, be a class not affected by the arrhythmia and a class affected by the arrhythmia, or a class affected by a first arrhythmia and another class affected by a second, different arrhythmia or cardiac rhythm. The classification can be performed by one or more computer processors configured for data classification and/or deep learning. The classification can be used by one or more computer processors configured for display, and/or moving and/or superimposing and/or aligning of virtual data.

For example, each group or class of virtual data and/or each individual virtual data set or structure, can be moved individually by the computer system of the one or more OHMDs using individually measured or derived data (including data about an arrhythmia) or data measured or derived for one or more groups of patient data (including data about an arrhythmia) about heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction measured or derived for the individual corresponding physical data or structures or the corresponding groups or classes of physical data or structures. Thus, different virtual data including individual and/or groups or classes of virtual data can be moved by the one or more OHMDs using one or more different heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction in order to maintain superimposition and/or alignment of each individual virtual data set or structure and/or each group or class of virtual data with the corresponding individual physical data set or structure and/or each group or class of physical data during portions of or the entire cardiac cycle, also in the presence of one or more arrhythmias. In any of the examples of superimposing and/or aligning virtual data with physical data or structures and of maintaining virtual data in superimposition and/or alignment with physical data or physical structures through portions of or the entire cardiac cycle, the virtual data can be a virtual representation of the entire physical structure or only a portion of a physical structure, e.g. a 2D or 3D outline or a portion of an anatomic physical structure, e.g. a virtual 2D or 3D outline or placement indicator of a physical device, physical instrument, physical catheter, physical guidewire, physical stent, physical coil, physical extraction device, physical cardiac valve replacement, physical cardiac valve repair, or physical electrode or electric or electrophysiologic probe or an ablation device.

Any of the lists throughout the specification are only exemplary in nature and are not meant to be limiting. Any other anatomic or physical structure of the heart, lung, or vessels can be displayed in the form of virtual data by the one or more OHMDs and maintained in superimposition and/or alignment with the corresponding physical data or structures of the patient during portions of or the entire cardiac cycle using the embodiments in the specification.

Pre-operative and/or intra-operative imaging can include, but are not limited to, x-ray imaging, cone beam CT, CT, MRI, CT angiography, e.g. in 2D and/or in 3D, CT cardiac motion studies, e.g. using ultrafast CT, MR angiography, MR cardiac motion studies, SPECT studies, PET studies, ultrasound and/or echocardiography including transesophageal echocardiography, as well as electrophysiological studies and/or mapping.

After one or more image acquisitions, for example during a procedure, the use of the imaging system can optionally be discontinued; in some embodiments, the measured movement of the one or more markers or of the organ or tissue surface, e.g. as detected directly (e.g. without markers) by a 3D scanner or video system, or a pulse measurement or ECG can then be used, for example using prediction models, e.g. using one or more computer processors configured for applying prediction models, to compute or estimate the movement or excursion the physical data or physical structures of the patient, e.g. an organ, for example the heart, or tissue or tissue surface, on an external and/or exposed surface or inside the body, e.g. in a subsurface location, e.g. below a skin or inside a pericardium or a myocardium or a pleura or a peritoneum or inside an organ or underneath an organ surface, or underneath a tissue surface with the cardiac or vascular movement and/or pulsation or excursion, e.g. using a correlation to the image acquisitions, and the display of the virtual data by the one or more OHMDs can be moved with the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, e.g. in x-, y- and/or z- and/or any other direction, and the display of the virtual data can be maintained aligned with and/or superimposed with the corresponding physical data or structures of the patient, e.g. a physical organ or physical tissue, e.g. a heart, a lung, a vessel, an artery, a vein, an aorta, an inferior vena cava, a pulmonary artery or vein, a tumor or lesion, or a target for surgical or other intervention associated with the patient's body, during cardiac or vascular movement and/or pulsation or excursion.

The physical data or physical structures of the patient, e.g. an organ or tissue or tissue surface, e.g. a heart or vessel, can be inside the body, e.g. in a subsurface location, e.g. below a skin or inside a pericardium or a pleura or a peritoneum or inside an organ or underneath an organ surface, or underneath a tissue surface, and can be visible by an image capture or imaging system, camera system or video system inserted into or near the subsurface location, inside the pericardium, inside the pleura, inside a cavity, inside a vessel, inside a cardiac chamber, inside a hollow organ, or inside a space created by a surgical instrument. By inserting the image capture system, camera system or video system or imaging system into or near the subsurface location, inside the pericardium, inside the pleura, inside the peritoneum, inside a cavity, inside a vessel, inside a cardiac chamber, inside a hollow organ, or inside a space created by a surgical instrument, the physical data of the patient can be registered in a coordinate system, e.g. a coordinate system in which one or more OHMDs are also registered. By inserting the image capture system, camera system or video system or imaging system into or near the subsurface location, inside the pericardium, inside the pleura, inside the peritoneum, inside a cavity, inside a vessel, inside a cardiac chamber, inside a hollow organ, or inside a space created by a surgical instrument, the image capture system, camera system or video system or imaging system can also be used to image or capture cardiac or vascular motion or pulsation, e.g. of the physical data or structures of the patient, including, for example, the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, e.g. in x-, y- and/or z- and/or any other direction.

One or more markers applied to the organ, tissue, tissue surface pericardium or myocardium or other portions of the heart and vessels can be used to measure cardiac and/or vascular movement and/or pulsation including, for example, one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, e.g. in x-, y- and/or z- and/or any other direction using, for example, an image capture, camera or video system or an imaging system and using, for example, one or more computer processors configured for image analysis and/or for detection and/or measurement of marker movement. The data obtained with use of the one or more markers and the data obtained with the image capture system, camera system or video system inside the patient can optionally be compared, e.g. to identify any differences in marker measurements and image capture, camera or video system or imaging system measurements, with optional correction of such differences in the marker measurements. In some embodiments, the measured movement of one or more markers or of the organ or tissue surface, e.g. as detected directly, e.g. without markers, by a 3D scanner or video system, can be used to compute or estimate the movement or excursion the physical data or physical structures of the patient, e.g. an organ or tissue or tissue surface, inside the body, e.g. in a subsurface location, e.g. below a skin or inside a pericardium or myocardium or a pleura or inside an organ, e.g. a heart, or underneath an organ surface, e.g. a pericardium or myocardium, or underneath a tissue surface with the cardiac and/or vascular movement and/or pulsation or excursion, and the display of the virtual data by the one or more OHMDs can be moved with the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, and the display of the virtual data can be maintained aligned with and/or superimposed with the corresponding physical data or structures of the patient, e.g. a physical organ or physical tissue, e.g. a heart, a lung, a vessel, an artery, a vein, or a tumor or lesion, a left atrium, a right atrium, a left ventricle, a right ventricle, a mitral valve, a tricuspid valve, a pulmonary valve, an aortic valve, a pericardium, a myocardium, an endocardium, a coronary artery or vein, an open or patent portion of a coronary artery or vein, a stenotic portion of a coronary artery or vein, an occluded portion of a coronary artery or vein, an aorta, an IVC, a pulmonary artery or vein, an area of abnormal electrophysiologic activity, an area of abnormal mobility or contractility, an area of ischemia, an area of infarction, an area of healthy cardiac tissue, e.g. myocardium, an area of normal electrophysiologic activity, or an area of normal mobility or contractility, or a target for surgical or other intervention associated with the patient's body, during cardiac and/or vascular movement and/or pulsation or excursion.

In some embodiments, the display of the virtual data can be aligned with and superimposed onto corresponding physical data or structures of the patient through the entire cardiac cycle, e.g. through all phases of systole and diastole, e.g. using one or more computer processors configured for displaying and/or moving and/or aligning and/or maintaining the display of virtual data. Thus, the display of the virtual data can be maintained aligned with and superimposed onto corresponding physical data or structures of the patient through the entire cardiac cycle, e.g. through all phases of systole and diastole. For example, a cardiac gating system can measure one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion. The measured data can be used to compute a synchronized movement of the virtual data by the one or more OHMDs to maintain superimposition and/or alignment of the virtual data onto the physical data or physical structures of the patient through the entire cardiac cycle.

In some embodiments, the display of the virtual data can be aligned with and superimposed onto corresponding physical data or structures of the patient through portions of the cardiac cycle, e.g. through select phases of systole and diastole. Thus, the display of the virtual data can be maintained aligned with and superimposed onto corresponding physical data or structures of the patient through portions of the cardiac cycle, e.g. through select phases of systole and diastole. For example, a cardiac gating system can measure one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion. The measured data can be used to compute a synchronized movement of the virtual data by the one or more OHMDs to maintain superimposition and/or alignment of the virtual data onto the physical data or physical structures of the patient through portions of the cardiac cycle.

Figure 20:
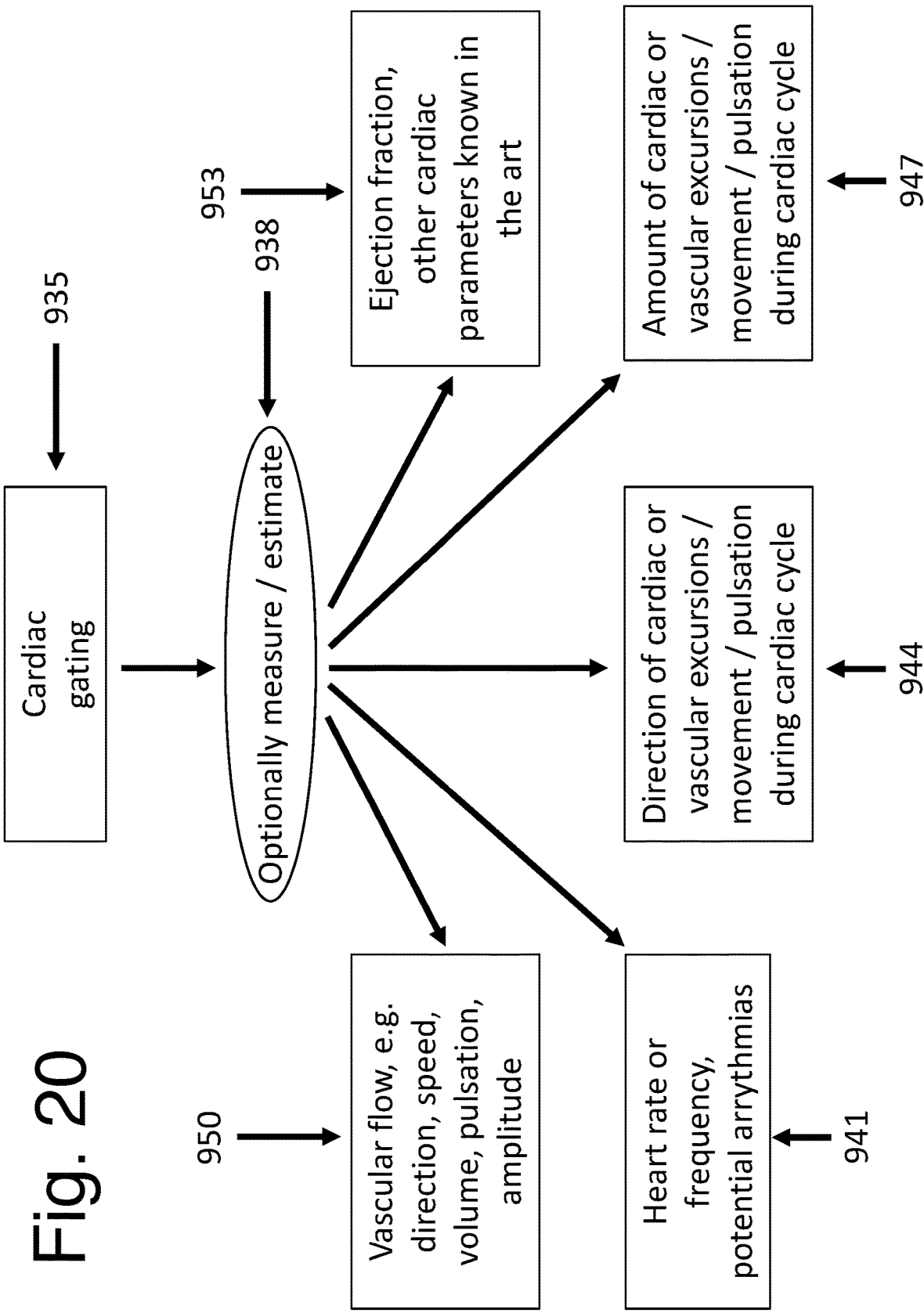
FIG. 20 is a diagram showing an example of cardiac gating for measuring or estimating one or more of heart rate or frequency including potential arrhythmias, the direction of cardiac and/or vascular excursions and/or movement and/or pulsation, the amount of cardiac and/or vascular excursions and/or movement and/or pulsation, vascular flow, e.g. speed, volume, pulsation, amplitude and/or ejection fraction and/or other cardiac parameters known in the art, according to some embodiments.

In any of the embodiments, one or more OHMDs can be registered in the same coordinate system in which the patient or any portion of the patient, e.g. a physical organ, a physical surface, a physical tissue, or a physical target on the surface, e.g. an exposed surface, of the patient or inside the patient, are registered. Subcoordinate systems can be used within a common coordinate system. For example, one or more subcoordinate systems can be used for registering and/or tracking one or more portions of the patient; one or more subcoordinate systems can be used for registering and/or tracking one or more OHMDs. The subcoordinate systems can be referenced to the same common coordinate system. By registering and tracking the one or more physical organs, physical structures or targets of the patient and the one or more OHMDs in a common coordinate system, and by performing cardiac gating using any of the techniques described in the specification, and by moving the display of the virtual data by the one or more OHMDs using one or more of the heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target or a lesion, the display of the virtual data can be maintained aligned with and/or superimposed with the physical organ or physical tissue or physical structure(s) of the patient or the target for one or more portions of the cardiac cycle or the cardiac respiratory cycle. FIG. 20 is an example of cardiac gating 935 for measuring or estimating 938 one or more of heart rate or frequency including potential arrhythmias 941, the direction of cardiac and/or vascular excursions and/or movement and/or pulsation 944, the amount of cardiac and/or vascular excursions and/or movement and/or pulsation 947, vascular flow, e.g. speed, volume, pulsation, amplitude 950 and/or ejection fraction and/or other cardiac parameters known in the art 953.

Throughout the specification, pulsation, e.g. of a vessel or a vascular structure or organs (e.g. adjacent to a heart) can, for example, be measured using an imaging test, e.g. fluoroscopy, ultrasound, echocardiography, CT, MRI, SPECT, PET, nuclear heart scan and any other imaging modality mentioned in the specification or known in the art. Throughout the specification, arrhythmias can include one or more of premature atrial contractions, premature ventricular contractions (PVCs), atrial fibrillation, atrial flutter, paroxysmal supraventricular tachycardia (PSVT), accessory pathway tachycardias, AV nodal reentrant tachycardia, ventricular fibrillation, ventricular tachycardia, long QT syndrome, bradyarrhythmias, sinus node dysfunction, or heart block. The information, e.g. heart rate and/or arrhythmias, can be used to move the display of virtual data by one or more OHMDs to maintain superimposition and/or alignment of the virtual data, for example a virtual surgical guide, e.g. a virtual axis for an instrument, with one or more physical organs, physical tissues, physical surfaces, physical structures or targets on the surface of the patient, e.g. an exposed surface, or inside the patient or inside an organ during at least portions of or the entire respiratory cycle. For example, if a patient is suffering from one or more arrhythmias, the movement of the virtual data by the one or more OHMDs can be controlled by a computer processor to be synchronized with portions or all of the cardiac rhythm including the arrhythmia. If the arrhythmia affects, for example, only the atria, the synchronization to the arrhythmia can be limited to the atria, e.g. in the case of atrial fibrillation. If the arrhythmia affects, for example, only the ventricles or a ventricle, the synchronization to the arrhythmia can be limited to the ventricles or the affected ventricle, e.g. in the case of atrial fibrillation. In some embodiments, an arrhythmia may have a frequency, e.g. a high frequency of 150, 200, 250 or more occurrences per minute that may make movement of the display of the virtual data displayed by the one or more OHMDs technically not feasible or that may be above a frequency perceptible by the human eye. In these embodiments, the display of the virtual data by the one or more OHMDs can optionally not be synchronized with the arrhythmia or can optionally be synchronized at a lower frequency, e.g. with a ratio of 2:1, 3:1, 4:1, 5:1, 10:1, 15:1, 20:1 or any other ratio between frequency of arrhythmia, e.g. beats per minute, and frequency of movement of the display of the virtual data by the one or more OHMDs.

For example, when OHMD guidance is desired for performing an electrophysiologic test or procedure, cardiac and/or respiratory gating of the virtual data displayed by the one or more OHMDs, e.g. pre-procedural or intra-procedural 2D or 3D images of the patient's heart, e.g. an ultrasound or echocardiogram, can be performed. Imaging can be performed at the beginning of or during the procedure to visualize the physical data or physical structures of the patient. The imaging can, for example, be performed using x-ray imaging, ultrasound, CT scan or MRI scan, or echocardiography or any other imaging modality known in the art. The image acquisition can be performed in select phases of the cardiac and/or respiratory cycle. The image acquisition can also be performed throughout the cardiac and/or respiratory cycle. Optionally, the image acquisition can be performed through the cardiac cycle to measure one or more of a heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s). The data obtained with use of the imaging system, e.g. an ultrasound system or echocardiogram, can optionally be compared to data obtained using cardiac gating systems using, for example, ECG or pulse measurements, or markers with one or more infrared or video systems. Once a correlation between the imaging data and the cardiac gating system(s) has been established, e.g. specific image coordinates of the heart or portion of the heart for a given or each phase of the cardiac cycle, the operator can optionally terminate the imaging procedure, while the cardiac gating and related data acquisition and analysis can continue. By moving and synchronizing the display of the virtual data, in this example virtual data or images of the heart, with the cardiac movement of the physical heart or physical portions of the heart, e.g. atria, ventricles, coronaries, valves, as measured with the imaging system and/or various cardiac gating systems known in the art or described in the specification, the OHMD display of the virtual data can be maintained superimposed and/or aligned with the physical heart and/or portions thereof during at least portions of or the entire cardiac cycle. The surgeon can thus see the virtual data displayed by the OHMD and projected inside the patient, e.g. a virtual focus of abnormal electrophysiologic activity, registered with and superimposed and/or aligned with the physical heart and/or portions thereof, e.g. a physical focus of abnormal electrophysiologic activity (including a physical focus of abnormal electrophysiologic activity in non-visible, e.g. subsurface, location), and maintained in superimposition and/or alignment with the physical heart and/or portions thereof, e.g. the physical focus of abnormal electrophysiologic activity, during at least portions of or the entire cardiac cycle. The surgeon can then direct a physical electrode or electric or electrophysiologic probe, e.g. an ablation device, towards the virtual focus of abnormal electrophysiologic activity projected by the OHMD and superimposed and maintained in superimposition with the physical heart or portions thereof, e.g. the physical focus of abnormal electrophysiologic activity, during the cardiac cycle or portions thereof and the surgeon can, for example, perform an ablation.

Optionally, the OHMD can also display virtual data of sensitive structures, e.g. adjacent arteries or veins or nerves, so that the surgeon can move a device or instrument or catheter or electrode or probe away from the displayed virtual sensitive structures while advancing it towards the target area. The display of the virtual data of sensitive structures near or adjacent to the target tissue, e.g. a focus of abnormal electrophysiologic activity, by the OHMD can also be moved and synchronized with the cardiac and/or respiratory movement of the physical sensitive structures so that the OHMD display of the virtual data of the sensitive structures of the patient can be maintained superimposed and/or aligned with the physical sensitive structures during at least portions of or the entire the cardiac and/or respiratory cycle.

In another example, when OHMD guidance is desired for resecting or ablating an area of abnormal tissue, e.g. inside the myocardium, cardiac gating of the virtual data displayed by the one or more OHMDs, e.g. pre-procedural or intra-procedural 2D or 3D images (for example using an ultrasound or echocardiogram) of the patient's organ e.g. the heart or myocardium, and/or of the area of abnormal tissue, e.g. an area of infarction and/or an area of abnormal contractility and/or an area of abnormal electrophysiologic activity can be performed. Imaging can be performed at the beginning of or during the procedure to visualize the physical data or physical structures of the patient, e.g. the heart or myocardium, and/or the area of abnormal tissue, e.g. an area of infarction and/or an area of abnormal contractility and/or an area of abnormal electrophysiologic activity. The imaging can, for example, be performed using x-ray imaging, ultrasound, CT scan or MRI scan, or echocardiography, or nuclear heart scan, or SPECT imaging or any other imaging modality known in the art. The image acquisition can be performed in select phases of the cardiac cycle. The image acquisition can also be performed throughout the cardiac cycle. Optionally, the image acquisition can be performed through the cardiac cycle to measure one or more of heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s).

The data obtained with use of the imaging system, e.g. an intra-operative ultrasound system using a sterile transducer probe, e.g. on the organ surface, can optionally be compared to data obtained using cardiac gating systems such as an ECG, or markers with one or more infrared or video systems. Once a correlation between the imaging data and the cardiac gating system(s) has been established, e.g. specific image coordinates of the heart or myocardium, and/or of the area of abnormal tissue, e.g. an area of infarction and/or an area of abnormal contractility and/or an area of abnormal electrophysiologic activity, for a given or each phase of the cardiac cycle, the operator can optionally terminate the imaging procedure, while the cardiac gating and related data acquisition and analysis can continue.

By moving and synchronizing the display of the virtual data, in this example virtual data or images of the heart or myocardium, and/or of the area of abnormal tissue, e.g. an area of infarction and/or an area of abnormal contractility and/or an area of abnormal electrophysiologic activity, with the cardiac movement of the physical heart or myocardium, and/or of the area of abnormal tissue, e.g. an area of infarction and/or an area of abnormal contractility and/or an area of abnormal electrophysiologic activity, as measured with the imaging system and/or the other cardiac gating systems, the OHMD display of the virtual data can be maintained superimposed and/or aligned with the physical heart or myocardium, and/or of the physical area of abnormal tissue, e.g. an area of infarction and/or an area of abnormal contractility and/or an area of abnormal electrophysiologic activity, during at least portions of or the entire cardiac cycle. The surgeon can thus see the virtual heart or myocardium, and/or of the virtual area of abnormal tissue, e.g. a virtual area of infarction and/or a virtual area of abnormal contractility and/or a virtual area of abnormal electrophysiologic activity, displayed by the OHMD and projected inside the patient, registered with and superimposed and/or aligned with the physical heart or myocardium, and/or of the physical area of abnormal tissue, e.g. a physical area of infarction and/or a physical area of abnormal contractility and/or a physical area of abnormal electrophysiologic activity, and maintained in superimposition and/or alignment with the physical heart or myocardium, and/or of the physical area of abnormal tissue, e.g. a physical area of infarction and/or a physical area of abnormal contractility and/or a physical area of abnormal electrophysiologic activity, during at least portions of or the entire cardiac cycle. A physical surgical instrument, e.g. a scalpel or a needle or a thermocoagulation probe, or an electrode or a probe, or another instrument or another device can then be directed, e.g. using a robot, towards the virtual heart or myocardium, and/or of the virtual area of abnormal tissue, e.g. a virtual area of infarction and/or a virtual area of abnormal contractility and/or a virtual area of abnormal electrophysiologic activity, projected by the OHMD and superimposed and maintained in superimposition with the physical heart or myocardium, and/or of the physical area of abnormal tissue, e.g. a physical area of infarction and/or a physical area of abnormal contractility and/or a physical area of abnormal electrophysiologic activity, during systole and/or diastole and the surgeon can place the scalpel or needle or thermocoagulation probe or electrode or probe or other instrument or other device inside the physical heart or myocardium, and/or of the physical area of abnormal tissue, e.g. a physical area of infarction and/or a physical area of abnormal contractility and/or a physical area of abnormal electrophysiologic activity. Optionally, the OHMD can also display virtual data of sensitive structures, e.g. adjacent arteries or veins or nerves, so that the surgeon can move the scalpel or needle or thermocoagulation probe, or electrode or probe, or other instrument or other device away from the displayed virtual sensitive structures while advancing it towards the physical heart or myocardium, and/or the physical area of abnormal tissue, e.g. a physical area of infarction and/or a physical area of abnormal contractility and/or a physical area of abnormal electrophysiologic activity.

The display of the virtual data of sensitive structures near or adjacent to the target tissue, e.g. the physical heart or myocardium, and/or of the physical area of abnormal tissue, e.g. a physical area of infarction and/or a physical area of abnormal contractility and/or a physical area of abnormal electrophysiologic activity, by the OHMD can also be moved and synchronized with the cardiac movement of the physical sensitive structures and/or the physical heart or myocardium, and/or of the physical area of abnormal tissue, e.g. a physical area of infarction and/or a physical area of abnormal contractility and/or a physical area of abnormal electrophysiologic activity, so that the OHMD display of the virtual data of the sensitive structures of the patient can be maintained superimposed and/or aligned with the physical sensitive structures during at least portions of or the entire the cardiac cycle.

In some embodiments, cardiac gating can be used to synchronize virtual data with physical data of the patient, e.g. a physical organ that is moving due to cardiac motion or pulsation. In this embodiment, the virtual data can be displayed by an AR or VR OHMD whenever a certain period or moment in the cardiac cycle is reached. For example, upon completion of systole or diastole or in mid-systole or diastole or in early systole or diastole, an OHMD can display virtual data of a patient, e.g. a virtual axis for a puncture or ablation, onto the physical organ of the patient, e.g. deep inside the patient, e.g. inside a myocardium.

Cardiac gating can be performed using any system or method known in the art. In any of the embodiments throughout the specification, see through augmented reality optical head mounted displays can be used. In any of the embodiments throughout the specification, non-see through virtual reality optical head mounted displays can be used; the use of VR optical head mounted displays can be accompanied by video capture of the physical data of the patient, e.g. a surgical site, onto which virtual data, e.g. virtual surgical guides or pre-operative imaging data, can optionally be superimposed.

In any of the embodiments, cardiac gating can be performed using ECG data and/or peripheral pulse data/measurements and/or vascular flow data/measurements, e.g. using ultrasound, which can, for example, be obtained during a procedure, including open heart surgery, endoscopic heart surgery, and/or vascular or other surgical procedures, including, for example, minimally invasive procedures. For example, cardiac contraction can be monitored using peripheral pulse data/measurements.

Cardiac gating can, for example, be performed prospectively by tracking a patient's cardiac cycle with an electrocardiogram (ECG). The system can detect specific points in the cyclic wave pattern of the ECG, e.g. peaks or valleys, the R-wave or the P-wave. The cyclic wave pattern can consist of repetitive periods that are usually identical or similar to each other. Any cardiac gating technique described in the specification or known in the art can be used. One or more of the following parameters can be measured for cardiac gating: heart rate, phase of the cardiac cycle, e.g. phase of systole or diastole, e.g. early, mid or late, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction, of the heart or vessel(s) or the amount of cardiac and/or vascular related movement or excursion of a physical organ or physical tissue or a target. Image acquisition and/or image display, e.g. the display of one or more virtual images by an OHMD, can then, for example, be triggered at a specific phase during that waveform relative to the detected points in the wave pattern, for example during diastole. Image data can be acquired at the same phase, e.g. systole or diastole, e.g. early, mid or late, in different periods of the cyclic wave pattern of the ECG. Image data can also be acquired at the same phase in the same period of the cyclic wave pattern of the ECG, e.g. with multi-detector spiral CT scanners or MRI scanners.

Image data acquired at the same phase in different locations can be combined. For example, CT or MRI data can be acquired in different locations at the same phase of the cardiac cycle. CT or MRI data can cover a spiral or volume of tissue, e.g. an upper third of the lung, a middle third of a lung, a lower third of a lung, a first portion of the heart, a second portion of the heart, a third portion of the heart, a fourth portion of the heart, etc., portions of an ascending aorta, portions of an aortic arch, portions of a descending aorta; different locations or volume data sets or spirals of the heart, lungs, vasculature, chest and/or abdomen can be acquired at the same phase of the cardiac cycle. Different locations or volume data sets or spirals of the heart, lungs, vasculature, chest and/or abdomen can be acquired at different phases of the cardiac cycle until ultimately the entire target anatomy, e.g. the heart, lung, vasculature, abdominal tissue or organs are covered or included in image data sets, volume data sets or spirals that include all phases of the cardiac cycle. The amount of tissue volume included in one image acquisition at the same phase of the cardiac cycle can depend on the speed of the image acquisition. The speed of the image acquisition can depend on multiple factors, e.g. spatial resolution, radiation dose (CT), number of detectors and detector rings used (CT), reconstruction algorithm, processor speed, gradient strength (MRI), field strength (MRI). If an image data set, volume data set or spiral cannot cover the entire anatomic structure of interest during one cardiac cycle, multiple image data sets, volume data sets or spirals from the same phase of the cardiac cycle can be acquired in different locations, sections or portions of the anatomic structure of interest, for example over multiple different cardiac cycles. Image data set, volume data sets or spirals acquired from the same phase of the cardiac cycle over multiple different cardiac cycles can then be combined, e.g. can be "stitched" together. For example, in CT imaging, various non-linear iterative reconstruction (IR) algorithms and/or linear filtered back projection (FBP) reconstruction algorithms can be used (see, for example, Haliburton S., et al., The role of advanced reconstruction algorithms in cardiac CT; Cardiovasc Diagn Ther, 2017, 7, 5, 527-538, which is hereby incorporated by reference in its entirety). Real-time or off console, off-line image reconstruction, e.g. after the image acquisition, can be used.

All image data, volume data and/or spirals from the same phase of the cardiac cycle, whether acquired during the same period or different period, e.g. of the cyclic wave pattern of the ECG, of the cardiac cycle or any combination thereof, can be combined into one or more 3D imaging data sets that can be used to generate a 3D model of the vasculature and/or the heart and/or the lungs and/or abdominal structures, tissues or organs for that phase of the cardiac cycle and, for example, all phases of the cardiac cycle.

This process can be repeated for a different phase of the cardiac cycle, e.g. systole or diastole, e.g. early, mid, late. This allows for creation of different 3D models of the vasculature and/or the heart and/or the lungs and/or abdominal structures, tissues or organs for different phases of the cardiac cycle.

In any of the embodiments, one or more computer processors can be configured to measure one or more of a respiratory rate or frequency, the phase of the respiratory cycle, the direction of respiratory excursions or movement during inspiration or expiration, the speed of respiratory excursions or movement during inspiration or expiration or the amount of respiratory excursions or movement during inspiration or expiration. One or more computer processors can be configured to synchronize and/or move one or more OHMD displays using the one or more of the respiratory rate or frequency, the phase of the respiratory cycle, the direction of respiratory excursions or movement during inspiration or expiration, the speed of respiratory excursions or movement during inspiration or expiration or the amount of respiratory excursions or movement during inspiration or expiration. One or more computer processors can be configured to measure one or more of a heart rate, arrhythmias, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. One or more computer processors can be configured to move and/or synchronize one or more OHMD displays using the heart rate, arrhythmias, direction of cardiac and/or vascular movement and/or pulsation, e.g. in x-, y- and/or z- and/or any other direction, speed of cardiac and/or vascular movement and/or pulsation, e.g. in x-, y- and/or z- and/or any other direction, amount of cardiac and/or vascular movement and/or pulsation, e.g. in x-, y- and/or z- and/or any other direction. One or more computer processors can be configured to register virtual data with physical data of the patient, including considering and/or using respiratory and/or cardiac gating information. One or more computer processors can be configured to superimpose and/or align virtual data with physical data of the patient and to maintain the superimposing and/or aligning of virtual data with the physical data during portions of or the entire respiratory and/or cardiac cycle. One or more computer processors can be configured to superimpose and/or align individual virtual data, e.g. individual virtual tissues, surfaces, organs or structures, or groups of virtual data, e.g. groups of virtual tissues, surfaces, organs or structures, with corresponding individual and/or groups of physical tissues, surfaces, organs or structures, optionally including cardiac and/or respiratory gating information. In any of the embodiments, the one or more computer processors can be the same or different. In any of the embodiments, the one or more computer processors can be part of the same or different computer systems, e.g. a computer system for a standalone computer monitor and/or a computer system for one or more OHMDs.

In some embodiments, gating of image acquisition and/or image display, e.g. by one or more OHMDs, can also be performed retrospectively. In these cases, image data is recorded continuously together with the respiratory gating and/or cardiac gating (e.g. ECG) information. Once the image data, volume data or spiral acquisition is complete, one or more specific phases of the respiratory and/or cardiac cycle can be selected and the corresponding image data, volume data or spiral acquisition from these time points, time segments or time intervals extracted from the continuous data set to create one or more virtual 3D models of the vasculature and/or heart and/or lungs, and or other tissues, organs, or structures, including in the abdomen for one or more of these different time points, time intervals or time segments. Different phases can be selected, e.g. early, mid, late systole and/or diastole, early, mid, late inspiration and/or expiration, to create the corresponding model for each phase.

Interpolation of Image Data, Volume Data or Spiral Acquisition Obtained at Different Time Points, Time Intervals or Time Segments Since the speed of scan, image data set, volume data set or spiral acquisition determines and/or limits the temporal resolution, the respiratory cycle and/or the cardiac cycle can, for example, be split or subdivided at a maximum into a number of time segments or time intervals that equals the length of the respiratory cycle (in sec) divided by the time required to obtain one scan, image data set, volume data set or spiral acquisition or the length of the cardiac cycle (in sec) divided by the time required to obtain one scan, image data set, volume data set or spiral acquisition. Depending on the speed of respiratory or cardiac movement, transitions between scans, image data sets, volume data sets or spiral acquisitions obtained at a first time segment or time interval and scans, image data sets, volume data sets or spiral acquisitions obtained at a second time segment or time interval can in some applications appear abrupt or "stepped"; in some embodiments, scans, image data sets, volume data sets or spiral acquisitions obtained at a first time segment or time interval and scans, image data sets, volume data sets or spiral acquisitions obtained at a second time segment or time interval can be interpolated creating one or more additional scans, image data sets, volume data sets or spiral acquisitions interpolated or generated for time segments or time intervals between the first and the second time segment or time interval through data interpolation. Interpolation techniques and/or algorithms can, for example, include linear interpolation or gray values, cubic interpolation of gray values, linear interpolation of coordinates, cubic interpolation of coordinates, linear interpolation of model landmarks, cubic interpolation of model landmarks, morphing techniques, statistical models, parameter models or any other technique that allows for computation of an intermediate image data set between a first image data set and a second image data set, or computation of an intermediate virtual anatomical model between a first virtual anatomical model and a second virtual anatomical model.

Combined Cardiac and Respiratory Gating

In some embodiments, cardiac and respiratory gating can be used in combination or simultaneously. Combined cardiac and respiratory gating can be used to optimize the superimposition and/or alignment of virtual data onto physical data or physical structures of the patient, e.g. a beating heart, a lung, a vessel, an artery, a vein, an aorta, an inferior vena cava, a coronary artery or vein etc., through the cardiac cycle despite cardiac and/or associated vascular motion or pulsation and/or despite respiratory motion. Combined cardiac and respiratory gating can be used to maintain the superimposition and/or alignment of virtual data onto physical data or physical structures of the patient, e.g. a beating heart, a lung, a vessel, an artery, a vein, an aorta, an inferior vena cava, a coronary artery or vein etc., through the cardiac cycle despite cardiac and/or associated vascular motion or pulsation and/or through respiratory motion for at least portions of or the entire the cardiac cycle and/or at least portions of or the entire respiratory cycle.

The virtual 3D models of the vasculature and/or heart and/or lungs, and/or other tissues, organs, or structures, including in the thorax or abdomen, e.g. obtained from a pre-operative image acquisition, can be displayed as virtual data, virtual images or virtual models overlaid onto, superimposed onto or aligned with the patient's physical anatomy or physical anatomic structures, or physical tissues or physical organs including the physical vasculature and/or physical heart and/or physical lungs, and or other physical tissues, physical organs, or physical structures, including in the thorax or abdomen, in the OHMD using the methods and techniques described in the specification, including registration and stereoscopic rendering. To synchronize the display of virtual 3D models of the vasculature and/or heart and/or lungs, and/or other tissues, organs, or structures, including in the thorax or abdomen from the different phases of the patient's respiratory and/or cardiac cycle with the live patient's respiratory and/or cardiac motion, e.g. during a procedure, cardiac and/or respiratory gating can be performed during the live procedure, e.g. a 2D or 3D angiogram, a vascular run-off or a bolus chase study, in the same fashion as for the pre-operative image acquisition. The same phases of the cardiac and/or respiratory cycle can then be used to display the virtual 3D models from the different time points, time intervals or time segments of the cardiac and/or respiratory cycle aligned with, superimposed onto or overlaid onto the live patients including for a given, particular phase of the cardiac or respiratory cycle in the live patient. Thus, the same phases of the cardiac and/or respiratory cycle can be matched or can be selected to display the virtual 3D models from the different time points, time intervals or time segments of the cardiac and/or respiratory cycle aligned with, superimposed onto or overlaid onto the live patients including for a given, particular phase of the cardiac or respiratory cycle in the live patient.

The virtual 3D models of the vasculature and/or heart and/or lungs, and/or other tissues, organs, or structures, including in the thorax or abdomen, e.g. obtained from a pre-operative image acquisition, can be displayed as virtual data, virtual images or virtual models overlaid onto, superimposed onto or aligned with the patient's virtual anatomy or virtual anatomic structures, or virtual tissues or virtual organs including the virtual vasculature and/or virtual heart and/or virtual lungs, and or other virtual tissues, virtual organs, or virtual structures, including in the thorax or abdomen, as imaged, for example, during a procedure, e.g. a 2D or 3D angiogram, a run-off or a bolus chase, in the OHMD using the methods and techniques described in the specification, including registration and stereoscopic rendering. To synchronize the display of virtual 3D models of the vasculature and/or heart and/or lungs, and/or other tissues, organs, or structures, including in the thorax or abdomen, e.g. from a pre-operative image acquisition, from the different phases of the patient's respiratory and/or cardiac cycle with the live patient's respiratory and/or cardiac motion, e.g. during a procedure, cardiac and/or respiratory gating can be performed during the live procedure, e.g. a 2D or 3D angiogram, a vascular run-off or a bolus chase study, in the same fashion as for the pre-operative image acquisition. The same phases of the cardiac and/or respiratory cycle can then be used to display the virtual 3D models from the different time points, time intervals or time segments of the cardiac and/or respiratory cycle from the pre-operative image acquisition aligned with, superimposed onto or overlaid onto the virtual images of the patient, e.g. an intra-operative 2D or 3D angiogram, run-off or bolus chase study, including for a given, particular phase of the cardiac or respiratory cycle in the live patient or in the live data of the intra-operative 2D or 3D angiogram, run-off or bolus chase study. Thus, the same phases of the cardiac and/or respiratory cycle can be matched or can be selected to display the virtual 3D models from the different time points, time intervals or time segments of the cardiac and/or respiratory cycle from the pre-operative image acquisition aligned with, superimposed onto or overlaid onto the virtual data or virtual images of the live patient, e.g. as seen in an angiogram, run-off or bolus chase study, including for a given, particular phase of the cardiac or respiratory cycle in the live patient. 3D models for time points, time intervals or time segments in between the pre-recorded phases of the cardiac and/or respiratory cycle can be interpolated. In this fashion, a dynamic 3D virtual model of the vasculature and/or heart can be displayed as a continuous cyclic sequence synchronized with the cardiac and/or respiratory cycles of the live, physical patient. Thus, virtual data from a pre-operative image acquisition, e.g. a CTA or MRA, obtained at different time points, time intervals or time segments of the cardiac or respiratory cycle, can be synchronized by the computer system and computer processors generating the OHMD display with cardiac and/or respiratory gating data of the live patient obtained during a surgical procedure or during an intervention, to superimpose or align the virtual data from the pre-operative image acquisition and to maintain the superimposition or alignment of the virtual data from the pre-operative image acquisition with the physical patient or the physical anatomic structures of the patient or the intra-operative images, e.g. a 2D or 3D angiogram, run-off or bolus chase (e.g. in real time), of the live physical patient obtained during the procedure, during portions of or all phases of the cardiac and/or respiratory cycle. The OHMD can display sequential virtual data, e.g. virtual data, for example, scans, images, image data sets, volume data sets, spirals or 3D models extracted from these, from sequential time points, time intervals, time segments, from a pre-operative imaging test. The scans, images, image data sets, volume data sets, spirals or 3D models extracted from these can optionally be marked or coded or tagged with the specific time point, time interval, time segment of the phase of the respiratory and/or cardiac cycle during which the scan, images, image data sets, volume data sets, spiral were acquired in the pre-operative scan, e.g. a CT or MRA. A computer system with one or more computer processors can then be used to display virtual data or virtual images from the time sequence of scans, images, image data sets, volume data sets, spirals obtained at the different time points, time intervals, time segments of the respiratory and/or cardiac cycle from the pre-operative image acquisition or scan that correspond to the phase of the respiratory or cardiac cycle of the patient, e.g. during an interventional procedure; the scans, images, image data sets, volume data sets, spirals obtained at the different time points, time intervals, time segments of the respiratory and/or cardiac cycle from the pre-operative image acquisition or scan can be marked or coded or tagged with the different time points, time intervals, time segments of the respiratory and/or cardiac cycle. Thus, the OHMD can display sequential virtual data or virtual images from the pre-operative scan that can match the phase of the cardiac and/or respiratory cycle of the patient during the intervention; in this manner, the computer system can maintain the display of the virtual data or virtual images superimposed onto and/or aligned with the corresponding anatomic structures, tissues and/or organs both in the physical patient and/or in virtual data acquired, for example, in real-time from the physical patient, e.g. an intra-operative angiogram, run-off or bolus chase, e.g. displayed by the OHMD and/or a computer monitor.

The display of virtual 3D models or virtual data of the vasculature and/or heart and/or lungs, and/or other tissues, organs, or structures, including in the thorax or abdomen obtained from a pre-operative imaging study in the OHMD can also be synchronized by a computer system with one or more computer processors by moving the virtual 3D models or virtual data from the pre-operative imaging study in the display of the OHMD. The moving by the display of the OHMD can be triggered or performed using one or more data or parameters obtained from the respiratory and/or cardiac cycle of the live patient during a surgical procedure or intervention. The moving can be reflective of and/or or correspond to, for example, a movement or excursion or pulsation of the heart, the lung, and/or a vessel measured using respiratory and/or cardiac gating techniques in the patient described in the specification or known in the art. The amount of movement (amplitude) can be adjusted based on the amount of respiratory and/or cardiac movement (amplitude). The amount of movement (amplitude) can also be adjusted based on the distance of the OHMD to the patient and/or a computer monitor (if virtual data or images are, for example, aligned with, superimposed onto or overlaid onto a computer monitor). Thus, the computer processor(s) can move virtual data or virtual images, e.g. from a pre-operative scan, in the OHMD display so as to match the movement of the tissues and/or organs during the cardiac and/or respiratory cycle of the patient during the surgical procedure or the intervention; in this manner, the computer system can maintain the display of the virtual data or virtual images superimposed onto and/or aligned with the corresponding anatomic structures, tissues and/or organs both inside the physical patient and/or in virtual data acquired, for example (e.g. in real-time) from the physical patient, e.g. an intra-operative angiogram, run-off or bolus chase study, e.g. displayed by the OHMD and/or a computer monitor.

In order to synchronize virtual data of a patient from a pre-operative image acquisition with the physical patient and/or physical anatomic structures of the patient during a procedure or virtual data of the physical patient obtained during a surgical procedure or an intervention, e.g. a 2D or 3D angiogram, a run-off or a bolus-chase, the computer system and computer processor can also perform a combination of moving of virtual data and displaying of sequential virtual data from the pre-operative imaging study, e.g. from two or more time points, time intervals or time segments of the respiratory and/or cardiac cycle.

Any of the embodiments pertaining to cardiac gating and/or respiratory gating can be combined.

Application Windows, Interfaces

In embodiments, the augmented reality display of the OHMD can be used to display a virtual 2-dimensional application window. This application window can be placed in an arbitrary plane in the 3-dimensional space of the OHMD. Optionally, the surgeon or interventionalist can interactively adjust the position and/or orientation of the virtual application window, for example using hand gesture control. As described elsewhere in this patent application, hand gestures can include finger taps or pinching gestures that are detected and interpreted by the OHMD software, for example to adjust position or size of the virtual application window. Additionally, head movement or eye movement can be used to control the virtual application window, alone or in combination with hand gestures.

The virtual application window can be used to display additional information pertaining to the procedure the patient is undergoing. For example, the additional information can include the angiographic images. The virtual application window can be used to display the image information in the same way as a conventional 2-dimensional monitor. The virtual application window can be used in addition to or in place of a conventional monitor. Using the techniques described, it can be placed according to the physician's preferences, including positions in the immediate vicinity or at a sterile field, thus allowing for better incorporation into the physician's workflow than would be possible with a conventional monitor.

The virtual application window can be used to project one or more 2D or 3D angiographic images. Additionally, the augmented reality OHMD can display a 3D hologram of a pre-operative image of the patient. The 3D hologram can, for example, be extracted from a CT angiography (CTA) or a MR angiography (MRA) scan. Using thresholding or maximum intensity projection or any other suitable technique to extract and/or display vascular structure information extracted from the preoperative scan, the hologram can be displayed near the virtual application window as a reference for the intra-procedural images, for example the angiographic images.

The information extracted from the preoperative images and displayed in the hologram can also be augmented with a visualization of information about the angiography catheter, e.g. the position of the catheter tip. The position of the catheter tip in the vascular tree can be determined from the intraoperative angiography and/or using tracking techniques, e.g. using RF trackers at the catheter tip.

Registration, Tracking, Coordinate Systems

In order to visualize information from the preoperative imaging scan, for example a CTA or MRA or ultrasound, in relationship with the intraoperative 2D or 3D angiographic images, the preoperative and intraoperative images can be registered. This process determines a transformation for one data set to transfer it into a common coordinate system with the other data set. Registrations can optionally be performed using image pixel or image voxel information, or using objects extracted from the pixel or voxel information, or both. Depending on the imaging source used, registrations can optionally be performed from 2D to 2D, 3D to 2D or 3D to 3D.

When used with 2D angiography systems, a 3D to 2D registration can be performed. This process can, for example, comprise the following image processing steps for image voxel/pixel information:
 Calculate 3D to 2D projection of preoperative scan using projection angle alpha
 Compare resulting 2D projection image with 2D angiography and measure difference, for example using a mutual information based technique (Wells, W. M. III et al., 1996. "Multi-modal volume registration by maximization of mutual information". Medical Image Analysis. 1 (1): 35-51
 Optimize the projection angle alpha such that the difference is minimized.
  Alternatively, an initial segmentation can be performed to extract the vascular tree as a separate object from the voxel/pixel information. The following steps describe an exemplary processing sequence with an initial segmentation:

Segment vascular tree from 3D preoperative scan to create a 3D representation of the vascular tree, for example using a thresholding or seed growing technique Segment vascular tree from 2D angiography image to create a 2D representation of the vascular tree, for example using a thresholding or seed growing technique Calculate 3D to 2D projection of 3D vascular tree representation using projection angle alpha Compare resulting 2D projection of vascular tree with 2D representation from angiography image, for example by calculating the overlapping area between the 2D projection of the vascular tree and the 2D representation from the angiography image Optimize the projection angle alpha such that the overlapping area is maximized When a 2D to 2D registration between a first, 2D preoperative image and a second, 2D angiography image is performed, the process can, for example, comprise the following image processing steps:

Calculate 2D transformation of preoperative image using transformation T

Compare resulting transformed 2D preoperative image with 2D angiography image and measure difference, for example using a mutual information based technique (Wells, W. M. Ill et al., 1996. *"Multi-modal volume registration by maximization of mutual information". Medical Image Analysis.* 1 (1): 35-51

Optimize the transformation T such that the difference is minimized.

Alternatively, an initial segmentation can be performed to extract the vascular tree as a separate object from the pixel information. The following steps describe an exemplary processing sequence with an initial segmentation:

Segment vascular tree from 2D preoperative image to create a first 2D representation of the vascular tree, for example using a thresholding or seed growing technique Segment vascular tree from 2D angiography image to create a second 2D representation of the vascular tree, for example using a thresholding or seed growing technique Calculate 2D transformation of first 2D vascular tree representation using transformation T Compare resulting 2D transformation of first 2D vascular tree representation with second 2D representation from angiography image, for example by calculating the overlapping area between the 2D transformation of first 2D vascular tree representation and second 2D representation from the angiography image Optimize the projection transformation T such that the overlapping area is maximized When used with 3D angiography systems, a 3D to 3D registration can be performed. This process can, for example, comprise the following image processing steps for image voxel information:

Calculate 3D transformation of preoperative scan using transformation T

Compare resulting transformed 3D preoperative scan with 3D angiography and measure difference, for example using a mutual information based technique (Wells, W. M. III et al., 1996. *"Multi-modal volume registration by maximization of mutual information". Medical Image Analysis.* 1 (1): 35-51

Optimize the transformation T such that the difference is minimized.

Alternatively, an initial segmentation can be performed to extract the vascular tree as a separate object from the voxel information. The following steps describe an exemplary processing sequence with an initial segmentation:

Segment vascular tree from 3D preoperative scan to create a first 3D representation of the vascular tree, for example using a thresholding or seed growing technique Segment vascular tree from 3D angiography image to create a second 3D representation of the vascular tree, for example using a thresholding or seed growing technique Calculate 3D transformation of first 3D vascular tree representation using transformation T Compare resulting 3D transformation of first 3D vascular tree representation with second 3D representation from angiography image, for example by calculating the overlapping volume between the 3D transformation of first 3D vascular tree representation and second 3D representation from the angiography image Optimize the projection transformation T such that the overlapping volume is maximized In any of the embodiments, one or more coordinate systems can be used. The coordinate system can be a common coordinate system. The common coordinate systems can have sub-coordinate systems, e.g. a sub-coordinate system for the patient, a sub-coordinate system for the OHMD, a sub-coordinate system for a computer monitor, a sub-coordinate system for virtual devices or virtual instruments, and a sub-coordinate system for physical devices or physical instruments.

One or more of the following can be registered in the coordinate system, e.g. a common coordinate system: one or more OHMDs, e.g. worn by a surgeon or interventionalist; the patient; the surgical site; a physical target organ or physical target tissue or physical tissue surface or physical anatomic structure; a virtual target organ or virtual target tissue or virtual tissue surface or virtual anatomic structure; virtual data or virtual images or virtual 3D model from a pre-operative image acquisition; virtual data or virtual images or virtual 3D model from an intra-operative image acquisition, e.g. a 2D or 3D angiogram, a run-off or a bolus chase, or an ultrasound; the movement in x, y, and/or z-direction and/or related x, y, and/or z-coordinates of a physical target organ or physical target tissue or physical tissue surface or physical anatomic structure during the cardiac and/or respiratory cycle of the patient; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a physical device; a physical instrument; a virtual device; a virtual instrument; tracking data; a virtual representation or virtual image generated or obtained from a tracked physical device; a virtual representation or virtual image generated or obtained from a tracked physical instrument. Any of the foregoing can be in a sub-coordinate system, e.g. registered in the common coordinate system.

By registering any of the foregoing in a coordinate system, e.g. a common coordinate system, one or more computer systems with one or more computer processors can co-display one or more of the virtual target organ or virtual target tissue or virtual tissue surface or virtual anatomic structure; virtual data or virtual images from a pre-operative image acquisition;

virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a virtual device; a virtual instrument; tracking data; a virtual representation or virtual image generated or obtained from a tracked physical device; a virtual representation or virtual image generated or obtained from a tracked physical instrument in one or more OHMD displays and/or on one or more computer monitors. By registering any of the foregoing in a coordinate system, e.g. a common coordinate system, one or more computer systems with one or more computer processors can superimpose and/or align the OHMD display of one or more of the virtual target organ or virtual target tissue or virtual tissue surface or virtual anatomic structure; virtual data or virtual images from a pre-operative image acquisition; virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a virtual device; a virtual instrument; tracking data; a virtual representation or virtual image generated or obtained from a tracked physical device; a virtual representation or virtual image generated or obtained from a tracked physical instrument.

By registering any of the foregoing in a coordinate system, e.g. a common coordinate system, one or more computer systems with one or more computer processors can superimpose and/or align the OHMD display of one or more of the virtual target organ or virtual target tissue or virtual tissue surface or virtual anatomic structure; virtual data or virtual images from a pre-operative image acquisition; virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a virtual device; a virtual instrument; tracking data; a virtual representation or virtual image generated or obtained from a tracked physical device; a virtual representation or virtual image generated or obtained from a tracked physical instrument with one or more of a physical surgical site; a physical target organ or physical target tissue or physical tissue surface or physical anatomic structure; the movement in x, y, and/or z-direction and/or related x, y, and/or z-coordinates of a physical target organ or physical target tissue or physical tissue surface or physical anatomic structure during the cardiac and/or respiratory cycle of the patient; a physical device; a physical instrument.

By registering any of the foregoing in a coordinate system, e.g. a common coordinate system, one or more computer systems with one or more computer processors can superimpose and/or align the OHMD display of one or more of the virtual target organ or virtual target tissue or virtual tissue surface or virtual anatomic structure; virtual data or virtual images from a pre-operative image acquisition; virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a virtual device; a virtual instrument; tracking data; a virtual representation or virtual image generated or obtained from a tracked physical device; a virtual representation or virtual image generated or obtained from a tracked physical instrument with a display on a computer monitor of one or more of the virtual target organ or virtual target tissue or virtual tissue surface or virtual anatomic structure; virtual data or virtual images from a pre-operative image acquisition; virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a virtual device; a virtual instrument; tracking data; a virtual representation or virtual image generated or obtained from a tracked physical device; a virtual representation or virtual image generated or obtained from a tracked physical instrument.

By registering any of the one or more OHMDs, e.g. worn by a surgeon or interventionalist; the patient; the surgical site; the physical target organ or physical target tissue or physical tissue surface or physical anatomic structure; the virtual target organ or virtual target tissue or virtual tissue surface or virtual anatomic structure; virtual data or virtual images from a pre-operative image acquisition; virtual data or virtual images from an intra-operative image acquisition, e.g. a 2D or 3D angiogram, a run-off or a bolus chase, or an ultrasound; the movement in x, y, and/or z-direction and/or related x, y, and/or z-coordinates of a physical target organ or physical target tissue or physical tissue surface or physical anatomic structure during the cardiac and/or respiratory cycle of the patient; the movement in x, y, and/or z-direction and/or related x, y, and/or z-coordinates of a virtual target organ or virtual target tissue or virtual tissue surface or virtual anatomic structure during the cardiac and/or respiratory cycle of the patient; the physical device; the physical instrument; the virtual device; the virtual instrument; tracking data; the virtual representation or virtual image generated or obtained from a tracked physical device; the virtual representation or virtual image generated or obtained from the tracked physical instrument in a coordinate system, e.g. a common coordinate system, one or more computer systems with one or more computer processors can maintain the superimposition and/or alignment of the virtual data displayed by the OHMD with the physical structures of the patient during at least portions of the cardiac and/or respiratory cycle, and of the virtual data displayed by the OHMD with the virtual data displayed by a computer monitor during at least portions of the cardiac and/or respiratory cycle. Any display combination and superimposition and/or alignment is possible between one or more OHMDs and one or more computer monitors and one or more OHMDs and the physical structures of the patient, as shown, for example, in Tables 11, 13 and 14. Any display combination of any of the foregoing virtual data is possible either on an OHMD or a computer monitor or a combination thereof.

In some embodiments, certain of the foregoing virtual data, e.g. a vascular tree can be displayed in stationary, non-moving form, e.g. by an OHMD or a computer monitor. In some embodiments, certain of the virtual data, e.g. a heart, can be displayed in moving form, e.g. through the cardiac cycle. In some embodiments, movement of a tracked physical device or instrument in the form of a moving virtual representation of the moving physical device or instrument (e.g. a catheter) can be displayed superimposed and/or aligned on a non-moving display, e.g. a vascular tree, e.g. from a pre-operative image acquisition or an intra-operative image acquisition or a combination of both. The virtual display of the tracked data (e.g. a moving catheter) can be in real time. The virtual display of the tracked data (e.g. a moving catheter) can be by an OHMD; the virtual display of the stationary virtual data, e.g. a vascular tree, can be by the OHMD or a computer monitor. In this manner, the computer system can visualize the movement of the virtual device or instrument, e.g. a virtual catheter, inside the virtual vascular tree, optionally in real time. The information can be used to direct the virtual device or instrument (and with that the physical device or instrument, e.g. using a robot for vascular procedures).

Registration of one or more of the following, e.g. one or more OHMDs, e.g. worn by a surgeon or interventionalist; the patient; the surgical site; a physical target organ or physical target tissue or physical tissue surface or physical anatomic structure; a virtual target organ or virtual target tissue or virtual tissue surface or virtual anatomic structure; virtual data or virtual images or virtual 3D model from a pre-operative image acquisition; virtual data or virtual images or virtual 3D model from an intra-operative image acquisition, e.g. a 2D or 3D angiogram, a run-off or a bolus chase, or an ultrasound; the movement in x, y, and/or z-direction and/or related x, y, and/or z-coordinates of a physical target organ or physical target tissue or physical tissue surface or physical anatomic structure during the cardiac and/or respiratory cycle of the patient; the movement in x, y, and/or z-direction and/or related x, y, and/or z-coordinates of a virtual target organ or virtual target tissue or virtual tissue surface or virtual anatomic structure during the cardiac and/or respiratory cycle of the patient; a physical device; a physical instrument; a virtual device; a virtual instrument; tracking data; a virtual representation or virtual image generated or obtained from a tracked physical device; a virtual representation or virtual image generated or obtained from a tracked physical instrument, into a common coordinate system can be performed for the same phase of the respiratory and/or cardiac cycle, or systole or diastole or peak of the R-wave. The registration can also be performed for a different phase, e.g. by taking into account a correction factor. The registration can also be performed for corresponding sets of data for two or more phases of the respiratory and/or cardiac cycle, e.g. for inspiration and expiration, or for systole and diastole. Registration parameters for phases in between can then be interpolated from the two or more phases.

Registration parameters can also be continuously updated to account for movement of the OHMD, e.g. in case of head movement of the surgeon or interventionalist. For example, if a head movement consisting of a translational component and/or a rotational component is detected using one or more of the OHMD tracking methods described in the specification, the view points for the superimposition of the virtual model in each of the stereoscopic OHMD displays can be corrected by the translational component and/or the view directions for each of the stereoscopic OHMD displays can be corrected by the rotational component.

In each phase of the respiratory and/or cardiac cycle, the 3D model can now be correctly displayed superimposed onto or aligned with the live patient or a computer monitor using the registration parameters corresponding to that phase and the current view points and view directions for the stereoscopic OHMD displays.

Alternatively, only a single registration for a single phase of the respiratory and/or cardiac cycle can be used. For example, systolic preoperative images can be registered with systolic intraoperative images. If preoperative images for other phases of the respiratory and/or cardiac cycle were all acquired in the same respective preoperative coordinate system, and the coordinate system for the intraoperative images can be fixed for the entire respiratory and/or cardiac cycle, the correct image for each phase of the respiratory and/or cardiac cycle can be displayed superimposed onto or aligned with the live patient or the computer monitor by using the gating information of the live patient, selecting the corresponding preoperative image or preoperative model for the gating phase, and applying the initial registration as well as the current OHMD view points and view angles.

Other Considerations for Vascular Applications

The embodiments in the specification pertaining to software and hardware for optical head mounted displays, systems for tracking the user's eyes, systems for measuring the location, orientation, coordinates and/or acceleration of anatomic structure, organs or body parts, novel user interfaces (e.g. virtual user interfaces including user interfaces with gesture recognition), techniques to move surgical instruments (for example using head movement), techniques to superimpose virtual data of the patient onto live data of the patient including intra-procedural imaging studies, techniques for image segmentation, techniques for registration of data (e.g. live data of the patient and virtual data including virtual instruments and devices and virtual data of the patient), techniques for superimposing and aligning virtual data onto live data, techniques of locking or moving virtual data, techniques of improving the accuracy of moving or re-orienting virtual data, use of virtual data in 2 or more dimensions, techniques of scrolling through, or moving virtual data superimposed onto live data of the patient, techniques for registration of virtual and live data using superimposition or object coordinate systems or spatial mapping or visual anatomic features or anatomic landmarks or implantable markers or optical markers or intraoperative imaging or skin or soft-tissue markers or calibration or registration phantoms, techniques to estimate the distance and/or orientation of an OHMD relative to a surgical or target site and/or relative to a standalone computer monitor, registration techniques accounting for soft-tissue deformation, registration techniques using CAD files or 3D data files of instruments and/or devices, registration techniques using non-anatomic data, registration techniques after performing a tissue alteration, virtual surgical plans, modifications of virtual surgical plans, placement rules, tissue morphing (e.g. from 2D images), stereoscopic and non-stereoscopic displays, refresh rates, automatic turning on and off of OHMD displays, managing bandwidth limitations, viewing 2D computer monitors through OHMD displays with superimposition of OHMD displays, magnified displays, and displaying virtual surgical instruments and/or virtual devices can be applied to various aspects of vascular interventions including, but not limited to, neurovascular interventions, cardiovascular interventions, cardiac interventions, thoracic including pulmonary vascular interventions, abdominal vascular interventions, pelvic vascular interventions, musculoskeletal vascular interventions, spinal vascular interventions, and/or extremity vascular interventions. It should be appreciated that the term "bone" can be exchanged for the term "vascular" or "vessel" in some embodiments. The term "cartilage" can be exchanged for the term "vascular" or "vessel" in some embodiments. The term "tissue" or "target tissue" can be exchanged for the term "vascular" or "vessel"

in some embodiments. The term "live data" can include intra-procedural imaging, e.g. 2D or 3D angiography, digital subtraction angiography, contrast studies, contrast imaging, flow studies, bolus studies, and bolus tracking, in some embodiments.

INCORPORATION BY REFERENCE

All publications, patents mentioned herein are hereby incorporated by references in their entirety as if each individual publication or patent was specifically and individually indicated to be incorporated by reference.

The invention claimed is:

1. A system comprising:
a stereoscopic optical head mounted display; and
a computer system comprising one or more processors,
wherein the one or more processors are configured to receive a first set of real time images obtained during a phase of systole and a second set of real time images obtained during a phase of diastole of a cardiac cycle of a patient, wherein the phases of the cardiac cycle of the patient are determined using an electrocardiogram (ECG),
wherein the first set of real time images is tagged with the ECG data from the phase of systole during image acquisition,
wherein the second set of real time images is tagged with the ECG data from the phase of diastole during image acquisition,
wherein the one or more processors are configured to generate a first set of ECG data tagged three-dimensional (3D) stereoscopic views based on information from the first set of tagged real time images, and a second set of ECG data tagged 3D stereoscopic views based on information from the second set of tagged real time images,
wherein the one or more processors are configured to receive real time intra-operative ECG data of a phase of systole and a phase of diastole of the cardiac cycle of the patient during a medical, radiologic, or surgical procedure,
wherein the one or more computer processors are configured to match the ECG data tags of the first set of 3D stereoscopic views with corresponding intra-operative ECG data of the phase of systole and to match the ECG data tags of the second set of 3D stereoscopic views with the corresponding intra-operative ECG data of the phase of the diastole, and
wherein the one or more computer processors are configured to display, by the stereoscopic optical head mounted display, (i) the first set of ECG data tagged 3D stereoscopic views superimposed or aligned with a beating heart or a pulsating physical vascular structure of the patient during the phase of systole, and (ii) the set of second ECG data tagged 3D stereoscopicviews superimposed or aligned with the beating heart or the pulsating physical vascular structure of the patient during the phase of diastole.

2. The system of claim 1, wherein the intra-operative ECG data from the phase of systole or the intra-operative ECG data from the phase of diastole comprise a portion of an ECG wave, a peak or valley in an ECG wave, or a combination thereof.

3. The system of claim 1, wherein the one or more processors are configured to display the first set of ECG data tagged 3D stereoscopic views superimposed or aligned with the beating heart or the pulsating physical vascular structure of the patient through the phase of systole and the second ECG data tagged 3D stereoscopic views superimposed or aligned with the beating heart or the pulsating physical vascular structure of the patient through the phase of diastole for successive cardiac cycles.

4. The system of claim 1, further comprising at least one infrared marker, a radiofrequency (RF) marker, an active marker, a passive marker, an inertial measurement unit (IMU), a light-emitting diode (LED), an optical marker, a geometric pattern, a surgical navigation system, a camera, a video system, an image capture system, a depth sensor, a laser scanner, a 3D scanner, a patient specific marker, a patient specific template, an x-ray, an imaging system, or combination thereof configured to obtain x, y, and z coordinates of the beating heart or the pulsating physical vascular structure, the stereoscopic optical head mounted display, a device, an instrument or combinations thereof in a coordinate system.

5. The system of claim 4, wherein the one or more processors are configured to adjust in real time the ECG data tagged 3D stereoscopic views displayed by the stereoscopic optical head mounted display responsive to movement of the beating heart or the pulsating physical vascular structure, the stereoscopic optical head mounted display, the device, the instrument or combinations thereof.

6. The system of claim 4, wherein the device comprises a catheter, catheter tip, guidewire, sheath, stent, coil, implant, or vascular prosthesis.

7. The system of claim 4, wherein the instrument comprises a grasper, vein valve cutter, vein extirpation set, or extraction instrument.

8. The system of claim 1, wherein the first and second set of tagged real time images comprise x-ray images, a two-dimensional (2D) angiogram, a 3D angiogram, a vascular run-off, a bolus chase study, a computed tomography (CT) scan, a contrast enhanced CT scan, a CT angiogram, a magnetic resonance imaging (MRI) scan, a contrast enhanced MRI scan, a magnetic resonance (MR) angiogram, an ultrasound, a contrast enhanced ultrasound, an echocardiogram, a contrast enhanced echocardiogram, a single photon emission computed tomography (SPECT) scan, a positron emission tomography (PET) scan, a nuclear heart scan, or combinations thereof.

9. The system of claim 8, wherein the first and second set of ECG data tagged real time images are obtained preoperatively, or wherein the first and second set of ECG data tagged real time images are obtained intraoperatively, or wherein the first and second set of ECG data tagged real time images are obtained preoperatively and intraoperatively.

10. The system of claim 1, wherein the first and second set of ECG data tagged real time 3D stereoscopic views further comprise a three-dimensional digital representation corresponding to at least one portion of a physical device, a physical instrument or a combination thereof.

11. The system of claim 1, wherein the first and second set of ECG data tagged real time 3D stereoscopic views further comprise a three-dimensional digital representation corresponding to at least one virtual guide, virtual path, virtual trajectory, virtual tissue resection, virtual tissue ablation, virtual device, virtual implant, virtual instrument or a combination thereof.

12. The system of claim 1, wherein the stereoscopic optical head mounted display is an optical see through stereoscopic optical head mounted display.

13. The system of claim 12, wherein the system is configured to adjust the transparency of the optical see through stereoscopic optical head mounted display.

14. The system of claim 1, wherein the first set of real time ECG data tagged images during the phase of systole and/or the second set of real time ECG data tagged images during the phase of diastole comprise information about a direction of cardiac or vascular movement or pulsation, speed of cardiac or vascular movement or pulsation, an amount of cardiac or vascular movement or pulsation, flow volume, flow amplitude, ejection fraction or a combination thereof.

15. The system of claim 1, wherein the one or more processors are configured to display the first set of systolic ECG data tagged 3D stereoscopic views superimposed or aligned with the beating heart or the pulsating physical vascular structure of the patient sequentially during the phase of systole and the second set of diastolic ECG data tagged 3D stereoscopic views superimposed or aligned with the beating heart or the pulsating physical vascular structure of the patient sequentially during the phase of diastole.

16. The system of claim 15, wherein the display is repeated for multiple cardiac cycles of the patient.

17. The system of claim 1, wherein the one or more processors are configured to adjust in real time the first set of systolic ECG data tagged 3D stereoscopic views and/or the second set of diastolic ECG data tagged 3D stereoscopic views displayed by the stereoscopic optical head mounted display responsive to movement of the beating heart or the pulsating physical vascular structure, the stereoscopic optical head mounted display, a device, an instrument or a combination thereof.

* * * * *